(12) United States Patent
Haddick et al.

(10) Patent No.: US 8,964,298 B2
(45) Date of Patent: Feb. 24, 2015

(54) VIDEO DISPLAY MODIFICATION BASED ON SENSOR INPUT FOR A SEE-THROUGH NEAR-TO-EYE DISPLAY

(71) Applicant: Microsoft Corporation, Redmond, WA (US)

(72) Inventors: John D. Haddick, Larkspur, CA (US); Ralph F. Osterhout, San Francisco, CA (US)

(73) Assignee: Microsoft Corporation, Redmond, WA (US)

( * ) Notice: Subject to any disclaimer, the term of this patent is extended or adjusted under 35 U.S.C. 154(b) by 7 days.

(21) Appl. No.: 13/627,930

(22) Filed: Sep. 26, 2012

(65) Prior Publication Data

US 2013/0127980 A1   May 23, 2013

Related U.S. Application Data

(63) Continuation-in-part of application No. 13/591,187, filed on Aug. 21, 2012, now abandoned, which is a continuation-in-part of application No. 13/441,145, filed on Apr. 6, 2012, application No. 13/627,930, (Continued)

(51) Int. Cl.
*G02B 27/14* (2006.01)
*G06F 3/01* (2006.01)
(Continued)

(52) U.S. Cl.
CPC .................. *G06F 3/013* (2013.01); *H04N 7/15* (2013.01); *G06F 1/163* (2013.01); *G02B 27/017* (2013.01);

(Continued)

(58) Field of Classification Search
USPC .......................................................... 359/630
See application file for complete search history.

(56) References Cited

U.S. PATENT DOCUMENTS 5,151,722 A   9/1992   Massof et al.
5,625,765 A   4/1997   Ellenby et al.
(Continued)

FOREIGN PATENT DOCUMENTS

EP    1637975 A1    3/2006
JP    H08136852 A   5/1996
(Continued)

OTHER PUBLICATIONS

Starner, Thad et al., "Augmented Reality Through Wearable Computing", MIT Media Laboratory Perceptual Computing Section Technical Report, vol. 397, Jan. 1, 1997, 9 pages.

(Continued)

*Primary Examiner* — James Jones
(74) *Attorney, Agent, or Firm* — Rachael Vaughn; Leonard Smith; Micky Minhas

(57) ABSTRACT

This disclosure concerns a near field communication (NFC) device which includes a wrist-worn NFC-enabled electronics device, wherein the wrist-worn NFC enabled electronics device includes a first communications link for communicating with a second NFC-enabled electronics device via NFC protocols, and a second communications link for communicating with an eyepiece via a medium-range communications protocol and receiving control commands. The wrist-worn NFC-enabled electronics device facilitates the transfer of data between the eyepiece and the second NFC-enabled electronics device. The eyepiece comprises optics enabling a see-through display on which is displayed the data.

8 Claims, 216 Drawing Sheets

Related U.S. Application Data which is a continuation-in-part of application No. 13/429,413, filed on Mar. 25, 2012, now Pat. No. 8,477,425, said application No. 13/591,187 is a continuation-in-part of application No. 13/341,758, filed on Dec. 30, 2011, application No. 13/627,930, which is a continuation-in-part of application No. 13/232,930, filed on Sep. 14, 2011, application No. 13/627,930, which is a continuation-in-part of application No. 13/037,324, filed on Feb. 28, 2011, application No. 13/627,930, which is a continuation-in-part of application No. 13/037,335, filed on Feb. 28, 2011.

(60) Provisional application No. 61/539,269, filed on Sep. 26, 2011, provisional application No. 61/679,522, filed on Aug. 3, 2012, provisional application No. 61/679,558, filed on Aug. 3, 2012, provisional application No. 61/679,542, filed on Aug. 3, 2012, provisional application No. 61/679,578, filed on Aug. 3, 2012, provisional application No. 61/679,601, filed on Aug. 3, 2012, provisional application No. 61/679,541, filed on Aug. 3, 2012, provisional application No. 61/679,548, filed on Aug. 3, 2012, provisional application No. 61/679,550, filed on Aug. 3, 2012, provisional application No. 61/679,557, filed on Aug. 3, 2012, provisional application No. 61/679,566, filed on Aug. 3, 2012, provisional application No. 61/644,078, filed on May 8, 2012, provisional application No. 61/670,457, filed on Jul. 11, 2012, provisional application No. 61/674,689, filed on Jul. 23, 2012, provisional application No. 61/598,885, filed on Feb. 14, 2012, provisional application No. 61/598,889, filed on Feb. 14, 2012, provisional application No. 61/598,896, filed on Feb. 14, 2012, provisional application No. 61/604,917, filed on Feb. 29, 2012, provisional application No. 61/584,029, filed on Jan. 6, 2012, provisional application No. 61/557,289, filed on Nov. 8, 2011, provisional application No. 61/382,578, filed on Sep. 14, 2010, provisional application No. 61/472,491, filed on Apr. 6, 2011, provisional application No. 61/483,400, filed on May 6, 2011, provisional application No. 61/487,371, filed on May 18, 2011, provisional application No. 61/504,513, filed on Jul. 5, 2011, provisional application No. 61/308,973, filed on Feb. 28, 2010, provisional application No. 61/373,791, filed on Aug. 13, 2010, provisional application No. 61/382,578, filed on Sep. 14, 2010, provisional application No. 61/410,983, filed on Nov. 8, 2010, provisional application No. 61/429,445, filed on Jan. 3, 2011, provisional application No. 61/429,447, filed on Jan. 3, 2011.

(51) Int. Cl.
*H04N 7/15* (2006.01)
*G06F 1/16* (2006.01)
*G02B 27/01* (2006.01)
*G02B 27/00* (2006.01)
*A61B 3/113* (2006.01)
*H04N 7/14* (2006.01)
*H04N 13/04* (2006.01)

(52) U.S. Cl.
CPC ............... *A61B 3/113* (2013.01); *H04N 7/142* (2013.01); *H04N 13/0468* (2013.01); *G02B 2207/113* (2013.01); *G02B 2207/115* (2013.01); *G02B 27/0093* (2013.01); *G02B 2027/0112* (2013.01); *G02B 2027/0178* (2013.01); *G02B 2027/0118* (2013.01); *G02B 2027/014* (2013.01)
USPC ........................................................ 359/630

(56) References Cited

U.S. PATENT DOCUMENTS

| | | |
|---|---|---|
| 5,699,194 A | 12/1997 | Takahashi |
| 5,949,583 A | 9/1999 | Rallison et al. |
| 6,040,945 A | 3/2000 | Karasawa |
| 6,091,546 A | 7/2000 | Spitzer |
| 6,204,974 B1 | 3/2001 | Spitzer |
| 2003/0030912 A1 | 2/2003 | Gleckman et al. |
| 2006/0028400 A1 | 2/2006 | Lapstun et al. |
| 2006/0152434 A1 | 7/2006 | Sauer et al. |
| 2006/0284791 A1 | 12/2006 | Chen et al. |
| 2007/0035563 A1 | 2/2007 | Biocca et al. |
| 2007/0052672 A1* | 3/2007 | Ritter et al. .................. 345/156 |
| 2007/0263137 A1 | 11/2007 | Shigeta et al. |
| 2008/0246694 A1 | 10/2008 | Fischer |
| 2010/0164990 A1 | 7/2010 | Van Doorn |
| 2011/0221896 A1 | 9/2011 | Haddick et al. |

FOREIGN PATENT DOCUMENTS

| | | | |
|---|---|---|---|
| JP | 2008176681 | A | 7/2008 |
| JP | 2009222774 | A | 10/2009 |
| KR | 20110063075 | A | 6/2011 |
| WO | 9636898 | A2 | 11/1996 |

OTHER PUBLICATIONS

ISA European Patent Office, International Search Report and Written Opinion for Patent Application No. PCT/US2011/026558, Aug. 11, 2011, 11 pages.

ISA European Patent Office, International Search Report and Written Opinion for Patent Application No. PCT/US2011/026559, Aug. 11, 2011, 11 pages.

ISA European Patent Office, International Search Report and Written Opinion for Patent Application No. PCT/US2011/051650, Jul. 11, 2012, 23 pages.

ISA Korean Intellectual Property Office, International Search Report and Written Opinion for Patent Application No. PCT/US2012/022492, Jul. 30, 2012, 10 pages.

ISA Korean Intellectual Property Office, International Search Report and Written Opinion for Patent Application No. PCT/US2012/022568, Oct. 31, 2012, 9 pages.

ISA Korean Intellectual Property Office, International Search Report and Written Opinion for Patent Application No. PCT/US2012/057387, Mar. 29, 2013, 11 pages.

* cited by examiner

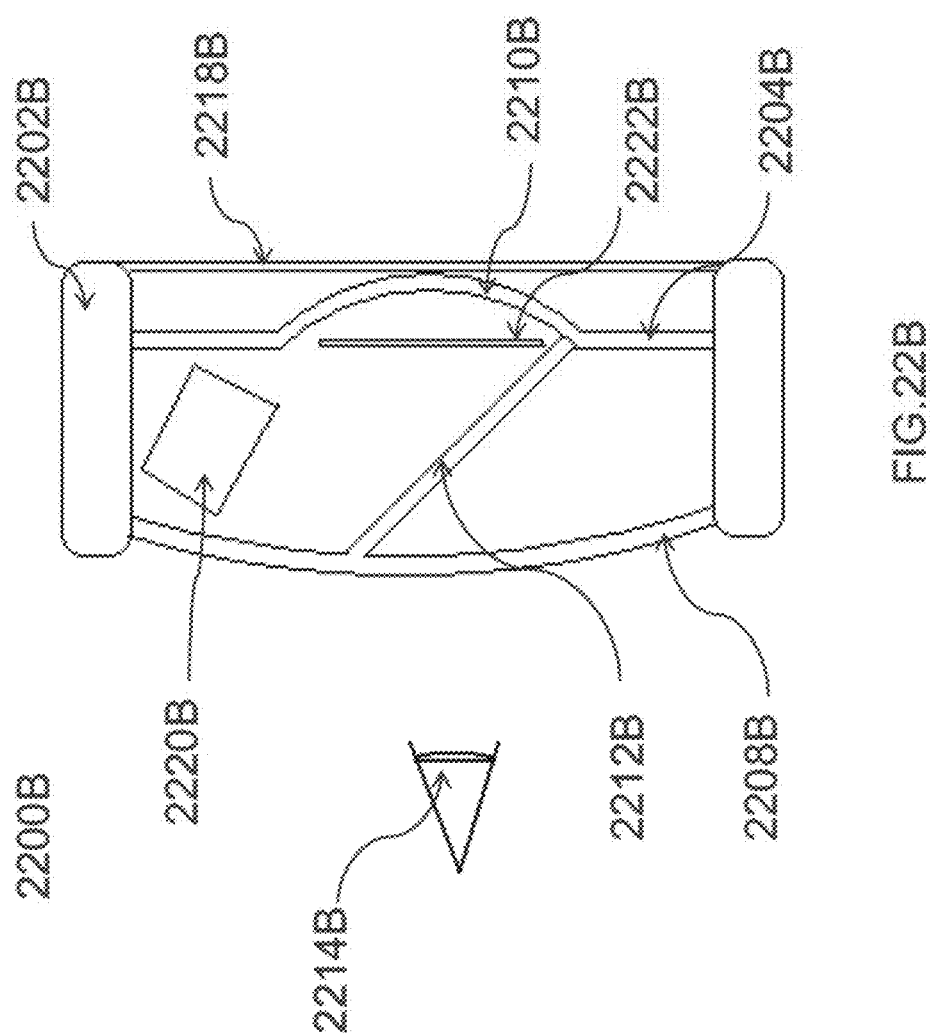

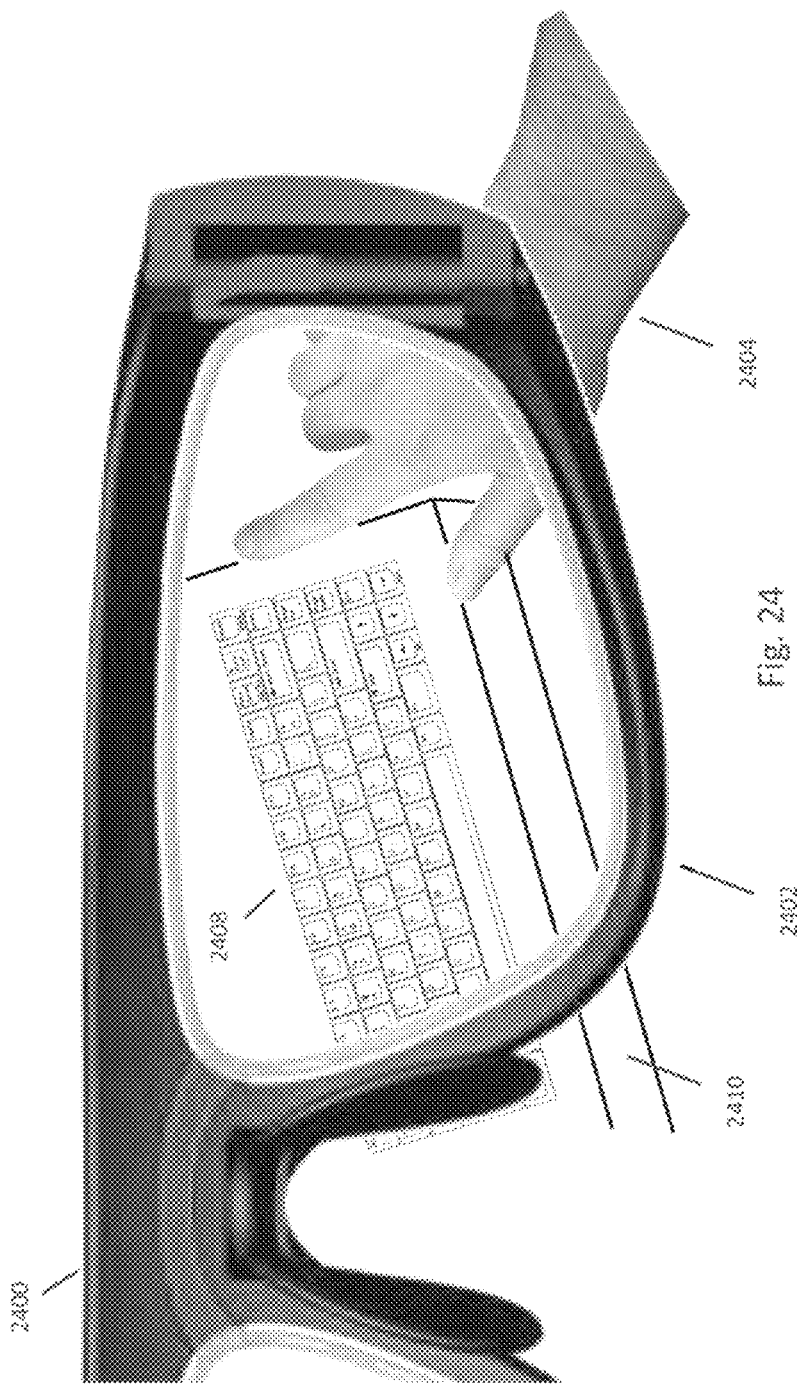

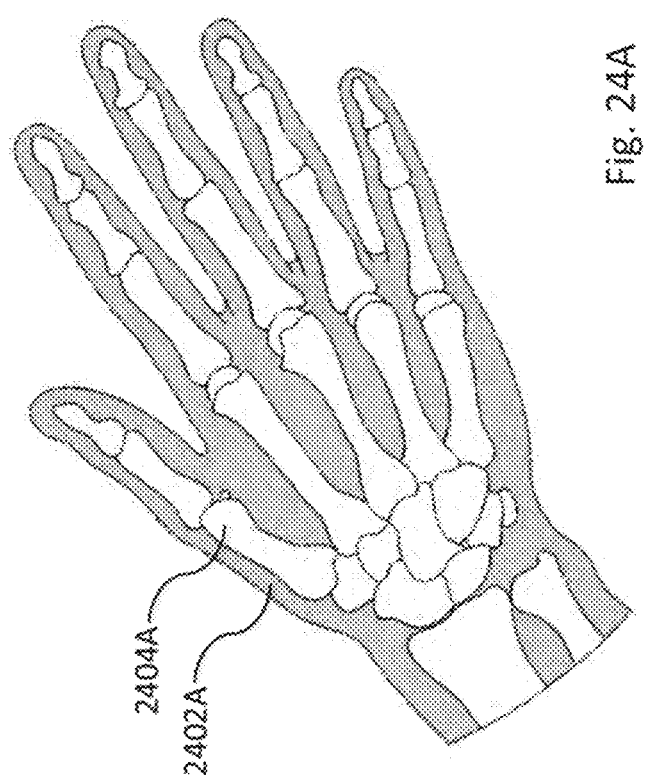

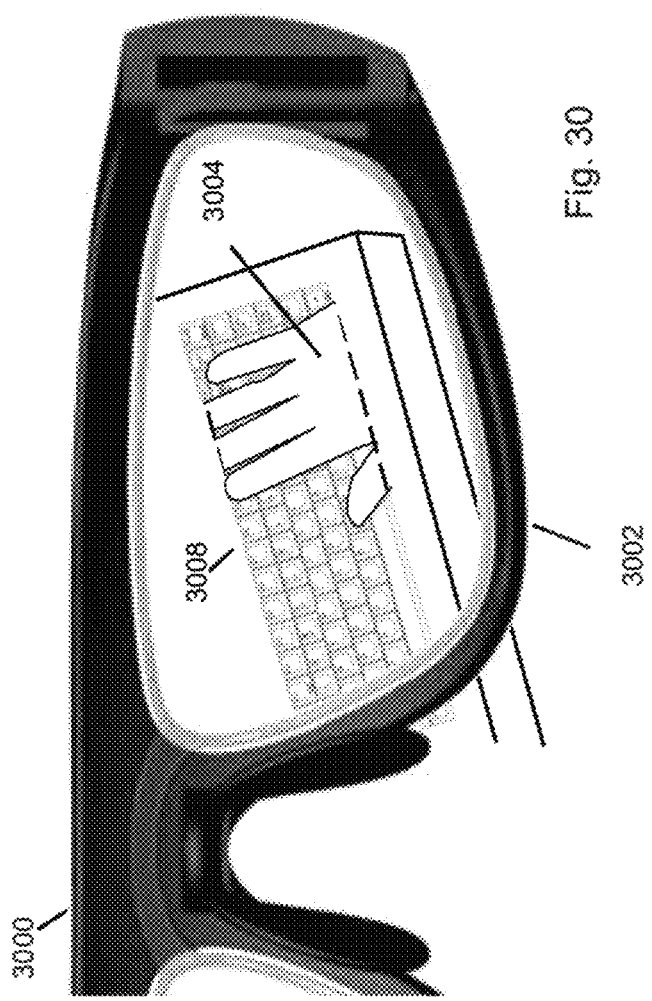

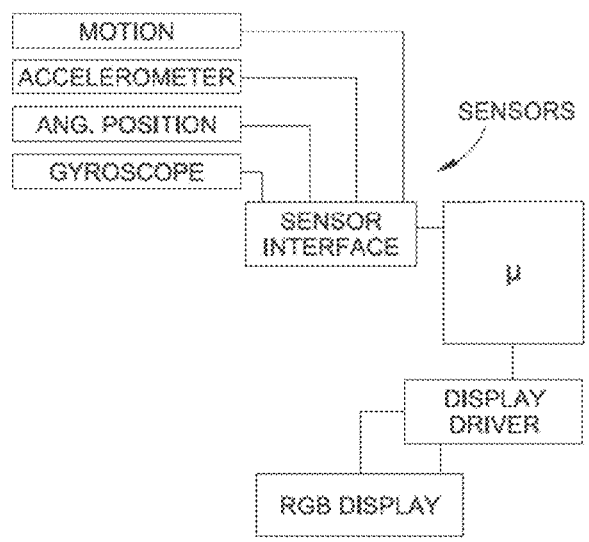
FIG. 34A
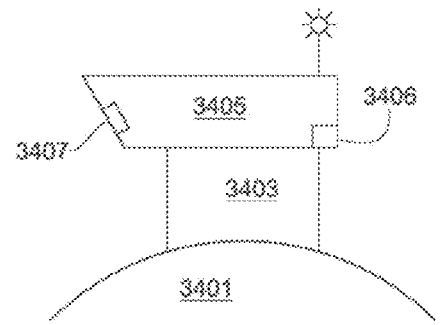
FIG. 34B
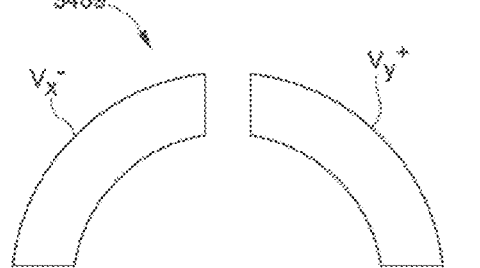
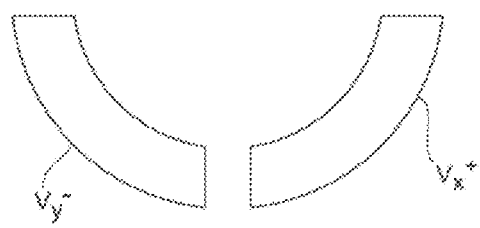
FIG. 34C

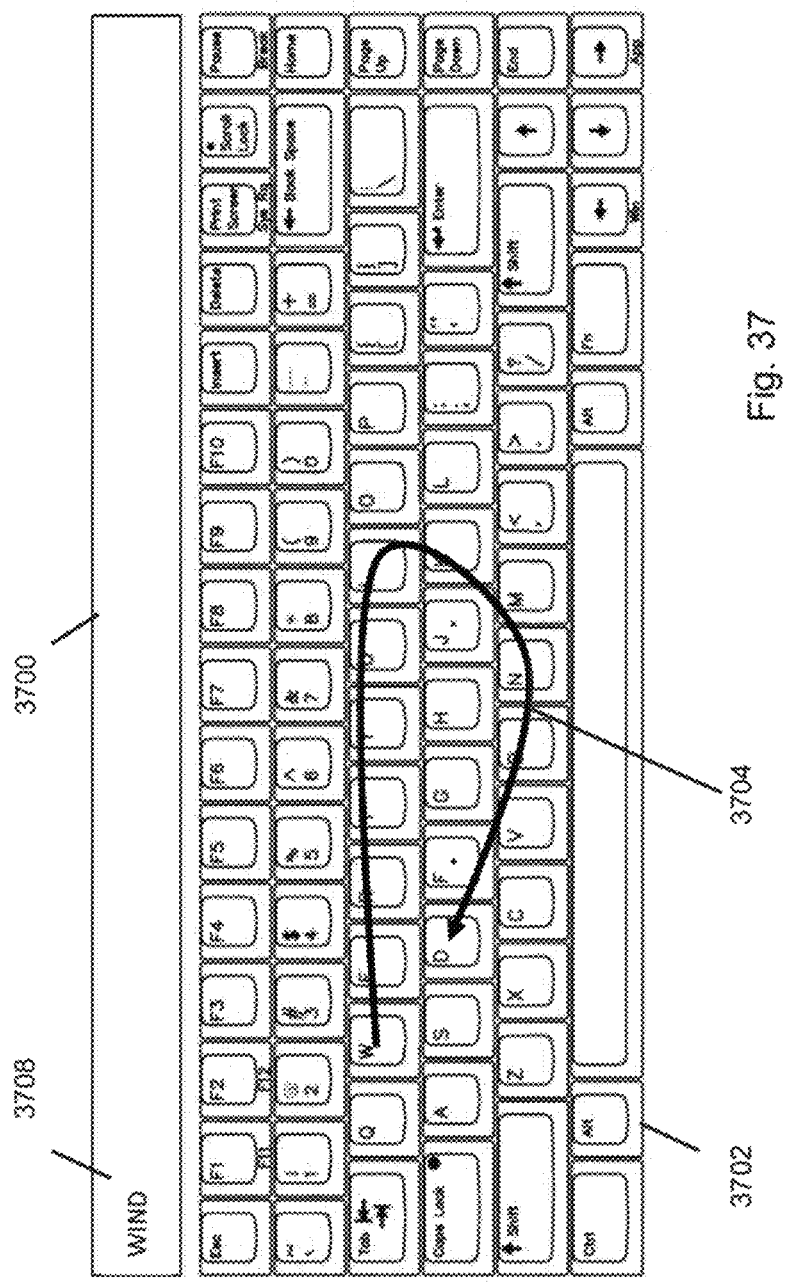

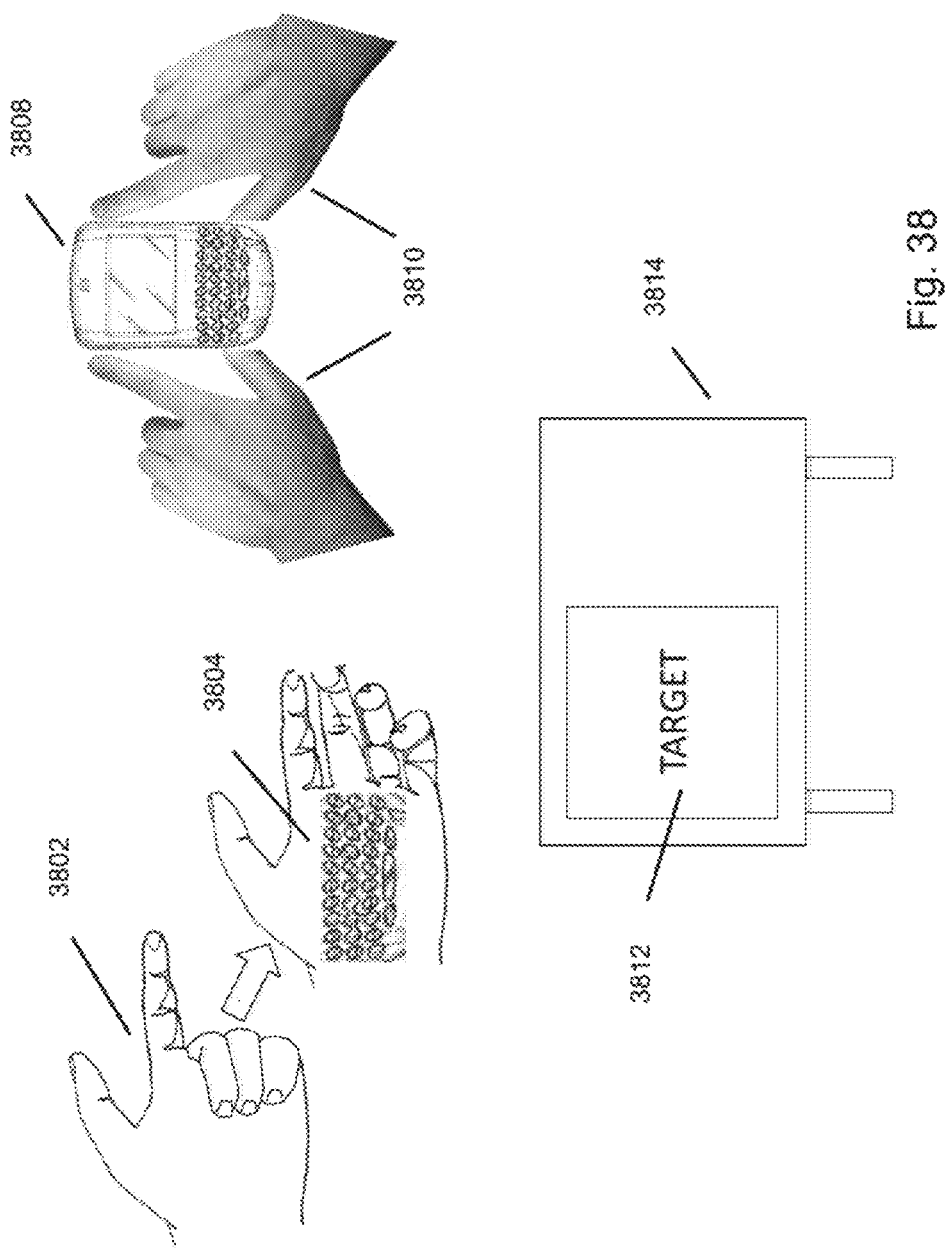

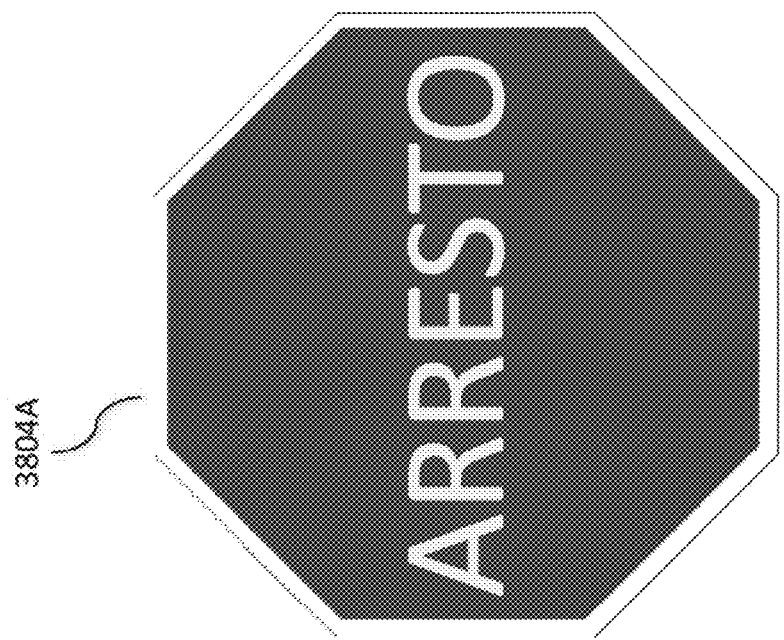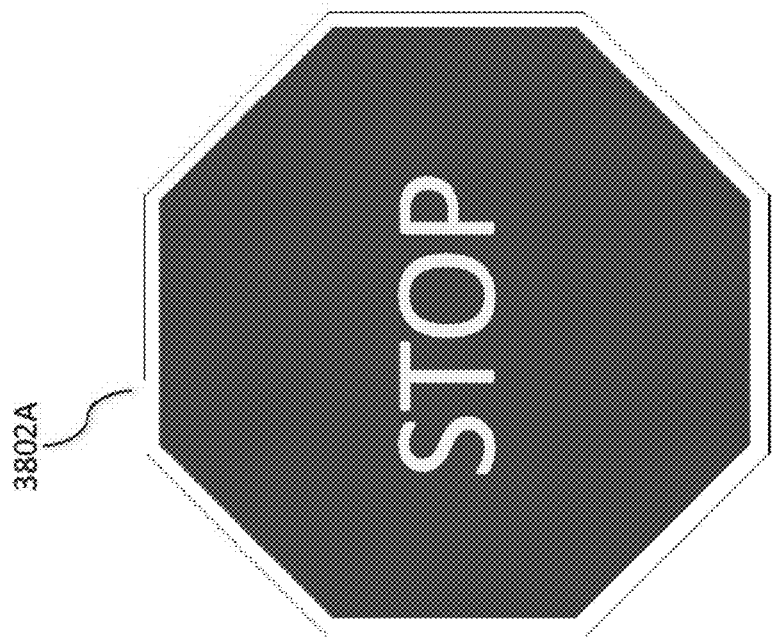
Fig. 38A

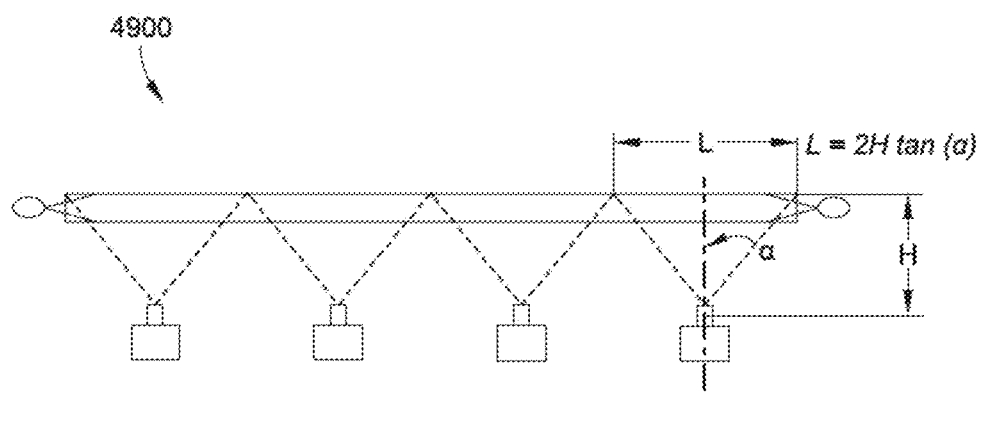
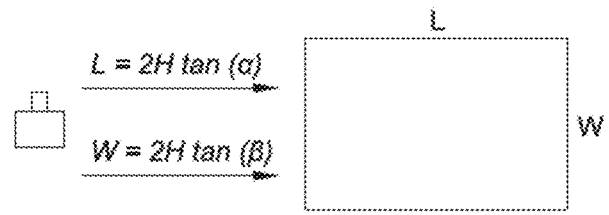
α = 1/2 CAMERA HORIZONTAL FOV
β = 1/2 CAMERA VERTICAL FOV
FIG. 49

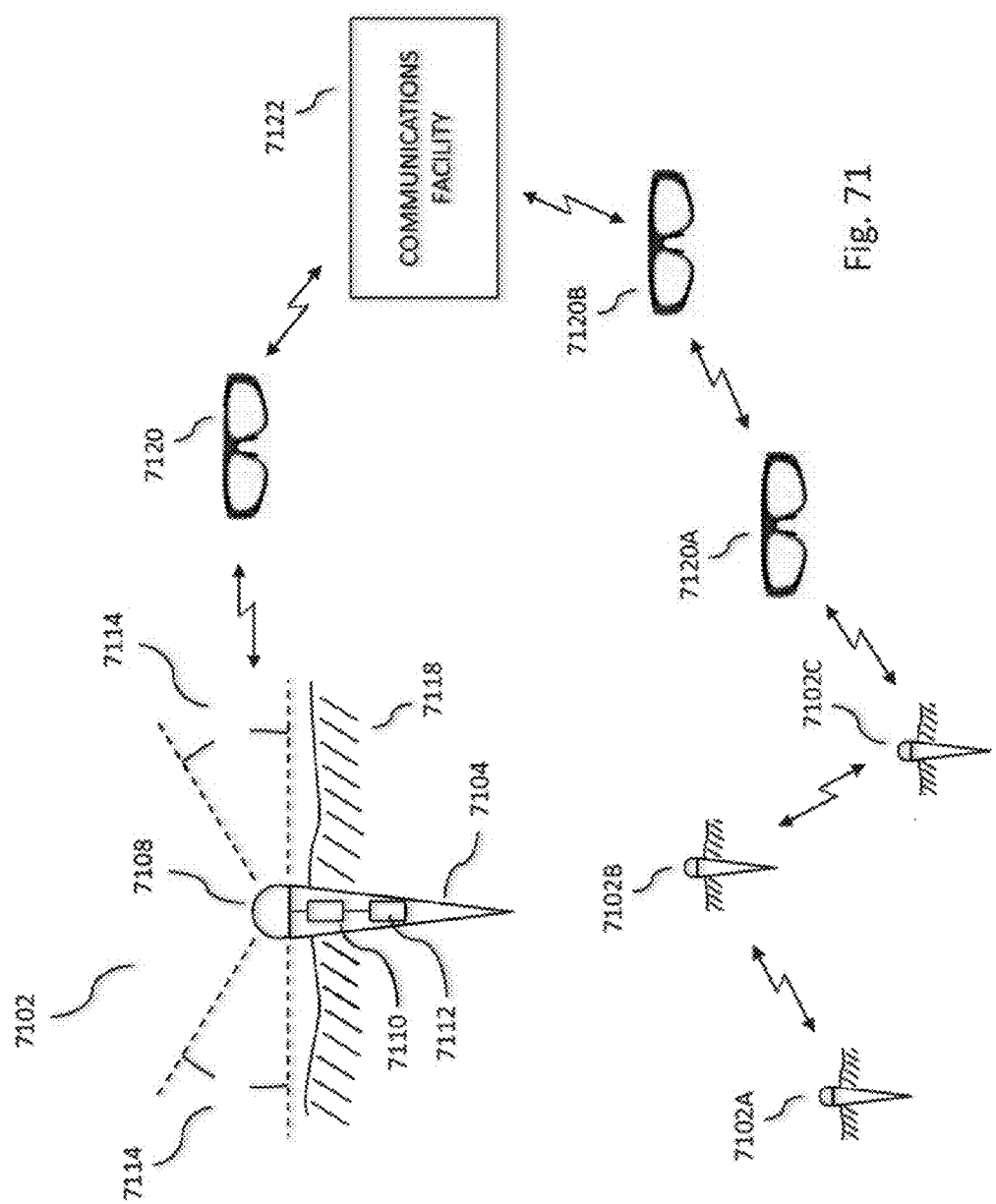

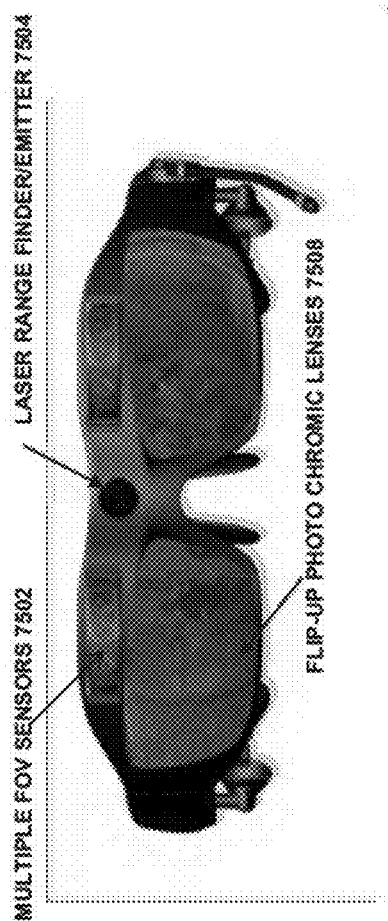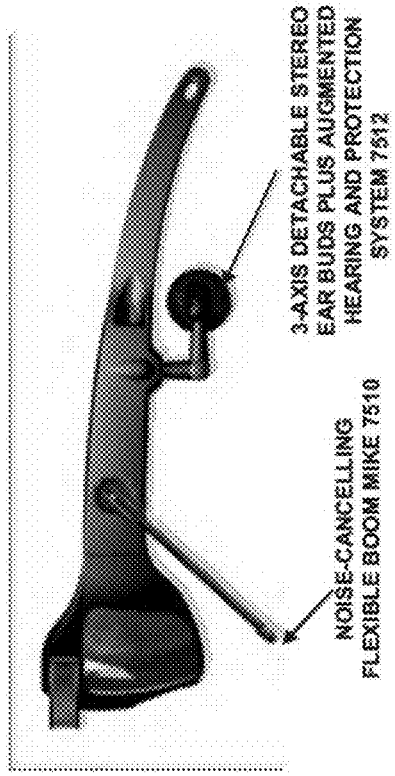
Fig. 75

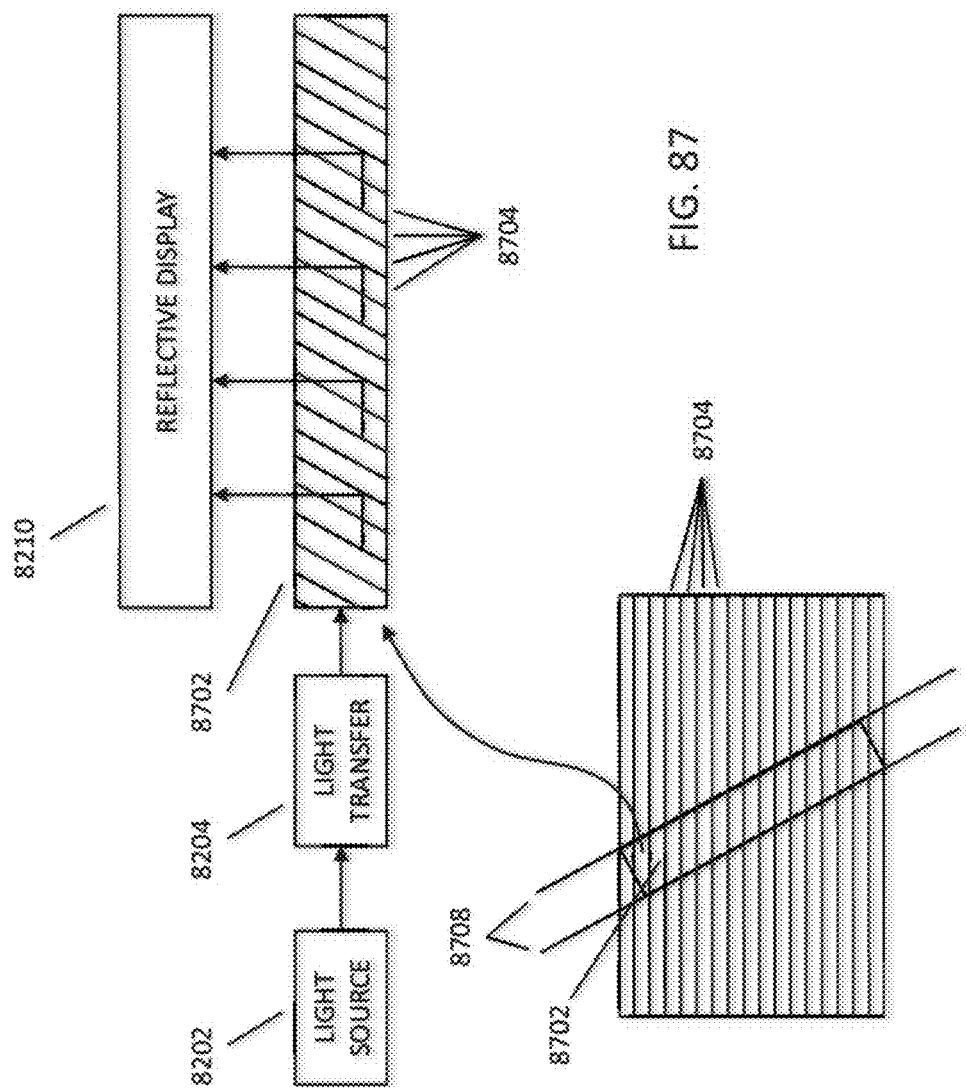

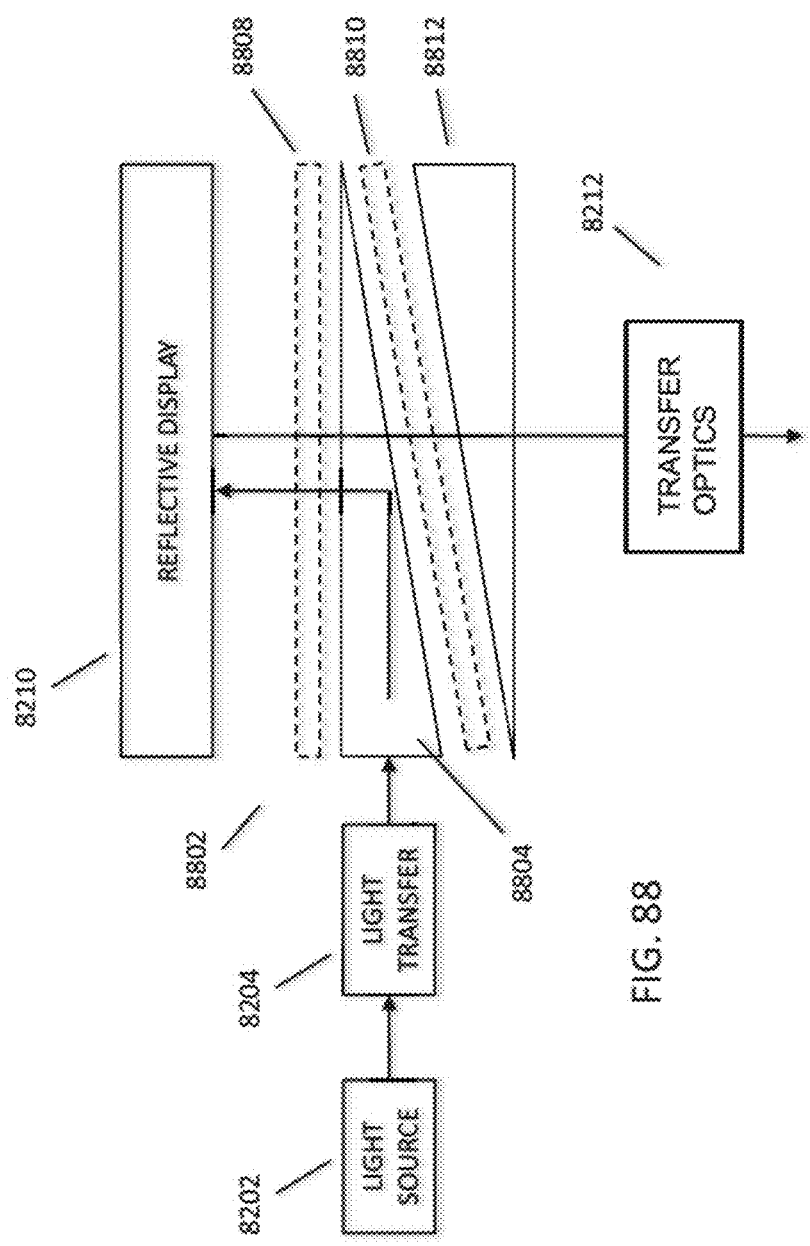

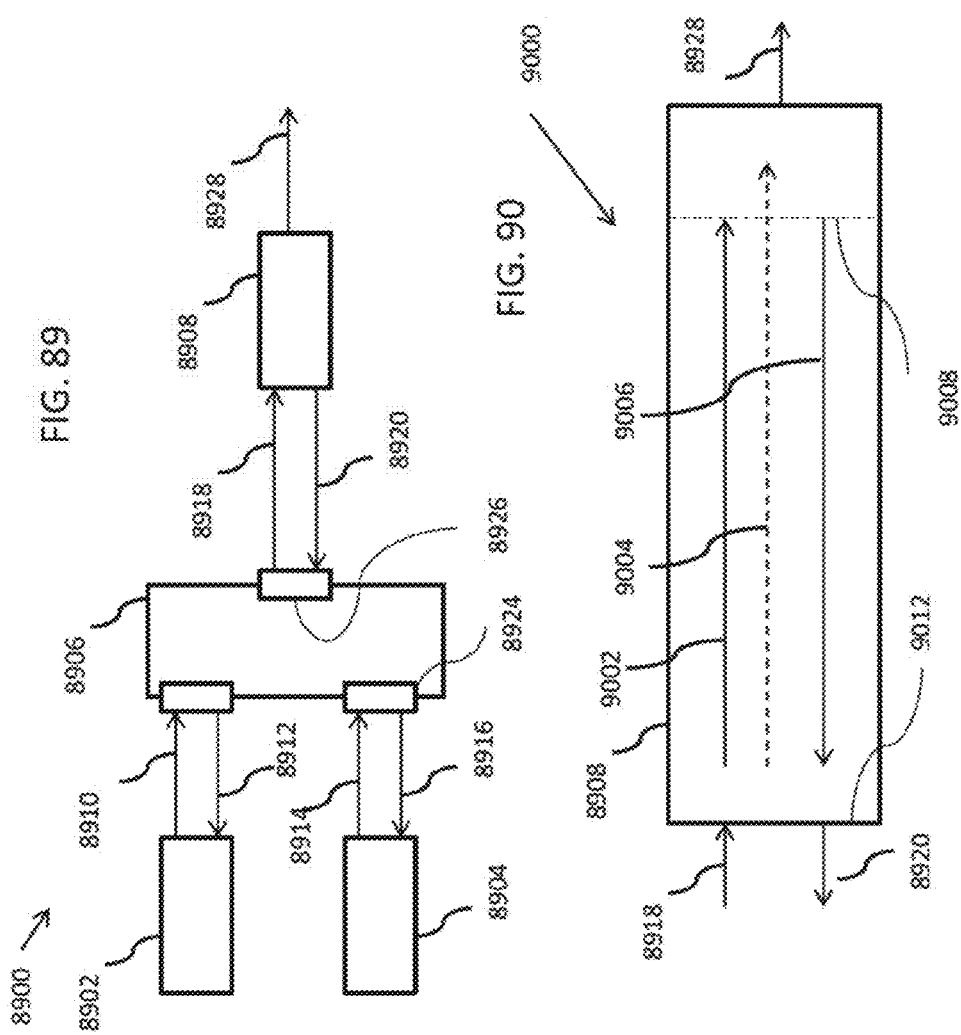

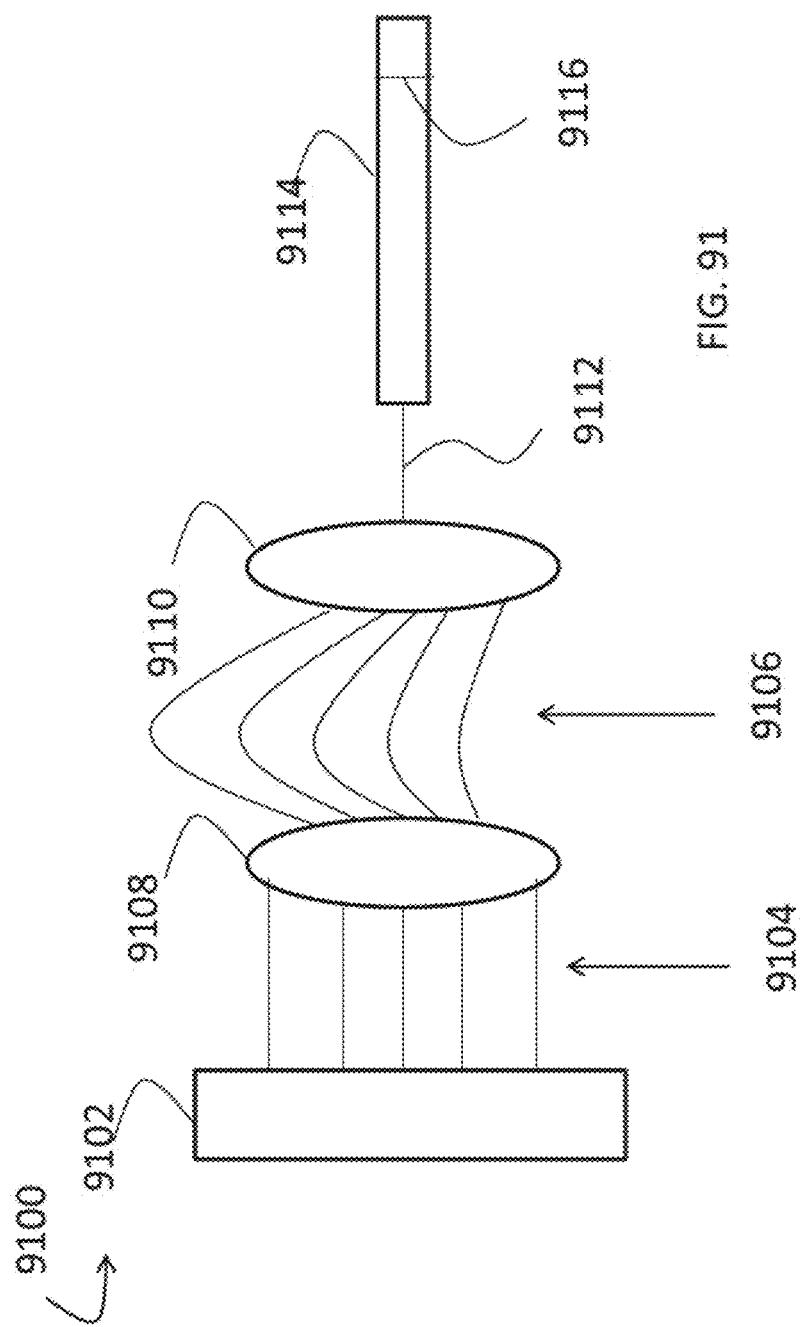

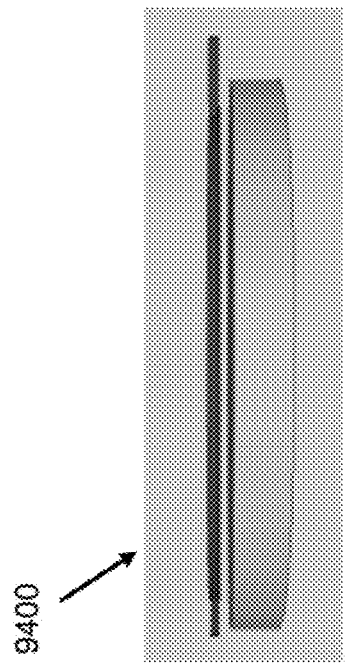
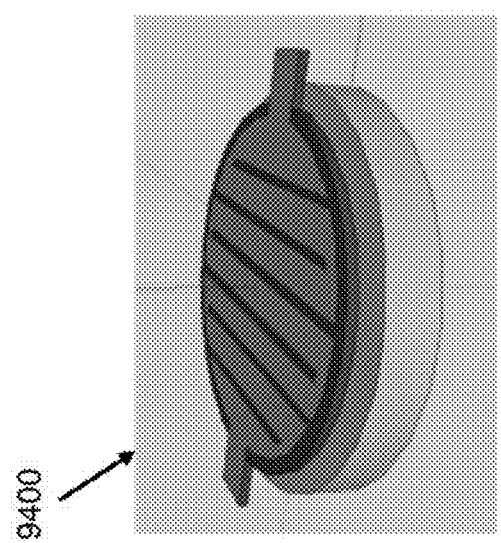
Fig. 94A
Fig. 94B

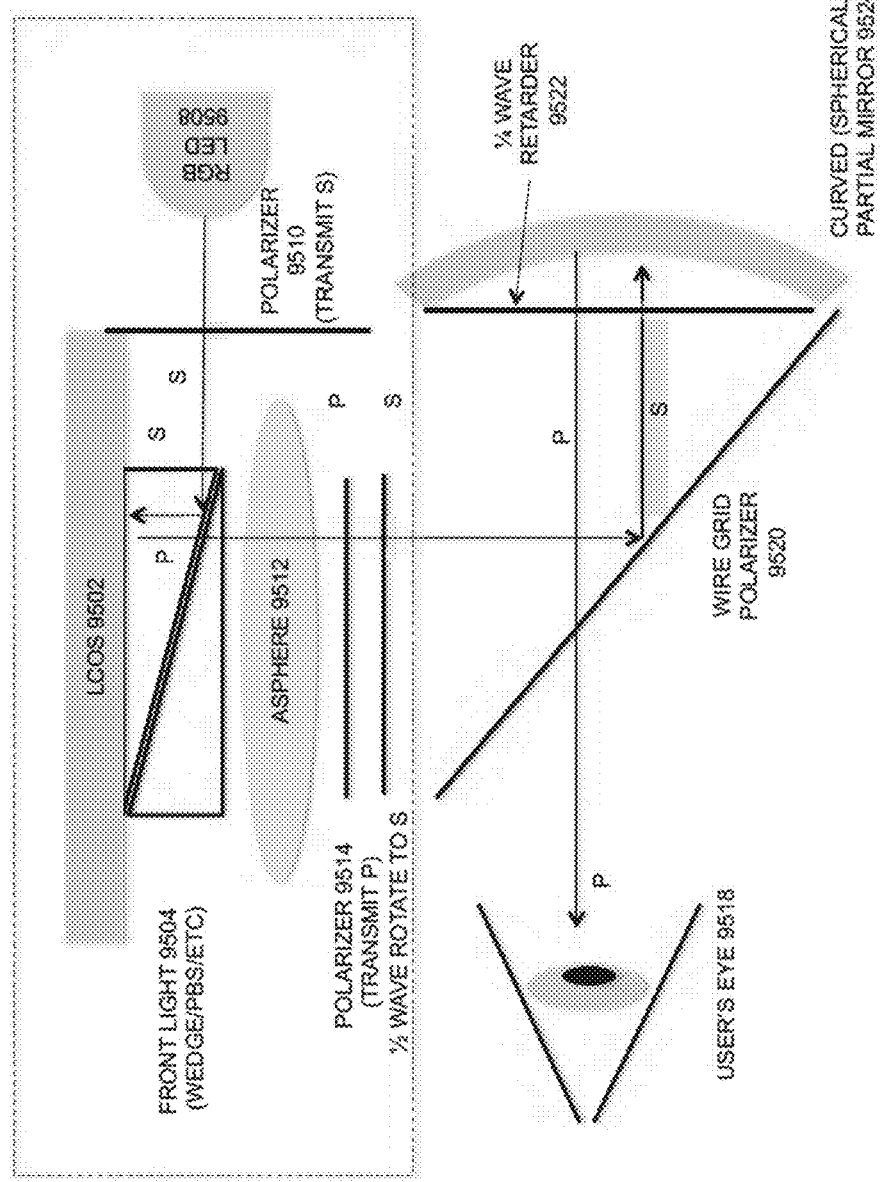

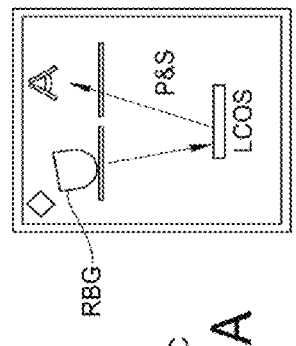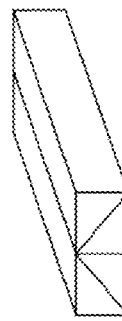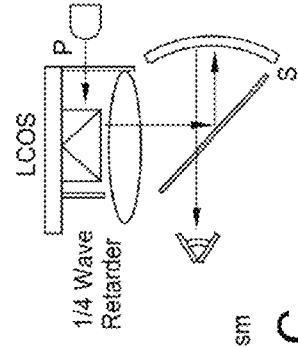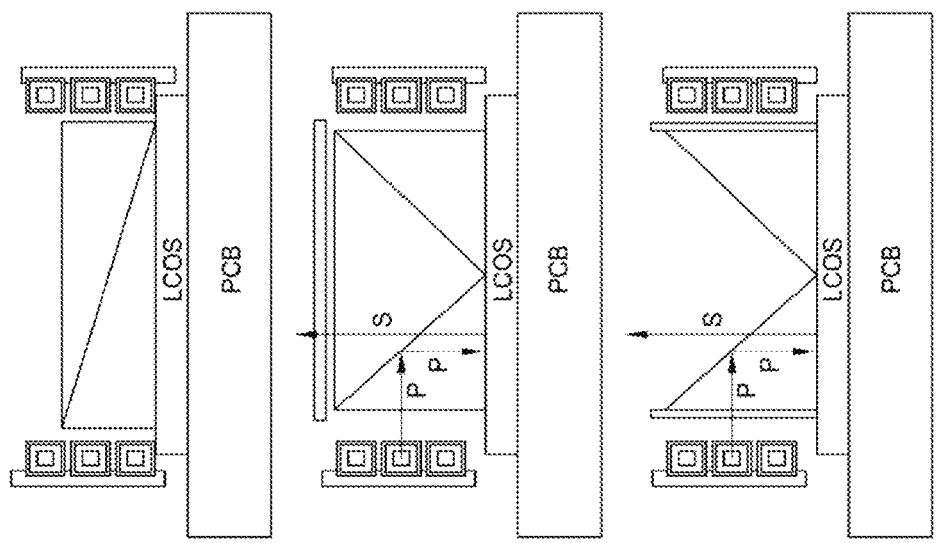
FIG. 98A Wedge + MLC
FIG. 98B PBS
FIG. 98C Right Angle Prism

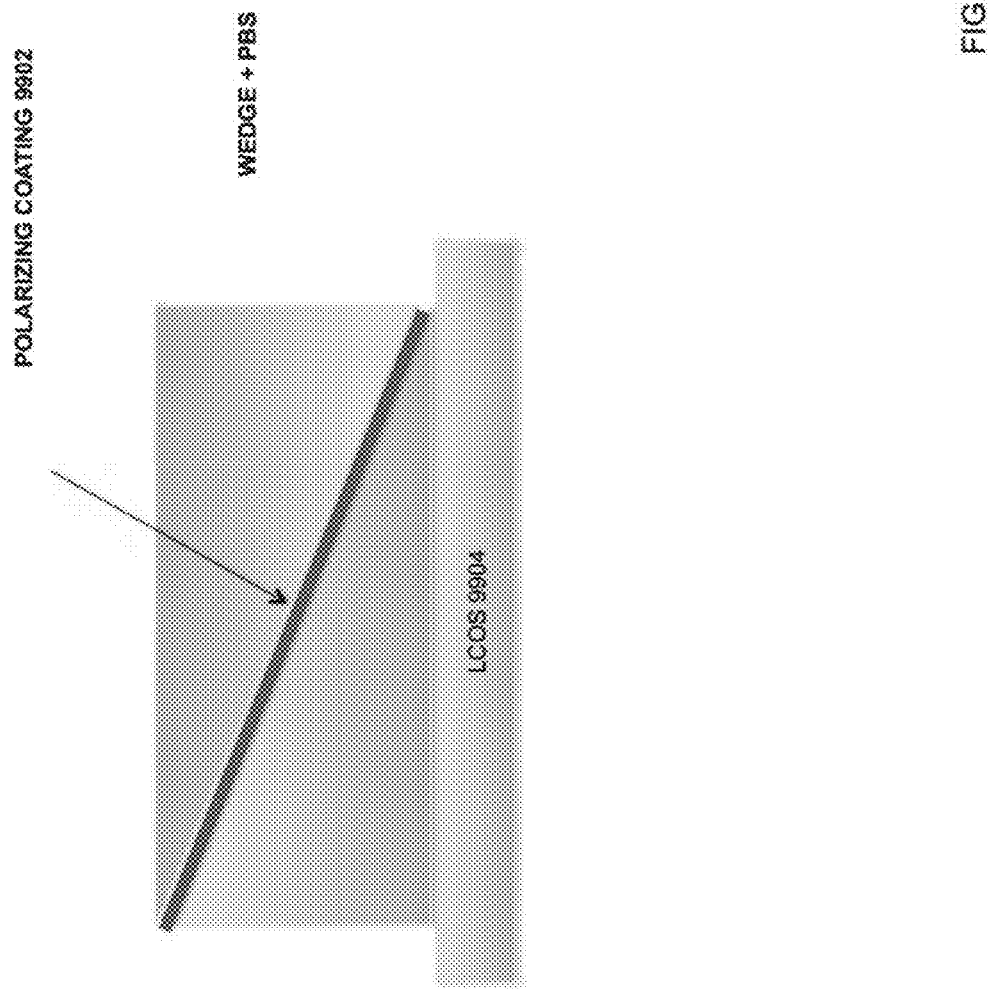

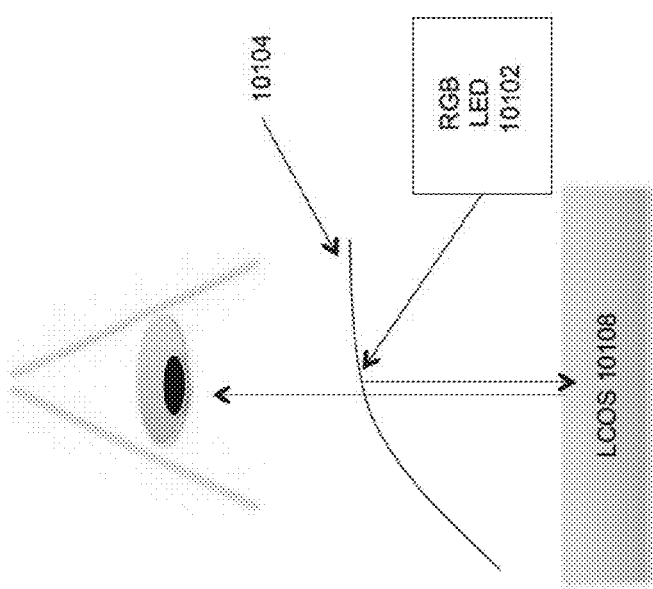

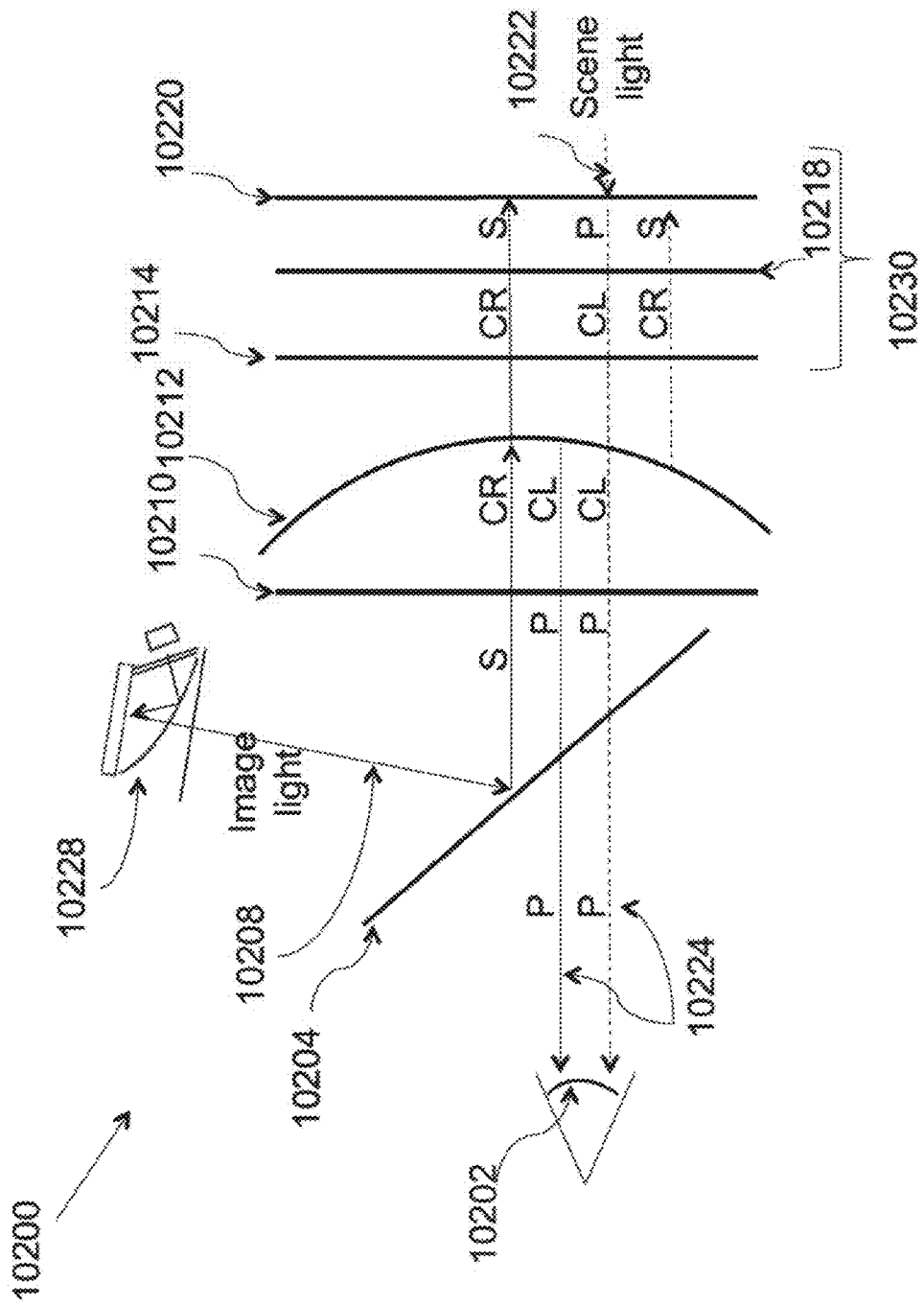

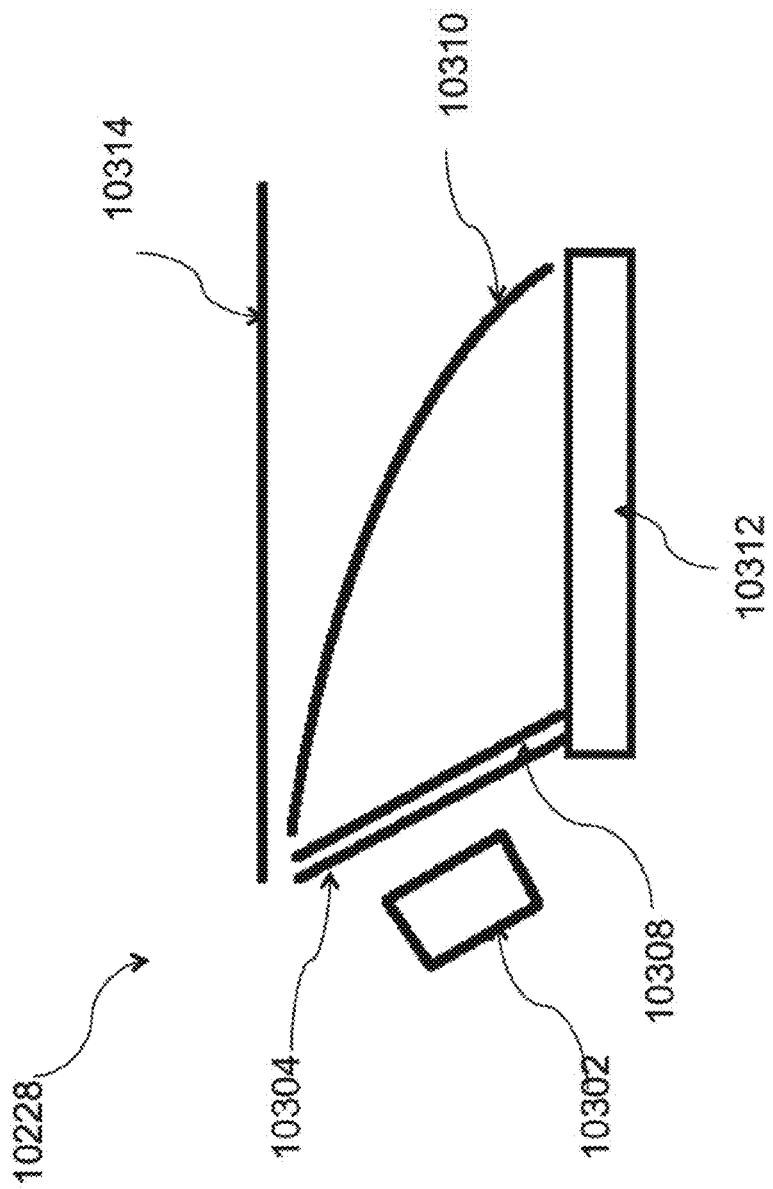

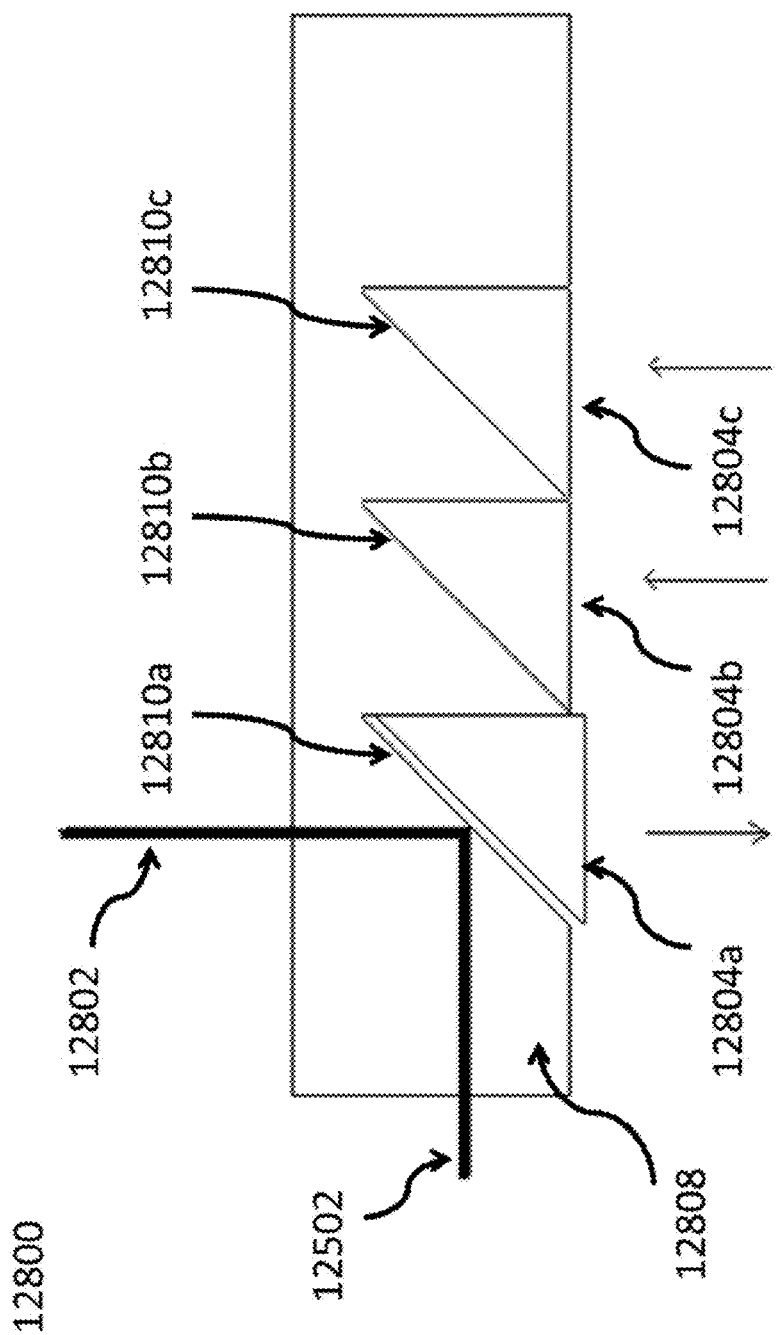

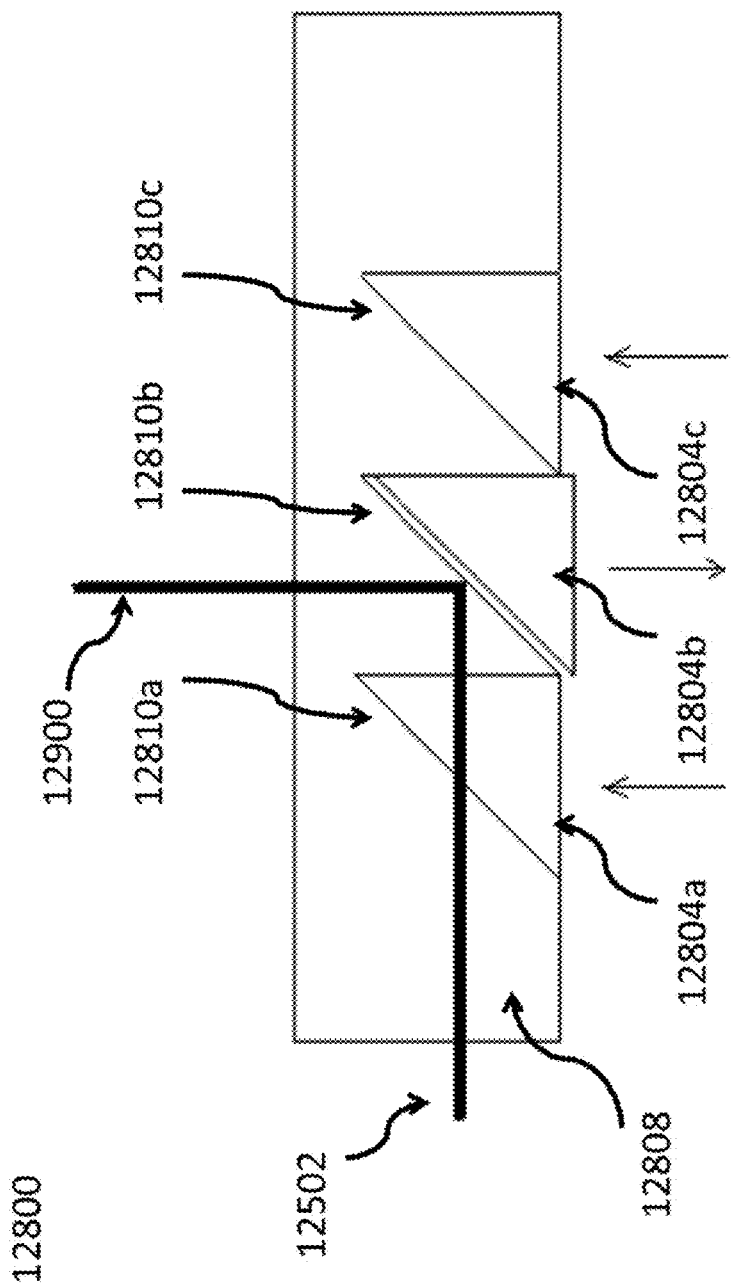

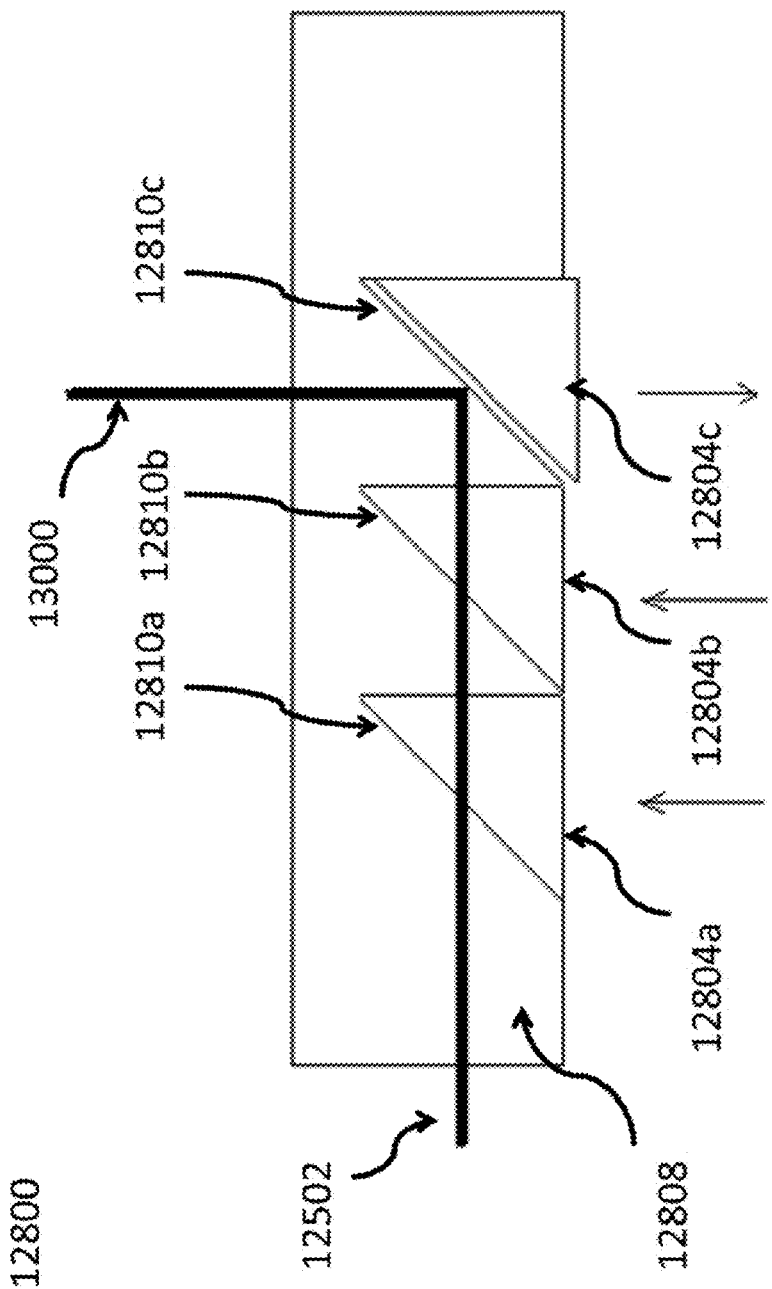

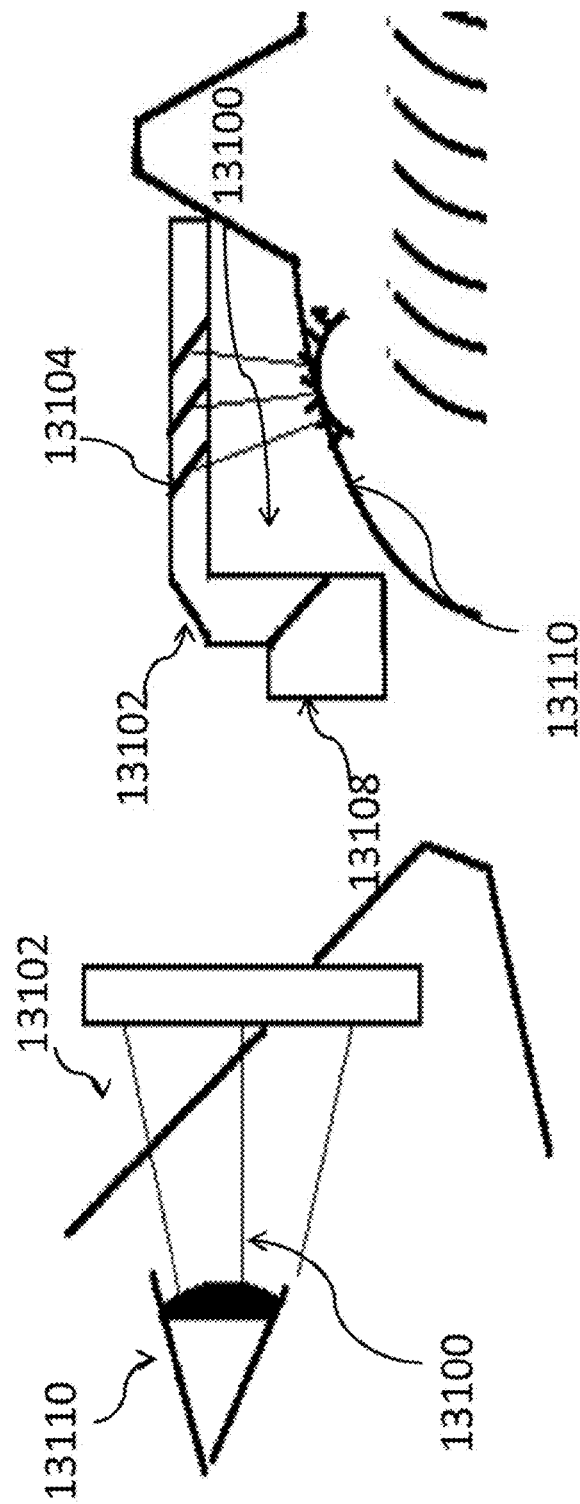

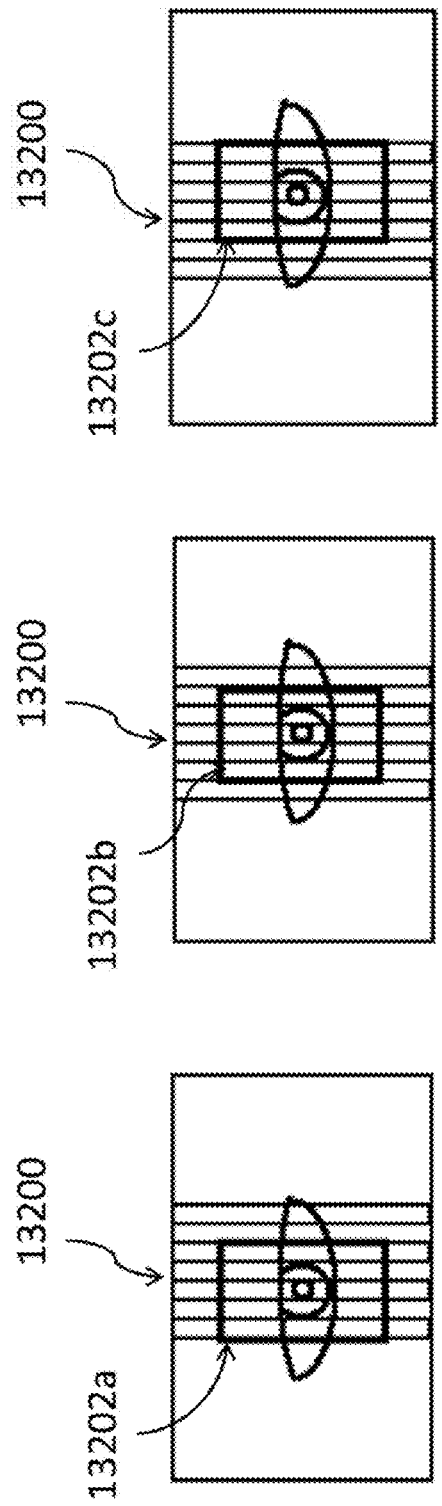

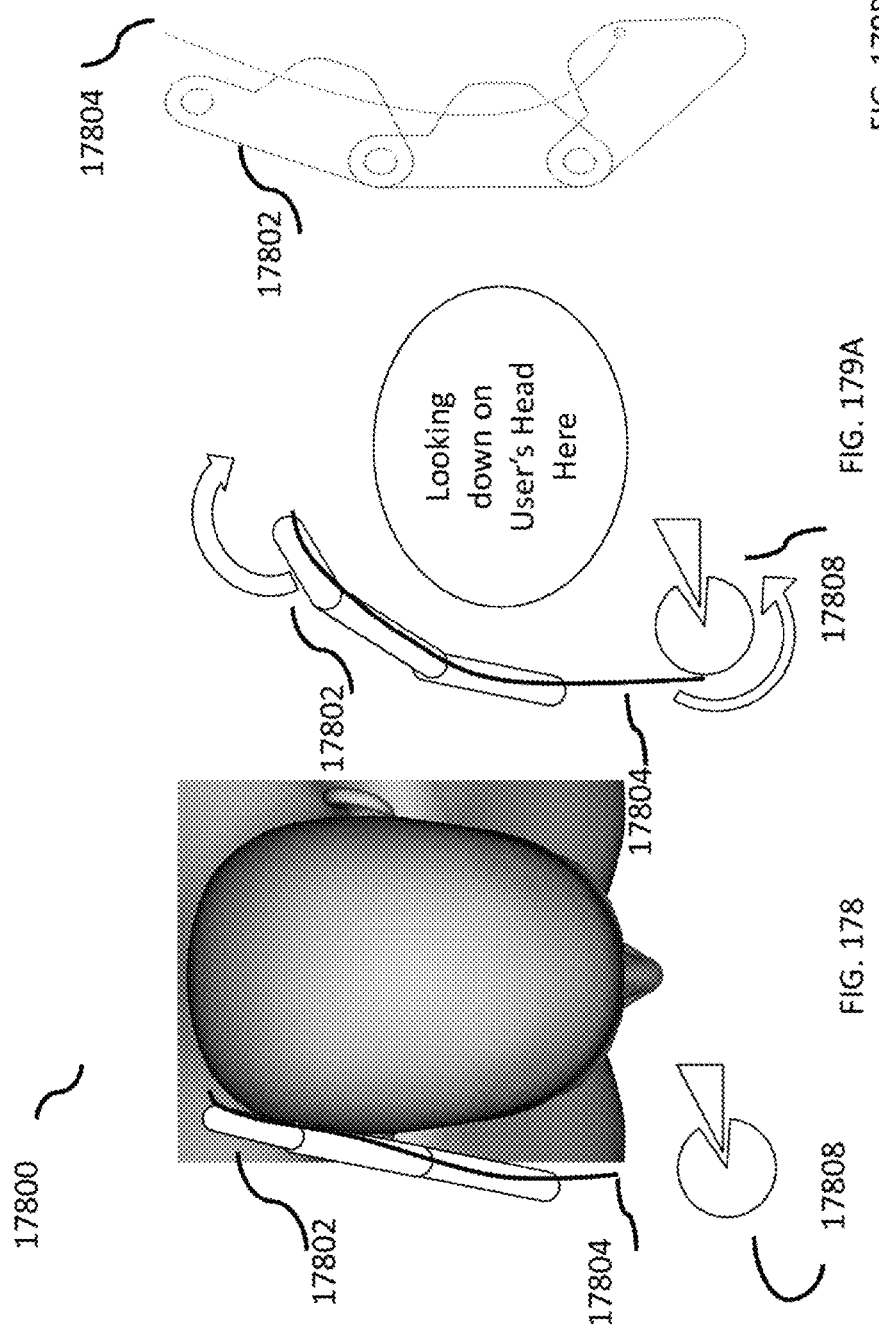

The blue (shorter segment) ear piece may comprise the back portion of the earpiece on the glasses from the arrow back or from other points, or may comprise the entire portions of the ear piece. The knob on the right of the earpiece may be a knob adjustor.

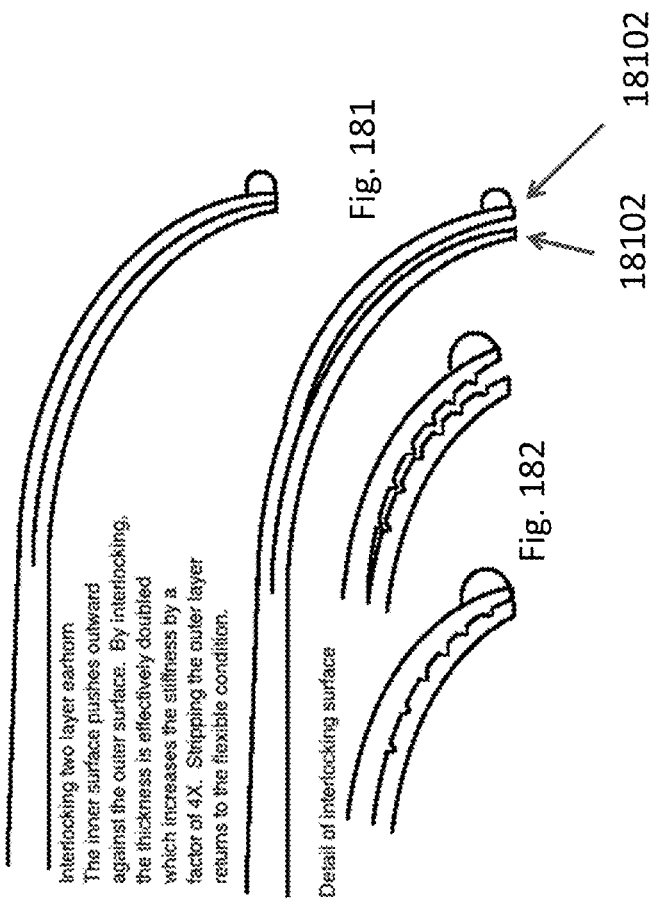
The ear horns (curved portion) may attach to glasses similarly as in Fig. 180 and may be oriented so that they are curving around the user's head.

VIDEO DISPLAY MODIFICATION BASED ON SENSOR INPUT FOR A SEE-THROUGH NEAR-TO-EYE DISPLAY

CROSS-REFERENCE TO RELATED APPLICATIONS

This application claims priority to the following United States Provisional patent applications, each of which is incorporated herein by reference in its entirety:

U.S. Provisional Application 61/539,269, filed Sep. 26, 2011.

This application is a continuation-in-part of the following United States non-provisional patent applications, each of which is incorporated herein by reference in its entirety:

U.S. Non-Provisional application Ser. No. 13/591,187, filed Aug. 21, 2012, which claims the benefit of the following provisional applications, each of which is hereby incorporated herein by reference in its entirety: U.S. Provisional Patent Application 61/679,522, filed Aug. 3, 2012; U.S. Provisional Patent Application 61/679,558, filed Aug. 3, 2012; U.S. Provisional Patent Application 61/679,542, filed Aug. 3, 2012; U.S. Provisional Patent Application 61/679,578, filed Aug. 3, 2012; U.S. Provisional Patent Application 61/679,601, filed Aug. 3, 2012; U.S. Provisional Patent Application 61/679,541, filed Aug. 3, 2012; U.S. Provisional Patent Application 61/679,548, filed Aug. 3, 2012; U.S. Provisional Patent Application 61/679,550, filed Aug. 3, 2012; U.S. Provisional Patent Application 61/679,557, filed Aug. 3, 2012; and U.S. Provisional Patent Application 61/679,566, filed Aug. 3, 2012; U.S. Provisional Patent Application 61/644,078, filed May 8, 2012; U.S. Provisional Patent Application 61/670,457, filed Jul. 11, 2012; and U.S. Provisional Patent Application 61/674,689, filed Jul. 23, 2012.

U.S. Non-Provisional application Ser. No. 13/441,145, filed Apr. 6, 2012, which claims the benefit of the following provisional applications, each of which is hereby incorporated herein by reference in its entirety: U.S. Provisional Patent Application 61/598,885, filed Feb. 14, 2012; U.S. Provisional Patent Application 61/598,889, filed Feb. 14, 2012; U.S. Provisional Patent Application 61/598,896, filed Feb. 14, 2012; and U.S. Provisional Patent Application 61/604,917, filed Feb. 29, 2012.

U.S. Non-Provisional application Ser. No. 13/429,413, filed Mar. 25, 2012, which claims the benefit of the following provisional applications, each of which is hereby incorporated herein by reference in its entirety: U.S. Provisional Patent Application 61/584,029, filed Jan. 6, 2012.

U.S. Non-Provisional application Ser. No. 13/341,758, filed Dec. 30, 2011, which claims the benefit of the following provisional applications, each of which is hereby incorporated herein by reference in its entirety: U.S. Provisional Patent Application 61/557,289, filed Nov. 8, 2011.

U.S. Non-Provisional application Ser. No. 13/232,930, filed Sep. 14, 2011, which claims the benefit of the following provisional applications, each of which is hereby incorporated herein by reference in its entirety: U.S. Provisional Application 61/382,578, filed Sep. 14, 2010; U.S. Provisional Application 61/472,491, filed Apr. 6, 2011; U.S. Provisional Application 61/483,400, filed May 6, 2011; U.S. Provisional Application 61/487,371, filed May 18, 2011; and U.S. Provisional Application 61/504,513, filed Jul. 5, 2011.

U.S. Non-Provisional patent application Ser. No. 13/037,324, filed Feb. 28, 2011 and United States Non-Provisional patent application Ser. No. 13/037,335, filed Feb. 28, 2011, each of which claim the benefit of the following provisional applications, each of which is hereby incorporated herein by reference in its entirety: U.S. Provisional Patent Application 61/308,973, filed Feb. 28, 2010; U.S. Provisional Patent Application 61/373,791, filed Aug. 13, 2010; U.S. Provisional Patent Application 61/382,578, filed Sep. 14, 2010; U.S. Provisional Patent Application 61/410,983, filed Nov. 8, 2010; U.S. Provisional Patent Application 61/429,445, filed Jan. 3, 2011; and U.S. Provisional Patent Application 61/429,447, filed Jan. 3, 2011.

BACKGROUND

Field

The present disclosure relates to an augmented reality eyepiece, associated control technologies, and applications for use, and more specifically to software applications running on the eyepiece.

This disclosure also relates to a thin display technology that uses switchable mirrors in a sequenced pattern to provide an image from a waveguide.

Head mounted displays with reflecting surfaces are well known in the industry. Head mounted displays with angled single partial reflecting beam splitter plates are described in U.S. Pat. No. 4,969,714. While this approach provides excellent uniformity of brightness and color over the displayed field of view, the optical system is relatively thick due to the angled beam splitter plate.

Head mounted displays with arrays of partially reflecting surfaces to provide a thinner optical system are described in U.S. Pat. Nos. 6,829,095 and 7,724,441 and shown in FIG. 124 wherein the array of partially reflecting surfaces 12408 is used to provide image light 12404 over a display field of view enabling a user to view displayed images combined with a view of the environment in front of the user. The image light 12404 viewed by the user is comprised of the combined reflected light from each of the multiple partially reflecting surfaces 12408. The light from the image source 12402 has to pass through the multiple partially reflecting surfaces 12408 where a portion of the light 12402 is reflected toward the user's eye thereby providing image light 12404. To provide a uniform image over the display field of view, the reflection characteristics of the partially reflecting surfaces 12408 must be precisely controlled. The reflectivity of the partially reflective surfaces 12408 must be lowest for surfaces that are closest to the image source and highest for surfaces that are farthest from the image source. Generally the reflectivity of the partially reflective surfaces 12408 must increase linearly in relation to the distance from the image source. This presents a manufacturing and cost problem as the reflectivity of each partially reflective surface 12408 is different from the neighboring surfaces and the reflectivity of each surface must be tightly controlled. As such, providing an image that is of uniform brightness and color over the entire display field of view is difficult with an array of partially reflective surfaces.

Alternately a diffractive grating is used to redirect the image light into and out of a waveguide to the display field of view as described in U.S. Pat. No. 4,711,512. However, diffraction gratings are costly and subject to color aberrations.

Therefore, the need persists for a relatively thin optical system for a head mounted display that also provides good image uniformity of brightness and color overt the display field of view.

This disclosure also concerns a compact and lightweight frontlight that includes a wire grid polarizer film as a partially reflective surface to deflect the illumination light downwards to the reflective image source.

In a display with a reflective image source and a frontlight as shown in FIG. 133, illumination light 13308 passes from an edge light source 13300 and is deflected by the frontlight 13304 to illuminate the reflective image source 13302. The illumination light 13308 then reflects from the reflective image source 13302 turning into image light 13310 which then passes back through the frontlight 13304 and into the display optics. As such, the frontlight 13304 simultaneously deflects illumination light 13308 entering from the edge light source 13300 and allows reflected image light 13310 to pass through without being deflected so it can pass into the display optics, where the display optics can be dispersive when the display is a flat screen display or refractive or diffractive when the display is a near eye display. In this embodiment, the display optics may include diffusers.

For a reflective image source such as a liquid crystal on silicon (LCoS) image source, the illumination light is polarized and the reflective image source includes a quarter wave retardation film that changes the polarization state during the reflection from the reflective image source. A polarizer is then included in the display optics which causes the polarization effects imparted by the liquid crystal to form an image as the image light passes through the display optics.

U.S. Pat. No. 7,163,330 describes a series of frontlights which include grooves in the upper surface of the frontlight to deflect light from the edge light source down to the reflective image source along with flat sections between the grooves to allow the reflected image light to pass into the display optics. FIG. 134 shows an illustration of the frontlight 13400 with the grooves 13410 and the flat sections 13408. The illumination light 13402 from the edge light source 13300, reflects from the grooves 13410 and is deflected downwards to illuminate the reflective image source 13302. The image light 13404 reflects from the reflective image source 13302 and passes through the flat sections 13408 of the frontlight 13400. Linear and curved grooves 13410 are described. However, for the grooves 13410 to effectively deflect the illumination light 13402, the grooves 13410 must occupy a substantial area of the frontlight thereby limiting the area of the flat sections 13408 and degrading the image quality provided to the display optics due to light scatter from the grooves as it passes back through the frontlight. Frontlights 13400 are typically formed from a solid plate of material and as such can be relatively heavy.

In U.S. Pat. No. 7,545,571, a wearable display system is presented which includes a reflective image source 13502 with a polarizing beam splitter 13512 as a frontlight to deflect and polarize illumination light 13504 supplied by an edge light source 13500 onto the reflective image source 13502 as shown in FIG. 135. The polarizing beam splitter 13512 is an angled plane in a solid block with a separate curved reflector 13514 associated with the edge light source 13500. The curved reflector 13514 can be a total internal reflection block 13510 that is connected to the polarizing beam splitter 13512. As such, the frontlight disclosed in this patent with the solid block of the polarizing beam splitter and the total internal reflection block provides a frontlight that is bulky and relatively heavy. Further, FIG. 135 also shows image light rays 13508.

There remains a need to provide a frontlight for displays with reflective image sources that provides good image quality with little scattered light and is also compact and light in weight.

The disclosure also pertains to optically flat surfaces produced with optical films. More particularly, the disclosure provides a method for making an optically flat beam splitter using an optical film.

Optical films can be obtained for a variety of purposes including: beam splitters, polarizing beam splitters, holographic reflectors and mirrors. In imaging applications and particularly in reflective imaging applications, it is important to provide that the optical film be very flat to preserve the wavefront of the image. Some optical films are available with pressure sensitive adhesive on one side to allow the optical films to be attached to a substrate for structural support and to aid in keeping the optical film flat. However, optical films attached to substrates in this manner tend to have surfaces with small-scale undulations and pock marks known orange peel that prevent the surface from reaching optical flatness and as a result, reflected images are degraded.

In United States Patent Application 20090052030 a method for producing an optical film is provided wherein the optical film is a wire grid polarizer. However, techniques for providing the film with optical flatness are not provided.

In U.S. Pat. Nos. 4,537,739 and 4,643,789, methods are provided for attaching artwork to molded structures using a strip to carry the artwork to the mold. However, these methods do not anticipate the special requirements for optical films.

In United States Patent Application 20090261490 a method is provided for making simple optical articles is provided which includes optical films and molding. The method is directed at curved surfaces generated as the method includes limits between the ratio of the radius of curvature to the diameter to avoid wrinkles in the film due to deforming of the film during molding. The special requirements for producing an optically flat surface with an optical film are not addressed.

In U.S. Pat. No. 7,820,081, a method is provided for lamination of a functional film to a lens. The method uses a thermally cured adhesive to adhere a functional film to a lens. However, this process includes thermoforming the optical film while the lens is hot so that the optical film, the adhesive and the lens are deformed together during the bonding process. As such this method is not suited to making optically flat surfaces.

Therefore the need persists for a method to use optical films such that surfaces including optical films can be provided with optical flatness.

SUMMARY

In embodiments, the eyepiece may include an internal software application running on an integrated multimedia computing facility that has been adapted for 3D augmented reality (AR) content display and interaction with the eyepiece. 3D AR software applications may be developed in conjunction with mobile applications and provided through application store(s), or as stand-alone applications specifically targeting the eyepiece as the end-use platform and through a dedicated 3D AR eyepiece store. Internal software applications may interface with inputs and output facilities provided by the eyepiece through facilities internal and external to the eyepiece, such as initiated from the surrounding environment, sensing devices, user action capture devices, internal processing facilities, internal multimedia processing facilities, other internal applications, camera, sensors, microphone, through a transceiver, through a tactile interface, from external computing facilities, external applications, event and/or data feeds, external devices, third parties, and the like. Command and control modes operating in conjunction with the eyepiece may be initiated by sensing inputs through input devices, user action, external device interaction, reception of events and/or data feeds, internal application execution, external application execution, and the like. In embodiments, there may be a series of steps included in the execution control as provided through the internal software application, including at least combinations of two of the following: events and/or data feeds, sensing inputs and/or sensing devices, user action capture inputs and/or outputs, user movements and/or actions for controlling and/or initiating commands, command and/or control modes and interfaces in which the inputs may be reflected, applications on the platform that may use commands to respond to inputs, communications and/or connection from the on-platform interface to external systems and/or devices, external devices, external applications, feedback to the user (such as related to external devices, external applications), and the like.

The disclosure also provides a method for providing a relatively thin optical system that provides an image with improved uniformity of brightness and color over the display field of view. The disclosure includes an integral array of narrow switchable mirrors over the display area, to provide a display field of view wherein the switchable mirrors are used sequentially to reflect portions of the light from an image source to present sequential portions of an image to a user. By rapidly switching the narrow switchable mirrors from transparent to reflective in a repeating sequence, the user perceives the portions of the image to be combined into the entire image as presented by the image source. Provided that each of the narrow switchable mirrors is switched at 60 Hz or greater, the user does not perceive flicker in portions of the image.

Various embodiments of the array of narrow switchable mirrors are presented. In one embodiment, the switchable mirrors are liquid crystal switchable mirrors. In another embodiment the switchable mirrors are moveable prism elements, which use an air gap to provide a switchable total internal reflective mirror.

In an alternate embodiment, not all the switchable mirrors are used in the sequence, instead the switchable mirrors are used in a selected group that varies based on the eye spacing of the user The present disclosure further provides a compact and light weight frontlight that includes a wire grid polarizer film as a partially reflective surface to deflect the illumination light downwards to the reflective image source. The edge light source is polarized and the wire grid polarizer is oriented such that the illumination light is reflected and the image light is allowed to pass through to the display optics. By using a wire grid polarizer film that is flexible, the disclosure provides a partially reflective surface that can be curved to focus the illumination light onto the reflective image source thereby increasing efficiency and increasing uniformity of image brightness. The wire grid polarizer also has very low light scattering as the image light passes through the frontlight on the way to the display optics, so image quality is preserved. In addition, since the partially reflective surface is a wire grid polarizer film, the majority of the frontlight is comprised of air and as such the frontlight is much lighter in weight.

This disclosure further provides methods for producing surfaces with optical flatness when using an optical film. In embodiments of the disclosure the optical film can comprise a beam splitter, a polarizing beam splitter, a wire grid polarizer, a mirror, a partial mirror or a holographic film. The advantage provided by the disclosure is that the surface of the optical film is optically flat so that the wavefront of the light is preserved to provide improved image quality.

In some embodiments, the disclosure provides an image display system including an optically flat optical film. The optically flat optical film includes a substrate to hold the optical film optically flat in a display module housing with an image source and a viewing location. Wherein the image provided by the image source is reflected from the optical film to the viewing location and the substrate with the optical film is replaceable within the display module housing.

In other embodiments of the disclosure, the optical film is attached to a molded structure so the optical film is part of the display module housing.

In a prior art display 18700 with a reflective image source 18720 and a solid beam splitter cube frontlight 18718 as shown in FIG. 187, light 18712 passes from an light source 18702 into a diffuser 18704 where it is made more uniform to provide illumination light 18714. The illumination light 18714 is redirected by a partially reflective layer 18708 to thereby illuminate the reflective image source 18720. The illumination light 18714 then reflects from the reflective image source 18720 turning into image light 18710 which then passes back through the partially reflective layer 18708 and into the associated imaging optics (not shown) which present the image to a viewer. As such, the solid beam splitter cube 18718 simultaneously redirects illumination light 18714 and allows reflected image light 18710 to pass through without being redirected so it can pass into the imaging optics, where the imaging optics can be dispersive when the display is a flat screen display or refractive or diffractive when the display is a projector or a near eye display.

For a reflective image source such as a liquid crystal on silicon (LCoS) image source, the illumination light is polarized and the reflective image source changes the polarization state when the illumination light is reflected from the reflective image source based on the image content presented by the image source thereby forming image light. An analyzer polarizer is then included which causes the polarization effects imparted by the LCOS to form an image as the image light passes through the imaging optics and an image is presented to a viewer.

In U.S. Pat. No. 7,545,571, a wearable display system is presented which includes a reflective image source with a polarizing beam splitter as a frontlight to deflect and polarize illumination light supplied by an edge light source onto the reflective image source. The polarizing beam splitter is an angled plane in a solid block with a separate curved reflector associated with the edge light source. The curved reflector can be a total internal reflection block that is connected to the polarizing beam splitter. As such, the frontlight disclosed in this patent with the solid block of the polarizing beam splitter and the total internal reflection block provides a frontlight that is bulky and relatively heavy.

U.S. Pat. No. 6,195,136 discloses a series of frontlight illumination methods for use with reflective image sources. A method using a curved beam splitter is disclosed for making the frontlight more compact. However, the curved beam splitter is located a substantial distance away from the image source to reduce the angle of the light from the light source that is then reflected by the beam splitter to the image source. Also, the light is provided only on one side of the frontlight so the size of the beam splitter must be at least as big as the image source. As a result, the overall size of the frontlight is still relatively large when measured along the optical axis compared to the illuminated area on the image source.

There remains a need to provide a frontlight for displays with reflective image sources that provides good image quality with little scattered light and is also compact, efficient and light in weight.

The present disclosure provides a compact, efficient and light weight frontlight in a display assembly that includes a partially reflective surface to redirect the illumination light from a light source at the side to a reflective image source, wherein the size of the display assembly as measured by the height of the diffuser area is substantially smaller than the width of the reflective image source that is illuminated. In some embodiments, the partially reflective surface can be curved to focus or concentrate the light from the light source onto the reflective image source. The light source can be polarized and a polarizing beam splitter film can be used as the curved partially reflective surface such that the illumination light is redirected and the reflected image light is allowed to pass through to the imaging optics. Polarizing beam splitter film is light in weight and has very low light scattering as the image light passes through the frontlight on the way to the display optics, so image quality is preserved.

In other embodiments of the disclosure, light sources are provided on opposing sides of the frontlight so that light is provided to opposing edges of the reflective image source. In this case, the partially reflective surface is comprised of two surfaces, wherein one surface deflects the illumination light from one light source to one half of the image source and the other surface deflects light to the other half of the image source. In this embodiment, the partially reflective surfaces can be curved or flat.

In a further embodiment of the disclosure, the partially reflective surface is a polarizing beam splitter and the light source is polarized so the light from the light source is first redirected by the polarizing beam splitter and then transmitted after being reflected and changed in polarization by the reflective image source.

In another embodiment, the light from the light source is unpolarized so the polarizing beam splitter reflects one polarization state of the light to illuminate half of the reflective image source while transmitting the other polarization state of the light. The transmitted polarization state of the light passes to the opposite side of the frontlight where the light is recycled. The recycling of the transmitted polarization state can be done by passing through a quarter wave film and being reflected by a mirror so that it passes back through the quarter wave film and thereby changes polarization state. After the polarization state of the transmitted and reflected light has changed, it is redirected by the polarizing beam splitter to illuminate the other half of the reflective image source. In an alternate embodiment, light from the two sidelights of the frontlight acts in a complimentary fashion where the transmitted polarization state of the light from the opposite side becomes unpolarized when it interacts with the diffuser on the opposite side and is thereby recycled.

In yet another embodiment of the disclosure, methods are provided for making frontlights with flexible partially reflecting films. The flexible films can be supported at the edges and freestanding over the reflective image source or the flexible films can be clamped between two or more solid pieces that are transparent. The solid pieces can be shaped prior to being placed in contact with the flexible films. The solid pieces can hold the flexible film in a flat geometry or a curved geometry. In yet another embodiment, the flexible film can be supported at the edges and then solid pieces can be cast in place so that the flexible film is embedded in the transparent solid material.

In an embodiment, a system may include an interactive head-mounted eyepiece worn by a user, wherein the eyepiece includes an optical assembly through which the user views a surrounding environment and displayed content, an integrated processor for handling content for display to the user, an integrated image source for introducing the content to the optical assembly; the processor adapted to modify the content, wherein the modification is made in response to a sensor input. The content may be a video image. The modification may be at least one of adjust brightness, adjust color saturation, adjust color balance, adjust color hue, adjust video resolution, adjust transparency, adjust compression rate, adjust frames per second rate, isolate part of the video, stop the video from playing, pause the video, or restart the video. The sensor input may be derived from at least one of a charge-coupled device, black silicon sensor, IR sensor, acoustic sensor, induction sensor, motion sensor, optical sensor, opacity sensor, proximity sensor, inductive sensor, Eddy-current sensor, passive infrared proximity sensor, radar, capacitance sensor, capacitive displacement sensor, hall-effect sensor, magnetic sensor, GPS sensor, thermal imaging sensor, thermocouple, thermistor, photoelectric sensor, ultrasonic sensor, infrared laser sensor, inertial motion sensor, MEMS internal motion sensor, ultrasonic 3D motion sensor, accelerometer, inclinometer, force sensor, piezoelectric sensor, rotary encoders, linear encoders, chemical sensor, ozone sensor, smoke sensor, heat sensor, magnetometer, carbon dioxide detector, carbon monoxide detector, oxygen sensor, glucose sensor, smoke detector, metal detector, rain sensor, altimeter, GPS, detection of being outside, detection of context, detection of activity, object detector (e.g. billboard), marker detector (e.g. geo-location marker for advertising), laser rangefinder, sonar, capacitance, optical response, heart rate sensor, or an RF/micropower impulse radio (MIR) sensor. The content may be stopped from playing in response to an indication from an accelerometer input that the user's head is moving. Audio sensor input may be generated by the speaking of at least one participant of a video conference. Visual sensor input may be a video image of at least one participant of a video conference or a video image of a visual presentation. The modification may be at least one of making the video image more or less transparent in response to an indication from a sensor that the user is moving.

In an embodiment, a system may include an interactive head-mounted eyepiece worn by a user, wherein the eyepiece includes an optical assembly through which the user views a surrounding environment and displayed content, an integrated processor for handling content for display to the user, an integrated image source for introducing the content to the optical assembly, the processor adapted to modify the content, wherein the modification is made in response to a sensor input; and further comprising, an integrated video image capture facility that records an aspect of the surrounding environment and provides the content for display.

These and other systems, methods, objects, features, and advantages of the present disclosure will be apparent to those skilled in the art from the following detailed description of the embodiments and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The present disclosure and the following detailed description of certain embodiments thereof may be understood by reference to the following figures:

FIG. 15A depicts hand mounted sensors in an embodiment of a virtual mouse.

FIG. 22B depicts a cross-section of the eyepiece with a light control element for reducing eyeglow.

FIG. 24 depicts a lock position of a virtual keyboard.

FIG. 24A depicts an embodiment of a virtually projected image on a part of the human body.

FIG. 30 depicts partial image removal by the eyepiece.

FIG. 37 depicts a swipe process with a virtual keyboard.

FIG. 38 depicts a target marker process for a virtual keyboard.

FIG. 38A depicts an embodiment of a visual word translator.

FIG. 49 illustrates the camera field of view and number of cameras used in a mosaic sensor according to another embodiment.

FIG. 71 depicts an embodiment of a ground stake data system.

FIG. 75 depicts an embodiment of situational awareness glasses.

FIG. 87 depicts an embodiment of a planar illumination facility fabricated from a laminate structure.

FIG. 88 depicts an embodiment of a planar illumination facility with a wedged optic assembly for redirecting light.

FIG. 89 depicts a block diagram of an illumination module, according to an embodiment of the disclosure.

FIG. 90 depicts a block diagram of an optical frequency converter, according to an embodiment of the disclosure.

FIG. 91 depicts a block diagram of a laser illumination module, according to an embodiment of the disclosure.

FIGS. 94A & B depict a lens with a photochromic element and a heater element in a top down and side view, respectively.

FIG. 95 depicts an embodiment of an LCoS front light design.

FIGS. 98A, 98B and 98C depict multiple embodiments of an LCoS front light design.

FIG. 99 depicts a wedge plus OBS overlaid on an LCoS.

FIG. 101 depicts a curved PBS film over the LCoS chip.

FIG. 102B depicts an embodiment of an optical assembly with an in-line camera.

FIG. 103 depicts an embodiment of an image source.

FIG. 104 depicts an embodiment of an image source.

FIG. 105 depicts embodiments of image sources.

FIG. 106 depicts a top-level block diagram showing software application facilities and markets in conjunction with functional and control aspects of the eyepiece in an embodiment of the present disclosure.

FIG. 107 depicts a functional block diagram of the eyepiece application development environment in an embodiment of the present disclosure.

FIG. 108 depicts a platform elements development stack in relation to software applications for the eyepiece in an embodiment of the present disclosure.

FIG. 109 is an illustration of a head mounted display with see-through capability according to an embodiment of the present disclosure.

FIG. 110 is an illustration of a view of an unlabeled scene as viewed through the head mounted display depicted in FIG. 109.

FIG. 111 is an illustration of a view of the scene of FIG. 110 with 2D overlaid labels.

FIG. 112 is an illustration of 3D labels of FIG. 111 as displayed to the viewer's left eye.

FIG. 113 is an illustration of 3D labels of FIG. 111 as displayed to the viewer's right eye.

Figure 111:
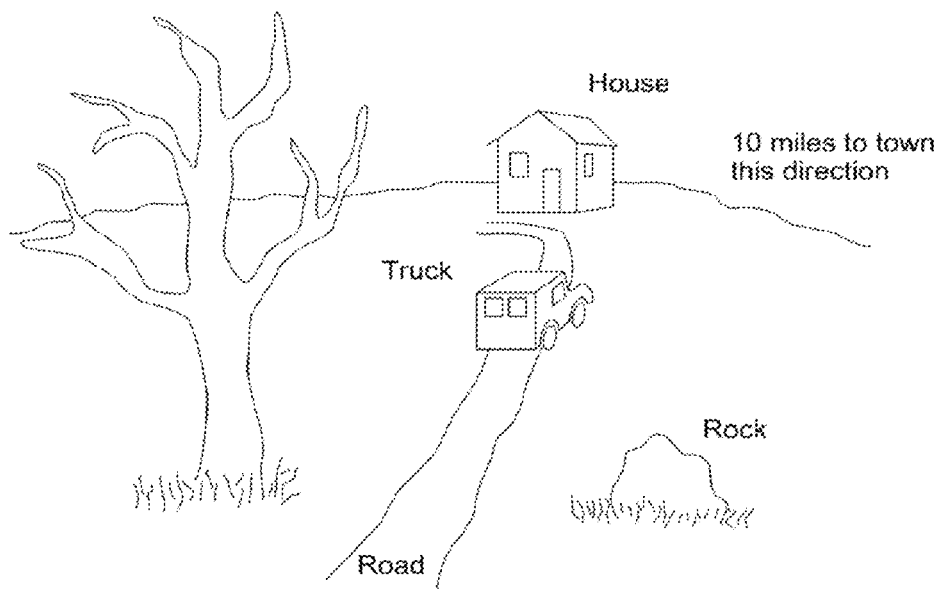
Figure 114:
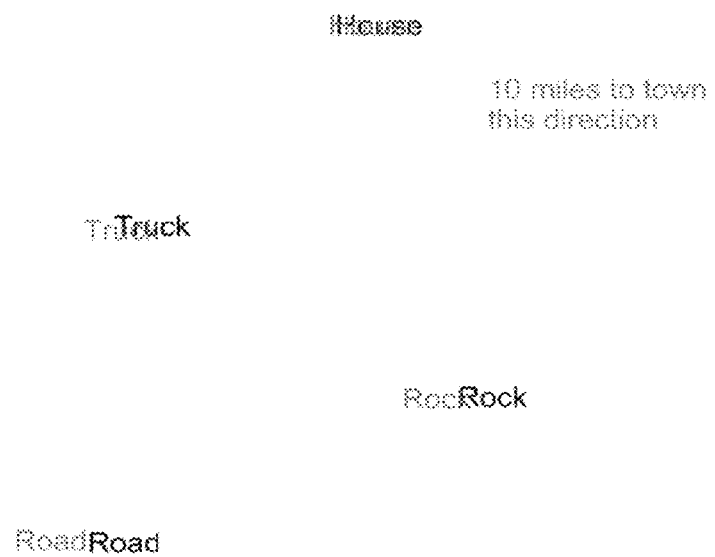

FIG. 114 is an illustration of the left and right 3D labels of FIG. 111 overlaid on one another to show the disparity.

Figure 110:
Figure 115:
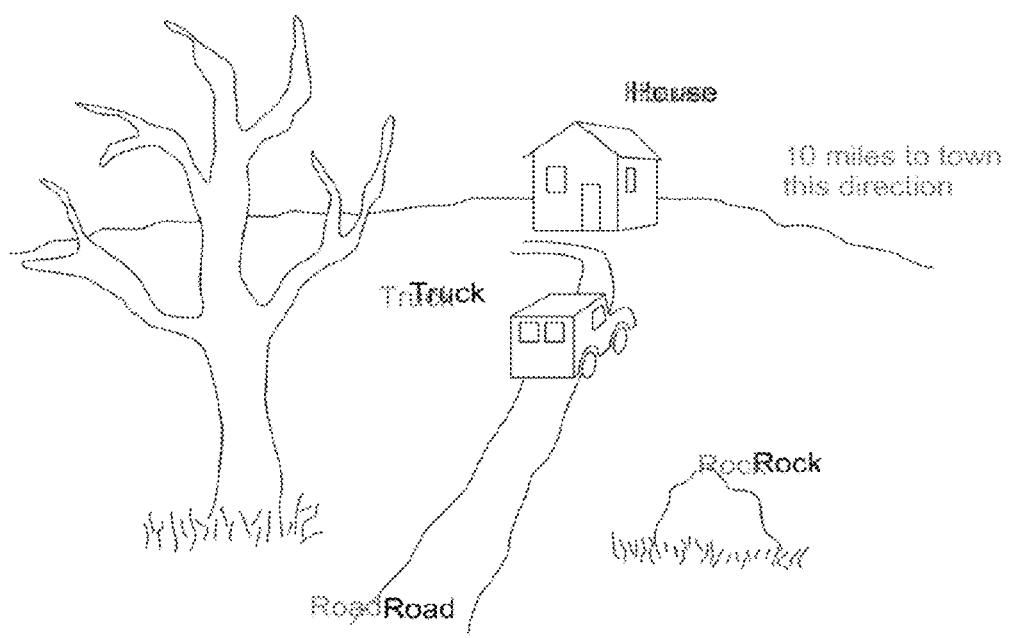

FIG. 115 is an illustration of the view of a scene of FIG. 110 with the 3D labels.

Figure 116:
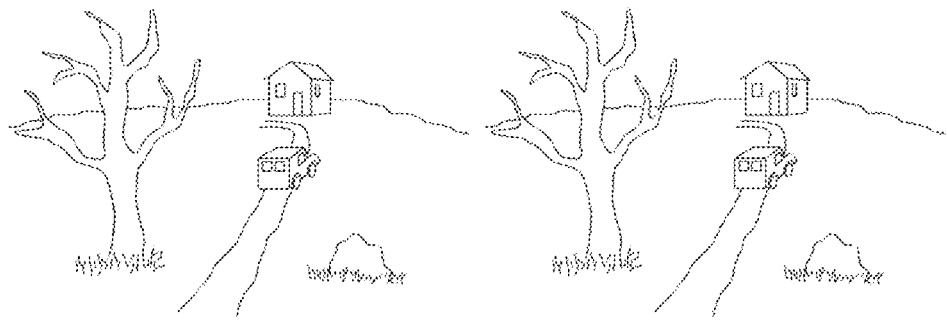

FIG. 116 is an illustration of stereo images captured of the scene of FIG. 110.

Figure 117:
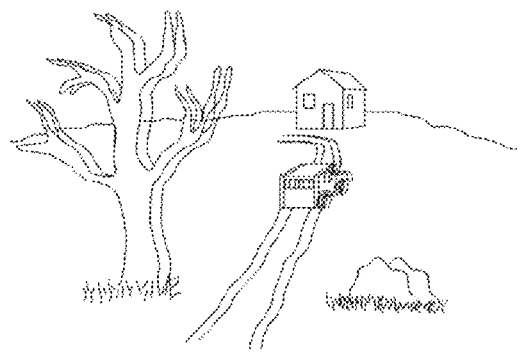

FIG. 117 is an illustration of the overlaid left and right stereo images of FIG. 116 showing the disparity between the images.

Figure 118:
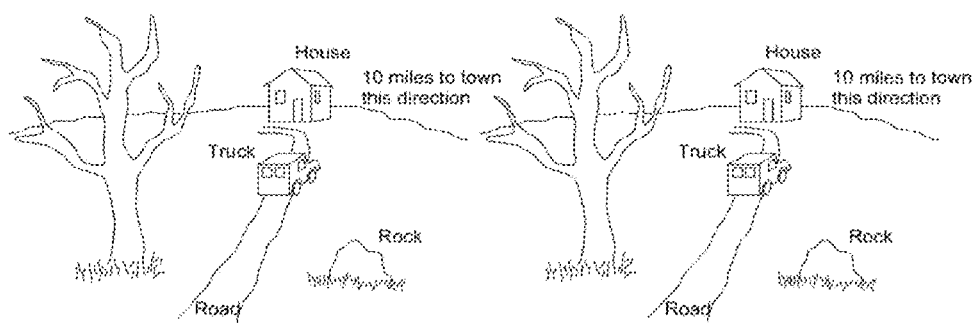

FIG. 118 is an illustration of the scene of FIG. 110 showing the overlaid 3D labels.

Figure 119:
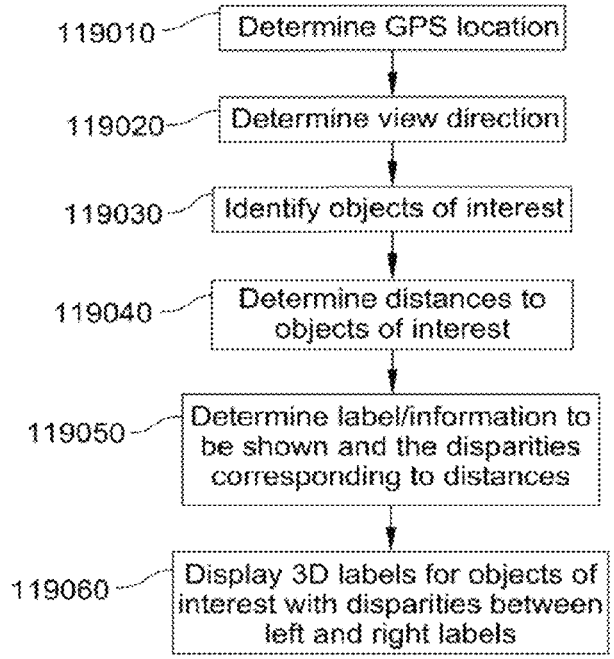

FIG. 119 is a flowchart for a depth cue method embodiment of the present disclosure for providing 3D labels.

Figure 120:
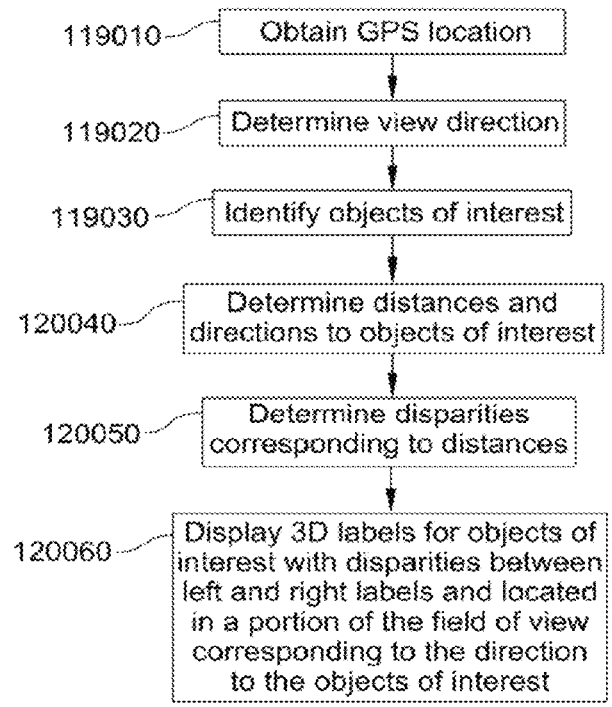

FIG. 120 is a flowchart for another depth cue method embodiment of the present disclosure for providing 3D labels.

Figure 121:
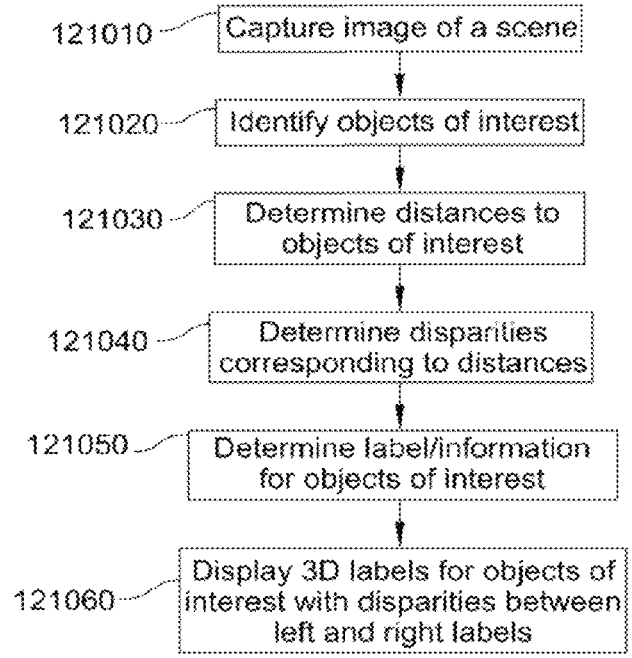

FIG. 121 is a flowchart for yet another depth cue method embodiment of the present disclosure for providing 3D labels.

Figure 122:
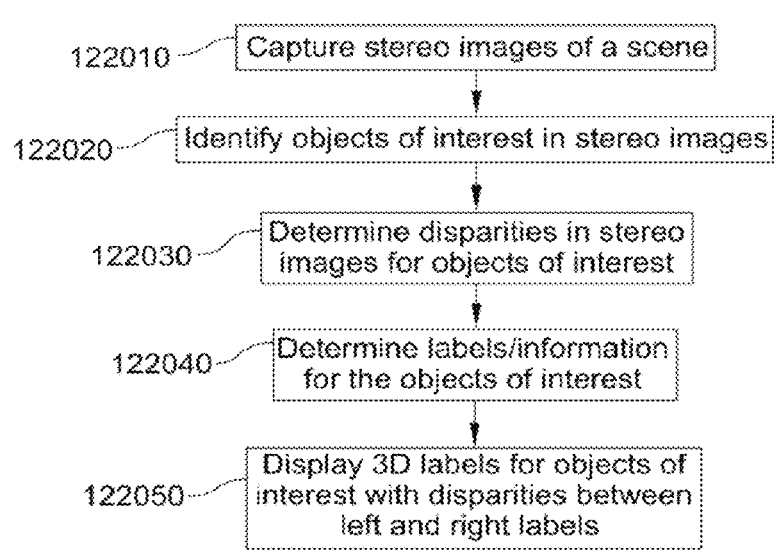

FIG. 122 is a flowchart for a still another depth cue method embodiment of the present disclosure for providing 3D labels.

Figure 123:
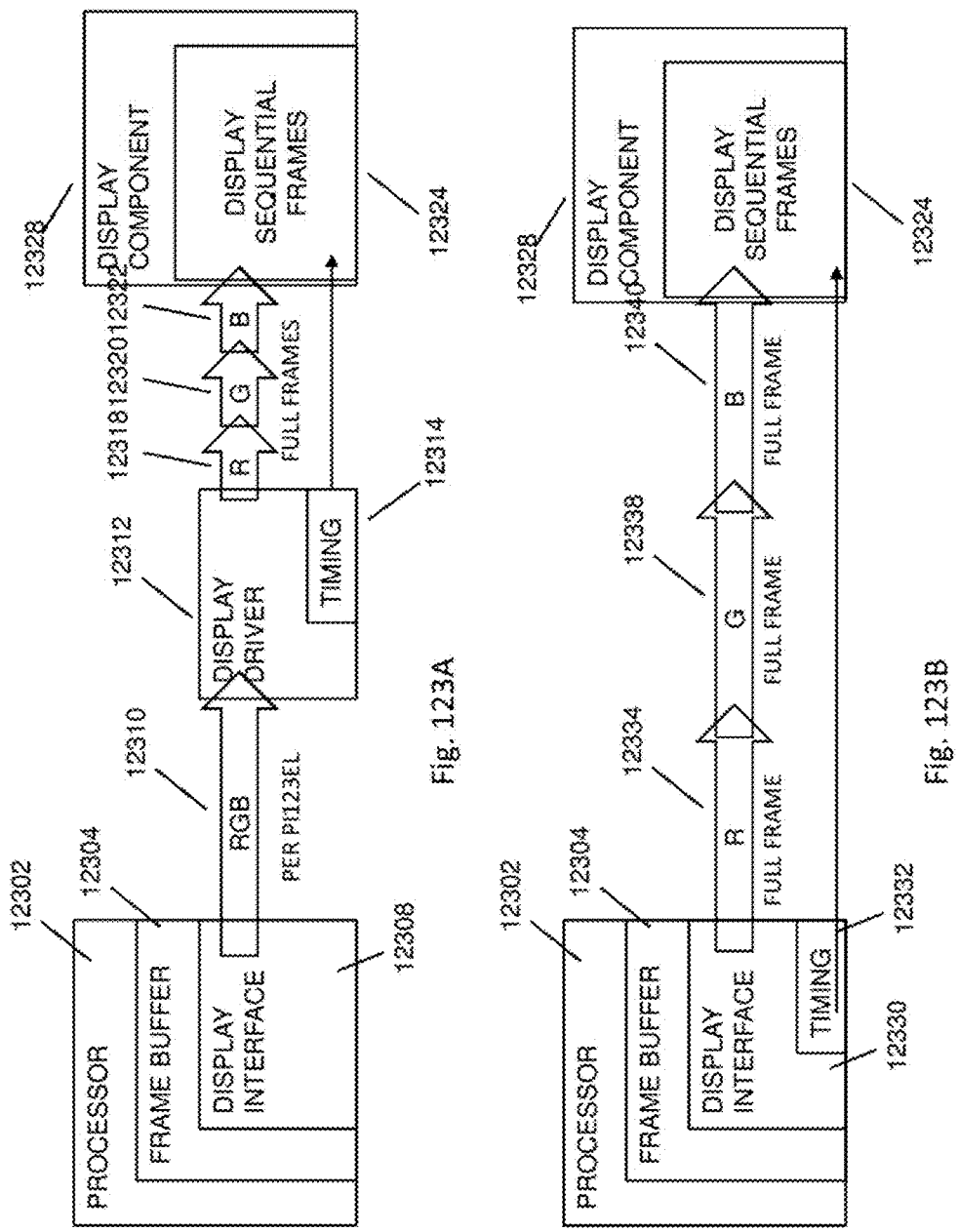

FIG. 123A depicts a processor for providing display sequential frames for image display through a display component.

FIG. 123B depicts a display interface configured to eliminate the display driver.

Figure 124:
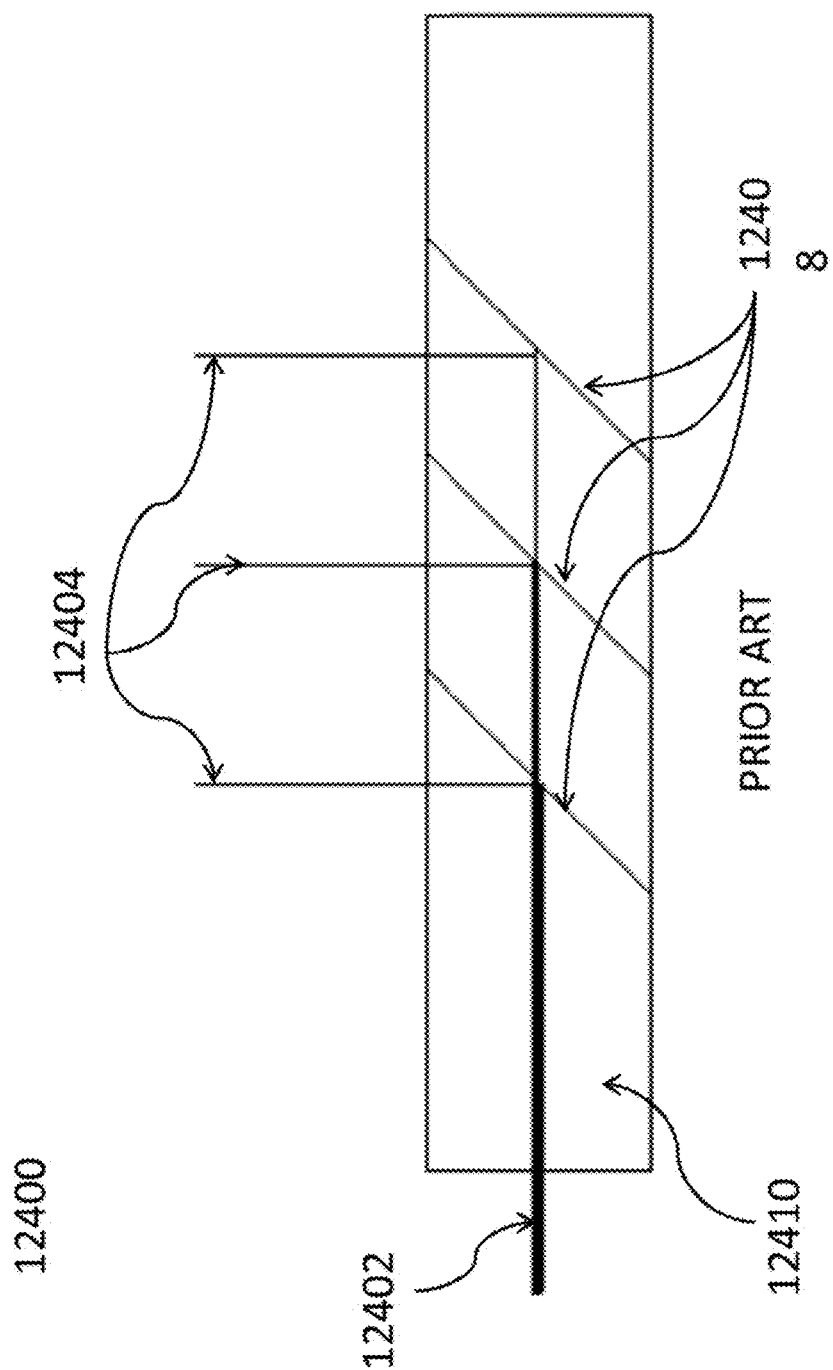
Figure 125:
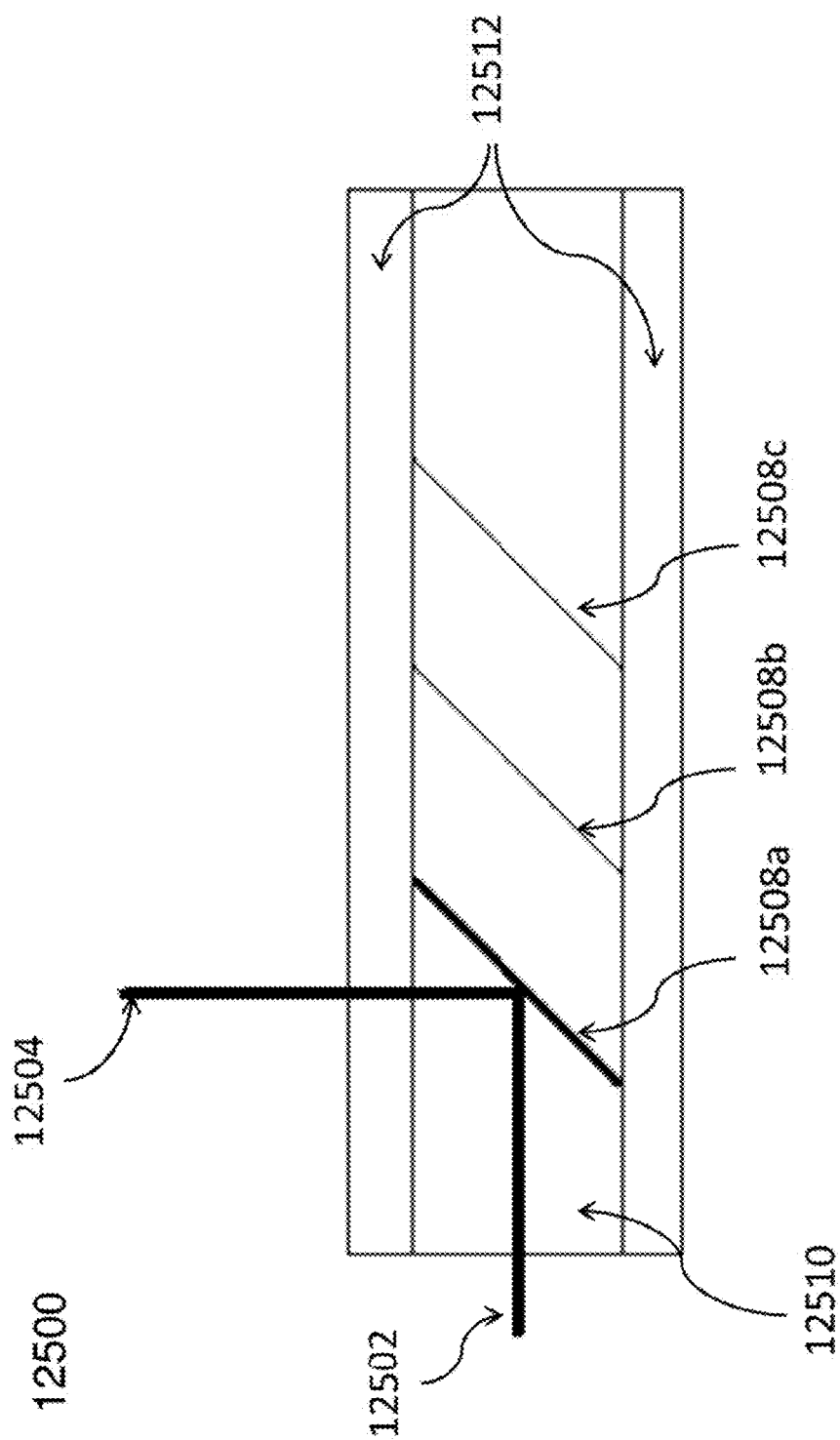
Figure 125A:
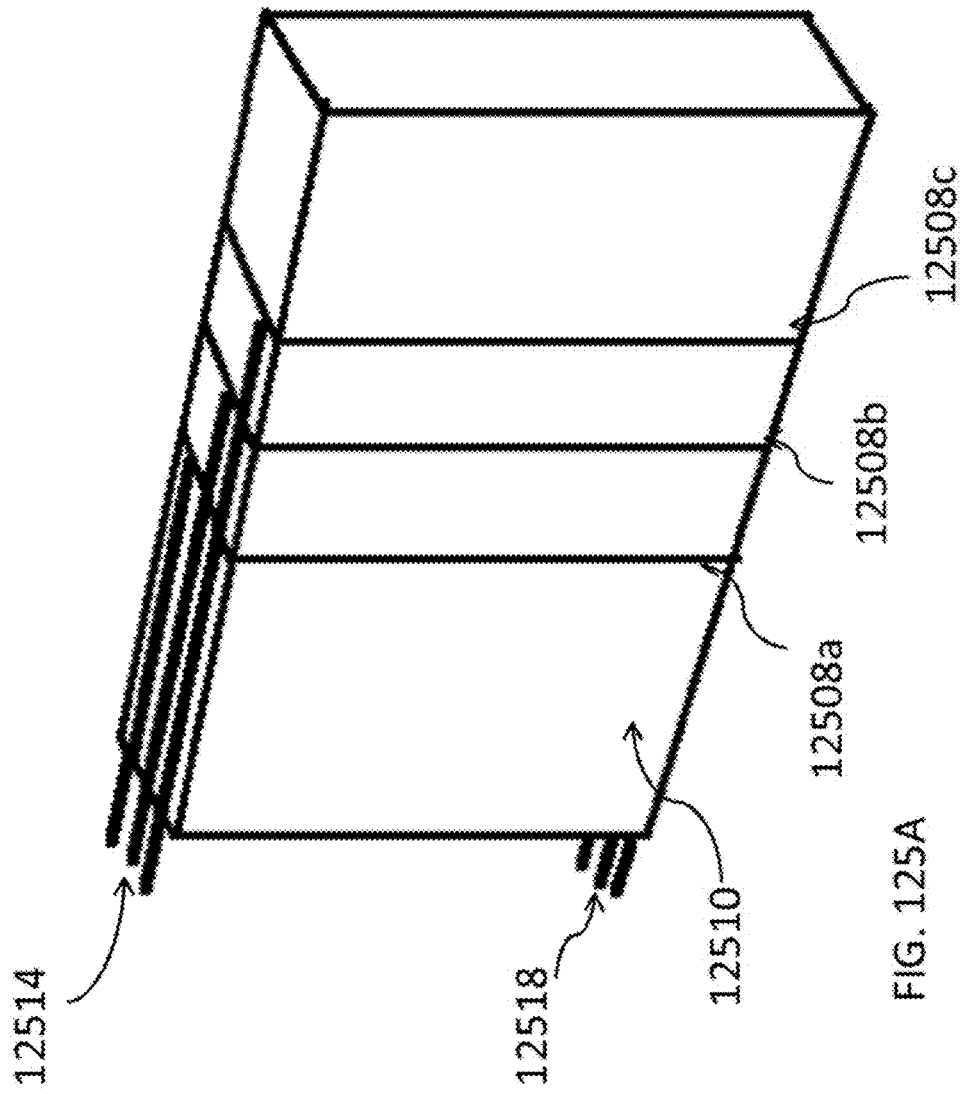
Figure 126:
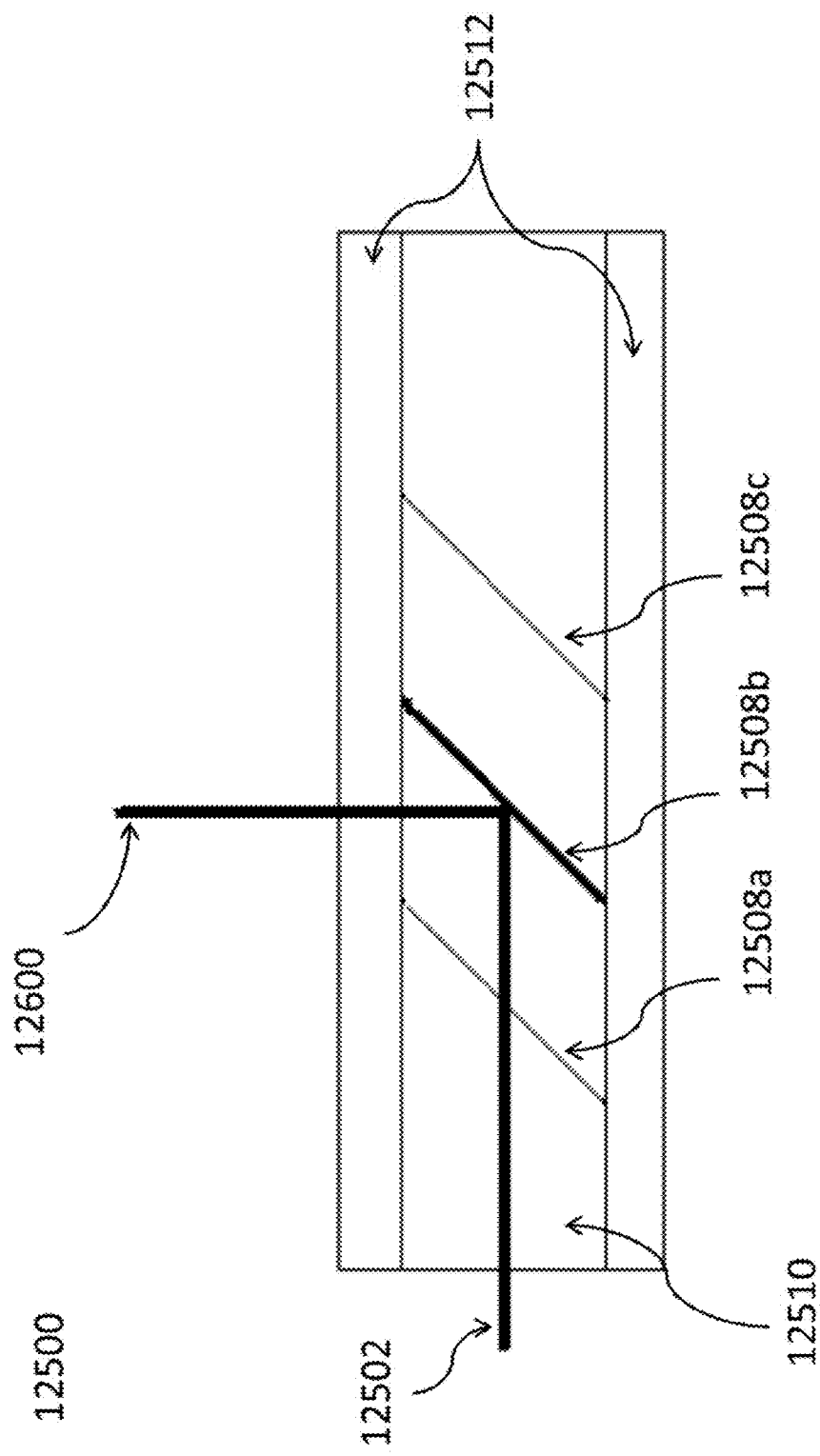
Figure 127:
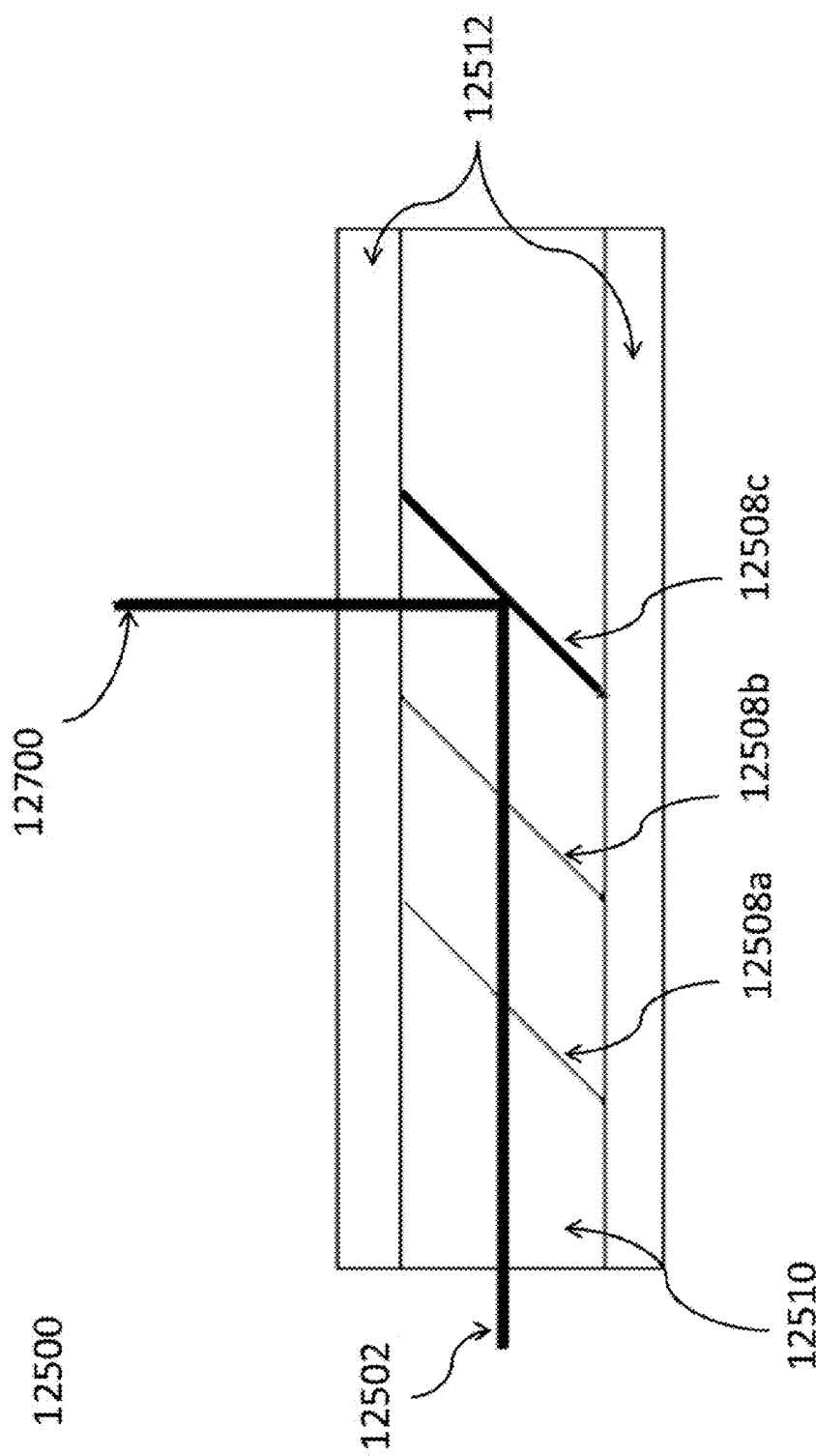
Figure 128A:
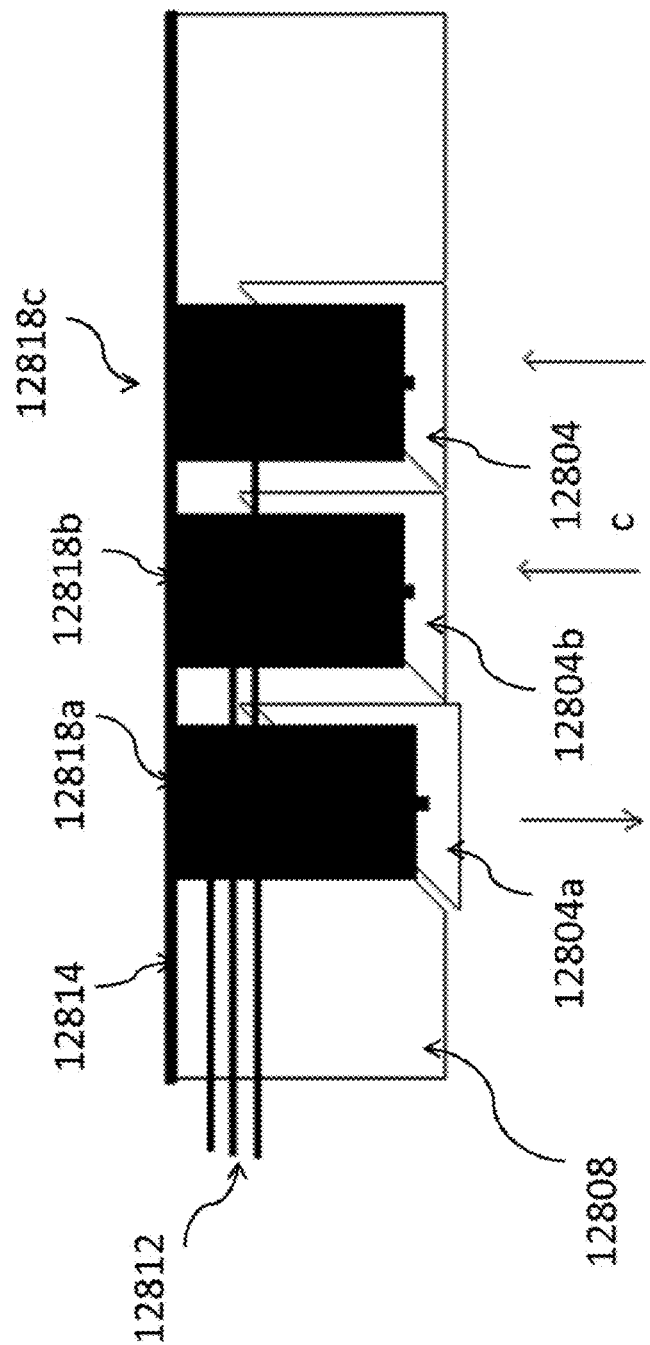

FIG. 124 is a schematic drawing of a prior art waveguide with multiple partial reflectors;

FIG. 125 is a schematic drawing of a waveguide with multiple electrically switchable mirrors in a first position;

FIG. 125A is an illustration of a waveguide assembly with electrical connections;

FIG. 126 is a schematic drawing of a waveguide with multiple electrically switchable mirrors in a second position;

FIG. 127 is a schematic drawing of a waveguide with multiple electrically switchable mirrors in a third position;

FIG. 128 is a schematic drawing of a waveguide with multiple mechanically switchable mirrors in a first position;

FIG. 128A is a schematic drawing of a waveguide assembly with microactuators and associated hardware;

FIG. 129 is a schematic drawing of a waveguide with multiple mechanically switchable mirrors in a second position;

FIG. 130 is a schematic drawing of a waveguide with multiple mechanically switchable mirrors in a third position;

FIG. 131A and FIG. 131B are illustrations of a waveguide display with switchable mirrors on the face of a user; and FIG. 132A-132C are illustrations of the display area provided for users with different eye spacings.

Figure 133:
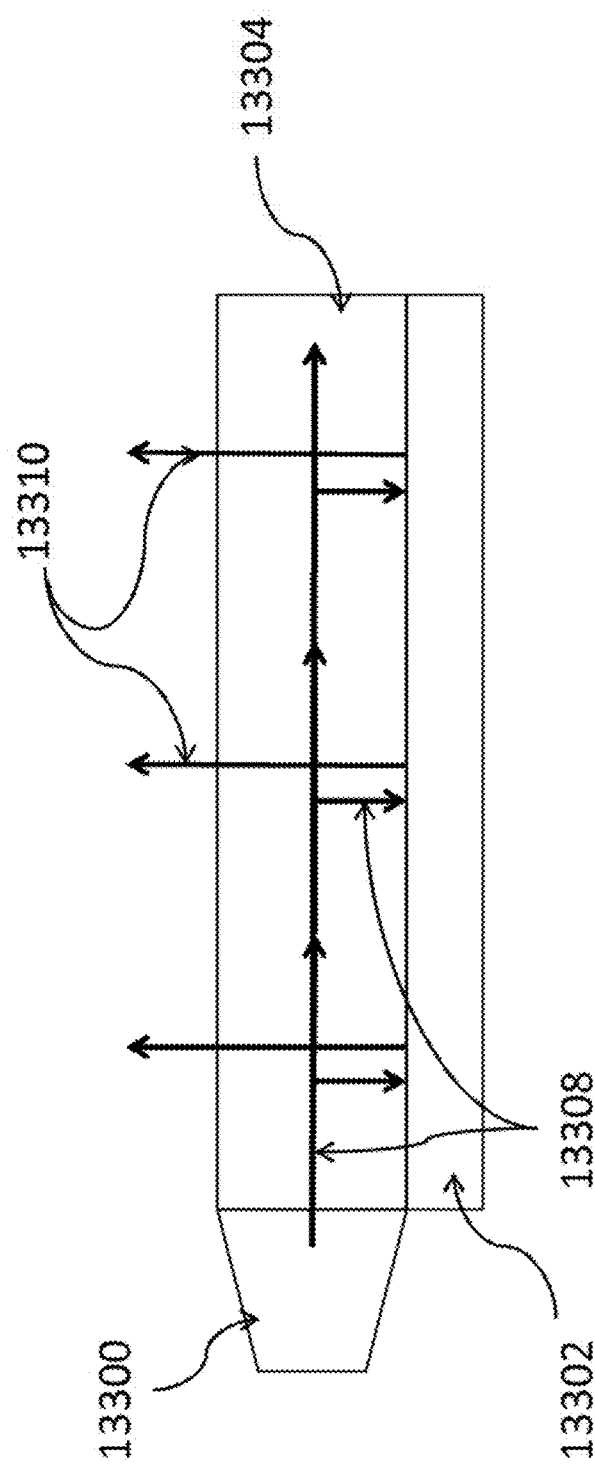
Figure 134:
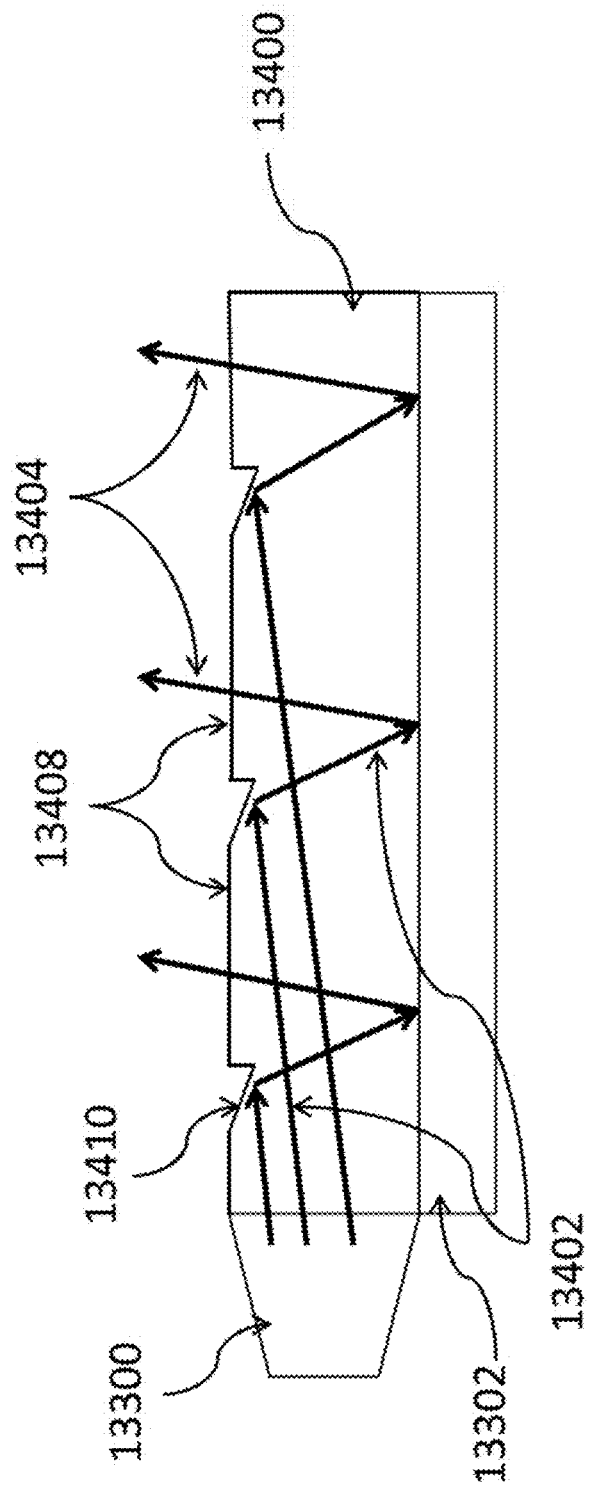
Figure 135:
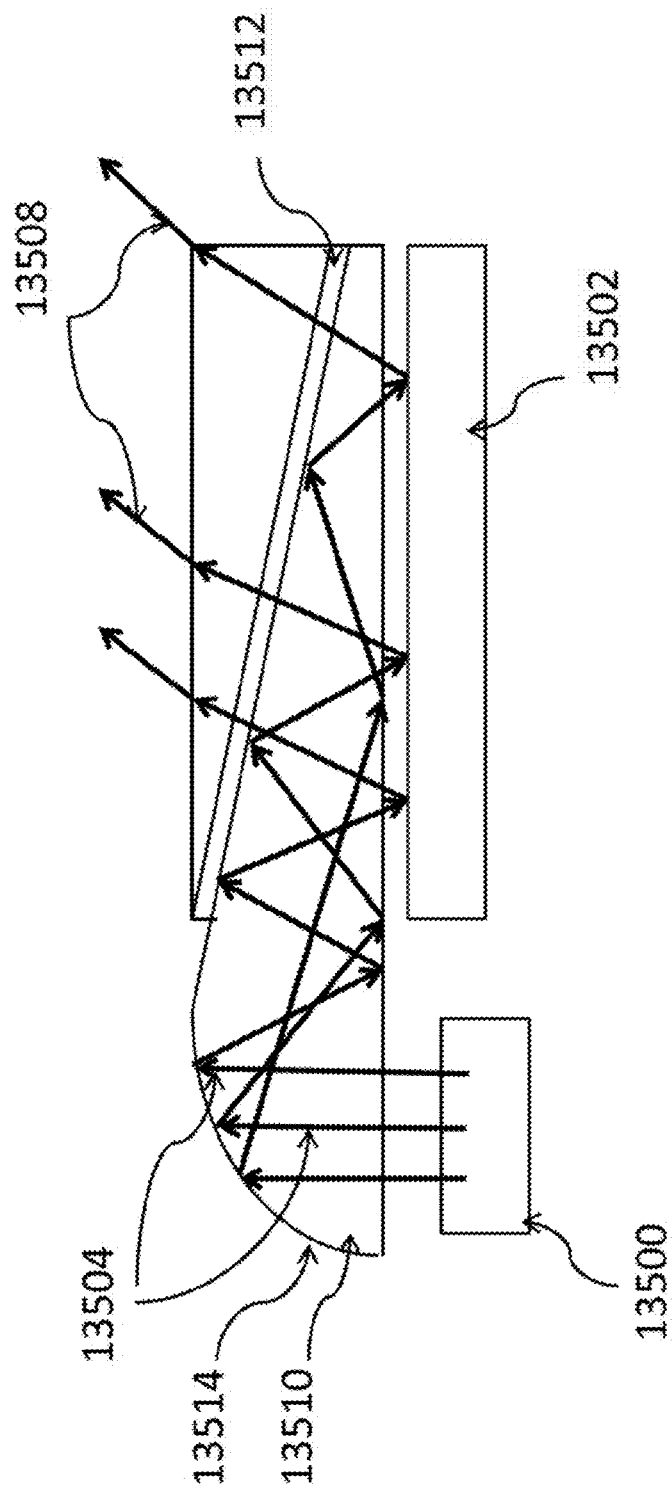
Figure 136:
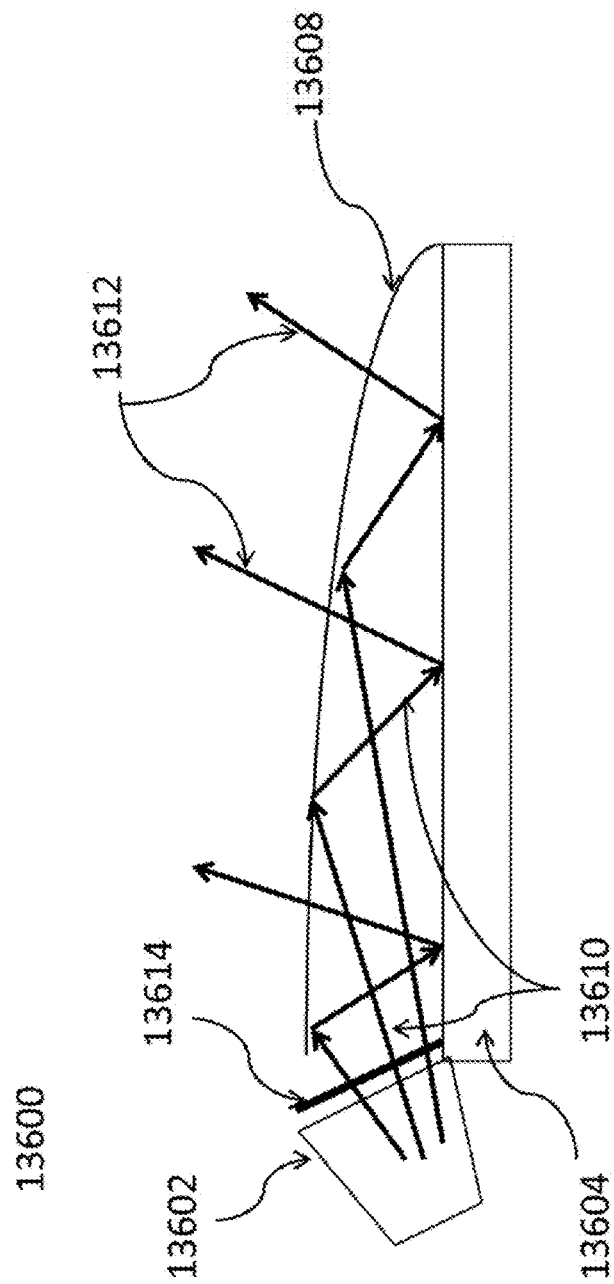
Figure 137:
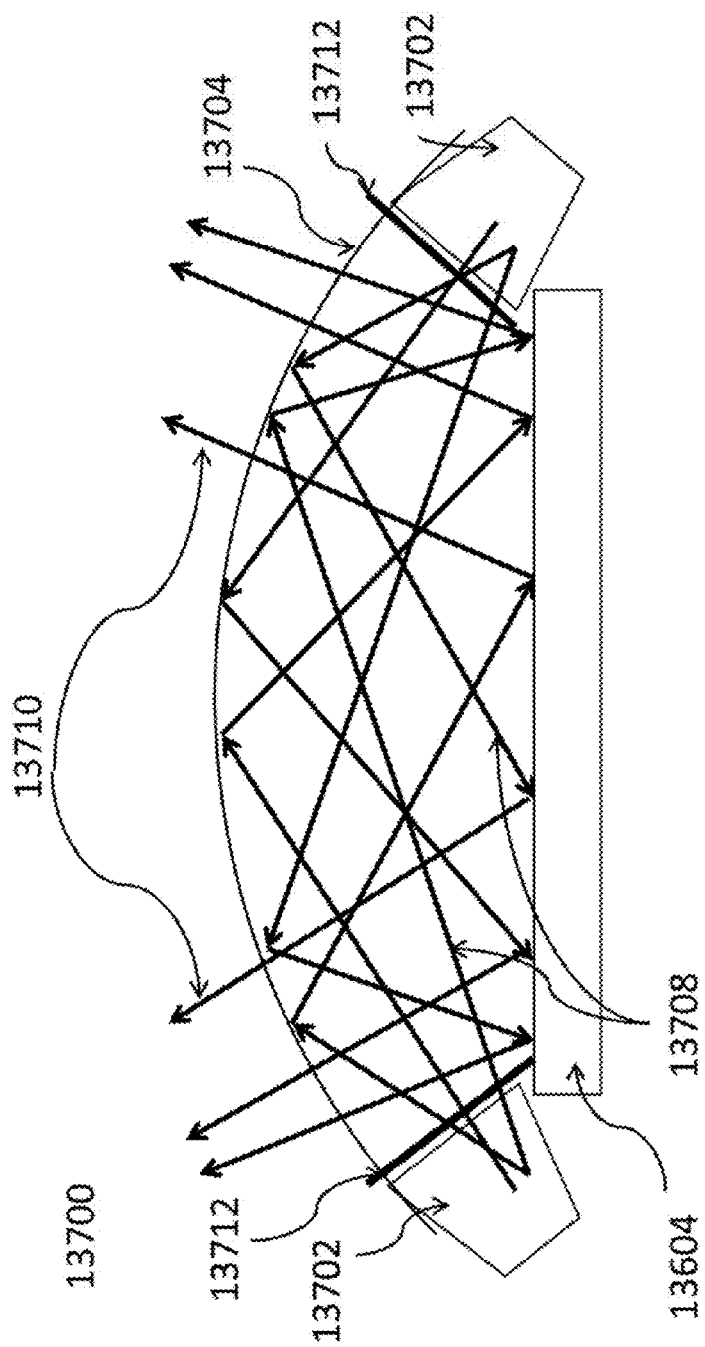
Figure 138:
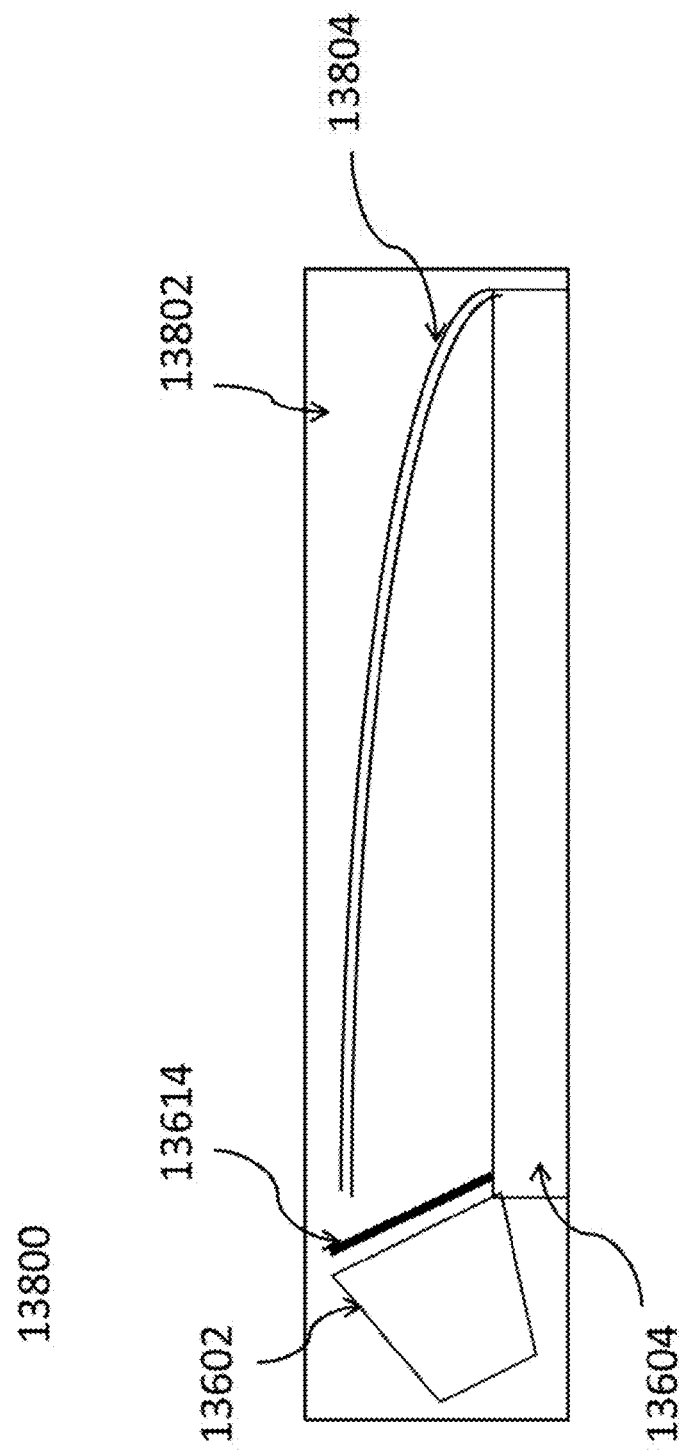
Figure 139:
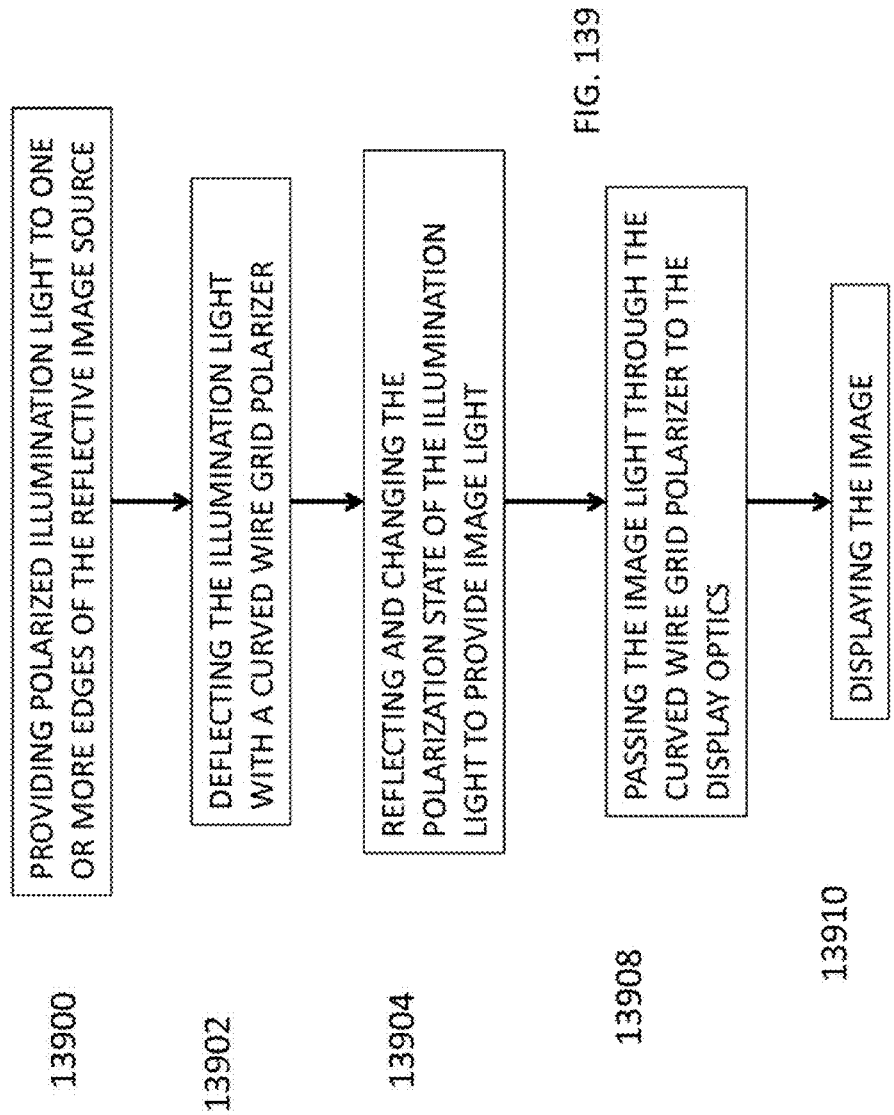

FIG. 133 is a schematic drawing of a reflective image source with an edge light source and a frontlight that shows the rays of light passing through;

FIG. 134 is a schematic drawing of a prior art frontlight which includes grooves;

FIG. 135 is a schematic drawing of a prior art frontlight which includes a planar polarizing beam splitter and the curved reflector in a solid block;

FIG. 136 is a schematic drawing of an embodiment of the present disclosure with a single edge light and a curved wire grid polarizer film;

FIG. 137 is a schematic drawing of an embodiment of the present disclosure with two edge lights and a curved wire grid polarizer film;

FIG. 138 is a schematic drawing of a side frame to hold the flexible wire grid polarizer film in the desired curved shape; and FIG. 139 is a flowchart of the method of the disclosure.

Figure 140:
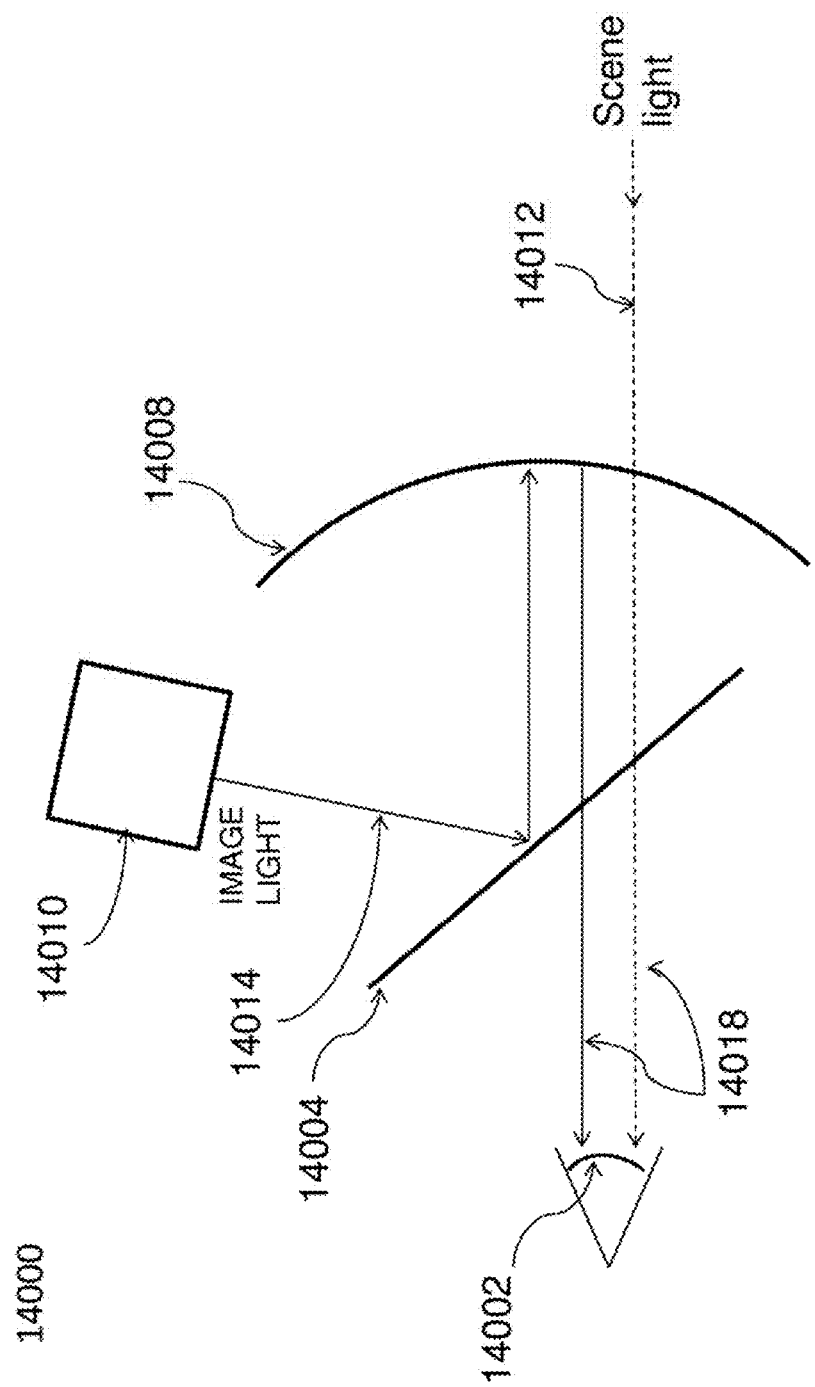
Figure 141:
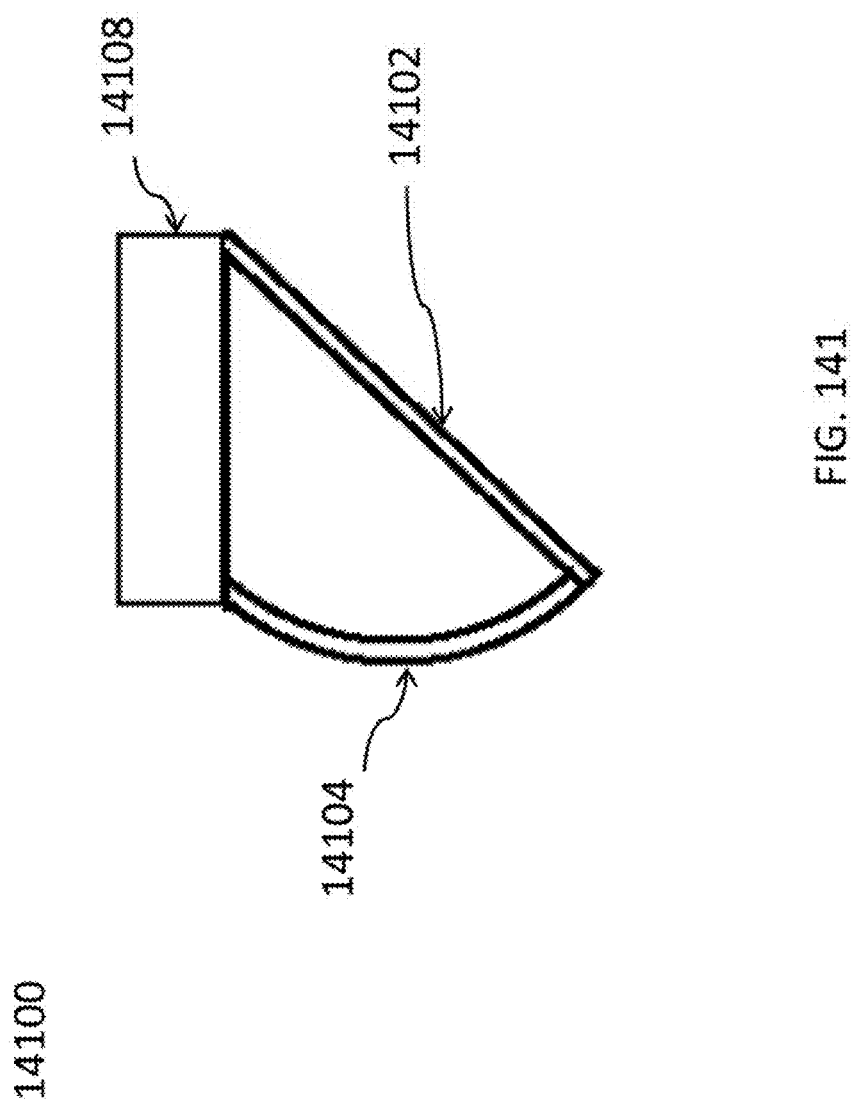
Figure 142:
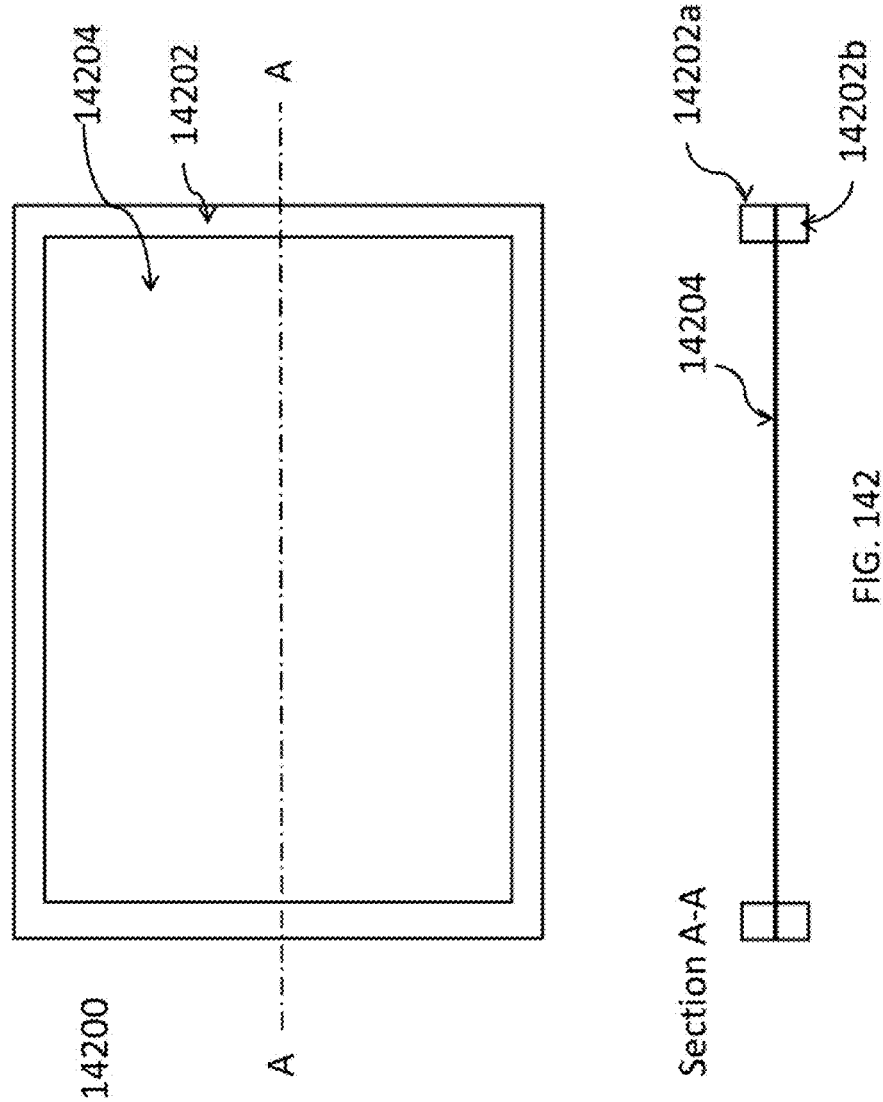
Figure 143:
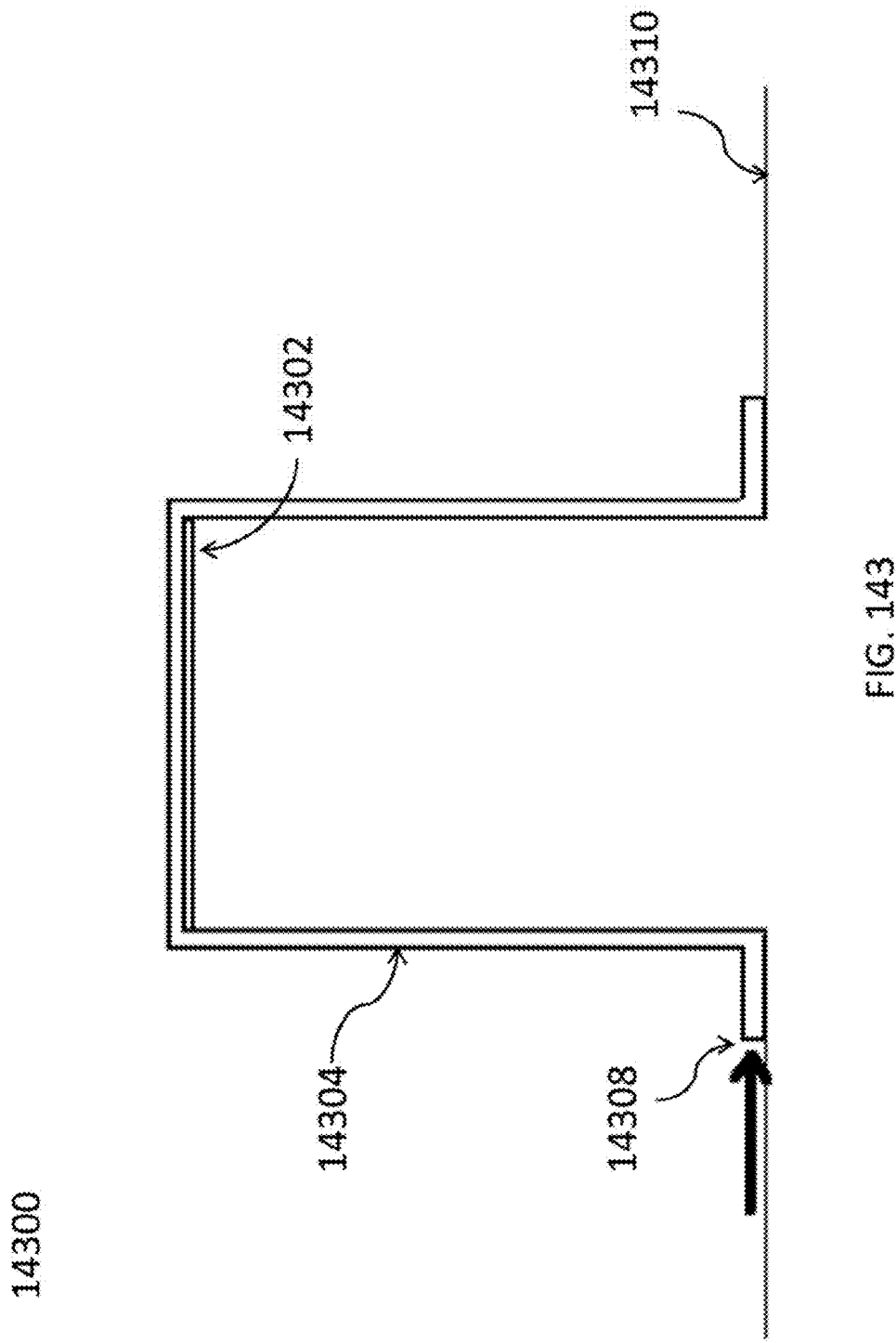
Figure 144:
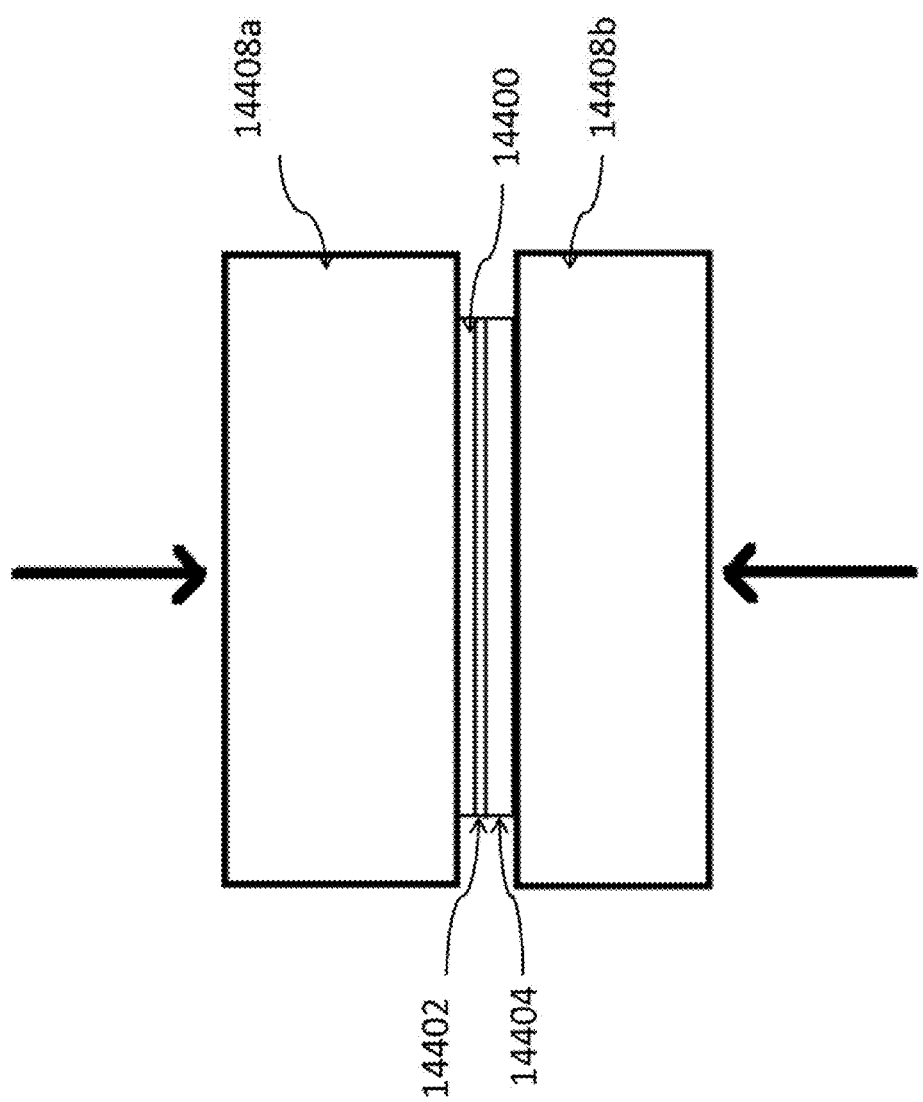

FIG. 140 is a schematic drawing of a near eye imaging system with a beam splitter;

FIG. 141 is a schematic drawing of an optics module for a near eye imaging system;

FIG. 142 is an illustration of a pellicle style optical plate;

FIG. 143 is an illustration of an insert molded module housing with an embedded optical plate;

FIG. 144 is an illustration of compression molding of a laminate style optical plate; and FIG. 145A-C is an illustration of the application of an optical film within a molded module housing.

Figure 146:
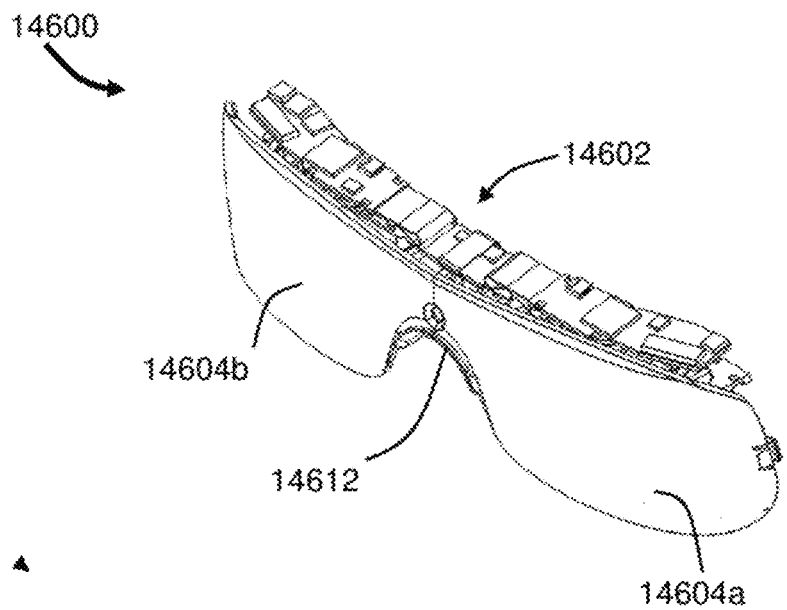

FIG. 146 depicts a schematic front perspective view of an AR eyepiece (without its temple pieces) according to an embodiment of the present disclosure.

Figure 147:
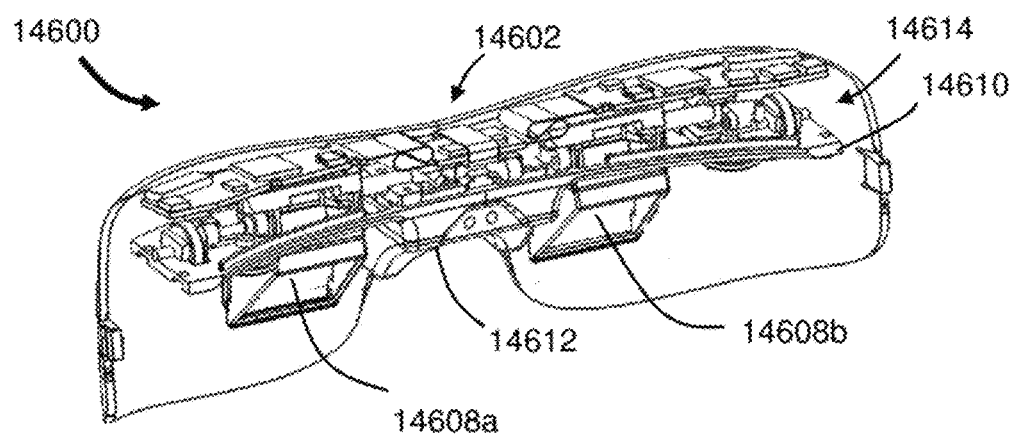

FIG. 147 depicts a schematic rear perspective view of the AR eyepiece of FIG. 146.

Figure 148:
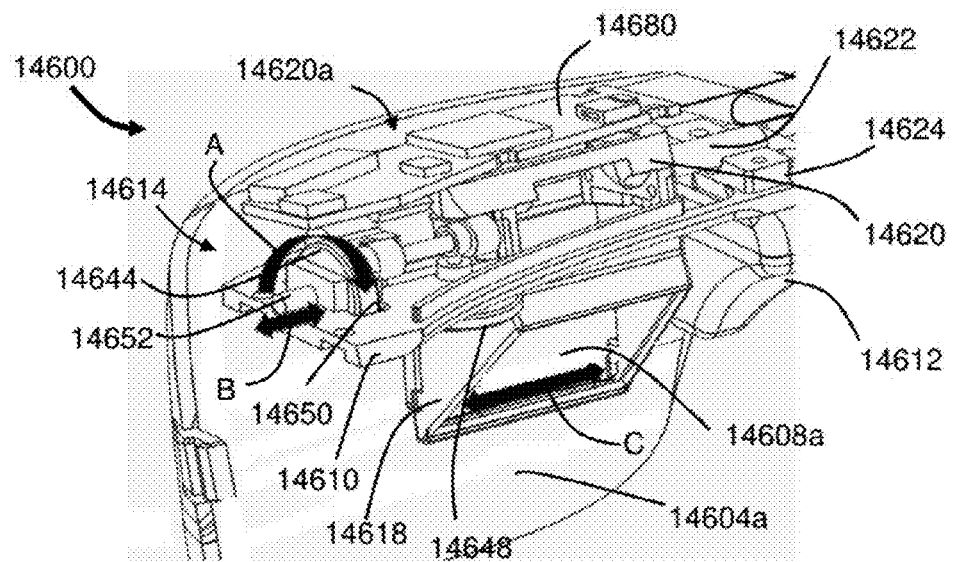

FIG. 148 depicts a schematic rear perspective partial view of the wearer's right side of the AR eyepiece of FIG. 146.

Figure 149:
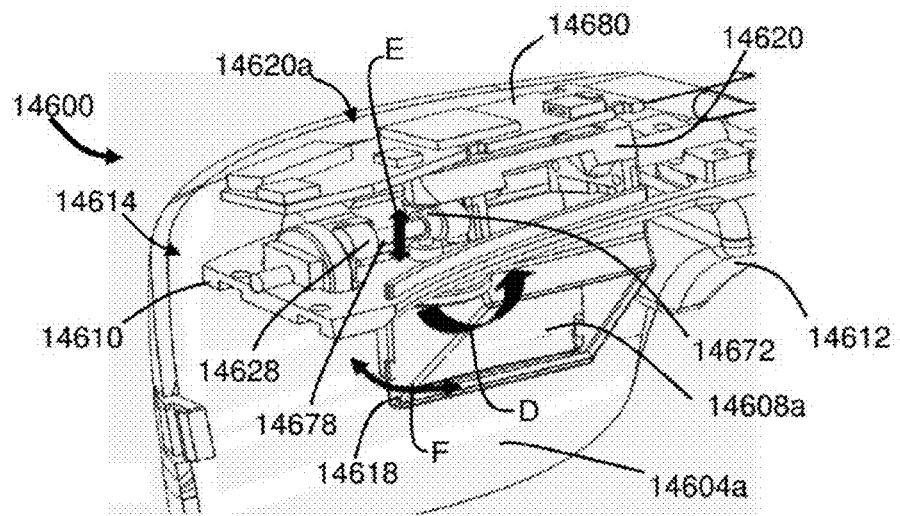

FIG. 149 depicts a schematic rear perspective partial view of the wearer's right side of the AR eyepiece of FIG. 146.

Figure 150:
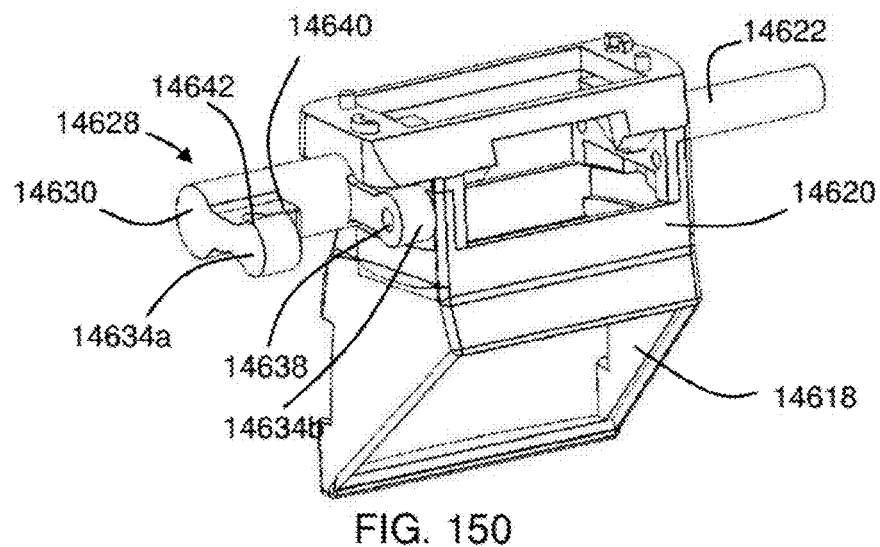

FIG. 150 depicts a schematic perspective view of components of the AR eyepiece shown in FIG. 146 for supporting one of the projection screens.

Figure 151:
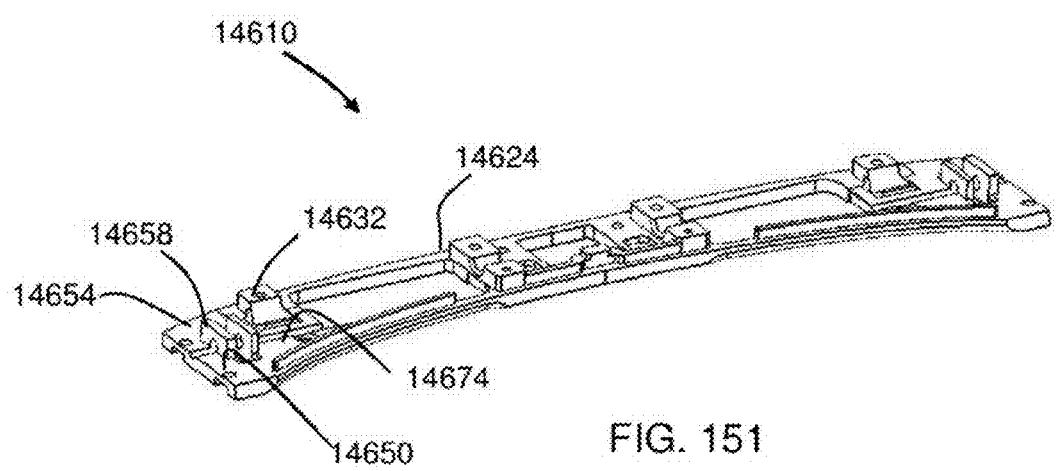

FIG. 151 depicts a schematic perspective view of the adjustment platform of the AR eyepiece shown in FIG. 146.

Figure 152:
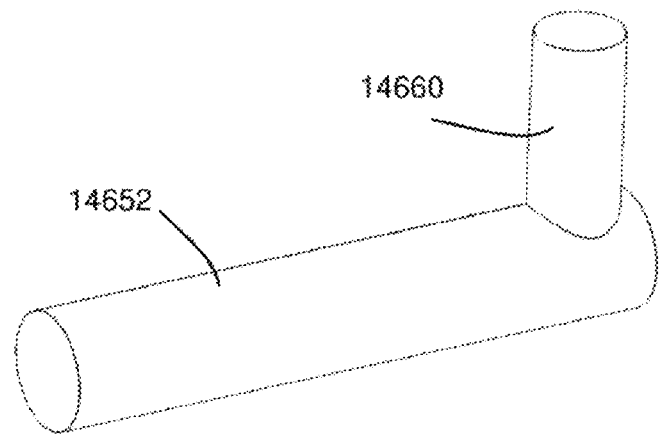

FIG. 152 depicts a schematic perspective view of a component of the lateral adjustment mechanism of the AR eyepiece shown in FIG. 146.

Figure 153:
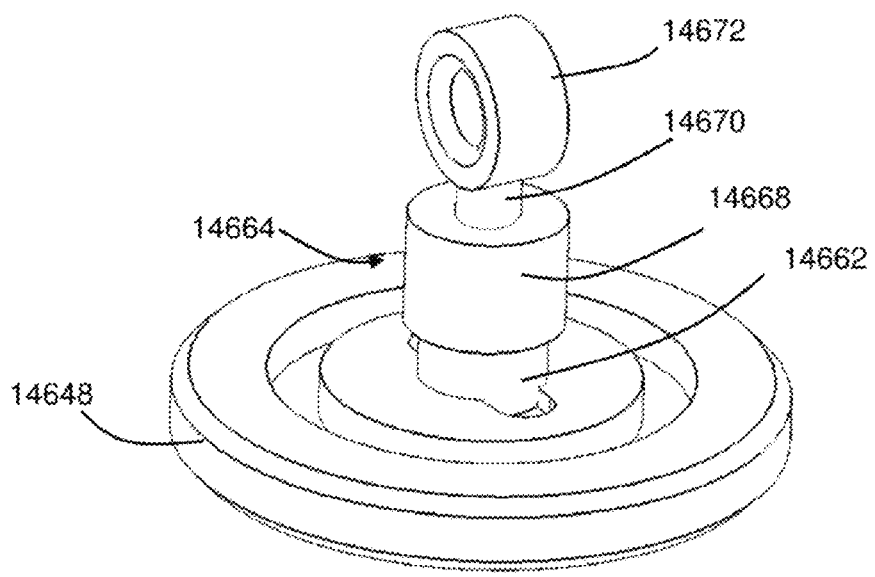

FIG. 153 depicts a schematic perspective view of a component of the tilt adjustment mechanism of the AR eyepiece shown in FIG. 146.

Figure 154:
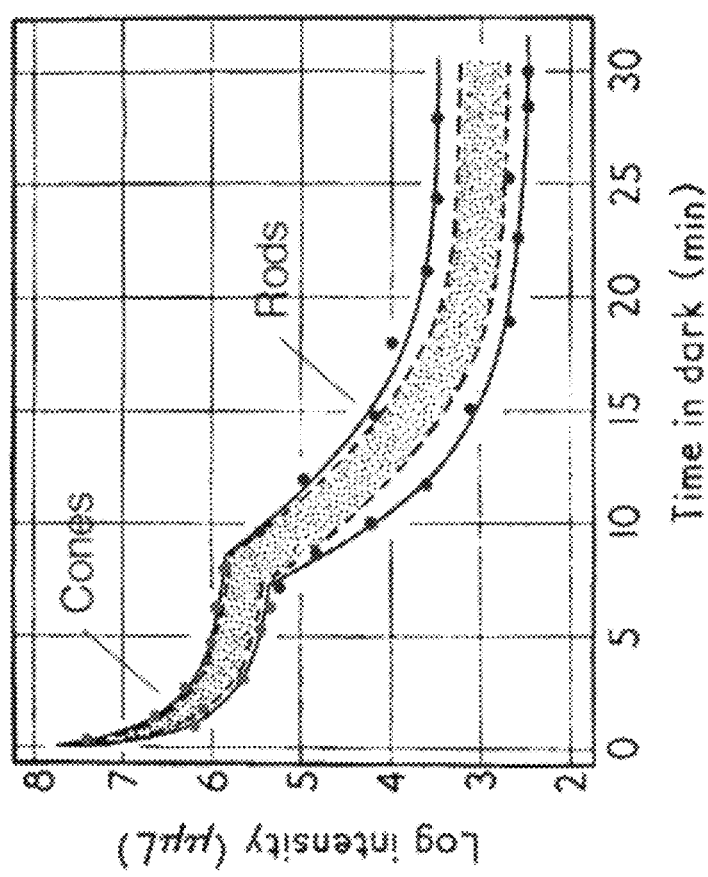

FIG. 154 is a chart showing the dark adaptation curve for a human eye.

Figure 155:
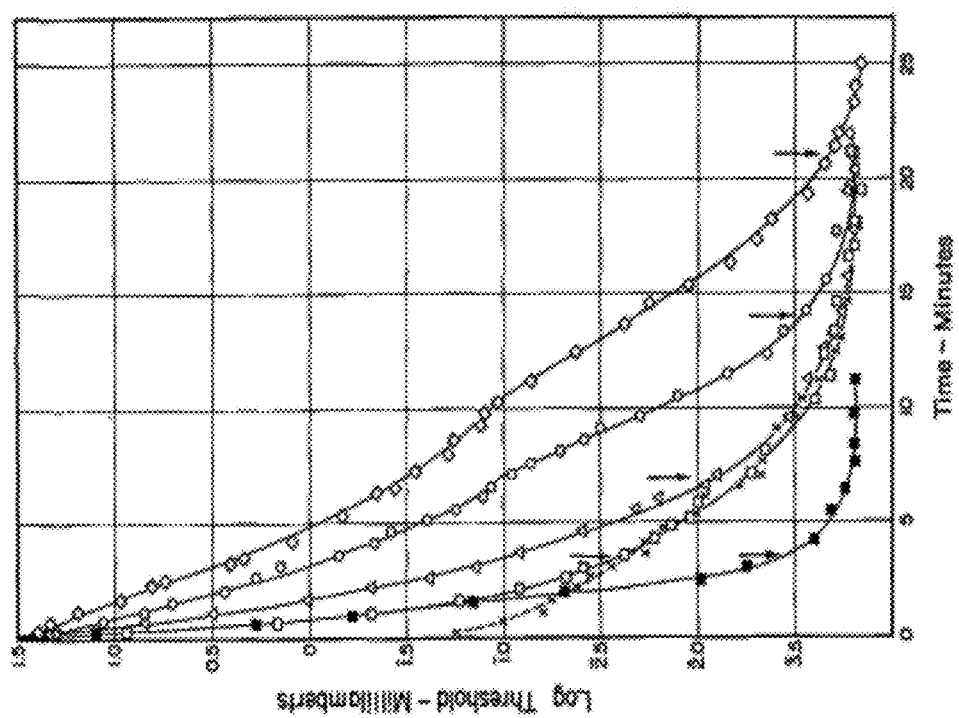

FIG. 155 is a chart showing the effect of progressively decreasing the illuminance on the dark adaptation curve for the human eye.

Figure 156:
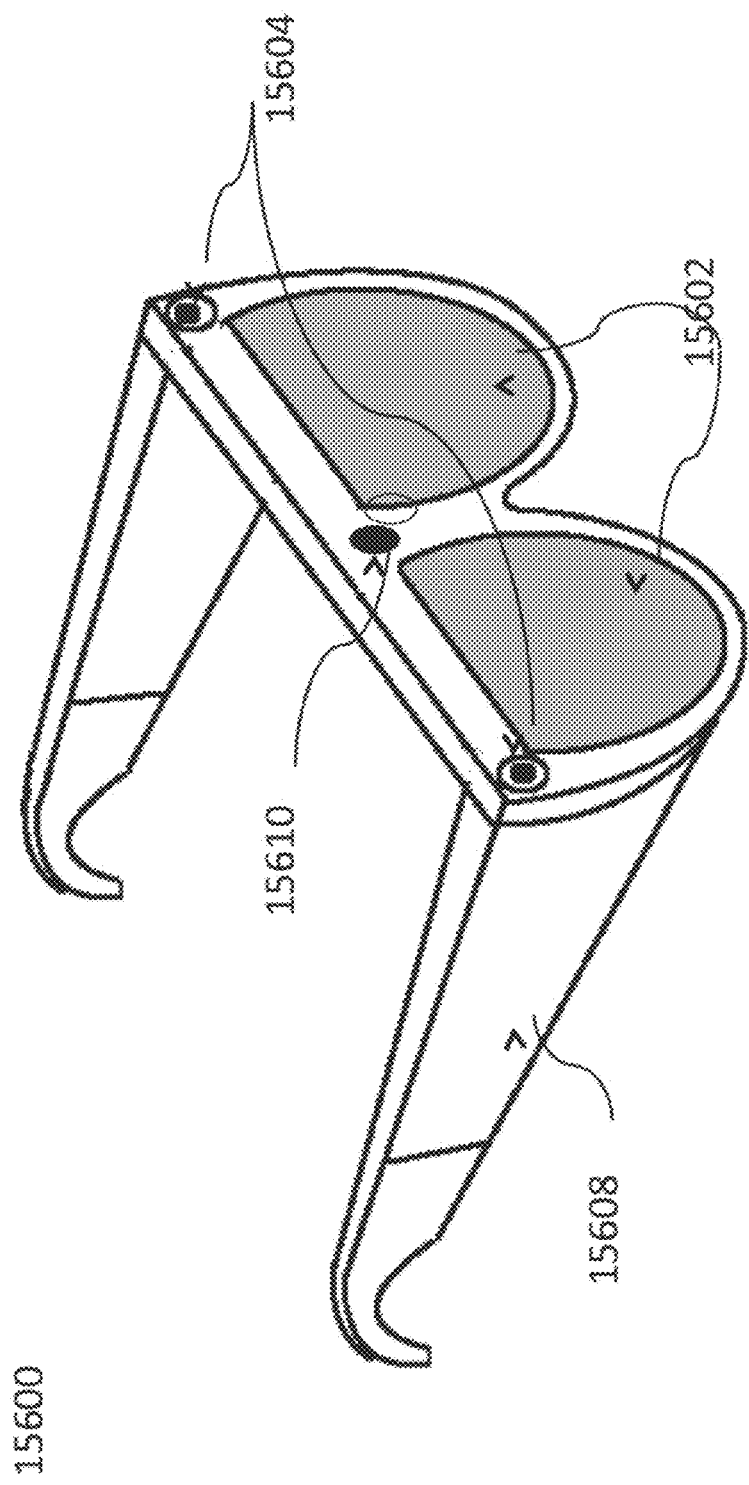

FIG. 156 is an illustration of a head mounted display with see-through capabilities.

Figure 157:
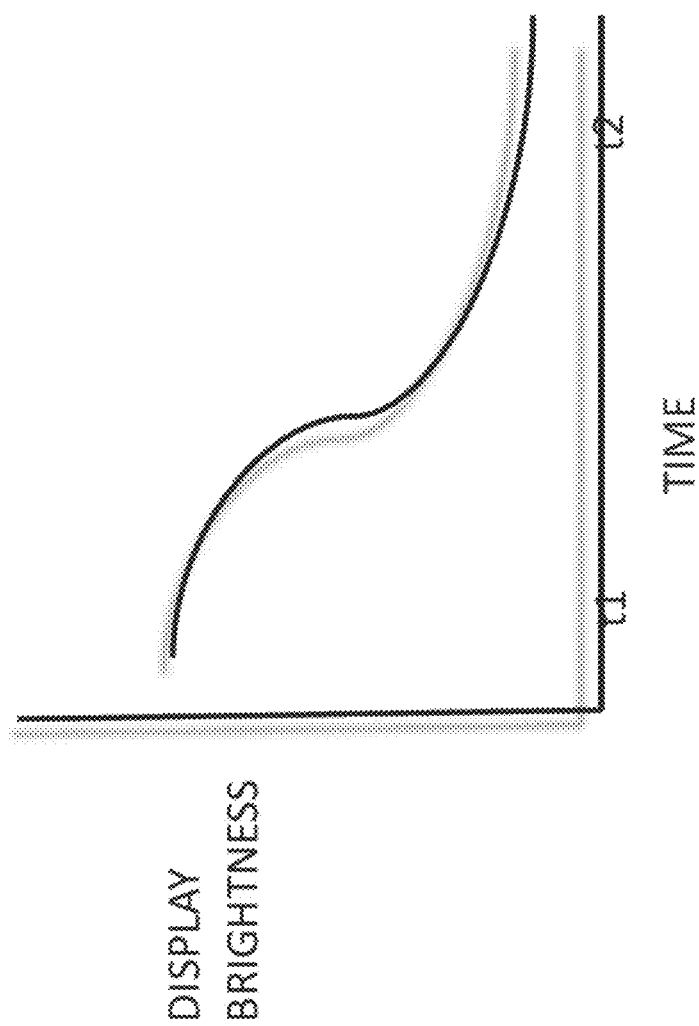

FIG. 157 is a graph showing a relationship between display brightness and time when entering a dark environment.

Figure 158:
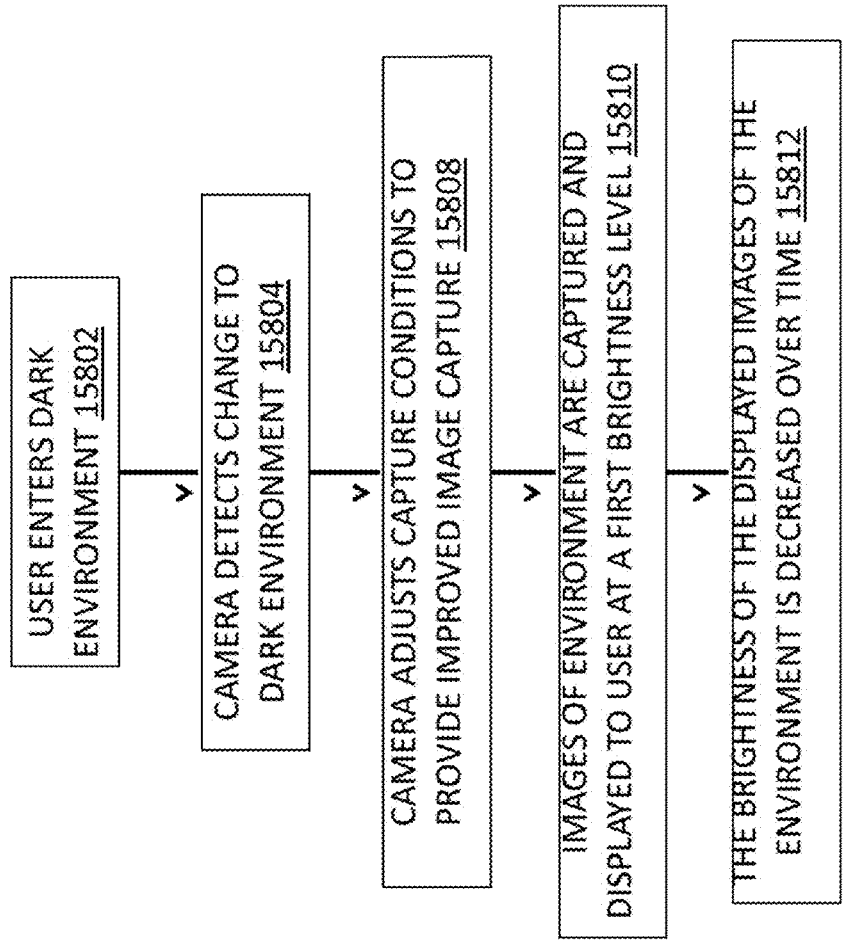

FIG. 158 is a flow chart for a method of dark adaptation.

Figure 159:

FIG. 159 depicts a virtual keyboard presented in a user's field of view.

Figure 160:
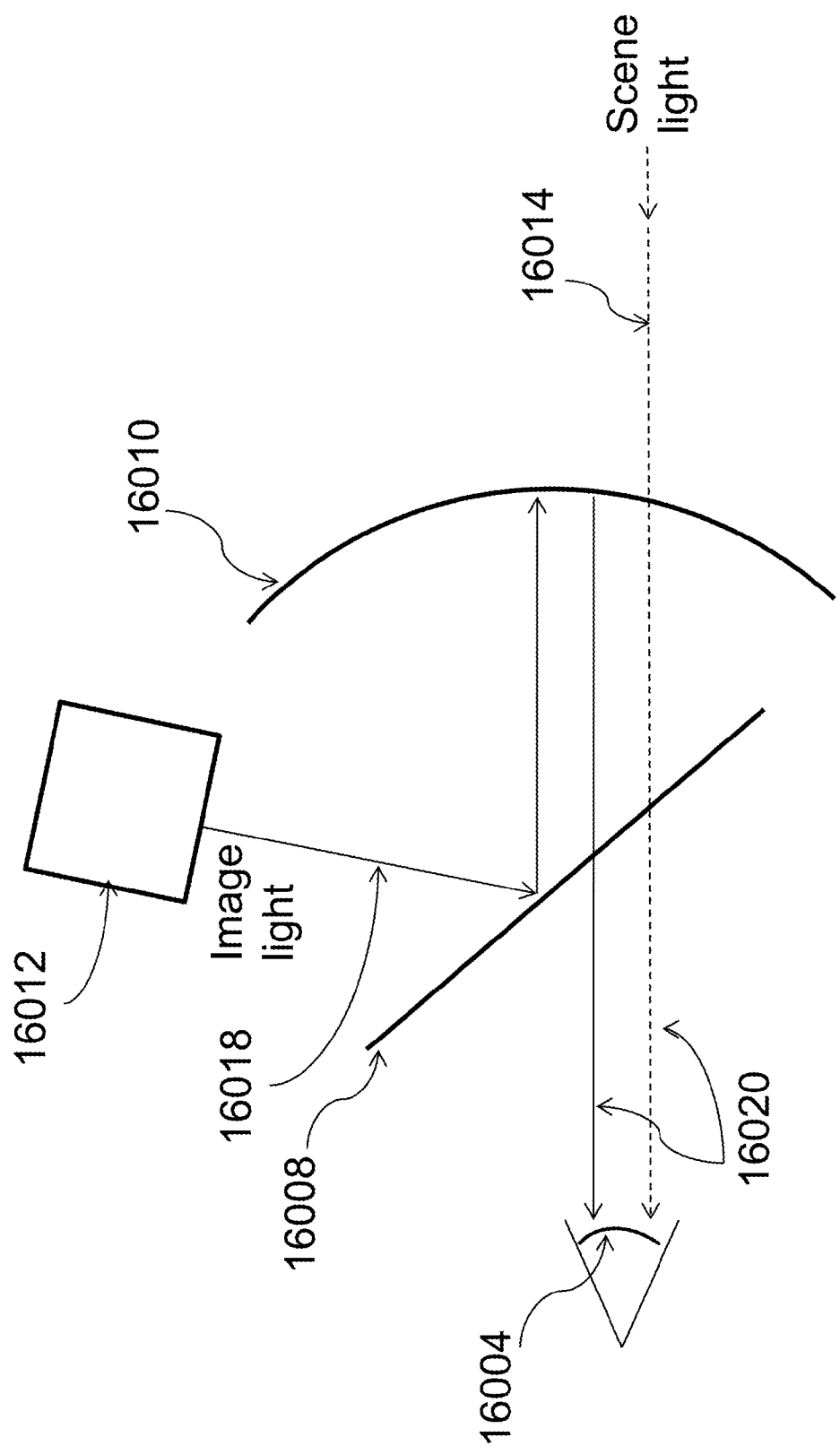

FIG. 160 depicts an example of a display system with an optically flat reflective surface.

Figure 161:
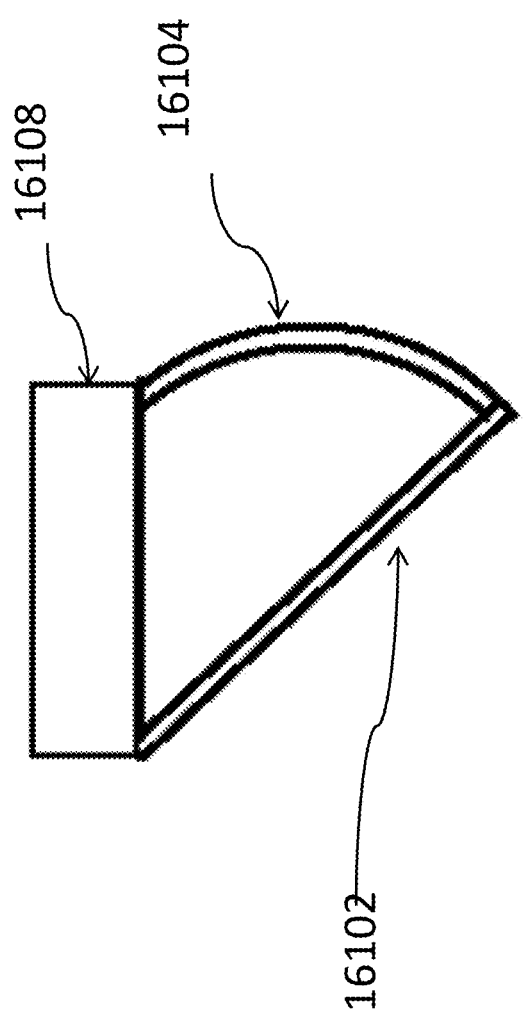

FIG. 161 shows an illustration of a near eye display module.

Figure 162:
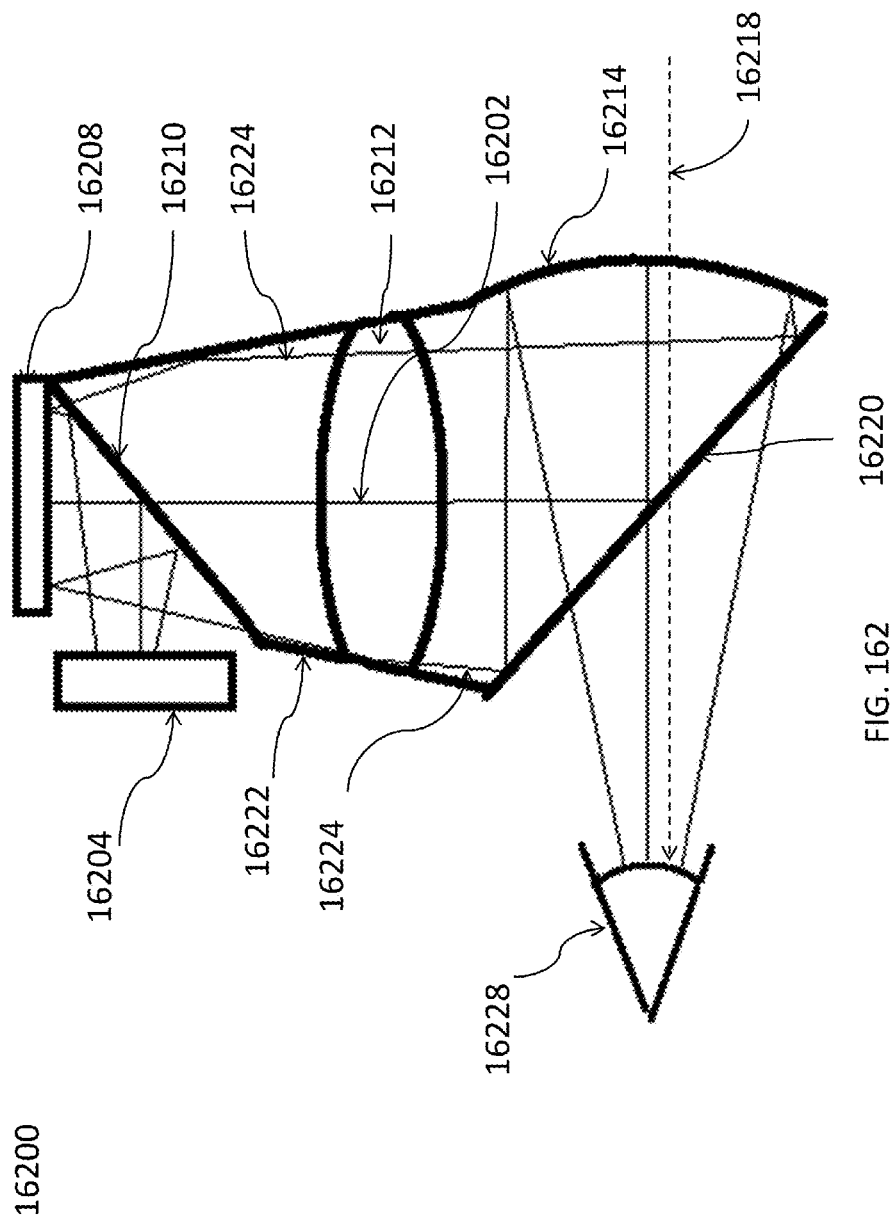

FIG. 162 shows an illustration of the optics associated with a type of head mounted display.

Figure 163:
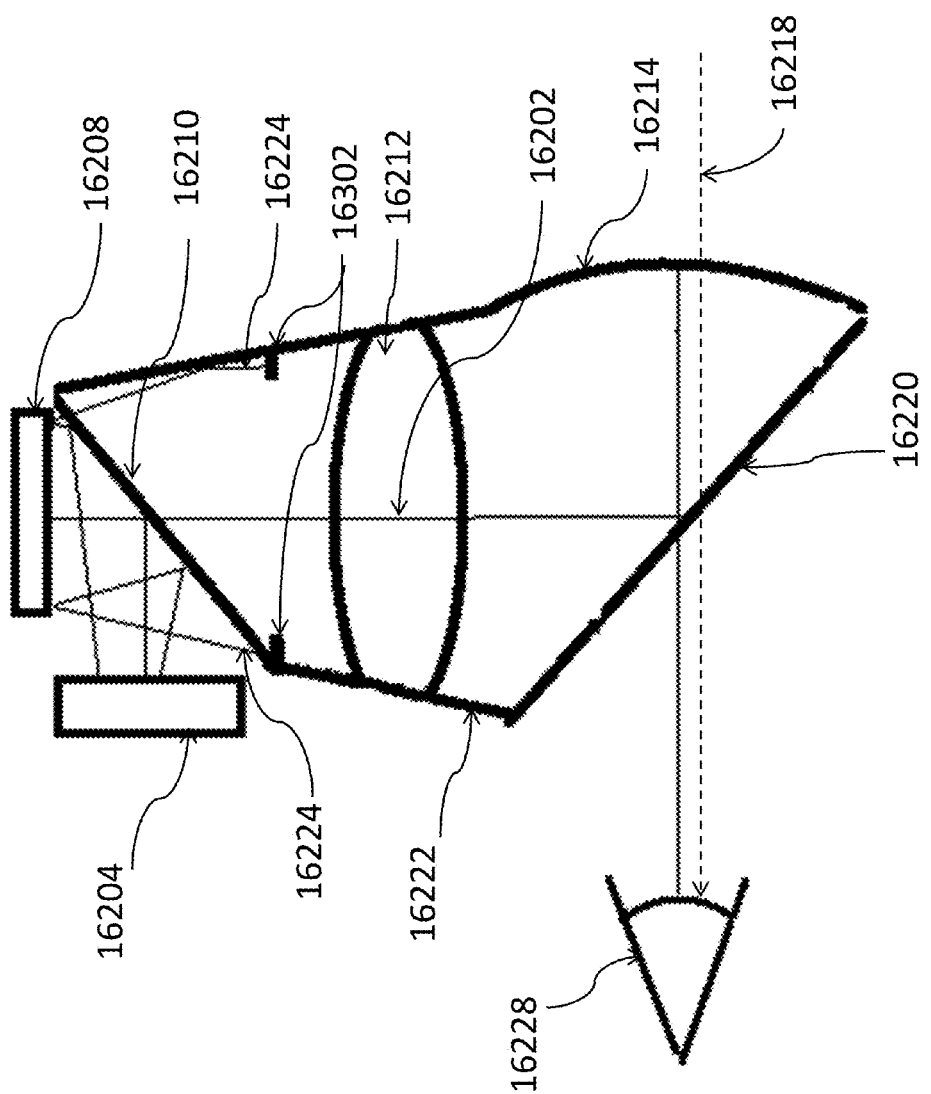

FIG. 163 shows an illustration in which baffles are added inside the housing between the illumination beam splitter and the lens.

Figure 164:
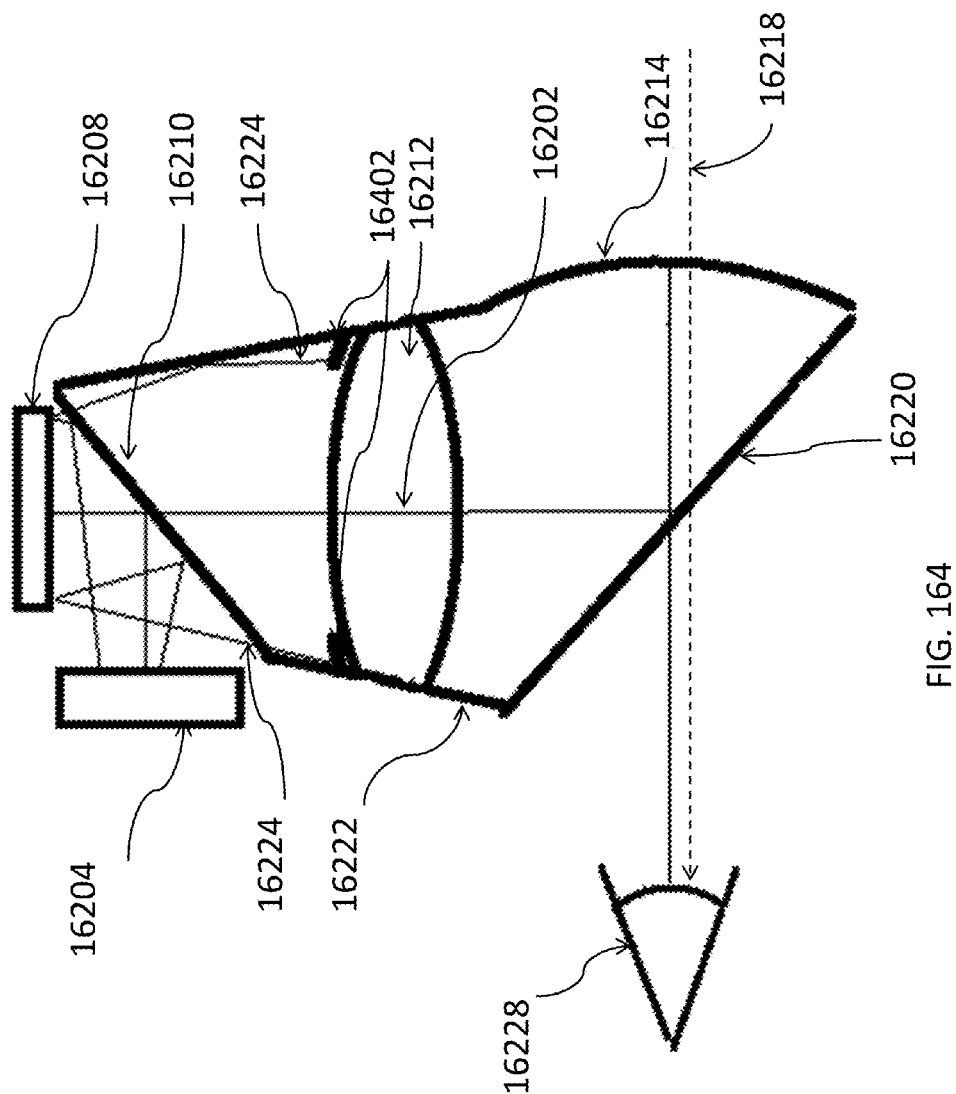

FIG. 164 shows an illustration of another embodiment of the disclosure in which baffles are added at the entering surface of the lens.

Figure 165:
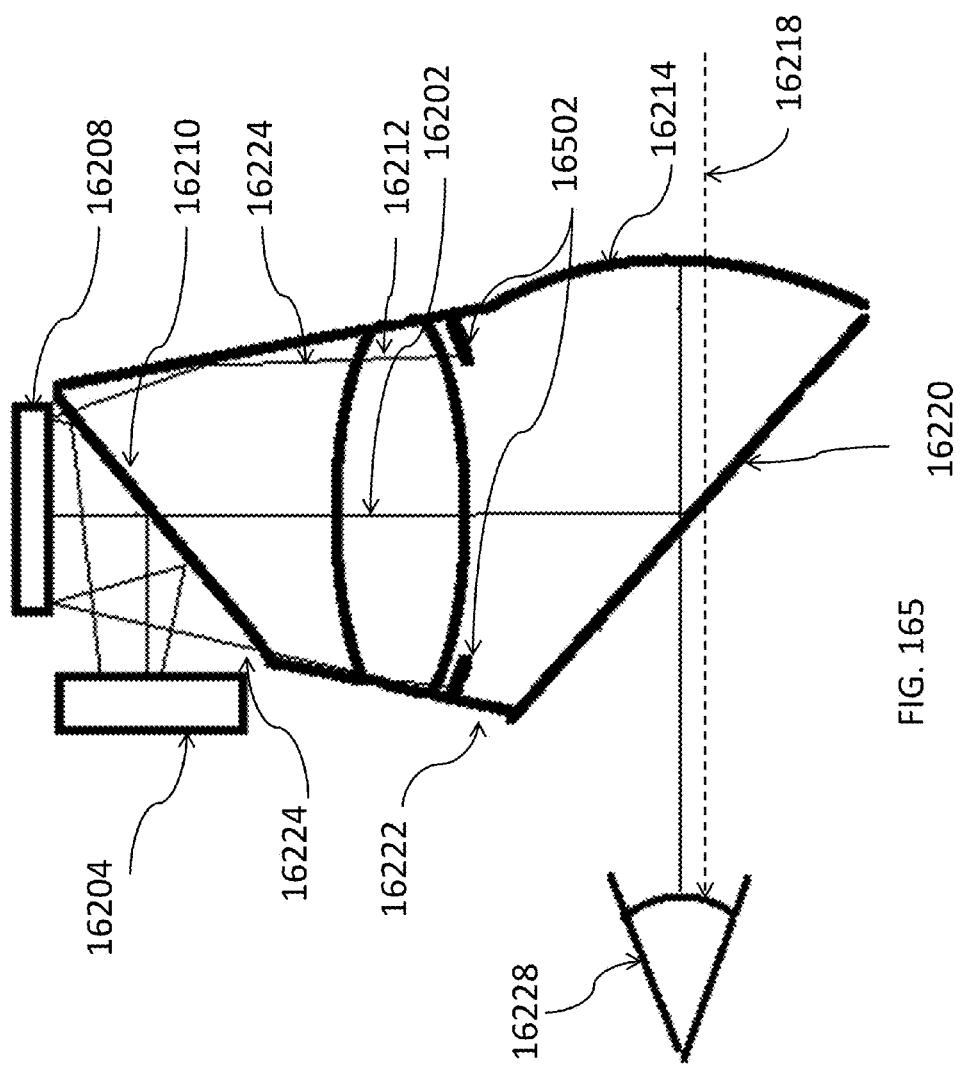

FIG. 165 shows an illustration of another embodiment of the disclosure in which baffles are added at the output of the lens.

Figure 166:
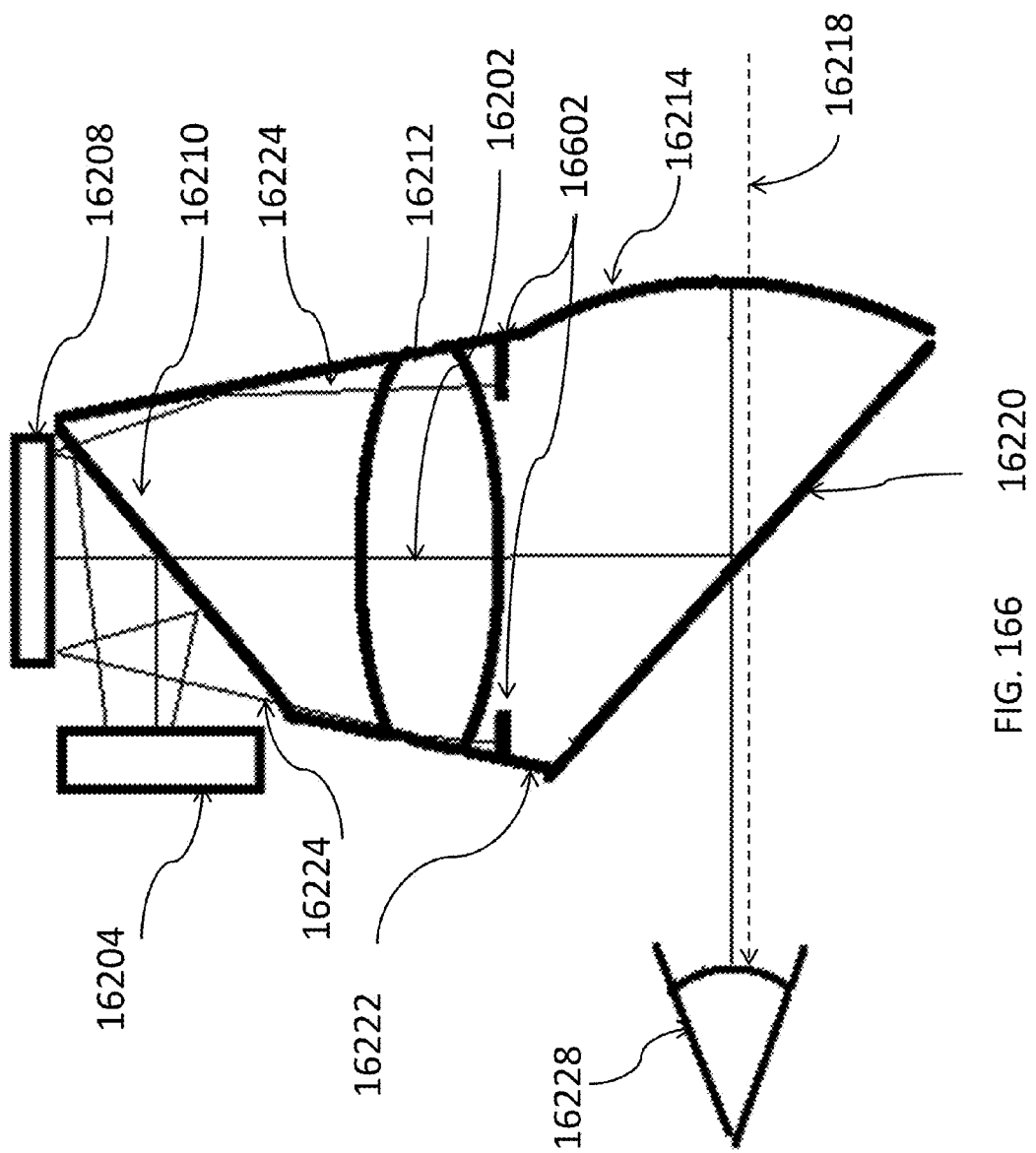

FIG. 166 shows an illustration of another embodiment of the disclosure in which a baffle is attached to the housing between the lens and the imaging beam splitter.

Figure 167:
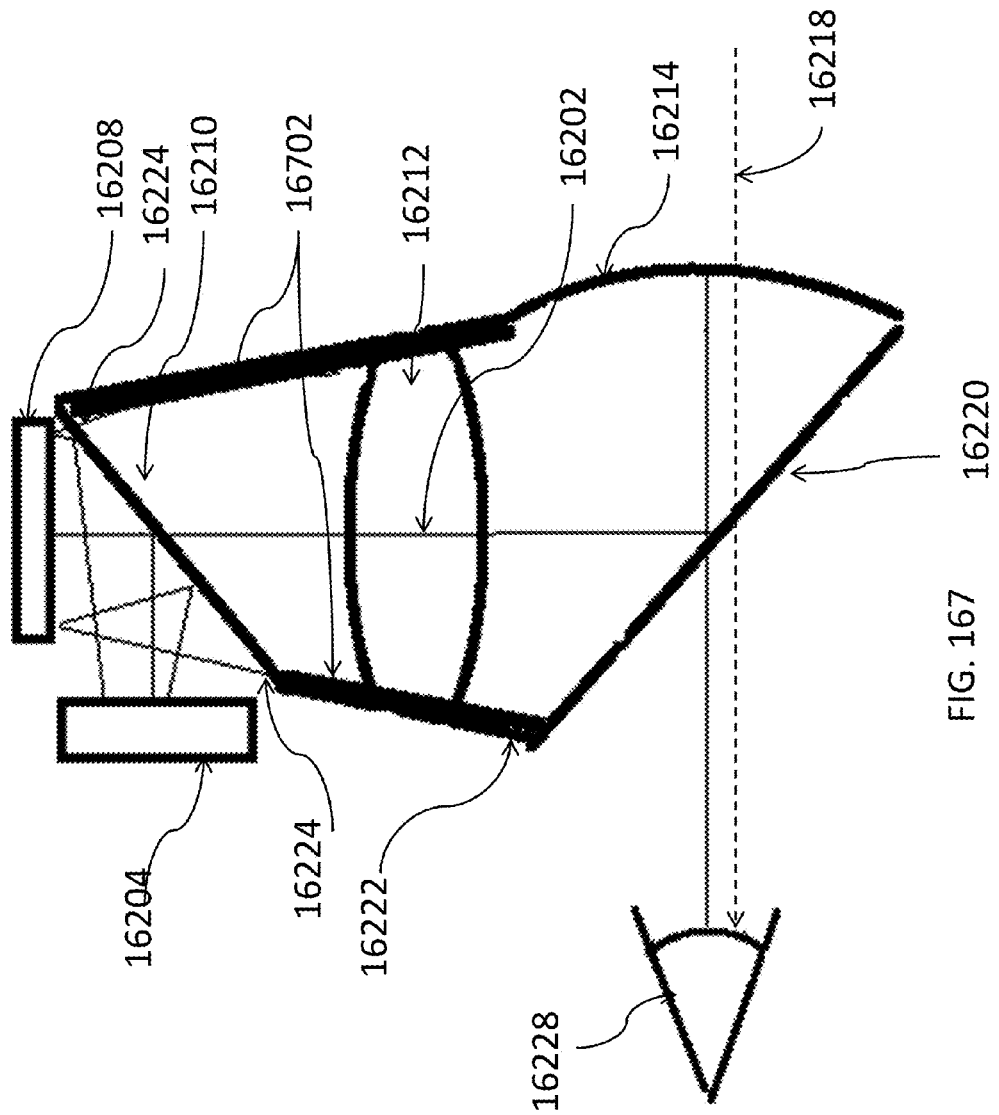

FIG. 167 shows an illustration of a further embodiment of the disclosure in which absorbing coatings are applied to the sidewalls of the housing.

Figure 168:
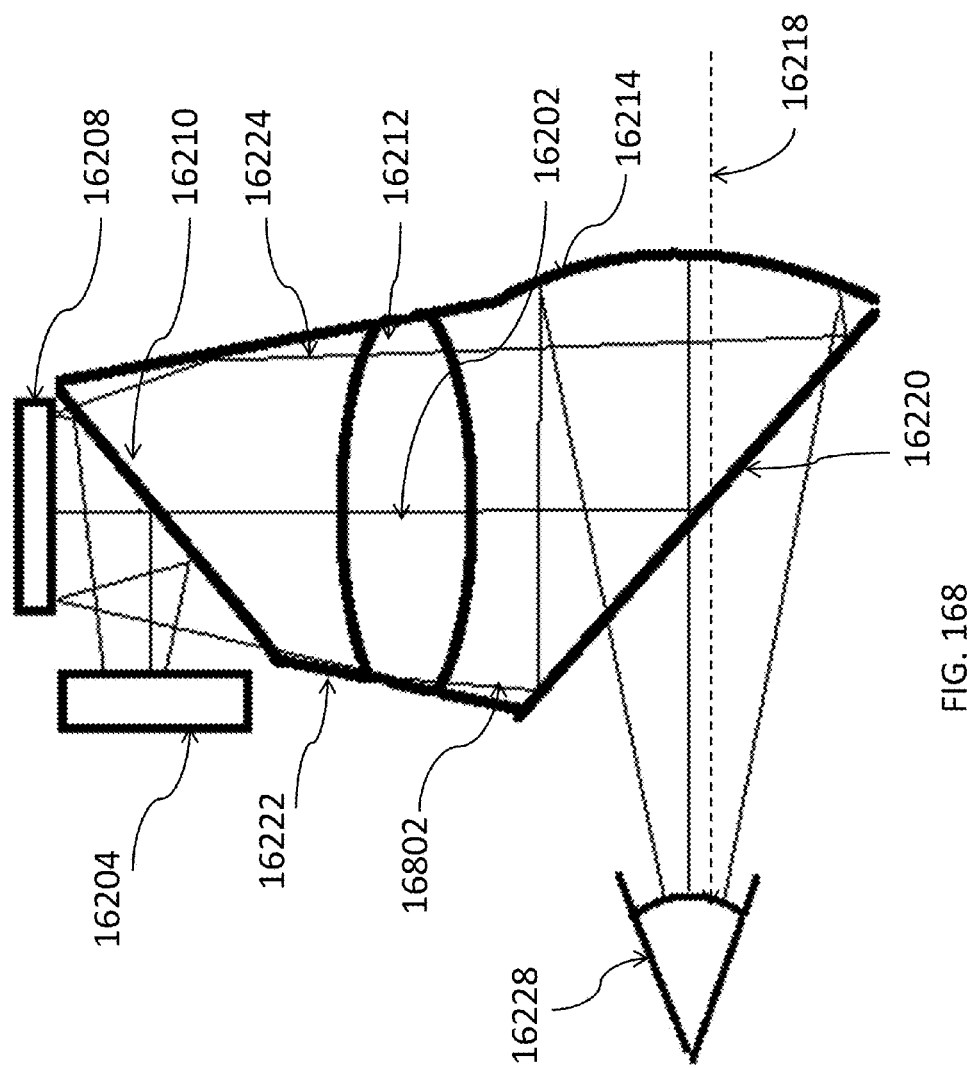

FIG. 168 shows an illustration of another source of stray light in a head mounted display wherein the stray light comes directly from the edge of the light source.

Figure 169:
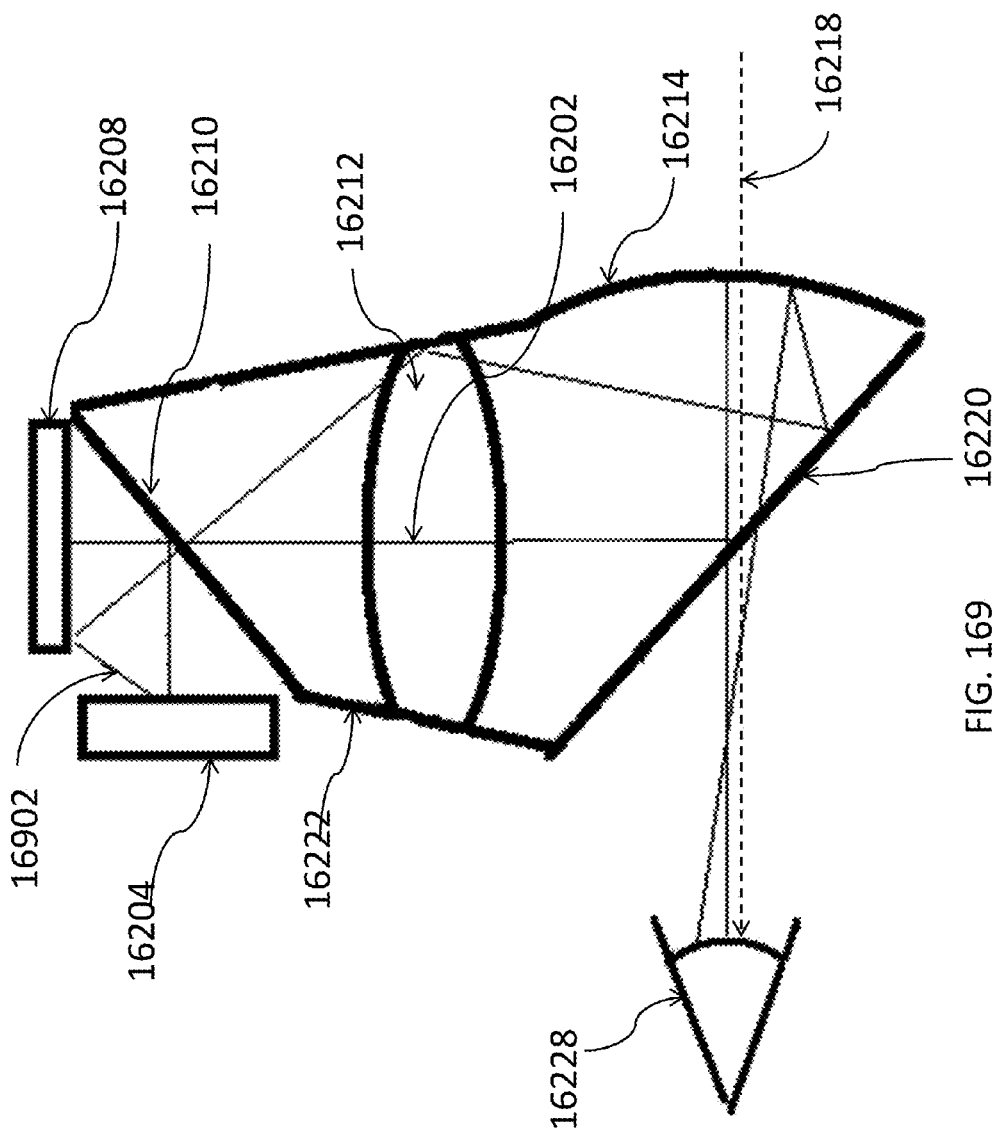

FIG. 169 depicts stray light reflecting off of any reflective surface in the housing or the edge of the lens.

Figure 170:
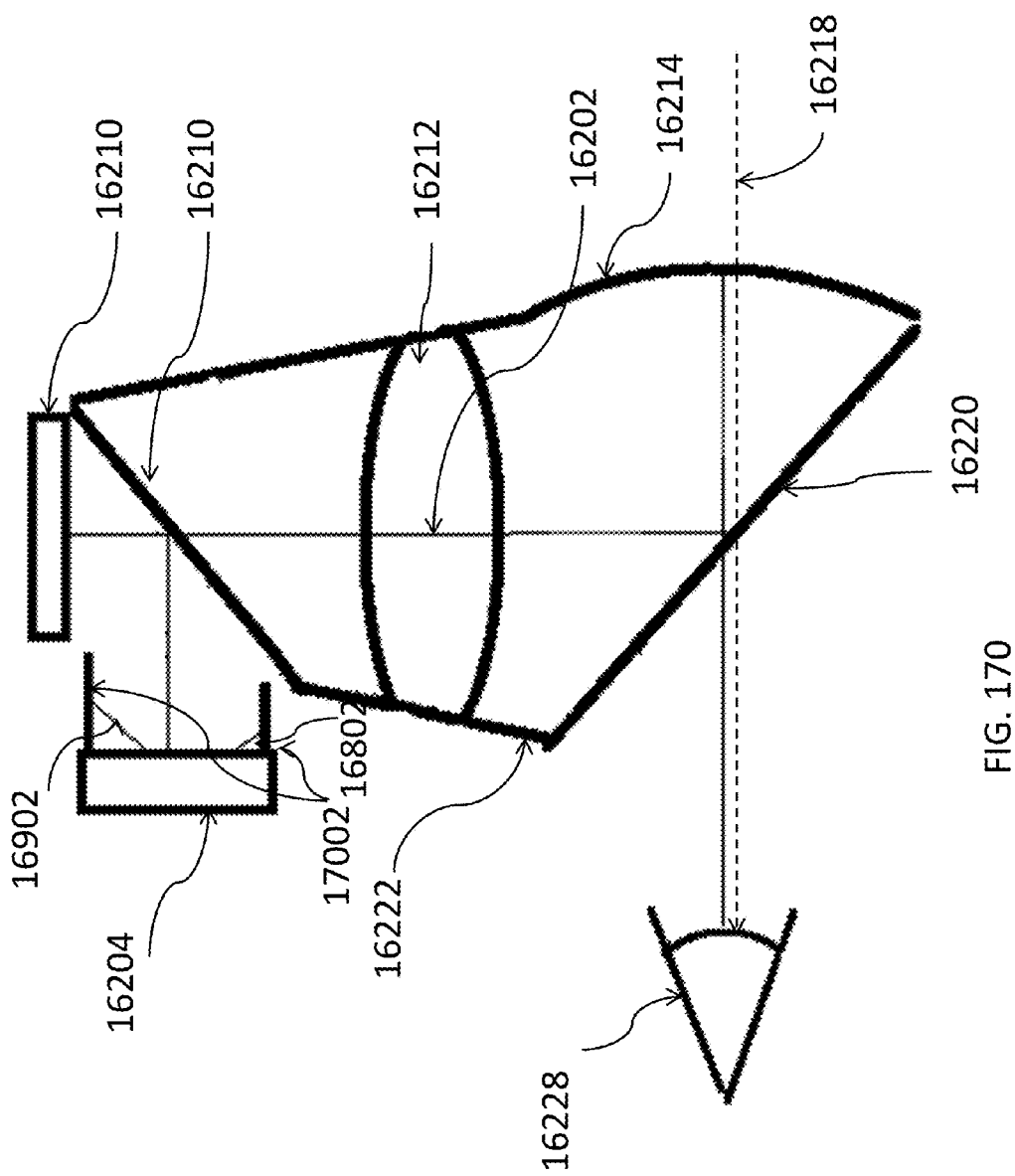

FIG. 170 shows an illustration of a yet further embodiment of the disclosure in which a baffle is provided adjacent to the light source.

Figure 171:
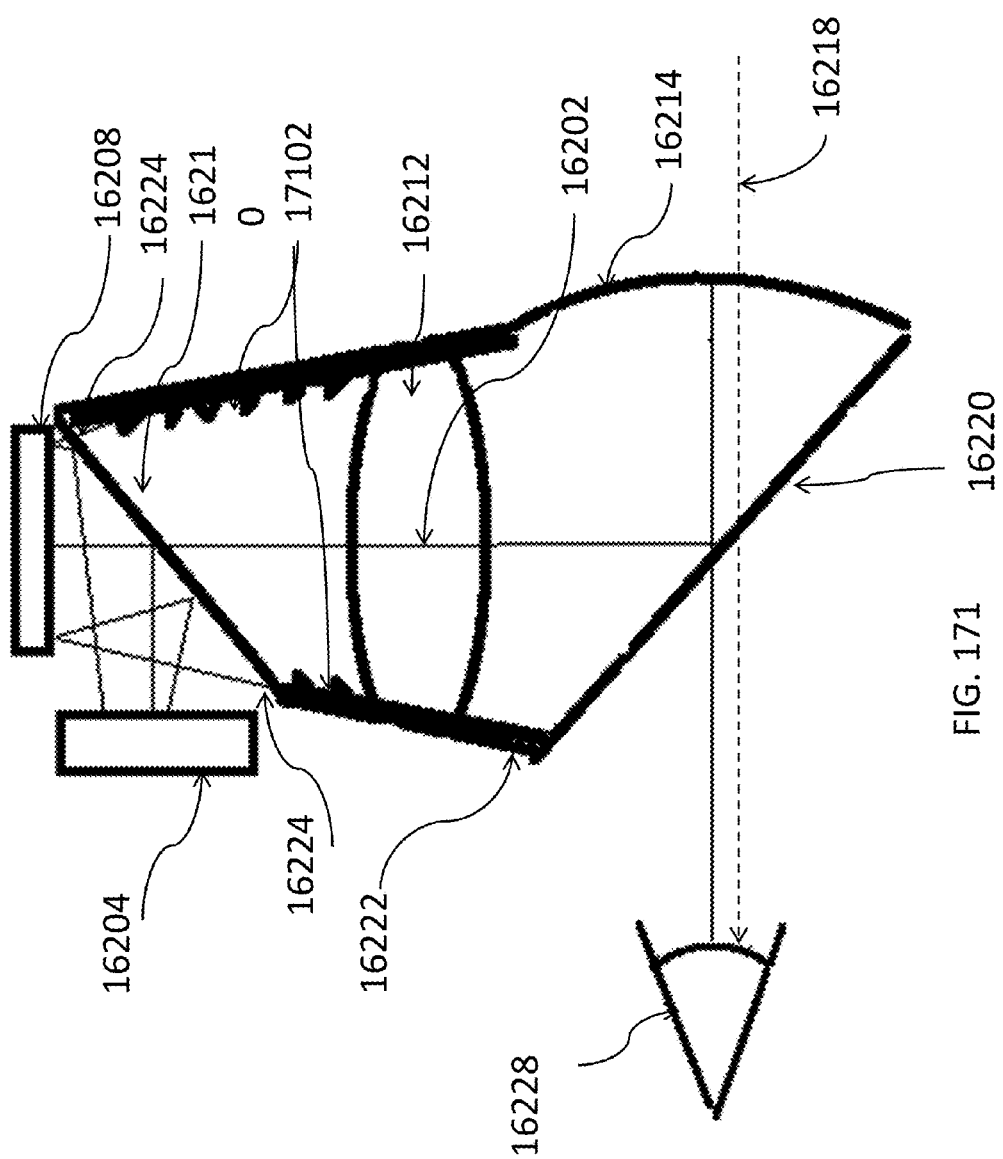

FIG. 171 depicts an absorbing coating with ridges can be used wherein a series of small ridges or steps act as a series of baffles to block or clip edge rays over the entire sidewall area of the housing.

Figure 172:
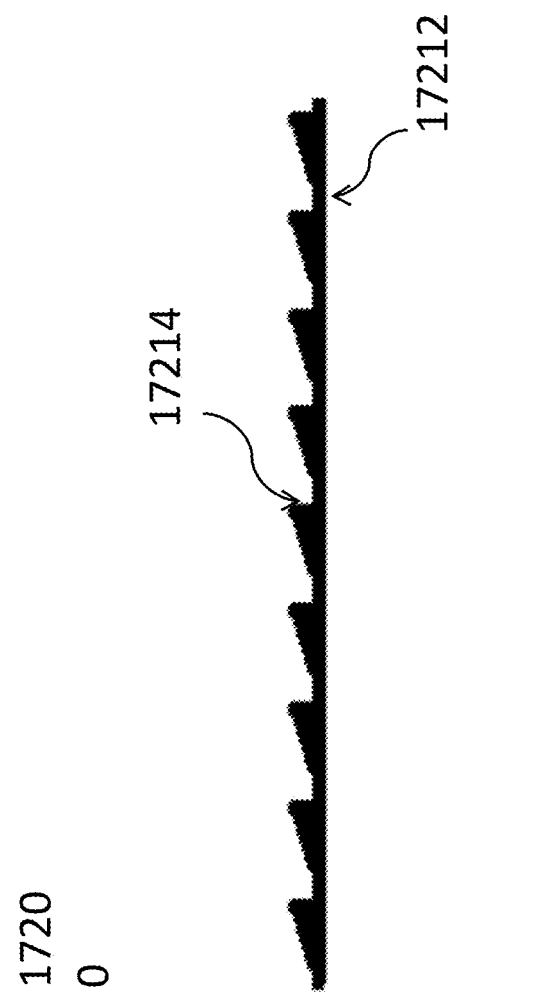

FIG. 172 shows a further embodiment of a tape or sheet which includes a carrier sheet and ridges that can be used to block reflected light.

Figure 173:
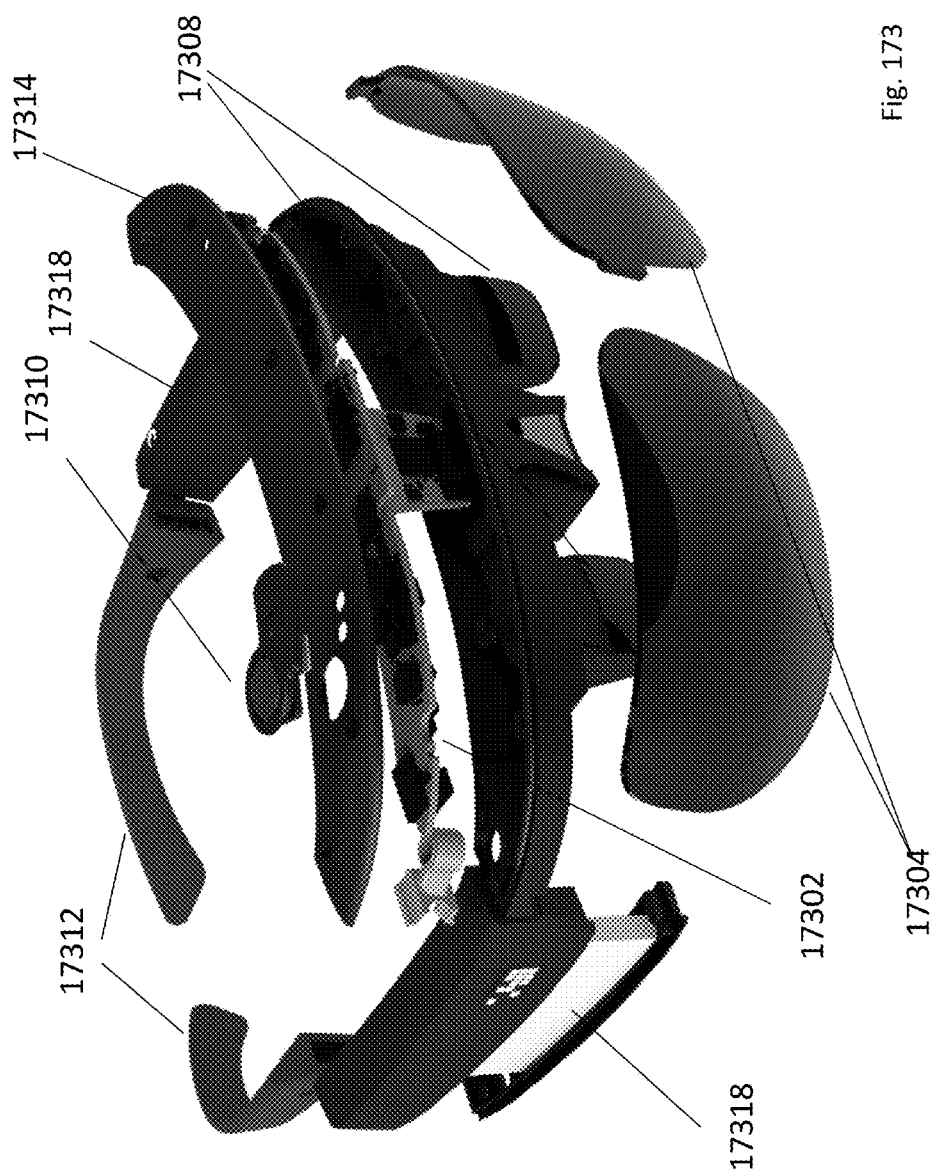

FIG. 173 depicts an exploded view of an embodiment of the glasses.

Figure 174:
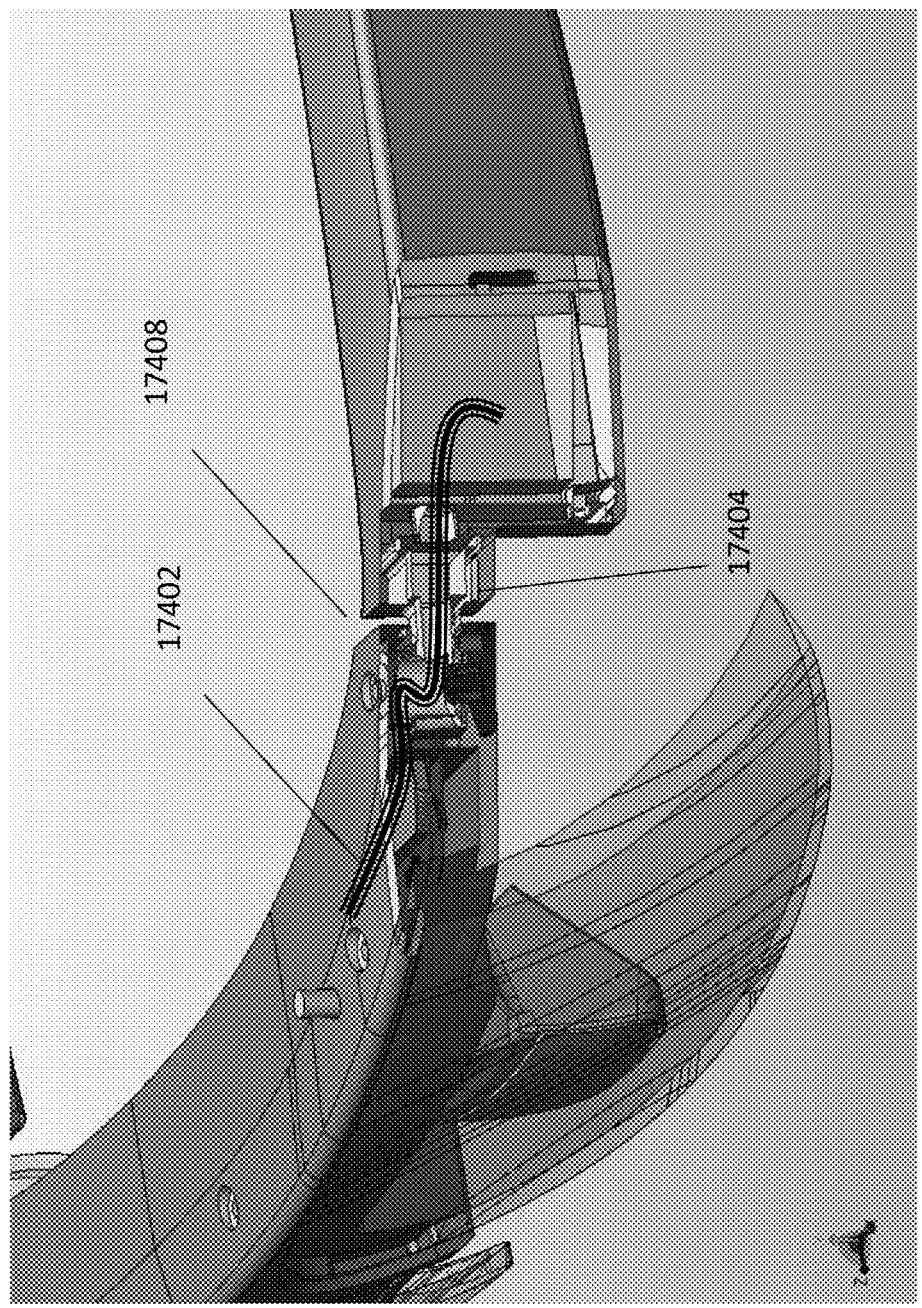

FIG. 174 depicts a wiring design and wire guide of the glasses.

Figure 175:
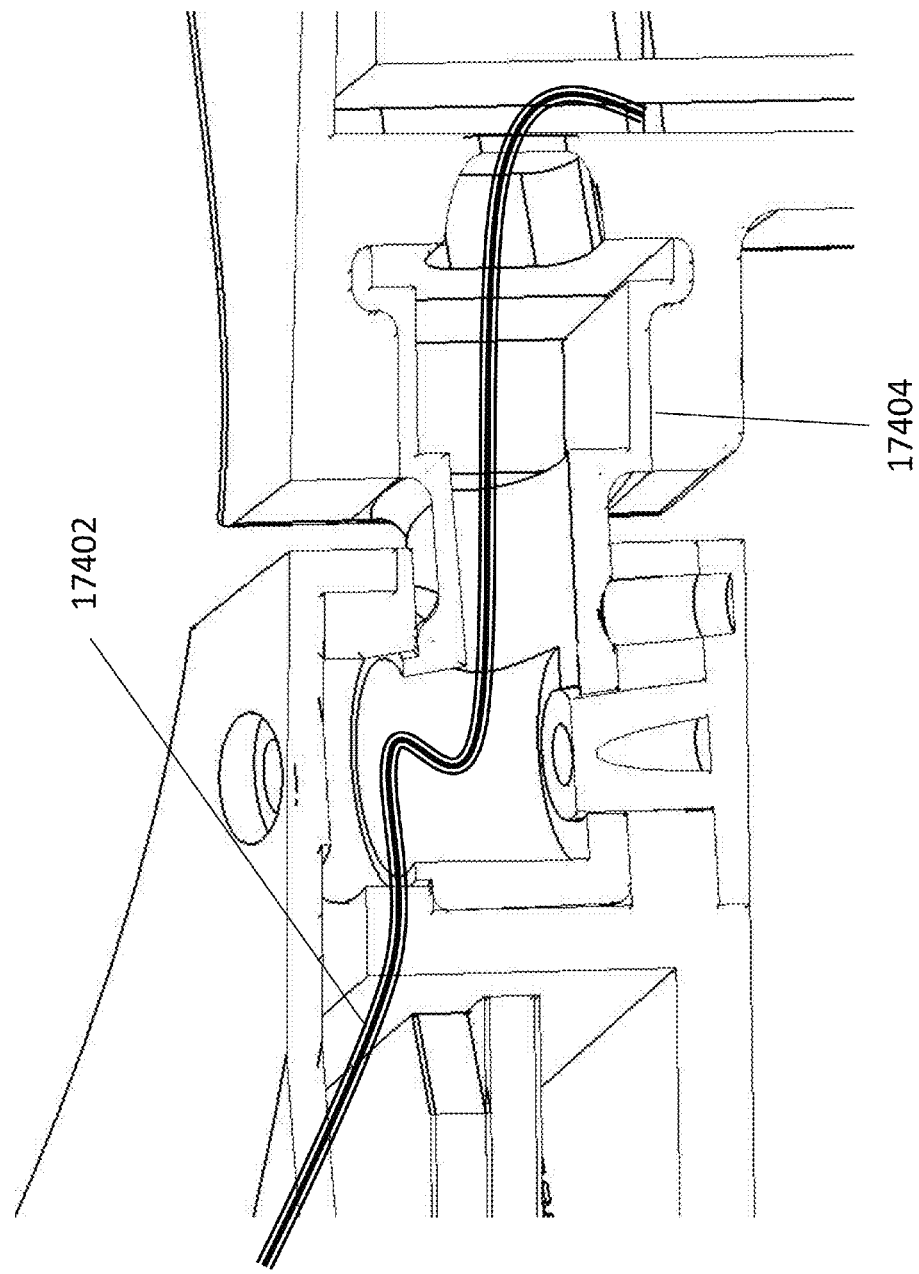

FIG. 175 depicts an enlarged version of the wiring design and wire guide of the glasses.

FIG. 176A shows a cutaway view of the wiring design and wire guide of the glasses.

FIG. 176B shows a cutaway view of the wiring design and wire guide of the glasses.

FIG. 176C shows an intact version of the wiring design and wire guide of the glasses.

Figure 177:
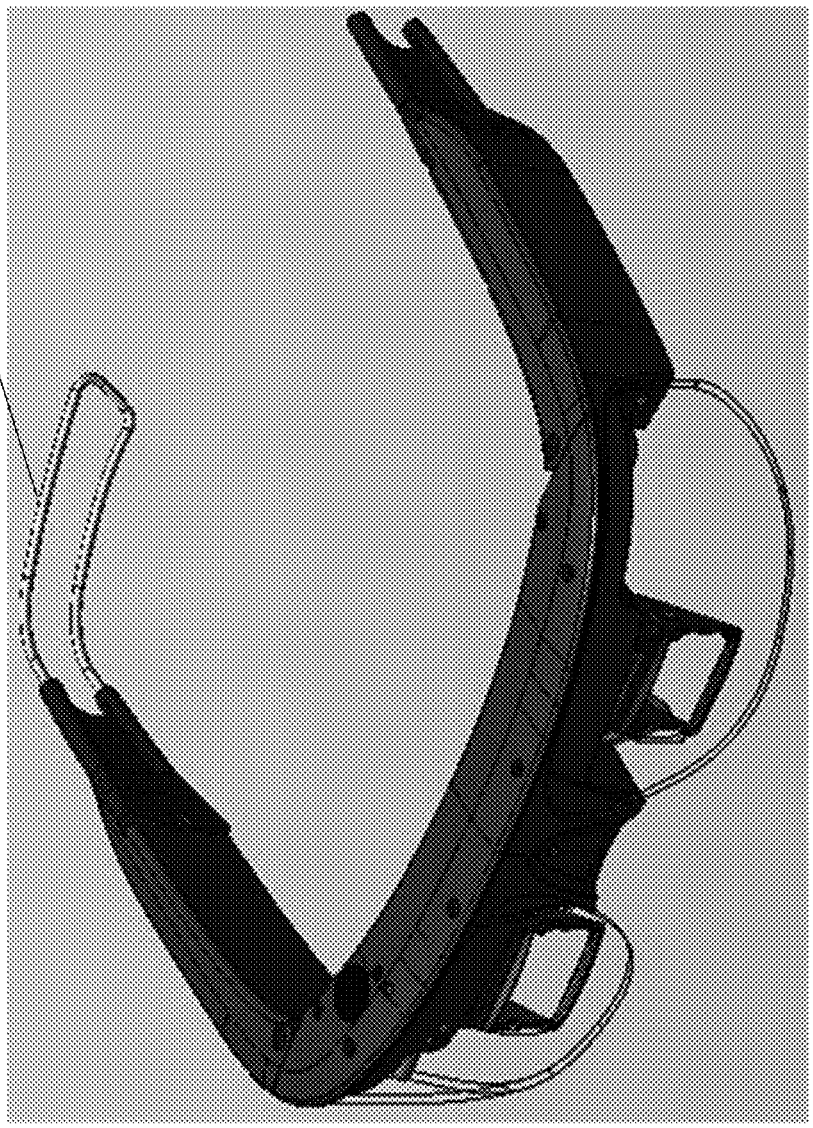

FIG. 177 depicts a U-shaped accessory for securing the glasses.

FIG. 178 depicts an embodiment of a cable-tensioned system for securing the glasses to a user's head.

FIG. 179A and FIG. 179B depicts an embodiment of a cable-tensioned system for securing the glasses to a user's head in a bent configuration.

Figure 180:
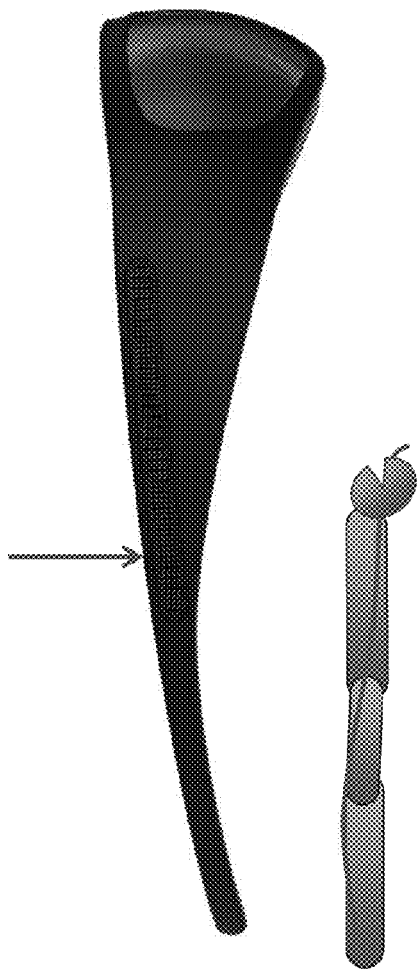

FIG. 180 depicts an embodiment of a cable-tensioned system for securing the glasses to a user's head.

FIG. 181 depicts an embodiment of a system for securing the glasses to a user's head.

FIG. 182 depicts an embodiment of a system for securing the glasses to a user's head.

Figure 183:
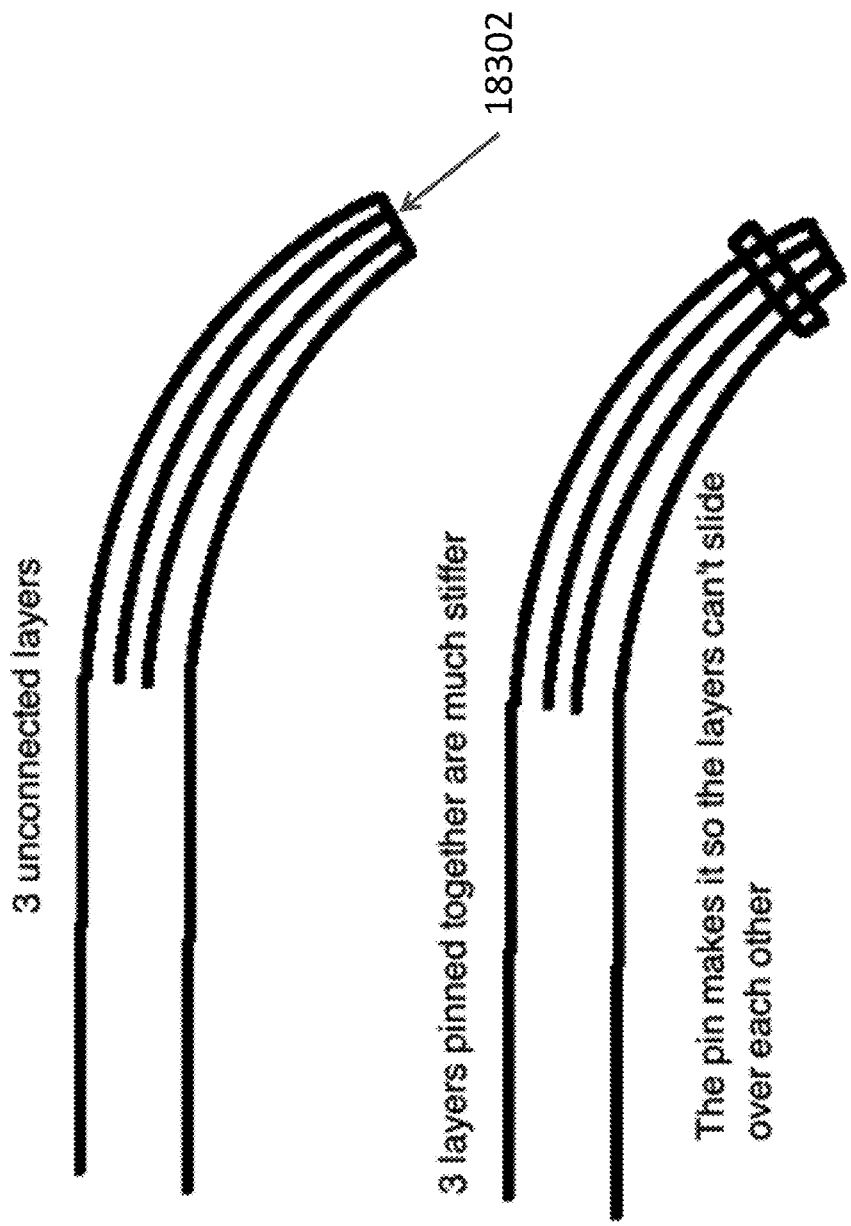

FIG. 183 depicts an embodiment of a system for securing the glasses to a user's head.

Figure 184:
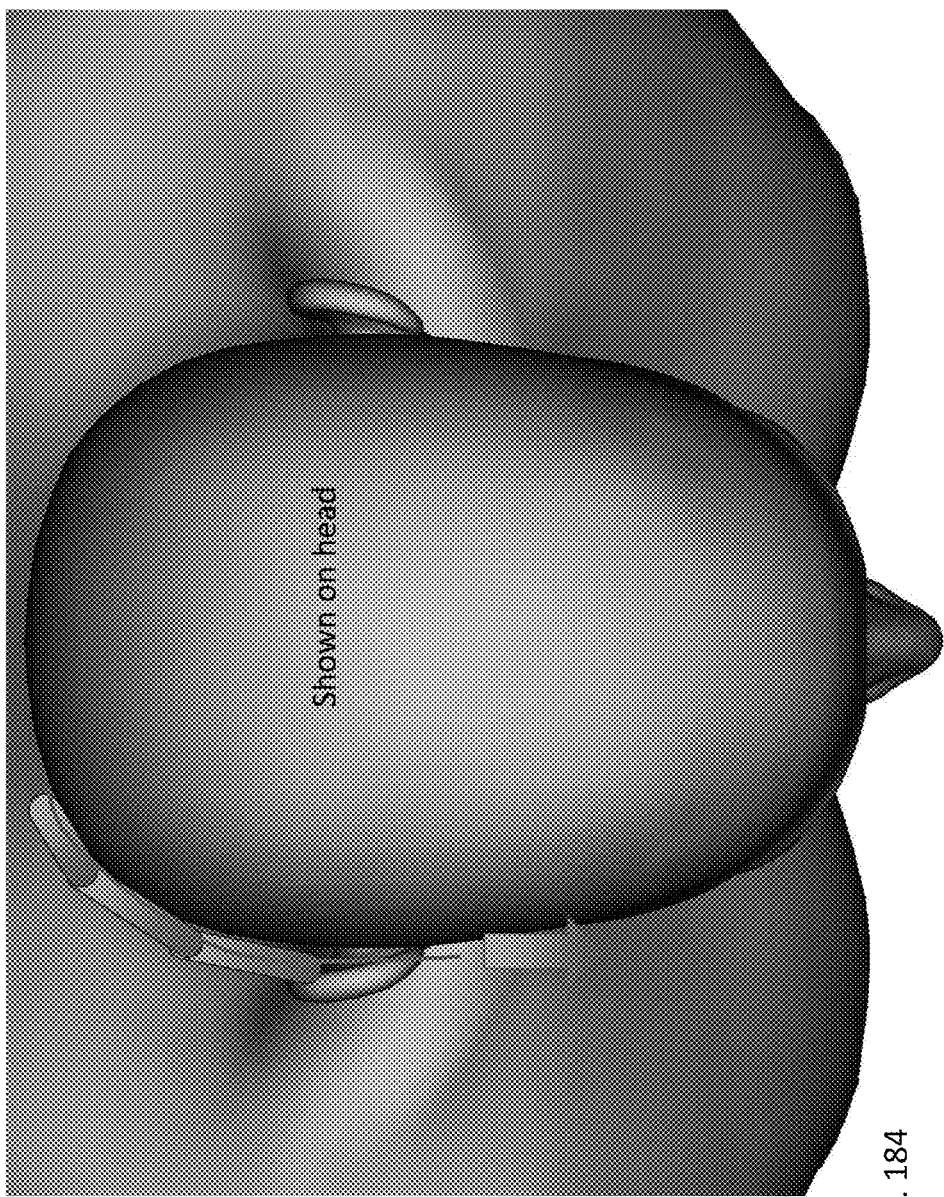

FIG. 184 depicts an embodiment of a system for securing the glasses to a user's head.

Figure 185B:
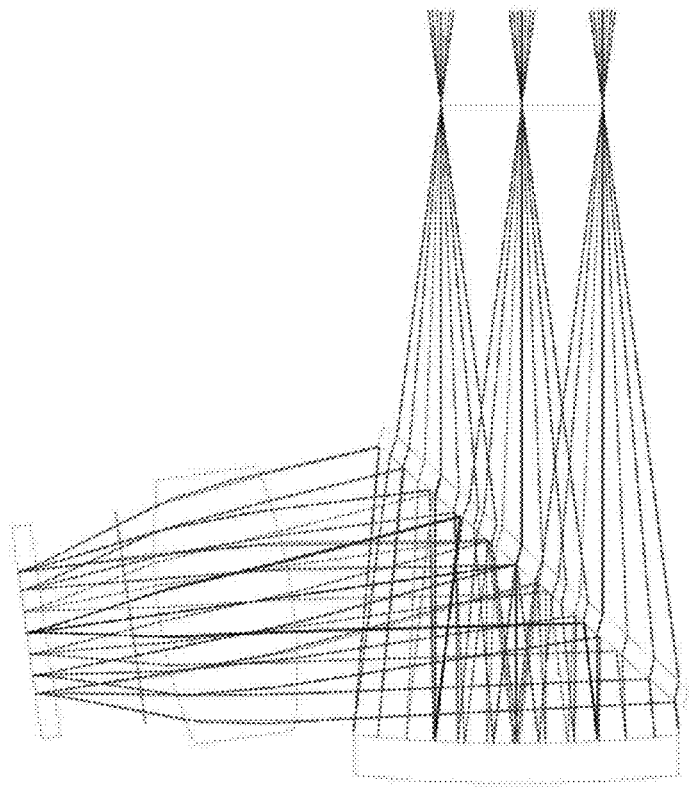
Figure 185A:
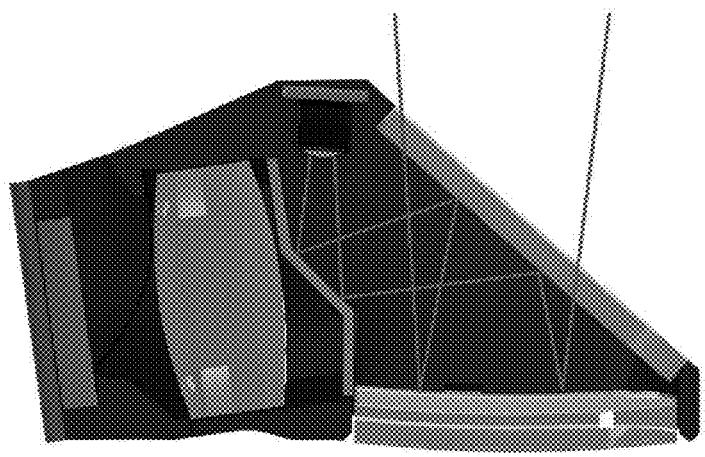

FIG. 185A depicts an embodiment of the optical train.

FIG. 185B depicts sample ray traces for light in an embodiment of the optical train.

Figure 186:
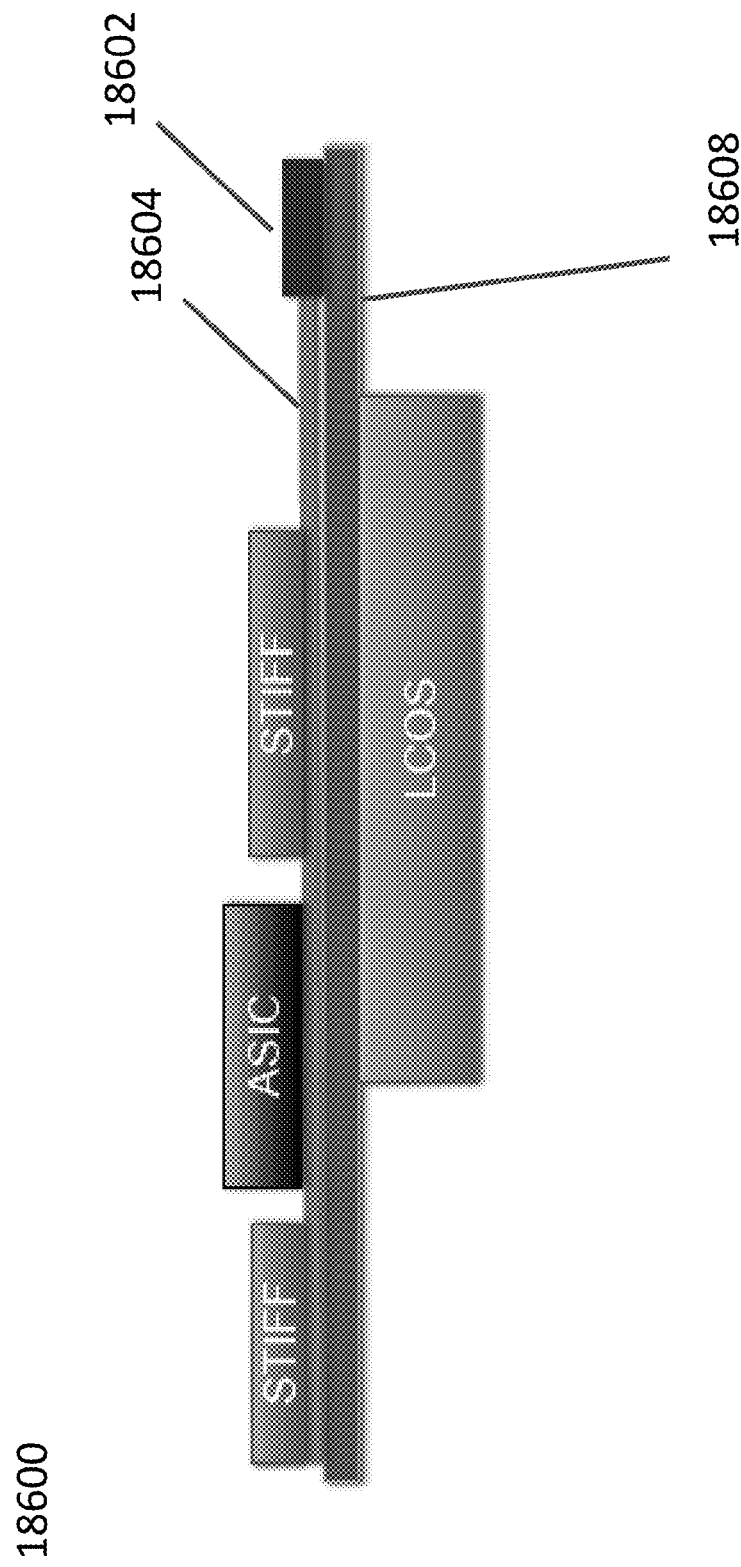

FIG. 186 depicts an embodiment of an LCoS plus ASIC package.

Figure 187:
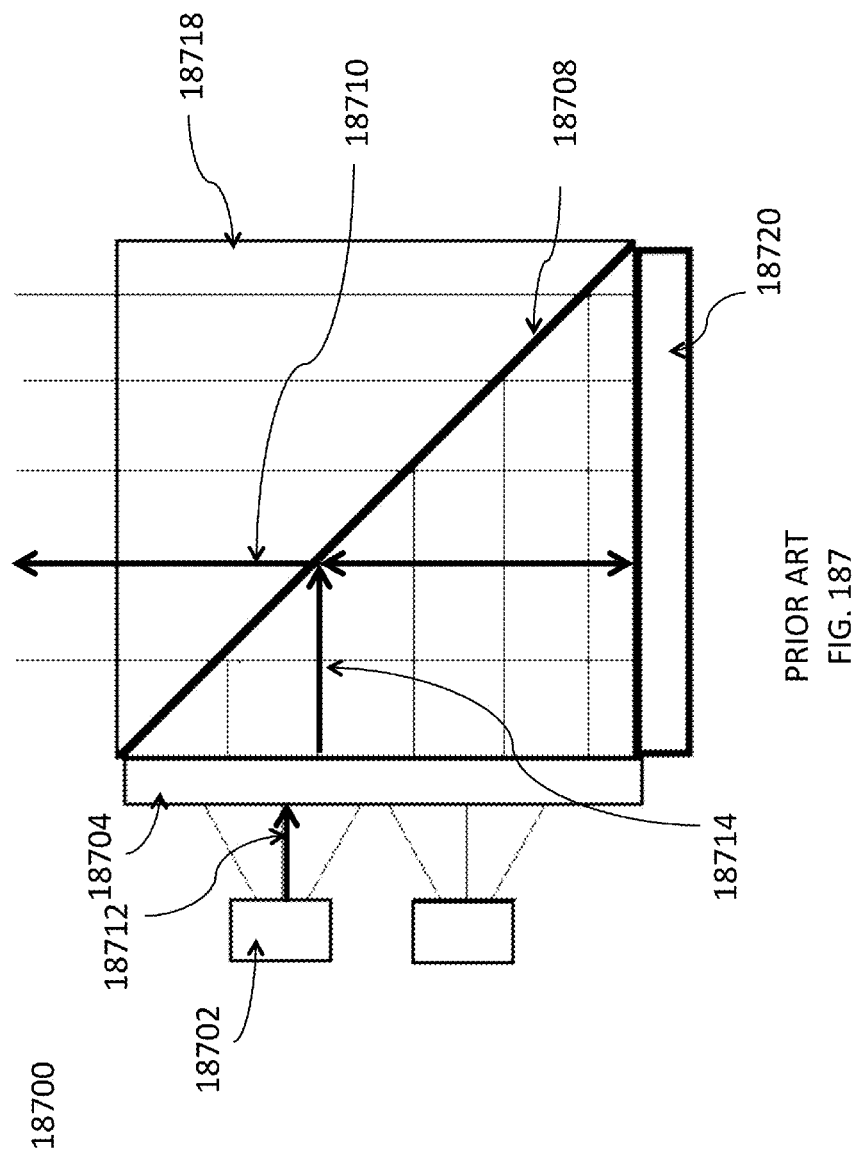
Figure 188:
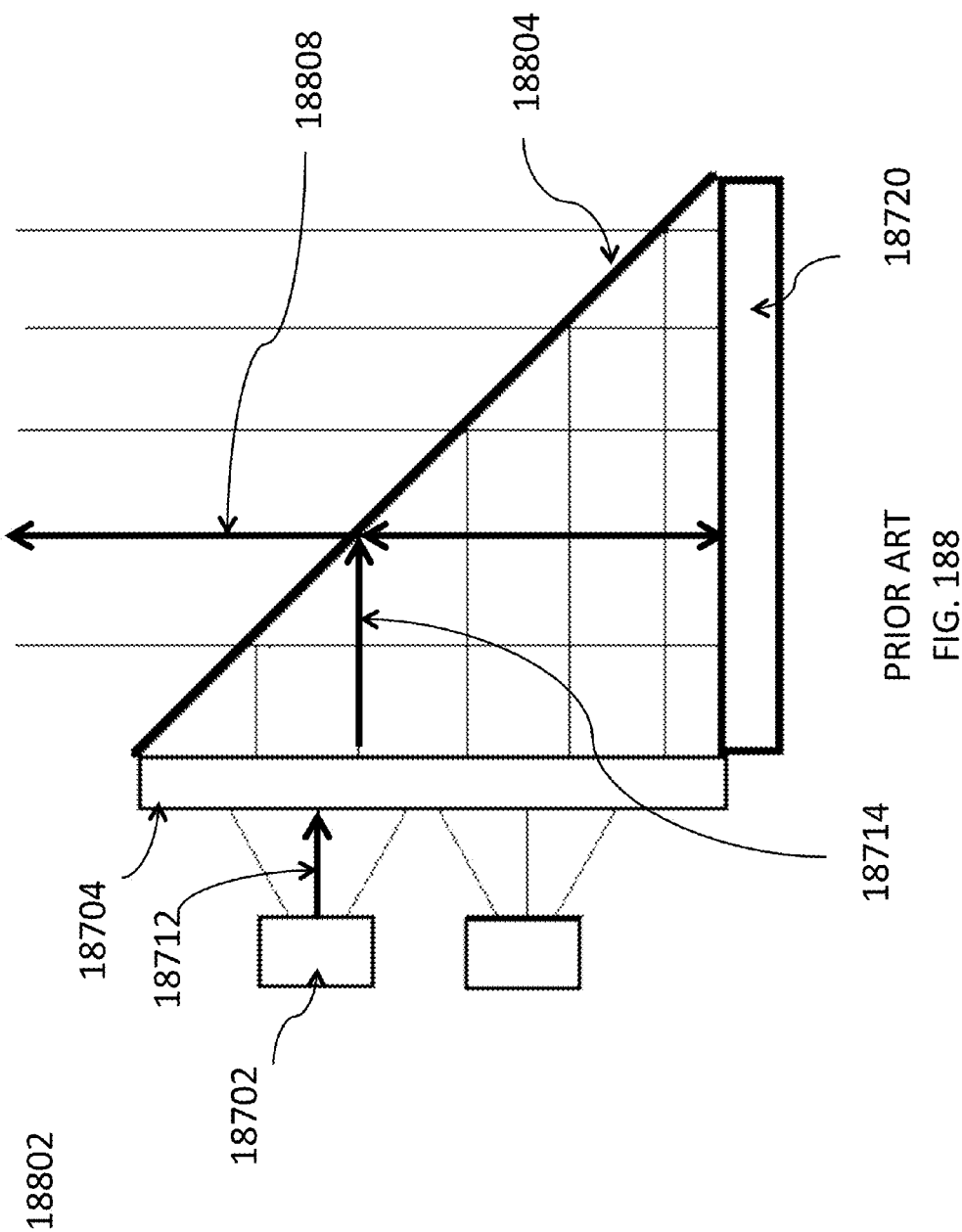
Figure 189:
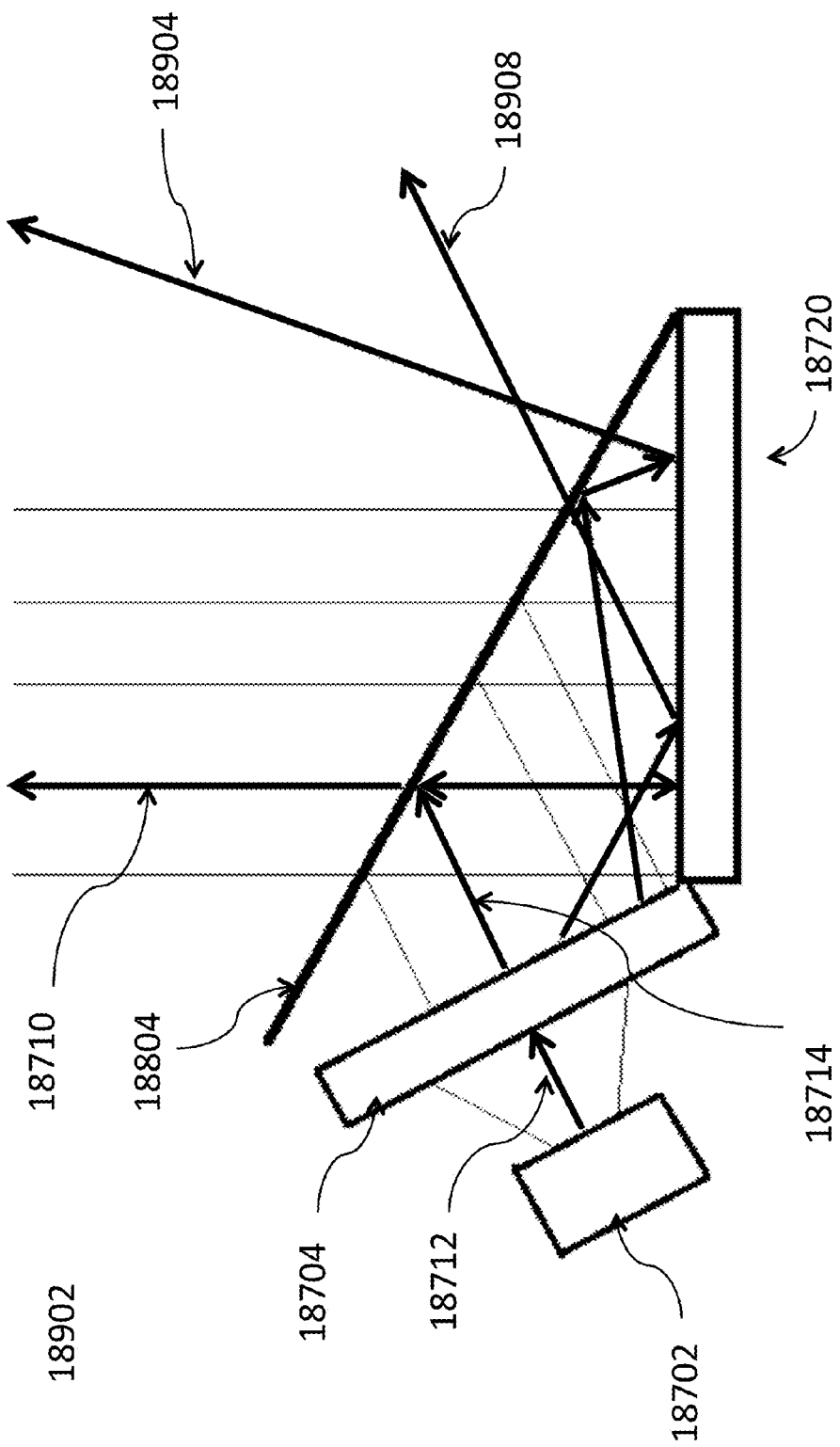
Figure 190:
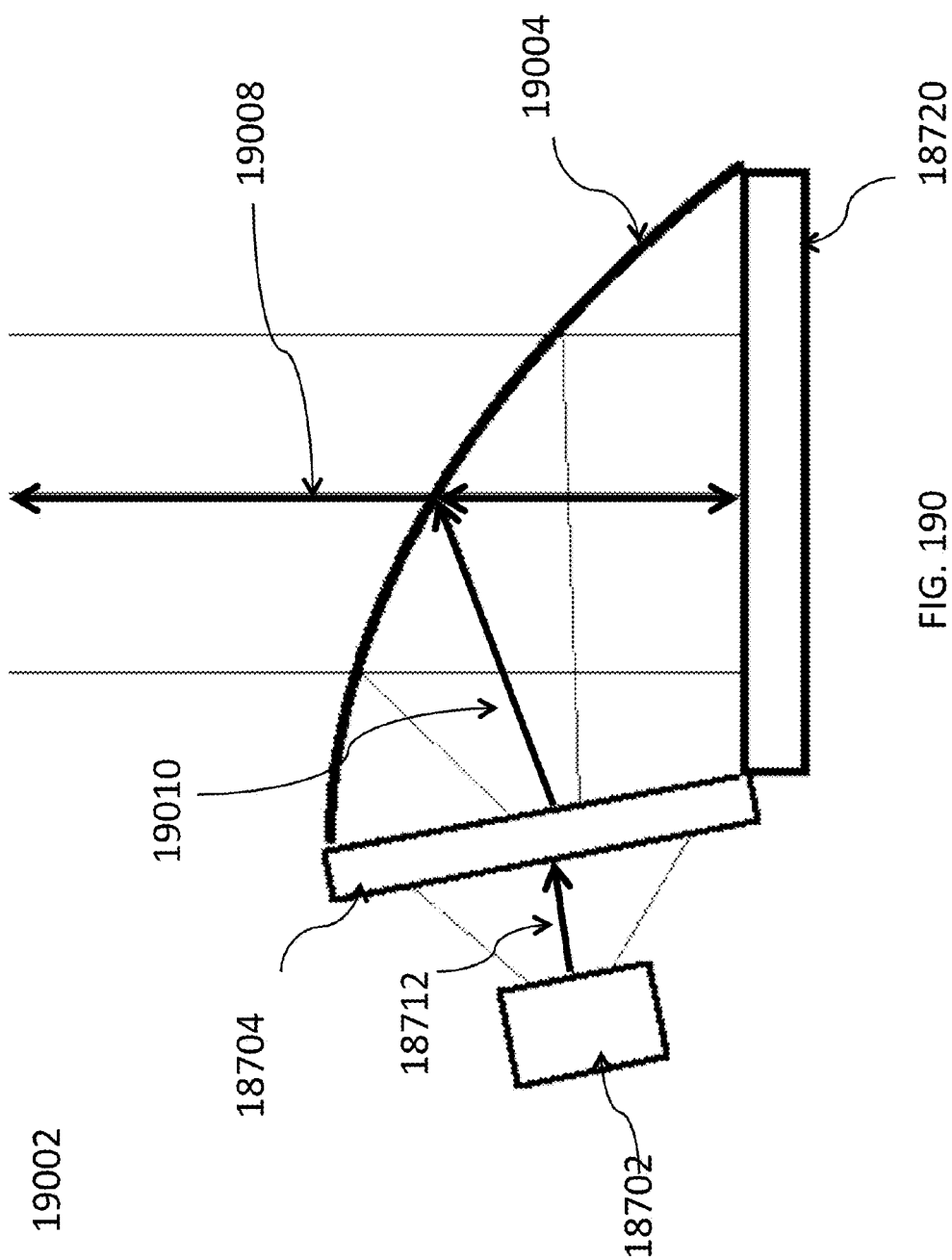
Figure 191:
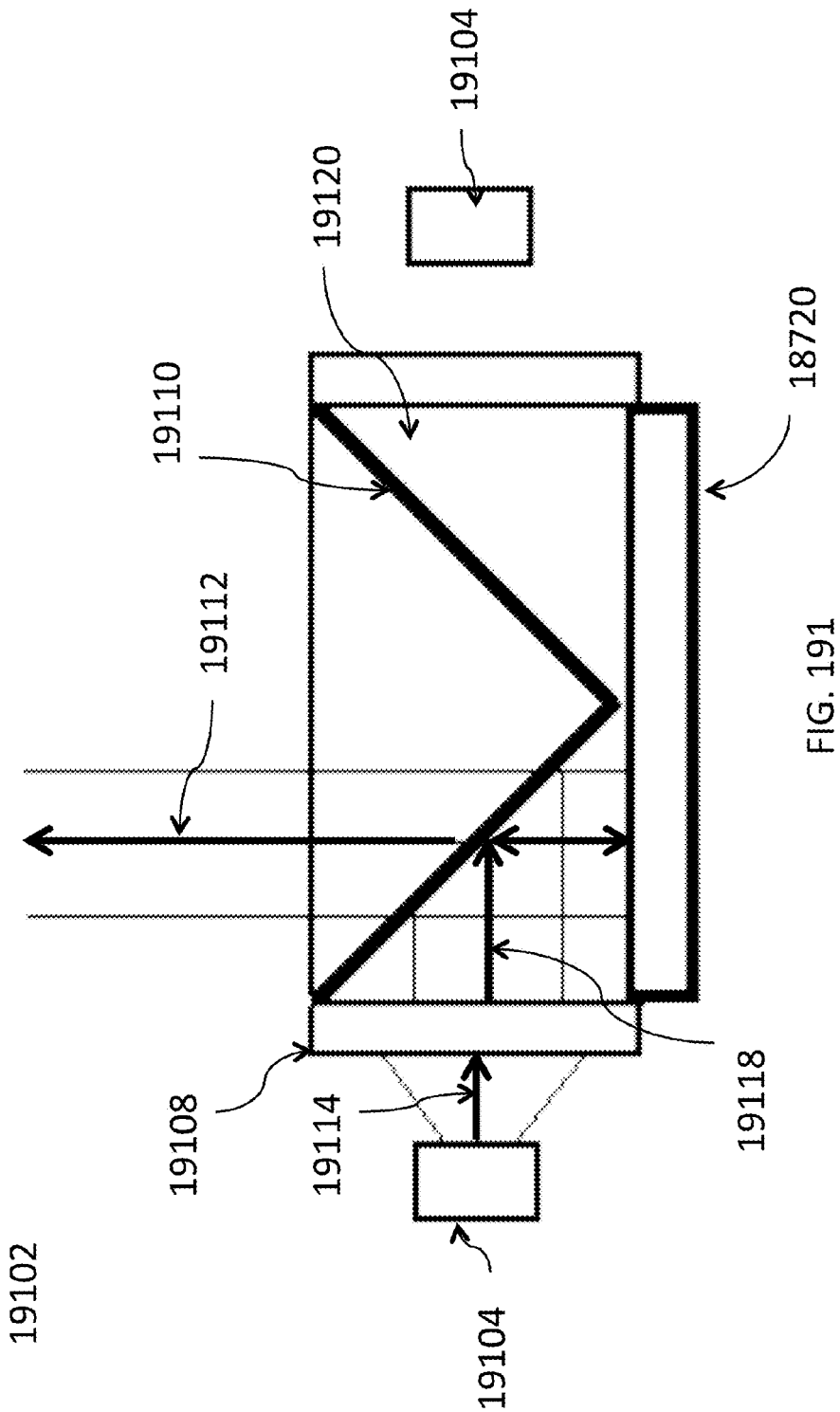
Figure 192:
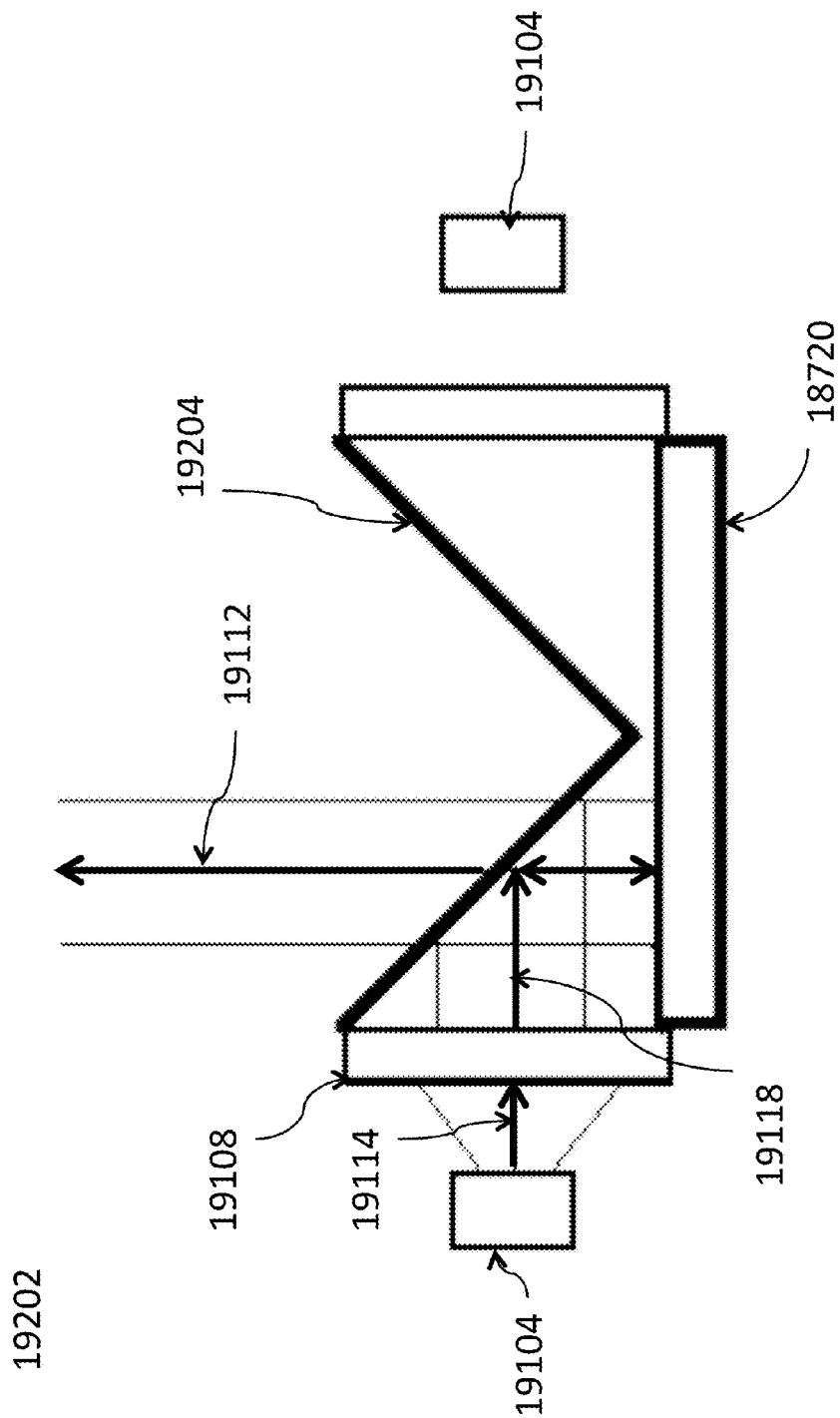
Figure 193:
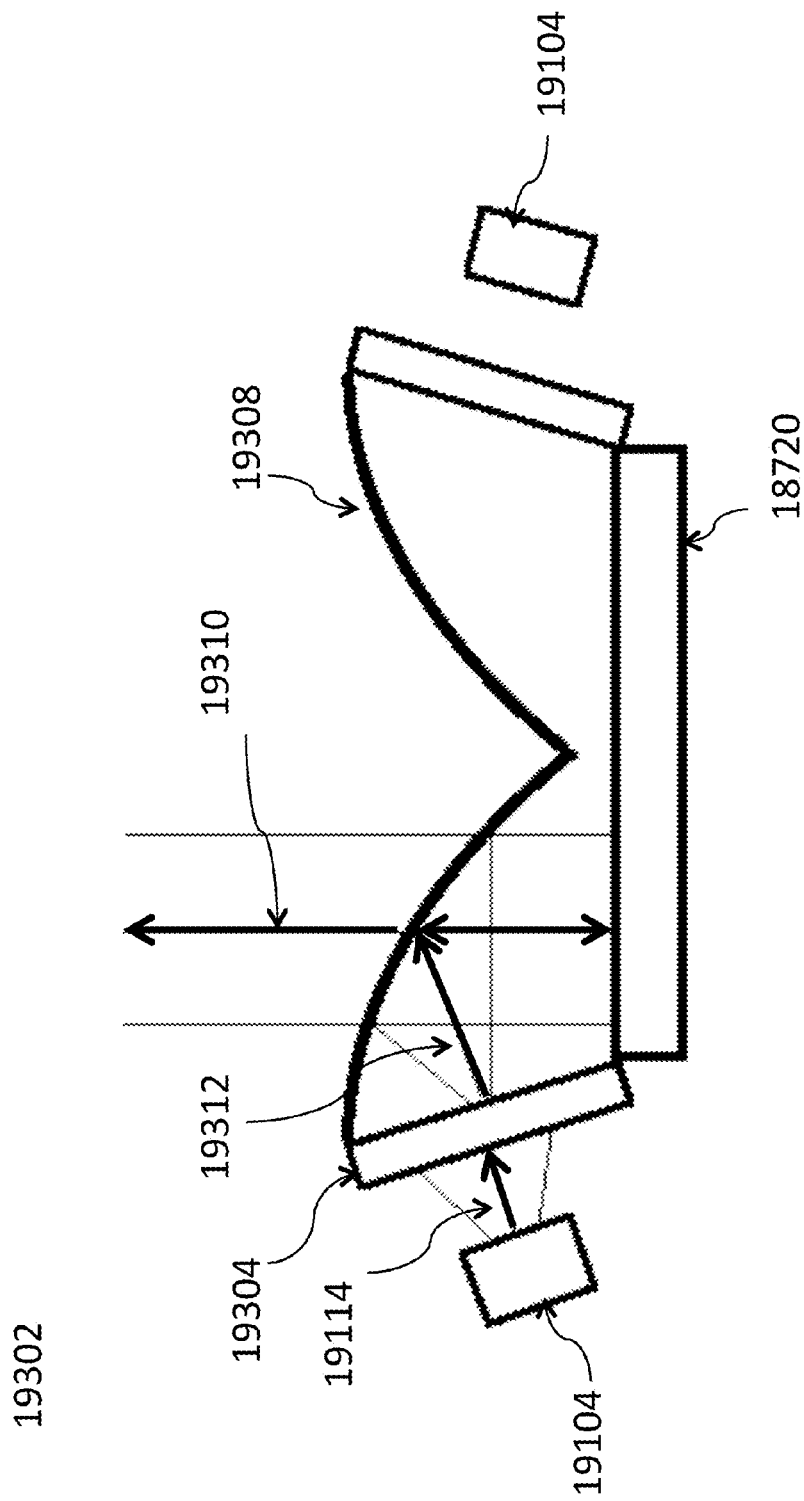
Figure 194:
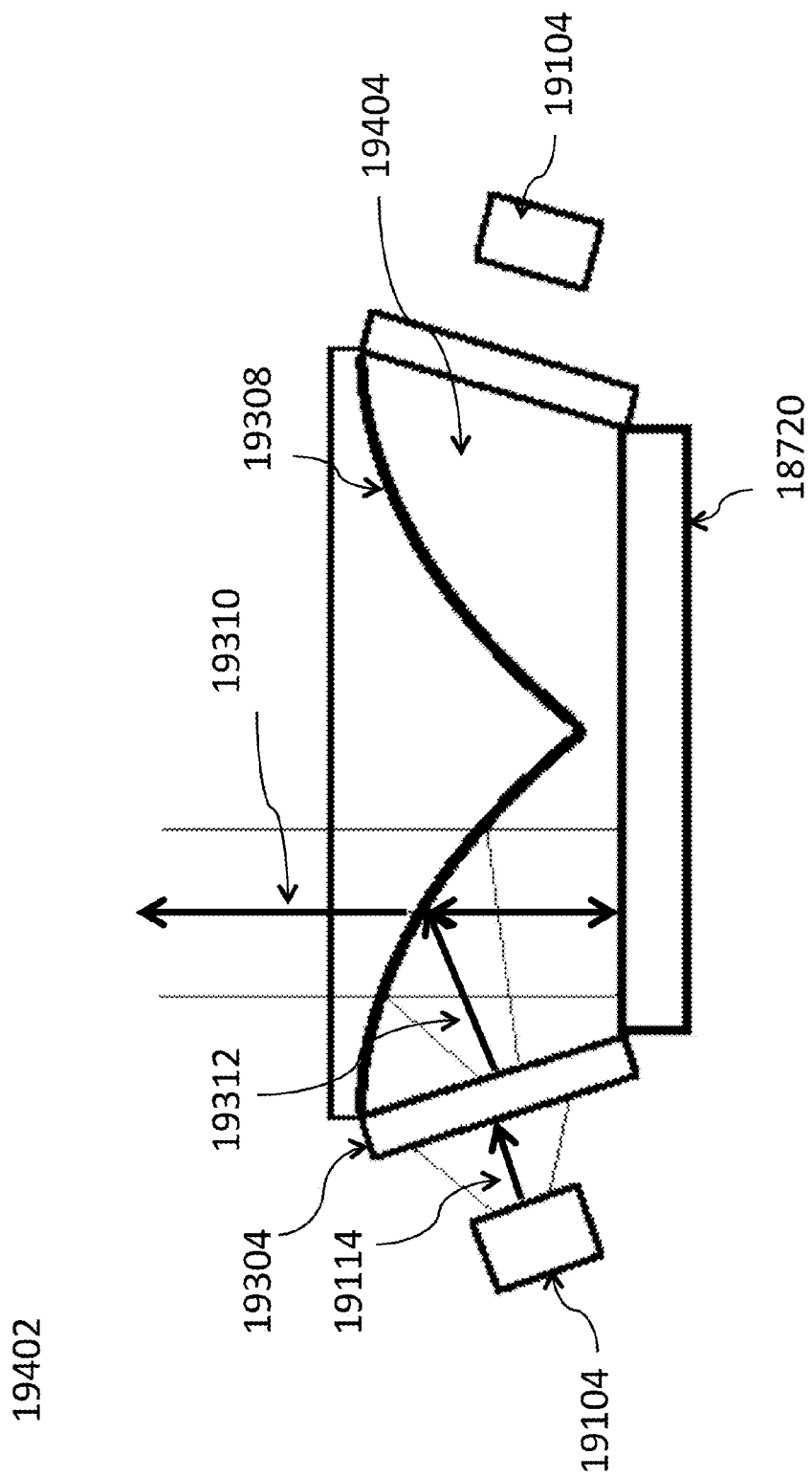
Figure 195:
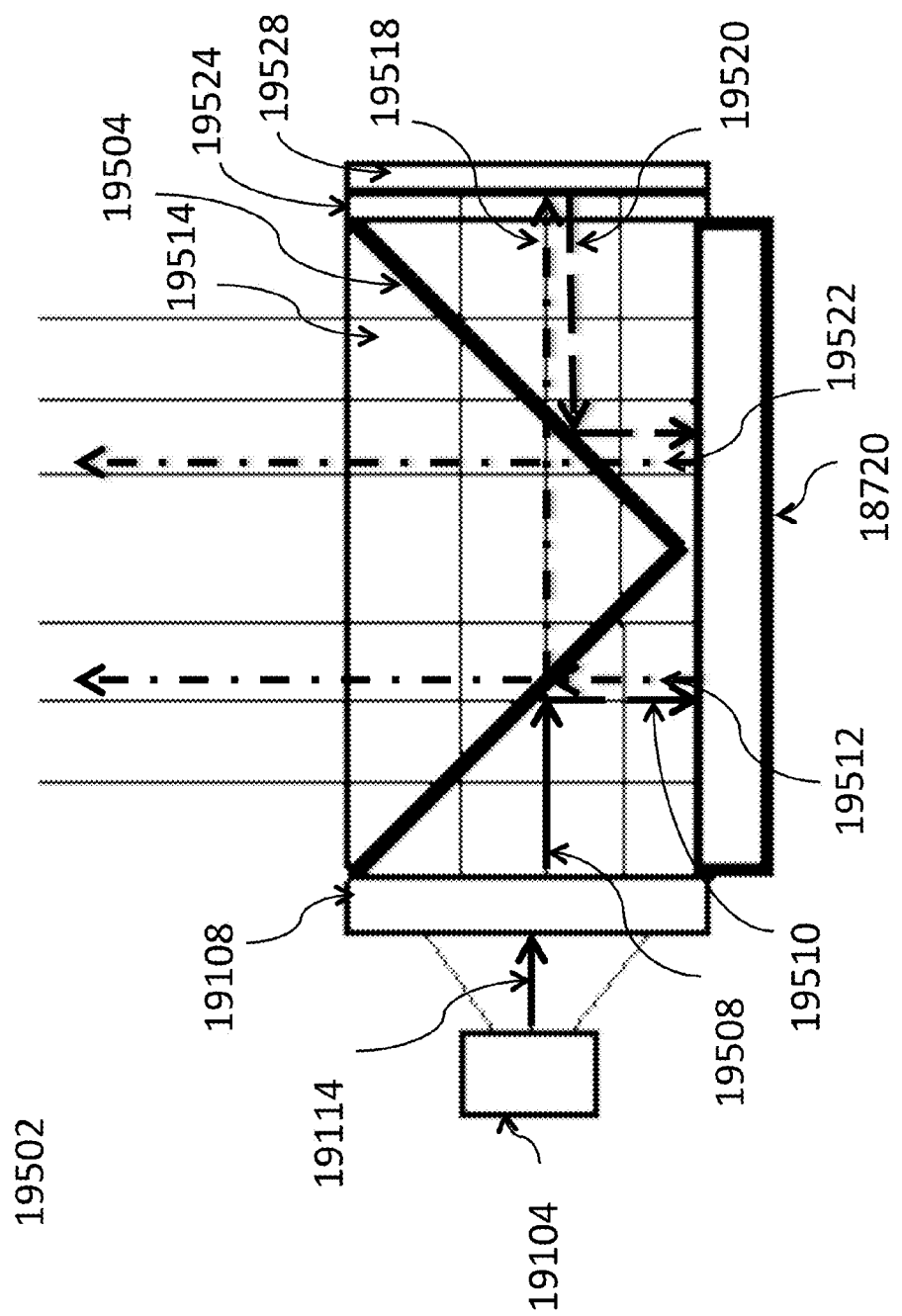
Figure 196:
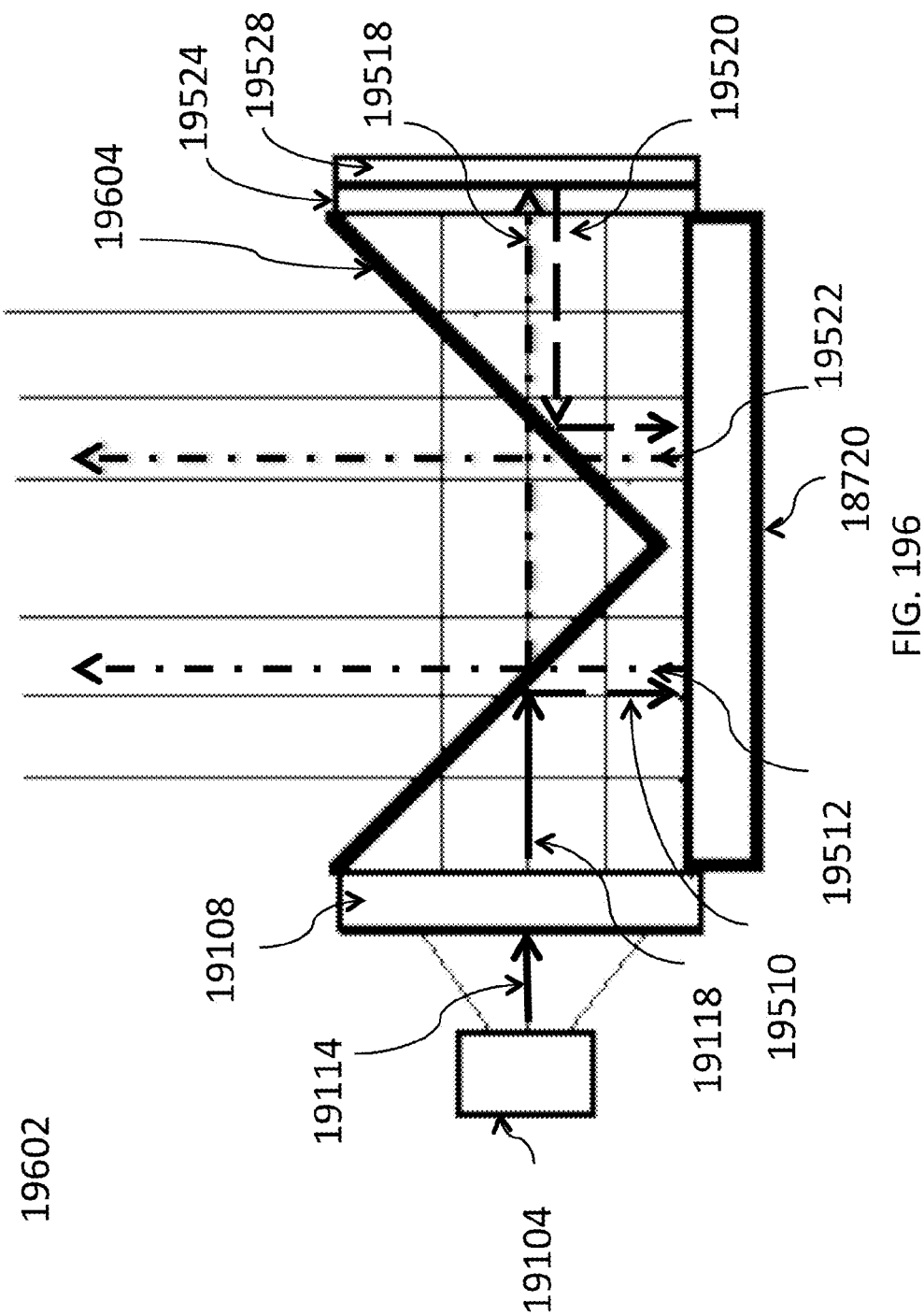
Figure 197:
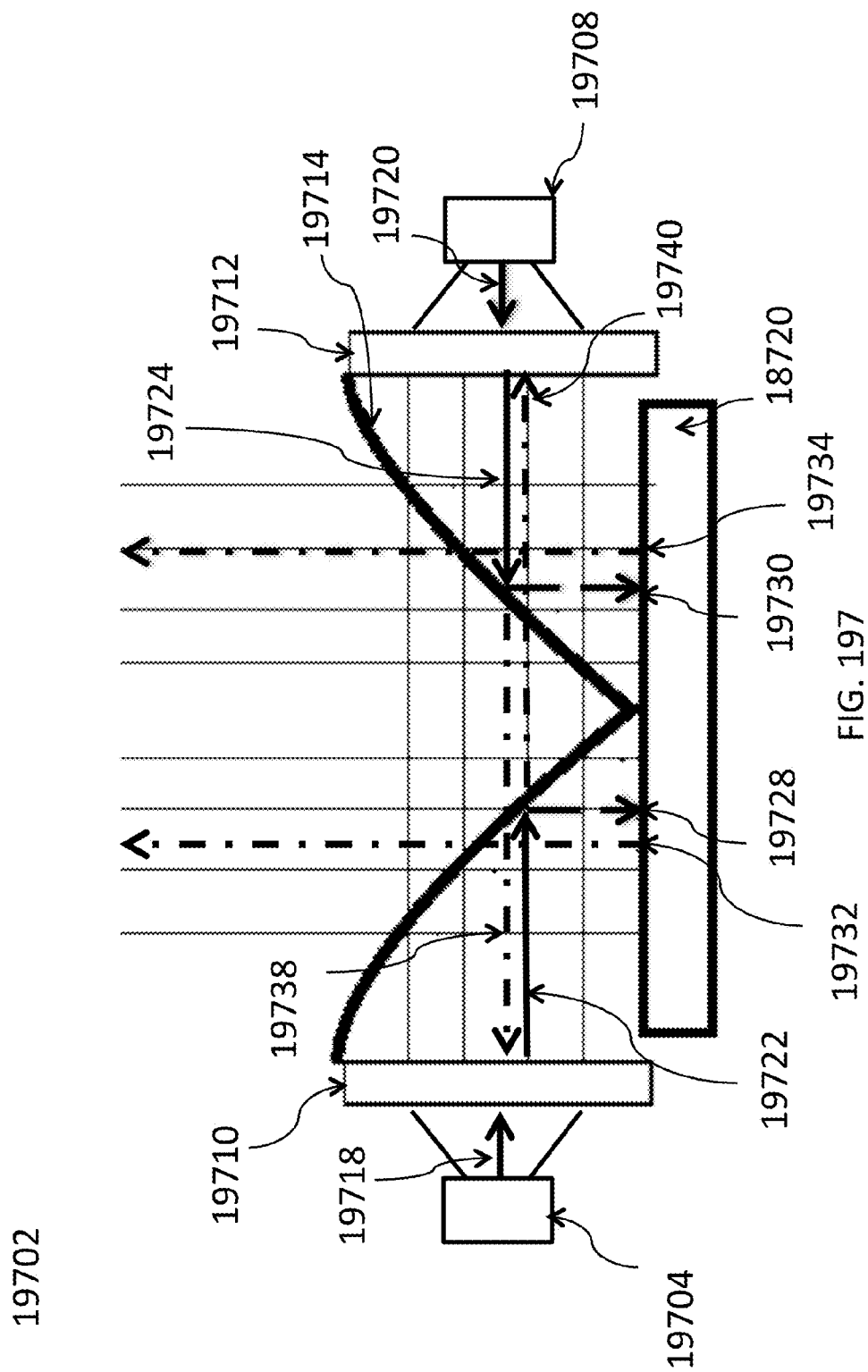
Figure 198:
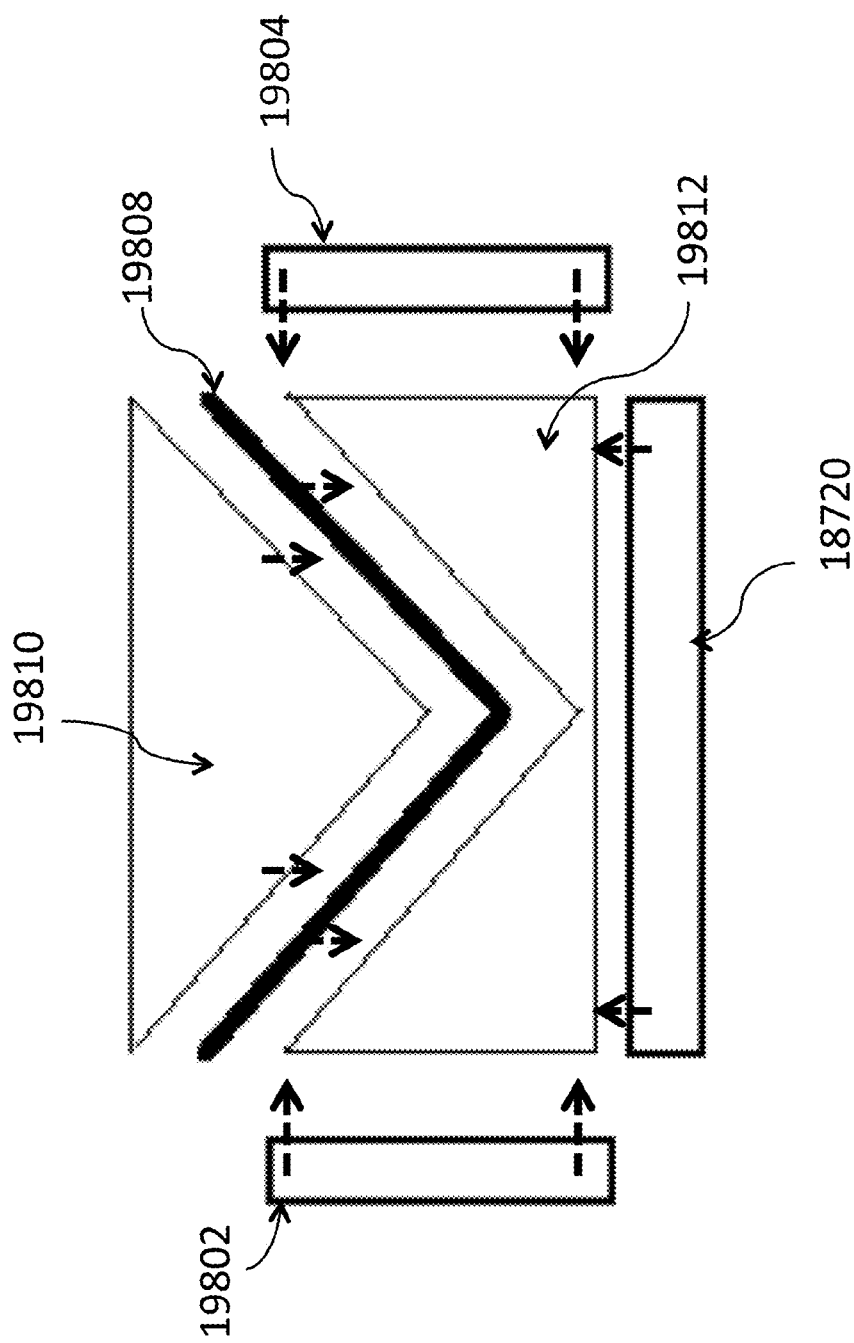
Figure 199:
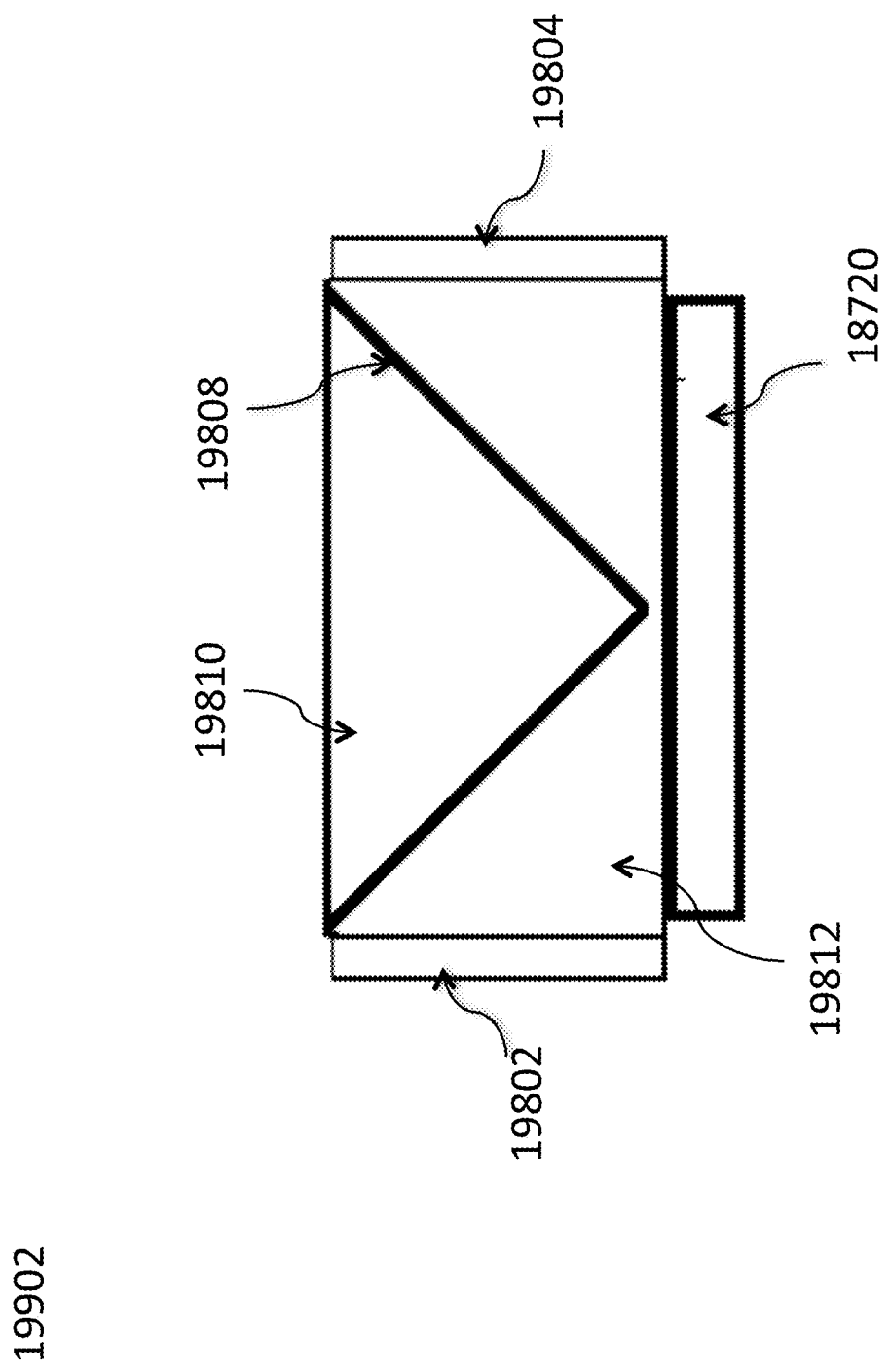
Figure 200:
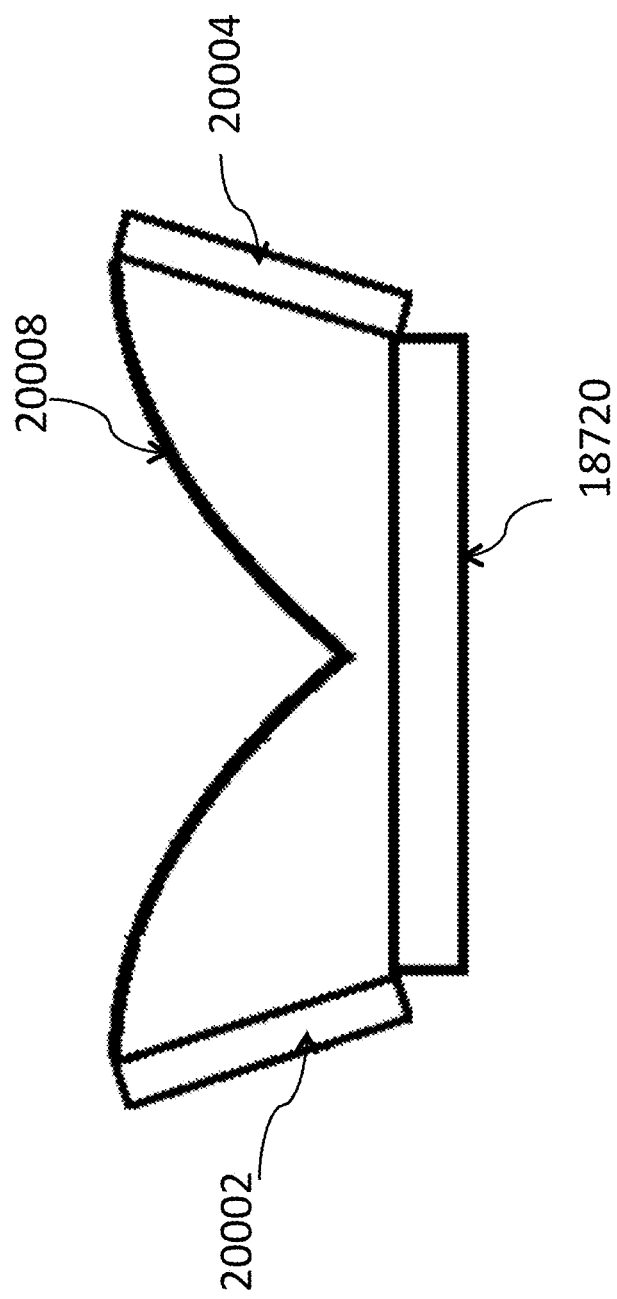
Figure 201:
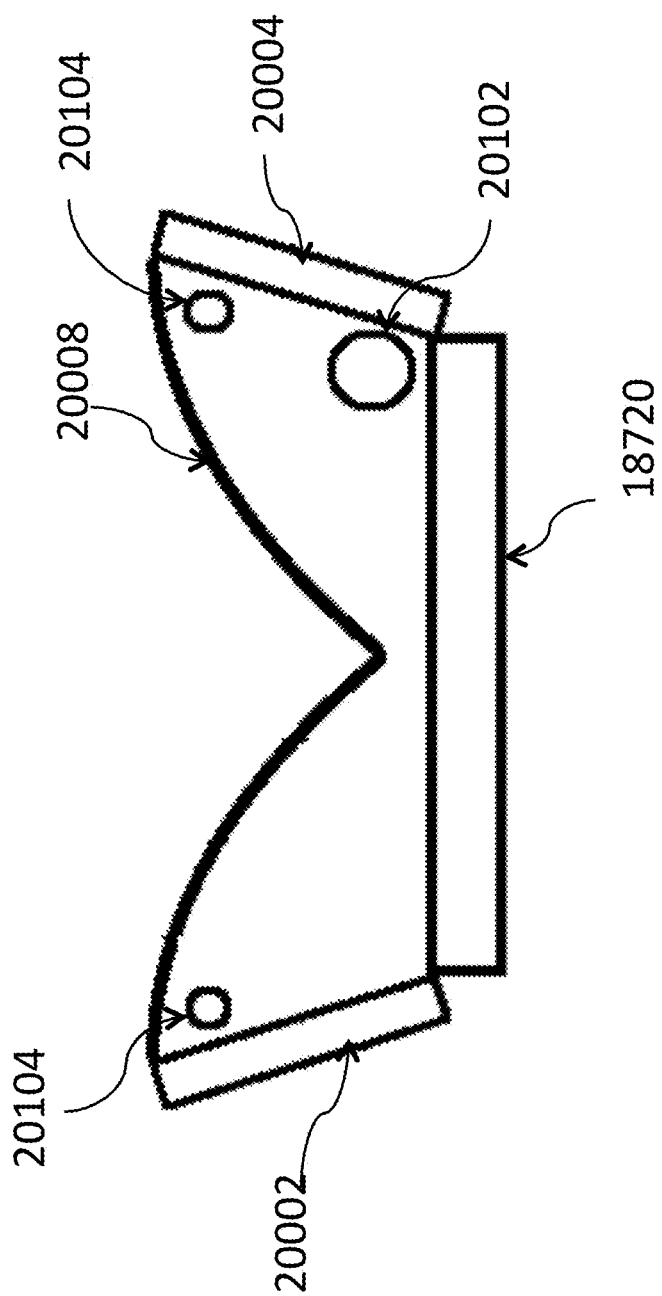
Figure 202:
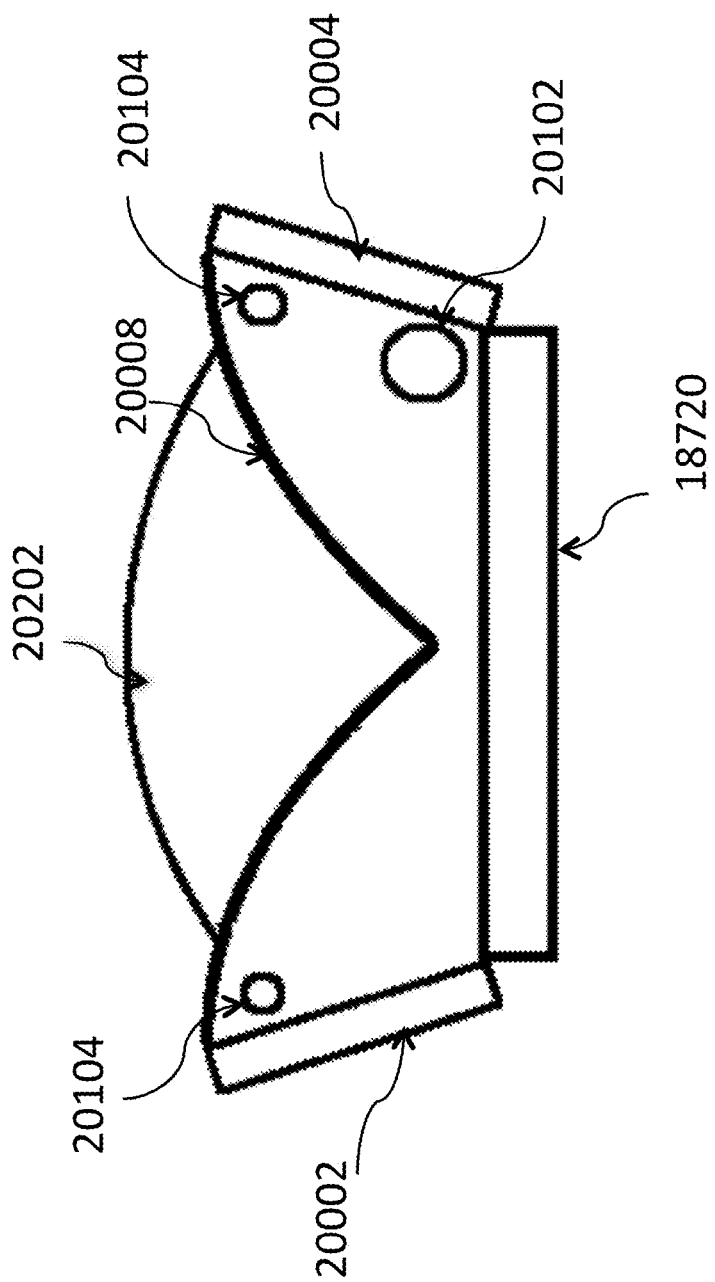
Figure 203:
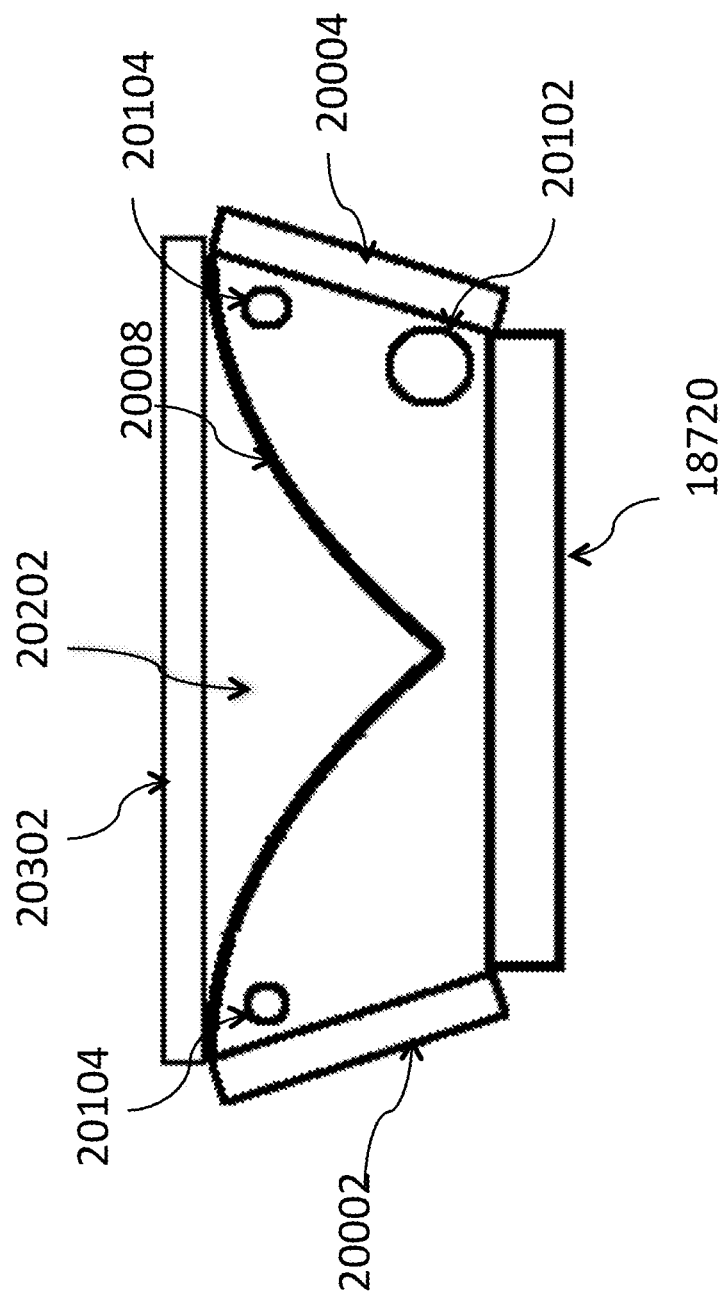
Figure 204:
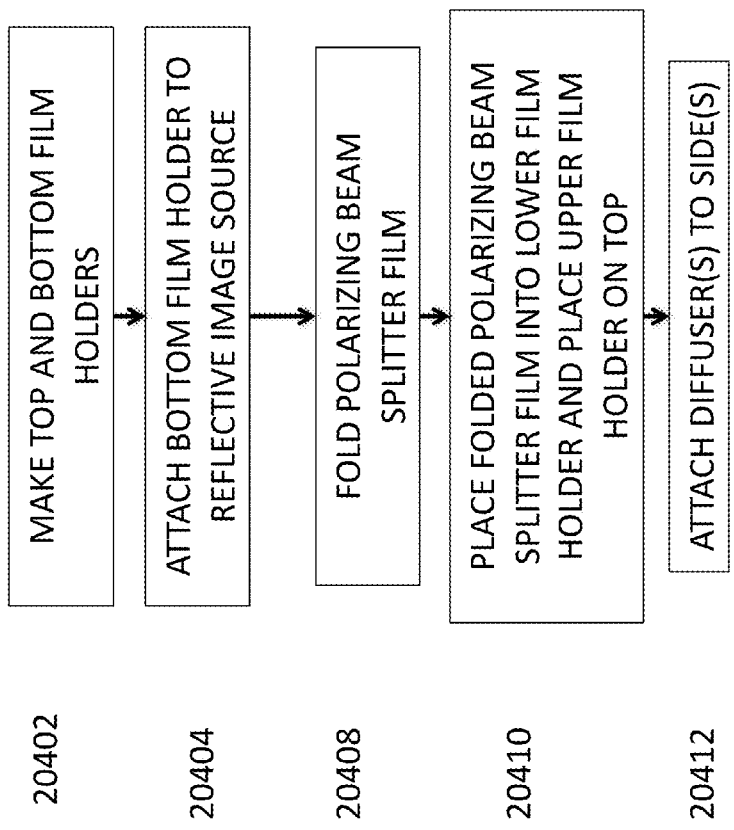
Figure 205:
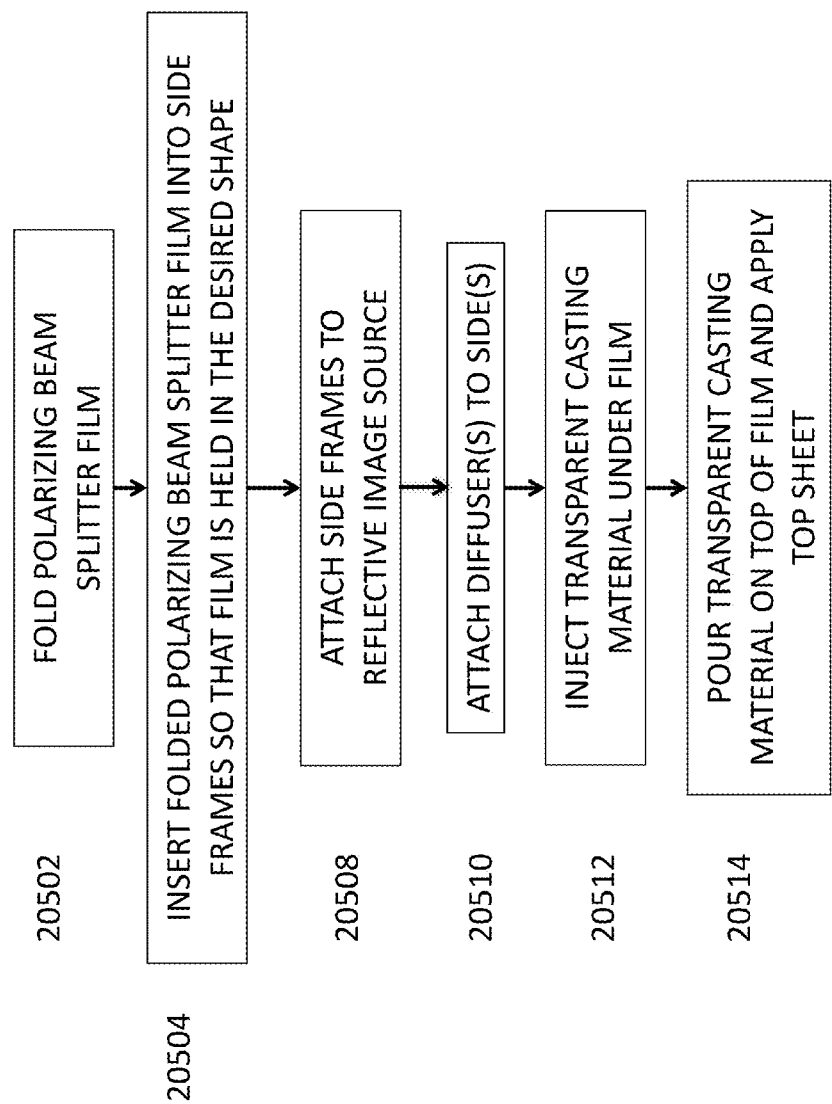
Figure 206:
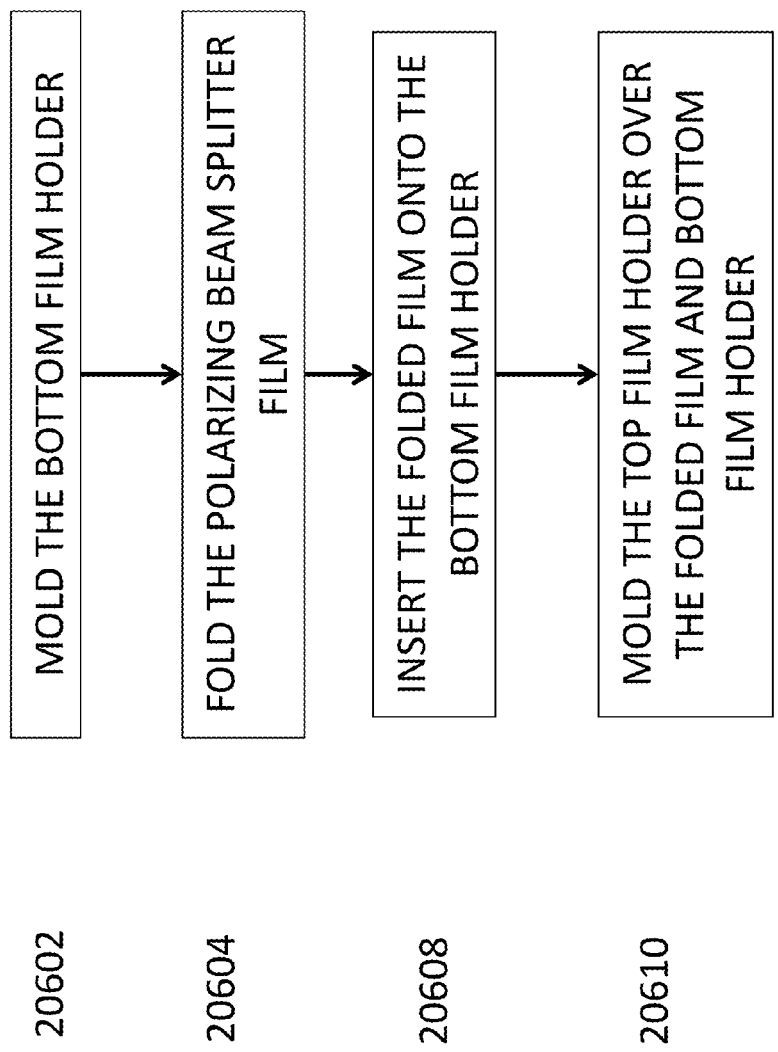

FIG. 187 is a schematic illustration of a prior art frontlight using a single light source and a beam splitter cube;

FIG. 188 is a schematic illustration of a prior art frontlight using a single light source and a reflective beam splitter layer;

FIG. 189 is a schematic illustration of a frontlight using a single light source wherein a flat reflective beam splitter layer is positioned at a reduced angle;

FIG. 190 is a schematic illustration of a frontlight using a single light source wherein the reflective beam splitter layer is curved;

FIG. 191 is a schematic illustration of a frontlight using dual light sources wherein a folded reflective beam splitter film with flat surfaces is positioned in a transparent solid;

FIG. 192 is a schematic illustration of a frontlight using a dual light sources wherein a folded free standing reflective beam splitter film with flat surfaces is used;

FIG. 193 is a schematic illustration of a frontlight using a dual light sources wherein a folded free standing reflective beam splitter film with curved surfaces is used;

FIG. 194 is a schematic illustration of a frontlight using a dual light sources wherein a folded reflective beam splitter film with curved surfaces is positioned in a transparent solid;

FIG. 195 is a schematic illustration of a frontlight using a single light source with an opposing mirror and a quarter wave film to recycle a portion of the polarized light wherein a folded reflective beam splitter film with flat surfaces is provided in a transparent solid;

FIG. 196 is a schematic illustration of a frontlight using a single light source with an opposing mirror and a quarter wave film to recycle a portion of the polarized light wherein a free standing folded reflective polarizer beam splitter film with flat surfaces is provided;

FIG. 197 is a schematic illustration of a frontlight using a single light source with an opposing mirror and a quarter wave film to recycle a portion of the polarized light wherein a free standing folded reflective polarizer beam splitter film with curved surfaces is provided;

FIG. 198 is a schematic illustration of a method for making a frontlight such as that shown in FIG. 197 but with the folded reflective beam splitter film with flat surfaces positioned in a transparent solid wherein top and bottom film holders are used to shape and position the reflective beam splitter film is provided and portions of the polarized light are recycled;

FIG. 199 is a schematic illustration of a frontlight for use with dual light sources and recycled portions of polarized light made using the method illustrated in FIG. 198;

FIG. 200 is a schematic illustration of a folded free standing reflective beam splitter film that is supported on the edges in a first step of a method for casting a solid frontlight;

FIG. 201 is a schematic illustration showing the holes for injecting the transparent casting material and venting the air in a method for casting a solid frontlight;

FIG. 202 is a schematic illustration showing the casting of the upper portion of the cast solid frontlight;

FIG. 203 is a schematic illustration showing the use of a flat transparent sheet to flatten the top of the cast solid frontlight;

FIG. 204 is a flow chart of a method for making a solid frontlight by assembly;

FIG. 205 is a flow chart of a method for making a solid frontlight by casting; and FIG. 206 is a flow chart of a method for making a solid film holder using a multi-step molding process.

Figure 207:
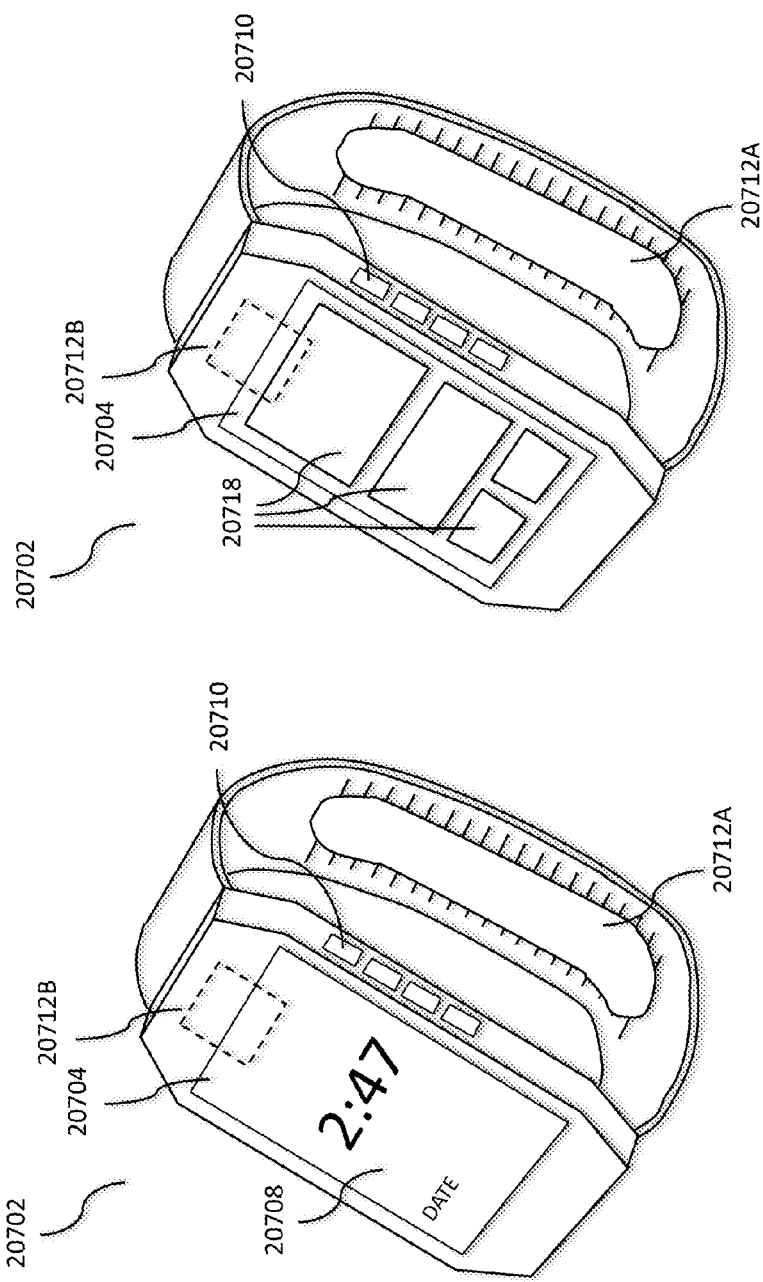

FIG. 207 depicts an embodiment of a near field communications watch.

Figure 208:
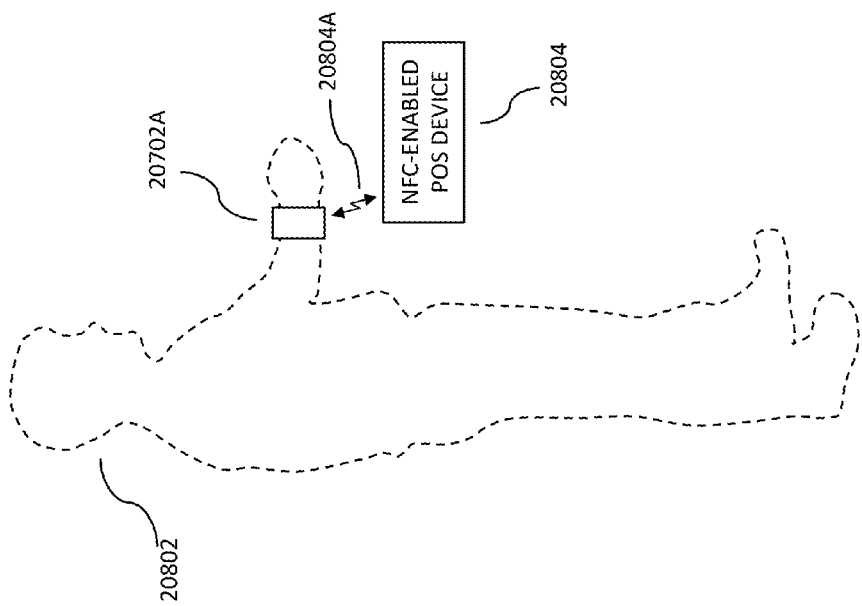

FIG. 208 depicts an embodiment of a near field communications watch interfacing with a near field communications enabled point of service device.

Figure 209:
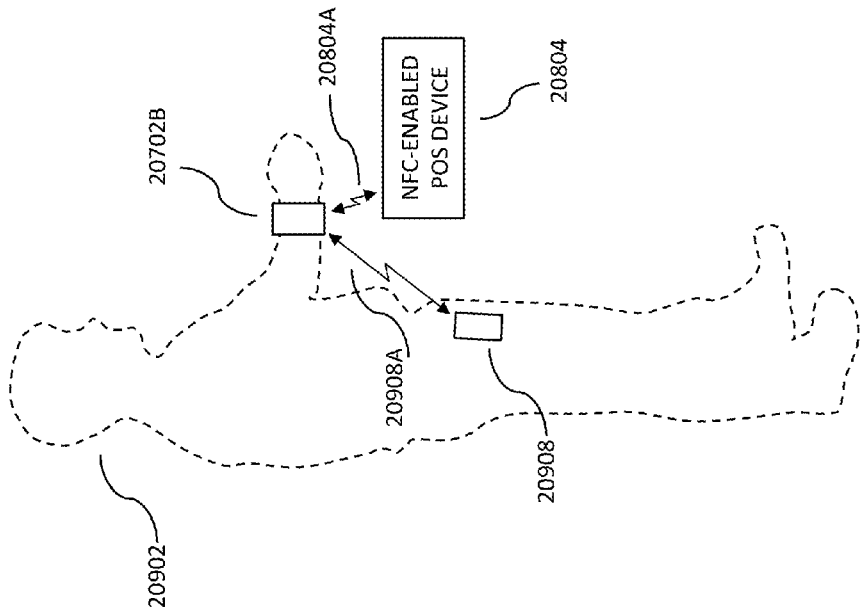

FIG. 209 depicts an embodiment of a near field communications watch interfacing with a near field communications enabled point of service device and with a user's smart phone.

DETAILED DESCRIPTION

The present disclosure relates to eyepiece electro-optics. The eyepiece may include projection optics suitable to project an image onto a see-through or translucent lens, enabling the wearer of the eyepiece to view the surrounding environment as well as the displayed image. The projection optics, also known as a projector, may include an RGB LED module that uses field sequential color. With field sequential color, a single full color image may be broken down into color fields based on the primary colors of red, green, and blue and imaged by an LCoS (liquid crystal on silicon) optical display 210 individually. As each color field is imaged by the optical display 210, the corresponding LED color is turned on. When these color fields are displayed in rapid sequence, a full color image may be seen. With field sequential color illumination, the resulting projected image in the eyepiece can be adjusted for any chromatic aberrations by shifting the red image relative to the blue and/or green image and so on. The image may thereafter be reflected into a two surface freeform waveguide where the image light engages in total internal reflections (TIR) until reaching the active viewing area of the lens where the user sees the image. A processor, which may include a memory and an operating system, may control the LED light source and the optical display. The projector may also include or be optically coupled to a display coupling lens, a condenser lens, a polarizing beam splitter, and a field lens.

Referring to FIGS. 123A and 123B, a processor 12302 (e.g. a digital signal processor) may provide display sequential frames 12324 for image display through a display component 12328 (e.g. an LCOS display component) of the eyepiece 100. In embodiments, the sequential frames 12324 may be produced with or without a display driver 12312 as an intermediate component between the processor 12302 and the display component 12328. For example, and referring to FIG. 123A, the processor 12302 may include a frame buffer 12304 and a display interface 12308 (e.g. a mobile industry processor interface (MIPI), with a display serial interface (DSI)). The display interface 12308 may provide per-pixel RGB data 12310 to the display driver 12312 as an intermediate component between the processor 12302 and the display component 12328, where the display driver 12312 accepts the per-pixel RGB data 12310 and generates individual full frame display data for red 12318, green 12320, and blue 12322, thus providing the display sequential frames 12324 to the display component 12328. In addition, the display driver 12312 may provide timing signals, such as to synchronize the delivery of the full frames 12318 12320 12322 as display sequential frames 12324 to the display component 12328. In another example, and referring to FIG. 123B, the display interface 12330 may be configured to eliminate the display driver 12312 by providing full frame display data for red 12334, green 12338, and blue 12340 directly to the display component 12328 as display sequential frames 12324. In addition, timing signals 12332 may be provided directly from the display interface 12330 to the display components. This configuration may provide significantly lower power consumption by removing the need for a display driver. Not only may this direct panel information remove the need for a driver, but also may simplify the overall logic of the configuration, and remove redundant memory required to reform panel information from pixels, to generate pixel information from frame, and the like.

Referring to FIG. 186, in embodiments, to improve yield of the LCoS+ASIC package 18600, the ASIC may be mounted onto a flexible printed circuit (FPC) 18604 with a stiffener on the topside. The topside stiffener does not add thickness to the overall package if it is as tall as the ASIC. The FPC can connect to a standard LCoS package, such as LCoS on fiberglass reinforced epoxy laminates (FR4) 18608 via a connector 18602, such as a zero insertion force (ZIF) connection or Board to Board connector for a higher pin count. A pressure sensitive adhesive may be used to bond the ASIC, stiffener(s) and LCoS to the FPC.

Figure 1:
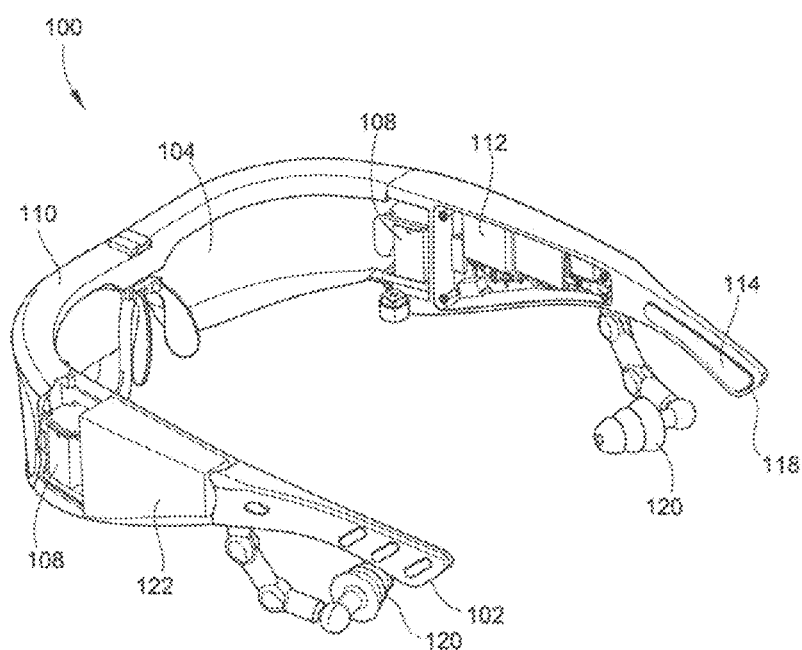
FIG. 1 depicts an illustrative embodiment of the optical arrangement.

Referring to FIG. 1, an illustrative embodiment of the augmented reality eyepiece 100 may be depicted. It will be understood that embodiments of the eyepiece 100 may not include all of the elements depicted in FIG. 1 while other embodiments may include additional or different elements. In embodiments, the optical elements may be embedded in the arm portions 122 of the frame 102 of the eyepiece. Images may be projected with a projector 108 onto at least one lens 104 disposed in an opening of the frame 102. One or more projectors 108, such as a nanoprojector, picoprojector, microprojector, femtoprojector, LASER-based projector, holographic projector, and the like may be disposed in an arm portion of the eyepiece frame 102. In embodiments, both lenses 104 are see-through or translucent while in other embodiments only one lens 104 is translucent while the other is opaque or missing. In embodiments, more than one projector 108 may be included in the eyepiece 100.

In embodiments such as the one depicted in FIG. 1, the eyepiece 100 may also include at least one articulating ear bud 120, a radio transceiver 118 and a heat sink 114 to absorb heat from the LED light engine, to keep it cool and to allow it to operate at full brightness. There are also one or more TI OMAP4 (open multimedia applications processors) 112, and a flex cable with RF antenna 110, all of which will be further described herein.

Figure 2:
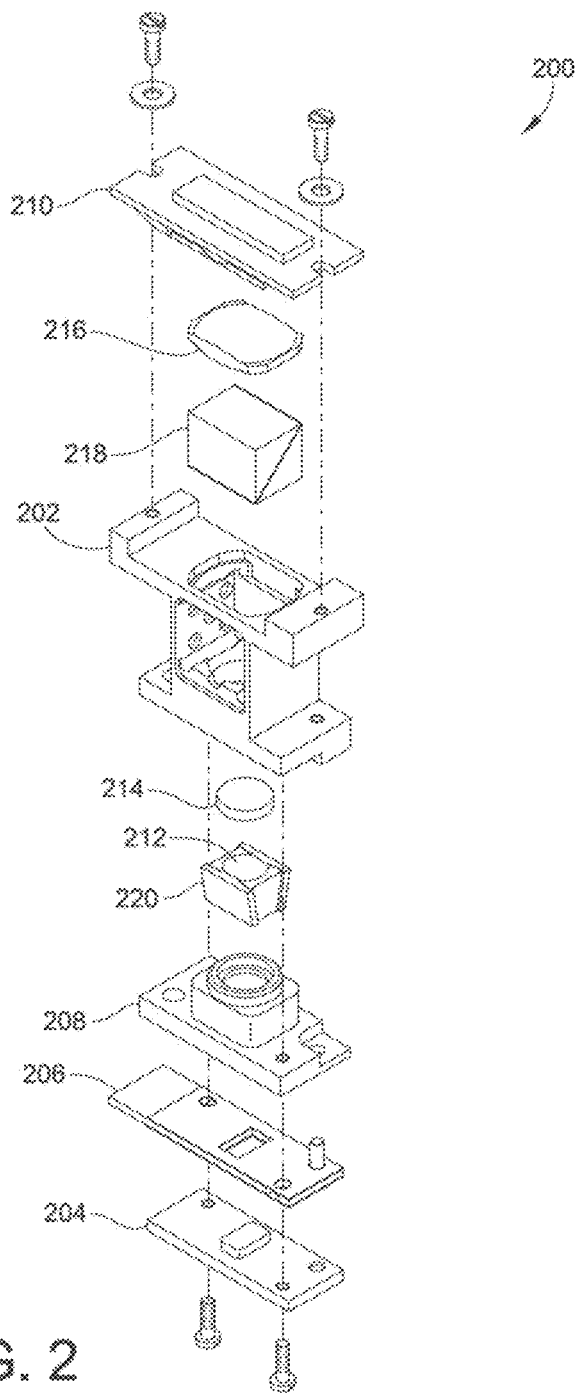
FIG. 2 depicts an RGB LED projector.

In an embodiment and referring to FIG. 2, the projector 200 may be an RGB projector. The projector 200 may include a housing 202, a heatsink 204 and an RGB LED engine or module 206. The RGB LED engine 206 may include LEDs, dichroics, concentrators, and the like. A digital signal processor (DSP) (not shown) may convert the images or video stream into control signals, such as voltage drops/current modifications, pulse width modulation (PWM) signals, and the like to control the intensity, duration, and mixing of the LED light. For example, the DSP may control the duty cycle of each PWM signal to control the average current flowing through each LED generating a plurality of colors. A still image co-processor of the eyepiece may employ noise-filtering, image/video stabilization, and face detection, and be able to make image enhancements. An audio back-end processor of the eyepiece may employ buffering, SRC, equalization and the like.

The projector 200 may include an optical display 210, such as an LCoS display, and a number of components as shown. In embodiments, the projector 200 may be designed with a single panel LCoS display 210; however, a three panel display may be possible as well. In the single panel embodiment, the display 210 is illuminated with red, blue, and green sequentially (aka field sequential color). In other embodiments, the projector 200 may make use of alternative optical display technologies, such as a back-lit liquid crystal display (LCD), a front-lit LCD, a transflective LCD, an organic light emitting diode (OLED), a field emission display (FED), a ferroelectric LCoS (FLCOS), liquid crystal technologies mounted on Sapphire, transparent liquid-crystal micro-displays, quantum-dot displays, and the like.

In various embodiments, the display may be a 3D display, LCD, thin film transistor LCD, LED, LCOS, ferroelectric liquid crystal on silicon display, CMOS display, OLED, QLED, OLED arrays that have CMOS style pixels sensors at the junctions between the OED pixels, transmissive LCoS display, CRT display, VGA display, SXGA display, QVGA display, display with video based gaze tracker, display with exit pupil expanding technology, Asahi film display, a free form optics display, an XY polynomial combiner display, a light guide transfer display, an Amoled display, and the like. In embodiments, the display may be a holographic display that allows the eyepiece to display an image from the image source as a hologram. In embodiments, the display may be a liquid crystal reflective micro-display. Such a display may contain polarization optics and may improve brightness as compared to certain OLED micro displays. In embodiments, the display may be a free form prism display. Free form prism displays may achieve 3D stereo imaging capability. In embodiments, the display may be similar or the same as those displays described by Cannon and/or Olympus in U.S. Pat. Nos. 6,384,983 and 6,181,475 respectively. In yet other embodiments, the display may contain a video based gaze tracker. In embodiments, a light beam of an infrared light source may be divided and expanded inside an exit pupil expander (EPE) to produce collimated beams from the EPE toward the eyes. A Miniature video camera may image the cornea and eye gaze direction may be calculated by locating the pupil and the glints of the infrared beams. After user calibration, the data from the gaze tracker may reflect the user focus point in the displayed image which may be used as an input device. Such a device may be similar to that provided by Nokia Research Center of Tampere, Finland. Further, in embodiments, the display may contain an exit pupil expander which enlarges the exit pupil and transfers the image to a new position. Therefore only a thin transparent plate may need to be placed in front of the user's eyes and the image source may be placed elsewhere. In yet other embodiments, the display may be an off axis optics display. In embodiments, such a display may not be coincident with the mechanical center of the aperture. This may avoid obstruction of the primary aperture by secondary optical elements, instrument packages and/or sensors and may provide access to instrument packages and/or sensors at the focus. For example, the active-maxtrix organic light-emitting diode (Amoled) display may use a pixel design, called PenTile, from Nouvoyance which lets more light through in a couple of ways. First, the red, blue, and green subpixels are larger than those in traditional displays. Second, one out of every four subpixels is clear. This means the backlight can use less power and shine brighter. Fewer subpixels would usually mean a lower resolution, but the PenTile display uses individual sub-pixels to trick the eye into perceiving the same resolution while using about one-third as many subpixels as an RGB stripe panel. The PenTile display also uses image processing algorithms to determine the brightness of a scene, automatically dimming the backlight for darker images.

To overcome the limitations of the prior art previously described, the disclosure provides an integral array of switchable mirrors in a waveguide that can be used sequentially to provide a progressive scan of portions of the image across the display field of view. By rapidly switching the mirrors from reflective to transmissive in a sequential manner, the image can be provided to the user without perceptible flicker. Since each switchable mirror is in the transmissive state more than the reflective state, the array of switchable mirrors appears to be transparent to the user while also presenting the displayed image to the user.

Presentation of light from an image source by a waveguide is well known to those skilled in the art and as such will not be discussed herein. Exemplary discussions of waveguides and the transport of light from an image source to a display area are provided in U.S. Pat. Nos. 5,076,664 and 6,829,095. The present disclosure includes methods and apparatus for redirecting image light in a waveguide to provide an image to a user where the image light in the waveguide has been provided from an image source.

FIG. 125 shows a waveguide display device 12500 with an integral array of switchable mirrors 12508a-12508c that redirect the light from the image source 12502 that is transported through the waveguide 12510 to provide image light 12504 to the user. Three switchable mirrors 12508a-12508c, are shown but the array can include a different number of switchable mirrors in the disclosure. The switchable mirrors shown in FIG. 125 are electrically switchable mirrors including liquid crystal switchable mirrors. Cover glasses 12512 are provided to contain the liquid crystal material in the thin layers which are shown as switchable mirrors 12508a-12508c. FIG. 125 further shows power wires 12514 and 12518.

The waveguide 12510 and the integral array of switchable mirrors 12508a-12508c, can be made from plastic or glass material so long as it is suitably flat. Thickness uniformity is not as important as in most liquid crystal devices since the switchable mirror has high reflectivity. Construction of a switchable liquid crystal mirror is described in U.S. Pat. No. 6,999,649.

FIGS. 126 and 127 show the sequential aspect of the disclosure in that only one of the switchable mirrors in the array is in the reflective state at a time, the other switchable mirrors in the array are then in the transmissive state. FIG. 124 shows the first switchable mirror 12508a in the reflective state thereby redirecting the light from the image source 12502 to become image light 12504 that presents a portion of the image to the user. The other switchable mirrors 12508b and 12508c are in the transmissive state. FIG. 124 further shows waveguide 12410.

In FIG. 126, switchable mirrors 12508a and 12508c are in the transmissive while switchable mirror 12508b is in the reflective state. This condition provides image light 12600 with its associated portion of the image to the user. Finally in FIG. 127, switchable mirrors 12508a and 12508b are in the transmissive state while switchable mirror 12508c is in the reflective state. This last condition provides image light 12700 with its associated portion of the image to the user. Following this last condition, the sequence is repeated as shown in FIG. 124, followed by that shown in FIG. 125 and then as shown in FIG. 126 to provide a progressive scan of the image. The sequence is repeated continuously while the user is viewing displayed images. Thus, all of the light from the image source 12502 is redirected by a single switchable mirror at any given time in the sequence. The image source can operate continuously while the switchable mirrors provide a progressive scan of the image light 12504 across the field of view. If the image light is perceived to be brighter or there is a different color balance for different switchable mirrors, the image source can be adjusted to compensate and the brightness or color balance of the image source can be modulated to synchronize with the switching sequence of the array of switchable mirrors. In another embodiment of the disclosure, the order of switching of the switchable mirrors can be changed to provide an interlaced image to the user such as 1, 3, 2, 4 in a repeating fashion for an array of four switchable mirrors.

FIG. 128 shows another embodiment of the disclosure in which an integral array of mechanically driven switchable mirrors is provided. In this case, the switchable mirrors in the waveguide display device 12800 comprise prisms 12804a-12804c that are moved to alternately provide an air gap or an optical contact with surfaces 12810a-12810c respectively. As shown in FIG. 128, prism 12804a has been moved downward to provide an air gap so that surface 12810a is a reflective surface that operates by total internal reflection. At the same time, prisms 12804b and 12804c are forced upwards to provide optical contact at surfaces 12810b and 12810c respectively so that surfaces 12810b and 12810c are transmissive. This condition redirects the light from the image source 12502 to become image light 12802 which presents a portion of the image to the user. In this embodiment, the switchable mirror moves from optical contact where the transmission is nearly 100% to total internal reflection where the reflectivity is nearly 100%. FIG. 128 also shows power wires 12812, mount and common ground connection 12814, and microactuators 12818a-c.

FIGS. 129 and 130 show other conditions in the sequence for the mechanically driven switchable mirrors in the switchable mirror array. In FIG. 129, prisms 12804a and 12804c are forced upwards to provide optical contact with surfaces 12810a and 12810c respectively thereby providing a transmissive state for the light from the image source 12502. At the same time prism 12804b is moved downward to create an air gap at surface 12810b so that the light from the image source 12502 is redirected to become image light 12900 that presents an associated portion of the image to the user. In the final step of the sequence shown in FIG. 130, prisms 12804a and 12804b are forced upwards to provide optical contact at surfaces 12810a and 12810b respectively so that the light from the image source passes through to surface 12810c. Prism 12804c is moved downwards to provide an air gap at surface 12810c so that surface 12810c becomes a reflecting surface with total internal reflection and the light from the image source 12502 is redirected to become image light 13000 with its associated portion of the image.

In the previous discussion, the conditions for total internal reflection are based on the optical properties of the material of the waveguide 12808 and the air as is well known to those skilled in the art. To obtain a 90 degree reflection as shown in FIGS. 128-130, the refractive index of the waveguide 12808 must be greater than 1.42. To provide for optical contact between the prisms 12804a-12804c and surfaces 12810a-12810c respectively, the surfaces of the prisms 12804a-12804c must match those of the surfaces 12810a-12810c within 1.0 micron. Lastly, for the light from the image source 12502 to proceed through the waveguide 12808 and the prisms 12804a-12804c without deflecting at interfaces, the refractive index of the prisms 12804a-12804c must be the same as the refractive index of the waveguide 12808 within approximately 0.1.

FIGS. 131a and 131b show illustrations of waveguide assemblies 13102 with arrays of switchable mirrors as included in the disclosure. FIG. 131a shows a side view of the waveguide assembly 13102 on the user's head wherein the long axis of the array of switchable mirrors is oriented vertically so that the image light 13100 is directed into the user's eye. FIG. 131b shows an overhead view of the waveguide assembly 13102 on the user's head wherein the short axis of the array of switchable mirrors 13104 can be seen and image light 13100 is provided to the user's eye 13110. In FIGS. 131a and 131b, the field of view provided in the image light 13100 can be clearly seen. In FIG. 131b, the respective portions of the image as provided by different switchable mirrors in the array can be seen as well. FIG. 131b also shows an embodiment of the waveguide assembly 13102 including the image source 13108 wherein the image source 13108 has an internal light source to provide light from a miniature display such as an LCOS display or an LCD display that is then transported by the waveguide to the switchable mirrors where it is redirected by the switchable mirrors and becomes image light 13100 that is presented to the user's eye 13110.

To reduce the perception of image flicker by the user as the switchable mirrors are operated to provide sequential portions of the image to the user, the switchable mirror sequence is preferentially operated at faster than 60 Hz. In this case, each of the n switchable mirrors in the array is in the reflective state for (1/60)×1/n seconds then in the transmissive state for (1/60)×(n−1)/n seconds in each cycle of the sequence. As such, each switchable mirror is in the transmissive state for a greater portion of each cycle in the sequence than it is in the reflective state and consequently the user perceives the array of switchable mirrors to be relatively transparent.

In another embodiment of the disclosure, the integral array of switchable mirrors has more switchable mirrors than are needed to cover the display area. The extra switchable mirrors are used to provide an adjustment for different users that have different eye spacings (also known as interpupillary distance). In this case, the switchable mirrors that are used to present the image to the user are adjacent to one another so that they present a contiguous image area. The switchable mirrors at the edges of the array are used depending on the eye spacing of the user. As an example illustrated in FIGS. 132A-132C, an array 13200 is provided with seven switchable mirrors each 3 mm wide. During use, five adjacent switchable mirrors are used to provide a 15 mm wide display area (13202a-13202c) with +/−3 mm of adjustment for eye spacing. In the narrow eye spacing case shown in FIG. 132A, the five switchable mirrors toward the inner edge are used to display while the two outer switchable mirrors are not used. In the wide eye spacing case shown in FIG. 132C, the five switchable mirrors toward the outer edge are used to display while the two inner switchable mirrors are not used. The centered case is shown in FIG. 132B where the center five switchable mirrors are used and the outer and inner switchable mirrors are not used. Where in this description, the term "not used" refers to the switchable mirror being held in the transmissive state while the other switchable mirrors are used in a repeating sequence between the transmissive state and the reflective state.

EXAMPLES

In a first example, a liquid crystal switchable mirror with a fast response is used as provided by Kent Optronics Inc., Hopewell Junction, N.Y. (http://www.kentoptronics.com/). The waveguide is made of glass or plastic and the liquid crystal is contained in spaces between layers so that the liquid crystal is 5 microns thick. Coverglasses contain the liquid crystal on the outer surfaces. The response time is 10 millisec with reflectivity of 87% in the reflective state and transmission of 87% in the transmissive state. Three switchable mirrors can be driven in a sequence that operates at 30 Hz. If the switchable mirrors are 5 mm wide, a 15 mm wide display area is provided which equates to a 38 degree field of view when viewed with the eye 10 mm from the waveguide with an 8 mm wide eyebox.

In a second example, a mechanically driven array of prisms is provided made of glass or plastic with a refractive index of 1.53, the waveguide is made of the same material with a refractive index of 1.53. The surfaces of the prisms are polished to provide a flatness of less than 1 micron and piezoelectric microactuators are used to move the prisms approximately 10 microns from the transmissive state to the reflective state. The waveguide is molded to provide a flatness of less than 1 micron on the mating surfaces to the prisms. Five switchable mirrors can be driven by the piezoelectric actuators to operate in a sequence at 100 Hz. The piezoelectric microactuators are obtained from Steiner & Martins Inc., Miami, Fla. (http://www.steminc.com/piezo/PZ_STAKPN ViewPN.asp?PZ_SM_MODEL=SMPAK155510D10) the microactuators provide a 10 micron movement with over 200 pounds of force in a 5×5×10 mm package driven by 150V. An array of 5 prisms that are each 5 mm wide are used to provide a 25 mm wide display area which equates to a 72 degree field of view when viewed with the eye 10 mm from the waveguide with an 8 mm wide eyebox. Alternately, only 3 prisms are used at a time to provide a 15 mm wide display area (38 degree field of view) with the ability to move the display area laterally by +/−5 mm to adjust for different spacing between the eyes for different users.

In embodiments, a waveguide display system may comprise an image source that provides image light from a displayed image, a waveguide to transport the image light to a display area, and an integral array of switchable mirrors to redirect the image light from the waveguide to the display area where the displayed image can be viewed by the user. In embodiments, the switchable mirrors may be electrically driven. The switchable mirrors may be mechanically driven in embodiments. In further embodiments, the microactuators may be used to mechanically drive the switchable mirrors. Further, the microactuators may be piezoelectric. The switchable mirrors may be switched between transmissive and reflective states to provide portions of the image light in a progressive scan across the display area.

In embodiments, a method of providing a displayed image from a waveguide may comprise providing image light from an image source to waveguide, providing an integral array of switchable mirrors in the waveguide over the display area and sequentially operating the switchable mirrors between transmissive and reflective states to provide portions of the image light in a progressive scan across the display area.

In yet other embodiments, a waveguide display system with interpupillary adjustment may comprise an image source that provides image light from a displayed image, a waveguide to transport the image light to a display area and an internal array of switchable mirrors to redirect the image light from the waveguide to the display. Further the array of switchable mirrors may have more mirrors than are needed to cover the display area and the switchable mirrors at the edges of the array may be used to provide a display area that matches the eye spacing of the user.

The eyepiece may be powered by any power supply, such as battery power, solar power, line power, and the like. The power may be integrated in the frame 102 or disposed external to the eyepiece 100 and in electrical communication with the powered elements of the eyepiece 100. For example, a solar energy collector may be placed on the frame 102, on a belt clip, and the like. Battery charging may occur using a wall charger, car charger, on a belt clip, in an eyepiece case, and the like.

The projector 200 may include the LED light engine 206, which may be mounted on heat sink 204 and holder 208, for ensuring vibration-free mounting for the LED light engine, hollow tapered light tunnel 220, diffuser 212 and condenser lens 214. Hollow tunnel 220 helps to homogenize the rapidly-varying light from the RGB LED light engine. In one embodiment, hollow light tunnel 220 includes a silvered coating. The diffuser lens 212 further homogenizes and mixes the light before the light is led to the condenser lens 214. The light leaves the condenser lens 214 and then enters the polarizing beam splitter (PBS) 218. In the PBS, the LED light is propagated and split into polarization components before it is refracted to a field lens 216 and the LCoS display 210. The LCoS display provides the image for the microprojector. The image is then reflected from the LCoS display and back through the polarizing beam splitter, and then reflected ninety degrees. Thus, the image leaves microprojector 200 in about the middle of the microprojector. The light then is led to the coupling lens 504, described below.

FIG. 2 depicts an embodiment of the projector assembly along with other supporting figures as described herein, but one skilled in the art will appreciate that other configurations and optical technologies may be employed. For instance, transparent structures, such as with substrates of Sapphire, may be utilized to implement the optical path of the projector system rather than with reflective optics, thus potentially altering and/or eliminating optical components, such as the beam splitter, redirecting mirror, and the like. The system may have a backlit system, where the LED RGB triplet may be the light source directed to pass light through the display. As a result the back light and the display may be mounted either adjacent to the wave guide, or there may be columnizing/directing optics after the display to get the light to properly enter the optic. If there are no directing optics, the display may be mounted on the top, the side, and the like, of the waveguide. In an example, a small transparent display may be implemented with a silicon active backplane on a transparent substrate (e.g. sapphire), transparent electrodes controlled by the silicon active backplane, a liquid crystal material, a polarizer, and the like. The function of the polarizer may be to correct for depolarization of light passing through the system to improve the contrast of the display. In another example, the system may utilize a spatial light modulator that imposes some form of spatially-varying modulation on the light path, such as a micro-channel spatial light modulator where a membrane-mirror light shutters based on micro-electromechanical systems (MEMS). The system may also utilize other optical components, such as a tunable optical filter (e.g. with a deformable membrane actuator), a high angular deflection micro-mirror system, a discrete phase optical element, and the like.

In other embodiments the eyepiece may utilize OLED displays, quantum-dot displays, and the like, that provide higher power efficiency, brighter displays, less costly components, and the like. In addition, display technologies such as OLED and quantum-dot displays may allow for flexible displays, and so allowing greater packaging efficiency that may reduce the overall size of the eyepiece. For example, OLED and quantum-dot display materials may be printed through stamping techniques onto plastic substrates, thus creating a flexible display component. For example, the OLED (organic LED) display may be a flexible, low-power display that does not require backlighting. It can be curved, as in standard eyeglass lenses. In one embodiment, the OLED display may be or provide for a transparent display. In embodiments, high modulation transfer functions permit the combination of resolution levels and device size, e.g., eyeframe thickness, that have been unachievable heretofore.

Figure 82:
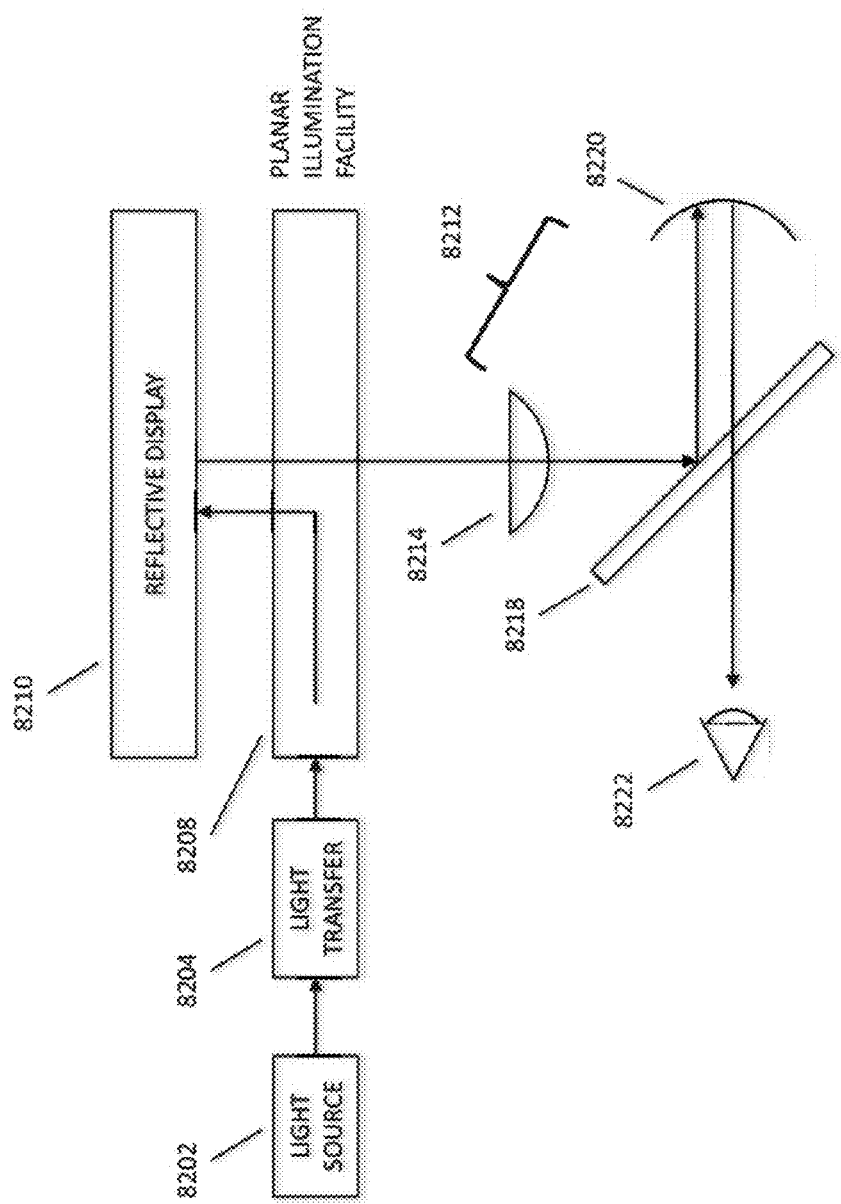
FIG. 82 depicts an embodiment of an optical display system utilizing a planar illumination facility with a reflective display.

Referring to FIG. 82, the eyepiece may utilize a planar illumination facility 8208 in association with a reflective display 8210, where light source(s) 8202 are coupled 8204 with an edge of the planar illumination facility 8208, and where the planar side of the planar illumination facility 8208 illuminates the reflective display 8210 that provides imaging of content to be presented to the eye 8222 of the wearer through transfer optics 8212. In embodiments, the reflective display 8210 may be an LCD, an LCD on silicon (LCoS), cholesteric liquid crystal, guest-host liquid crystal, polymer dispersed liquid crystal, phase retardation liquid crystal, and the like, or other liquid crystal technology know in the art. In other embodiments, the reflective display 8210 may be a bi-stable display, such as electrophoretic, electrofluidic, electrowetting, electrokinetic, cholesteric liquid crystal, and the like, or any other bi-stable display known to the art. The reflective display 8210 may also be a combination of an LCD technology and a bi-stable display technology. In embodiments, the coupling 8204 between a light source 8202 and the 'edge' of the planar illumination facility 8208 may be made through other surfaces of the planar illumination facility 8208 and then directed into the plane of the planar illumination facility 8208, such as initially through the top surface, bottom surface, an angled surface, and the like. For example, light may enter the planar illumination facility from the top surface, but into a 45° facet such that the light is bent into the direction of the plane. In an alternate embodiment, this bending of direction of the light may be implemented with optical coatings.

In an example, the light source 8202 may be an RGB LED source (e.g. an LED array) coupled 8204 directly to the edge of the planar illumination facility. The light entering the edge of the planar illumination facility may then be directed to the reflective display for imaging, such as described herein. Light may enter the reflective display to be imaged, and then redirected back through the planar illumination facility, such as with a reflecting surface at the backside of the reflective display. Light may then enter the transfer optics 8212 for directing the image to the eye 8222 of the wearer, such as through a lens 8214, reflected by a beam splitter 8218 to a reflective surface 8220, back through the beam splitter 8218, and the like, to the eye 8222. Although the transfer optics 8212 have been described in terms of the 8214, 8218, and 8220, it will be appreciated by one skilled in the art that the transfer optics 8212 may include any transfer optics configuration known, including more complex or simpler configurations than describe herein. For instance, with a different focal length in the field lens 8214, the beam splitter 8218 could bend the image directly towards the eye, thus eliminating the curved mirror 8220, and achieving a simpler design implementation. In embodiments, the light source 8202 may be an LED light source, a laser light source, a white light source, and the like, or any other light source known in the art. The light coupling mechanism 8204 may be direct coupling between the light source 8202 and the planar illumination facility 8208, or through coupling medium or mechanism, such as a waveguide, fiber optic, light pipe, lens, and the like. The planar illumination facility 8208 may receive and redirect the light to a planar side of its structure through an interference grating, optical imperfections, scattering features, reflective surfaces, refractive elements, and the like. The planar illumination facility 8208 may be a cover glass over the reflective display 8210, such as to reduce the combined thickness of the reflective display 8210 and the planar illumination facility 8208. The planar illumination facility 8208 may further include a diffuser located on the side nearest the transfer optics 8212, to expand the cone angle of the image light as it passes through the planar illumination facility 8208 to the transfer optics 8212. The transfer optics 8212 may include a plurality of optical elements, such as lenses, mirrors, beam splitters, and the like, or any other optical transfer element known to the art.

Figure 83:
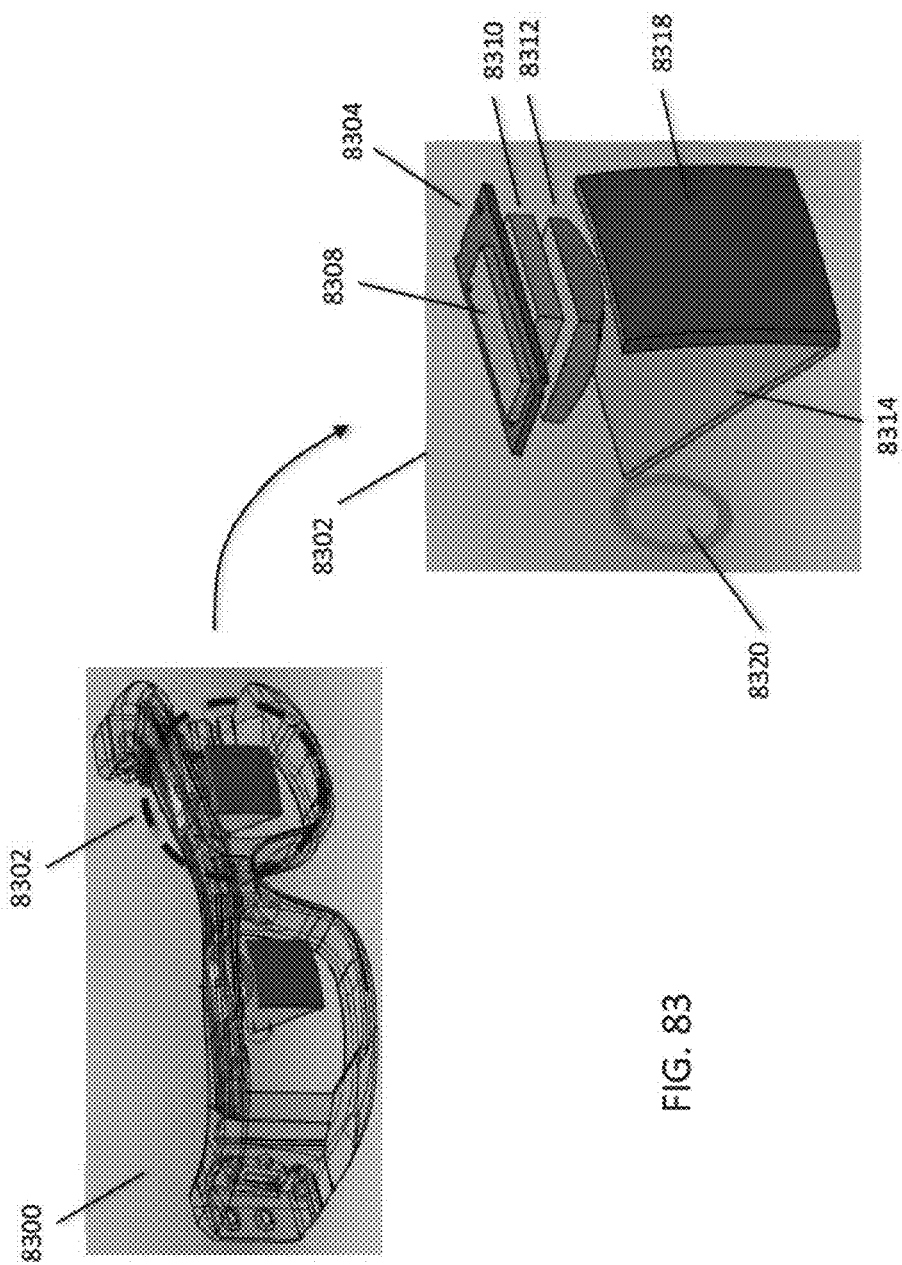
FIG. 83 depicts a structural embodiment of a planar illumination optical system.

FIG. 83 presents an embodiment of an optical system 8302 for the eyepiece 8300, where a planar illumination facility 8310 and reflective display 8308 mounted on substrate 8304 are shown interfacing through transfer optics 8212 including an initial diverging lens 8312, a beam splitter 8314, and a spherical mirror 8318, which present the image to the eyebox 8320 where the wearer's eye receives the image. In an example, the flat beam splitter 8314 may be a wire-grid polarizer, a metal partially transmitting mirror coating, and the like, and the spherical reflector 8318 may be a series of dielectric coatings to give a partial mirror on the surface. In another embodiment, the coating on the spherical mirror 8318 may be a thin metal coating to provide a partially transmitting mirror.

Figure 84:
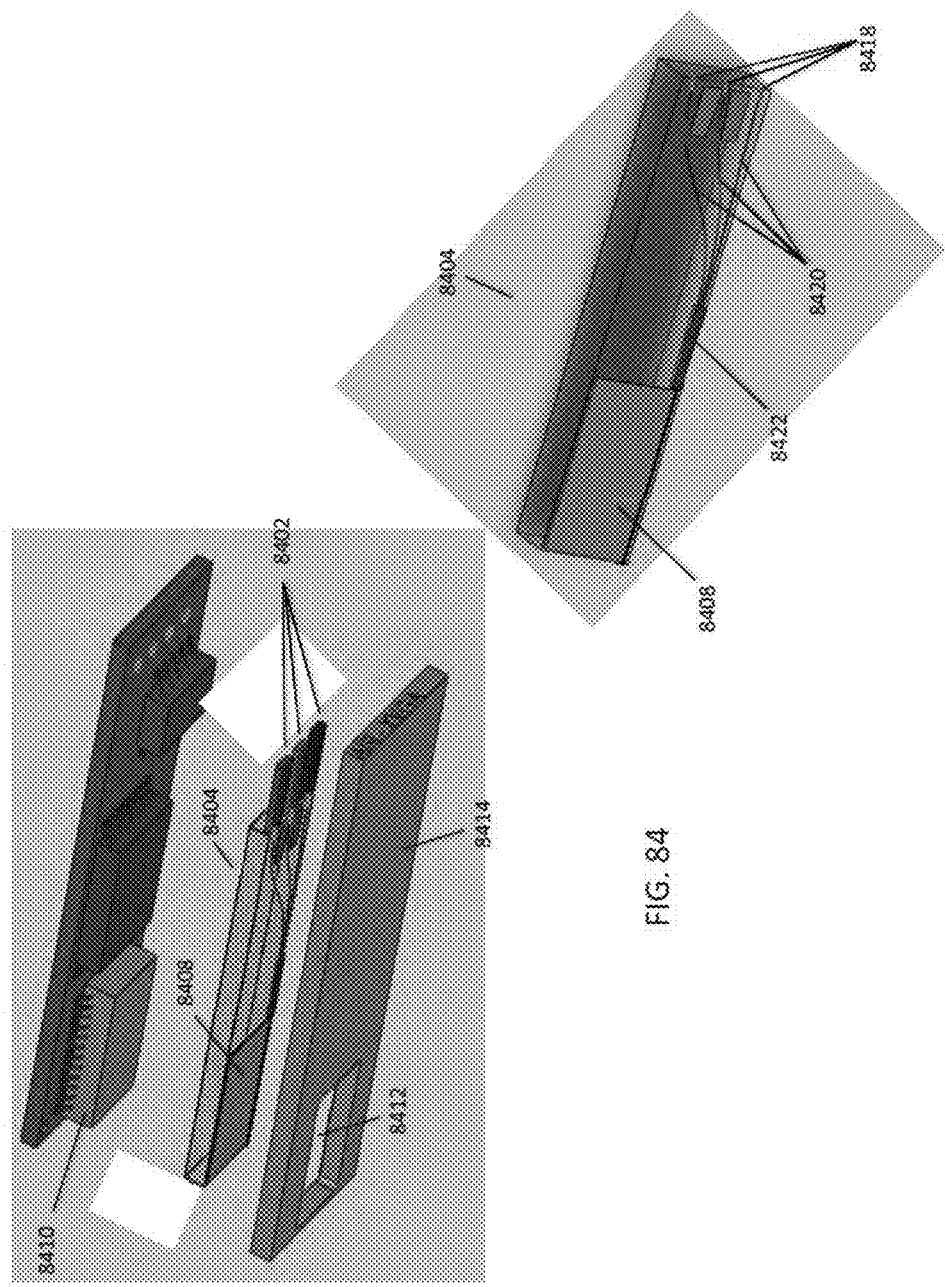
FIG. 84 depicts an embodiment assembly of a planar illumination facility and a reflective display with laser speckle suppression components.

In an embodiment of an optics system, FIG. 84 shows a planar illumination facility 8408 as part of a ferroelectric light-wave circuit (FLC) 8404, including a configuration that utilizes laser light sources 8402 coupling to the planar illumination facility 8408 through a waveguide wavelength converter 8420 8422, where the planar illumination facility 8408 utilizes a grating technology to present the incoming light from the edge of the planar illumination facility to the planar surface facing the reflective display 8410. The image light from the reflective display 8410 is then redirected back though the planar illumination facility 8408 through a hole 8412 in the supporting structure 8414 to the transfer optics. Because this embodiment utilizes laser light, the FLC also utilizes optical feedback to reduce speckle from the lasers, by broadening the laser spectrum as described in U.S. Pat. No. 7,265,896. In this embodiment, the laser source 8402 is an IR laser source, where the FLC combines the beams to RGB, with back reflection that causes the laser light to hop and produce a broadened bandwidth to provide the speckle suppression. In this embodiment, the speckle suppression occurs in the wave-guides 8420. The laser light from laser sources 8402 is coupled to the planar illumination facility 8408 through a multi-mode interference combiner (MMI) 8422. Each laser source port is positioned such that the light traversing the MMI combiner superimposes on one output port to the planar illumination facility 8408. The grating of the planar illumination facility 8408 produces uniform illumination for the reflective display. In embodiments, the grating elements may use a very fine pitch (e.g. interferometric) to produce the illumination to the reflective display, which is reflected back with very low scatter off the grating as the light passes through the planar illumination facility to the transfer optics. That is, light comes out aligned such that the grating is nearly fully transparent. Note that the optical feedback utilized in this embodiment is due to the use of laser light sources, and when LEDs are utilized, speckle suppression may not be required because the LEDs are already broadband enough.

Figure 85:
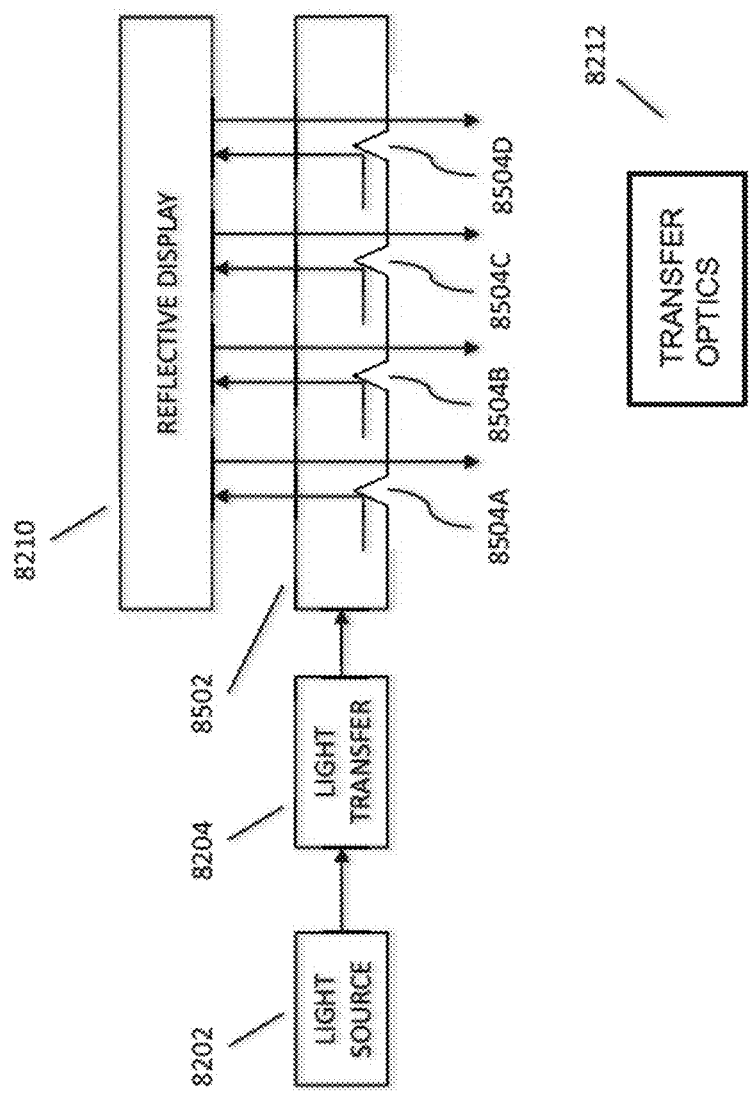
FIG. 85 depicts an embodiment of a planar illumination facility with grooved features for redirecting light.

In an embodiment of an optics system utilizing a planar illumination facility 8502 that includes a configuration with optical imperfections, in this case a 'grooved' configuration, is shown in FIG. 85. In this embodiment, the light source(s) 8202 are coupled 8204 directly to the edge of the planar illumination facility 8502. Light then travels through the planar illumination facility 8502 and encounters small grooves 8504A-D in the planar illumination facility material, such as grooves in a piece of Poly-methyl methacrylate (PMMA). In embodiments, the grooves 8504A-D may vary in spacing as they progress away from the input port (e.g. less 'aggressive' as they progress from 8504A to 8504D), vary in heights, vary in pitch, and the like. The light is then redirected by the grooves 8504A-D to the reflective display 8210 as an incoherent array of light sources, producing fans of rays traveling to the reflective display 8210, where the reflective display 8210 is far enough away from the grooves 8504A-D to produce illumination patterns from each groove that overlap to provide uniform illumination of the area of the reflective display 8210. In other embodiments, there may be an optimum spacing for the grooves, where the number of grooves per pixel on the reflective display 8210 may be increased to make the light more incoherent (more fill), but where in turn this produces lower contrast in the image provided to the wearer with more grooves to interfere within the provided image. While this embodiment has been discussed with respect to grooves, other optical imperfections, such as dots, are also possible.

Figure 86:
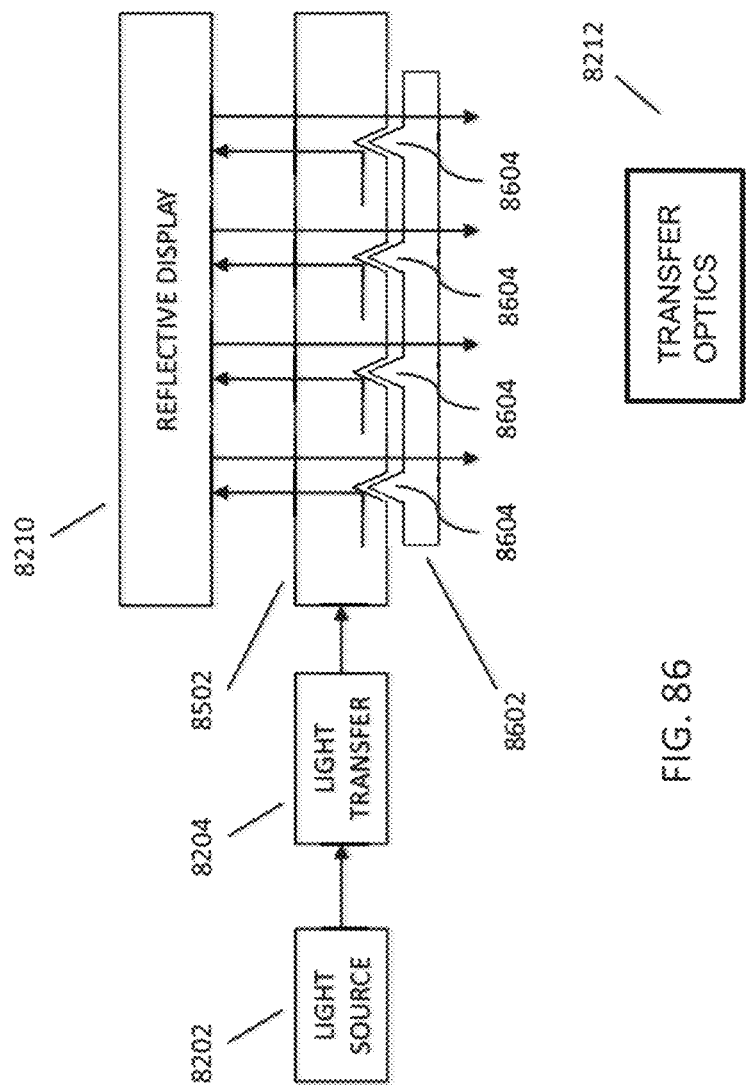
FIG. 86 depicts an embodiment of a planar illumination facility with grooved features and anti-grooved features paired to reduce image aberrations.

In embodiments, and referring to FIG. 86, counter ridges 8604 (or 'anti-grooves') may be applied into the grooves of the planar illumination facility, such as in a 'snap-on' ridge assembly 8602. Wherein the counter ridges 8604 are positioned in the grooves 8504A-D such that there is an air gap between the groove sidewalls and the counter ridge sidewalls. This air gap provides a defined change in refractive index as perceived by the light as it travels through the planar illumination facility that promotes a reflection of the light at the groove sidewall. The application of counter ridges 8604 reduces aberrations and deflections of the image light caused by the grooves. That is, image light reflected from reflective display 8210 is refracted by the groove sidewall and as such it changes direction because of Snell's law. By providing counter ridges in the grooves, where the sidewall angle of the groove matches the sidewall angle of the counter ridge, the refraction of the image light is compensated for and the image light is redirected toward the transfer optics 8214.

In embodiments, and referring to FIG. 87, the planar illumination facility 8702 may be a laminate structure created out of a plurality of laminating layers 8704 wherein the laminating layers 8704 have alternating different refractive indices. For instance, the planar illumination facility 8702 may be cut across two diagonal planes 8708 of the laminated sheet. In this way, the grooved structure shown in FIGS. 85 and 86 is replaced with the laminate structure 8702. For example, the laminating sheet may be made of similar materials (PMMA 1 versus PMMA 2—where the difference is in the molecular weight of the PMMA). As long as the layers are fairly thick, there may be no interference effects, and act as a clear sheet of plastic. In the configuration shown, the diagonal laminations will redirect a small percentage of light source 8202 to the reflective display, where the pitch of the lamination is selected to minimize aberration.

In an embodiment of an optics system, FIG. 88 shows a planar illumination facility 8802 utilizing a 'wedge' configuration. In this embodiment, the light source(s) are coupled 8204 directly to the edge of the planar illumination facility 8802. Light then travels through the planar illumination facility 8802 and encounters the slanted surface of the first wedge 8804, where the light is redirected to the reflective display 8210, and then back to the illumination facility 8802 and through both the first wedge 8804 and the second wedge 8812 and on to the transfer optics. In addition, multi-layer coatings 8808 8810 may be applied to the wedges to improve transfer properties. In an example, the wedge may be made from PMMA, with dimensions of ½ mm high-10 mm width, and spanning the entire reflective display, have 1 to 1.5 degrees angle, and the like. In embodiments, the light may go through multiple reflections within the wedge 8804 before passing through the wedge 8804 to illuminate the reflective display 8210. If the wedge 8804 is coated with a highly reflecting coating 8808 and 8810, the ray may make many reflections inside wedge 8804 before turning around and coming back out to the light source 8202 again. However, by employing multi-layer coatings 8808 and 8810 on the wedge 8804, such as with SiO2, Niobium Pentoxide, and the like, light may be directed to illuminate the reflective display 8210. The coatings 8808 and 8810 may be designed to reflect light at a specified wavelength over a wide range of angles, but transmit light within a certain range of angles (e.g. theta out angles). In embodiments, the design may allow the light to reflect within the wedge until it reaches a transmission window for presentation to the reflective display 8210, where the coating is then configured to enable transmission. The angle of the wedge directs light from an LED lighting system to uniformly irradiate a reflective image display to produce an image that is reflected through the illumination system. By providing light from the light source 8202 such that a wide cone angle of light enters the wedge 8804, different rays of light will reach transmission windows at different locations along the length of the wedge 8804 so that uniform illumination of the surface of the reflective display 8210 is provided and as a result, the image provided to the wearer's eye has uniform brightness as determined by the image content in the image.

In embodiments, the see-through optics system including a planar illumination facility 8208 and reflective display 8210 as described herein may be applied to any head-worn device known to the art, such as including the eyepiece as described herein, but also to helmets (e.g. military helmets, pilot helmets, bike helmets, motorcycle helmets, deep sea helmets, space helmets, and the like) ski goggles, eyewear, water diving masks, dusk masks, respirators, Hazmat head gear, virtual reality headgear, simulation devices, and the like. In addition, the optics system and protective covering associated with the head-worn device may incorporate the optics system in a plurality of ways, including inserting the optics system into the head-worn device in addition to optics and covering traditionally associated with the head-worn device. For instance, the optics system may be included in a ski goggle as a separate unit, providing the user with projected content, but where the optics system doesn't replace any component of the ski goggle, such as the see-through covering of the ski goggle (e.g. the clear or colored plastic covering that is exposed to the outside environment, keeping the wind and snow from the user's eyes). Alternatively, the optics system may replace, at least in part, certain optics traditionally associated with the head-worn gear. For instance, certain optical elements of the transfer optics 8212 may replace the outer lens of an eyewear application. In an example, a beam splitter, lens, or mirror of the transfer optics 8212 could replace the front lens for an eyewear application (e.g. sunglasses), thus eliminating the need for the front lens of the glasses, such as if the curved reflection mirror 8220 is extended to cover the glasses, eliminating the need for the cover lens. In embodiments, the see-through optics system including a planar illumination facility 8208 and reflective display 8210 may be located in the head-worn gear so as to be unobtrusive to the function and aesthetic of the head-worn gear. For example, in the case of eyewear, or more specifically the eyepiece, the optics system may be located in proximity with an upper portion of the lens, such as in the upper portion of the frame.

In embodiments, the optical assembly may be used in configurations such as a head or helmet mounted display, and/or further may comprise a single lens, binocular, holographic binocular, helmet visor, head mounted display with mangin mirror, integrated helmet and display sighting system, helmet integrated display sight system, link advanced head mounted display (AHMD), and multiple micro-display optics. In embodiments, the optical assembly may include a telescopic lens. Such lens may be spectacle mounted or otherwise. Such an embodiment may be beneficial to those with visual impairments. In embodiments, Eli Peli's wide-field Keplerian telescope may be built within the spectacle lens. Such design may use embedded mirrors inside of a carrier lens to fold the optical path and power elements for higher magnification. This may allow the wearer to simultaneously view the magnified and unmagnified field within the eyeglass format. In embodiments, the optical assembly may be used in configurations with the Q-Sight helmet mounted display developed by BAE Systems of London, United Kingdom. Such a configuration may provide heads-up and eyes-out capability delivering situational awareness. Furthermore, various embodiments may use any of the optical assemblies in the configurations as noted above.

A planar illumination facility, also known as an illumination module, may provide light in a plurality of colors including Red-Green-Blue (RGB) light and/or white light. The light from the illumination module may be directed to a 3LCD system, a Digital Light Processing (DLP®) system, a Liquid Crystal on Silicon (LCoS) system, or other micro-display or micro-projection systems. The illumination module may use wavelength combining and nonlinear frequency conversion with nonlinear feedback to the source to provide a source of high-brightness, long-life, speckle-reduced or speckle-free light. Various embodiments of the disclosure may provide light in a plurality of colors including Red-Green-Blue (RGB) light and/or white light. The light from the illumination module may be directed to a 3LCD system, a Digital Light Processing (DLP) system, a Liquid Crystal on Silicon (LCoS) system, or other micro-display or micro-projection systems. The illumination modules described herein may be used in the optical assembly for the eyepiece 100.

One embodiment of the disclosure includes a system comprising a laser, LED or other light source configured to produce an optical beam at a first wavelength, a planar lightwave circuit coupled to the laser and configured to guide the optical beam, and a waveguide optical frequency converter coupled to the planar lightwave circuit, and configured to receive the optical beam at the first wavelength, convert the optical beam at the first wavelength into an output optical beam at a second wavelength. The system may provide optically coupled feedback which is nonlinearly dependent on the power of the optical beam at the first wavelength to the laser.

Another embodiment of the disclosure includes a system comprising a substrate, a light source, such as a laser diode array or one or more LEDs disposed on the substrate and configured to emit a plurality of optical beams at a first wavelength, a planar lightwave circuit disposed on the substrate and coupled to the light source, and configured to combine the plurality of optical beams and produce a combined optical beam at the first wavelength, and a nonlinear optical element disposed on the substrate and coupled to the planar lightwave circuit, and configured to convert the combined optical beam at the first wavelength into an optical beam at a second wavelength using nonlinear frequency conversion. The system may provide optically coupled feedback which is nonlinearly dependent on a power of the combined optical beam at the first wavelength to the laser diode array.

Another embodiment of the disclosure includes a system comprising a light source, such as a semiconductor laser array or one or more LEDs configured to produce a plurality of optical beams at a first wavelength, an arrayed waveguide grating coupled to the light source and configured to combine the plurality of optical beams and output a combined optical beam at the first wavelength, a quasi-phase matching wavelength-converting waveguide coupled to the arrayed waveguide grating and configured to use second harmonic generation to produce an output optical beam at a second wavelength based on the combined optical beam at the first wavelength.

Power may be obtained from within a wavelength conversion device and fed back to the source. The feedback power has a nonlinear dependence on the input power provided by the source to the wavelength conversion device. Nonlinear feedback may reduce the sensitivity of the output power from the wavelength conversion device to variations in the nonlinear coefficients of the device because the feedback power increases if a nonlinear coefficient decreases. The increased feedback tends to increase the power supplied to the wavelength conversion device, thus mitigating the effect of the reduced nonlinear coefficient.

Referring to FIGS. 109A and 109B, a processor 10902 (e.g. a digital signal processor) may provide display sequential frames 10924 for image display through a display component 10928 (e.g. an LCOS display component) of the eyepiece 100. In embodiments, the sequential frames 10924 may be produced with or without a display driver 10912 as an intermediate component between the processor 10902 and the display component 10928. For example, and referring to FIG. 109A, the processor 10902 may include a frame buffer 10904 and a display interface 10908 (e.g. a mobile industry processor interface (MIPI), with a display serial interface (DSI)). The display interface 10908 may provide per-pixel RGB data 10910 to the display driver 10912 as an intermediate component between the processor 10902 and the display component 10928, where the display driver 10912 accepts the per-pixel RGB data 10910 and generates individual full frame display data for red 10918, green 10920, and blue 10922, thus providing the display sequential frames 10924 to the display component 10928. In addition, the display driver 10912 may provide timing signals, such as to synchronize the delivery of the full frames 10918 10920 10922 as display sequential frames 10924 to the display component 10928. In another example, and referring to FIG. 109B, the display interface 10930 may be configured to eliminate the display driver 10912 by providing full frame display data for red 10934, green 10938, and blue 10940 directly to the display component 10928 as display sequential frames 10924. In addition, timing signals 10932 may be provided directly from the display interface 10930 to the display components. This configuration may provide significantly lower power consumption by removing the need for a display driver. Not only may this direct panel information remove the need for a driver, but also may simplify the overall logic of the configuration, and remove redundant memory required to reform panel information from pixels, to generate pixel information from frame, and the like.

FIG. 89 is a block diagram of an illumination module, according to an embodiment of the disclosure. Illumination module 8900 comprises an optical source, a combiner, and an optical frequency converter, according to an embodiment of the disclosure. An optical source 8902, 8904 emits optical radiation 8910, 8914 toward an input port 8922, 8924 of a combiner 8906. Combiner 8906 has a combiner output port 8926, which emits combined radiation 8918. Combined radiation 8918 is received by an optical frequency converter 8908, which provides output optical radiation 8928. Optical frequency converter 8908 may also provide feedback radiation 8920 to combiner output port 8926. Combiner 8906 splits feedback radiation 8920 to provide source feedback radiation 8912 emitted from input port 8922 and source feedback radiation 8916 emitted from input port 8924. Source feedback radiation 8912 is received by optical source 8902, and source feedback radiation 8916 is received by optical source 8904. Optical radiation 8910 and source feedback radiation 8912 between optical source 8902 and combiner 8906 may propagate in any combination of free space and/or guiding structure (e.g., an optical fiber or any other optical waveguide). Optical radiation 8914, source feedback radiation 8916, combined radiation 8918 and feedback radiation 8920 may also propagate in any combination of free space and/or guiding structure.

Suitable optical sources 8902 and 8904 include one or more LEDs or any source of optical radiation having an emission wavelength that is influenced by optical feedback. Examples of sources include lasers, and may be semiconductor diode lasers. For example, optical sources 8902 and 8904 may be elements of an array of semiconductor lasers. Sources other than lasers may also be employed (e.g., an optical frequency converter may be used as a source). Although two sources are shown on FIG. 89, the disclosure may also be practiced with more than two sources. Combiner 8906 is shown in general terms as a three port device having ports 8922, 8924, and 8926. Although ports 8922 and 8924 are referred to as input ports, and port 8926 is referred to as a combiner output port, these ports may be bidirectional and may both receive and emit optical radiation as indicated above.

Combiner 8906 may include a wavelength dispersive element and optical elements to define the ports. Suitable wavelength dispersive elements include arrayed waveguide gratings, reflective diffraction gratings, transmissive diffraction gratings, holographic optical elements, assemblies of wavelength-selective filters, and photonic band-gap structures. Thus, combiner 8906 may be a wavelength combiner, where each of the input ports has a corresponding, non-overlapping input port wavelength range for efficient coupling to the combiner output port.

Various optical processes may occur within optical frequency converter 8908, including but not limited to harmonic generation, sum frequency generation (SFG), second harmonic generation (SHG), difference frequency generation, parametric generation, parametric amplification, parametric oscillation, three-wave mixing, four-wave mixing, stimulated Raman scattering, stimulated Brillouin scattering, stimulated emission, acousto-optic frequency shifting and/or electro-optic frequency shifting.

In general, optical frequency converter 8908 accepts optical inputs at an input set of optical wavelengths and provides an optical output at an output set of optical wavelengths, where the output set differs from the input set.

Optical frequency converter 8908 may include nonlinear optical materials such as lithium niobate, lithium tantalate, potassium titanyl phosphate, potassium niobate, quartz, silica, silicon oxynitride, gallium arsenide, lithium borate, and/or beta-barium borate. Optical interactions in optical frequency converter 8908 may occur in various structures including bulk structures, waveguides, quantum well structures, quantum wire structures, quantum dot structures, photonic bandgap structures, and/or multi-component waveguide structures.

In cases where optical frequency converter 8908 provides a parametric nonlinear optical process, this nonlinear optical process is preferably phase-matched. Such phase-matching may be birefringent phase-matching or quasi-phase-matching. Quasi-phase matching may include methods disclosed in U.S. Pat. No. 7,116,468 to Miller, the disclosure of which is hereby incorporated by reference.

Optical frequency converter 8908 may also include various elements to improve its operation, such as a wavelength selective reflector for wavelength selective output coupling, a wavelength selective reflector for wavelength selective resonance, and/or a wavelength selective loss element for controlling the spectral response of the converter.

In embodiments, multiple illumination modules as described in FIG. 89 may be associated to form a compound illumination module.

One component of the illumination module may be a diffraction grating, or grating, as further described herein. A diffraction grating plate may be less than 1 mm thick but may still be rigid enough to bond in place permanently or replace cover glass of the LCOS. One advantage of using the grating in the illumination module is that it would use laser illumination sources to increase efficiency and reduce power. The grating may have inherently less stray light and due to the narrow band, would enable more options for filtering out eye glow with less reduction of the see through brightness.

FIG. 90 is a block diagram of an optical frequency converter, according to an embodiment of the disclosure. FIG. 90 illustrates how feedback radiation 8920 is provided by an exemplary optical frequency converter 8908 which provides parametric frequency conversion. Combined radiation 8918 provides forward radiation 9002 within optical frequency converter 8908 that propagates to the right on FIG. 90, and parametric radiation 9004, also propagating to the right on FIG. 90, is generated within optical frequency converter 8908 and emitted from optical frequency converter 8908 as output optical radiation 8928. Typically there is a net power transfer from forward radiation 9002 to parametric radiation 9004 as the interaction proceeds (i.e., as the radiation propagates to the right in this example). A reflector 9008, which may have wavelength-dependent transmittance, is disposed in optical frequency converter 8908 to reflect (or partially reflect) forward radiation 9002 to provide backward radiation 9006 or may be disposed externally to optical frequency converter 8908 after endface 9010. Reflector 9008 may be a grating, an internal interface, a coated or uncoated endface, or any combination thereof. The preferred level of reflectivity for reflector 9008 is greater than 90%. A reflector located at an input interface 9012 provides purely linear feedback (i.e., feedback that does not depend on the process efficiency). A reflector located at an endface 9010 provides a maximum degree of nonlinear feedback, since the dependence of forward power on process efficiency is maximized at the output interface (assuming a phase-matched parametric interaction).

FIG. 91 is a block diagram of a laser illumination module, according to an embodiment of the disclosure. While lasers are used in this embodiment, it is understood that other light sources, such as LEDs, may also be used. Laser illumination module 9100 comprises an array of diode lasers 9102, waveguides 9104 and 9106, star couplers 9108 and 9110 and optical frequency converter 9114. An array of diode lasers 9102 has lasing elements coupled to waveguides 9104 acting as input ports (such as ports 8922 and 8924 on FIG. 89) to a planar waveguide star coupler 9108. Star coupler 9108 is coupled to another planar waveguide star coupler 9110 by waveguides 9106 which have different lengths. The combination of star couplers 9108 and 9110 with waveguides 9106 may be an arrayed waveguide grating, and acts as a wavelength combiner (e.g., combiner 8906 on FIG. 89) providing combined radiation 8918 to waveguide 9112. Waveguide 9112 provides combined radiation 8918 to optical frequency converter 9114. Within optical frequency converter 9114, an optional reflector 9116 provides a back reflection of combined radiation 8918. As indicated above in connection with FIG. 90, this back reflection provides nonlinear feedback according to embodiments of the disclosure. One or more of the elements described with reference to FIG. 91 may be fabricated on a common substrate using planar coating methods and/or lithography methods to reduce cost, parts count and alignment requirements.

A second waveguide may be disposed such that its core is in close proximity with the core of the waveguide in optical frequency converter 8908. As is known in the art, this arrangement of waveguides functions as a directional coupler, such that radiation in waveguide may provide additional radiation in optical frequency converter 8908. Significant coupling may be avoided by providing radiation at wavelengths other than the wavelengths of forward radiation 9002 or additional radiation may be coupled into optical frequency converter 8908 at a location where forward radiation 9002 is depleted.

While standing wave feedback configurations where the feedback power propagates backward along the same path followed by the input power are useful, traveling wave feedback configurations may also be used. In a traveling wave feedback configuration, the feedback re-enters the gain medium at a location different from the location at which the input power is emitted from.

Figure 92:
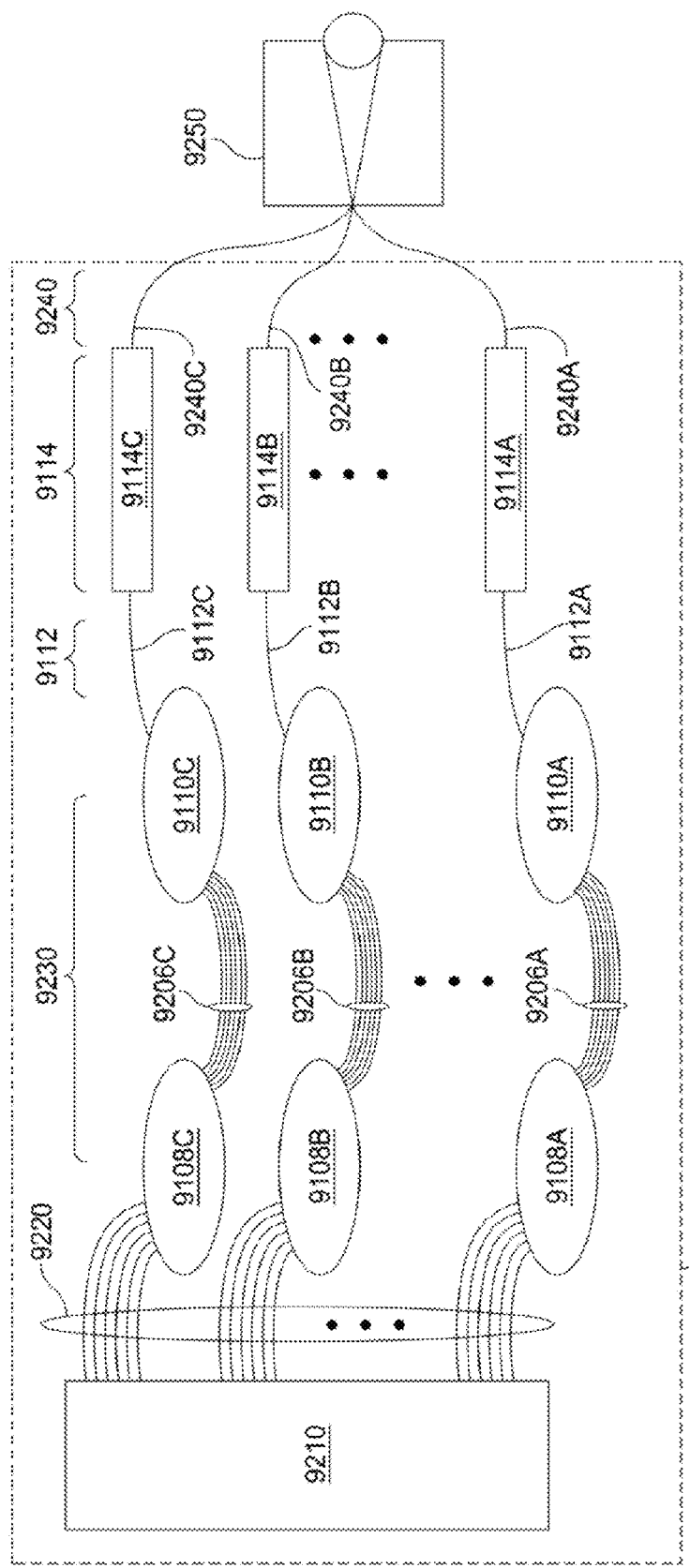
FIG. 92 depicts a block diagram of a laser illumination system, according to another embodiment of the disclosure.

FIG. 92 is a block diagram of a compound laser illumination module, according to another embodiment of the disclosure. Compound laser illumination module 9200 comprises one or more laser illumination modules 9100 described with reference to FIG. 91. Although FIG. 92 illustrates compound laser illumination module 9200 including three laser illumination modules 9100 for simplicity, compound laser illumination module 9200 may include more or fewer laser illumination modules 9100. An array of diode lasers 9210 may include one or more arrays of diode lasers 9102 which may be an array of laser diodes, a diode laser array, and/or a semiconductor laser array configured to emit optical radiation within the infrared spectrum, i.e., with a wavelength shorter than radio waves and longer than visible light.

Laser array output waveguides 9220 couple to the diode lasers in the array of diode lasers 9210 and directs the outputs of the array of diode lasers 9210 to star couplers 9108A-C. The laser array output waveguides 9220, the arrayed waveguide gratings 9230, and the optical frequency converters 9114A-C may be fabricated on a single substrate using a planar lightwave circuit, and may comprise silicon oxynitride waveguides and/or lithium tantalate waveguides.

Arrayed waveguide gratings 9230 comprise the star couplers 9108A-C, waveguides 9106A-C, and star couplers 9110A-C. Waveguides 9112A-C provide combined radiation to optical frequency converters 9114A-C and feedback radiation to star couplers 9110A-C, respectively.

Optical frequency converters 9114A-C may comprise nonlinear optical (NLO) elements, for example optical parametric oscillator elements and/or quasi-phase matched optical elements.

Compound laser illumination module 9200 may produce output optical radiation at a plurality of wavelengths. The plurality of wavelengths may be within a visible spectrum, i.e., with a wavelength shorter than infrared and longer than ultraviolet light. For example, waveguide 9240A may similarly provide output optical radiation between about 450 nm and about 470 nm, waveguide 9240B may provide output optical radiation between about 525 nm and about 545 nm, and waveguide 9240C may provide output optical radiation between about 615 nm and about 660 nm. These ranges of output optical radiation may again be selected to provide visible wavelengths (for example, blue, green and red wavelengths, respectively) that are pleasing to a human viewer, and may again be combined to produce a white light output.

The waveguides 9240A-C may be fabricated on the same planar lightwave circuit as the laser array output waveguides 9220, the arrayed waveguide gratings 9230, and the optical frequency converters 9114A-C. In some embodiments, the output optical radiation provided by each of the waveguides 9240A-C may provide an optical power in a range between approximately 1 watts and approximately 20 watts.

The optical frequency converter 9114 may comprise a quasi-phase matching wavelength-converting waveguide configured to perform second harmonic generation (SHG) on the combined radiation at a first wavelength, and generate radiation at a second wavelength. A quasi-phase matching wavelength-converting waveguide may be configured to use the radiation at the second wavelength to pump an optical parametric oscillator integrated into the quasi-phase matching wavelength-converting waveguide to produce radiation at a third wavelength, the third wavelength optionally different from the second wavelength. The quasi-phase matching wavelength-converting waveguide may also produce feedback radiation propagated via waveguide 9112 through the arrayed waveguide grating 9230 to the array of diode lasers 9210, thereby enabling each laser disposed within the array of diode lasers 9210 to operate at a distinct wavelength determined by a corresponding port on the arrayed waveguide grating.

For example, compound laser illumination module 9200 may be configured using an array of diode lasers 9210 nominally operating at a wavelength of approximately 830 nm to generate output optical radiation in a visible spectrum corresponding to any of the colors red, green, or blue.

Compound laser illumination module 9200 may be optionally configured to directly illuminate spatial light modulators without intervening optics. In some embodiments, compound laser illumination module 9200 may be configured using an array of diode lasers 9210 nominally operating at a single first wavelength to simultaneously produce output optical radiation at multiple second wavelengths, such as wavelengths corresponding to the colors red, green, and blue. Each different second wavelength may be produced by an instance of laser illumination module 9100.

The compound laser illumination module 9200 may be configured to produce diffraction-limited white light by combining output optical radiation at multiple second wavelengths into a single waveguide using, for example, waveguide-selective taps (not shown).

The array of diode lasers 9210, laser array output waveguides 9220, arrayed waveguide gratings 9230, waveguides 9112, optical frequency converters 9114, and frequency converter output waveguides 9240 may be fabricated on a common substrate using fabrication processes such as coating and lithography. The beam shaping element 9250 is coupled to the compound laser illumination module 9200 by waveguides 9240A-C, described with reference to FIG. 92.

Beam shaping element 9250 may be disposed on a same substrate as the compound laser illumination module 9200. The substrate may, for example, comprise a thermally conductive material, a semiconductor material, or a ceramic material. The substrate may comprise copper-tungsten, silicon, gallium arsenide, lithium tantalate, silicon oxynitride, and/or gallium nitride, and may be processed using semiconductor manufacturing processes including coating, lithography, etching, deposition, and implantation.

Some of the described elements, such as the array of diode lasers 9210, laser array output waveguides 9220, arrayed waveguide gratings 9230, waveguides 9112, optical frequency converters 9114, waveguides 9240, beam shaping element 9250, and various related planar lightwave circuits may be passively coupled and/or aligned, and in some embodiments, passively aligned by height on a common substrate. Each of the waveguides 9240A-C may couple to a different instance of beam shaping element 9250, rather than to a single element as shown.

Beam shaping element 9250 may be configured to shape the output optical radiation from waveguides 9240A-C into an approximately rectangular diffraction-limited optical beam, and may further configure the output optical radiation from waveguides 9240A-C to have a brightness uniformity greater than approximately 95% across the approximately rectangular beam shape.

The beam shaping element 9250 may comprise an aspheric lens, such as a "top-hat" microlens, a holographic element, or an optical grating. In some embodiments, the diffraction-limited optical beam output by the beam shaping element 9250 produces substantially reduced or no speckle. The optical beam output by the beam shaping element 9250 may provide an optical power in a range between approximately 1 watt and approximately 20 watts, and a substantially flat phase front.

Figure 93:
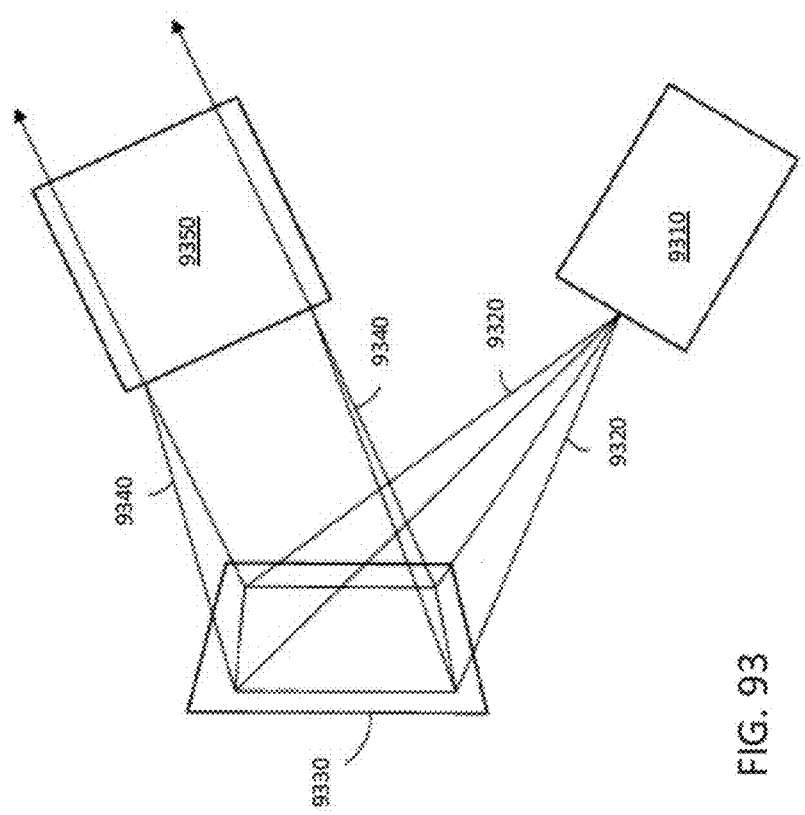
FIG. 93 depicts a block diagram of an imaging system, according to an embodiment of the disclosure.

FIG. 93 is a block diagram of an imaging system, according to an embodiment of the disclosure. Imaging system 9300 comprises light engine 9310, optical beams 9320, spatial light modulator 9330, modulated optical beams 9340, and projection lens 9350. The light engine 9310 may be a compound optical illumination module, such as multiple illumination modules described in FIG. 89, a compound laser illumination module 9200, described with reference to FIG. 92, or a laser illumination system 9300, described with reference to FIG. 93. Spatial light modulator 9330 may be a 3LCD system, a DLP system, a LCoS system, a transmissive liquid crystal display (e.g. transmissive LCoS), a liquid-crystal-on-silicon array, a grating-based light valve, or other micro-display or micro-projection system or reflective display.

The spatial light modulator 9330 may be configured to spatially modulate the optical beam 9320. The spatial light modulator 9330 may be coupled to electronic circuitry configured to cause the spatial light modulator 9330 to modulate a video image, such as may be displayed by a television or a computer monitor, onto the optical beam 9320 to produce a modulated optical beam 9340. In some embodiments, modulated optical beam 9340 may be output from the spatial light modulator on a same side as the spatial light modulator receives the optical beam 9320, using optical principles of reflection. In other embodiments, modulated optical beam 9340 may be output from the spatial light modulator on an opposite side as the spatial light modulator receives the optical beam 9320, using optical principles of transmission. The modulated optical beam 9340 may optionally be coupled into a projection lens 9350. The projection lens 9350 is typically configured to project the modulated optical beam 9340 onto a display, such as a video display screen.

A method of illuminating a video display may be performed using a compound illumination module such as one comprising multiple illumination modules 8900, a compound laser illumination module 9100, a laser illumination system 9200, or an imaging system 9300. A diffraction-limited output optical beam is generated using a compound illumination module, compound laser illumination module 9100, laser illumination system 9200 or light engine 9310. The output optical beam is directed using a spatial light modulator, such as spatial light modulator 9330, and optionally projection lens 9350. The spatial light modulator may project an image onto a display, such as a video display screen.

The illumination module may be configured to emit any number of wavelengths including one, two, three, four, five, six, or more, the wavelengths spaced apart by varying amounts, and having equal or unequal power levels. An illumination module may be configured to emit a single wavelength per optical beam, or multiple wavelengths per optical beam. An illumination module may also comprise additional components and functionality including polarization controller, polarization rotator, power supply, power circuitry such as power FETs, electronic control circuitry, thermal management system, heat pipe, and safety interlock. In some embodiments, an illumination module may be coupled to an optical fiber or a lightguide, such as glass (e.g. BK7).

Some options for an LCoS front light design include: 1) Wedge with MultiLayer Coating (MLC). This concept uses MLC to define specific reflected and transmitted angles.; 2) Wedge with polarized beamsplitter coating. This concept works like a regular PBS Cube, but at a much shallower angle. This can be PBS coating or a wire grid film.; 3) PBS Prism bars (these are similar to Option #2) but have a seam down the center of the panel.; 4) Wire Grid Polarizer plate beamsplitter (similar to the PBS wedge, but just a plate, so that it is mostly air instead of solid glass); and 5) a polarizing beamsplitter (PBS) comprising a flexible film, such as a 3M polarizing beamsplitter made of alternating layers of different plastics with the refractive indices tailored so that they match in one in-plane direction but not the other. In the unmatched direction, a highly reflective quarter-wave stack is formed, while in the matched direction the film acts as a transparent slab of plastic. This film is laminated between glass prisms to form a wide angle PBS that provides high performance for a fast beam throughout the visible range. The MLC wedge may be rigid and may be robustly glued in place with no air gaps for condensation or thermal deflection. It may work with a broadband LED light source. In embodiments, the MLC wedge may replace the cover glass of the LCOS for a complete module. The MLC wedge may be about less than 4 mm thick. In an embodiment, the MLC wedge may be 2 mm thick or less.

It is to be understood that the present disclosure provides the employment of the frontlighting systems as have been described herein in all types of optical configurations that may include, but do not necessarily include, an augmented reality eyepiece. The frontlighting systems may be used as a component in any type of optical system as a source of direct or indirect illumination, and are particularly preferred for illumination of any type or types of optical element, optical surface, or optical sensor, most preferably those which have a selectively configurable optical path, e.g., such as LCoS or liquid crystal displays, and/or reflect light. In some embodiments, at least some of the light produced by the frontlighting system will be reflected so as to pass back through a portion of the frontlighting system on its way to its final destination, e.g., an eye, a light sensor, etc., while in other embodiments none of the produced light passes back through the frontlighting system on its way to its final destination. For example, the frontlighting system may illuminate an optical device such as an LCoS to create image light which may be directed back through a component of the frontlighting system and thereafter pass through one or more additional optical systems that condition the image light for ultimate reception by a user's eye. Such other optical systems may be, or include among their components, one or more of a waveguide (which may be a freeform waveguide), a beam splitter, a collimator, a polarizer, a mirror, a lens, and a diffraction grating.

FIG. 95 depicts an embodiment of an LCoS front light design. In this embodiment, light from an RGB LED 9508 illuminates a front light 9504, which can be a wedge, PBS, and the like. The light strikes a polarizer 9510 and is transmitted in its S state to an LCoS 9502 where it gets reflected as image light in its P state back through an asphere 9512. An inline polarizer 9514 may polarize the image light again and/or cause a ½ wave rotation to the S state. The image light then hits a wire grid polarizer 9520 and reflects to a curved (spherical) partial mirror 9524, passing through a ½ wave retarder 9522 on its way. The image light reflects from the mirror to the user's eye 9518, once more traversing the ½ wave retarder 9522 and wire grid polarizer 9520. Various examples of the front light 9504 will now be described.

In embodiments, the optical assembly includes a partially reflective, partially transmitting optical element that reflects respective portions of image light from the image source and transmits scene light from a see-through view of the surrounding environment, so that a combined image comprised of portions of the reflected image light and the transmitted scene light is provided to a user's eye.

In portable display systems, it is important to provide a display that is bright, compact and light in weight. Portable display systems include cellphone, laptop computers, tablet computers and head mounted displays.

The disclosure provides a compact and lightweight front light for a portable display system comprised of a curved or other non-planar wire grid polarizer film as a partial reflector to efficiently deflect light from an edge light source to illuminate a reflective image source. Wire grid polarizers are known to provide efficient reflection of one polarization state while simultaneously allowing the other polarization state to pass through. While glass plate wire grid polarizers are well known in the industry and a rigid wire grid polarizer can be used in the disclosure, in a preferred embodiment of the present disclosure a flexible wire grid polarizer film is used for the curved wire grid polarizer. Suitable wire grid polarizer film is available from Asahi-Kasei E-materials Corp, Tokyo Japan.

An edge light provides a compact form of lighting for a display, but since it is located at the edge of the image source, the light must be deflected by 90 degrees to illuminate the image source. In an embodiment of the disclosure, a curved wire grid polarizer film is used as a partially reflective surface to deflect the light provided by the edge light source downward to illuminate the reflective image source. A polarizer is provided adjacent to the edge light source to polarize the illumination light provided to the curved wire grid polarizer. The polarizer and the wire grid polarizer are oriented such that the light passing through the polarizer is reflected by the wire grid polarizer. Due to the quarter wave retarder film that is included in the reflective image source, the polarization of the reflected image light is the opposite polarization state compared to the illumination light. As such, the reflected image light passes through the wire grid polarizer film and continues to the display optics. By using a flexible wire grid polarizer film as a partial reflector, the partially reflective surface can be curved in a lightweight structure where the wire grid polarizer performs the dual role of being a reflector for the illumination light and a transparent member for the image light. An advantage provided by the wire grid polarizer film is that it can receive image light over a wide range of incident angles so that the curve doesn't interfere with the image light passing through to the display optics. In addition, since the wire grid polarizer film is thin (e.g. less than 200 micron), the curved shape doesn't noticeably distort the image light as it passes through to the display optics. Finally, the wire grid polarizer has a very low tendency to scatter light so high image contrast can be maintained.

FIG. 136 shows a schematic drawing of the frontlighted image source 13600 of the present disclosure. The edge light source 13602 provides illumination light that passes through a polarizer 13614 so that the illumination light 13610 is polarized, where the polarizer 13614 can be an absorptive polarizer or a reflective polarizer. The polarizer is oriented so that the polarization state of the illumination light 13610 is such that the light is reflected by the curved wire grid polarizer 13608, thereby deflecting the illumination light 13610 downwards toward the reflective image source 13604. Thus, the passing axis of the polarizer 13614 is perpendicular to the passing axis of the wire grid polarizer 13608. It will be noted by those skilled in the art that while FIG. 136 shows the frontlighted image source 13600 oriented horizontally, other orientations are equally possible. As has already been stated, typically reflective image sources such as LCOS image sources, include a quarter wave retarder film so that the polarization state of the illuminating light is changed during the reflection by the reflective image source and as a result the image light has in general the opposite polarization state compared to the illumination light. This change in polarization state is fundamental to the operation of all liquid crystal based displays as is well known to those skilled in the art and as described in U.S. Pat. No. 4,398,805. For individual portions of the image, the liquid crystal element of the reflective image source 13604 will cause more or less change in polarization state so that the reflected image light 13612 before passing through the curved wire grid polarizer has a mixed elliptical polarization state. After passing through the curved wire grid polarizer 13608 and any additional polarizer that can be included in the display optics, the polarization state of the image light 13612 is determined by the curved wire grid polarizer 13608 and the image content contained in the image light 13612 determines the local intensity of the image light 13612 in the image displayed by the portable display system.

The flexible nature of the wire grid polarizer film that is used in the curved wire grid polarizer 13608 allows it to be formed into a shape that focuses the illumination light 13610 onto the reflective image source 13604. The shape of the curve of the curved wire grid polarizer is selected to provide uniform illumination of the reflective image source. FIG. 136 shows a curved wire grid polarizer 13608 with a parabolic shape, but radiused curves, complex splined curves or planes are possible as well to uniformly deflect the illumination light 13610 onto the reflective image source 13604 depending on the nature of the edge light source 13602. Experiments have shown that parabolic, radiused and complex splined curves all provide more uniform illumination than a flat surface. But in some very thin frontlighted image sources, a flat wire grid polarizer film can be used effectively to provide a lightweight portable display system. The shape of the flexible wire grid polarizer film can be maintained with side frames that have shaped slots of the appropriate curve to hold the wire grid polarizer film in place as shown in FIG. 138 which shows a schematic drawing of a frontlighted image source assembly 13800. Side frame 13802 is shown with a curved slot 13804 for the flexible wire grid polarizer film to be held in the desired curved shape. While only one side frame 13802 is shown in FIG. 138, two side frames 13802 would be used to support the curved shape on either side along with the other components of the frontlighted image source. In any case, because a large part of the frontlighted image source that is the disclosure is comprised of air and the wire grid polarizer film is very thin, weight is substantially lower compared to prior art front light systems.

In a further embodiment of the disclosure, a frontlighted image source 13700 is provided with two or more edge light sources 13702 positioned along two or more edges of a reflective image source 13604 as shown in FIG. 137. Polarizers 13712 are provided adjacent to each edge light source 13702 to polarize the illumination light 13708. The illumination light 13708 is deflected by the curved wire grid polarizer 13704 to illuminate the reflective image source 13604. The reflected image light 13710 then passes through the curved wire grid polarizer 13704 and on to the display optics. The advantage of using two or more edge light sources 13702 is that more light can be applied to the reflective image source 13604 thereby providing for brighter images.

The edge light source can be a fluorescent light, an incandescent light, an organic light emitting diode, a laser or an electroluminescent light. In a preferred embodiment of the disclosure, the edge light source is an array of 3 or more light emitting diodes. To uniformly illuminate the reflective image source, the edge light source should have a substantial cone angle, for example the edge light source can be a Lambertian light source. For the case of a laser light source, the cone angle of the light would need to be expanded. By using an array of light sources or multiple edge light sources, the distribution of light onto the reflective image source can be adjusted to provide more uniform illumination and as a result, the brightness of the displayed image can be made to be more uniform.

The image light provided by the frontlighted image source of the disclosure passes into display optics for the portable display system. Various display optics are possible depending on how the displayed image is to be used. For example, the display optics can be dispersive when the display is a flat screen display or alternately the display optics can be refractive or diffractive when the display is a near eye display or a head mounted display.

FIG. 139 is a flowchart of the method of the disclosure for the portable display system with a reflective image source. In Step 13900, polarized illumination light is provided to one or more edges of the reflective image source. In Step 13902, the curved wire grid polarizer receives the illumination light and deflects it to illuminate the reflective image source, wherein the curve of the wire grid polarizer is selected to improve the uniformity of illumination of the area of the reflective image source. In Step 13904, the reflective image source receives the illumination light, reflecting the illumination light and simultaneously changing the polarization state of the illumination light in correspondence to the image being displayed. The image light then passes through the curved wire grid polarizer in Step 13908 and passes into the display optics. In Step 13910, the image is displayed by the portable display system.

In embodiments, a lightweight portable display system with a reflective liquid crystal image source for displaying an image may comprise one or more edge light sources providing polarized illumination light adjacent to one or more edges of the reflective liquid crystal image source, a curved wire grid polarizer partial reflector that may receive the polarized illumination light and may deflect it to illuminate the reflective liquid crystal image source, and display optics that receive reflected image light from the reflective liquid crystal image source and display the image. Further, the one or more ledge light sources may comprise a light emitting diode. In embodiments, the wire grid polarizer may be a flexible film, and the flexible film may be held in a curved shape by side frames. In embodiments, the curved wire grid polarizer of the display system may be parabolic, radiused or complex splined curve. Further, the reflective liquid crystal image source of the display system may be an LCOS. In embodiments, the display optics of the display system may comprise diffusers and the display system may be a flat screen display. In embodiments, the display optics of the display system may comprise refractive or diffractive elements and the display system may be a near eye display or a head mounted display.

In embodiments, a method for providing and image on a lightweight portable display system with a reflective liquid crystal image source may comprise providing polarized illumination light to one or more edges of the reflective liquid crystal image source, receiving the illumination light with a curved wire grid polarizer and deflecting the light to illuminate the reflective liquid crystal image source, reflecting and changing the polarization state of the illumination light relative to the image to be displayed with the reflective liquid crystal image source to provide image light, passing the image light through the curved wire grid polarizer, receiving the image light with display optics, and displaying the image. In embodiments of the method, the curved shape of the curved wire grid polar may be selected to improve uniformity of illumination of the reflective liquid crystal image source. Further, the one or more edge light sources may comprise a light emitting diode. In embodiments, the wire grid polarizer may be a flexible film. Further, the flexible film may be held in a curved shape by side frames. In embodiments of the method, the cured wire grid polarizer may be a parabolic radiused or complex splined curve. Further, the embodiments of the above method, the reflexive liquid crystal image source may be an LCOS. In embodiments, the display optics may comprise diffusers and the display system may be a flat screen display. In embodiments of the method above, the display optics may comprise refractive or diffractive elements and the display system may be a near eye display or a head mounted display.

Figure 96:
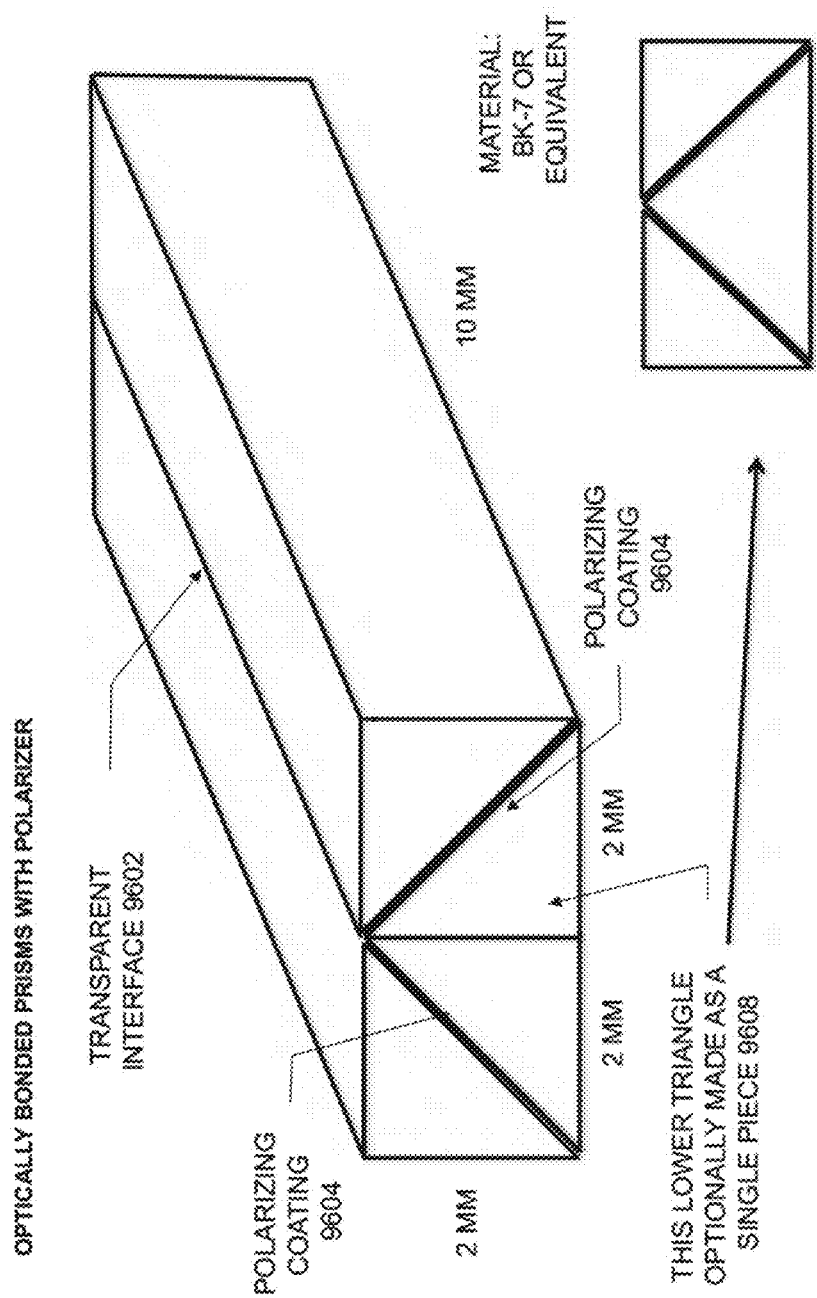
FIG. 96 depicts optically bonded prisms with a polarizer.
Figure 97:
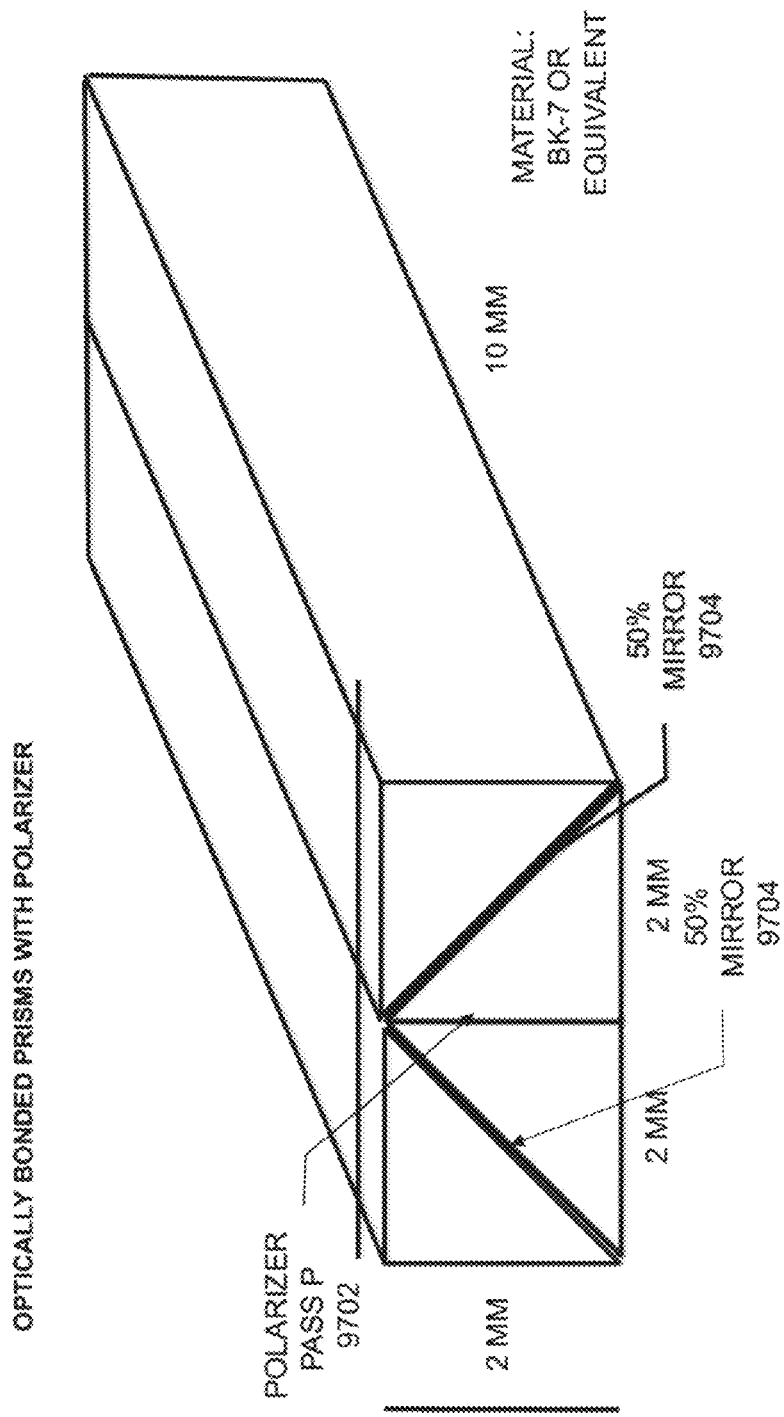
FIG. 97 depicts optically bonded prisms with a polarizer.

FIG. 96 depicts an embodiment of a front light 9504 comprising optically bonded prisms with a polarizer. The prisms appear as two rectangular solids with a substantially transparent interface 9602 between the two. Each rectangular is diagonally bisected and a polarizing coating 9604 is disposed along the interface of the bisection. The lower triangle formed by the bisected portion of the rectangular solid may optionally be made as a single piece 9608. The prisms may be made from BK-7 or the equivalent. In this embodiment, the rectangular solids have square ends that measure 2 mm by 2 mm. The length of the solids in this embodiment is 10 mm. In an alternate embodiment, the bisection comprises a 50% mirror 9704 surface and the interface between the two rectangular solids comprises a polarizer 9702 that may pass light in the P state.

FIGS. 98A, 98B and 98C depict three versions of an LCoS front light design. FIG. 98A depicts a wedge with MultiLayer Coating (MLC). This concept uses MLC to define specific reflected and transmitted angles. In this embodiment, image light of either P or S polarization state is observed by the user's eye. FIG. 98B depicts a PBS with a polarizer coating. Here, only S-polarized image light is transmitted to the user's eye. FIG. 98C depicts a right angle prism, eliminating much of the material of the prism enabling the image light to be transmitted through air as S-polarized light.

FIG. 99 depicts a wedge plus PBS with a polarizing coating 9902 layered on an LCoS 9904.

Figure 100A:
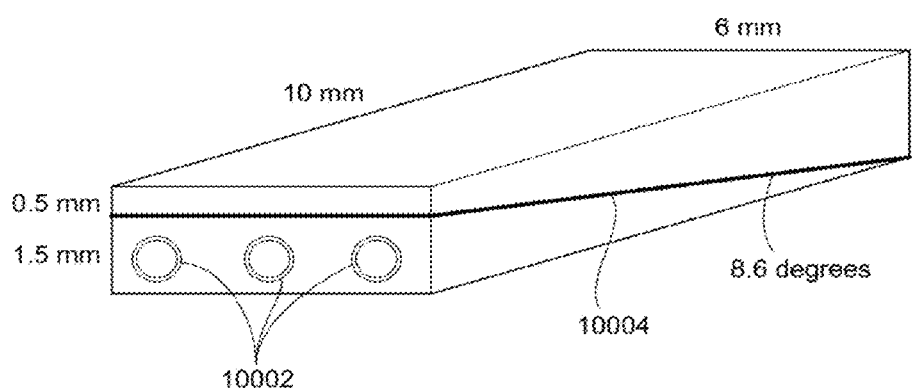
FIGS. 100A and 100B depict two versions of a wedge.
Figure 100B:
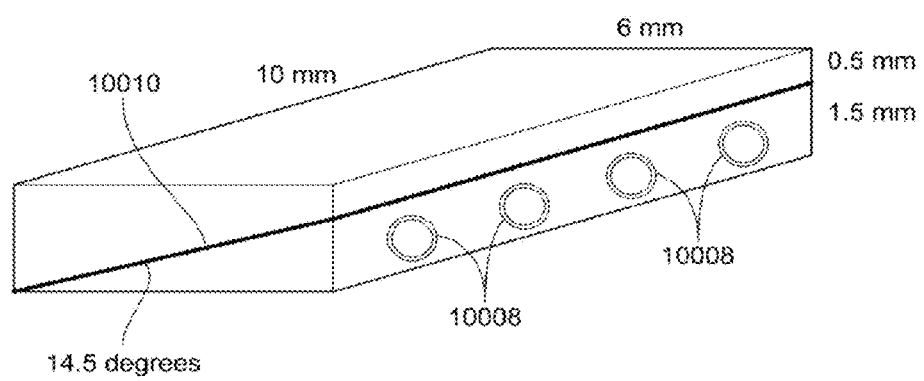

FIGS. 100A-100B depict two embodiments of prisms with light entering the short end (A) and light entering along the long end (B). In FIG. 100A, a wedge is formed by offset bisecting a rectangular solid to form at least one 8.6 degree angle at the bisect interface. In this embodiment, the offset bisection results in a segment that is 0.5 mm high and another that is 1.5 mm on the side through which the RGB LEDs 10002 are transmitting light. Along the bisection, a polarizing coating 10004 is disposed. In FIG. 100B, a wedge is formed by offset bisecting a rectangular solid to form at least one 14.3 degree angle at the bisect interface. In this embodiment, the offset bisection results in a segment that is 0.5 mm high and another that is 1.5 mm on the side through which the RGB LEDs 10008 are transmitting light. Along the bisection, a polarizing coating 10010 is disposed.

FIG. 101 depicts a curved PBS film 10104 illuminated by an RGB LED 10102 disposed over an LCoS chip 10108. The PBS film 10104 reflects the RGB light from the LED array 10102 onto the LCOS chip's surface 10108, but lets the light reflected from the imaging chip pass through unobstructed to the optical assembly and eventually to the user's eye. Films used in this system include Asahi Film, which is a Tri-Acetate Cellulose or cellulose acetate substrate (TAC). In embodiments, the film may have UV embossed corrugations at 100 nm and a calendared coating built up on ridges that can be angled for incidence angle of light. The Asahi film may come in rolls that are 20 cm wide by 30 m long and has BEF properties when used in LCD illumination. The Asahi film may support wavelengths from visible through IR and may be stable up to 100° C.

Figure 21:
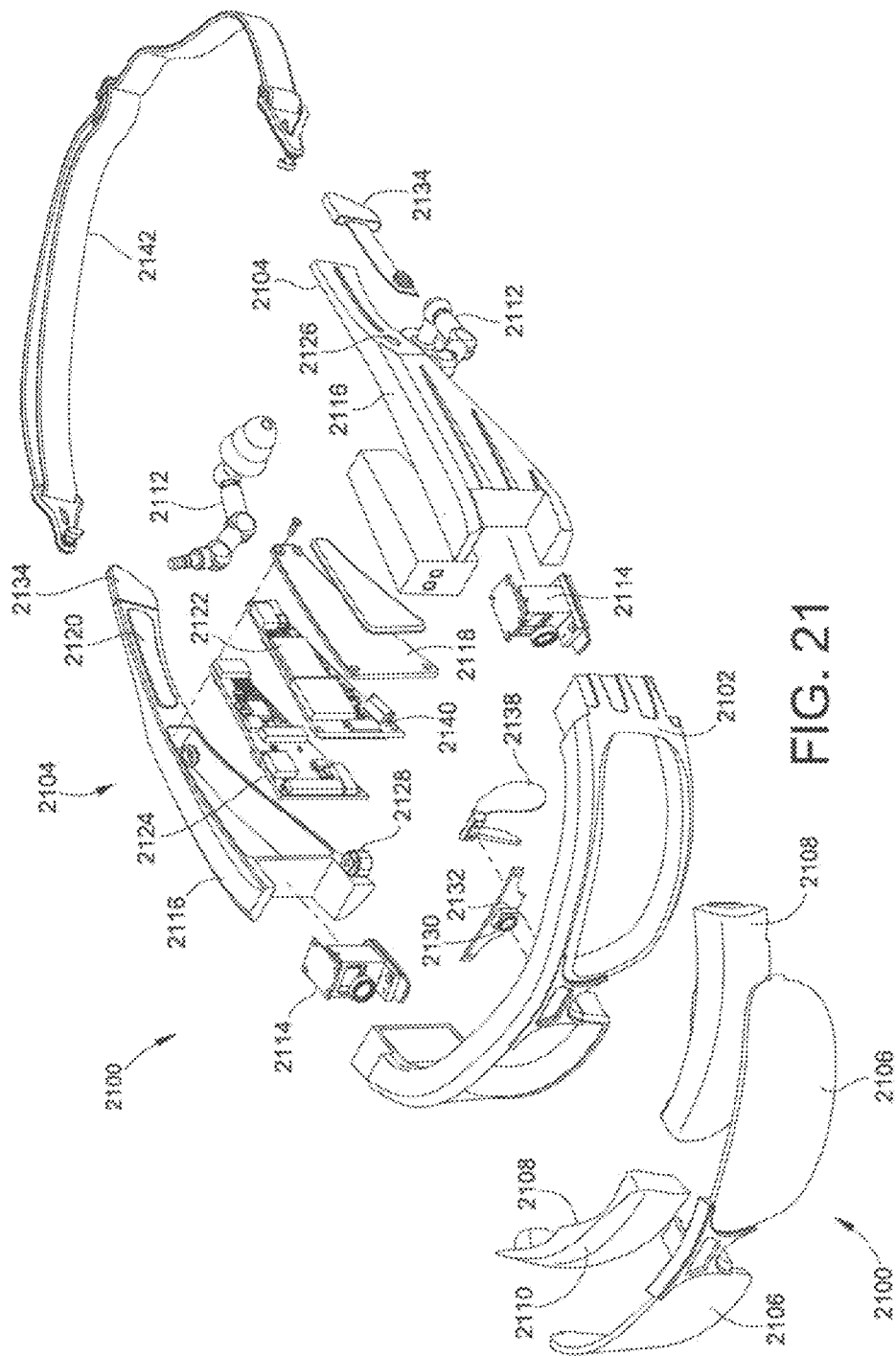
FIG. 21 depicts an alternative arrangement of the eyepiece optics and electronics.
Figure 22:
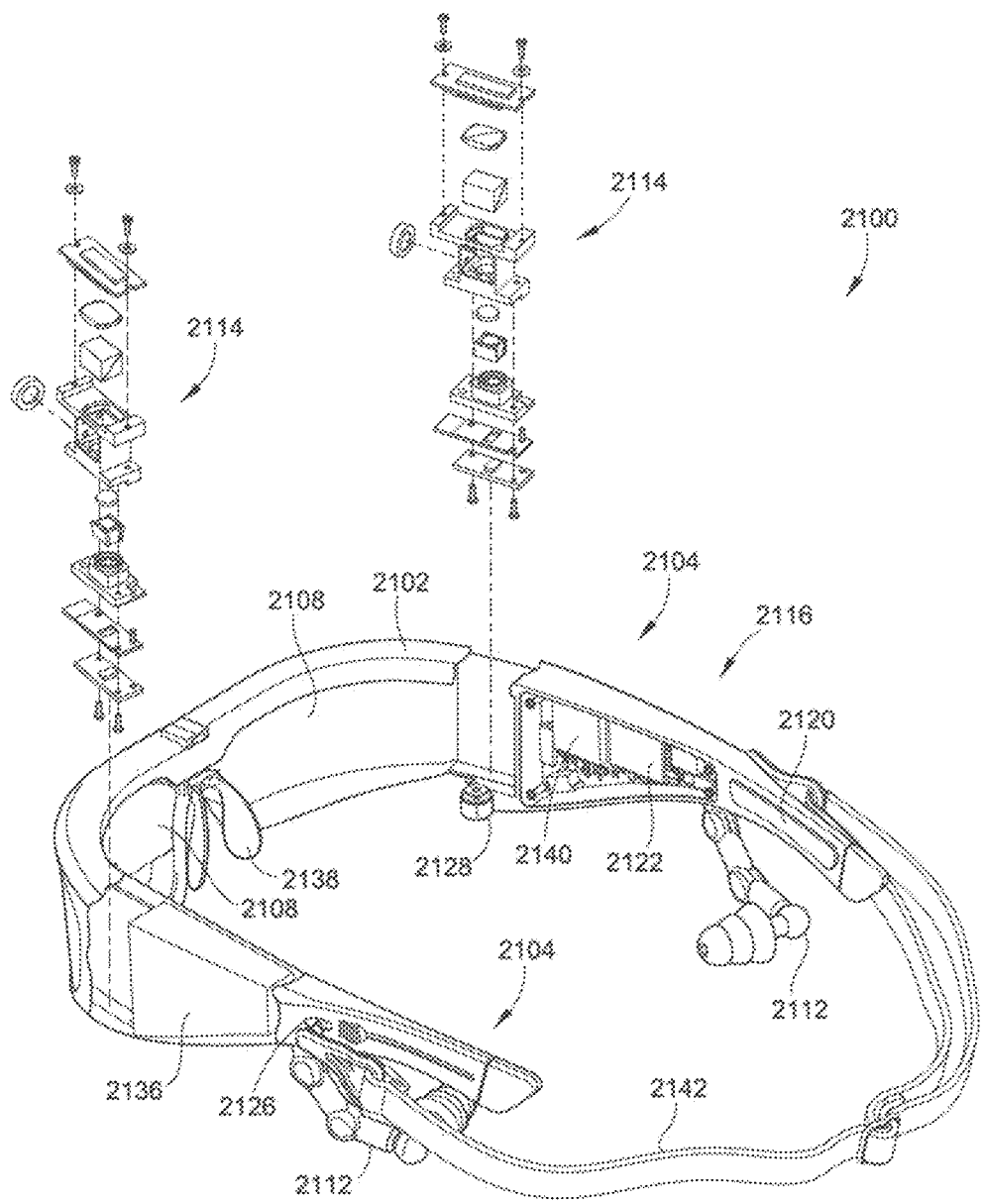
FIG. 22 depicts an alternative arrangement of the eyepiece optics and electronics.

In another embodiment, FIGS. 21 and 22 depict an alternate arrangement of the waveguide and projector in exploded view. In this arrangement, the projector is placed just behind the hinge of the arm of the eyepiece and it is vertically oriented such that the initial travel of the RGB LED signals is vertical until the direction is changed by a reflecting prism in order to enter the waveguide lens. The vertically arranged projection engine may have a PBS 218 at the center, the RGB LED array at the bottom, a hollow, tapered tunnel with thin film diffuser to mix the colors for collection in an optic, and a condenser lens. The PBS may have a pre-polarizer on an entrance face. The pre-polarizer may be aligned to transmit light of a certain polarization, such as p-polarized light and reflect (or absorb) light of the opposite polarization, such as s-polarized light. The polarized light may then pass through the PBS to the field lens 216. The purpose of the field lens 216 may be to create near telecentric illumination of the LCoS panel. The LCoS display may be truly reflective, reflecting colors sequentially with correct timing so the image is displayed properly. Light may reflect from the LCoS panel and, for bright areas of the image, may be rotated to s-polarization. The light then may refract through the field lens 216 and may be reflected at the internal interface of the PBS and exit the projector, heading toward the coupling lens. The hollow, tapered tunnel 220 may replace the homogenizing lenslet from other embodiments. By vertically orienting the projector and placing the PBS in the center, space is saved and the projector is able to be placed in a hinge space with little moment arm hanging from the waveguide.

Figure 22A:
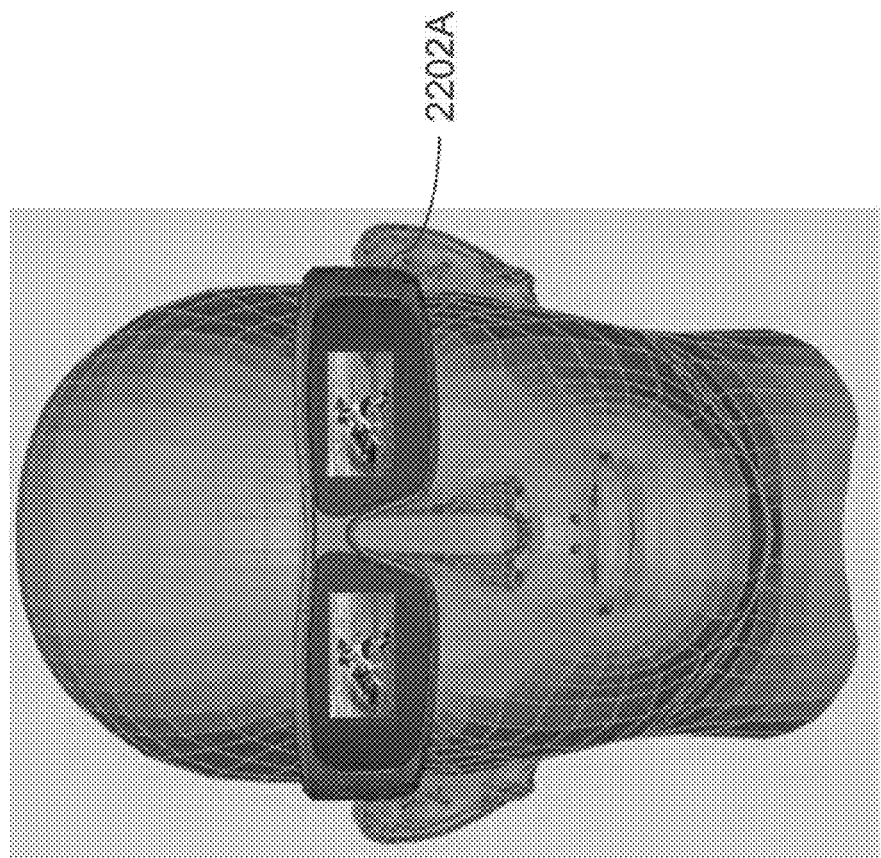
FIG. 22A depicts the eyepiece with an example of eyeglow.

Light reflected or scattered from the image source or associated optics of the eyepiece may pass outward into the environment. These light losses are perceived by external viewers as 'eyeglow' or 'night glow' where portions of the lenses or the areas surrounding the eyepiece appear to be glowing when viewed in a dimly lit environment. In certain cases of eyeglow as shown in FIG. 22A, the displayed image can be seen as an observable image 2202A in the display areas when viewed externally by external viewers. To maintain privacy of the viewing experience for the user both in terms of maintaining privacy of the images being viewed and in terms of making the user less noticeable when using the eyepiece in a dimly lit environment, it is preferable to reduce eyeglow. Methods and apparatus may reduce eyeglow through a light control element, such as with a partially reflective mirror in the optics associated with the image source, with polarizing optics, and the like. For instance, light entering the waveguide may be polarized, such as s-polarized. The light control element may include a linear polarizer. Wherein the linear polarizer in the light control element is oriented relative to the linearly polarized image light so that the second portion of the linearly polarized image light that passes through the partially reflecting mirror is blocked and eyeglow is reduced. In embodiments, eyeglow may be minimized or eliminated by attaching lenses to the waveguide or frame, such as the snap-fit optics described herein, that are oppositely polarized from the light reflecting from the user's eye, such as p-polarized in this case.

In embodiments, the light control element may include a second quarter wave film and a linear polarizer. The second quarter wave film converts a second portion of a circularly polarized image light into linearly polarized image light with a polarization state that is blocked by the linear polarizer in the light control element so that eyeglow is reduced. For example, when the light control element includes a linear polarizer and a quarter wave film, incoming unpolarized scene light from the external environment in front of the user is converted to linearly polarized light while 50% of the light is blocked. The first portion of scene light that passes through the linear polarizer is linearly polarized light which is converted by the quarter wave film to circularly polarized light. The third portion of scene light that is reflected from the partially reflecting mirror has reversed circular polarization which is then converted to linearly polarized light by the second quarter wave film. The linear polarizer then blocks the reflected third portion of the scene light thereby reducing escaping light and reducing eyeglow. FIG. 22B shows an example of a see-through display assembly with a light control element in a glasses frame. The glasses cross-section 2200B shows the components of see-through display assembly in a glasses frame 2202B. The light control element covers the entire see-through view seen by the user. Supporting members 2204B and 2208B are shown supporting the partially reflecting mirror 2210B and the beam splitter layer 2212B respectively in the field of view of the user's eye 2214B. The supporting members 2204B and 2208B along with the light control element 2218B are connected to the glasses frame 2202B. The other components such as the folding mirror 2220B and the first quarter wave film 2222B are also connected to the supporting members 2204B and 2208B so that the combined assembly is structurally sound.

Stray light in a compact optical system such as a head mounted display, typically comes from scattering off sidewalls of the housing or other structures where the light encounters the surface at a steep angle. This type of stray light produces bright areas of scattered light that surround the displayed image.

There are two approaches to reducing this type of stray light. One is to darken or roughen the sidewalls or other structures to reduce the reflectance of light. However, while this does increase the absorbance at the surface, the reflected light scattered off the surface may still be noticeable. The other is to provide baffles to block or clip the stray light. Blocking or clipping the reflected light scattered off the surface greatly reduces the effects of this stray light. In a head mounted display, it is beneficial to use both approaches to reducing stray light as bright areas around the displayed image are eliminated and the contrast of the displayed image is increased.

U.S. Pat. No. 5,949,583 provides a visor on the top of a head mounted display to block stray light from entering from above. However, this does not address the need for controls to reduce stray light that comes from inside the head mounted display system.

U.S. Pat. No. 6,369,952 provides two masks to block light that comes from around the edge of a liquid crystal display image source in a head mounted display. The first mask is located on the input side of the liquid crystal image source adjacent to the backlight, while the second mask is located on the output side of the liquid crystal display. Since the two masks are located close to the liquid crystal display, "both the first mask 222 and the second mask 224 have opening or windows 232, 234, respectively which are substantially equal and congruent to the active area of the LCD" (Col 15, lines 15-19). By locating the masks close to the image source, the masks can have little effect on light that is emitted by the image source in a broad cone angle from areas of the image source that are nearer the center of the active area of the image source. This broad cone angle light can reflect off the sidewalls of the housing in a variety of ways and thereby contribute stray light in the form of bright areas and reduced contrast.

Therefore, there remains a need for a method to reduce stray light from sources inside of head mounted displays.

FIG. 160 shows an example of a display system with an optically flat reflective surface that is a beam splitter comprised of an optical film on a substrate wherein the display system is a near eye display 16002. In this example, the image source 16012 includes a projection system (not shown) to provide image light with an optical layout that includes a folded optical axis 16018 located in the near eye display 16002. The optics along the optical axis 16018 can include lenses to focus the image light to provide a focused image from the image source 16012 to the user's eye 16004. A beam splitter 16008 folds the optical axis 16018 from the image source 16012 to a spherical or aspherical reflector 16010. The beam splitter 16008 can be a partially reflecting mirror or a polarizing beam splitter. The beam splitter 16008 in the near eye display 16002 is oriented at an angle to redirect at least a portion of the image light from the image source 16012 to the reflector 16010. From the reflector 16010, at least a further portion of the image light is reflected back to the user's eye 16004. The reflected further portion of the image light passes back through the beam splitter 16008 and is focused at the user's eye 16004. The reflector 16010 can be a mirror or a partial mirror. In the case where the reflector 16010 is a partial mirror, scene light from the scene in front of the near eye display 16002 can be combined with the image light and thereby present combined image light 16020 comprised of image light along axis 16018 and scene light 16014 to the user's eye 16004. The combined image light 16020 presents a combined image of the scene with an overlaid image from the image source to the user's eye 16004.

FIG. 161 shows an illustration of a near eye display module 200. The module 200 is comprised of a reflector 16104, an image source module 16108 and a beam splitter 16102. The module can be open at the sides with attachments between at least some of the joining edges between the reflector 16104, the image source module 16108 and the beam splitter 16102. Alternately, the module 200 can be closed at the sides by sidewalls to provide an enclosed module to prevent dust, dirt and water from reaching the inner surfaces of the module 200. The reflector 16104, the image source module 16108 and the beam splitter 16102 can be manufactured separately and then joined together, or at least some of the pieces can be manufactured together in joined subassemblies. In the module 200, optical films can be used on the beam splitter 16102 or the reflector 16104. In FIG. 161, the beam splitter 16102 is shown as a flat surface while the reflector 16104 is shown as a spherical surface. In the near eye display module 200, both the reflector 16104 and the beam splitter 16102 are used to provide an image to the user's eye as shown in FIG. 160 and as such it is important that the surfaces be optically flat or optically uniform.

Given that the image source 16108 includes a projection system with a light source with a wide cone angle of light the image light also has a wide cone angle. As a result, image light interacts with the sidewalls of the module 200 and this interaction can provide reflected and scattered light in the form of bright areas, which are observed by the user as bright areas surrounding the displayed image. These bright areas can be very distracting to the user as they can look like halos surrounding the displayed image. In addition, scattered light can degrade the contrast in the displayed image by contributing low level light randomly across the image.

FIG. 162 shows an illustration of the optics associated with a type of head mounted display 16200. In the optics, a light source 16204 provides a broad cone angle of light rays including a center ray 16202 and edge rays 16224. The light source 16204 can provide polarized light. The light rays pass from the light source 16204 to an illumination beam splitter 16210, which reflects a portion of the light toward a reflective image source 16208 which can be an LCOS display. A first portion of the light is reflected by the image source 16208 and simultaneously changed in polarization state in correspondence to the image content that is being displayed. A second portion of the light then passes through the illumination beam splitter 16210 and then passes through one or more lenses 16212 which expand the cone angle of light rays. A third portion of the light is reflected at an angle by an imaging beam splitter 16220 toward a spherical (or aspherical) partial mirror 16214. The partial mirror 16214 reflects a fourth portion of light while causing the light to converge and focus the image at the user's eye 16228. After the fourth portion of light is reflected by the partial mirror 16214, a fifth portion of light passes through the imaging beam splitter 16220 and passes on to the user's eye 16228 where an enlarged version of the image displayed by the image source 16208 is provided to the user's eye 16228. In a see-through head mounted display, light 16218 from the environment (or scene light) passes through the partial mirror 16214 and the imaging beam splitter 16220 to provide a see-through image of the environment. The user then is provided with a combined image comprised of the displayed image from the image source and the see-through image of the environment.

The center ray 16202 passes through the center of the optics of the head mounted display along the optical axis of the optics. The optics include: the illumination beam splitter 16210, the image source 16208, the lens 16212, the imaging beam splitter 16220 and the partial mirror 16214. The edge rays 16224 pass along the sides of the housing 16222 where they can interact with the sidewalls of the housing 16222 where the edge rays 16224 can be reflected or scattered by the sidewalls as shown in FIG. 162. This reflected or scattered light from the edge rays 16224 is visible to the user as bright areas surrounding the displayed image or as a reduction in the contrast in the image. The disclosure provides methods to reduce the bright areas by reducing reflections and scattered light from the sidewalls by blocking or clipping the reflected or scattered light.

FIG. 163 shows an illustration of a first embodiment of the disclosure in which baffles 16302 are added inside the housing 16222 between the illumination beam splitter 16210 and the lens 16212. The baffles 16302 block or clip edge rays 16224 before they pass into the lens 16212. The baffles 16302 can be made of any material that is opaque so that the edge rays 16224 are blocked or clipped. In a preferential embodiment, the baffles 16302 may be made of a black material with a matte finish so that incident light is absorbed by the baffle. The baffles 16302 can be made from a flat sheet of material with an aperture that is positioned in the housing 16222 or the baffles 16302 can be made as part of the housing 16222. Since the baffles 16302 are positioned at a distance from the image source 16208 and the image light is diverging, the aperture created by the surrounding baffles 16302 is larger than the active area of the image source 16208 so the image provided by the image source 16208 is not clipped at the edges by the baffles and as a result, the entire image provided by the image source 16208 is visible by the user's eye as shown in FIG. 163. In addition, the baffles are preferentially provided with thin cross section (as shown in FIG. 163) or a sharp edge so that light is not scattered from the edge of the baffle.

FIG. 164 shows an illustration of another embodiment of the disclosure in which baffles 16402 are added at the entering surface of the lens 16212. The baffles 16402 can be manufactured as part of the housing 16222 or the baffles 16402 can be applied as a mask on the lens 16212. In either case, the baffles 16402 should be opaque and preferentially black with a matte finish to block and absorb incident light.

FIG. 165 shows an illustration of an embodiment of the disclosure that is similar to the embodiment shown in FIG. 164 but located on the output side of the lens 16212. In this embodiment, baffles 16502 are provided to block or clip edge rays 16224 after they have passed through lens 16212.

FIG. 166 shows an illustration of another embodiment of the disclosure in which a baffle 16602 is attached to the housing 16222 between the lens 16212 and the imaging beam splitter 16220. The baffle 16602 can be part of the housing 16222 or the baffle 16602 can be a separate structure that is positioned in the housing 16222. The baffle 16602 blocks or clips edge rays 16224 so that bright areas are not provided to the user's eye 16228 around the displayed image.

FIG. 167 shows an illustration of a further embodiment of the disclosure in which absorbing coatings 16702 are applied to the sidewalls of the housing 16222 to reduce reflections and scattering of incident light and edge light 16224. The absorbing coatings 16702 can be combined with baffles 16302, 16402, 16502 or 16602.

FIG. 168 shows an illustration of another source of stray light in a head mounted display wherein the stray light 16802 comes directly from the edge of the light source 16204. This stray light 16802 can be particularly bright because it comes directly from the light source 16204 without first reflecting from the illuminating beam splitter 16210 and then reflecting from the image source 16208. FIG. 169 shows an illustration of another source of stray light 16902 that comes from the light source 16204 wherein the stray light 16902 reflects off the surface of the image source 16208 where the polarization state is changed and the stray light 16902 can then pass through the illuminating beam splitter at a relatively steep angle. This stray light 16902 can then reflect off of any reflective surface in the housing or the edge of the lens 16212 as shown in FIG. 169. FIG. 170 shows an illustration of a yet further embodiment of the disclosure in which a baffle 17002 is provided adjacent to the light source 16204. The baffle 17002 is opaque and extended from the light source 16204 so that stray light 16802 and 16902 is blocked or clipped immediately after the light source 16204 and thereby prevented from reaching the user's eye 16228.

In a further embodiment, baffles or coatings shown in FIGS. 163-167 and 169-170 are combined to further reduce stray light in the head mounted display and thereby reduce bright areas surrounding the displayed image or increase the contrast in the displayed image. Multiple baffles can be used between the light source 16204 and the imaging beam splitter 16220. In addition, as shown in FIG. 171, an absorbing coating with ridges 17102 can be used wherein a series of small ridges or steps act as a series of baffles to block or clip edge rays over the entire sidewall area of the housing 16222. The ridges 17102 can be made as part of the housing 16222 or attached as a separate layer to the inside walls of the housing 16222.

FIG. 172 shows a further embodiment of a tape or sheet 17210 which includes a carrier sheet 17212 and ridges 17214 that can be used to block reflected light as shown in FIG. 171. The ridges 17214 are obliquely inclined on one side and sharply inclined on the other side so that incident light approaching from the sharply inclined side is blocked. The ridges 17214 can be solid ridges with a triangular cross section with a sharp edge as shown in FIG. 172, or they can be thin inclined scales attached at one edge, or they can be inclined fibers attached at one end so that a surface is angled relative to the sidewall and incident light is blocked. The advantage of the tape or sheet 17210 is that the ridges 17214 can be relatively thin and the ridges can cover a substantial area of the housing 16222. A further advantage of the tape or sheet 17210 is that the ridges 17214 can be made more easily than the ridges shown in FIG. 171, which may be difficult to mold as part of the housing.

In all embodiments, the surrounding baffles may create apertures whose size corresponds to the distance they are located along the optical axis from the image source so that the image light can diverge along the optical axis and thereby provide an unclipped view of the image source 16208 to the user's eye 16228.

In an embodiment, an absorptive polarizer in the optical assembly is used to reduce stray light. The absorptive polarizer may include an anti-reflective coating. The absorptive polarizer may be disposed after a focusing lens of the optical assembly to reduce light passing through an optically flat film of the optical assembly. The light from the image source may be polarized to increase contrast.

In an embodiment, an anti-reflective coating in the optical assembly may be used to reduce stray light. The anti-reflective coating may be disposed on a polarizer of the optical assembly or a retarding film of the optical assembly. The retarding film may be a quarter wave film or a half wave film. The anti-reflective coating may be disposed on an outer surface of a partially reflecting mirror. The light from the image source may be polarized to increase contrast.

Figure 102B:
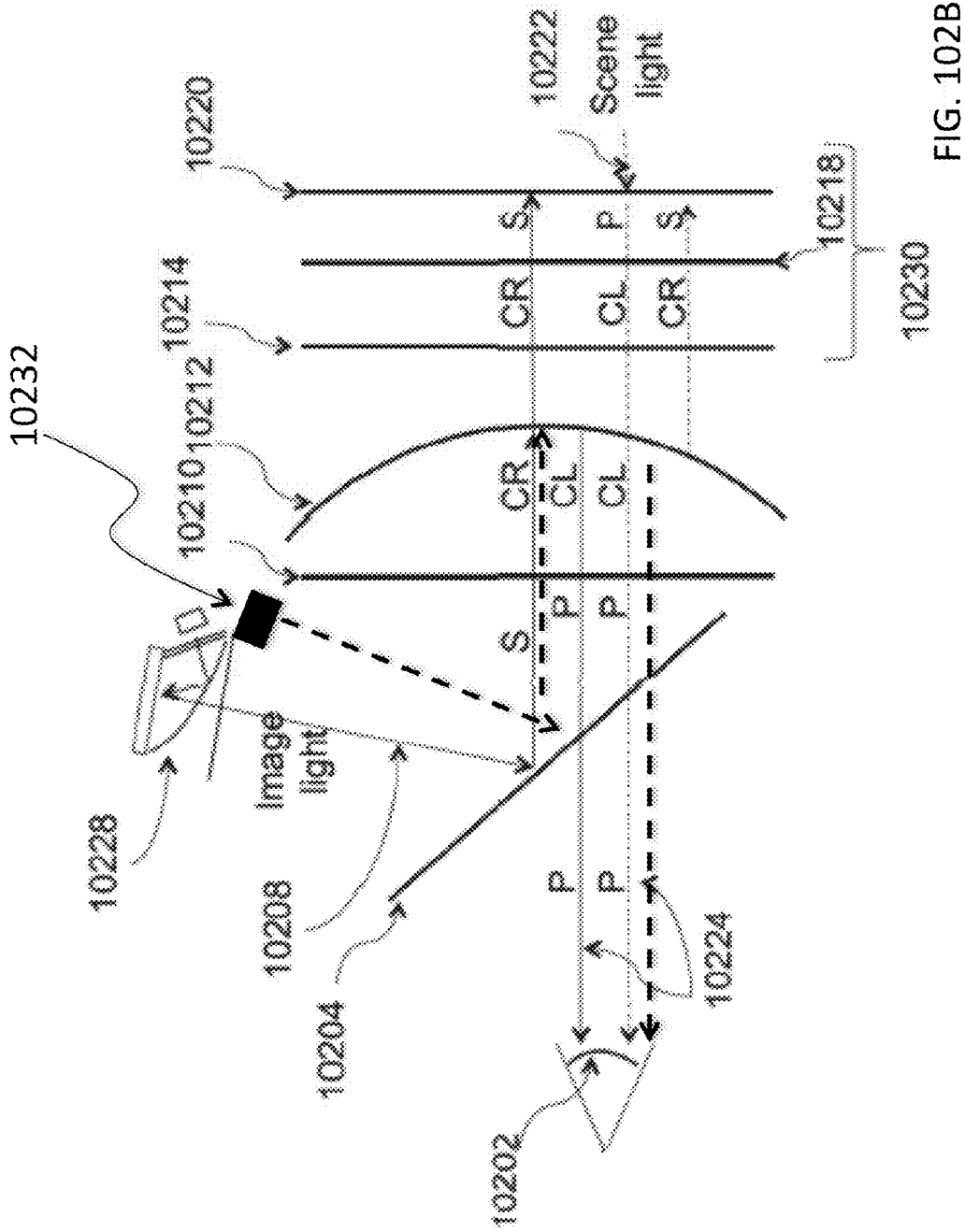
FIG. 102A depicts an embodiment of an optical assembly.

Referring to FIG. 102A, an image source 10228 directs image light to a beam splitter layer of the optical assembly. FIG. 103 depicts a blow-up of the image source 10228. In this particular embodiment, the image source 10228 is shown containing a light source (LED Bar 10302) that directs light through a diffuser 10304 and prepolarizer 10308 to a curved wire grid polarizer 10310 where the light is reflected to an LCoS display 10312. Image light from the LCoS is then reflected back through the curved wire grid polarizer 10310 and a half wave film 10312 to the beam splitter layer of the optical assembly 10200. In embodiments, an optical assembly including optical components 10204, 10210, 10212, 10212, 10230 may be provided as a sealed optical assembly, such as being detachable (e.g. snaps on and off), exchangeable, and the like, and the image source 10228 provided as an integral component within the frame of the eyepiece. This may enable the sealed optical assembly to be water proof, dust proof, exchangeable, customizable, and the like. For instance, a given sealed optical assembly may be provided with corrective optics for a one person, and be replaceable with a second sealed optical assembly for another person who has different corrective optics needs (e.g. a different prescription). In embodiments, there may be applications where both eyes do not have to receive an input from the eyepiece. In this instance, a person may simply detach one side, and only use the single side for projection of content. In this way, the user would now have an unobstructed optical path for the eye where the assembly has been removed, the eyepiece would preserve battery life with only one half of the system running, and the like.

The optics assembly may be considered partitioned into separate portions with respect to what portion is being sealed, such as being comprised of an image generation facility 10228 and a directive optics facility 10204, 10210, 10212, and 10230, as shown in FIG. 102A. In further illustration, FIG. 147 shows an embodiment configuration of the eyepiece showing the directive optics as 'projection screens' 14608*a* and 14608*b*. FIG. 102A also shows the eyepiece electronics and the portions of the projections system 14602, where this portion of the projection system may be referred to as the image generation facility. The image generation facility and directive optics facility may be sealed subassemblies, such as to project the optics therein from contaminants in the surrounding environment. In addition, the directive optics may be detachable, such as for replacement, for removing to allow for an unobstructed view by the user, to accommodate a non-destructive forced removal (e.g. where the directive optics are hit, and break away from the main body of the eyepiece without damage), and the like. In embodiments, the present disclosure may comprise an interactive head-mounted eyepiece worn by a user, wherein the eyepiece includes an optical assembly through which the user views a surrounding environment and displayed content, and an integrated image source adapted to introduce the content to the optical assembly, wherein the optical assembly includes an image generation facility mounted within the frame of the eyepiece and a directive optics facility positioned in front of the user's eye and detachable from the frame of the eyepiece, where the image generation facility is sealed within the frame to reduce contamination from the surrounding environment. In embodiments, the seal may be a sealed optical window. As described herein, the eyepiece may further comprise a processing facility, power management facility, a detachment sensor, a battery, and the like, where the power management facility may detect the detachment of the directive optics facility through a detachment indication from the detachment sensor, and selectively reduce power to components of the eyepiece to reduce power consumed from the battery. For instance, the component that is reduced in power may be the image source, such as reducing the brightness of the image source, turning off the power to the image source, and the like, where the power management facility may monitor for the reattachment of a directive optics facility and return the power usage of the image source to a pre-detachment operational level. The directive optics facility may be detachable in a break-away manner, such that when if the directive optics facility is inadvertently forced to detach, that it will do so without damaging the eyepiece. The directive optics facility may be detachable through a connection mechanism, such as a magnet, pin, rail, a snap-on connector, and the like. The directive optics facility may provide for vision correction for a user that requires corrective eyewear, where the directive optics facility is replaceable for the purpose of changing the vision correction prescription of the eyepiece. The eyepiece may have two separate detachable optical assemblies for each eye, where one of the separate optical assemblies is removed to enable monocular usage with the remaining of the separate optical assemblies. For instance, the monocular usage may be a firearms sighting usage where the side of the eyepiece with the detached directive optics facility is used for sighting the firearm, allowing the user with an unobstructed visual path the firearm's sight, while retaining facilities provided by the eyepiece to the other eye. The directive optics facility may be detachable to enable exchanging between a directive optics facility adapted to indoor use with a directive optics facility adapted to indoor use. For instance, there may be different filters, field of view, contrast, shielding, and the like for indoor use verses outdoor use. The directive optics facility may be adapted to accept an additional element, such as an optical element, a mechanical element, an adjustment element, and the like. For instance, an optical element may inserted to adjust for a user's optical prescription. The directive optics facility may also be replaceable in order to change the field of view provided, such as by replacing a directive optics facility with a first field of view with a directive optics facility with a second field of view.

Figure 104:
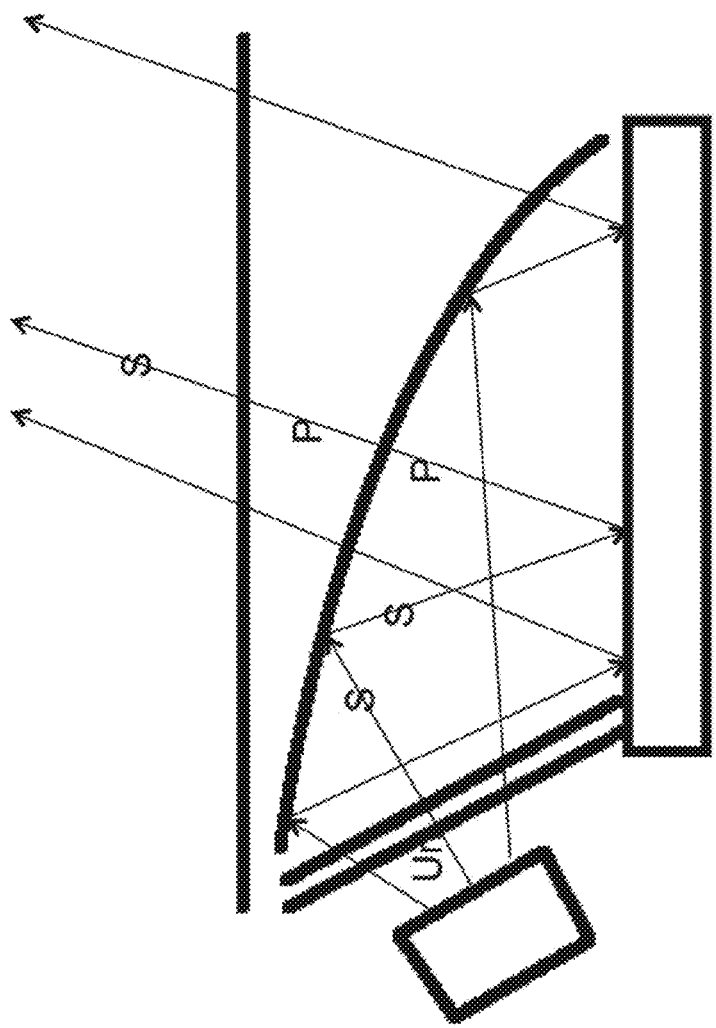

Referring to FIG. 104, LEDs provide unpolarized light. The diffuser spreads and homogenizes the light from the LEDs. The absorptive prepolarizer converts the light to S polarization. The S polarized light is then reflected toward the LCOS by the curved wire grid polarizer. The LCOS reflects the S polarized light and converts it to P polarized light depending on local image content. The P polarized light passes through the curved wire grid polarizer becoming P polarized image light. The half wave film converts the P polarized image light to S polarized image light.

Referring again to FIG. 102A, the beam splitter layer 10204 is a polarizing beam splitter, or the image source provides polarized image light 10208 and the beam splitter layer 10204 is a polarizing beam splitter, so that the reflected image light 10208 is linearly polarized light, this embodiment and the associated polarization control is shown in FIG. 102A. For the case where the image source provides linearly polarized image light and the beam splitter layer 10204 is a polarizing beam splitter, the polarization state of the image light is aligned to the polarizing beam splitter so that the image light 10208 is reflected by the polarizing beam splitter. FIG. 102A shows the reflected image light as having S state polarization. In cases where the beam splitter layer 10204 is a polarizing beam splitter, a first quarter wave film 10210 is provided between the beam splitter layer 10204 and the partially reflecting mirror 10212. The first quarter wave film 10210 converts the linearly polarized image light to circularly polarized image light (shown as S being converted to CR in FIG. 102A). The reflected first portion of image light 10208 is then also circularly polarized where the circular polarization state is reversed (shown as CL in FIG. 102A) so that after passing back through the quarter wave film, the polarization state of the reflected first portion of image light 10208 is reversed (to P polarization) compared to the polarization state of the image light 10208 provided by the image source (shown as S). As a result, the reflected first portion of the image light 10208 passes through the polarizing beam splitter without reflection losses. When the beam splitter layer 10204 is a polarizing beam splitter and the see-through display assembly 10200 includes a first quarter wave film 10210, the light control element 10230 is a second quarter wave film and a linear polarizer 10220. In embodiments, the light control element 10230 includes a controllable darkening layer 10214. Wherein the second quarter wave film 10218 converts the second portion of the circularly polarized image light 10208 into linearly polarized image light 10208 (shown as CR being converted to S) with a polarization state that is blocked by the linear polarizer 10220 in the light control element 10230 so that eyeglow is reduced.

When the light control element 10230 includes a linear polarizer 10220 and a quarter wave film 10218, incoming unpolarized scene light 10222 from the external environment in front of the user is converted to linearly polarized light (shown as P polarization state in FIG. 102A) while 50% of the light is blocked. The first portion of scene light 10222 that passes through the linear polarizer 10220 is linearly polarized light which is converted by the quarter wave film to circularly polarized light (shown as P being converted to CL in FIG. 102A). The third portion of scene light that is reflected from the partially reflecting mirror 10212 has reversed circular polarization (shown as converting from CL to CR in FIG. 102A) which is then converted to linearly polarized light by the second quarter wave film 10218 (shown as CR converting to S polarization in FIG. 102A). The linear polarizer 10220 then blocks the reflected third portion of the scene light thereby reducing escaping light and reducing eyeglow.

As shown in FIG. 102A, the reflected first portion of image light 10208 and the transmitted second portion of scene light have the same circular polarization state (shown as CL) so that they combine and are converted by the first quarter wave film 10210 into linearly polarized light (shown as P) which passes through the beam splitter when the beam splitter layer 10204 is a polarizing beam splitter. The linearly polarized combined light 10224 then provides a combined image to the user's eye 10202 located at the back of the see-through display assembly 10200, where the combined image is comprised of overlaid portions of the displayed image from the image source and the see-through view of the external environment in front of the user.

The beamsplitter layer 10204 includes an optically flat film, such as the Asahi TAC film discussed herein. The beamsplitter layer 10204 may be disposed at an angle in front of a user's eye so that it reflects and transmits respective portions of image light and transmits scene light from a see-through view of the surrounding environment, so that a combined image comprised of portions of the image light and the transmitted scene light is provided to a user's eye. The optically flat film may be a polarizer, such as a wire grid polarizer. The optically flat film may be laminated to a transparent substrate. The optically flat film may be molded, over-molded, glued, and the like into or onto a surface of one of the optical surfaces of the eyepiece, such as the beamsplitter 10202. The optically flat film may be positioned at less than 40 degrees from vertical. The curved polarizing film may have a less than 1:1 ratio of height of light source to width of illuminated area. The highest point of the curved film is lower than the length of the narrowest axis of the display. In embodiments, once the optically thin film(s) are on the beamsplitter, additional optics, such as corrective optics, prescriptions, and the like, may be added to the surface, such as to keep the film flat in a sandwich layer in between.

This disclosure further provides methods for providing an optically flat surface with an optical film. Optical films are a convenient way to form an optical structure with optical characteristics that are very different from the rest of the structure of an imaging device. To provide function for the imaging device, the optical film needs to be attached to the optical device. When the optical film is used in a reflective manner, it is critical that the reflective surface be optically flat or the wavefront of the light reflecting from the reflective surface will not be preserved and the image quality will be degraded. An optically flat surface may be defined as a surface that is uniform within 5 wavelengths of light per inch of surface, as measured for the wavelength of light that the imaging device is used with and compared to either a flat surface or a desired optical curve.

Optically flat surfaces including optical films as described in the present disclosure can be included in display systems including: projectors, projection televisions, near eye displays, head mounted displays, see-thru displays, and the like.

FIG. 140 shows an example of a display system with an optically flat reflective surface that is a beam splitter comprised of an optical film on a substrate wherein the display system is a near eye display 14000. In this example, the image source 14010 includes a projection system (not shown) to provide image light with an optical layout that includes a folded optical axis 14014 located in the near eye display 14000. The optics along the optical axis 14014 can include lenses to focus the image light to provide a focused image from the image source 14010 to the user's eye 14002. A beam splitter 14004 folds the optical axis 14014 from the image source 14010 to a spherical or aspherical reflector 14008. The beam splitter 14004 can be a partially reflecting mirror or a polarizing beam splitter layer. The beam splitter 14004 in the near eye display 14000 is oriented at an angle to redirect at least a portion of the image light from the image source 14010 to the reflector 14008. From the reflector 14008, at least a further portion of the image light is reflected back to the user's eye 14002. The reflected further portion of the image light passes back through the beam splitter 14004 and is focused at the user's eye 14002. The reflector 14008 can be a mirror or a partial mirror. In the case where the reflector 14008 is a partial mirror, scene light from the scene in front of the near eye display 14000 can be combined with the image light and thereby present combined image light 14018 comprised of image light along axis 14014 and scene light along axis 14012 to the user's eye 14002. The combined image light 14018 presents a combined image of the scene with an overlaid image from the image source to the user's eye.

FIG. 141 shows an illustration of a near eye display module 14100. The module 14100 is comprised of a reflector 14104, an image source module 14108 and a beam splitter 14102. The module can be open at the sides with attachments between at least some of the joining edges between the reflector 14104, the image source module 14108 and the beam splitter 14102. Alternately, the module 14100 can be closed at the sides by sidewalls to provide an enclosed module to prevent dust, dirt and water from reaching the inner surfaces of the module 14100. The reflector 14104, the image source module 14108 and the beam splitter 14102 can be manufactured separately and then joined together, or at least some of the pieces can be manufactured together in joined subassemblies. In the module 14100, optical films can be used on the beam splitter 14102 or the reflector. In FIG. 141 the beam splitter 14102 is shown as a flat surface while the reflector 14104 is shown as a spherical surface. In the near eye display module 14100, both the reflector 14104 and the beam splitter 14102 are used to provide an image to the user's eye as shown in FIG. 140 and as such it is important that the surfaces be optically flat or optically uniform.

FIG. 142 shows a schematic drawing of an embodiment of the disclosure, a pellicle style film assembly 14200. The pellicle style film assembly 14200 includes a frame 14202 comprised of upper and lower frame members 14202a and 14202b. The optical film 14204 is held between the frame members 14202a and 14202b with an adhesive or fasteners. To improve the flatness of the optical film 14204, the optical film 14204 can be stretched in one or more directions while the adhesive is applied and the frame members 14202a and 14202b are bonded to the optical film 14204. After the optical film 14204 is bonded to the frame 14202, the edges of the optical film can be trimmed to provide a smooth surface to the outer edges of the frame 14202.

In some embodiments of the disclosure, the optical film 14204 is a folded film comprised of a series of optically flat surfaces and the interface of the frame members 14202a and 14202b have a matching folded shape. The folded film is then stretched along the direction of the folds and bonded into position so that the frame members 14202a and 14202b hold the optical film 14204 in the folded shape and each of the series of optically flat surfaces is held in place.

In all cases, after the frame members 14202a and 14202b are bonded to the optical film 14204, the resulting pellicle style film assembly 14200 is a rigid assembly that can be placed into an optical device such as the near eye display module 14100 to form the beam splitter 14102. In this embodiment, the pellicle style film assembly 14200 is a replaceable beam splitter 14102 assembly in the near eye display module 14100. Sidewalls in the near eye display module 14100 can have grooves that the frame 14202 fits into, or alternately a flat surface can be provided that connects the sidewalls and the frame 14202 can sit on top of the flat surface.

FIG. 143 shows an illustration of an insert molded assembly 14300 which includes an optical film 14302. In this embodiment the optical film 14302 is placed into a mold and a viscous plastic material is injected into the mold through a molding gate 14308 so that the plastic fills the mold cavity and forms a molded structure 14304 adjacent to the optical film 14302 and behind the optical film 14302. When the plastic material hardens in the mold, the mold is opened along the parting line 14310 and the insert molded assembly 14300 is removed from the mold. The optical film 14302 is then embedded into and attached to the insert molded assembly 14300. To improve the optical flatness of the optical film 14302 in the insert molded assembly 14300, the inner surface of the mold that the optical film 14302 is placed against is an optically flat surface. In this way, the viscous plastic material forces the optical film 14302 against the optically flat surface of the mold during the molding process. This process can be used to provide optically flat surfaces as described above that are flat or have a desired optical curve. In a further embodiment, the optical film 14302 can be provided with an adhesive layer or a tie layer to increase the adhesion between the optical film 14302 and the molded structure 14304.

In yet another embodiment, the optical film 14302 is placed into the mold with a protective film between the mold surface and the optical film 14302. The protective film can be attached to the optical film 14302 or the mold. The protective film can be smoother or flatter than the mold surface to provide a smoother or flatter surface for the optical film 14302 to be molded against. As such, the protective film can be any material such as for example plastic or metal.

FIG. 144 shows an illustration of a laminating process for making a laminated plate with an optical film 14400. In this embodiment, upper and lower press plates 14408a and 14408b are used to laminate an optical film 14400 onto a substrate 14404. An adhesive 14402 can be optionally used to bond the substrate 14404 to the optical film 14400. In addition, one or more of the press plates 14408a and 14408b can be heated or the substrate 14404 can be heated to provide a higher level of adhesion between the substrate 14404 and the optical film 14400. Heating of the substrate or one or more of the press plates 14408a and 14408b can also be used to soften the substrate 14404 and thereby provide a more uniform pressure behind the optical film 14400 to improve the smoothness or flatness of the optical film 14400 in the laminated plate. The laminated plate with an optical film 14400 of this embodiment can be used as a replaceable beam splitter in a near eye optical module 14100 as previously described for the pellicle style film assembly 14200.

Figure 145:
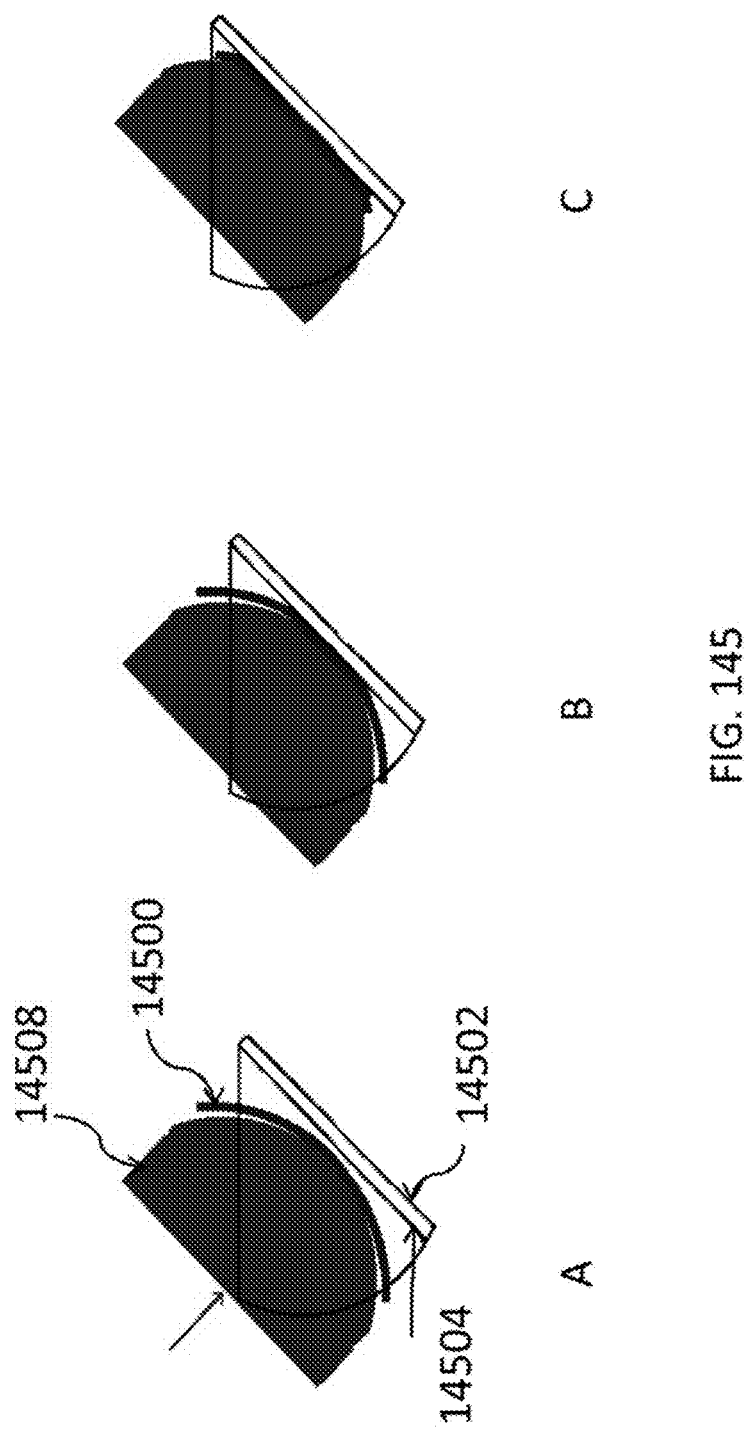

FIG. 145 A-C shows an illustration of an application process for making a molded structure 14502 with an optical surface including an optical film 14500. In this embodiment, the optical film 14500 is applied to an optically flat surface 14504 in a molded structure 14502 with a rubber applicator 14508. An adhesive layer may be applied to either the optically flat surface 14504 of the molded structure 14502 or the bottom surface of the optical film 14500 to adhere the optical film 14500 to the molded structure 14502. The rubber applicator 14508 may be a relatively soft and rubbery material with a curved surface so that the center portion of the optical film 14500 is forced to contact the optically flat surface 14504 of the molded structure 14502 first. As the rubber applicator 14508 pushes down further, the contact area between the optical film 14500 and the optically flat surface 14504 of the molded structure 14502 grows in size as shown in FIGS. 145A, 145B and 145C. This progressive application process provides a very uniform application of pressure that allows the air at the interface to be expelled during the application process. The progressive application process along with the optically flat surface 14504 of the molded structure 14502 provides an optically flat optical film 14500 attached to the interior surface of the molded structure 14502 as shown in FIG. 145C. The adhesive layer used to bond the optical film 14500 to the molded structure 14502 can be attached to the optical film 14500 or the optically flat surface 14504 on the interior of the molded structure 14502. Those skilled in the art will realize that this application process can be similarly used to apply an optical film to an outer surface of a molded structure. In addition, the optically flat surface can be a flat surface or a surface with a desired optical curve, or a series of optically flat surfaces wherein the rubber applicator is shaped to provide a progressive application of pressure as the optical film is applied.

In embodiments, an image display system may include an optically flat optical film comprising a display module housing, wherein the housing comprises a substrate to hold the optical film optically flat, an image source and a viewing location wherein the image provided by the image source is reflected from the optical film to the viewing location. In embodiments, the optical film of the image display system may be molded into the display module. The optical film may be applied to the display module in embodiments. Further, in embodiments, the optical film of the display system may be a wire grid polarizer, a mirror, a partial mirror, holographic film, and the like. In embodiments, the image display system may be a near eye display. In embodiments, were the optical film is molded into the display module, or otherwise, the optical film may be held against an optically flat surface when the optical film is molded into the display module. In embodiments, the optical film of the image display system may comprise an optical flatness of 5 wavelengths of light per inch.

In an embodiment, an image display system including an optically flat optical film may comprise a substrate to hold the optical film optically flat, a display module housing, an image source, and a viewing location wherein the image provided by the image source may be reflected from the optical film to the viewing location and the substrate with the optical film may be replaceable within the display module housing. In such embodiments, the substrate of the image display system may be a frame and the optical film may be held under tension by the frame, the substrate may be a plate molded behind the file, and/or the substrate may be a laminated plate. Further, the optical film of the image display system may be a beam splitter, a polarizing beam splitter, a wire grid polarizer, a mirror, a partial mirror, a holographic film, and the like. Further, the image display system may be a near eye display. In embodiments, the optical film of the image display system may be held against an optically flat surface when the plate is molded behind the optical film. Further, in embodiments, the optical film of the image display system may be held against an optically flat surface when the plate is laminated to the optical film. In various embodiments, the optical film of the image display system may comprise an optical flatness of 5 wavelengths of light per inch.

In an embodiment, the components in FIG. 102A collectively form an electro-optic module. The angle of the optical axis associated with the display may be 10 degrees or more forward of vertical. This degree of tilt refers to how the upper part of the optics module leans forward. This allows the beamsplitter angle to be reduced which makes the optics module thinner.

The ratio of the height of the curved polarizing film to the width of the reflective image display is less than 1:1. The curve on the polarizing film determines the width of the illuminated area on the reflective display, and the tilt of the curved area determines the positioning of the illuminated area on the reflective display. The curved polarizing film reflects illumination light of a first polarization state onto the reflective display, which changes the polarization of the illumination light and generates image light, and the curved polarizing film passes reflected image light. The curved polarizing film includes a portion that is parallel to the reflective display over the light source. The height of the image source may be at least 80% of the display active area width, at least 3.5 mm, or less than 4 mm.

In portable display systems, it is important to provide a display that is bright, compact and light in weight. Portable display systems include cellphones, laptop computers, tablet computers, near eye displays and head mounted displays.

The disclosure provides a compact and lightweight frontlight for a portable display system comprised of a partially reflective film to redirect light from an edge light source to illuminate a reflective image source. The partially reflective film can be a partial mirror beam splitter film or a polarizing beam splitter film. The polarizing beam splitter film can be a multi-layer dielectric film or a wire grid polarizer film. Polarizing beam splitter films are known to provide efficient reflection of one polarization state while simultaneously allowing the other polarization state to pass through. Multilayer dielectric films are available from 3M in Minneapolis, Minn. under the name DBEF. Wire grid polarizing films are available from Asahi-Kasei E-Materials in Tokyo, Japan under the name WGF.

An edge light provides a compact light source for a display, but since it is located at the edge of the image source, the light must be redirected by 90 degrees to illuminate the image source. When the image source is a reflective image source such as a liquid crystal on silicon (LCoS) image source, the illuminating light must be polarized. The polarized light is reflected by the surface of the image source and the polarization state of the light is changed in correspondence with the image content being displayed. The reflected light then passes back through the frontlight.

FIG. 187 shows a schematic illustration of a prior art display assembly 18700 with a solid beam splitter cube 18718 as a frontlight. A display assembly includes a frontlight, one or more light sources and an image source. In display assembly 18700, one or more light sources 18702 are included to provide light shown as light rays 18712. The light source can be LEDs, fluorescent lights, OLEDs, incandescent lights or solid state lights. The light rays 18712 pass through a diffuser 18704 to spread the light laterally for more uniform illumination. If the diffused light is polarized, the diffuser includes a linear polarizer. The diffused light rays 18714 are emitted through the solid beam splitter cube 18718 toward the partially reflective layer 18708 where they are partially reflected toward the reflective image source 18720. The diffused light rays 18714 are then reflected by the reflective image source 18720 thereby forming image light 18710 which is transmitted by the partially reflective layer 18708. The image light 18710 can then pass into associated imaging optics (not shown) to present an image to a viewer. However, as can be seen in FIG. 187, the height of the lighted area of the light source herein shown as the diffuser 18704 is the same as the width of the reflective image source 18720 that is illuminated. The partially reflective layer 18708 is positioned at a 45 degree included angle to provide image light rays 18710 that proceed straight or vertically into the associated imaging optics. As a result, the frontlight shown in FIG. 187 is relatively large in size.

In imaging systems in general, it is important to preserve the wavefront from the image source to provide a high quality image with good resolution and contrast. As such, the image light 18710 must proceed perpendicularly from the reflective image source 18720 to provide a uniform wavefront to the associated imaging optics for a high quality image to be provided to a viewer, as is known by those skilled in the art. As such, the diffused light rays 18714 must be redirected by the partially reflective film 18708 to be perpendicular to the reflective image source 18720 so they can be reflected and pass vertically (as shown in FIGS. 187-198) into the associated imaging optics.

FIG. 188 shows another prior art display assembly 18802, which includes a partially reflective film 18804, which is supported at the edges and is free-standing over the reflective image source 18720. This display assembly works in a similar fashion to the display assembly shown in FIG. 187 with the difference being that display assembly 18802 is lighter in weight than display assembly 18700 due to the lack of solid beam splitter cube 18718. As can be seen in FIG. 188, the height of the diffuser 18704 is again the same as the width of the reflective image source 18720 to provide image light 18808 which when reflected by the reflective image source 18720 proceeds vertically into the associated imaging optics.

FIG. 189 shows a schematic illustration of what happens to the light in a display assembly 18902 if the partially reflective film 18804 is positioned at an included angle of less than 45 degrees. In this case, portions of the reflective image source 18720 are not illuminated uniformly. Light rays that illuminate the portion of the reflective image source that are farthest away from the diffuser either do not proceed straight to the associated imaging optics (as in the case of rays 18904) or have previously reflected from the surface of the reflective image source (as in the case of rays 18908) which changes the polarization state and the light rays then pass through the partially reflective film if the film is a polarizing beam splitter film (also known as a reflective polarizer film). As such, when the associated imaging optics can only use image light that proceeds straight from the reflective image source 18720, when the partially reflective film 18804 is positioned at an angle of less than 45 degrees, the area of the reflective image source 18720 that is illuminated is reduced and correspondingly dark portions of the image are produced.

In an embodiment of the disclosure shown in FIG. 190, a curved partially reflective surface 19004 is provided to redirect the diffused light 19010 provided by the light source 18702 downward to illuminate the reflective image source 18720. The curved partially reflective surface 19004 can be a polarizing beam splitter film, which is thin and flexible. In this case, the diffuser 18704 includes a linear polarizer so that the light 18712 is diffused and then linearly polarized, so the diffused light 19010 is polarized. The linear polarizer in the diffuser 18704 and the polarizing beam splitter film 19004 are oriented such that light passing through the linear polarizer is reflected by the polarizing beam splitter film. In this way, when the reflective image source 18720 changes the polarization of the diffused light 19010, the polarization of the reflected image light 19008 is the opposite polarization state compared to the diffused light 19010. The reflected image light 19008 then passes through the partially reflective film 19004 and continues to the display optics. By using a flexible polarizing beam splitter film as the partially reflecting surface 19004, the partially reflective surface 19004 can be curved and lightweight. The polarizing beam splitter film performs the dual role of being a reflector for the diffused light 19010 that illuminates the reflective image source 18720 and a transparent member for the reflected image light 19008. An advantage provided by polarizing beam splitter films as is known by those skilled in the art is that they can receive light over a wide range of incident angles so that a curve doesn't interfere with light passing through to the film. In addition, since polarizing beam splitter film is thin (e.g. less than 200 micron), the curved shape doesn't noticeably distort the image light 19008 as it passes through the film to the display optics. Finally, the polarizing beam splitter films have a low tendency to scatter light so high image contrast can be maintained.

The flexible nature of polarizing beam splitter films allows them to be formed into curved shapes that redirect and focus light from the diffuser onto the reflective image source. The shape of the curve of the polarizing beam splitter film can be selected based on the light distribution provided by the diffuser to provide uniform illumination of the reflective image source. FIG. 190 shows a curved partially reflective film 19004 with a parabolic shape, but radiused curves, complex splined curves, relatively flat curves, flats or segmented planes are possible as well to uniformly redirect and focus the diffused light 19010 onto the reflective image source 18720 depending on the nature of the light source 18702 and the effectiveness of the diffuser 18704. Experiments have shown that curved surfaces on the partially reflective surface 19004 tend to concentrate the diffused light 19010 into the center of the reflective image source 18720 so that curved surfaces are best used when the diffuser 18704 provides a distribution of light that is brighter at the edges. Conversely, experiments have shown that a relatively flat surface on the partially reflective surface 19004 is best used when the diffuser 18704 provides a distribution of light that is brighter at the center. The shape of the partially reflective surface 19004 when it is comprised of a flexible film, can be maintained with side frames that have slots of the appropriate curve to hold the flexible film in place as shown in FIG. 190 as a free standing film. Two side frames are used to support the curved shape on either side of the display assembly 19002 along with the other components. Because a large part of the display assembly 19002 is comprised of air and the partially reflective surface 19004 is thin film, weight is substantially lower compared to the prior art display assembly 18700 shown in FIG. 187. In addition, as can be seen in FIG. 190, the width of the reflective image source 18720 that is illuminated is greater than the height of the diffuser 18704 so that the display assembly 19002 is more compact than the prior art display assembly shown in FIG. 188.

FIG. 191 shows another embodiment of the disclosure in which dual light sources 19104 are used in display assembly 19102 with two relatively flat partially reflective surfaces positioned back to back. The arrangement shown in FIG. 191 provides a solid film holder 19120 in the frontlight with two sides, so that the display assembly 19102 is similar to using two display assemblies 18700 as shown in FIG. 187 positioned back to back. In FIG. 191 the light rays are only shown for one side, but the parts and the light rays in the other side are symmetrical with the side shown. In the solid film holder 19120 is a partially reflective film 19110 that extends continuously between the two sides. The solid film holder 19120 is also continuous between the two sides so that the image light 19112 is not interrupted or deflected by a seam line between the two sides of the display assembly 19102. The solid film holder 19120 and the partially reflective film 19110 together present a constant optical thickness so the image light is not deflected or distorted. As such, image light 19112 with continuous image quality can be provided while being illuminated by light from two light sources 19104. Each light source 19104 provides light 19114 to a diffuser 19108 which spreads the light 19114 laterally to provide diffused light 19118 to illuminate one half of the reflective image source 18720. The solid film holder 19120 holds the partially reflective film 19110 in the desired shape. Most importantly, the height of the diffuser 19108 is reduced to half of the prior art diffuser 18704 shown in FIG. 187 for display assembly 18700 when compared to the illuminated width of the reflective image source 18720.

FIG. 192 shows a schematic illustration of a display assembly 19202 with dual light sources 19104 and a freestanding partially reflecting film 19204 that is supported only at the edges. In FIG. 192 the light rays are only shown for one side, but the parts and the light rays for the other side are symmetrical with the side shown. The functions of the various components of the display assembly 19202 are the same as those shown in FIG. 191, but with the added benefit that the display assembly 19202 is lighter in weight than the display assembly 19102 since the major portion of the display assembly 19202 is comprised of air.

FIG. 193 shows a display assembly 19302 with dual light sources 19104 and a freestanding partially reflective film 19308 where the film is supported at the edges such that two curved surfaces are provided. In FIG. 193 the light rays are only shown for one side, but the parts and the light rays for the other side are symmetrical with the side shown. The partially reflective film 19308 is continuous across both sides with similar curves on both sides. The curves are chosen to reflect and focus the diffused light 19312 provided by the diffuser onto the reflective image source 18720. The reflective image source 18720 reflects the diffused light 19312 thereby forming image light 19310. The height of the diffuser 19304 is less than half of the prior art diffuser 18704 shown in FIG. 187 so that the frontlight and display assembly 19302 is very compact.

FIG. 194 shows a schematic illustration of a display assembly 19402 with a continuous partially reflective film 19308 inside a solid film holder 19404 that is otherwise similar to display assembly 19302 shown in FIG. 193. In FIG. 194 the light rays are only shown for one side, but the parts and the light rays for the other side are symmetrical with the side shown. The solid film holder 19404 is used on either side of the partially reflective film 19308 to hold the film into a prescribed two sided curve and also to protect the partially reflective film 19308. The two sides of the solid film holder 19404 are connected by a relatively thin section in the middle of the bottom portion of the solid film holder 19404 to further avoid presenting a seam line that would disrupt the image light 19310 in the center of the image.

In preferred embodiments of the disclosure, the partially reflective films in the display assemblies shown in FIGS. 191-194 are polarizing beam splitting films. In these embodiments the diffusers include linear polarizers so that the diffused light is polarized. The linear polarizer is aligned to the polarizing beam splitter film so that the diffused light has the polarization state that is reflected by the polarizing beam splitter film. The polarizing beam splitter film also acts as an analyzer to the image light. The advantage of using polarized diffused light with a polarizing beam splitter film in the frontlight is that stray light is reduced in the display assemblies since all of the polarized diffused light is reflected by the polarizing beam splitter film toward the reflective image source, where it is converted into image light. If the diffused light were not polarized, the polarization state of the diffused light that was not reflected would be transmitted through the polarizing beam splitter film and if this light were not controlled, it would contribute scattered light to the image light, which would reduce contrast in the image presented to the viewer.

FIG. 195 shows a schematic illustration of a display assembly 19502 with a single light source 19104 on one side and polarization control to effectively illuminate the reflective image source 18720 from both sides. In this case, the light source 19104 provides unpolarized light 19114 and unpolarized diffused light 19508. The partially reflective film is a polarizing beam splitter film 19504 in a solid film holder 19514. The polarizing beam splitter film 19504 reflects one polarization state of the diffused light (shown as ray 19510) while transmitting the other polarization state (shown as ray 19518). The polarizing beam splitter film 19504 is folded and continuous so that the light with the other polarization state 19518 passes through both sides of the folded polarizing beam splitter film 19504. This light 19518 then passes through a quarter wave retarder film 19524, which changes the polarization state from linear to circular. The circularly polarized light is then reflected by a mirror 19528 and passes back through the quarter wave retardation film 19524 which changes the polarization state from circular polarization to linear polarization but of the one polarization state (shown as ray 19520) so that the light 19520 is then reflected toward the reflective image source 18720 by the polarizing beam splitter film 19504. Thus the light provided by the light source 19104 in display assembly 19502 illuminates the reflective image source 18720 on both sides with light of the same polarization state. Since the diffused light 19508 is unpolarized, and both polarization states (19510, 19518) are used to illuminate the reflective image source 18720, essentially all of the light provided by the light source 18720 is converted into image light (19512, 19522). The image light (19512, 19522) is provided straight to the associated imaging optics. Again, the height of diffuser 19108 is half of the diffuser 18704 shown in FIG. 187 thereby providing a frontlight and display assembly that is compact and efficient.

FIG. 196 shows a display assembly 19602 with similar geometry to that shown in FIG. 195, but the polarizing beam slitter film 19604 is free standing and supported only at the edges to reduce the weight of the frontlight while still providing a low height of the diffuser relative to the width of the reflective image source that is illuminated.

FIG. 197 shows yet another embodiment of the disclosure including display assembly 19702 with dual light sources 19704 and 19708 and a folded polarizing beam splitter film 19714 wherein the two sides of the folded polarizing beam splitter film 19714 are curved. The light 19718, 19720 from the light sources 19704, 19708 is unpolarized and the diffusers 19710, 19712 do not include polarizers so that the diffuse light 19722, 19724 is unpolarized as well. The curved and angled sides of the polarizing beam splitter film 19714 redirect one polarization state of the diffuse light (shown as rays 19728, 19730) toward the reflective image source 18720 while also concentrating the light 19728, 19730 onto the imaging area of the reflective image source 18720. In this display assembly, the dual light sources 19704, 19708 and the folded polarizing beam splitter 19714 work in a complimentary fashion since the polarizing beam splitter film 19714 is continuous. As such, unpolarized diffused light 19722, 19724 is provided respectively on each side of the display assembly 19702 and a first polarization state (typically S) is redirected toward the reflective image source 18720 by the polarizing beam splitter film 19714 while light 19740, 19738 with the other polarization state (typically P) is transmitted by the polarizing beam splitter film 19714. The transmitted light 19740, 19738 with the other polarization state passes through both sides of the folded polarizing beam splitter film 19714 so that it reaches diffusers 19712, 19710 respectively on the opposite side. When the light 19740, 19738 impacts the diffuser 19712, 19710 respectively on the opposite side, it is diffusely reflected by the diffuser and in the process it becomes unpolarized. A reflector can be added to the light sources 19704, 19708 and the surrounding area to increase the reflection of the light 19740, 19738. This diffusely reflected unpolarized light then mixes with the diffuse light 19722, 19724 provided by the light source 19704, 19708 on the respective side and then passes back toward the polarizing beam splitter film 19714 where the light 19730, 19728 with the first polarization state is reflected toward the reflective image source, the light 19738, 19740 while the other polarization state is transmitted and the process continuously repeats. As such, in this embodiment of the disclosure the light of the other polarization state is continuously recycled thereby increasing the efficiency of the display assembly 19702 since both polarization states of the light 19718, 19720 supplied by the dual light sources 19704, 19708 is utilized to illuminate the reflective image source 18720. The increased diffuse reflection of the recycled light also improves the uniformity of the illuminating light provided to the reflective image source 18720. The image light (19732, 19734) may be provided straight to the associated imaging optics.

A similar approach to that presented in FIG. 197 and described above can be used in another embodiment with a display assembly that has flat surfaces in the sides of the folded polarizing beam splitter film. In this embodiment, since the sides of the reflective polarizing film are flat, the light from the sidelights retains the illumination uniformity provided by the diffuser.

In a further embodiment to the display assembly shown in FIG. 197, a solid film holder can be used wherein the light of the other polarization state is recycled to improved efficiency. The sides of the folded polarizing beam splitter film can be flat or curved in this embodiment.

FIG. 198 shows a schematic illustration of a method for making a frontlight 19902 such as that shown in FIG. 199 with a folded reflective beam splitter film 19808 and dual light sources on the sides. In FIG. 198, the dual light sources are not shown, as they can be part of another assembly step or in a surrounding module. A flowchart of the assembly method is provided in FIG. 204. In this method, top 19810 and bottom 19812 film holders are provided in Step 20402. The top and bottom film holders 19810, 19812 can be made from any transparent material by diamond turning, injection molding, compression molding or grinding. The combination of material and manufacturing technique are chosen to provide top 19810 and bottom 19812 film holders with low birefringence. Suitable low birefringence materials for the films holders 19810, 19812 include glass materials or plastics such as Zeonex F52R from Zeon Chemicals, APL5514 from Mitsui or OKP4 from Osaka Gas. The surfaces in the top and bottom film holders that will contact the folded polarizing beam splitter film 19808, are matched to hold the film 19808 in place with the desired shape and angle without introducing significant airgap, so the image light can pass through the frontlight 19902 without being substantially deflected. In Step 20404, the bottom film holder 19812 is attached to the reflective image source 18720 either by adhesive binding or by providing a surrounding structure that holds the bottom film holder 19812 in relationship (either in contact or at a specified distance) to the reflective image source 18720. The polarizing beam splitter film is folded in Step 20408. Then in Step 20410, the folded polarizing beam splitter film 19808 is placed into the lower film holder 19812 and the upper film holder 19810 is placed on top, thereby forcing the polarizing beam splitter film 19808 to conform with the matched surfaces of the top 19810 and bottom 19812 film holders. In an alternate embodiment of this method, an adhesive is applied to the surface of the top 19810 or bottom 19812 film holder so that the polarizing beam splitter film 19808 is bonded to the top 19810 or bottom 19812 film holder. The diffusers 19802, 19804 are attached to the sides of the lower 19812 film holder in Step 20412. A schematic illustration of the assembled frontlight 19902 is shown in FIG. 199. Similar methods can be used to make the frontlights shown in FIGS. 191, 194 and 195. The order of assembly can be changed within the scope of the disclosure.

In an alternate embodiment to the method described above, the film holders 19810, 19812 are assembled with the folded polarizing beam splitter film 19808 prior to being attached to the diffusers 19802, 19804 or the reflective image source 18720 or any other pieces. Steps 20402, 20408 and 20410 are then done in sequence to make a solid film holder with the folded polarizing beam splitter film 19808 inside as shown similarly in FIGS. 191, 194 and 195. The reflective image source 18720 and the diffusers 19802, 19804 are attached at a later time (Steps 20404, 20412).

Various methods can be used to hold the reflective beam splitter film in place between the top and bottom film holders. The film can be bonded in place to the top or bottom film holder. The top or bottom film holder can be bonded to a surrounding structural piece (not shown) or to associated imaging optics (not shown). When the reflective beam splitter film is a polarizing beam splitter film with a wire grid polarizer, the performance of the wire grid polarizer can be compromised if adhesive is used on the side of the wire grid structure. In this case, the polarizing beam splitter film can be bonded on the opposite side to the wire grid structure to either the top or bottom film holder depending on which is adjacent the wire grid structure. Adhesives used to bond the polarizing beam splitter film to the film holder must be transparent and low birefringence. Examples of suitable adhesives include UV curing adhesives or pressure sensitive adhesives.

FIGS. 200-203 show a series of schematic illustrations of another method for making a frontlight with dual sidelights. FIG. 205 is a flowchart that lists the steps of the method. In this method, the top and bottom film holders are cast in place around the folded reflective beam splitter film. In Step 20502, the polarizing beam splitter film 20008 is folded. In Step 20504, the folded polarizing beam splitter film 20008 is inserted into side frames, which have slots or matching pieces to hold the polarizing beam splitter film 20008 in the desired shape for the frontlight (see the dual curved shape shown in FIG. 200). The side frames are then attached to the reflective image source 18720 in Step 20508. The diffusers 20002, 20004 are attached to the sides of the side frames in Step 20510. At this point, the folded polarizing beam splitter film 20008 is surrounded on the sides by the side frames and the diffusers 20002, 20004 and on the bottom by the reflective image source 18720. FIG. 200 shows a schematic illustration of the reflective image source 18720 with attached diffusers 20002, 20004 and a free standing reflective beam splitter film 20008 that is supported at the edges so that the desired shape is imparted to the reflective beam splitter film 20008.

FIG. 201 shows holes in the side frames or surrounding structure, which are used to introduce the transparent casting material under the folded reflective beam splitter film. As shown, the larger hole 20102 near the reflective image source 18720 is used to introduce the transparent casting material, while the smaller holes 20104 are used to allow the air to escape from under the folded reflective beam splitter film 20008. In this method, the folded reflective beam splitter film 20008 forms an enclosed cavity over the reflective image source 18720 and contained by the diffusers 20002, 20004 and the side frames or surrounding structure. As the transparent casting resin is slowly injected into hole 20102, the air from the enclosed cavity passes out the smaller holes 20104. When the cavity is full, portions of the transparent casting material flow out of the holes 20104 thereby preventing pressures from forming under the reflective beam splitter film 20008 that would distort the shape of the film. The holes 20102 and 20104 can then be plugged to prevent the transparent casting material from leaking back out.

In Step 20512, transparent liquid casting material 20202 is poured on top of the polarizing beam splitter film 20008 as shown in FIG. 202. A transparent top sheet or plate 20302 is then applied in Step 20514 to provide a flat top surface to material 20202 as shown in FIG. 203. Care must be taken to prevent air from being entrapped under the flat sheet of transparent material when it is applied to the transparent casting material. Stops can be provided in the surrounding structure to hold the flat sheet of transparent material parallel to the reflective image source.

The transparent liquid casting material can be any transparent liquid casting material such as epoxy, acrylic or urethane. The same transparent liquid casting material should be used for the top film holder as the bottom film holder so the image light is exposed to a uniform optical thickness solid block and the image light is not deflected by the surfaces of the folded polarizing beam splitter film. The transparent liquid casting material can be cured after casting by allowing a cure time, exposing to UV or exposing to heat. Curing of the transparent casting material can be done in a single step or in multiple steps. Curing of the lower portion as shown in FIG. 201 can be done prior to the casting of the upper portion shown in FIG. 202. Alternately, curing of the entire cast frontlight can be done after the step shown in FIG. 203.

The advantage of the method shown in FIGS. 200-203 is that intimate contact is obtained between the transparent casting material and the reflective beam splitter film so that light can pass unimpeded through the portions of the frontlight. The casting method can also be used with a solid top or bottom film holder so that only the top or bottom film holder is cast. While FIGS. 200-203 show a frontlight being made with curved surfaces, the method can be used to make a frontlight with flat surfaces as well.

In a further embodiment, one of the film holders is made as a solid piece and the other film holder is cast with the folded polarizing beam splitter film in place. The folded polarizing beam splitter film can be bonded to the solid piece prior to casting the other film holder in place. In this way, the cast film holder will have intimate contact with the surfaces of the polarizing beam splitter film. The materials used for the solid film holder should have the same refractive index as the cast film holder to avoid deflecting the image light as it passes through from the reflective image source to the associated imaging optics. An example of suitably matched materials is APEC 2000 from Bayer which has a refractive index of 1.56 and is injection moldable with EpoxAcast 690 from Smooth-On which has an refractive index of 1.565 and is castable.

In a yet further embodiment of the method, a solid film holder is made using a multi-step molding process as shown in the flowchart of FIG. 206. In Step 20602, the bottom film holder is molded. Suitable molding techniques include injection molding, compression molding or casting. In Step 20604, the polarizing beam splitter film is folded. In Step 20608, the folded polarizing beam splitter film is placed on the molded bottom film holder and then placed as an insert into a mold for the top film holder. In Step 20610, the top film holder is then molded over the folded polarizing beam splitter film and the bottom film holder. The end result is a solid film holder with the folded polarizing beam splitter film inside such as is shown in FIGS. 191, 194 and 195. The advantage of this multi-step molding technique is that the folded polarizing beam splitter film is forced to conform to the surface of the bottom film holder and the top and bottom film holders are in intimate contact with the folded polarizing beam splitter film. In a preferred embodiment, the refractive index of the top and bottom film holders is the same within 0.03. In a further preferred embodiment, the glass transition point of the material for the bottom film holder is higher than the glass transition point for the material of the top film holder or the material for the bottom film holder is crosslinked so that the bottom film holder doesn't deform when the top film holder is molded over the folded polarizing beam splitter film and the bottom film holder. An example of a suitable combination of injection moldable materials are cyclic olefin materials such as Zeonex E48R from Zeon Chemicals with a Tg of 139 C and refractive index of 1.53 and Topas 6017 from Topas Advanced Polymers with a Tg of 177 C and refractive index of 1.53.

It is to be understood that some embodiments of the AR eyepieces of the present disclosure have high modulation transfer functions that permit combinations of resolution levels and device size, e.g., eyeframe thickness, that have been unachievable heretofore. For example, in some embodiments, the virtual image pixel resolution levels presented to the user may be in the range of from about 28 to about 46 pixels per degree.

Figure 105:
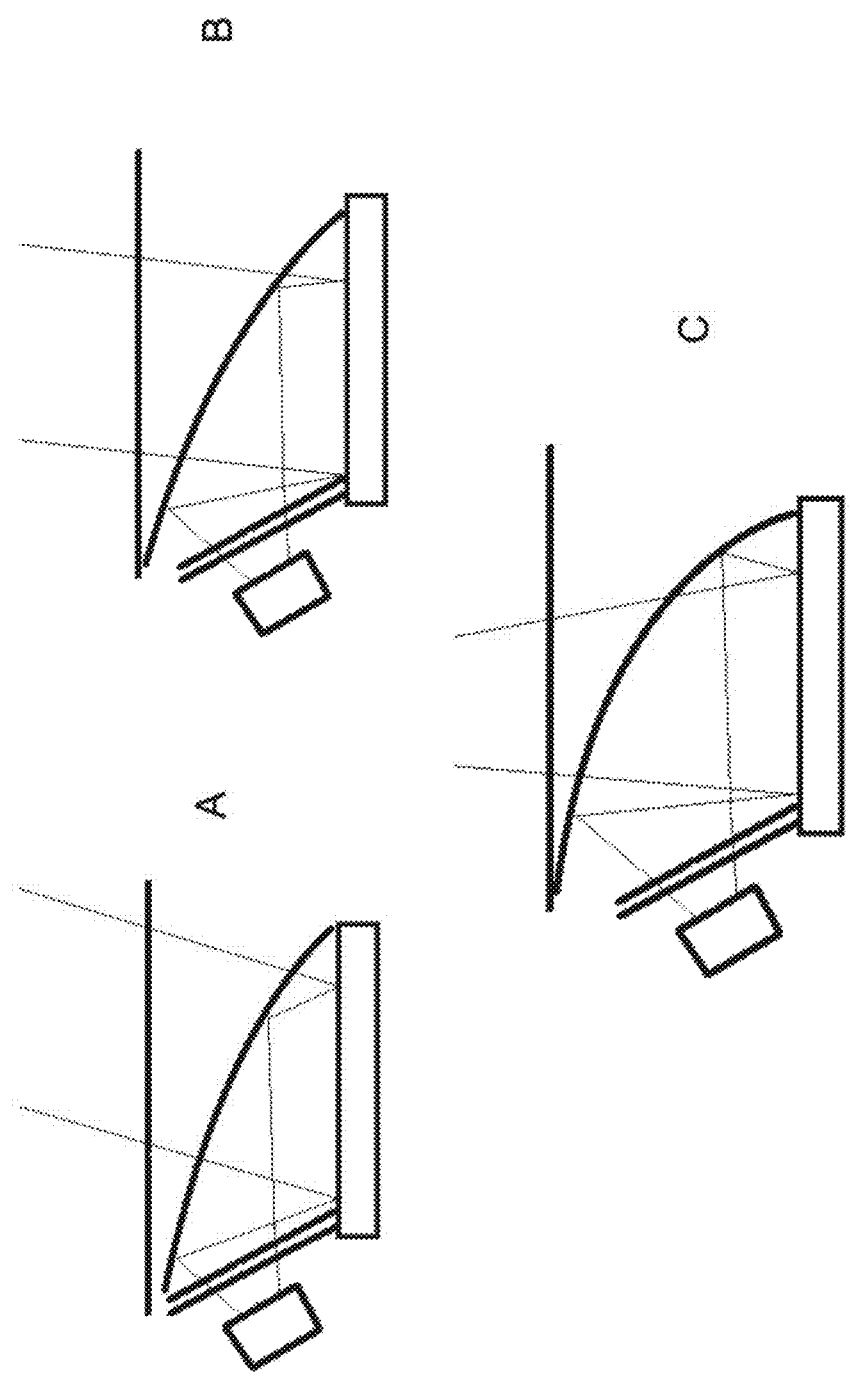

Referring to FIGS. 105 A through C, the angle of the curved wire grid polarizer controls the direction of the image light. The curve of the curved wire grid polarizer controls the width of the image light. The curve enables use of a narrow light source because it spreads the light when the light strikes it and then folds it/reflects it to uniformly illuminate an image display. Image light passing back through the wire grid polarizer is unperturbed. Thus, the curve also enables the miniaturization of the optical assembly.

In FIGS. 21-22, augmented reality eyepiece 2100 includes a frame 2102 and left and right earpieces or temple pieces 2104. Protective lenses 2106, such as ballistic lenses, are mounted on the front of the frame 2102 to protect the eyes of the user or to correct the user's view of the surrounding environment if they are prescription lenses. The front portion of the frame may also be used to mount a camera or image sensor 2130 and one or more microphones 2132. Not visible in FIG. 21, waveguides are mounted in the frame 2102 behind the protective lenses 2106, one on each side of the center or adjustable nose bridge 2138. The front cover 2106 may be interchangeable, so that tints or prescriptions may be changed readily for the particular user of the augmented reality device. In one embodiment, each lens is quickly interchangeable, allowing for a different prescription for each eye. In one embodiment, the lenses are quickly interchangeable with snap-fits as discussed elsewhere herein. Certain embodiments may only have a projector and waveguide combination on one side of the eyepiece while the other side may be filled with a regular lens, reading lens, prescription lens, or the like. The left and right ear pieces 2104 may each vertically mount a projector or microprojector 2114 or other image source atop a spring-loaded hinge 2128 for easier assembly and vibration/shock protection. Each temple piece also includes a temple housing 2116 for mounting associated electronics for the eyepiece, and each may also include an elastomeric head grip pad 2120, for better retention on the user. Each temple piece also includes extending, wrap-around ear buds 2112 and an orifice 2126 for mounting a headstrap 2142.

As noted, the temple housing 2116 contains electronics associated with the augmented reality eyepiece. The electronics may include several circuit boards, as shown, such as for the microprocessor and radios 2122, the communications system on a chip (SOC) 2124, and the open multimedia applications processor (OMAP) processor board 2140. The communications system on a chip (SOC) may include electronics for one or more communications capabilities, including a wide local area network (WLAN), BlueTooth™ communications, frequency modulation (FM) radio, a global positioning system (GPS), a 3-axis accelerometer, one or more gyroscopes, and the like. In addition, the right temple piece may include an optical trackpad (not shown) on the outside of the temple piece for user control of the eyepiece and one or more applications.

In an embodiment, a digital signal processor (DSP) may be programmed and/or configured to receive video feed information and configure the video feed to drive whatever type of image source is being used with the optical display. The DSP may include a bus or other communication mechanism for communicating information, and an internal processor coupled with the bus for processing the information. The DSP may include a memory, such as a random access memory (RAM) or other dynamic storage device (e.g., dynamic RAM (DRAM), static RAM (SRAM), and synchronous DRAM (SDRAM)), coupled to the bus for storing information and instructions to be executed. The DSP can include a non-volatile memory such as for example a read only memory (ROM) or other static storage device (e.g., programmable ROM (PROM), erasable PROM (EPROM), and electrically erasable PROM (EEPROM)) coupled to the bus for storing static information and instructions for the internal processor. The DSP may include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The DSP may include at least one computer readable medium or memory for holding instructions programmed and for containing data structures, tables, records, or other data necessary to drive the optical display. Examples of computer readable media suitable for applications of the present disclosure may be compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read. Various forms of computer readable media may be involved in carrying out one or more sequences of one or more instructions to the optical display for execution. The DSP may also include a communication interface to provide a data communication coupling to a network link that can be connected to, for example, a local area network (LAN), or to another communications network such as the Internet. Wireless links may also be implemented. In any such implementation, an appropriate communication interface can send and receive electrical, electromagnetic or optical signals that carry digital data streams representing various types of information (such as the video information) to the optical display.

The eyepiece may be able to do context-aware capture of video that adjusts video capture parameters based on the motion of the viewer, where a parameter may be image resolution, video compression, frames per second rate, and the like. The eyepiece may be used for a plurality of video applications, such as recording video taken through an integrated camera or as transmitted from an external video device, playing back video to the wearer through the eyepiece (by methods and systems as described herein), streaming live video either from an external source (e.g. a conference call, a live news feed, a video stream from another eyepiece) or from an integrated camera (e.g. from an integrated non-line-of-sight camera), and the like. In embodiments, the eyepiece may accommodate multiple video applications being presented to the wearer at once, such as for example viewing a streamed external video link concurrent with a playback of a video file stored on the eyepiece. The eyepiece may provide for a 3D viewing experience, such as through providing images to either eyes, or alternately, a reduced 3D experience, such as providing a reduced amount of content to one of two eyes. The eyepiece may provide for text-enhanced video, such as when audio conditions are too loud to hear the included audio, the audio is in a language foreign to the user, the user wants to record a transcription of the audio, and the like.

In embodiments, the eyepiece may provide for context-aware video applications, such as adjusting at least one parameter of video capture and/or viewing as a function of the environment of the wearer. For instance, a wearer of the eyepiece may be presented video through the eyepiece in the context of an external environment that requires the wearer to concentrate on the external environment more than the video, where the at least one parameter adjusts the presented video in a manner that makes the presentation less distracting (e.g. adjustment of spatial resolution; adjustment of frames per second; replacement of the video presentation with a static image representative of the content of the video, such as a stored picture of the person, a single frame from the video); and the like. In another instance, video may be captured by an integrated camera on the eyepiece in the context of the wearer being in motion (e.g. walking, running, biking, driving) where the at least one parameter adjusts the video being captured to help accommodate for the motion (e.g. making adjustments during periods where the eyepiece senses rapid motion where the video would be blurred, making adjustments during periods where the wearer is walking or moving slowly).

In embodiments, the at least one parameter may be a spatial resolution parameter (e.g. pixels per area, specific color pixels per area, limiting to only a single ('black and white') pixel per area), field-of-view, frames recorded per time, frames presented per time, data compression, periods of time not recorded/presented, and the like.

In embodiments, the at least one parameter may be adjusted based on a sensed input by the eyepiece, such as from a motion detection input (as described herein) for determining head motion (e.g. to determine rapid head motion, slow head motion), motion of the surrounding video-captured environment or within the environment through processing of images received through the integrated camera for determining relative motion between the wearer and the environment, eye motion of the wearer (as described herein) to determine whether the wearer is being distracted by video being presented to the wearer, ambient light and/or sound conditions, and the like.

In embodiments, the eyepiece may provide image processing with respect to reducing the effects of motion or the environment on the quality of a video experience by the wearer or as stored when capturing video, such as for the compensation for gentle movements, bouncing, rapid motion; adjustment of background lighting and/or sound environment, such as by adjusting the color mixture, brightness; and the like. Selection of processing may be a function of sensed inputs, environmental conditions, video content, and the like. For instance, a high quality image may be preferred in some instances, such that under certain circumstances a reduction in quality is not acceptable, and so video may be paused under those circumstances. In another instance, video and/or audio compression may be applied where it is determined that circumstances preclude the capture of an acceptable level of quality, but where some continuity of capture is still desired. Processing may also be applied differently to each eye of the eyepiece, such as with respect to a wearer's dominant eye, to varying environmental conditions experienced in one eye verses the other, and the like. Processing may compensate for a bright environment, where an embedded sensor is used to check ambient light levels for possible adjustments to the display of content, such as to determine what color channel compression and/or manipulation to perform based on the environment, modifying a color curve/palette to be more or less visible relative to the ambient environment, to vary color depth, color curve, vary how the color is compressed, and the like.

In embodiments, the eyepiece may initiate an action as a result of a sensed condition, such as going to a screen-shot mode while continuing the audio portion of the video when a condition is exceeded, such as exceeding a predetermined amount of movement by the eyepiece, stop taking video if the motion is such as would degrade a predetermined quality level, trigger a change in the video presentation as the motion level is exceeded in the received video, and the like.

In embodiments, the eyepiece may initiate an action as a result of the receipt of a control signal. The control signal could be based on the location of the eyepiece, on what is currently being viewed by the eyepiece or a user gesture. The action could be the upload or download of the video being captured by the eyepiece from a storage location. The action may be initiated solely upon receipt of the control signal itself or by the receipt of the control signal and a confirmation control signal initiated by the user. The action could be the initiation of a process to move to a specific position within the video being displayed by the glasses, bookmark a specific position within the video being displayed by the glasses, and the like.

In embodiments, adjustments made as a result of sensed conditions may be controlled through user preferences, an organizations policy, state or federal regulations, and the like. For instance, it may be a preference to always provide a certain quality, resolution, compression, and the like, no matter what the sensed inputs indicate.

In an example, the wearer of the eyepiece may be in an environment where their head, and thus the integrated camera of the eyepiece, is rapidly shaking while the eyepiece is recording video. In this case the eyepiece may adjust at least one parameter to reduce the extent to which the shaky video is captured, such as increasing the compression being applied to the video, reducing the number of frames being captured per period of time (e.g. capturing a frame every few seconds), discarding frames that have a large change in the image from frame to frame, reducing the spatial resolution, and the like.

In an example, the wearer of the eyepiece may be using video conferencing through the eyepiece where the eyepiece senses through a motion sensor that the wearer is moving. As a result, static images may replace the participant's video feed during this motion, such as for the image of one of the other participants or the user's image as transmitted to the other members. In this way, the distracting effects of the motion of the wearer may be reduced for the wearer and/or the other participants in the videoconference.

In an example, the wearer may be viewing a video and then begin driving a car, where it may become a safety issue if the wearer continues to view the video as currently displayed. In this instance, the eyepiece may be able to detect the motion of the environment as indicative of being in a car, and alter the viewing experience to be less distracting, such as if the eye movement of the wearer indicates that the user is quickly alternating between the line-of-sight (driving direction) or the field of view directly behind the car, and the displayed video. The eyepiece may for instance halt the video, and present the viewer with options to continue. The eyepiece may further be able to sense the motion of the environment as differentiated between being in a car, a bike, walking, and the like, and adjust accordingly.

In an example, the wearer may need assistance in navigating to a location, whether in a car, on a bike, walking, or the like. In this instance, the eyepiece would display a video navigation application to the user. The navigation instructions that are displayed by the eyepiece to the user could be selected by a control signal. The control signal could be generated by a location specified by the wearer, by what is currently being displayed in the glasses or on a destination spoken by wearer. The location may be one of an eating/drinking, education, event, exercise, home, outdoors, retail, transportation location, or the like.

In an example, the wearer may be capturing video where the ambient environment is distracting or lowers the quality of the video in some regard, such as because of color contrast, mixture, depth, resolution, brightness, and the like. The eyepiece may adjust for conditions where the wearer is outside verses inside, under different lighting conditions, under unfavorable sound conditions, and the like. In this case, the eyepiece may adjust the image and sound as recorded so as to create a video product that is a more effective representation of the content being captured.

In embodiments, the eyepiece may provide an external interface to computer peripheral devices, such as a monitor, display, TV, keyboards, mice, memory storage (e.g. external hard drive, optical drive, solid state memory), network interface (e.g. to the Internet), and the like. For instance, the external interface may provide direct connectivity to external computer peripheral devices (e.g. connect directly to a monitor), indirect connectivity to external computer peripheral devices (e.g. through a central external peripheral interface device), through a wired connection, though a wireless connection, and the like. In an example, the eyepiece may be able to connect to a central external peripheral interface device that provides connectivity to external peripheral devices, where the external peripheral interface device may include computer interface facilities, such as a computer processor, memory, operating system, peripheral drivers and interfaces, USB port, external display interface, network port, speaker interface, microphone interface, and the like. In embodiments, the eyepiece may be connected to the central external peripheral interface by a wired connection, wireless connection, directly in a cradle, and the like, and when connected may provide the eyepiece with computational facilities similar to or identical to a personal computer. In embodiments, the device selected to be controlled by the eyepiece may be chosen the user looking at the eyepiece, pointing at the eyepiece, selecting from a user interface displayed on the eyepiece, and the like. In other embodiments, the eyepiece may display the user interface of the device when a user looks or points at the device.

The frame 2102 is in a general shape of a pair of wraparound sunglasses. The sides of the glasses include shape-memory alloy straps 2134, such as nitinol straps. The nitinol or other shape-memory alloy straps are fitted for the user of the augmented reality eyepiece. The straps are tailored so that they assume their trained or preferred shape when worn by the user and warmed to near body temperature. In embodiments, the fit of the eyepiece may provide user eye width alignment techniques and measurements. For instance, the position and/or alignment of the projected display to the wearer of the eyepiece may be adjustable in position to accommodate the various eye widths of the different wearers. The positioning and/or alignment may be automatic, such as though detection of the position of the wearer's eyes through the optical system (e.g. iris or pupil detection), or manual, such as by the wearer, and the like.

Other features of this embodiment include detachable, noise-cancelling earbuds. As seen in the figure, the earbuds are intended for connection to the controls of the augmented reality eyepiece for delivering sounds to ears of the user. The sounds may include inputs from the wireless internet or telecommunications capability of the augmented reality eyepiece. The earbuds also include soft, deformable plastic or foam portions, so that the inner ears of the user are protected in a manner similar to earplugs. In one embodiment, the earbuds limit inputs to the user's ears to about 85 dB. This allows for normal hearing by the wearer, while providing protection from gunshot noise or other explosive noises and listening in high background noise environments. In one embodiment, the controls of the noise-cancelling earbuds have an automatic gain control for very fast adjustment of the cancelling feature in protecting the wearer's ears.

Figure 23:
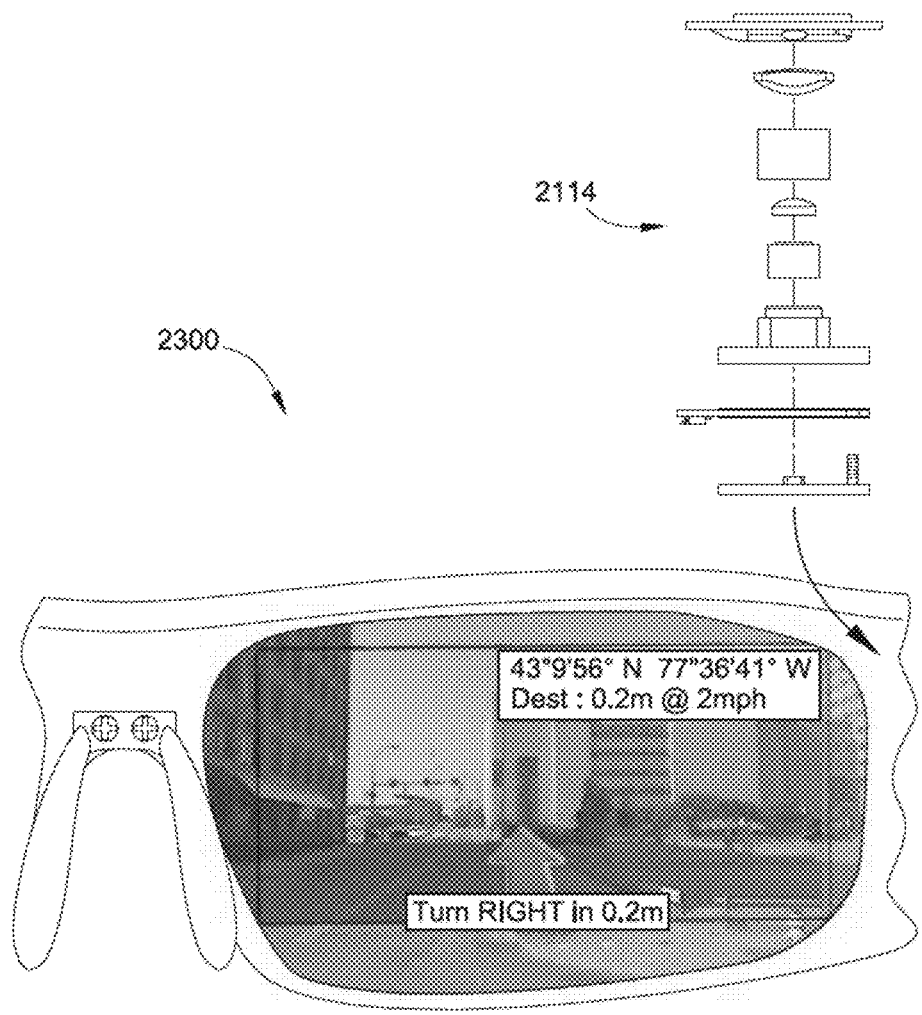
FIG. 23 depicts an alternative arrangement of the eyepiece optics and electronics.

FIG. 23 depicts a layout of the vertically arranged projector 2114 in an eyepiece 2300, where the illumination light passes from bottom to top through one side of the PBS on its way to the display and imager board, which may be silicon backed, and being refracted as image light where it hits the internal interfaces of the triangular prisms which constitute the polarizing beam splitter, and is reflected out of the projector and into the waveguide lens. In this example, the dimensions of the projector are shown with the width of the imager board being 11 mm, the distance from the end of the imager board to the image centerline being 10.6 mm, and the distance from the image centerline to the end of the LED board being about 11.8 mm.

Figure 25:
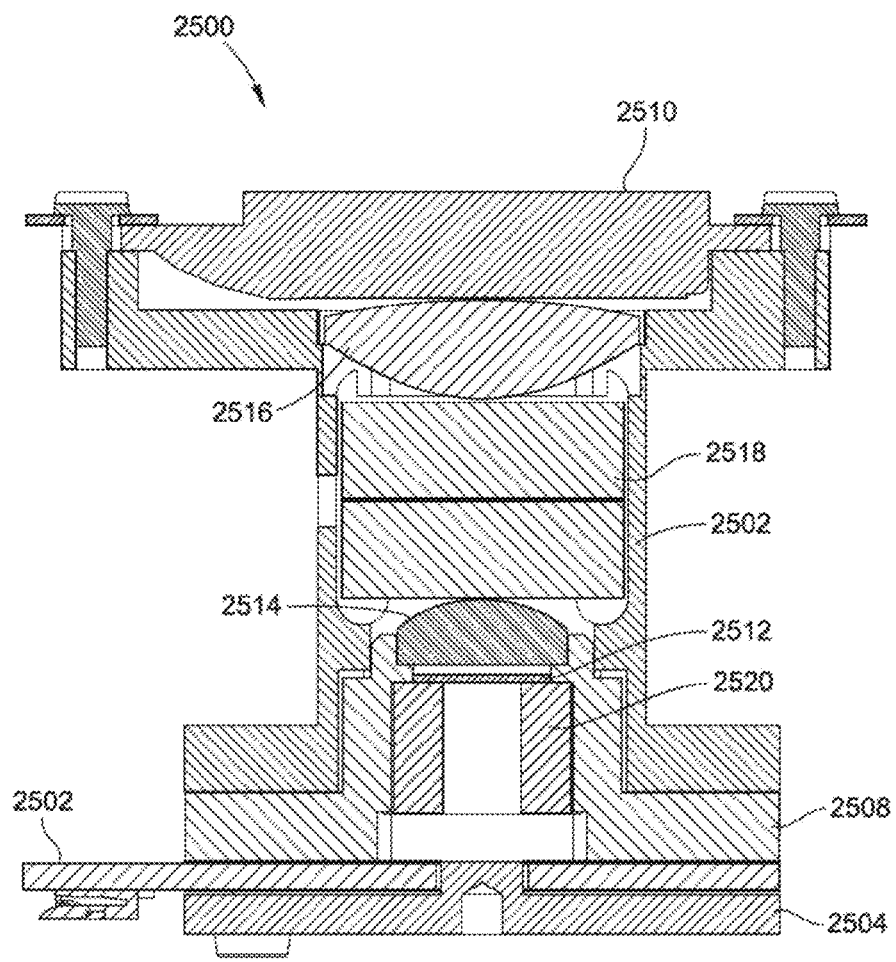
FIG. 25 depicts a detailed view of the projector.

A detailed and assembled view of the components of the projector discussed above may be seen in FIG. 25. This view depicts how compact the micro-projector 2500 is when assembled, for example, near a hinge of the augmented reality eyepiece. Microprojector 2500 includes a housing and a holder 2508 for mounting certain of the optical pieces. As each color field is imaged by the optical display 2510, the corresponding LED color is turned on. The RGB LED light engine 2502 is depicted near the bottom, mounted on heat sink 2504. The holder 2508 is mounted atop the LED light engine 2502, the holder mounting light tunnel 2520, diffuser lens 2512 (to eliminate hotspots) and condenser lens 2514. Light passes from the condenser lens into the polarizing beam splitter 2518 and then to the field lens 2516. The light then refracts onto the LCoS (liquid crystal on silicon) chip 2510, where an image is formed. The light for the image then reflects back through the field lens 2516 and is polarized and reflected 90° through the polarizing beam splitter 2518. The light then leaves the microprojector for transmission to the optical display of the glasses.

Figure 26:
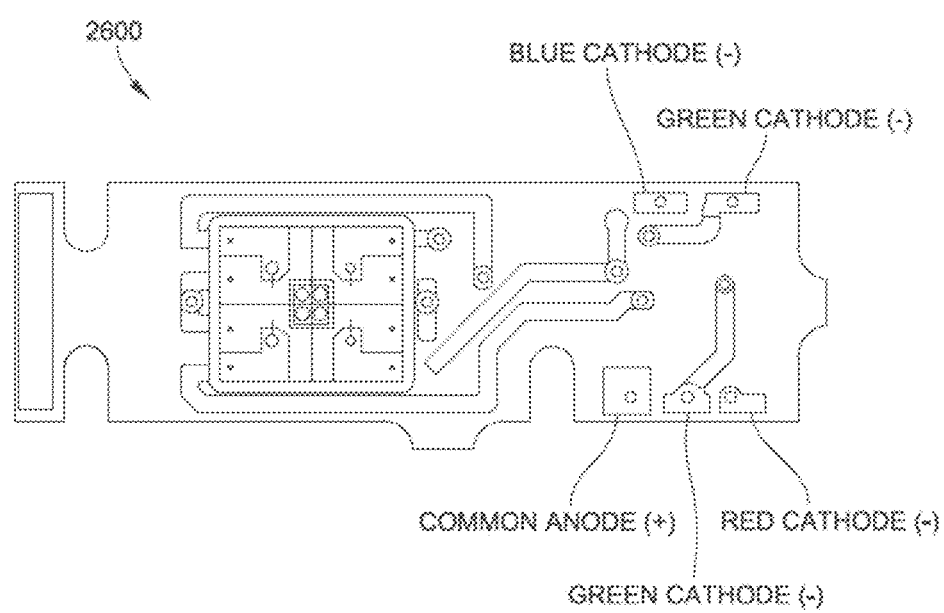
FIG. 26 depicts a detailed view of the RGB LED module.

FIG. 26 depicts an exemplary RGB LED module 2600. In this example, the LED is a 2×2 array with 1 red, 1 blue and 2 green die and the LED array has 4 cathodes and a common anode. The maximum current may be 0.5 A per die and the maximum voltage (≈4V) may be needed for the green and blue die.

In embodiments, the system may utilize an optical system that is able to generate a monochrome display to the wearer, which may provide advantages to image clarity, image resolution, frame rate, and the like. For example, the frame rate may triple (over an RGB system) and this may be useful in a night vision and the like situation where the camera is imaging the surroundings, where those images may be processed and displayed as content. The image may be brighter, such as be three times brighter if three LEDs are used, or provide a space savings with only one LED. If multiple LEDs are used, they may be the same color or they could be different (RGB). The system may be a switchable monochrome/color system where RGB is used but when the wearer wants monochrome they could either choose an individual LED or a number of them. All three LEDs may be used at the same time, as opposed to sequencing, to create white light. Using three LEDs without sequencing may be like any other white light where the frame rate goes up by a factor of three. The "switching" between monochrome and color may be done "manually" (e.g. a physical button, a GUI interface selection) or it may be done automatically depending on the application that is running. For instance, a wearer may go into a night vision mode or fog clearing mode, and the processing portion of the system automatically determines that the eyepiece needs to go into a monochrome high refresh rate mode.

Figure 3:
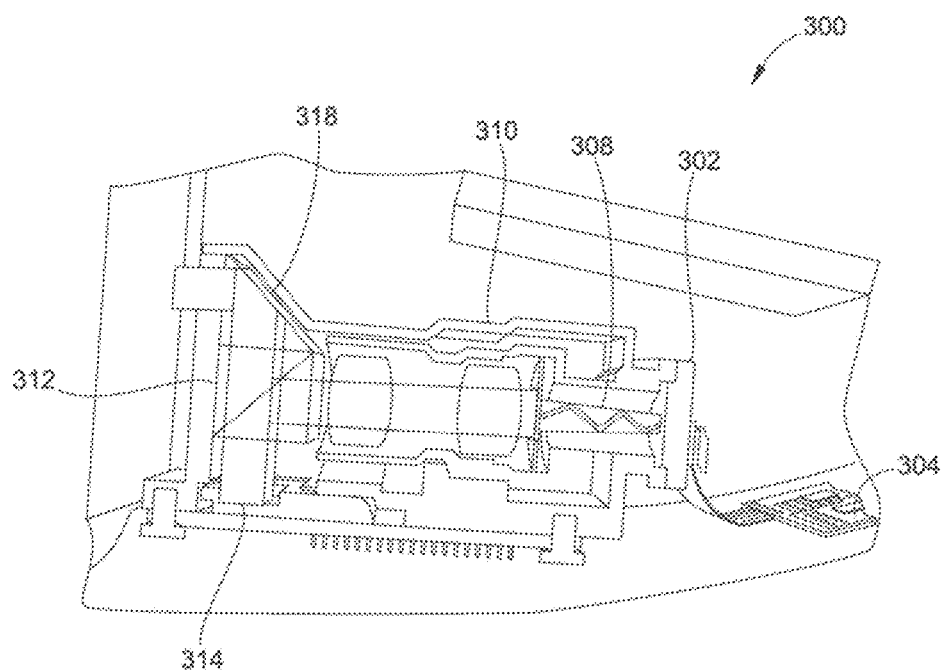
FIG. 3 depicts the projector in use.

FIG. 3 depicts an embodiment of a horizontally disposed projector in use. The projector 300 may be disposed in an arm portion of an eyepiece frame. The LED module 302, under processor control 304, may emit a single color at a time in rapid sequence. The emitted light may travel down a light tunnel 308 and through at least one homogenizing lenslet 310 before encountering a polarizing beam splitter 312 and being deflected towards an LCoS display 314 where a full color image is displayed. The LCoS display may have a resolution of 1280×720p. The image may then be reflected back up through the polarizing beam splitter, reflected off a fold mirror 318 and travel through a collimator on its way out of the projector and into a waveguide. The projector may include a diffractive element to eliminate aberrations.

In an embodiment, the interactive head-mounted eyepiece includes an optical assembly through which a user views a surrounding environment and displayed content, wherein the optical assembly includes a corrective element that corrects the user's view of the surrounding environment, a freeform optical waveguide enabling internal reflections, and a coupling lens positioned to direct an image from an optical display, such as an LCoS display, to the optical waveguide. The eyepiece further includes one or more integrated processors for handling content for display to the user and an integrated image source, such as a projector facility, for introducing the content to the optical assembly. In embodiments where the image source is a projector, the projector facility includes a light source and the optical display. Light from the light source, such as an RGB module, is emitted under control of the processor and traverses a polarizing beam splitter where it is polarized before being reflected off the optical display, such as the LCoS display or LCD display in certain other embodiments, and into the optical waveguide. A surface of the polarizing beam splitter may reflect the color image from the optical display into the optical waveguide. The RGB LED module may emit light sequentially to form a color image that is reflected off the optical display. The corrective element may be a see-through correction lens that is attached to the optical waveguide to enable proper viewing of the surrounding environment whether the image source is on or off. This corrective element may be a wedge-shaped correction lens, and may be prescription, tinted, coated, or the like. The freeform optical waveguide, which may be described by a higher order polynomial, may include dual freeform surfaces that enable a curvature and a sizing of the waveguide. The curvature and the sizing of the waveguide enable its placement in a frame of the interactive head-mounted eyepiece. This frame may be sized to fit a user's head in a similar fashion to sunglasses or eyeglasses. Other elements of the optical assembly of the eyepiece include a homogenizer through which light from the light source is propagated to ensure that the beam of light is uniform and a collimator that improves the resolution of the light entering the optical waveguide.

In embodiments, the prescription lens may be mounted on the inside of the eyepiece lens or on the outside. In some embodiments, the prescription power may be divided into prescription lenses mounted on the outside and inside of the eyepiece lens. In embodiments, the prescription correction is provided by corrective optics that cling to eyepiece lens or a component of the optical assembly, such as the beamsplitter, such as through surface tension. In embodiments, the corrective optics may be provided in part in one location in the optical path, and in part in another location in the optical path. For example, half of the corrective optics may be provided on the outside of the converging surface of the beamsplitter and the other half on the inside of the converging surface. In this way, correction may be provided differently to the image light from the internal source and to the scene light. That is, the light from the source may only be corrected by the portion of the corrective optics on the inside of the converging lens, as the image is reflected to the eye of the user, and the scene light may be corrected through both portions as the light is transmitted through the beamsplitter, thus being exposed to different optical corrections. In another embodiment, the optical assembly associated with the beamsplitter may be a sealed assembly, such as to make the assembly water proof, dust proof, and the like, where an inner surface of the sealed optical assembly has one portion of the corrective optics and the outside surface of the sealed optical assembly has another portion of the corrective optics. Suitable optics may be provided by 3M's Press-On Optics, which are available at least as Prisms (a.k.a. Fresnel Prisms), Aspheric Minus Lenses, Aspheric Plus Lenses, and Bifocal Lenses. The corrective optics may be a user removable and replaceable diopter correction facility adapted to be removably attached in a position between the user's eye and the displayed content such that the diopter correction facility corrects the user's eyesight with respect to the displayed content and the surrounding environment. The diopter correction facility may be adapted to mount to the optical assembly. The diopter correction facility may be adapted to mount to the head-mounted eyepiece. The diopter correction facility may mount using a friction fit. The diopter correction facility may mount using a magnetic attachment facility. The user may select from a plurality of different diopter correction facilities depending on the user's eyesight.

In embodiments, the present disclosure may provide for corrective optics that 'snap on' to the eyepiece, such as where a user removable and replaceable diopter correction facility is adapted to be removably attached in a position between the user's eye and the displayed content such that the diopter correction facility corrects the users eyesight with respect to the displayed content and the surrounding environment. The diopter correction facility may be adapted to mount to the optical assembly, to the head-mounted eyepiece, and the like. The diopter correction facility may be mounted using a friction fit, a magnetic attachment facility, and the like. The user may be able to select from a plurality of different diopter correction facilities depending on the user's eyesight.

Figure 4:
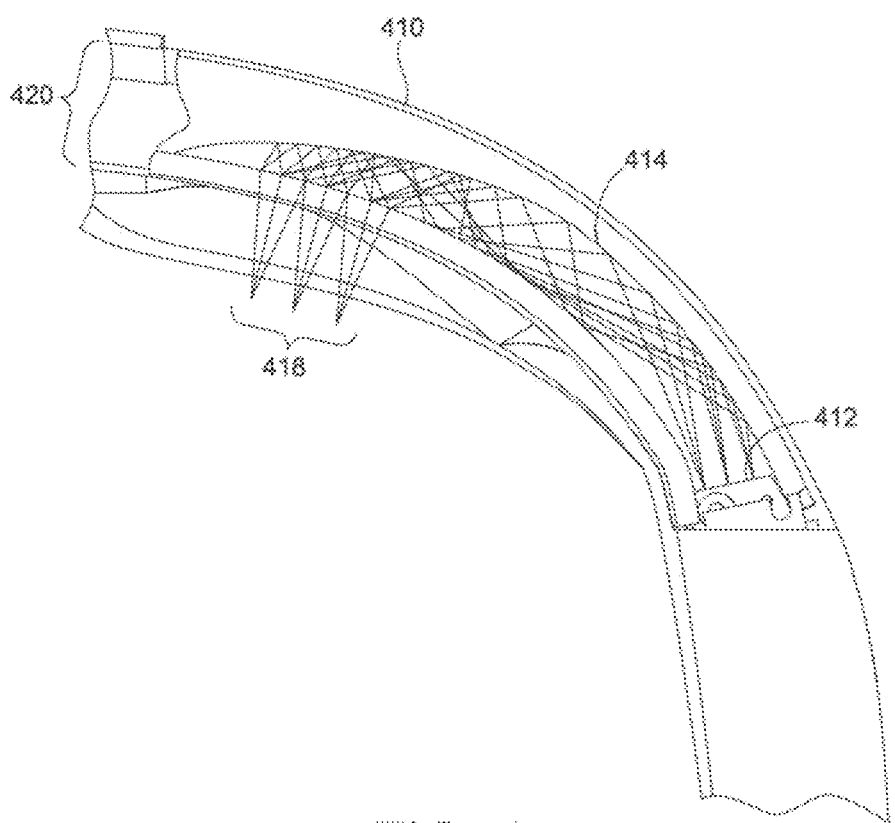
FIG. 4 depicts an embodiment of the waveguide and correction lens disposed in a frame.

Referring to FIG. 4, the image light, which may be polarized and collimated, may optionally traverse a display coupling lens 412, which may or may not be the collimator itself or in addition to the collimator, and enter the waveguide 414. In embodiments, the waveguide 414 may be a freeform waveguide, where the surfaces of the waveguide are described by a polynomial equation. The waveguide may be rectilinear. The waveguide 414 may include two reflective surfaces. When the image light enters the waveguide 414, it may strike a first surface with an angle of incidence greater than the critical angle above which total internal reflection (TIR) occurs. The image light may engage in TIR bounces between the first surface and a second facing surface, eventually reaching the active viewing area 418 of the composite lens. In an embodiment, light may engage in at least three TIR bounces. Since the waveguide 414 tapers to enable the TIR bounces to eventually exit the waveguide, the thickness of the composite lens 420 may not be uniform. Distortion through the viewing area of the composite lens 420 may be minimized by disposing a wedge-shaped correction lens 410 along a length of the freeform waveguide 414 in order to provide a uniform thickness across at least the viewing area of the lens 420. The correction lens 410 may be a prescription lens, a tinted lens, a polarized lens, a ballistic lens, and the like, mounted on the inside or outside of the eyepiece lens, or in some embodiments, mounted on both the inside and outside of the eyepiece lens.

In some embodiments, while the optical waveguide may have a first surface and a second surface enabling total internal reflections of the light entering the waveguide, the light may not actually enter the waveguide at an internal angle of incidence that would result in total internal reflection. The eyepiece may include a mirrored surface on the first surface of the optical waveguide to reflect the displayed content towards the second surface of the optical waveguide. Thus, the mirrored surface enables a total reflection of the light entering the optical waveguide or a reflection of at least a portion of the light entering the optical waveguide. In embodiments, the surface may be 100% mirrored or mirrored to a lower percentage. In some embodiments, in place of a mirrored surface, an air gap between the waveguide and the corrective element may cause a reflection of the light that enters the waveguide at an angle of incidence that would not result in TIR.

In an embodiment, the eyepiece includes an integrated image source, such as a projector, that introduces content for display to the optical assembly from a side of the optical waveguide adjacent to an arm of the eyepiece. As opposed to prior art optical assemblies where image injection occurs from a top side of the optical waveguide, the present disclosure provides image injection to the waveguide from a side of the waveguide. The displayed content aspect ratio is between approximately square to approximately rectangular with the long axis approximately horizontal. In embodiments, the displayed content aspect ratio is 16:9. In embodiments, achieving a rectangular aspect ratio for the displayed content where the long axis is approximately horizontal may be done via rotation of the injected image. In other embodiments, it may be done by stretching the image until it reaches the desired aspect ratio.

Figure 5:
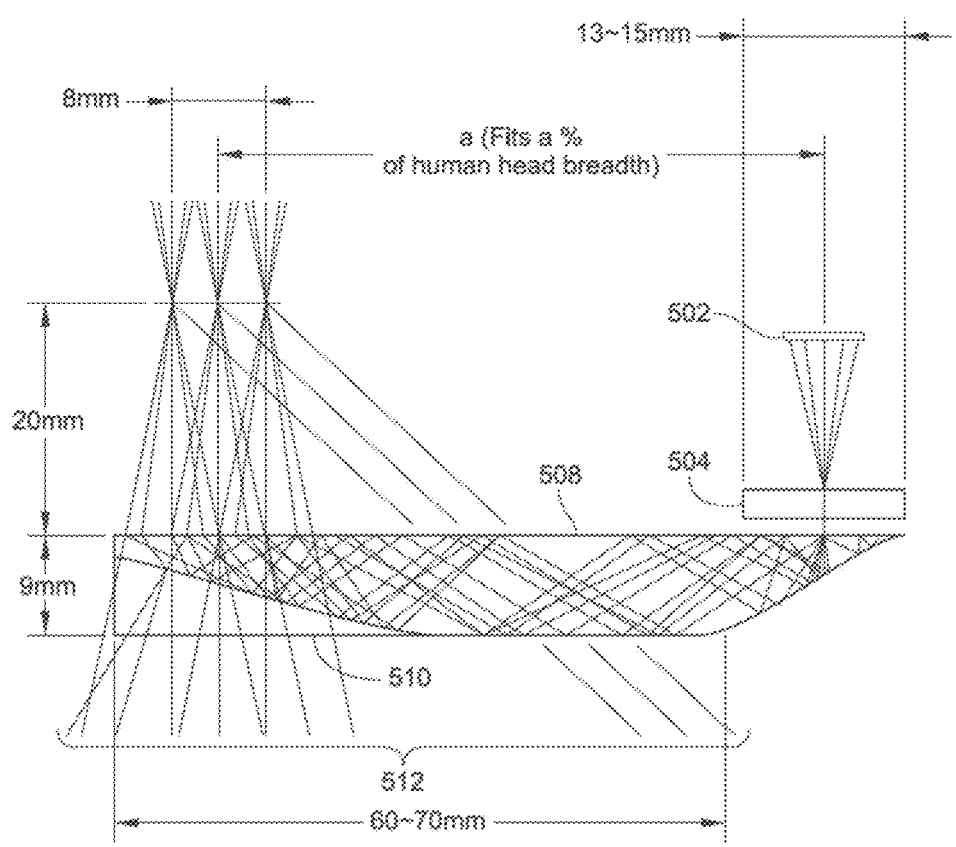
FIG. 5 depicts a design for a waveguide eyepiece.

FIG. 5 depicts a design for a waveguide eyepiece showing sample dimensions. For example, in this design, the width of the coupling lens 504 may be 13~15 mm, with the optical display 502 optically coupled in series. These elements may be disposed in an arm or redundantly in both arms of an eyepiece. Image light from the optical display 502 is projected through the coupling lens 504 into the freeform waveguide 508. The thickness of the composite lens 520, including waveguide 508 and correction lens 510, may be 9 mm. In this design, the waveguide 502 enables an exit pupil diameter of 8 mm with an eye clearance of 20 mm. The resultant see-through view 512 may be about 60~70 mm. The distance from the pupil to the image light path as it enters the waveguide 502 (dimension a) may be about 50~60 mm, which can accommodate a large % of human head breadths. In an embodiment, the field of view may be larger than the pupil. In embodiments, the field of view may not fill the lens. It should be understood that these dimensions are for a particular illustrative embodiment and should not be construed as limiting. In an embodiment, the waveguide, snap-on optics, and/or the corrective lens may comprise optical plastic. In other embodiments, the waveguide snap-on optics, and/or the corrective lens may comprise glass, marginal glass, bulk glass, metallic glass, palladium-enriched glass, or other suitable glass. In embodiments, the waveguide 508 and correction lens 510 may be made from different materials selected to result in little to no chromatic aberrations. The materials may include a diffraction grating, a holographic grating, and the like.

In embodiments such as that shown in FIG. 1, the projected image may be a stereo image when two projectors 108 are used for the left and right images. To enable stereo viewing, the projectors 108 may be disposed at an adjustable distance from one another that enables adjustment based on the inter-pupillary distance for individual wearers of the eyepiece. For example, a single optical assembly may include two independent electro-optic modules with individual adjustments for horizontal, vertical and tilt positioning. Alternatively, the optical assembly may include only a single electro-optic module.

FIGS. 146 through 149 schematically show an embodiment of an augmented reality (AR) eyepiece 14600 (without its temple pieces) in which the placement of the images may be adjusted. FIGS. 146 and 147 show, respectively, front and rear perspective views of the AR eyepiece 14600. In this embodiment, the electronics and portions of the projection systems (collectively 14602) are located above the lenses 14604*a*, 14604*b*. The AR eyepiece 14600 has two projection screens 14608*a*, 14608*b* which are adjustably suspended from an adjustment platform 14610 on the wearer-side of the lenses 14604*a*, 14604*b*. The adjustment platform 14610 has mounted on it mechanisms for independently adjusting the lateral position relative to the bridge 14612 of the AR eyepiece 14600 and tilt of each of the projection screens 14608*a*, 14608*b*.

The mechanisms for adjusting the positions of one or both of the display screens may be controlled by manually-activated (e.g., by way of buttons) or software-activated motors, by manual control devices (such as thumbwheels, lever arms, etc.) or a combination of both motorized and manual devices. The AR eyepiece 14600 employs manual devices, which will now be described. Those skilled in the art will understand that the adjustment mechanism is designed to decouple lateral adjustments from tilt adjustments.

FIG. 148 shows a perspective rear view of a portion of wearer's left side of the AR eyepiece 14600 in which the adjustment mechanism 14614 on adjustment platform 14610 for projection screen 14608*a* is shown more clearly. The projection screen 14608*a* is mounted on a frame 14618 which is fixedly attached to (or is part of) a movable carriage 14620. On its bridge 14612 side, the carriage 14620 is rotatably and slidably supported by the carriage shaft 14622 in an arcuate groove of first block 14624, which is attached to adjustment platform 14610. On its temple-side, the carriage 14620 is rotatably and slidably supported by a yoke 14628. Referring to FIG. 150, the yoke 14628 has a shaft portion 14630 that is fixedly attached to the carriage 14620 and coaxial with carriage shaft 14622 to provide the carriage 14620 with an axis of rotation. The yoke 14628 is slidably and rotatably supported in an arcuate groove of a second support block 14632, which is attached to adjustment platform 14610 (see FIG. 151).

The yoke 14628 also has two parallel arms 14634*a*, 14634*b* extending radially outward from the shaft portion 14630. The free end of each of the arms 14634*a*, 14634*b* has a hole, e.g., hole 14638 of arm 14634*b*, for fixedly capturing a shaft 14678 therebetween, as is discussed below (see FIG. 149). The arm 14634*a* has an anchor portion 14640 where it attaches to the shaft portion 14630 of the yoke 14628. The anchor portion 14640 has a through-hole 14642 for slidably capturing a pin 14660, as is discussed below (see FIG. 152).

Referring again to FIG. 148, the adjustment mechanism has a first thumbwheel 14644 for controlling the lateral position of the projection screen 14608*a* and a second thumbwheel 14648 for controlling the tilt of the projection screen 14608*a*. The first thumbwheel 14644 extends partially through a slot 14650 in the adjustment platform 14610 and is threadably engaged and supported by the first threaded shaft

14652. The first threaded shaft 14652 is slidably supported in through-holes in third and fourth support blocks 14654, 14658 (see FIG. 151). The third and fourth blocks 14654, 14658 and/or the sides of the slot 14650 act to prevent the first thumbwheel 14644 from moving laterally. Thus, rotating the thumbwheel 14644 around its axis (indicated by arrow A) causes the first threaded shaft 14652 to move laterally (indicated by arrow B). As best seen in FIG. 152, the first threaded shaft 14652 has a pin 14660 extending radially outward from its bridge-side end. (Note that the threads of the first threaded shaft 14652 are not depicted in the drawings, but may be single or multiple pitch threads.) The pin 14660 is slidably captured by the vertically-oriented through-hole 14642 of the anchor portion 14640 of arm 14634a of yoke 14628. When the first thumbwheel 14644 is turned in a direction that causes the first threaded shaft 14652 to advance laterally towards the bridge 14612, the pin 14660 pushes against the bridge 14612 side of through-hole 14642 which, in turn, makes the yoke 14628, the carriage 14620, the frame 14618, and the first projection screen 14608a all move laterally toward the bridge 14612 (see arrow C). Similarly, turning the first thumbwheel 14644 in the opposite direction results in the first projection screen 14608a moving laterally away from the bridge 14612.

The second thumbwheel 14648 is used to control the tilt of the first projection screen 14608a around the axis defined by the carriage shaft 14622 and the yoke shaft portion 14630. Referring now to FIG. 153, the second thumbwheel 14648 is fixedly attached to the narrow portion 14662 of a hollow flanged shaft 14664. The flange portion 14668 of the flanged shaft 14664 threadably receives a threaded shaft portion 14670 of an eyehook 14672. (Note that the threads of the threaded shaft portion 14670 are not depicted in the drawings, but may be single or multiple pitch threads.) In use, the narrow portion 14662 of the flanged shaft 14664 rotatably passes through a countersunk hole 14674 in the adjustment platform 14610 (see FIG. 151) so that the thumbwheel 14648 is on the bottom side of the adjustment platform 14610 and the eyehook 14672 is on the top side and the flange portion 14668 of the flanged shaft 14664 is captured within the countersunk portion of the countersunk hole 14674. Referring again to FIG. 149, the eye of the eyehook 14672 is slidably engaged around the shaft 14678 which is captured within the holes at the free ends of the yoke arms 14634a, 14634b. Thus, turning the second thumbwheel 14644 around its axis (as indicated by arrow D) causes the flanged shaft 14664 to turn with it which causes the threaded shaft portion 14670 of the eyehook 14672 to move vertically in or out of the flange portion 14668 (as indicated by arrow E) which cause the eye of the eyehook 14672 to push against the shaft 14678 which, in turn, causes the yoke 14628 to move around its axis thus causing the first projection screen 14608a to tilt away from or towards the wearer (as indicated by arrow F).

Referring again to FIG. 148, it is to be noted that the electronics and portions of the projection system 14602a are located on a platform 14680 that is fixed to the top of the carriage 14620. Thus, the spatial relationship between the projection screen 14608a and its associated electronics and portion of its projection system 14602a remains substantially unchanged by any lateral or tilt adjustment that is made to the projection screen 14608a.

The AR eyeglass 14600 also includes a similar adjustment mechanism to the adjustment mechanism 14614 just described for laterally positioning and tilting the second projection screen 14608b which is located on the wearer's right side of the AR eyepiece 14600.

In an embodiment, the eyepiece may include a slanted or curved guide rail for IPD adjustment that keeps the optics module more in the curved frame. In some embodiments, a display is operably connected to such a slanted or curved guide rail.

In embodiments, the display screen or screens of the AR eyepieces are arranged so as to be parallel to the line connecting the user's eyes. In some embodiment, the display screen or screens are rotated about their vertical axis so that their ends which are near the nose are rotated inward toward the eye, that is "toed-in", at an angle that is in the range of about 0.1 to about 5 degrees from being parallel to the line connecting the user's eyes. In some of these latter embodiments, the toe-in angle is permanently fixed, while in other embodiments, the toe-in angle is user-adjustable. In some of the user-adjustable embodiments, the adjustability is limited to two or more preset positions, e.g., those representing near convergence, medium distance convergence, and distant convergence. In other embodiments, the adjustability is continuous. Preferably, in embodiments of the AR eyeglasses which also include automatic vergence corrections as disclosed herein, the amount of toe-in is taken into consideration in the vergence corrections. In embodiments where the toe-in is permanently fixed, the toe-in amount may be included directly in the automatic vergence corrections without the need for a position sensor, but in the user-adjustable embodiments, a position sensor is preferably used to communicate to the processor the amount of toe-in present to use in the vergence correction calculations. In the embodiments in which the toe-in angle is user-adjustable, the adjustment may be made either manually, e.g., by use of a turnwheel that directly or indirectly, e.g., through a drive train, selectably rotates one or both display screens about their vertical axes, or may be motorized to accomplish the selectable rotation when activated by the user through a user interface or a control switch.

In some cases, the toe-in feature may be used to relax the user's eyes during lengthy sessions of activity during which the user's eyes are kept at a particular focus distance, e.g., while reading, watching a monitor, a ball game, or a horizon. The toe-in feature described above may be used in order to adjust for the user's interpupillary distance by effectively rotating the display screens to be better aligned with the user's eyes.

In embodiments, the present disclosure may provide for a mechanical pupil distance adjustment, such as where the optical assembly of the eyepiece is adapted to be user position adjustable within a glasses frame such that the user has the ability to change the position of the optical assembly with respect to the user's eye. The position adjustment may control the horizontal position, the vertical position, the tilt, and the like, of the optical assembly within the glasses frame.

In embodiments, the present disclosure may provide for digital pupil distance adjustment, such as where an integrated processor executes a pupil alignment procedure that enables the user to adjust the position of the placement of the displayed content within a field of view presented on the eyepiece optical assembly to set a pupil alignment calibration factor to be used in the placement of other display content. The calibration factor may comprise horizontal and/or vertical adjustments of the displayed content within the field of view. The calibration factor may comprise a plurality of calibration factors, each representing a distance to a real-world object distance calibration factor to be used when positioning content within the field of view based on a distance to real-world object calculation. The calibration factor may comprise a calibration process based on a plurality of calibration factors, each representing a distance to a real-world object distance calibration factor to be used when positioning content within the field of view based on a distance to real-world object calculation. The positioning of the image can be adjusted on the display to move it within the field of view. Moving the two images further apart will make it appear that the imaged object is getting further away, while moving the images closer together will make the object appear to be closer. The difference in the position of an object within the field of view for each eye is known as the disparity. The disparity relates to the perceived distance that the object is away from the user.

Referring now to FIG. 173, an exploded view of the glasses is depicted. The electronics 17302 are in the front frame of the glasses above the eyes, including the CPU, display drivers, camera, radios, processor, user interfaces, and the like. The optics modules 17308 are attached to the frame with lenses 17304, which may be optional, covering them. The lenses 17304 may be tinted or tintable. A stereo embodiment is shown here, but it should be understood that a single optics module 17308 may also be used. The electronics 17302 are sealed with a cover 17314 that includes a physical user interface 17310, which may be a button, touch interface, rollerball, switch, or any other physical user interface. The physical user interface 17310 may control various aspects of the glasses, such as functions of the glasses, applications running on the glasses, or applications controlling an external device. The user can easily utilize this control feature by grasping the lower part of the frame to stabilize it while touching the control feature/UI on the top of the frame. The arms 17312 rest on the ears and may include straps for securing the glasses, audio/ear phone functionality or jacks for external audio devices, battery 17318 or power functionality, and the like. Batteries 17318, options for which are disclosed herein but also include any available battery types, may be placed in either arm. The straps may be ear bands made from Nitinol or other shape memory alloy. The ear bands may be in a band format or, as in FIG. 177, the ear bands 17702 may be in a bent wire format to thin it down, lighten it up, and lower the cost. For aesthetic purposes, the frame may be in any color, the lenses may be in any color, and the eyepiece arms, or at least the tips of the arms, may be colored. For example, the nitinol forming the tip of the arm may be colored.

Figure 176:
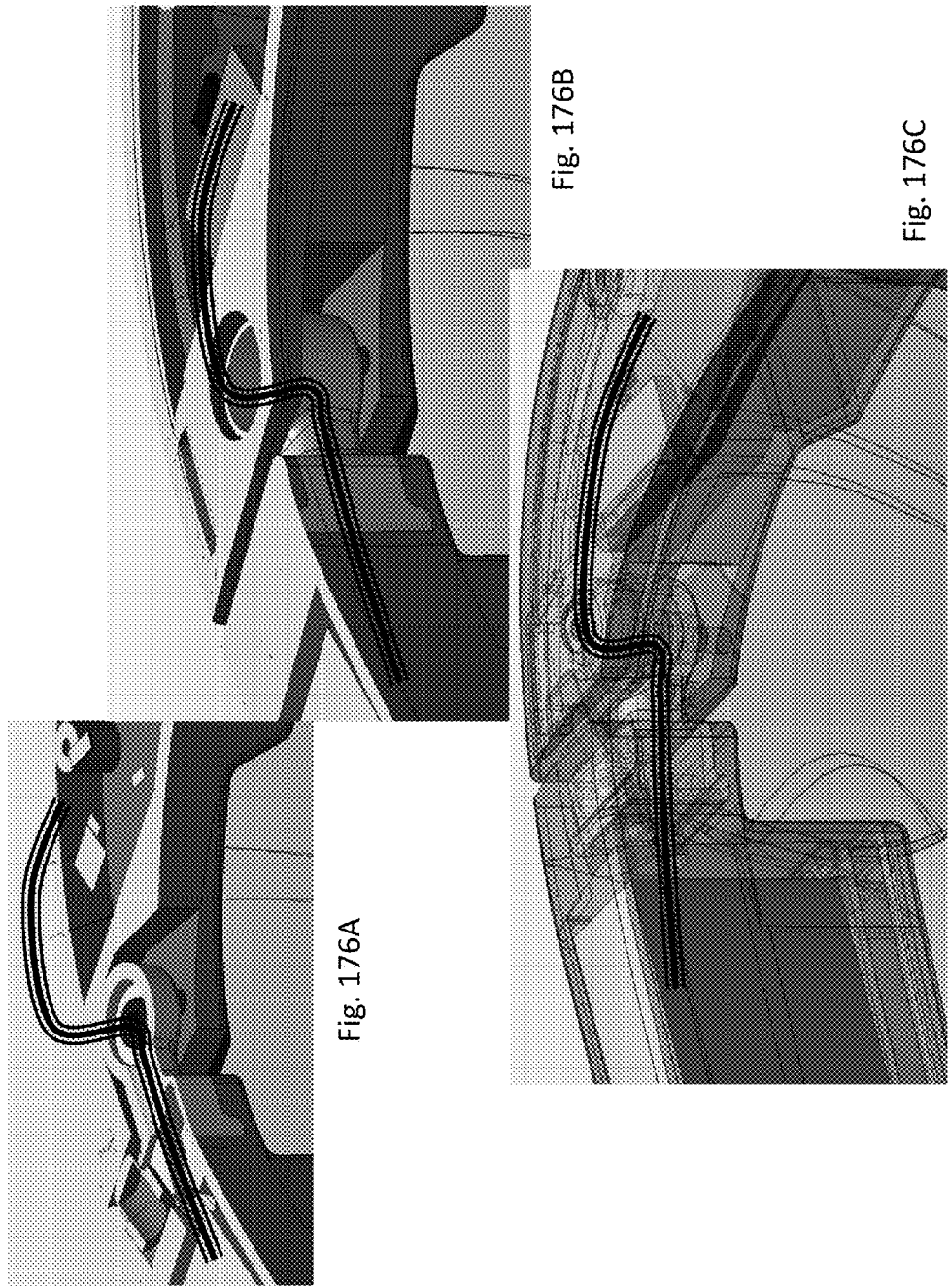

Referring now to FIG. 174, the batteries are enabled to power the electronics in the front frame, even through an operable hinge 17408, using a wiring design that uses a minimal number of wires and passes through the hinge in a wire guide 17404. The wiring design may include wires 17402 running from the front frame electronics to earbuds located on the arms. FIG. 175 depicts an enlarged version of FIG. 174 with a focus on the wires 17402 traversing the wire guide 17404. FIG. 176 A-C depict the wire guide with various portions of the frame and internal glasses workings cutaway. The view is from the user's side of the frame looking at the hinge. FIG. 176A shows the most material cutaway, FIG. 176B shows the next most material cutaway, while FIG. 176C shows an intact version of the glasses.

Figure 6:
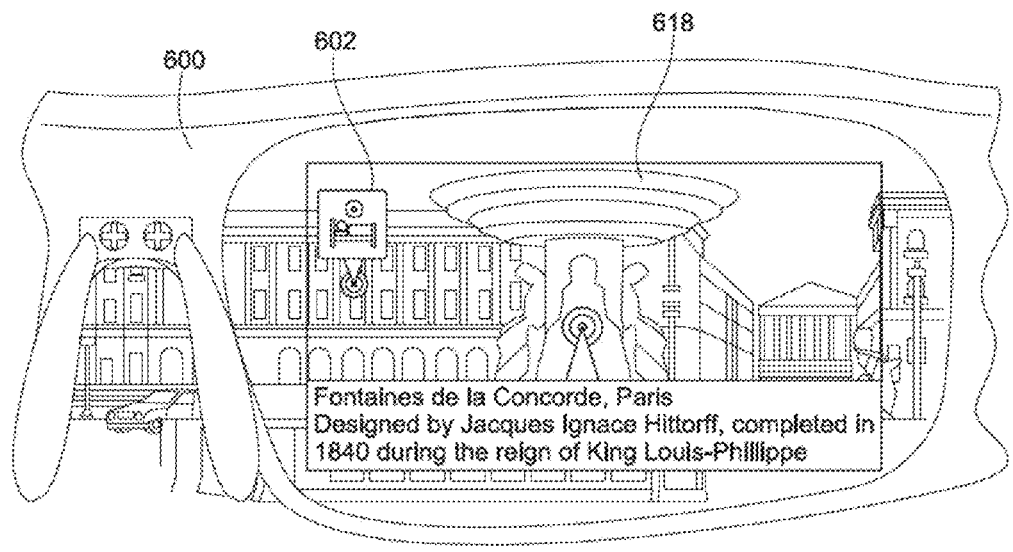
FIG. 6 depicts an embodiment of the eyepiece with a see-through lens.

FIG. 6 depicts an embodiment of the eyepiece 600 with a see-through or translucent lens 602. A projected image 618 can be seen on the lens 602. In this embodiment, the image 618 that is being projected onto the lens 602 happens to be an augmented reality version of the scene that the wearer is seeing, wherein tagged points of interest (POI) in the field of view are displayed to the wearer. The augmented reality version may be enabled by a forward facing camera embedded in the eyepiece (not shown in FIG. 6) that images what the wearer is looking and identifies the location/POI. In one embodiment, the output of the camera or optical transmitter may be sent to the eyepiece controller or memory for storage, for transmission to a remote location, or for viewing by the person wearing the eyepiece or glasses. For example, the video output may be streamed to the virtual screen seen by the user. The video output may thus be used to help determine the user's location, or may be sent remotely to others to assist in helping to locate the location of the wearer, or for any other purpose. Other detection technologies, such as GPS, RFID, manual input, and the like, may be used to determine a wearer's location. Using location or identification data, a database may be accessed by the eyepiece for information that may be overlaid, projected or otherwise displayed with what is being seen. Augmented reality applications and technology will be further described herein.

Figure 7:
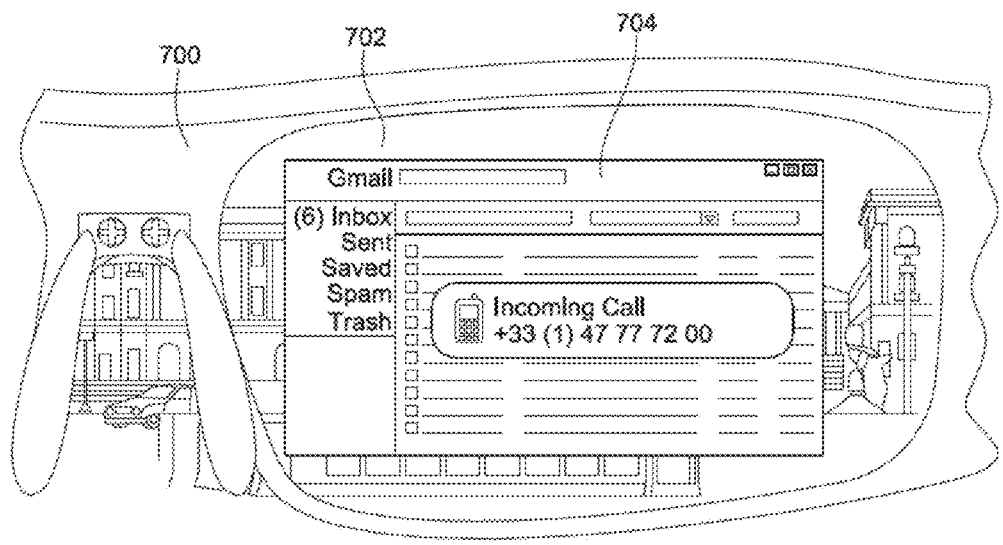
FIG. 7 depicts an embodiment of the eyepiece with a see-through lens.

In FIG. 7, an embodiment of the eyepiece 700 is depicted with a translucent lens 702 on which is being displayed streaming media (an e-mail application) and an incoming call notification 704. In this embodiment, the media obscures a portion of the viewing area, however, it should be understood that the displayed image may be positioned anywhere in the field of view. In embodiments, the media may be made to be more or less transparent.

In an embodiment, the eyepiece may receive input from any external source, such as an external converter box. The source may be depicted in the lens of eyepiece. In an embodiment, when the external source is a phone, the eyepiece may use the phone's location capabilities to display location-based augmented reality, including marker overlay from marker-based AR applications. In embodiments, a VNC client running on the eyepiece's processor or an associated device may be used to connect to and control a computer, where the computer's display is seen in the eyepiece by the wearer. In an embodiment, content from any source may be streamed to the eyepiece, such as a display from a panoramic camera riding atop a vehicle, a user interface for a device, imagery from a drone or helicopter, and the like. For example, a gun-mounted camera may enable shooting a target not in direct line of sight when the camera feed is directed to the eyepiece.

Figure 9:
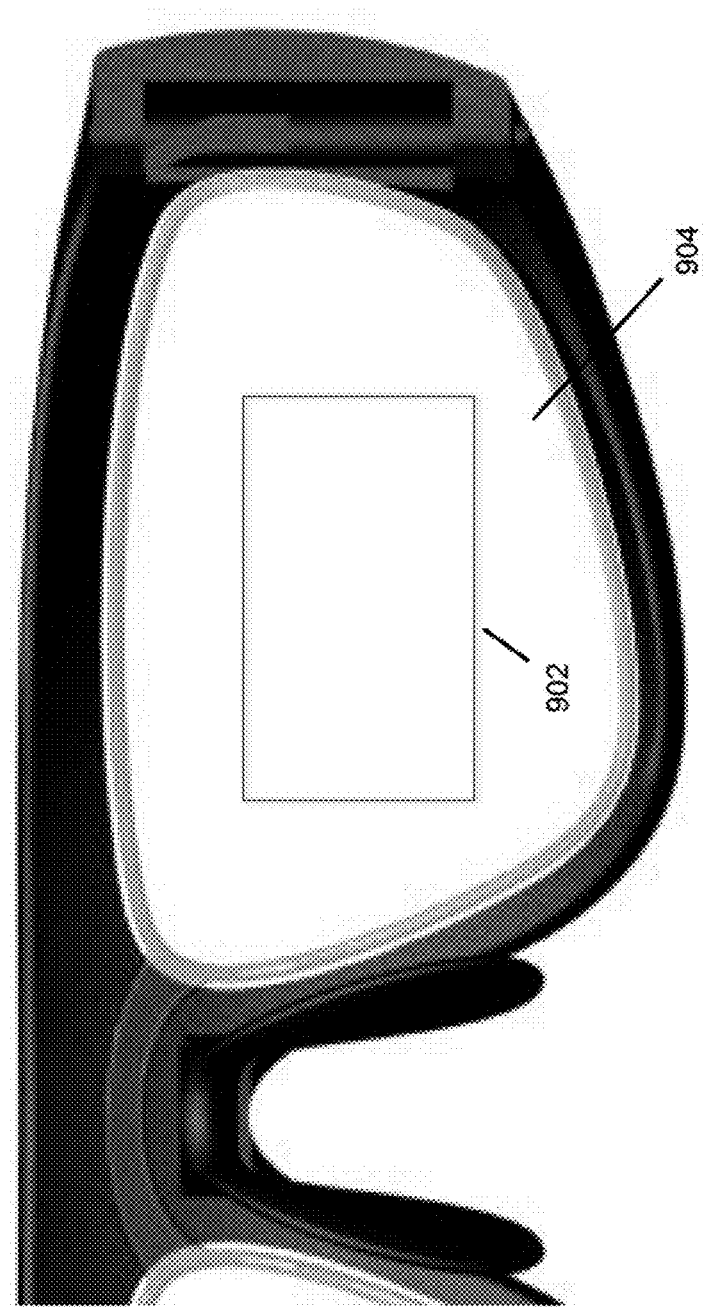
FIG. 9 depicts an electrochromic layer of the eyepiece.

The lenses may be chromic, such as photochromic or electrochromic. The electrochromic lens may include integral chromic material or a chromic coating which changes the opacity of at least a portion of the lens in response to a burst of charge applied by the processor across the chromic material. For example, and referring to FIG. 9, a chromic portion 902 of the lens 904 is shown darkened, such as for providing greater viewability by the wearer of the eyepiece when that portion is showing displayed content to the wearer. In embodiments, there may be a plurality of chromic areas on the lens that may be controlled independently, such as large portions of the lens, sub-portions of the projected area, programmable areas of the lens and/or projected area, controlled to the pixel level, and the like. Activation of the chromic material may be controlled via the control techniques further described herein or automatically enabled with certain applications (e.g. a streaming video application, a sun tracking application, an ambient brightness sensor, a camera tracking brightness in the field of view) or in response to a frame-embedded UV sensor. In embodiments, an electrochromic layer may be located between optical elements and/or on the surface of an optical element on the eyepiece, such as on a corrective lens, on a ballistic lens, and the like. In an example, the electrochromic layer may consist of a stack, such as an Indium Tin Oxide (ITO) coated PET/PC film with two layers of electrochromic (EC) between, which may eliminate another layer of PET/PC, thereby reducing reflections (e.g. a layer stack may comprise a PET/PC-EC-PET/PC-EC-PET/PC). In embodiments, the electrically controllable optical layer may be provided as a liquid crystal based solution with a binary state of tint. In other embodiments, multiple layers of liquid crystal or an alternative e-tint forming the optical layer may be used to provide variable tint such that certain layers or segments of the optical layer may be turned on or off in stages. Electrochromic layers may be used generically for any of the electrically controlled transparencies in the eyepiece, including SPD, LCD, electrowetting, and the like.

In embodiments, the lens may have an angular sensitive coating which enables transmitting light-waves with low incident angles and reflecting light, such as s-polarized light, with high incident angles. The chromic coating may be controlled in portions or in its entirety, such as by the control technologies described herein. The lenses may be variable contrast and the contrast may be under the control of a push button or any other control technique described herein. In embodiments, the user may wear the interactive head-mounted eyepiece, where the eyepiece includes an optical assembly through which the user views a surrounding environment and displayed content. The optical assembly may include a corrective element that corrects the user's view of the surrounding environment, an integrated processor for handling content for display to the user, and an integrated image source for introducing the content to the optical assembly. The optical assembly may include an electrochromic layer that provides a display characteristic adjustment that is dependent on displayed content requirements and surrounding environmental conditions. In embodiments, the display characteristic may be brightness, contrast, and the like. The surrounding environmental condition may be a level of brightness that without the display characteristic adjustment would make the displayed content difficult to visualize by the wearer of the eyepiece, where the display characteristic adjustment may be applied to an area of the optical assembly where content is being displayed.

In embodiments, the eyepiece may have brightness, contrast, spatial, resolution, and the like control over the eyepiece projected area, such as to alter and improve the user's view of the projected content against a bright or dark surrounding environment. For example, a user may be using the eyepiece under bright daylight conditions, and in order for the user to clearly see the displayed content the display area my need to be altered in brightness and/or contrast. Alternatively, the viewing area surrounding the display area may be altered. In addition, the area altered, whether within the display area or not, may be spatially oriented or controlled per the application being implemented. For instance, only a small portion of the display area may need to be altered, such as when that portion of the display area deviates from some determined or predetermined contrast ratio between the display portion of the display area and the surrounding environment. In embodiments, portions of the lens may be altered in brightness, contrast, spatial extent, resolution, and the like, such as fixed to include the entire display area, adjusted to only a portion of the lens, adaptable and dynamic to changes in lighting conditions of the surrounding environment and/or the brightness-contrast of the displayed content, and the like. Spatial extent (e.g. the area affected by the alteration) and resolution (e.g. display optical resolution) may vary over different portions of the lens, including high resolution segments, low resolution segments, single pixel segments, and the like, where differing segments may be combined to achieve the viewing objectives of the application(s) being executed. In embodiments, technologies for implementing alterations of brightness, contrast, spatial extent, resolution, and the like, may include electrochromic materials, LCD technologies, embedded beads in the optics, flexible displays, suspension particle device (SPD) technologies, colloid technologies, and the like.

In embodiments, there may be various modes of activation of the electrochromic layer. For example, the user may enter sunglass mode where the composite lenses appear only somewhat darkened or the user may enter "Blackout" mode, where the composite lenses appear completely blackened.

In an example of a technology that may be employed in implementing the alterations of brightness, contrast, spatial extent, resolution, and the like, may be electrochromic materials, films, inks, and the like. Electrochromism is the phenomenon displayed by some materials of reversibly changing appearance when electric charge is applied. Various types of materials and structures can be used to construct electrochromic devices, depending on the specific applications. For instance, electrochromic materials include tungsten oxide ($WO_3$), which is the main chemical used in the production of electrochromic windows or smart glass. In embodiments, electrochromic coatings may be used on the lens of the eyepiece in implementing alterations. In another example, electrochromic displays may be used in implementing 'electronic paper', which is designed to mimic the appearance of ordinary paper, where the electronic paper displays reflected light like ordinary paper. In embodiments, electrochromism may be implemented in a wide variety of applications and materials, including gyricon (consisting of polyethylene spheres embedded in a transparent silicone sheet, with each sphere suspended in a bubble of oil so that they can rotate freely), electro-phoretic displays (forming images by rearranging charged pigment particles using an applied electric field), E-Ink technology, electro-wetting, electro-fluidic, interferometric modulator, organic transistors embedded into flexible substrates, nano-chromics displays (NCD), and the like.

In another example of a technology that may be employed in implementing the alterations of brightness, contrast, spatial extent, resolution, and the like, may be suspended particle devices (SPD). When a small voltage is applied to an SPD film, its microscopic particles, which in their stable state are randomly dispersed, become aligned and allow light to pass through. The response may be immediate, uniform, and with stable color throughout the film. Adjustment of the voltage may allow users to control the amount of light, glare and heat passing through. The system's response may range from a dark blue appearance, with up to full blockage of light in its off state, to clear in its on state. In embodiments, SPD technology may be an emulsion applied on a plastic substrate creating the active film. This plastic film may be laminated (as a single glass pane), suspended between two sheets of glass, plastic or other transparent materials, and the like.

Figure 8A:
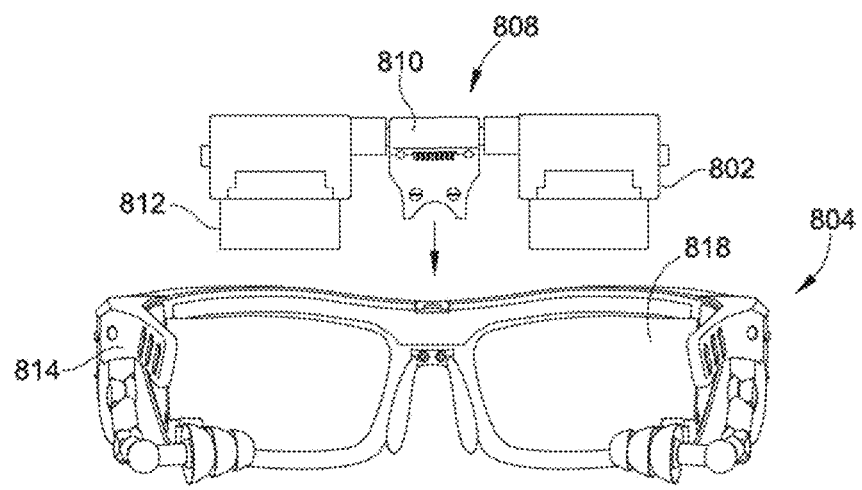
FIG. 8A-C depicts embodiments of the eyepiece arranged in a flip-up/flip-down configuration.
Figure 8B:
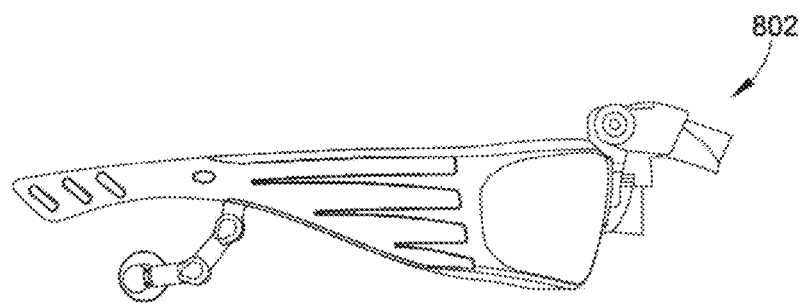
Figure 8C:
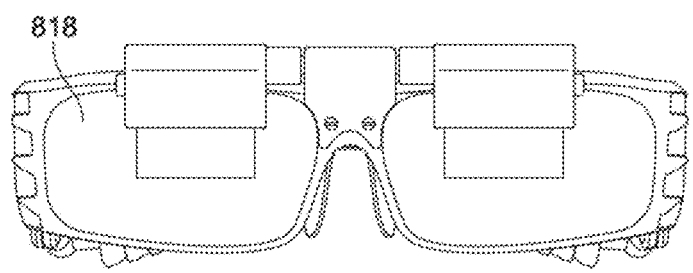

Referring to FIGS. 8A-C, in certain embodiments, the electro-optics may be mounted in a monocular or binocular flip-up/flip-down arrangement in two parts: 1) electro-optics; and 2) correction lens. FIG. 8A depicts a two part eyepiece where the electro-optics are contained within a module 802 that may be electrically connected to the eyepiece 804 via an electrical connector 810, such as a plug, pin, socket, wiring, and the like. In this arrangement, the lens 818 in the frame 814 may be a correction lens entirely. The interpupillary distance (IPD) between the two halves of the electro-optic module 802 may be adjusted at the bridge 808 to accommodate various IPDs. Similarly, the placement of the display 812 may be adjusted via the bridge 808. FIG. 8B depicts the binocular electro-optics module 802 where one half is flipped up and the other half is flipped down. The nose bridge may be fully adjustable and elastomeric. This enables 3-point mounting on nose bridge and ears with a head strap to assure the stability of images in the user's eyes, unlike the instability of helmet-mounted optics, that shift on the scalp. Referring to FIG. 8C, the lens 818 may be ANSI-compliant, hard-coat scratch-resistant polycarbonate ballistic lenses, may be chromic, may have an angular sensitive coating, may include a UV-sensitive material, and the like. In this arrangement, the electro-optics module may include a CMOS-based VIS/NIR/SWIR black silicon sensor for night vision capability. The electro-optics module 802 may feature quick disconnect capability for user flexibility, field replacement and upgrade. The electro-optics module 802 may feature an integrated power dock.

Figure 79:
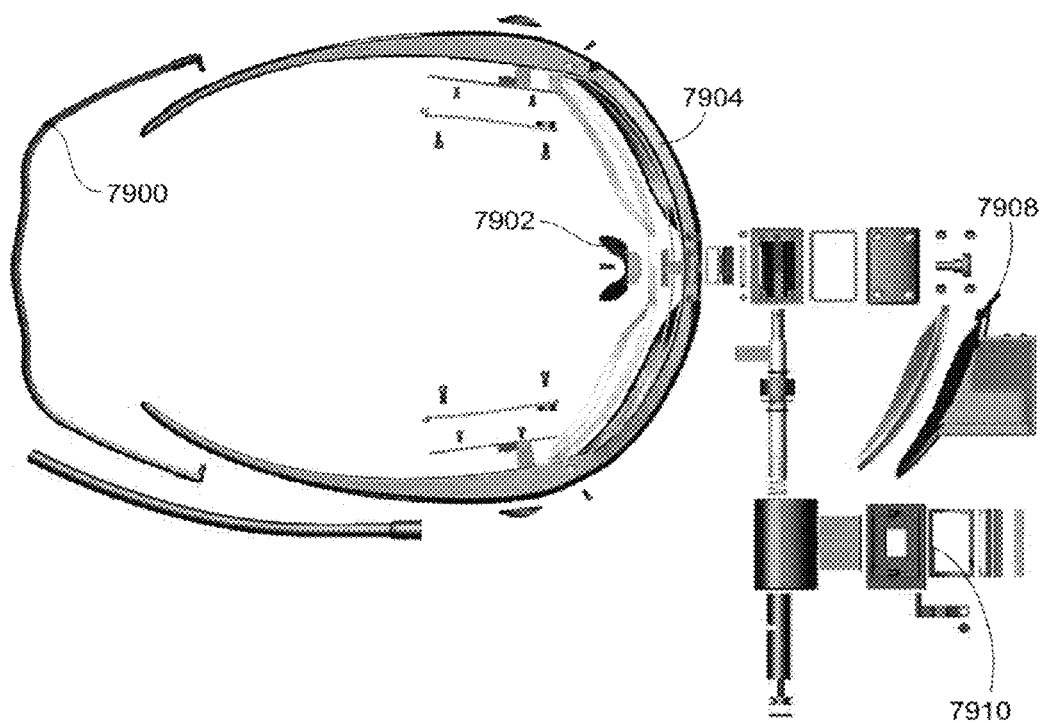
FIG. 79 depicts an exploded top view of the eyepiece.
Figure 80:
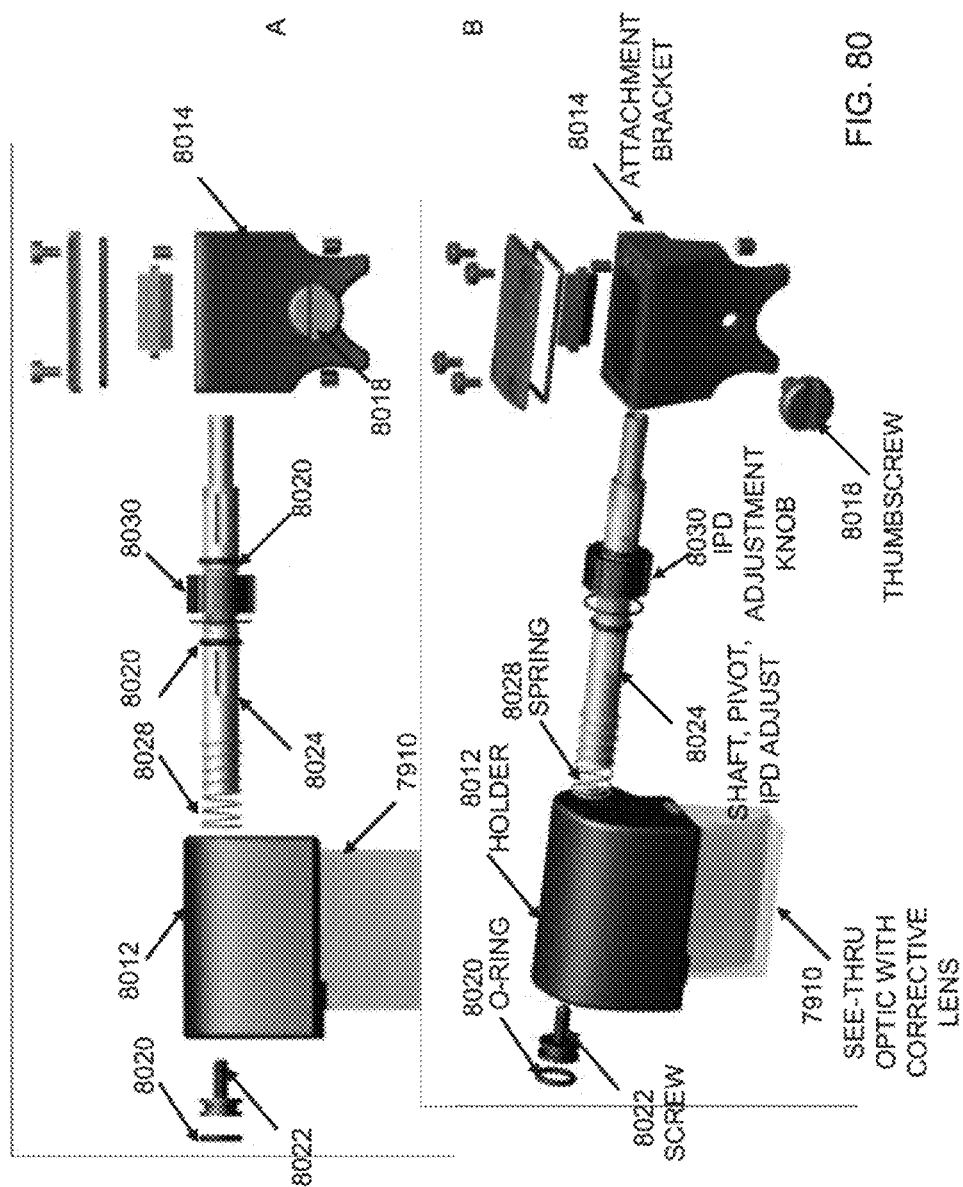
FIG. 80 depicts an exploded electro-optic assembly.
Figure 81:
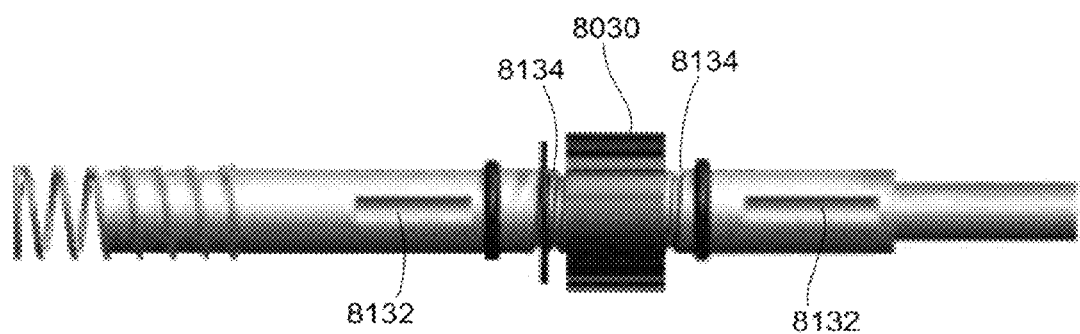
FIG. 81 depicts an exploded view of the shaft of the electro-optic assembly.

As in FIG. 79, the flip-up/flip-down lens 7910 may include a light block 7908. Removable, elastomeric night adapters/light dams/light blocks 7908 may be used to shield the flip-up/flip-down lens 7910, such as for night operations. The exploded top view of the eyepiece also depicts a headstrap 7900, frame 7904, and adjustable nose bridge 7902. FIG. 80 depicts an exploded view of the electro-optic assembly in a front (A) and side angle (B) view. A holder 8012 holds the see-through optic with corrective lens 7910. An O-ring 8020 and screw 8022 secures the holder to the shaft 8024. A spring 8028 provides a spring-loaded connection between the holder 8012 and shaft 8024. The shaft 8024 connects to the attachment bracket 8014, which secures to the eyepiece using the thumbscrew 8018. The shaft 8024 serves as a pivot and an IPD adjustment tool using the IPD adjustment knob 8030. As seen in FIG. 81, the knob 8030 rotates along adjustment threads 8134. The shaft 8024 also features two set screw grooves 8132.

In embodiments, a photochromic layer may be included as part of the optics of the eyepiece. Photochromism is the reversible transformation of a chemical species between two forms by the absorption of electromagnetic radiation, where the two forms have different absorption spectra, such as a reversible change of color, darkness, and the like, upon exposure to a given frequency of light. In an example, a photochromic layer may be included between the waveguide and corrective optics of the eyepiece, on the outside of the corrective optic, and the like. In embodiments, a photochromic layer (such as used as a darkening layer) may be activated with a UV diode, or other photochromic responsive wavelength known in the art. In the case of the photochromic layer being activated with UV light, the eyepiece optics may also include a UV coating outside the photochromic layer to prevent UV light from the Sun from accidentally activating it.

Photochromics are presently fast to change from light to dark and slow to change from dark to light. This due to the molecular changes that are involved with the photochromic material changing from clear to dark. Photochromic molecules are vibrating back to clear after the UV light, such as UV light from the sun, is removed. By increasing the vibration of the molecules, such as by exposure to heat, the optic will clear quicker. The speed at which the photochromic layer goes from dark to light may be temperature-dependent. Rapid changing from dark to light is particularly important for military applications where users of sunglasses often go from a bright outside environment to a dark inside environment and it is important to be able to see quickly in the inside environment.

This disclosure provides a photochromic film device with an attached heater that is used to accelerate the transition from dark to clear in the photochromic material. This method relies on the relationship between the speed of transition of photochromic materials from dark to clear wherein the transition is faster at higher temperatures. To enable the heater to increase the temperature of the photochromic material rapidly, the photochromic material is provided as a thin layer with a thin heater. By keeping the thermal mass of the photochromic film device low per unit area, the heater only has to provide a small amount of heat to rapidly produce a large temperature change in the photochromic material. Since the photochromic material only needs to be at a higher temperature during the transition from dark to clear, the heater only needs to be used for short periods of time so the power requirement is low.

The heater may be a thin and transparent heater element, such as an ITO heater or any other transparent and electrically conductive film material. When a user needs the eyepiece to go clear quickly, the user may activate the heater element by any of the control techniques discussed herein.

In an embodiment, the heater element may be used to calibrate the photochromic element to compensate for cold ambient conditions when the lenses might go dark on their own.

In another embodiment, a thin coat of photochromic material may be deposited on a thick substrate with the heater element layered on top. For example, the cover sunglass lens may comprise an accelerated photochromic solution and still have a separate electrochromic patch over the display area that may optionally be controlled with or without UV light.

FIG. 94A depicts a photochromic film device with a serpentine heater pattern and FIG. 94B depicts a side view of a photochromic film device wherein the device is a lens for sunglasses. The photochromic film device is shown above and not contacting a protective cover lens to reduce the thermal mass of the device.

U.S. Pat. No. 3,152,215 describes a heater layer combined with a photochromic layer to heat the photochromic material for the purpose of reducing the time to transition from dark to clear. However, the photochromic layer is positioned in a wedge which would greatly increase the thermal mass of the device and thereby decrease the rate that the heater could change the temperature of the photochromic material or alternately greatly increase the power required to change the temperature of the photochromic material.

This disclosure includes the use of a thin carrier layer that the photochromic material is applied to. The carrier layer can be glass or plastic. The photochromic material can be applied by vacuum coating, by dipping or by thermal diffusion into the carrier layer as is well known in the art. The thickness of the carrier layer can be 150 microns or less. The selection of the thickness of the carrier layer is selected based on the desired darkness of the photochromic film device in the dark state and the desired speed of transition between the dark state and the clear state. Thicker carrier layers can be darker in the dark state while being slower to heat to an elevated temperature due to having more thermal mass. Conversely, thinner carrier layers can be less dark in the dark state while being faster to heat to an elevated temperature due to having less thermal mass.

The protective layer shown in FIG. 94 is separated from the photochromic film device to keep the thermal mass of the photochromic film device low. In this way, the protective layer can be made thicker to provide higher impact strength. The protective layer can be glass or plastic, for example the protective layer can be polycarbonate.

The heater can be a transparent conductor that is patterned into a conductive path that is relatively uniform so that the heat generated over the length of the patterned heater is relatively uniform. An example of a transparent conductor that can be patterned is titanium dioxide. A larger area is provided at the ends of the heater pattern for electrical contacts such as is shown in FIG. 94.

As noted in the discussion for FIG. 8A-C, the augmented reality glasses may include a lens 818 for each eye of the wearer. The lenses 818 may be made to fit readily into the frame 814, so that each lens may be tailored for the person for whom the glasses are intended. Thus, the lenses may be corrective lenses, and may also be tinted for use as sunglasses, or have other qualities suitable for the intended environment. Thus, the lenses may be tinted yellow, dark or other suitable color, or may be photochromic, so that the transparency of the lens decreases when exposed to brighter light. In one embodiment, the lenses may also be designed for snap fitting into or onto the frames, i.e., snap on lenses are one embodiment. For example, the lenses may be made from high-quality Schott optical glass and may include a polarizing filter.

Of course, the lenses need not be corrective lenses; they may simply serve as sunglasses or as protection for the optical system within the frame. In non-flip up/flip down arrangements, it goes without saying that the outer lenses are important for helping to protect the rather expensive waveguides, viewing systems and electronics within the augmented reality glasses. At a minimum, the outer lenses offer protection from scratching by the environment of the user, whether sand, brambles, thorns and the like, in one environment, and flying debris, bullets and shrapnel, in another environment. In addition, the outer lenses may be decorative, acting to change a look of the composite lens, perhaps to appeal to the individuality or fashion sense of a user. The outer lenses may also help one individual user to distinguish his or her glasses from others, for example, when many users are gathered together.

It is desirable that the lenses be suitable for impact, such as a ballistic impact. Accordingly, in one embodiment, the lenses and the frames meet ANSI Standard Z87.1-2010 for ballistic resistance. In one embodiment, the lenses also meet ballistic standard CE EN166B. In another embodiment, for military uses, the lenses and frames may meet the standards of MIL-PRF-31013, standards 3.5.1.1 or 4.4.1.1. Each of these standards has slightly different requirements for ballistic resistance and each is intended to protect the eyes of the user from impact by high-speed projectiles or debris. While no particular material is specified, polycarbonate, such as certain Lexan® grades, usually is sufficient to pass tests specified in the appropriate standard.

Figure 8D:
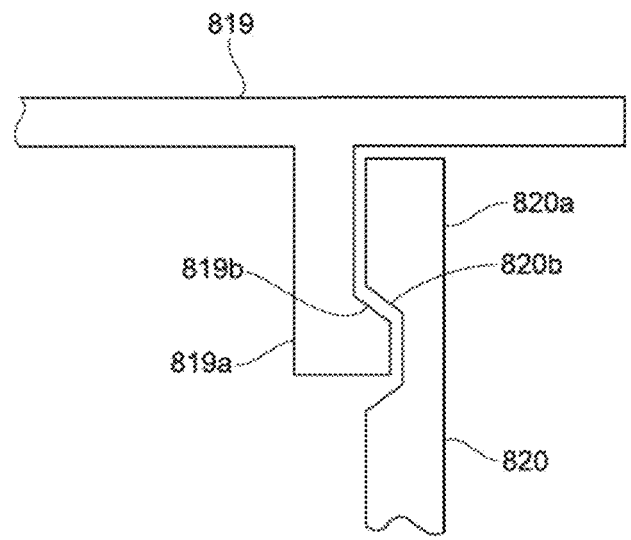
FIG. 8D-E depicts embodiments of snap-fit elements of a secondary optic.

In one embodiment, as shown in FIG. 8D, the lenses snap in from the outside of the frame, not the inside, for better impact resistance, since any impact is expected from the outside of the augmented reality eyeglasses. In this embodiment, replaceable lens 819 has a plurality of snap-fit arms 819a which fit into recesses 820a of frame 820. The engagement angle 819b of the arm is greater than 90°, while the engagement angle 820b of the recess is also greater than 90°. Making the angles greater than right angles has the practical effect of allowing removal of lens 819 from the frame 820. The lens 819 may need to be removed if the person's vision has changed or if a different lens is desired for any reason. The design of the snap fit is such that there is a slight compression or bearing load between the lens and the frame. That is, the lens may be held firmly within the frame, such as by a slight interference fit of the lens within the frame.

The cantilever snap fit of FIG. 8D is not the only possible way to removably snap-fit the lenses and the frame. For example, an annular snap fit may be used, in which a continuous sealing lip of the frame engages an enlarged edge of the lens, which then snap-fits into the lip, or possibly over the lip. Such a snap fit is typically used to join a cap to an ink pen. This configuration may have an advantage of a sturdier joint with fewer chances for admission of very small dust and dirt particles. Possible disadvantages include the fairly tight tolerances required around the entire periphery of both the lens and frame, and the requirement for dimensional integrity in all three dimensions over time.

Figure 8E:
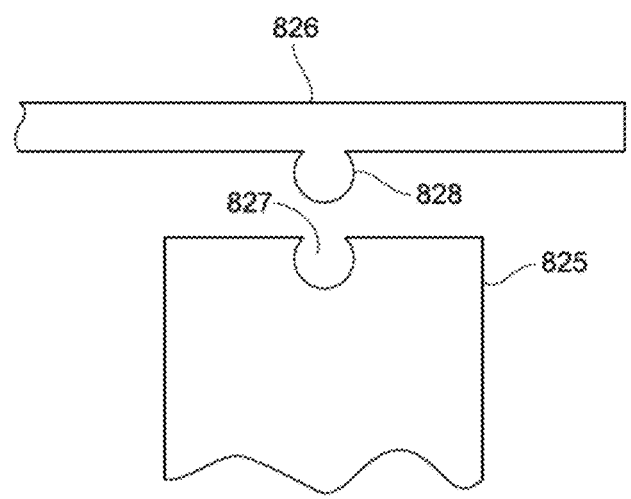

It is also possible to use an even simpler interface, which may still be considered a snap-fit. A groove may be molded into an outer surface of the frame, with the lens having a protruding surface, which may be considered a tongue that fits into the groove. If the groove is semi-cylindrical, such as from about 270° to about 300°, the tongue will snap into the groove and be firmly retained, with removal still possible through the gap that remains in the groove. In this embodiment, shown in FIG. 8E, a lens or replacement lens or cover 826 with a tongue 828 may be inserted into a groove 827 in a frame 825, even though the lens or cover is not snap-fit into the frame. Because the fit is a close one, it will act as a snap-fit and securely retain the lens in the frame.

In another embodiment, the frame may be made in two pieces, such as a lower portion and an upper portion, with a conventional tongue-and-groove fit. In another embodiment, this design may also use standard fasteners to ensure a tight grip of the lens by the frame. The design should not require disassembly of anything on the inside of the frame. Thus, the snap-on or other lens or cover should be assembled onto the frame, or removed from the frame, without having to go inside the frame. As noted in other parts of this disclosure, the augmented reality glasses have many component parts. Some of the assemblies and subassemblies may require careful alignment. Moving and jarring these assemblies may be detrimental to their function, as will moving and jarring the frame and the outer or snap-on lens or cover.

Figure 8F:
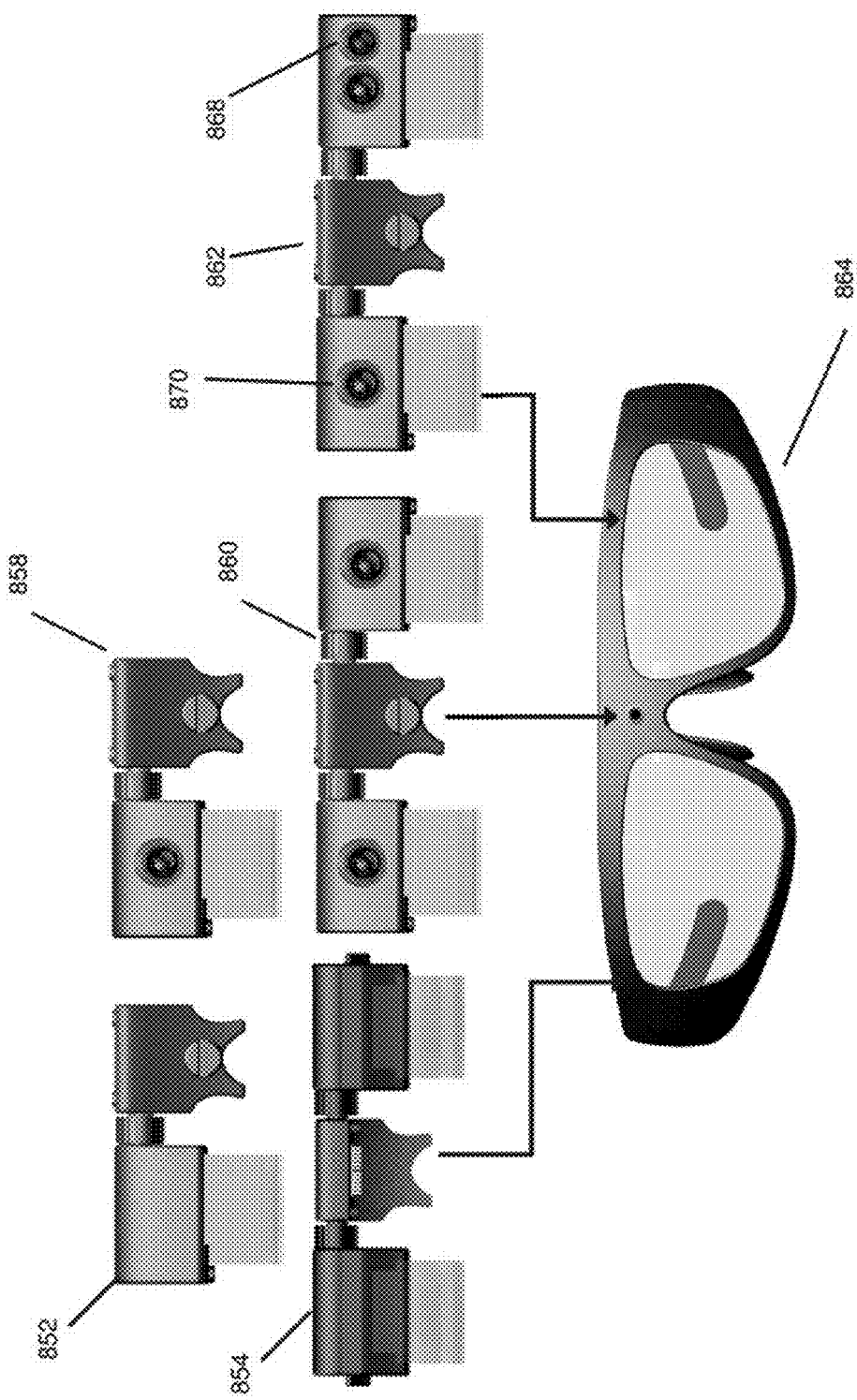
FIG. 8F depicts embodiments of flip-up/flip-down electro-optics modules.

In embodiments, the flip-up/flip-down arrangement enables a modular design for the eyepiece. For example, not only can the eyepiece be equipped with a monocular or binocular module 802, but the lens 818 may also be swapped. In embodiments, additional features may be included with the module 802, either associated with one or both displays 812. Referring to FIG. 8F, either monocular or binocular versions of the module 802 may be display only 852 (monocular), 854 (binocular) or may be equipped with a forward-looking camera 858 (monocular), and 860 & 862 (binocular). In some embodiments, the module may have additional integrated electronics, such as a GPS, a laser range finder, and the like. In the embodiment 862 enabling urban leader tactical response, awareness & visualization, also known as 'Ultra-Vis', a binocular electro-optic module 862 is equipped with stereo forward-looking cameras 870, GPS, and a laser range finder 868. These features may enable the Ultra-Vis embodiment to have panoramic night vision, and panoramic night vision with laser range finder and geo location.

In an embodiment, the electro-optics characteristics may be, but not limited to, as follows:

| Optic Characteristics | Value |
|---|---|
| WAVEGUIDE | |
| virtual display field of view (Diagonal) | ~25-30 degrees (equivalent to the FOV of a 24" monitor viewed at 1 m distance) |
| see-through field of view | more than 80 degrees |
| eye clearance | more than 18 mm |
| Material | zeonex optical plastic |
| weight approx | 15 grams |
| Wave Guide dimensions | 60 × 30 × 10 mm (or 9) |
| Size | 15.5 mm (diagonal) |
| Material | PMMA (optical plastics) |
| FOV | 53.5° (diagonal) |
| Active display area | 12.7 mm × 9.0 mm |
| Resolution | 800 × 600 pixels |
| VIRTUAL IMAGING SYSTEM | |
| Type | Folded FFS prism |
| Effective focal length | 15 mm |
| Exit pupil diameter | 8 mm |

-continued

| Optic Characteristics | Value |
| --- | --- |
| Eye relief | 18.25 mm |
| F# | 1.875 |
| Number of free form surfaces | 2-3 |
| AUGMENTED VIEWING SYSTEM | |
| Type | Free form Lens |
| Number of free form surfaces | 2 |
| Other Parameters | |
| Wavelength | 656.3-486.1 nm |
| Field of view | 45°H × 32°V |
| Vignetting | 0.15 for the top and bottom fields |
| Distortion | <12% at the maximum field |
| Image quality | MTF > 10% at 30 lp/mm |

In an embodiment, the Projector Characteristics may be as follows:

| Projector Characteristics | Value |
| --- | --- |
| Brightness | Adjustable, .25-2 Lumens |
| Voltage | 3.6 VDC |
| Illumination | Red, Green and Blue LEDs |
| Display | SVGA 800 × 600 dpi Syndiant LCOS Display |
| Power Consumption | Adjustable, 50 to 250 mw |
| Target MPE Dimensions | Approximately 24 mm × 12 mm × 6 mm |
| Focus | Adjustable |
| Optics Housing | 6061-T6 Aluminum and Glass-filled ABS/PC |
| Weight | 5 gms |
| RGB Engine | Adjustable Color Output |
| ARCHITECTURE | 2 × 1 GHZ processor cores |
| | 633 MHZ DSPs |
| | 30M polygons/sec DC graphics accelerator |
| IMAGE CORRECTION | real-time sensing |
| | image enhancement |
| | noise reduction |
| | keystone correction |
| | perspective correction |

In another embodiment, an augmented reality eyepiece may include electrically-controlled lenses as part of the microprojector or as part of the optics between the microprojector and the waveguide. FIG. 21 depicts an embodiment with such liquid lenses 2152.

The glasses may also include at least one camera or optical sensor 2130 that may furnish an image or images for viewing by the user. The images are formed by a microprojector 2114 on each side of the glasses for conveyance to the waveguide 2108 on that side. In one embodiment, an additional optical element, a variable focus lens 2152 may also be furnished. The lens may be electrically adjustable by the user so that the image seen in the waveguides 2108 are focused for the user. In embodiments, the camera may be a multi-lens camera, such as an 'array camera', where the eyepiece processor may combine the data from the multiple lenses and multiple viewpoints of the lenses to build a single high-quality image. This technology may be referred to as computational imaging, since software is used to process the image. Computational imaging may provide image-processing advantages, such as allowing processing of the composite image as a function of individual lens images. For example, since each lens may provide its own image, the processor may provide image processing to create images with special focusing, such as foveal imaging, where the focus from one of the lens images is clear, higher resolution, and the like, and where the rest of the image is defocused, lower resolution, and the like. The processor may also select portions of the composite image to store in memory, while deleting the rest, such as when memory storage is limited and only portions of the composite image are critical to save. In embodiments, use of the array camera may provide the ability to alter the focus of an image after the image has been taken. In addition to the imaging advantages of an array camera, the array camera may provide a thinner mechanical profile than a traditional single-lens assembly, thus making it easier to integrate into the eyepiece.

Variable lenses may include the so-called liquid lenses furnished by Varioptic, S. A., Lyons, France, or by LensVector, Inc., Mountain View, Calif., U.S.A. Such lenses may include a central portion with two immiscible liquids. Typically, in these lenses, the path of light through the lens, i.e., the focal length of the lens is altered or focused by applying an electric potential between electrodes immersed in the liquids. At least one of the liquids is affected by the resulting electric or magnetic field potential. Thus, electrowetting may occur, as described in U.S. Pat. Appl. Publ. 2010/0007807, assigned to LensVector, Inc. Other techniques are described in LensVector Pat. Appl. Publs. 2009/021331 and 2009/0316097. All three of these disclosures are incorporated herein by reference, as though each page and figures were set forth verbatim herein.

Other patent documents from Varioptic, S. A., describe other devices and techniques for a variable focus lens, which may also work through an electrowetting phenomenon. These documents include U.S. Pat. Nos. 7,245,440 and 7,894,440 and U.S. Pat. Appl. Publs. 2010/0177386 and 2010/0295987, each of which is also incorporated herein by reference, as though each page and figures were set forth verbatim herein. In these documents, the two liquids typically have different indices of refraction and different electrical conductivities, e.g., one liquid is conductive, such as an aqueous liquid, and the other liquid is insulating, such as an oily liquid. Applying an electric potential may change the thickness of the lens and does change the path of light through the lens, thus changing the focal length of the lens.

The electrically-adjustable lenses may be controlled by the controls of the glasses. In one embodiment, a focus adjustment is made by calling up a menu from the controls and adjusting the focus of the lens. The lenses may be controlled separately or may be controlled together. The adjustment is made by physically turning a control knob, by indicating with a gesture, or by voice command. In another embodiment, the augmented reality glasses may also include a rangefinder, and focus of the electrically-adjustable lenses may be controlled automatically by pointing the rangefinder, such as a laser rangefinder, to a target or object a desired distance away from the user.

As shown in U.S. Pat. No. 7,894,440, discussed above, the variable lenses may also be applied to the outer lenses of the augmented reality glasses or eyepiece. In one embodiment, the lenses may simply take the place of a corrective lens. The variable lenses with their electric-adjustable control may be used instead of or in addition to the image source- or projector-mounted lenses. The corrective lens inserts provide corrective optics for the user's environment, the outside world, whether the waveguide displays are active or not.

It is important to stabilize the images presented to the wearer of the augmented reality glasses or eyepiece(s), that is, the images seen in the waveguide. The view or images presented travel from one or two digital cameras or sensors mounted on the eyepiece, to digital circuitry, where the images are processed and, if desired, stored as digital data before they appear in the display of the glasses. In any event, and as discussed above, the digital data is then used to form an image, such as by using an LCOS display and a series of RGB light emitting diodes. The light images are processed using a series of lenses, a polarizing beam splitter, an electrically-powered liquid corrective lens and at least one transition lens from the projector to the waveguide.

The process of gathering and presenting images includes several mechanical and optical linkages between components of the augmented reality glasses. It seems clear, therefore, that some form of stabilization will be required. This may include optical stabilization of the most immediate cause, the camera itself, since it is mounted on a mobile platform, the glasses, which themselves are movably mounted on a mobile user. Accordingly, camera stabilization or correction may be required. In addition, at least some stabilization or correction should be used for the liquid variable lens. Ideally, a stabilization circuit at that point could correct not only for the liquid lens, but also for any aberration and vibration from many parts of the circuit upstream from the liquid lens, including the image source. One advantage of the present system is that many commercial off-the-shelf cameras are very advanced and typically have at least one image-stabilization feature or option. Thus, there may be many embodiments of the present disclosure, each with a same or a different method of stabilizing an image or a very fast stream of images, as discussed below. The term optical stabilization is typically used herein with the meaning of physically stabilizing the camera, camera platform, or other physical object, while image stabilization refers to data manipulation and processing.

One technique of image stabilization is performed on digital images as they are formed. This technique may use pixels outside the border of the visible frame as a buffer for the undesired motion. Alternatively, the technique may use another relatively steady area or basis in succeeding frames. This technique is applicable to video cameras, shifting the electronic image from frame to frame of the video in a manner sufficient to counteract the motion. This technique does not depend on sensors and directly stabilizes the images by reducing vibrations and other distracting motion from the moving camera. In some techniques, the speed of the images may be slowed in order to add the stabilization process to the remainder of the digital process, and requiring more time per image. These techniques may use a global motion vector calculated from frame-to-frame motion differences to determine the direction of the stabilization.

Optical stabilization for images uses a gravity- or electronically-driven mechanism to move or adjust an optical element or imaging sensor such that it counteracts the ambient vibrations. Another way to optically stabilize the displayed content is to provide gyroscopic correction or sensing of the platform housing the augmented reality glasses, e.g., the user. As noted above, the sensors available and used on the augmented reality glasses or eyepiece include MEMS gyroscopic sensors. These sensors capture movement and motion in three dimensions in very small increments and can be used as feedback to correct the images sent from the camera in real time. It is clear that at least a large part of the undesired and undesirable movement probably is caused by movement of the user and the camera itself. These larger movements may include gross movements of the user, e.g., walking or running, riding in a vehicle. Smaller vibrations may also result within the augmented reality eyeglasses, that is, vibrations in the components in the electrical and mechanical linkages that form the path from the camera (input) to the image in the waveguide (output). These gross movements may be more important to correct or to account for, rather than, for instance, independent and small movements in the linkages of components downstream from the projector. In embodiments, the gyroscopic stabilization may stabilize the image when it is subject to a periodic motion. For such periodic motion, the gyroscope may determine the periodicity of the user's motion and transmit the information to a processor to correct for the placement of content in the user's view. The gyroscope may utilize a rolling average of two or three or more cycles of periodic motion in determining the periodicity. Other sensors may also be used to stabilize the image or correctly place the image in the user's field of view, such as an accelerometer, a position sensor, a distance sensor, a rangefinder, a biological sensor, a geodetic sensor, an optical sensor, a video sensor, a camera, an infrared sensor, a light sensor, a photocell sensor, or an RF sensor. When a sensor detects user head or eye movement, the sensor provides an output to a processor which may determine the direction, speed, amount, and rate of the user's head or eye movement. The processor may convert this information into a suitable data structure for further processing by the processor controlling the optical assembly (which may be the same processor). The data structure may be one or more vector quantities. For example, the direction of the vector may define the orientation of the movement, and the length of the vector may define the rate of the movement. Using the processed sensor output, the display of content is adjusted accordingly.

Motion sensing may thus be used to sense the motion and correct for it, as in optical stabilization, or to sense the motion and then correct the images that are being taken and processed, as in image stabilization. An apparatus for sensing motion and correcting the images or the data is depicted in FIG. 34A. In this apparatus, one or more kinds of motion sensors may be used, including accelerometers, angular position sensors or gyroscopes, such as MEMS gyroscopes. Data from the sensors is fed back to the appropriate sensor interfaces, such as analog to digital converters (ADCs) or other suitable interface, such as digital signal processors (DSPs). A microprocessor then processes this information, as discussed above, and sends image-stabilized frames to the display driver and then to the see-through display or waveguide discussed above. In one embodiment, the display begins with the RGB display in the microprojector of the augmented reality eyepiece.

In another embodiment, a video sensor or augmented reality glasses, or other device with a video sensor may be mounted on a vehicle. In this embodiment, the video stream may be communicated through a telecommunication capability or an Internet capability to personnel in the vehicle. One application could be sightseeing or touring of an area. Another embodiment could be exploring or reconnaissance, or even patrolling, of an area. In these embodiments, gyroscopic stabilization of the image sensor would be helpful, rather than applying a gyroscopic correction to the images or digital data representing the images. An embodiment of this technique is depicted in FIG. 34B. In this technique, a camera or image sensor 3407 is mounted on a vehicle 3401. One or more motion sensors 3406, such as gyroscopes, are mounted in the camera assembly 3405. A stabilizing platform 3403 receives information from the motion sensors and stabilizes the camera assembly 3405, so that jitter and wobble are minimized while the camera operates. This is true optical stabilization. Alternatively, the motion sensors or gyroscopes may be mounted on or within the stabilizing platform itself. This technique would actually provide optical stabilization, stabilizing the camera or image sensor, in contrast to digital stabilization, correcting the image afterwards by computer processing of the data taken by the camera.

In one technique, the key to optical stabilization is to apply the stabilization or correction before an image sensor converts the image into digital information. In one technique, feedback from sensors, such as gyroscopes or angular velocity sensors, is encoded and sent to an actuator that moves the image sensor, much as an autofocus mechanism adjusts a focus of a lens. The image sensor is moved in such a way as to maintain the projection of the image onto the image plane, which is a function of the focal length of the lens being used. Autoranging and focal length information, perhaps from a range finder of the interactive head-mounted eyepiece, may be acquired through the lens itself. In another technique, angular velocity sensors, sometimes also called gyroscopic sensors, can be used to detect, respectively, horizontal and vertical movements. The motion detected may then be fed back to electromagnets to move a floating lens of the camera. This optical stabilization technique, however, would have to be applied to each lens contemplated, making the result rather expensive.

Stabilization of the liquid lens is discussed in U.S. Pat. Appl. Publ. 2010/0295987, assigned to Varioptic, S.A., Lyon, France. In theory, control of a liquid lens is relatively simple, since there is only one variable to control: the level of voltage applied to the electrodes in the conducting and non-conducting liquids of the lens, using, for examples, the lens housing and the cap as electrodes. Applying a voltage causes a change or tilt in the liquid-liquid interface via the electrowetting effect. This change or tilt adjusts the focus or output of the lens. In its most basic terms, a control scheme with feedback would then apply a voltage and determine the effect of the applied voltage on the result, i.e., a focus or an astigmatism of the image. The voltages may be applied in patterns, for example, equal and opposite + and − voltages, both positive voltages of differing magnitude, both negative voltages of differing magnitude, and so forth. Such lenses are known as electrically variable optic lenses or electro-optic lenses.

Voltages may be applied to the electrodes in patterns for a short period of time and a check on the focus or astigmatism made. The check may be made, for instance, by an image sensor. In addition, sensors on the camera or in this case the lens, may detect motion of the camera or lens. Motion sensors would include accelerometers, gyroscopes, angular velocity sensors or piezoelectric sensors mounted on the liquid lens or a portion of the optic train very near the liquid lens. In one embodiment, a table, such as a calibration table, is then constructed of voltages applied and the degree of correction or voltages needed for given levels of movement. More sophistication may also be added, for example, by using segmented electrodes in different portions of the liquid so that four voltages may be applied rather than two. Of course, if four electrodes are used, four voltages may be applied, in many more patterns than with only two electrodes. These patterns may include equal and opposite positive and negative voltages to opposite segments, and so forth. An example is depicted in FIG. 34C. Four electrodes 3409 are mounted within a liquid lens housing (not shown). Two electrodes are mounted in or near the non-conducting liquid and two are mounted in or near the conducting liquid. Each electrode is independent in terms of the possible voltage that may be applied.

Look-up or calibration tables may be constructed and placed in the memory of the augmented reality glasses. In use, the accelerometer or other motion sensor will sense the motion of the glasses, i.e., the camera on the glasses or the lens itself. A motion sensor such as an accelerometer will sense in particular, small vibration-type motions that interfere with smooth delivery of images to the waveguide. In one embodiment, the image stabilization techniques described here can be applied to the electrically-controllable liquid lens so that the image from the projector is corrected immediately. This will stabilize the output of the projector, at least partially correcting for the vibration and movement of the augmented reality eyepiece, as well as at least some movement by the user. There may also be a manual control for adjusting the gain or other parameter of the corrections. Note that this technique may also be used to correct for near-sightedness or far-sightedness of the individual user, in addition to the focus adjustment already provided by the image sensor controls and discussed as part of the adjustable-focus projector.

Another variable focus element uses tunable liquid crystal cells to focus an image. These are disclosed, for example, in U.S. Pat. Appl. Publ. Nos. 2009/0213321, 2009/0316097 and 2010/0007807, which are hereby incorporated by reference in their entirety and relied on. In this method, a liquid crystal material is contained within a transparent cell, preferably with a matching index of refraction. The cell includes transparent electrodes, such as those made from indium tin oxide (ITO). Using one spiral-shaped electrode, and a second spiral-shaped electrode or a planar electrode, a spatially non-uniform magnetic field is applied. Electrodes of other shapes may be used. The shape of the magnetic field determines the rotation of molecules in the liquid crystal cell to achieve a change in refractive index and thus a focus of the lens. The liquid crystals can thus be electromagnetically manipulated to change their index of refraction, making the tunable liquid crystal cell act as a lens.

Figure 34D:
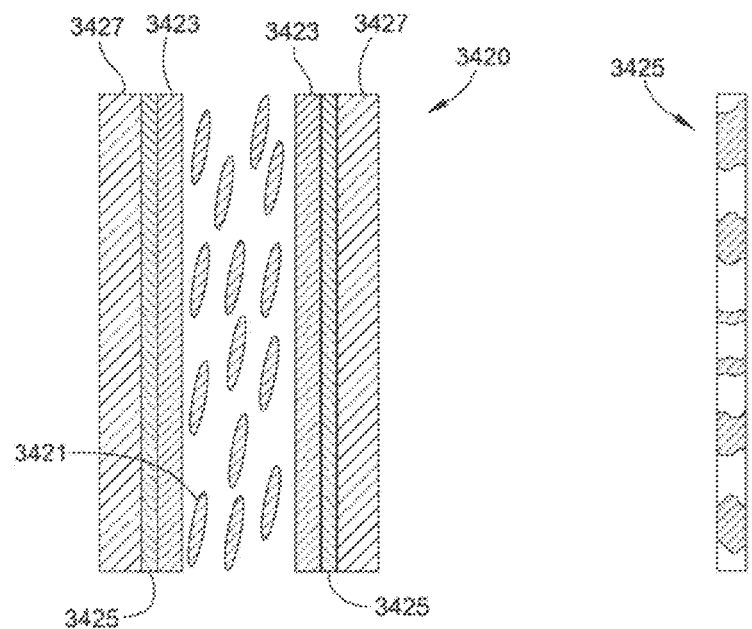
FIG. 34 depicts embodiments of the eyepiece for optical or digital stabilization.
Figure 34E:
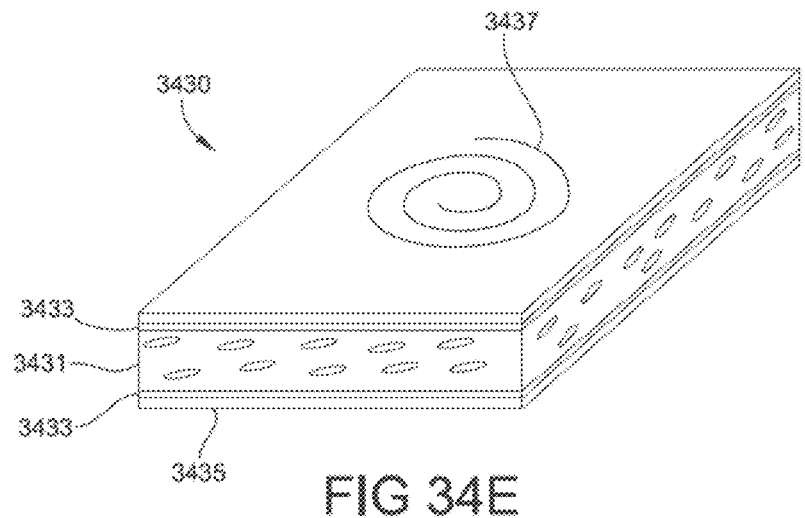

In a first embodiment, a tunable liquid crystal cell 3420 is depicted in FIG. 34D. The cell includes an inner layer of liquid crystal 3421 and thin layers 3423 of orienting material such as polyimide. This material helps to orient the liquid crystals in a preferred direction. Transparent electrodes 3425 are on each side of the orienting material. An electrode may be planar, or may be spiral shaped as shown on the right in FIG. 34D. Transparent glass substrates 3427 contain the materials within the cell. The electrodes are formed so that they will lend shape to the magnetic field. As noted, a spiral shaped electrode on one or both sides, such that the two are not symmetrical, is used in one embodiment. A second embodiment is depicted in FIG. 34E. Tunable liquid crystal cell 3430 includes central liquid crystal material 3431, transparent glass substrate walls 3433, and transparent electrodes. Bottom electrode 3435 is planar, while top electrode 3437 is in the shape of a spiral. Transparent electrodes may be made of indium tin oxide (ITO).

Additional electrodes may be used for quick reversion of the liquid crystal to a non-shaped or natural state. A small control voltage is thus used to dynamically change the refractive index of the material the light passes through. The voltage generates a spatially non-uniform magnetic field of a desired shape, allowing the liquid crystal to function as a lens.

In one embodiment, the camera includes the black silicon, short wave infrared (SWIR) CMOS sensor described elsewhere in this patent. In another embodiment, the camera is a 5 megapixel (MP) optically-stabilized video sensor. In one embodiment, the controls include a 3 GHz microprocessor or microcontroller, and may also include a 633 MHz digital signal processor with a 30 M polygon/second graphic accelerator for real-time image processing for images from the camera or video sensor. In one embodiment, the augmented reality glasses may include a wireless internet, radio or telecommunications capability for wideband, personal area network (PAN), local area network (LAN), a wide local area network, WLAN, conforming to IEEE 802.11, or reach-back communications. The equipment furnished in one embodiment includes a Bluetooth capability, conforming to IEEE 802.15. In one embodiment, the augmented reality glasses include an encryption system, such as a 256-bit Advanced Encryption System (AES) encryption system or other suitable encryption program, for secure communications.

In one embodiment, the wireless telecommunications may include a capability for a 3G or 4G network and may also include a wireless internet capability. In order for an extended life, the augmented reality eyepiece or glasses may also include at least one lithium-ion battery, and as discussed above, a recharging capability. The recharging plug may comprise an AC/DC power converter and may be capable of using multiple input voltages, such as 120 or 240 VAC. The controls for adjusting the focus of the adjustable focus lenses in one embodiment comprises a 2D or 3D wireless air mouse or other non-contact control responsive to gestures or movements of the user. A 2D mouse is available from Logitech, Fremont, Calif., USA. A 3D mouse is described herein, or others such as the Cideko AVK05 available from Cideko, Taiwan, R.O.C, may be used.

In an embodiment, the eyepiece may comprise electronics suitable for controlling the optics, and associated systems, including a central processing unit, non-volatile memory, digital signal processors, 3-D graphics accelerators, and the like. The eyepiece may provide additional electronic elements or features, including inertial navigation systems, cameras, microphones, audio output, power, communication systems, sensors, stopwatch or chronometer functions, thermometer, vibratory temple motors, motion sensor, a microphone to enable audio control of the system, a UV sensor to enable contrast and dimming with photochromic materials, and the like.

In an embodiment, the central processing unit (CPU) of the eyepiece may be an OMAP 4, with dual 1 GHz processor cores. The CPU may include a 633 MHz DSP, giving a capability for the CPU of 30 million polygons/second.

The system may also provide dual micro-SD (secure digital) slots for provisioning of additional removable non-volatile memory.

An on-board camera may provide 1.3 MP color and record up to 60 minutes of video footage. The recorded video may be transferred wirelessly or using a mini-USB transfer device to off-load footage.

The communications system-on-a-chip (SOC) may be capable of operating with wide local area networks (WLAN), Bluetooth version 3.0, a GPS receiver, an FM radio, and the like.

The eyepiece may operate on a 3.6 VDC lithium-ion rechargeable battery for long battery life and ease of use. An additional power source may be provided through solar cells on the exterior of the frame of the system. These solar cells may supply power and may also be capable of recharging the lithium-ion battery.

The total power consumption of the eyepiece may be approximately 400 mW, but is variable depending on features and applications used. For example, processor-intensive applications with significant video graphics demand more power, and will be closer to 400 mW. Simpler, less video-intensive applications will use less power. The operation time on a charge also may vary with application and feature usage.

The micro-projector illumination engine, also known herein as the projector, may include multiple light emitting diodes (LEDs). In order to provide life-like color, Osram red, Cree green, and Cree blue LEDs are used. These are die-based LEDs. The RGB engine may provide an adjustable color output, allowing a user to optimize viewing for various programs and applications.

In embodiments, illumination may be added to the glasses or controlled through various means. For example, LED lights or other lights may be embedded in the frame of the eyepiece, such as in the nose bridge, around the composite lens, or at the temples.

The intensity of the illumination and or the color of illumination may be modulated. Modulation may be accomplished through the various control technologies described herein, through various applications, filtering and magnification.

By way of example, illumination may be modulated through various control technologies described herein such as through the adjustment of a control knob, a gesture, eye movement, or voice command. If a user desires to increase the intensity of illumination, the user may adjust a control knob on the glasses or he may adjust a control knob in the user interface displayed on the lens or by other means. The user may use eye movements to control the knob displayed on the lens or he may control the knob by other means. The user may adjust illumination through a movement of the hand or other body movement such that the intensity or color of illumination changes based on the movement made by the user. Also, the user may adjust the illumination through a voice command such as by speaking a phrase requesting increased or decreased illumination or requesting other colors to be displayed. Additionally, illumination modulation may be achieved through any control technology described herein or by other means.

Further, the illumination may be modulated per the particular application being executed. As an example, an application may automatically adjust the intensity of illumination or color of illumination based on the optimal settings for that application. If the current levels of illumination are not at the optimal levels for the application being executed, a message or command may be sent to provide for illumination adjustment.

In embodiments, illumination modulation may be accomplished through filtering and or through magnification. For example, filtering techniques may be employed that allow the intensity and or color of the light to be changed such that the optimal or desired illumination is achieved. Also, in embodiments, the intensity of the illumination may be modulated by applying greater or less magnification to reach the desired illumination intensity.

The projector may be connected to the display to output the video and other display elements to the user. The display used may be an SVGA 800×600 dots/inch SYNDIANT liquid crystal on silicon (LCoS) display.

The target MPE dimensions for the system may be 24 mm×12 mm×6 mm.

The focus may be adjustable, allowing a user to refine the projector output to suit their needs.

The optics system may be contained within a housing fabricated for 6061-T6 aluminum and glass-filled ABS/PC.

The weight of the system, in an embodiment, is estimated to be 3.75 ounces, or 95 grams.

Figure 11:
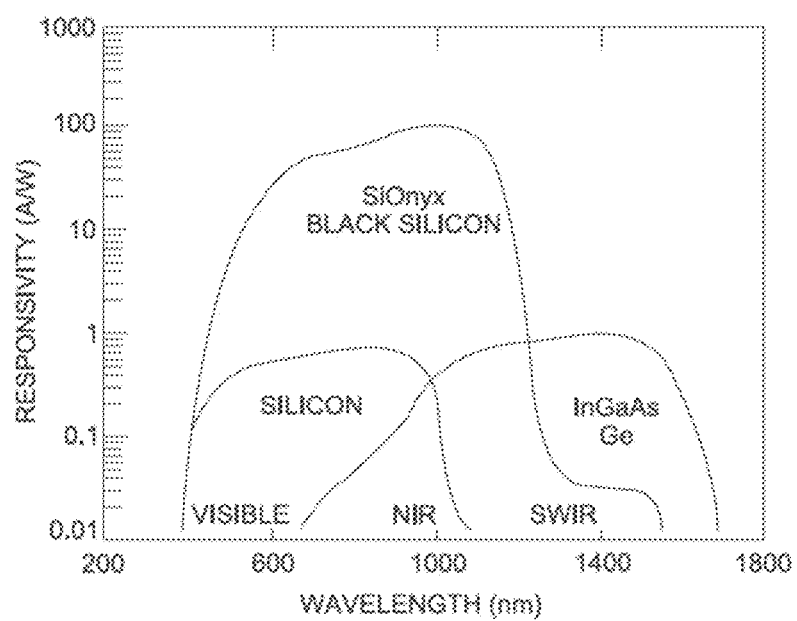
FIG. 11 depicts a plot of responsivity versus wavelength for three substrates.

In an embodiment, the eyepiece and associated electronics provide night vision capability. This night vision capability may be enabled by a black silicon SWIR sensor. Black silicon is a complementary metal-oxide silicon (CMOS) processing technique that enhances the photo response of silicon over 100 times. The spectral range is expanded deep into the short wave infra-red (SWIR) wavelength range. In this technique, a 300 nm deep absorbing and anti-reflective layer is added to the glasses. This layer offers improved responsivity as shown in FIG. 11, where the responsivity of black silicon is much greater than silicon's over the visible and NIR ranges and extends well into the SWIR range. This technology is an improvement over current technology, which suffers from extremely high cost, performance issues, as well as high volume manufacturability problems. Incorporating this technology into night vision optics brings the economic advantages of CMOS technology into the design.

Unlike current night-vision goggles (NVGs), which amplify starlight or other ambient light from the visible light spectrum, SWIR sensors pick up individual photons and convert light in the SWIR spectrum to electrical signals, similar to digital photography. The photons can be produced from the natural recombination of oxygen and hydrogen atoms in the atmosphere at night, also referred to as "Night Glow." Shortwave infrared devices see objects at night by detecting the invisible, shortwave infrared radiation within reflected star light, city lights or the moon. They also work in daylight, or through fog, haze or smoke, whereas the current NVG Image Intensifier infrared sensors would be overwhelmed by heat or brightness. Because shortwave infrared devices pick up invisible radiation on the edge of the visible spectrum, the SWIR images look like the images produced by visible light with the same shadows and contrast and facial details, only in black and white, dramatically enhancing recognition so people look like people; they don't look like blobs often seen with thermal Imagers. One of the important SWIR capabilities is of providing views of targeting lasers on the battlefield. Targeting lasers (1.064 um) are not visible with current night-vision goggles. With SWIR Electro-optics, soldiers will be able to view every targeting laser in use, including those used by the enemy. Unlike Thermal Imagers, which do not penetrate windows on vehicles or buildings, the Visible/Near Infrared/Short Wave Infrared Sensor can see through them—day or night, giving users an important tactical advantage.

Certain advantages include using active illumination only when needed. In some instances there may be sufficient natural illumination at night, such as during a full moon. When such is the case, artificial night vision using active illumination may not be necessary. With black silicon CMOS-based SWIR sensors, active illumination may not be needed during these conditions, and is not provided, thus improving battery life.

Figure 12:
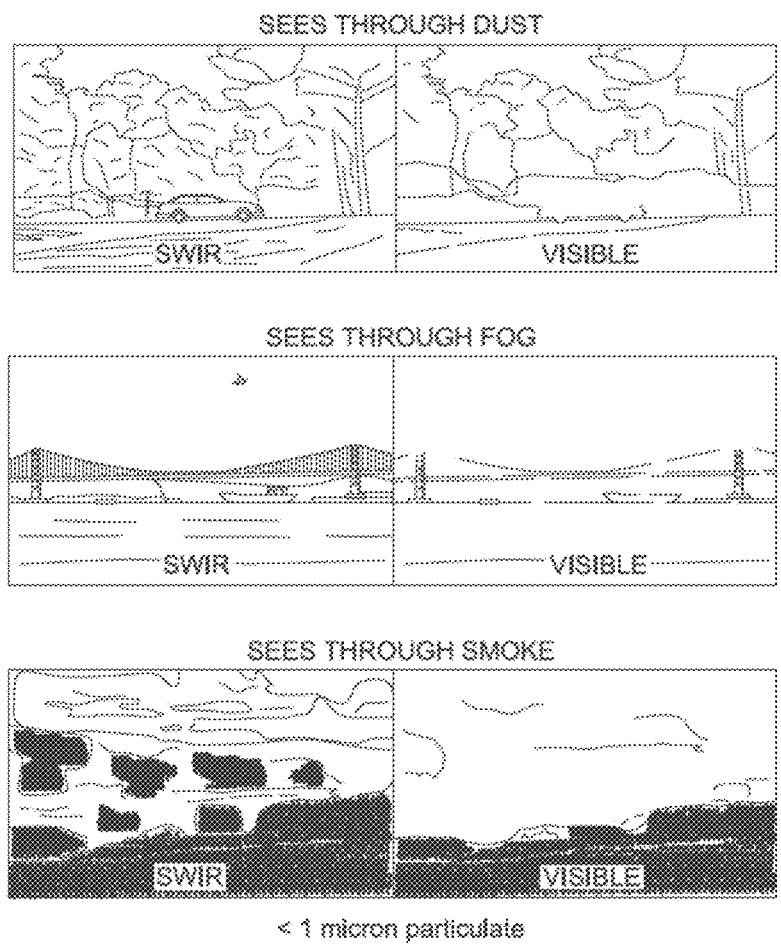
FIG. 12 illustrates the performance of the black silicon sensor.

In addition, a black silicon image sensor may have over eight times the signal to noise ratio found in costly indium-gallium arsenide image sensors under night sky conditions. Better resolution is also provided by this technology, offering much higher resolution than available using current technology for night vision. Typically, long wavelength images produced by CMOS-based SWIR have been difficult to interpret, having good heat detection, but poor resolution. This problem is solved with a black image silicon SWIR sensor, which relies on much shorter wavelengths. SWIR is highly desirable for battlefield night vision glasses for these reasons. FIG. 12 illustrates the effectiveness of black silicon night vision technology, providing both before and after images of seeing through a) dust; b) fog, and c) smoke. The images in FIG. 12 demonstrate the performance of the new VIS/NIR/SWIR black silicon sensor. In embodiments, the image sensor may be able to distinguish between changes in the natural environment, such as disturbed vegetation, disturbed ground, and the like. For example, an enemy combatant may have recently placed an explosive device in the ground, and so the ground over the explosive will be 'disturbed ground', and the image sensor (along with processing facilities internal or external to the eyepiece) may be able to distinguish the recently disturbed ground from the surrounding ground. In this way, a soldier may be able to detect the possible placement of an underground explosive device (e.g. an improvised explosive device (IED)) from a distance.

Figure 17:
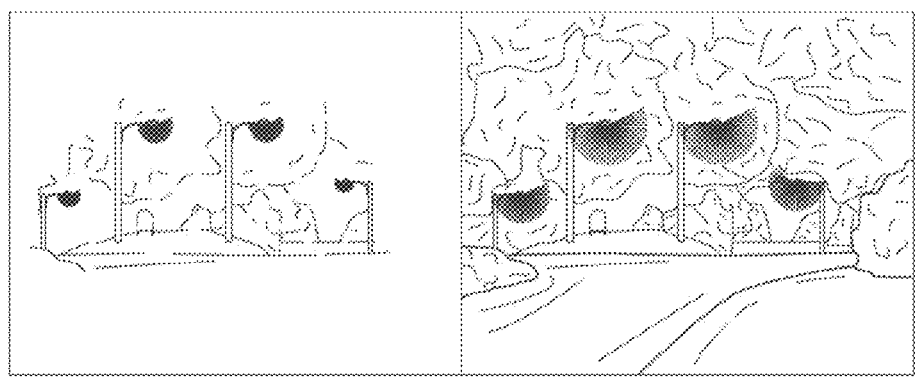
FIG. 17 shows the difference in image quality between A) a flexible platform of uncooled CMOS image sensors capable of VIS/NIR/SWIR imaging and B) an image intensified night vision system

Previous night vision systems suffered from "blooms" from bright light sources, such as streetlights. These "blooms" were particularly strong in image intensifying technology and are also associated with a loss of resolution. In some cases, cooling systems are necessary in image intensifying technology systems, increasing weight and shortening battery power lifespan. FIG. 17 shows the difference in image quality between A) a flexible platform of uncooled CMOS image sensors capable of VIS/NIR/SWIR imaging and B) an image intensified night vision system.

Figure 13A:
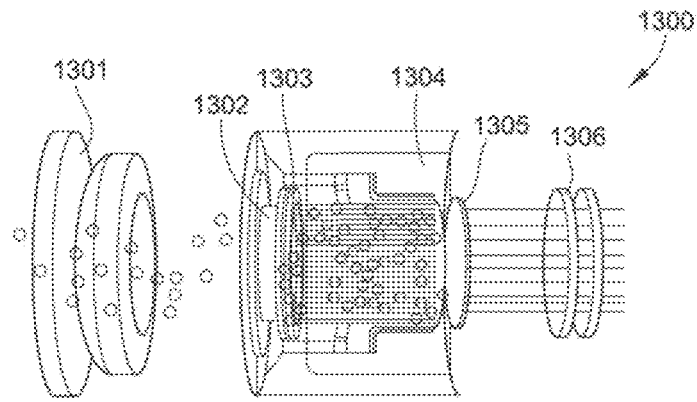
FIG. 13A depicts an incumbent night vision system.
Figure 13B:
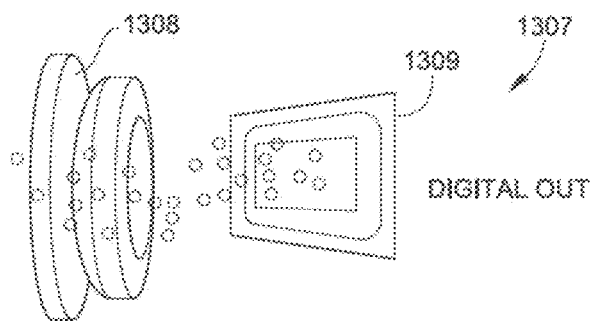
FIG. 13B depicts the night vision system of the present disclosure.

FIG. 13 depicts the difference in structure between current or incumbent vision enhancement technology 1300 and uncooled CMOS image sensors 1307. The incumbent platform (FIG. 13A) limits deployment because of cost, weight, power consumption, spectral range, and reliability issues. Incumbent systems are typically comprised of a front lens 1301, photocathode 1302, micro channel plate 1303, high voltage power supply 1304, phosphorous screen 1305, and eyepiece 1306. This is in contrast to a flexible platform (FIG. 13B) of uncooled CMOS image sensors 1307 capable of VIS/NIR/SWIR imaging at a fraction of the cost, power consumption, and weight. These much simpler sensors include a front lens 1308 and an image sensor 1309 with a digital image output.

Figure 13C:
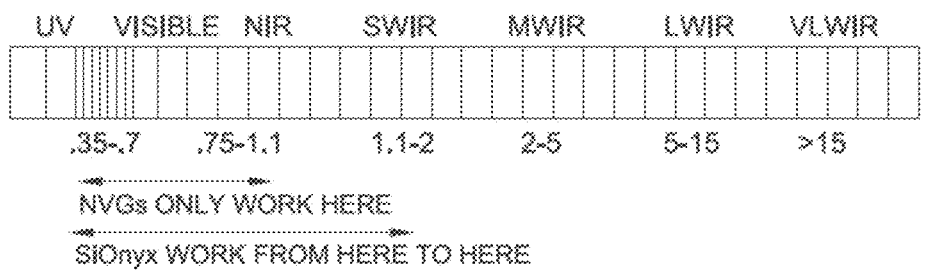
FIG. 13C illustrates the difference in responsivity between the two.

These advantages derive from the CMOS compatible processing technique that enhances the photo response of silicon over 100 times and extends the spectral range deep into the short wave infrared region. The difference in responsivity is illustrated in FIG. 13C. While typical night vision goggles are limited to the UV, visible and near infrared (NIR) ranges, to about 1100 nm (1.1 micrometers) the newer CMOS image sensor ranges also include the short wave infrared (SWIR) spectrum, out to as much as 2000 nm (2 micrometers).

The black silicon core technology may offer significant improvement over current night vision glasses. Femtosecond laser doping may enhance the light detection properties of silicon across a broad spectrum. Additionally, optical response may be improved by a factor of 100 to 10,000. The black silicon technology is a fast, scalable, and CMOS compatible technology at a very low cost, compared to current night vision systems. Black silicon technology may also provide a low operation bias, with 3.3 V typical. In addition, uncooled performance may be possible up to 50° C. Cooling requirements of current technology increase both weight and power consumption, and also create discomfort in users. As noted above, the black silicon core technology offers a high-resolution replacement for current image intensifier technology. Black silicon core technology may provide high speed electronic shuttering at speeds up to 1000 frames/second with minimal cross talk. In certain embodiments of the night vision eyepiece, an OLED display may be preferred over other optical displays, such as the LCoS display.

The eyepiece incorporating the VIS/NIR/SWIR black silicon sensor may provide for better situational awareness (SAAS) surveillance and real-time image enhancement.

In some embodiments, the VIS/NIR/SWIR black silicon sensor may be incorporated into a form factor suitable for night vision only, such as a night vision goggle or a night vision helmet. The night vision goggle may include features that make it suitable for the military market, such as ruggedization and alternative power supplies, while other form factors may be suitable for the consumer or toy market. In one example, the night vision goggles may have extended range, such as 500-1200 nm, and may also useable as a camera.

In some embodiments, the VIS/NIR/SWIR black silicon sensor as well as other outboard sensors may be incorporated into a mounted camera that may be mounted on transport or combat vehicles so that the real-time feed can be sent to the driver or other occupants of the vehicle by superimposing the video on the forward view without obstructing it. The driver can better see where he or she is going, the gunner can better see threats or targets of opportunity, and the navigator can better sense situational awareness (SAAS) while also looking for threats. The feed could also be sent to off-site locations as desired, such as higher headquarters of memory/storage locations for later use in targeting, navigation, surveillance, data mining, and the like.

Further advantages of the eyepiece may include robust connectivity. This connectivity enables download and transmission using Bluetooth, Wi-Fi/Internet, cellular, satellite, 3G, FM/AM, TV, and UVB transceiver for sending/receiving vast amounts of data quickly. For example, the UWB transceiver may be used to create a very high data rate, low-probability-of-intercept/low-probability-of-detection (LPI/LPD), Wireless Personal Area Network (WPAN) to connect weapons sights, weapons-mounted mouse/controller, E/O sensors, medical sensors, audio/video displays, and the like. In other embodiments, the WPAN may be created using other communications protocols. For example, a WPAN transceiver may be a COTS-compliant module front end to make the power management of a combat radio highly responsive and to avoid jeopardizing the robustness of the radio. By integrating the ultra wideband (UWB) transceiver, baseband/MAC and encryption chips onto a module, a physically small dynamic and configurable transceiver to address multiple operational needs is obtained. The WPAN transceivers create a low power, encrypted, wireless personal area network (WPAN) between soldier worn devices. The WPAN transceivers can be attached or embedded into nearly any fielded military device with a network interface (handheld computers, combat displays, etc.). The system is capable of supporting many users, AES encryption, robust against jamming and RF interference as well as being ideal for combat providing low probabilities of interception and detection (LPI/LPD). The WPAN transceivers eliminate the bulk, weight and "snagability" of data cables on the soldier. Interfaces include USB 1.1, USB 2.0 OTG, Ethernet 10-, 100 Base-T and RS232 9-pin D-Sub. The power output may be −10, −20 dBm outputs for a variable range of up to 2 meters. The data capacity may be 768 Mbps and greater. The bandwidth may be 1.7 GHz. Encryption may be 128-bit, 192-bit or 256-bit AES. The WPAN transceiver may include Optimized Message Authentication Code (MAC) generation. The WPAN transceiver may comply to MIL-STD-461F. The WPAN transceiver may be in the form of a connector dust cap and may attach to any fielded military device. The WPAN transceiver allows simultaneous video, voice, stills, text and chat, eliminates the need for data cables between electronic devices, allows hands-free control of multiple devices without distraction, features an adjustable connectivity range, interfaces with Ethernet and USB 2.0, features an adjustable frequency 3.1 to 10.6 GHz and 200 mw peak draw and nominal standby.

Figure 58:
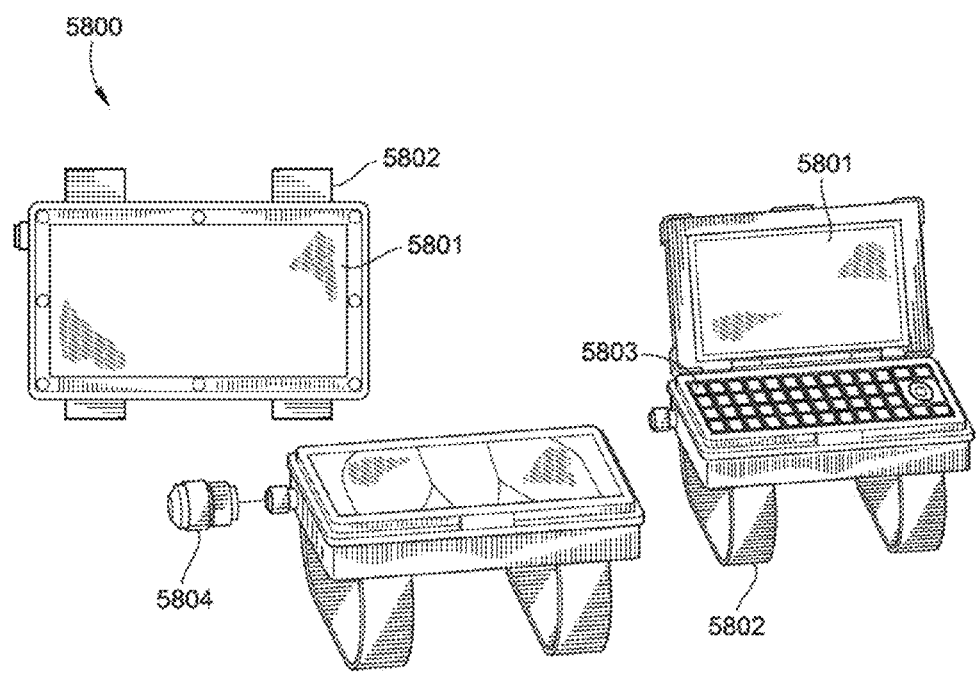
FIG. 58 illustrates a fingerprint, palm print, geo-location, and POI enrollment forearm wearable device according to an embodiment.

For example, the WPAN transceiver may enable creating a WPAN between the eyepiece 100 in the form of a GSE stereo heads-up combat display glasses, a computer, a remote computer controller, and biometric enrollment devices like that seen in FIG. 58. In another example, the WPAN transceiver may enable creating a WPAN between the eyepiece in the form of flip-up/-down heads-up display combat glasses, the HUD CPU (if it is external), a weapon fore-grip controller, and a forearm computer similar to that seen in FIG. 58.

The eyepiece may provide its own cellular connectivity, such as though a personal wireless connection with a cellular system. The personal wireless connection may be available for only the wearer of the eyepiece, or it may be available to a plurality of proximate users, such as in a Wi-Fi hot spot (e.g. WiFi), where the eyepiece provides a local hotspot for others to utilize. These proximate users may be other wearers of an eyepiece, or users of some other wireless computing device, such as a mobile communications facility (e.g. mobile phone). Through this personal wireless connection, the wearer may not need other cellular or Internet wireless connections to connect to wireless services. For instance, without a personal wireless connection integrated into the eyepiece, the wearer may have to find a WiFi connection point or tether to their mobile communications facility in order to establish a wireless connection. In embodiments, the eyepiece may be able to replace the need for having a separate mobile communications device, such as a mobile phone, mobile computer, and the like, by integrating these functions and user interfaces into the eyepiece. For instance, the eyepiece may have an integrated WiFi connection or hotspot, a real or virtual keyboard interface, a USB hub, speakers (e.g. to stream music to) or speaker input connections, integrated camera, external camera, and the like. In embodiments, an external device, in connectivity with the eyepiece, may provide a single unit with a personal network connection (e.g. WiFi, cellular connection), keyboard, control pad (e.g. a touch pad), and the like.

Communications from the eyepiece may include communication links for special purposes. For instance, an ultra-wide bandwidth communications link may be utilized when sending and/or receiving large volumes of data in a short amount of time. In another instance, a near-field communications (NFC) link may be used with very limited transmission range in order to post information to transmit to personnel when they are very near, such as for tactical reasons, for local directions, for warnings, and the like. For example, a soldier may be able to post/hold information securely, and transmit only to people very nearby with a need-to-know or need-to-use the information. In another instance, a wireless personal area network (PAN) may be utilized, such as to connect weapons sights, weapons-mounted mouse/controller, electro-optic sensors, medical sensors, audio-visual displays, and the like.

The eyepiece may include MEMS-based inertial navigation systems, such as a GPS processor, an accelerometer (e.g. for enabling head control of the system and other functions), a gyroscope, an altimeter, an inclinometer, a speedometer/odometer, a laser rangefinder, and a magnetometer, which also enables image stabilization.

The eyepiece may include integrated headphones, such as the articulating earbud 120, that provide audio output to the user or wearer.

In an embodiment, a forward facing camera (see FIG. 21) integrated with the eyepiece may enable basic augmented reality. In augmented reality, a viewer can image what is being viewed and then layer an augmented, edited, tagged, or analyzed version on top of the basic view. In the alternative, associated data may be displayed with or over the basic image. If two cameras are provided and are mounted at the correct interpupillary distance for the user, stereo video imagery may be created. This capability may be useful for persons requiring vision assistance. Many people suffer from deficiencies in their vision, such as near-sightedness, far-sightedness, and so forth. A camera and a very close, virtual screen as described herein provides a "video" for such persons, the video adjustable in terms of focal point, nearer or farther, and fully in control by the person via voice or other command. This capability may also be useful for persons suffering diseases of the eye, such as cataracts, retinitis pigmentosa, and the like. So long as some organic vision capability remains, an augmented reality eyepiece can help a person see more clearly. Embodiments of the eyepiece may feature one or more of magnification, increased brightness, and ability to map content to the areas of the eye that are still healthy. Embodiments of the eyepiece may be used as bifocals or a magnifying glass. The wearer may be able to increase zoom in the field of view or increase zoom within a partial field of view. In an embodiment, an associated camera may make an image of the object and then present the user with a zoomed picture. A user interface may allow a wearer to point at the area that he wants zoomed, such as with the control techniques described herein, so the image processing can stay on task as opposed to just zooming in on everything in the camera's field of view.

A rear-facing camera (not shown) may also be incorporated into the eyepiece in a further embodiment. In this embodiment, the rear-facing camera may enable eye control of the eyepiece, with the user making application or feature selection by directing his or her eyes to a specific item displayed on the eyepiece.

A further embodiment of a device for capturing biometric data about individuals may incorporate a microcassegrain telescoping folded optic camera into the device. The microcassegrain telescoping folded optic camera may be mounted on a handheld device, such as the bio-print device, the bio-phone, and could also be mounted on glasses used as part of a bio-kit to collect biometric data.

A cassegrain reflector is a combination of a primary concave mirror and a secondary convex mirror. These reflectors are often used in optical telescopes and radio antennas because they deliver good light (or sound) collecting capability in a shorter, smaller package.

In a symmetrical cassegrain both mirrors are aligned about the optical axis, and the primary mirror usually has a hole in the center, allowing light to reach the eyepiece or a camera chip or light detection device, such as a CCD chip. An alternate design, often used in radio telescopes, places the final focus in front of the primary reflector. A further alternate design may tilt the mirrors to avoid obstructing the primary or secondary mirror and may eliminate the need for a hole in the primary mirror or secondary mirror. The microcassegrain telescoping folded optic camera may use any of the above variations, with the final selection determined by the desired size of the optic device.

Figure 35:
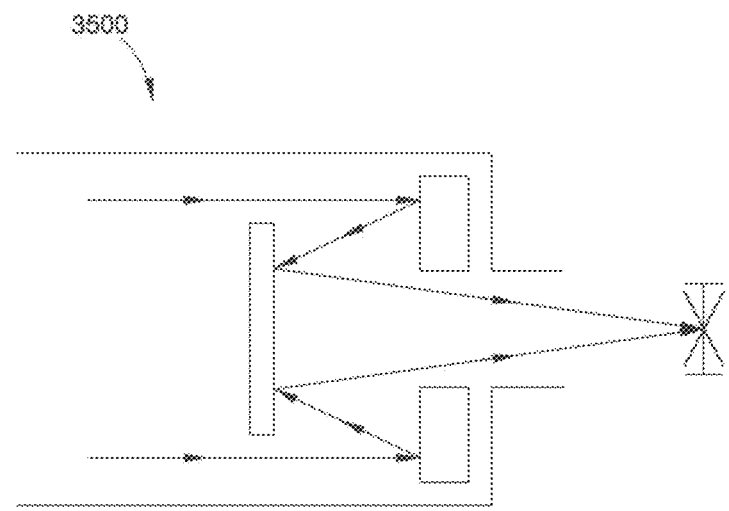
FIG. 35 depicts an embodiment of a classic cassegrain configuration.

The classic cassegrain configuration 3500 uses a parabolic reflector as the primary mirror and a hyperbolic mirror as the secondary mirror. Further embodiments of the microcassegrain telescoping folded optic camera may use a hyperbolic primary mirror and/or a spherical or elliptical secondary mirror. In operation the classic cassegrain with a parabolic primary mirror and a hyperbolic secondary mirror reflects the light back down through a hole in the primary, as shown in FIG. 35. Folding the optical path makes the design more compact, and in a "micro" size, suitable for use with the bio-print sensor and bio-print kit described herein. In a folded optic system, the beam is bent to make the optical path much longer than the physical length of the system. One common example of folded optics is prismatic binoculars. In a camera lens the secondary mirror may be mounted on an optically flat, optically clear glass plate that closes the lens tube. This support eliminates "star-shaped" diffraction effects that are caused by a straight-vaned support spider. This allows for a sealed closed tube and protects the primary mirror, albeit at some loss of light collecting power.

The cassegrain design also makes use of the special properties of parabolic and hyperbolic reflectors. A concave parabolic reflector will reflect all incoming light rays parallel to its axis of symmetry to a single focus point. A convex hyperbolic reflector has two foci and reflects all light rays directed at one focus point toward the other focus point. Mirrors in this type of lens are designed and positioned to share one focus, placing the second focus of the hyperbolic mirror at the same point as where the image is observed, usually just outside the eyepiece. The parabolic mirror reflects parallel light rays entering the lens to its focus, which is coincident with the focus of the hyperbolic mirror. The hyperbolic mirror then reflects those light rays to the other focus point, where the camera records the image.

Figure 36:
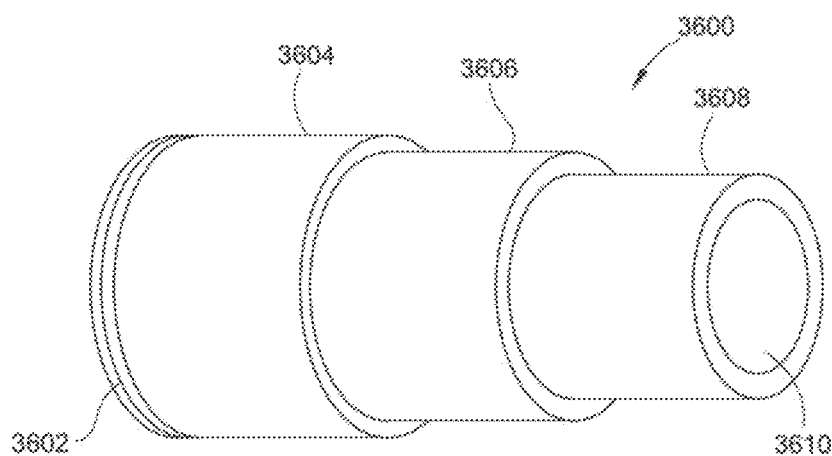
FIG. 36 depicts the configuration of the micro-cassegrain telescoping folded optic camera.

FIG. 36 shows the configuration of the microcassegrain telescoping folded optic camera. The camera may be mounted on augmented reality glasses, a bio-phone, or other biometric collection device. The assembly, 3600 has multiple telescoping segments that allow the camera to extend with cassegrain optics providing for a longer optical path. Threads 3602 allow the camera to be mounted on a device, such as augmented reality glasses or other biometric collection device. While the embodiment depicted in FIG. 36 uses threads, other mounting schemes such as bayonet mount, knobs, or press-fit, may also be used. A first telescoping section 3604 also acts as an external housing when the lens is in the fully retracted position. The camera may also incorporate a motor to drive the extension and retraction of the camera. A second telescoping section 3606 may also be included. Other embodiments may incorporate varying numbers of telescoping sections, depending on the length of optical path needed for the selected task or data to be collected. A third telescoping section 3608 includes the lens and a reflecting mirror. The reflecting mirror may be a primary reflector if the camera is designed following classic cassegrain design. The secondary mirror may be contained in first telescoping section 3604.

Further embodiments may utilize microscopic mirrors to form the camera, while still providing for a longer optical path through the use of folded optics. The same principles of cassegrain design are used.

Lens 3610 provides optics for use in conjunction with the folded optics of the cassegrain design. The lens 3610 may be selected from a variety of types, and may vary depending on the application. The threads 3602 permit a variety of cameras to be interchanged depending on the needs of the user.

Eye control of feature and option selection may be controlled and activated by object recognition software loaded on the system processor. Object recognition software may enable augmented reality, combine the recognition output with querying a database, combine the recognition output with a computational tool to determine dependencies/likelihoods, and the like.

Three-dimensional viewing is also possible in an additional embodiment that incorporates a 3D projector. Two stacked picoprojectors (not shown) may be used to create the three dimensional image output.

Figure 10:
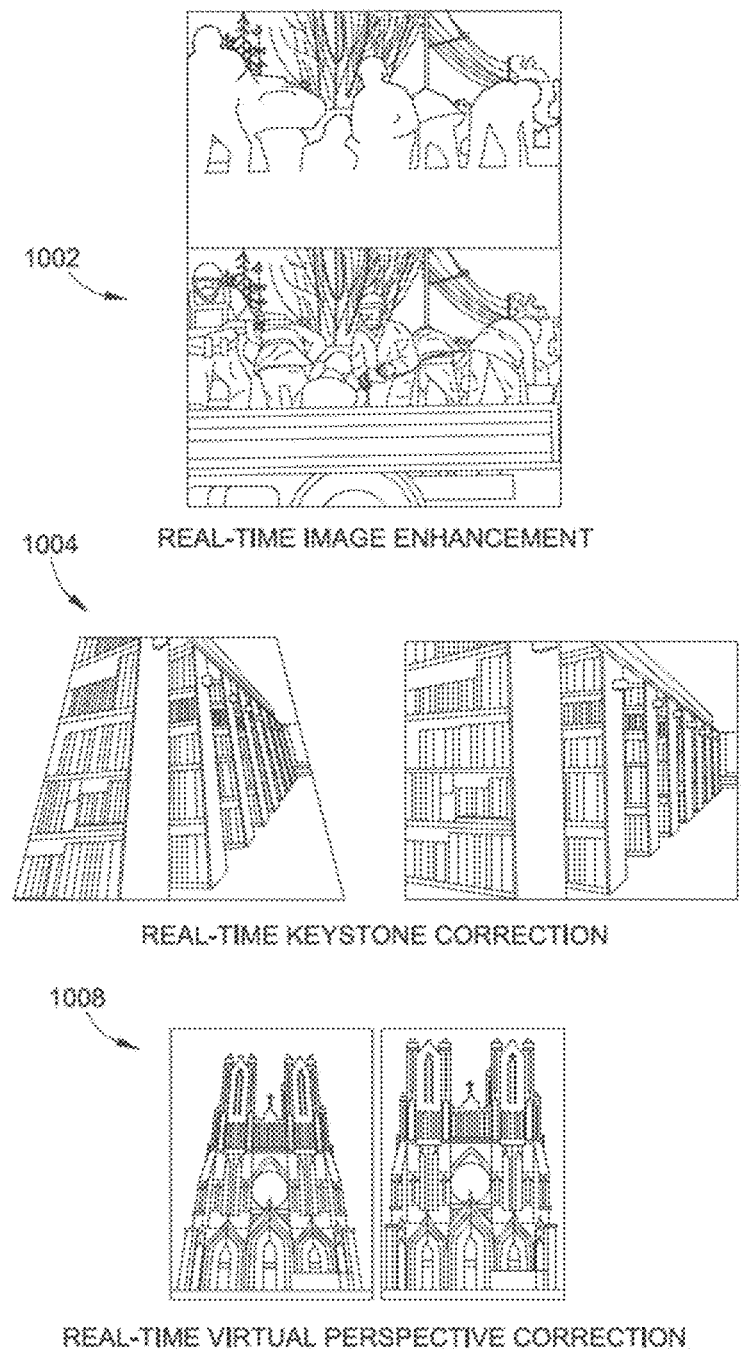
FIG. 10 depicts the advantages of the eyepiece in real-time image enhancement, keystone correction, and virtual perspective correction.

Referring to FIG. 10, a plurality of digital CMOS Sensors with redundant micros and DSPs for each sensor array and projector detect visible, near infrared, and short wave infrared light to enable passive day and night operations, such as real-time image enhancement 1002, real-time keystone correction 1004, and real-time virtual perspective correction 1008. The eyepiece may utilize digital CMOS image sensors and directional microphones (e.g. microphone arrays) as described herein, such as for visible imaging for monitoring the visible scene (e.g. for biometric recognition, gesture control, coordinated imaging with 2D/3D projected maps), IR/UV imaging for scene enhancement (e.g. seeing through haze, smoke, in the dark), sound direction sensing (e.g. the direction of a gunshot or explosion, voice detection), and the like. In embodiments, each of these sensor inputs may be fed to a digital signal processor (DSP) for processing, such as internal to the eyepiece or as interfaced to external processing facilities. The outputs of the DSP processing of each sensor input stream may then be algorithmically combined in a manner to generate useful intelligence data. For instance, this system may be useful for a combination of real-time facial recognition, real time voice detection, and analysis through links to a database, especially with distortion corrections and contemporaneous GPS location for soldiers, service personnel, and the like, such as in monitoring remote areas of interest, e.g., known paths or trails, or high-security areas. In an embodiment, the sound direction sensor input to the DSP may be processed to produce one or more of a visible, auditory or vibration queue to a user of the eyepiece to indicate a direction of the sound. For example, if hearing protection is used to cut off the sound of a loud blast or gunfire to protect the soldiers hearing or if a an explosion is so loud that the soldier can't tell where it came from and now their ears could be ringing so loud they can't hear anything, a visible, auditory or vibration queue to the operator may be used to indicate the direction of the original threat.

The augmented reality eyepiece or glasses may be powered by any stored energy system, such as battery power, solar power, line power, and the like. A solar energy collector may be placed on the frame, on a belt clip, and the like. Battery charging may occur using a wall charger, car charger, on a belt clip, in a glasses case, and the like. In one embodiment, the eyepiece may be rechargeable and be equipped with a mini-USB connector for recharging. In another embodiment, the eyepiece may be equipped for remote inductive recharging by one or more remote inductive power conversion technologies, such as those provided by Powercast, Ligonier, Pa., USA; and Fulton Int'l. Inc., Ada, Mich., USA, which also owns another provider, Splashpower, Inc., Cambridge, UK.

The augmented reality eyepiece also includes a camera and any interface necessary to connect the camera to the circuit. The output of the camera may be stored in memory and may also be displayed on the display available to the wearer of the glasses. A display driver may also be used to control the display. The augmented reality device also includes a power supply, such as a battery, as shown, power management circuits and a circuit for recharging the power supply. As noted elsewhere, recharging may take place via a hard connection, e.g., a mini-USB connector, or by means of an inductor, a solar panel input, and so forth.

The control system for the eyepiece or glasses may include a control algorithm for conserving power when the power source, such as a battery, indicates low power. This conservation algorithm may include shutting power down to applications that are energy intensive, such as lighting, a camera, or sensors that require high levels of energy, such as any sensor requiring a heater, for example. Other conservation steps may include slowing down the power used for a sensor or for a camera, e.g., slowing the sampling or frame rates, going to a slower sampling or frame rate when the power is low; or shutting down the sensor or camera at an even lower level. Thus, there may be at least three operating modes depending on the available power: a normal mode; a conserve power mode; and an emergency or shutdown mode.

Applications of the present disclosure may be controlled through movements and direct actions of the wearer, such as movement of his or her hand, finger, feet, head, eyes, and the like, enabled through facilities of the eyepiece (e.g. accelerometers, gyros, cameras, optical sensors, GPS sensors, and the like) and/or through facilities worn or mounted on the wearer (e.g. body mounted sensor control facilities). In this way, the wearer may directly control the eyepiece through movements and/or actions of their body without the use of a traditional hand-held remote controller. For instance, the wearer may have a sense device, such as a position sense device, mounted on one or both hands, such as on at least one finger, on the palm, on the back of the hand, and the like, where the position sense device provides position data of the hand, and provides wireless communications of position data as command information to the eyepiece. In embodiments, the sense device of the present disclosure may include a gyroscopic device (e.g. electronic gyroscope, MEMS gyroscope, mechanical gyroscope, quantum gyroscope, ring laser gyroscope, fiber optic gyroscope), accelerometers, MEMS accelerometers, velocity sensors, force sensors, pressure sensors, optical sensors, proximity sensor, RFID, and the like, in the providing of position information. For example, a wearer may have a position sense device mounted on their right index finger, where the device is able to sense motion of the finger. In this example, the user may activate the eyepiece either through some switching mechanism on the eyepiece or through some predetermined motion sequence of the finger, such as moving the finger quickly, tapping the finger against a hard surface, and the like. Note that tapping against a hard surface may be interpreted through sensing by accelerometers, force sensors, pressure sensors, and the like. The position sense device may then transmit motions of the finger as command information, such as moving the finger in the air to move a cursor across the displayed or projected image, moving in quick motion to indicate a selection, and the like. In embodiments, the position sense device may send sensed command information directly to the eyepiece for command processing, or the command processing circuitry may be co-located with the position sense device, such as in this example, mounted on the finger as part of an assembly including the sensors of the position sense device. Command information may be accompanied by a visual indicator. For example, the cursor may change color when interacting with different content. For example, in order to know where your finger is when you are using an external device to control the glasses, a visual indication of the command information may be displayed in the glasses.

In embodiments, the wearer may have a plurality of position sense devices mounted on their body. For instance, and in continuation of the preceding example, the wearer may have position sense devices mounted on a plurality of points on the hand, such as with individual sensors on different fingers, or as a collection of devices, such as in a glove. In this way, the aggregate sense command information from the collection of sensors at different locations on the hand may be used to provide more complex command information. For instance, the wearer may use a sensor device glove to play a game, where the glove senses the grasp and motion of the user's hands on a ball, bat, racket, and the like, in the use of the present disclosure in the simulation and play of a simulated game. In embodiments, the plurality of position sense devices may be mounted on different parts of the body, allowing the wearer to transmit complex motions of the body to the eyepiece for use by an application.

In embodiments, the sense device may have a force sensor, pressure sensor, and the like, such as for detecting when the sense device comes in contact with an object. For instance, a sense device may include a force sensor at the tip of a wearer's finger. In this case, the wearer may tap, multiple tap, sequence taps, swipe, touch, and the like to generate a command to the eyepiece. Force sensors may also be used to indicate degrees of touch, grip, push, and the like, where predetermined or learned thresholds determine different command information. In this way, commands may be delivered as a series of continuous commands that constantly update the command information being used in an application through the eyepiece. In an example, a wearer may be running a simulation, such as a game application, military application, commercial application, and the like, where the movements and contact with objects, such as through at least one of a plurality of sense devices, are fed to the eyepiece as commands that influence the simulation displayed through the eyepiece. For instance, a sense device may be included in a pen controller, where the pen controller may have a force sensor, pressure sensor, inertial measurement unit, and the like, and where the pen controller may be used to produce virtual writing, control a cursor associated with the eyepiece's display, act as a computer mouse, provide control commands though physical motion and/or contact, and the like.

In embodiments, the sense device may include an optical sensor or optical transmitter as a way for movement to be interpreted as a command. For instance, a sense device may include an optical sensor mounted on the hand of the wearer, and the eyepiece housing may include an optical transmitter, such that when a user moves their hand past the optical transmitter on the eyepiece, the motions may be interpreted as commands. A motion detected through an optical sensor may include swiping past at different speeds, with repeated motions, combinations of dwelling and movement, and the like. In embodiments, optical sensors and/or transmitters may be located on the eyepiece, mounted on the wearer (e.g. on the hand, foot, in a glove, piece of clothing), or used in combinations between different areas on the wearer and the eyepiece, and the like.

In one embodiment, a number of sensors useful for monitoring the condition of the wearer or a person in proximity to the wearer are mounted within the augmented reality glasses. Sensors have become much smaller, thanks to advances in electronics technology. Signal transducing and signal processing technologies have also made great progress in the direction of size reduction and digitization. Accordingly, it is possible to have not merely a temperature sensor in the AR glasses, but an entire sensor array. These sensors may include, as noted, a temperature sensor, and also sensor to detect: pulse rate; beat-to-beat heart variability; EKG or ECG; respiration rate; core body temperature; heat flow from the body; galvanic skin response or GSR; EMG; EEG; EOG; blood pressure; body fat; hydration level; activity level; oxygen consumption; glucose or blood sugar level; body position; and UV radiation exposure or absorption. In addition, there may also be a retinal sensor and a blood oxygenation sensor (such as an $SpO_2$ sensor), among others. Such sensors are available from a variety of manufacturers, including Vermed, Bellows Falls, Vt., USA; VTI, Ventaa, Finland; and ServoFlow, Lexington, Mass., USA.

In some embodiments, it may be more useful to have sensors mounted on the person or on equipment of the person, rather than on the glasses themselves. For example, accelerometers, motion sensors and vibration sensors may be usefully mounted on the person, on clothing of the person, or on equipment worn by the person. These sensors may maintain continuous or periodic contact with the controller of the AR glasses through a Bluetooth® radio transmitter or other radio device adhering to IEEE 802.11 specifications. For example, if a physician wishes to monitor motion or shock experienced by a patient during a foot race, the sensors may be more useful if they are mounted directly on the person's skin, or even on a T-shirt worn by the person, rather than mounted on the glasses. In these cases, a more accurate reading may be obtained by a sensor placed on the person or on the clothing rather than on the glasses. Such sensors need not be as tiny as the sensors which would be suitable for mounting on the glasses themselves, and be more useful, as seen.

The AR glasses or goggles may also include environmental sensors or sensor arrays. These sensors are mounted on the glasses and sample the atmosphere or air in the vicinity of the wearer. These sensors or sensor array may be sensitive to certain substances or concentrations of substances. For example, sensors and arrays are available to measure concentrations of carbon monoxide, oxides of nitrogen ("$NO_x$"), temperature, relative humidity, noise level, volatile organic chemicals (VOC), ozone, particulates, hydrogen sulfide, barometric pressure and ultraviolet light and its intensity. Vendors and manufacturers include: Sensares, Crolles, FR; Cairpol, Ales, FR; Critical Environmental Technologies of Canada, Delta, B.C., Canada; Apollo Electronics Co., Shenzhen, China; and AV Technology Ltd., Stockport, Cheshire, UK. Many other sensors are well known. If such sensors are mounted on the person or on clothing or equipment of the person, they may also be useful. These environmental sensors may include radiation sensors, chemical sensors, poisonous gas sensors, and the like.

In one embodiment, environmental sensors, health monitoring sensors, or both, are mounted on the frames of the augmented reality glasses. In another embodiment, the sensors may be mounted on the person or on clothing or equipment of the person. For example, a sensor for measuring electrical activity of a heart of the wearer may be implanted, with suitable accessories for transducing and transmitting a signal indicative of the person's heart activity.

The signal may be transmitted a very short distance via a Bluetooth® radio transmitter or other radio device adhering to IEEE 802.15.1 specifications. Other frequencies or protocols may be used instead. The signal may then be processed by the signal-monitoring and processing equipment of the augmented reality glasses, and recorded and displayed on the virtual screen available to the wearer. In another embodiment, the signal may also be sent via the AR glasses to a friend or squad leader of the wearer. Thus, the health and well-being of the person may be monitored by the person and by others, and may also be tracked over time.

In another embodiment, environmental sensors may be mounted on the person or on equipment of the person. For example, radiation or chemical sensors may be more useful if worn on outer clothing or a web-belt of the person, rather than mounted directly on the glasses. As noted above, signals from the sensors may be monitored locally by the person through the AR glasses. The sensor readings may also be transmitted elsewhere, either on demand or automatically, perhaps at set intervals, such as every quarter-hour or half-hour. Thus, a history of sensor readings, whether of the person's body readings or of the environment, may be made for tracking or trending purposes.

In an embodiment, an RF/micropower impulse radio (MIR) sensor may be associated with the eyepiece and serve as a short-range medical radar. The sensor may operate on an ultra-wide band. The sensor may include an RF/impulse generator, receiver, and signal processor, and may be useful for detecting and measuring cardiac signals by measuring ion flow in cardiac cells within 3 mm of the skin. The receiver may be a phased array antenna to enable determining a location of the signal in a region of space. The sensor may be used to detect and identify cardiac signals through blockages, such as walls, water, concrete, dirt, metal, wood, and the like. For example, a user may be able to use the sensor to determine how many people are located in a concrete structure by how many heart rates are detected. In another embodiment, a detected heart rate may serve as a unique identifier for a person so that they may be recognized in the future. In an embodiment, the RF/impulse generator may be embedded in one device, such as the eyepiece or some other device, while the receiver is embedded in a different device, such as another eyepiece or device. In this way, a virtual "tripwire" may be created when a heart rate is detected between the transmitter and receiver. In an embodiment, the sensor may be used as an in-field diagnostic or self-diagnosis tool. EKG's may be analyzed and stored for future use as a biometric identifier. A user may receive alerts of sensed heart rate signals and how many heart rates are present as displayed content in the eyepiece.

Figure 29:
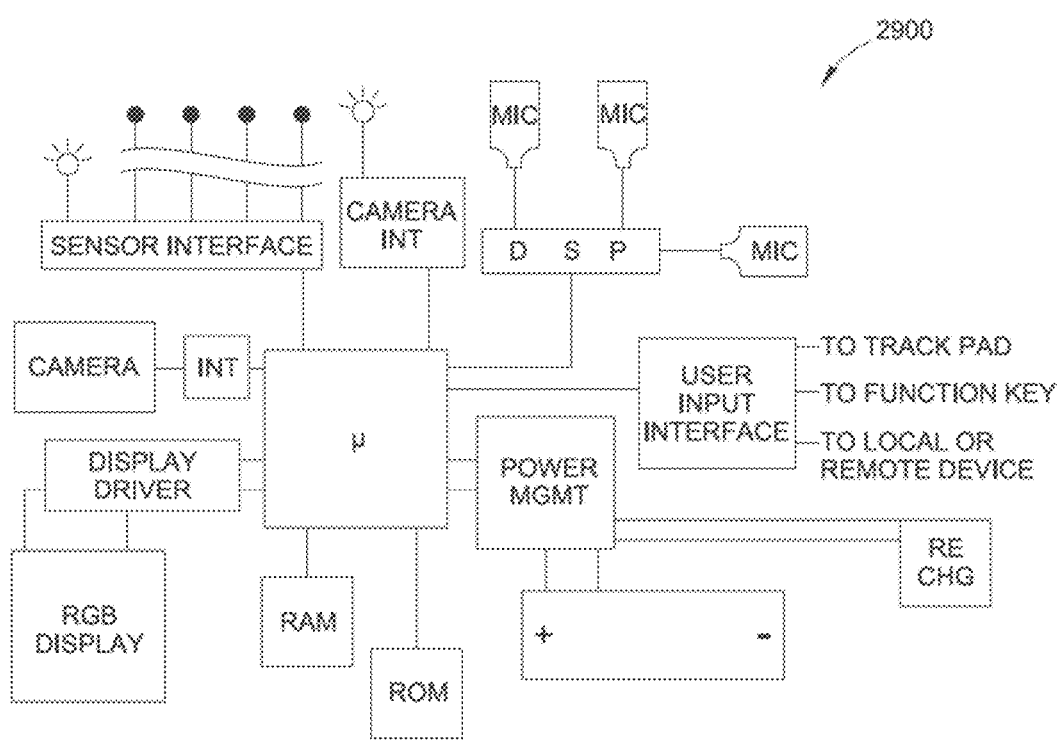
FIG. 29 depicts an exemplary electronic circuit diagram for an augmented reality eyepiece.

FIG. 29 depicts an embodiment 2900 of an augmented reality eyepiece or glasses with a variety of sensors and communication equipment. One or more than one environmental or health sensors are connected to a sensor interface locally or remotely through a short range radio circuit and an antenna, as shown. The sensor interface circuit includes all devices for detecting, amplifying, processing and sending on or transmitting the signals detected by the sensor(s). The remote sensors may include, for example, an implanted heart rate monitor or other body sensor (not shown). The other sensors may include an accelerometer, an inclinometer, a temperature sensor, a sensor suitable for detecting one or more chemicals or gasses, or any of the other health or environmental sensors discussed in this disclosure. The sensor interface is connected to the microprocessor or microcontroller of the augmented reality device, from which point the information gathered may be recorded in memory, such as random access memory (RAM) or permanent memory, read only memory (ROM), as shown.

In an embodiment, a sense device enables simultaneous electric field sensing through the eyepiece. Electric field (EF) sensing is a method of proximity sensing that allows computers to detect, evaluate and work with objects in their vicinity. Physical contact with the skin, such as a handshake with another person or some other physical contact with a conductive or a non-conductive device or object, may be sensed as a change in an electric field and either enable data transfer to or from the eyepiece or terminate data transfer. For example, videos captured by the eyepiece may be stored on the eyepiece until a wearer of the eyepiece with an embedded electric field sensing transceiver touches an object and initiates data transfer from the eyepiece to a receiver. The transceiver may include a transmitter that includes a transmitter circuit that induces electric fields toward the body and a data sense circuit, which distinguishes transmitting and receiving modes by detecting both transmission and reception data and outputs control signals corresponding to the two modes to enable two-way communication. An instantaneous private network between two people may be generated with a contact, such as a handshake. Data may be transferred between an eyepiece of a user and a data receiver or eyepiece of the second user. Additional security measures may be used to enhance the private network, such as facial or audio recognition, detection of eye contact, fingerprint detection, biometric entry, iris or retina tracking, and the like.

In embodiments, there may be an authentication facility associated with accessing functionality of the eyepiece, such as access to displayed or projected content, access to restricted projected content, enabling functionality of the eyepiece itself (e.g. as through a login to access functionality of the eyepiece) either in whole or in part, and the like. Authentication may be provided through recognition of the wearer's voice, iris, retina, fingerprint, and the like, or other biometric identifier. For example, the eyepiece or an associated controller may have an IR, ultrasonic or capacitive tactile sensor for receiving control input related to authentication or other eyepiece functions. A capacitance sensor can detect a fingerprint and launch an application or otherwise control an eyepiece function. Each finger has a different fingerprint so each finger can be used to control different eyepiece functions or quick launch different applications or provide various levels of authentication. Capacitance does not work with gloves but an ultrasonic sensor does and can be used in the same way to provide biometric authentication or control. Ultrasonic sensors useful in the eyepiece or associated controller include Sonavation's SonicTouch™ technology used in Sonavation's SonicSlide™ sensors, which works by acoustically measuring the ridges and valleys of the fingerprint to image the fingerprint in 256 shades of gray in order to discern the slightest fingerprint detail. The key imaging component of the SonicSlide™ sensor is the ceramic Micro-Electro Mechanical System (MEMS) piezoelectric transducer array that is made from a ceramic composite material.

The authentication system may provide for a database of biometric inputs for a plurality of users such that access control may be provided for use of the eyepiece based on policies and associated access privileges for each of the users entered into the database. The eyepiece may provide for an authentication process. For instance, the authentication facility may sense when a user has taken the eyepiece off, and require re-authentication when the user puts it back on. This better ensures that the eyepiece only provides access to those users that are authorized, and for only those privileges that the wearer is authorized for. In an example, the authentication facility may be able to detect the presence of a user's eye or head as the eyepiece is put on. In a first level of access, the user may only be able to access low-sensitivity items until authentication is complete. During authentication, the authentication facility may identify the user, and look up their access privileges. Once these privileges have been determined, the authentication facility may then provide the appropriate access to the user. In the case of an unauthorized user being detected, the eyepiece may maintain access to low-sensitivity items, further restrict access, deny access entirely, and the like.

In an embodiment, a receiver may be associated with an object to enable control of that object via touch by a wearer of the eyepiece, wherein touch enables transmission or execution of a command signal in the object. For example, a receiver may be associated with a car door lock. When a wearer of the eyepiece touches the car, the car door may unlock. In another example, a receiver may be embedded in a medicine bottle. When the wearer of the eyepiece touches the medicine bottle, an alarm signal may be initiated. In another example, a receiver may be associated with a wall along a sidewalk. As the wearer of the eyepiece passes the wall or touches the wall, advertising may be launched either in the eyepiece or on a video panel of the wall.

In an embodiment, when a wearer of the eyepiece initiates a physical contact, a WiFi exchange of information with a receiver may provide an indication that the wearer is connected to an online activity such as a game or may provide verification of identity in an online environment. In the embodiment, a representation of the person could change color or undergo some other visual indication in response to the contact.

Figure 14:
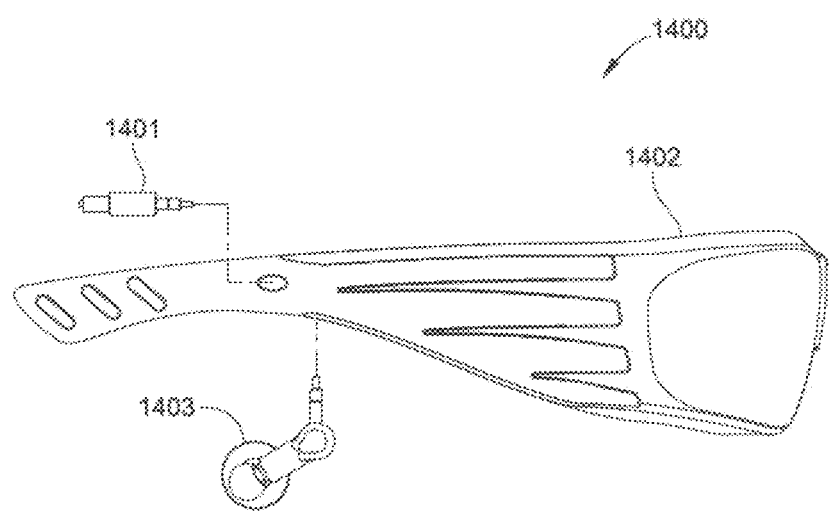
FIG. 14 depicts a tactile interface of the eyepiece.

In embodiments, the eyepiece may include a tactile interface as in FIG. 14, such as to enable haptic control of the eyepiece, such as with a swipe, tap, touch, press, click, roll of a rollerball, and the like. For instance, the tactile interface 1402 may be mounted on the frame of the eyepiece 1400, such as on an arm, both arms, the nosepiece, the top of the frame, the bottom of the frame, and the like. In embodiments, the tactile interface 1402 may include controls and functionality similar to a computer mouse, with left and right buttons, a 2D position control pad such as described herein, and the like. For example, the tactile interface may be mounted on the eyepiece near the user's temple and act as a 'temple mouse' controller for the eyepiece projected content to the user and may include a temple-mounted rotary selector and enter button. In another example, the tactile interface may be one or more vibratory temple motors which may vibrate to alert or notify the user, such as to danger left, danger right, a medical condition, and the like. The tactile interface may be mounted on a controller separate from the eyepiece, such as a worn controller hand-carried controller, and the like. If there is an accelerometer in the controller then it may sense the user tapping, such as on a keyboard, on their hand (either on the hand with the controller or tapping with the hand that has the controller), and the like. The wearer may then touch the tactile interface in a plurality of ways to be interpreted by the eyepiece as commands, such as by tapping one or multiple times on the interface, by brushing a finger across the interface, by pressing and holding, by pressing more than one interface at a time, and the like. In embodiments, the tactile interface may be attached to the wearer's body (e.g. their hand, arm, leg, torso, neck), their clothing, as an attachment to their clothing, as a ring 1500, as a bracelet, as a necklace, and the like. For example, the interface may be attached on the body, such as on the back of the wrist, where touching different parts of the interface provides different command information (e.g. touching the front portion, the back portion, the center, holding for a period of time, tapping, swiping, and the like). In embodiments, user contact with the tactile interface may be interpreted through force, pressure, movement, and the like. For instance, the tactile interface may incorporate resistive touch technologies, capacitive touch technologies, proportional pressure touch technologies, and the like. In an example, the tactile interface may utilize discrete resistive touch technologies where the application requires the interface to be simple, rugged, low power, and the like. In another example, the tactile interface may utilize capacitive tough technologies where more functionality is required through the interface, such as though movement, swiping, multi-point contacts, and the like. In another example, the tactile interface may utilize pressure touch technologies, such as when variable pressure commanding is required. In embodiments, any of these, or like touch technologies, may be used in any tactile interface as described herein.

In an embodiment, a hand held accessory may be used to control a virtual keyboard for input to the glasses. For example, If the hand held device has a touch screen, the user may interact with the touch screen that either presents an on-screen keyboard or is adapted to allow users to interact with the device which coordinates with a virtual keyboard to provide input to the glasses. For example, the virtual keyboard may be presented in the glasses, but instead of selecting items in the air, the user can adapt the touch screen device to accept input corresponding to the virtual keyboard. The device may track fingers as they slide across the capacitive module, and a click of the device would give a key strike sensation. The device may have a touch surface on the front and one or more action buttons on the back or top that allow the user to click to select without lifting their fingers off the touch surface. The letters the user has selected may be highlighted. The user could still do swipe texting, lift their fingers to end a word, insert a space, double tap to insert a period, and the like. FIG. 159 depicts a virtual keyboard 15902 presented in a user's field of view. On the keyboard, two keys are highlighted, 'D' and 'Enter'. A touchscreen accessory device 15904 is being used in the figure to provide this input to the keyboard, which is then transmitted to the glasses as input. Thus is provided a visual indicator indicating of having executed input or control commands using a virtual interface or actual touch screen on an external device.

In embodiments, the eyepiece may include a haptic communication interface that utilizes magnetic fields to transmit and/or receive a command, telemetry, information, and the like, between the eyepiece and an external device or directly to/from the user. For instance, a user may have a patterned magnetic material applied directly to some part of their body (e.g., skin, finger nail, internal to the body, and the like), where the patterned magnetic material physically responds (e.g. vibration, forces, motion, and the like) to an oscillating magnetic field generated by the haptic communication interface. The oscillating magnetic field may convey information through modulations of the field, such as through the amplitude of the signal, a time-wise variance of the signal, frequencies of the signal, and the like. The information conveyed may be an alert, an indication of an incoming call, for entertainment, for communication, an indication associated with a eyepiece application, to indicate the proximity of the user to the eyepiece, to provide haptic feedback to the user from the eyepiece, and the like. Different commands may induce different stimulus effects to the patterned magnetic material for different commands or indicators. For example, the different stimulus effects may be implemented with different frequencies and/or sequence patterns for incoming calls from different people in a user's contact list, different intensities for different alert levels, interesting patterns for purposes of entertainment, and the like.

The haptic communication interface may include coils that transmit and/or receive oscillating magnetic signals. The magnetic material may be a ferromagnetic material, a paramagnetic material, and the like, and may be applied as a power, ink, a tattoo, a decal, tape, a rub-on, sprayed-on, and the like. In embodiments, the magnetic material may have the ability to be demagnetized when the user is not using the eyepiece, un-magnetized when the magnetic material is not in the presence of the magnetic field from the eyepiece, and the like. The applied magnetic material may be applied in a spatial pattern that is functional, such as to respond to specific communication signal modulations, have a specific impedance, respond to specific frequencies, and the like. The applied magnetic material may be a visible image, invisible image, tattoo, marking, label, symbol, and the like. The applied magnetic material may include a pattern that utilizes the incoming magnetic signal to generate a transmitted signal back to the eyepiece haptic communication interface, such as with an identifier for the user, as a signal to indicate proximity between the eyepiece and the magnetic material, and the like. For example, an identifier could be a user ID that is compared to a stored ID on the eyepiece to confirm that the user is an authorized user of the eyepiece. In another example, the magnetic material may only be able to generate a transmitted signal back to the eyepiece if the magnetic material is close to the eyepiece. For instance, the user may have the magnetic material applied to a fingernail, and the user may provide a command indicator to the eyepiece by bringing their finger close to a user tactile interface.

Figure 15:
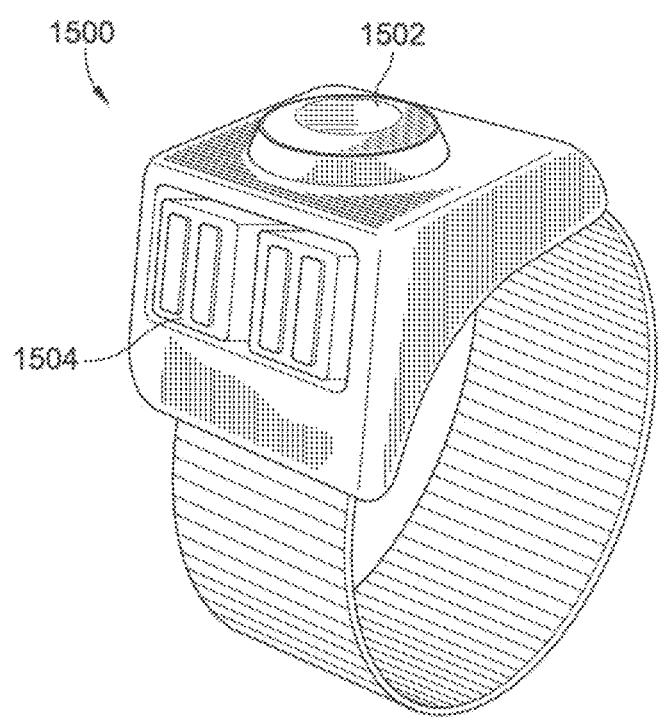
FIG. 15 depicts a ring that controls the eyepiece.

In another example, the wearer may have an interface mounted in a ring as shown in FIG. 15, a hand piece, and the like, where the interface may have at least one of a plurality of command interface types, such as a tactile interface, a position sensor device, and the like with wireless command connection to the eyepiece. In an embodiment, the ring 1500 may have controls that mirror a computer mouse, such as buttons 1504 (e.g. functioning as a one-button, multi-button, and like mouse functions), a 2D position control 1502, scroll wheel, and the like. The buttons 1504 and 2D position control 1502 may be as shown in FIG. 15, where the buttons are on the side facing the thumb and the 2D position controller is on the top. Alternately, the buttons and 2D position control may be in other configurations, such as all facing the thumb side, all on the top surface, or any other combination. The 2D position control 1502 may be a 2D button position controller (e.g. such as the TrackPoint pointing device embedded in some laptop keyboards to control the position of the mouse), a pointing stick, joystick, an optical track pad, an opto touch wheel, a touch screen, touch pad, track pad, scrolling track pad, trackball, any other position or pointing controller, and the like. In embodiments, control signals from the tactile interface (such as the ring tactile interface 1500) may be provided with a wired or wireless interface to the eyepiece, where the user is able to conveniently supply control inputs, such as with their hand, thumb, finger, and the like. In embodiments, the ring may be able to expand to fit any finger, or contract for a better fit. For example, the ring may have a customizable strap or a spring-mounted hinge. For example, the user may be able to articulate the controls with their thumb, where the ring is worn on the user's index finger. In embodiments, a method or system may provide an interactive head-mounted eyepiece worn by a user, wherein the eyepiece includes an optical assembly through which the user views a surrounding environment and displayed content, a processor for handling content for display to the user, and an integrated projector facility for projecting the content to the optical assembly, and a control device worn on the body of the user, such as a hand of the user, including at least one control component actuated by the user, and providing a control command from the actuation of the at least one control component to the processor as a command instruction. The command instruction may be directed to the manipulation of content for display to the user. The control device may be worn on a first digit of the hand of the user, and the at least one control component may be actuated by a second digit of a hand of the user. The first digit may be the index finger, the second digit the thumb, and the first and second digit on the same hand of the user. The control device may have at least one control component mounted on the index finger side facing the thumb. The at least one control component may be a button. The at least one control component may be a 2D position controller. The control device may have at least one button actuated control component mounted on the index finger side facing the thumb, and a 2D position controller actuated control component mounted on the top facing side of the index finger. The control components may be mounted on at least two digits of the user's hand. The control device may be worn as a glove on the hand of the user. The control device may be worn on the wrist of the user. The at least one control component may be worn on at least one digit of the hand, and a transmission facility may be worn separately on the hand. The transmission facility may be worn on the wrist. The transmission facility may be worn on the back of the hand. The control component may be at least one of a plurality of buttons. The at least one button may provide a function substantially similar to a conventional computer mouse button. Two of the plurality of buttons may function substantially similar to primary buttons of a conventional two-button computer mouse. The control component may be a scrolling wheel. The control component may be a 2D position control component. The 2D position control component may be a button position controller, pointing stick, joystick, optical track pad, opto-touch wheel, touch screen, touch pad, track pad, scrolling track pad, trackball, capacitive touch screen, and the like. The 2D position control component may be controlled with the user's thumb. The control component may be a touch-screen capable of implementing touch controls including button-like functions and 2D manipulation functions. The control component may be actuated when the user puts on the projected processor content pointing and control device. The ring controller may be powered by an on-board battery that may be disposable, rechargeable, solar, and the like.

Figure 15A:
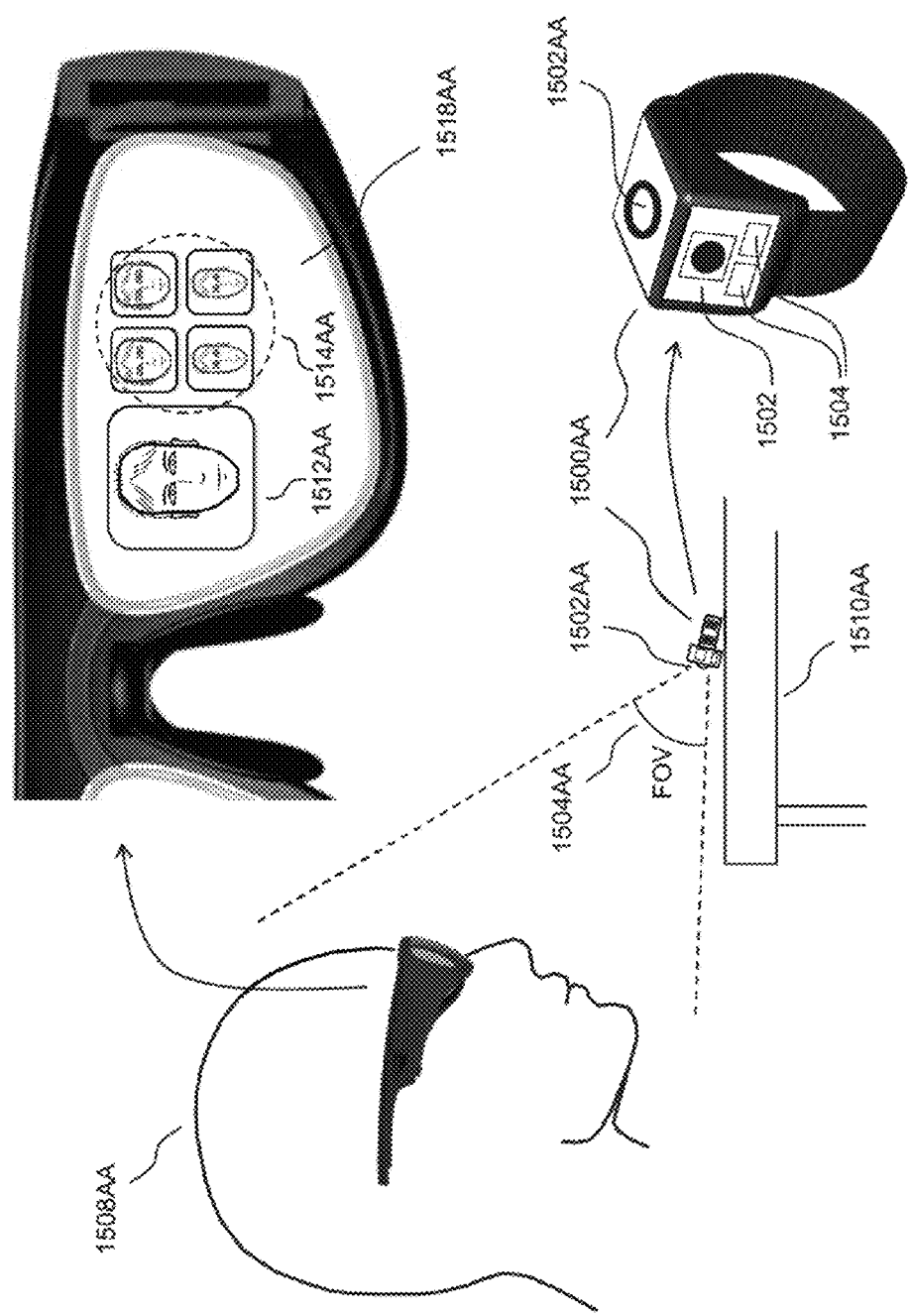
FIG. 15AA depicts a ring that controls the eyepiece with an integrated camera, where in an embodiment may allow the user to provide a video image of themselves as part of a videoconference.
Figure 15A:
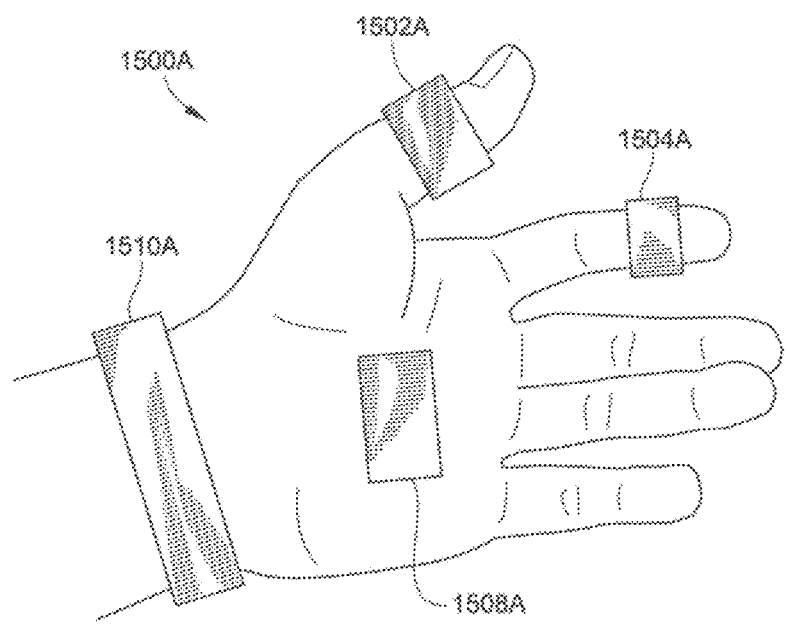
Figure 32:
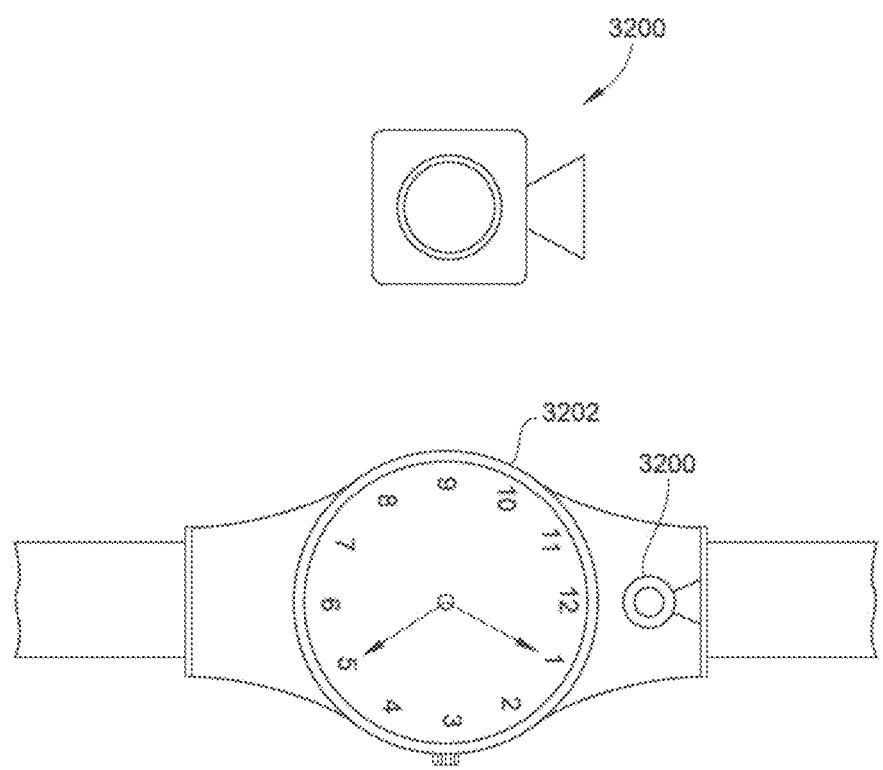
FIG. 32 depicts a typical camera for use in video calling or conferencing.
Figure 33:
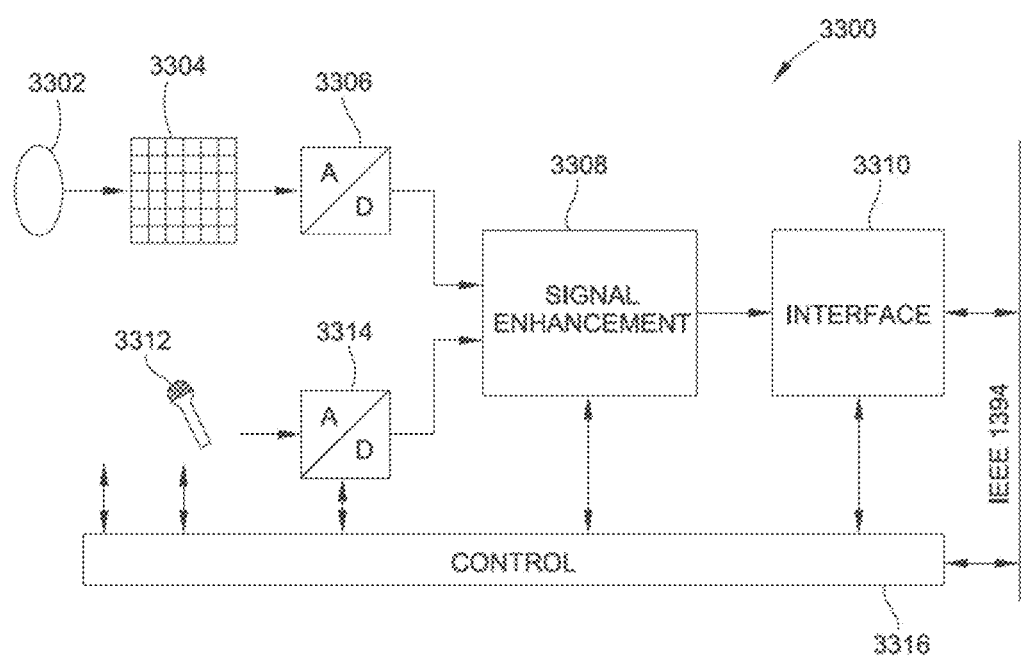
FIG. 33 illustrates an embodiment of a block diagram of a video calling camera.

In embodiments, the wearer may have an interface mounted in a ring 1500AA that includes a camera 1502AA, such as shown in FIG. 15AA. In embodiments, the ring controller 1502AA may have control interface types as described herein, such as through buttons 1504, 2D position control 1502, 3D position control (e.g. utilizing accelerometers, gyros), and the like. The ring controller 1500AA may then be used to control functions within the eyepiece, such as controlling the manipulation of the projected display content to the wearer. In embodiments, the control interfaces 1502, 1504 may provide control aspects to the embedded camera 1502AA, such as on/off, zoom, pan, focus, recording a still image picture, recording a video, and the like. Alternately, the functions may be controlled through other control aspects of the eyepiece, such as through voice control, other tactile control interfaces, eye gaze detection as described herein, and the like. The camera may also have automatic control functions enabled, such as auto-focus, timed functions, face detection and/or tracking, auto-zoom, and the like. For example, the ring controller 1500AA with integrated camera 1502AA may be used to view the wearer 1508AA during a videoconference enabled through the eyepiece, where the wearer 1508AA may hold the ring controller (e.g. as mounted on their finger) out in order to allow the camera 1502AA a view of their face for transmission to at least one other participant on the videoconference. Alternately, the wearer may take the ring controller 1500AA off and place it down on a surface 1510AA (e.g. a table top) such that the camera 1502AA has a view of the wearer. An image of the wearer 1512AA may then be displayed on the display area 1518AA of the eyepiece and transmitted to others on the videoconference, such as along with the images 1514AA of other participants on the videoconference call. In embodiments, the camera 1502AA may provide for manual or automatic FOV 1504AA adjustment. For instance, the wearer may set the ring controller 1500AA down on a surface 1510AA for use in a video conference call, and the FOV 1504AA may be controlled either manually (e.g. through button controls 1502, 1504, voice control, other tactile interface) or automatically (e.g. though face recognition) in order for the camera's FOV 1504AA to be directed to the wearer's face. The FOV 1504AA may be enabled to change as the wearer moves, such as by tracking by face recognition. The FOV 1504AA may also zoomed in/out to adjust to changes in the position of the wearer's face. In embodiments, the camera 1502AA may be used for a plurality of still and/or video applications, where the view of the camera is provided to the wearer on the display area 1518AA of the eyepiece, and where storage may be available in the eyepiece for storing the images/videos, which may be transferred, communicated, and the like, from the eyepiece to some external storage facility, user, web-application, and the like. In embodiments, a camera may be incorporated in a plurality of different mobile devices, such as worn on the arm, hand, wrist, finger, and the like, such as the watch 3202 with embedded camera 3200 as shown in FIGS. 32-33. As with the ring controller 1502AA, any of these mobile devices may include manual and/or automatic functions as described for the ring controller 1502AA. In embodiments, the ring controller 1502AA may have additional sensors, embedded functions, control features, and the like, such as a fingerprint scanner, tactile feedback, and LCD screen, an accelerometer, Bluetooth, and the like. For instance, the ring controller may provide for synchronized monitoring between the eyepiece and other control components, such as described herein.

In embodiments, the eyepiece may provide a system and method for providing an image of the wearer to videoconference participants through the use of an external mirror, where the wearer views themselves in the mirror and an image of themselves is captured through an integrated camera of the eyepiece. The captured image may be used directly, or the image may be flipped to correct for the image reversal of the mirror. In an example, the wearer may enter into a videoconference with a plurality of other people, where the wearer may be able to view live video images of the others though the eyepiece. By utilizing an ordinary mirror, and an integrated camera in the eyepiece, the user may be able to view themselves in the mirror, have the image captured by the integrated camera, and provide the other people with an image of themselves for purposes of the videoconference. This image may also be available to the wearer as a projected image to the eyepiece, such as in addition to the images of the other people involved in the videoconference.

In embodiments, a control component may provide a surface-sensing component in the control device for detecting motion across a surface may also be provided. The surface sensing component may be disposed on the palmar side of the user's hand. The surface may be at least one of a hard surface, a soft surface, surface of the user's skin, surface of the user's clothing, and the like. Providing control commands may be transmitted wirelessly, through a wired connection, and the like. The control device may control a pointing function associated with the displayed processor content. The pointing function may be control of a cursor position; selection of displayed content, selecting and moving displayed content; control of zoom, pan, field of view, size, position of displayed content; and the like. The control device may control a pointing function associated with the viewed surrounding environment. The pointing function may be placing a cursor on a viewed object in the surrounding environment. The viewed object's location position may be determined by the processor in association with a camera integrated with the eyepiece. The viewed object's identification may be determined by the processor in association with a camera integrated with the eyepiece. The control device may control a function of the eyepiece. The function may be associated with the displayed content. The function may be a mode control of the eyepiece. The control device may be foldable for ease of storage when not worn by the user. In embodiments, the control device may be used with external devices, such as to control the external device in association with the eyepiece. External devices may be entertainment equipment, audio equipment, portable electronic devices, navigation devices, weapons, automotive controls, and the like.

In embodiments, a body worn control device (e.g. as worn on a finger, attached to the hand at the palm, on the arm, leg, torso, and the like) may provide 3D position sensor information to the eyepiece. For instance, the control device may act as an 'air mouse', where 3D position sensors (e.g. accelerometers, gyros, and the like) provide position information when a user commands so, such as with the click of a button, a voice command, a visually detected gesture, and the like. The user may be able to use this feature to navigate either a 2D or 3D image being projected to the user via the eyepiece projection system. Further, the eyepiece may provide an external relay of the image for display or projection to others, such as in the case of a presentation. The user may be able to change the mode of the control device between 2D and 3D, in order to accommodate different functions, applications, user interfaces, and the like. In embodiments, multiple 3D control devices may be utilized for certain applications, such as in simulation applications.

In embodiments, a system may comprise an interactive head-mounted eyepiece worn by a user, wherein the eyepiece includes an optical assembly through which the user views a surrounding environment and displayed content, wherein the optical assembly comprises a corrective element that corrects the user's view of the surrounding environment, an integrated processor for handling content for display to the user, and an integrated image source for introducing the content to the optical assembly; and a tactile control interface mounted on the eyepiece that accepts control inputs from the user through at least one of a user touching the interface and the user being proximate to the interface.

In embodiments, control of the eyepiece, and especially control of a cursor associated with displayed content to the user, may be enabled through hand control, such as with a worn device 1500 as in FIG. 15, as a virtual computer mouse 1500A as in FIG. 15A, and the like. For instance, the worn device 1500 may transmit commands through physical interfaces (e.g. a button 1502, scroll wheel 1504), and the virtual computer mouse 1500A may be able to interpret commands though detecting motion and actions of the user's thumb, fist, hand, and the like. In computing, a physical mouse is a pointing device that functions by detecting two-dimensional motion relative to its supporting surface. A physical mouse traditionally consists of an object held under one of the user's hands, with one or more buttons. It sometimes features other elements, such as "wheels", which allow the user to perform various system-dependent operations, or extra buttons or features that can add more control or dimensional input. The mouse's motion translates into the motion of a cursor on a display, which allows for fine control of a graphical user interface. In the case of the eyepiece, the user may be able to utilize a physical mouse, a virtual mouse, or combinations of the two. In embodiments, a virtual mouse may involve one or more sensors attached to the user's hand, such as on the thumb 1502A, finger 1504A, palm 1508A, wrist 1510A, and the like, where the eyepiece receives signals from the sensors and translates the received signals into motion of a cursor on the eyepiece display to the user. In embodiments, the signals may be received through an exterior interface, such as the tactile interface 1402, through a receiver on the interior of the eyepiece, at a secondary communications interface, on an associated physical mouse or worn interface, and the like. The virtual mouse may also include actuators or other output type elements attached to the user's hand, such as for haptic feedback to the user through vibration, force, pressure, electrical impulse, temperature, and the like. Sensors and actuators may be attached to the user's hand by way of a wrap, ring, pad, glove, and the like. As such, the eyepiece virtual mouse may allow the user to translate motions of the hand into motion of the cursor on the eyepiece display, where 'motions' may include slow movements, rapid motions, jerky motions, position, change in position, and the like, and may allow users to work in three dimensions, without the need for a physical surface, and including some or all of the six degrees of freedom. Note that because the 'virtual mouse' may be associated with multiple portions of the hand, the virtual mouse may be implemented as multiple 'virtual mouse' controllers, or as a distributed controller across multiple control members of the hand. In embodiments, the eyepiece may provide for the use of a plurality of virtual mice, such as for one on each of the user's hands, one or more of the user's feet, and the like.

In embodiments, the eyepiece virtual mouse may need no physical surface to operate, and detect motion such as through sensors, such as one of a plurality of accelerometer types (e.g. tuning fork, piezoelectric, shear mode, strain mode, capacitive, thermal, resistive, electromechanical, resonant, magnetic, optical, acoustic, laser, three dimensional, and the like), and through the output signals of the sensor(s) determine the translational and angular displacement of the hand, or some portion of the hand. For instance, accelerometers may produce output signals of magnitudes proportional to the translational acceleration of the hand in the three directions. Pairs of accelerometers may be configured to detect rotational accelerations of the hand or portions of the hand. Translational velocity and displacement of the hand or portions of the hand may be determined by integrating the accelerometer output signals and the rotational velocity and displacement of the hand may be determined by integrating the difference between the output signals of the accelerometer pairs. Alternatively, other sensors may be utilized, such as ultrasound sensors, imagers, IR/RF, magnetometer, gyro magnetometer, and the like. As accelerometers, or other sensors, may be mounted on various portions of the hand, the eyepiece may be able to detect a plurality of movements of the hand, ranging from simple motions normally associated with computer mouse motion, to more highly complex motion, such as interpretation of complex hand motions in a simulation application. In embodiments, the user may require only a small translational or rotational action to have these actions translated to motions associated with user intended actions on the eyepiece projection to the user.

In embodiments, the virtual mouse may have physical switches associated with it to control the device, such as an on/off switch mounted on the hand, the eyepiece, or other part of the body. The virtual mouse may also have on/off control and the like through pre-defined motions or actions of the hand. For example, the operation of the virtual mouse may be enabled through a rapid back and forth motion of the hand. In another example, the virtual mouse may be disabled through a motion of the hand past the eyepiece, such as in front of the eyepiece. In embodiments, the virtual mouse for the eyepiece may provide for the interpretation of a plurality of motions to operations normally associated with physical mouse control, and as such, familiar to the user without training, such as single clicking with a finger, double clicking, triple clicking, right clicking, left clicking, click and drag, combination clicking, roller wheel motion, and the like. In embodiments, the eyepiece may provide for gesture recognition, such as in interpreting hand gestures via mathematical algorithms.

In embodiments, gesture control recognition may be provided through technologies that utilize capacitive changes resulting from changes in the distance of a user's hand from a conductor element as part of the eyepiece's control system, and so would require no devices mounted on the user's hand. In embodiments, the conductor may be mounted as part of the eyepiece, such as on the arm or other portion of the frame, or as some external interface mounted on the user's body or clothing. For example, the conductor may be an antenna, where the control system behaves in a similar fashion to the touch-less musical instrument known as the theremin. The theremin uses the heterodyne principle to generate an audio signal, but in the case of the eyepiece, the signal may be used to generate a control input signal. The control circuitry may include a number of radio frequency oscillators, such as where one oscillator operates at a fixed frequency and another controlled by the user's hand, where the distance from the hand varies the input at the control antenna. In this technology, the user's hand acts as a grounded plate (the user's body being the connection to ground) of a variable capacitor in an L-C (inductance-capacitance) circuit, which is part of the oscillator and determines its frequency. In another example, the circuit may use a single oscillator, two pairs of heterodyne oscillators, and the like. In embodiments, there may be a plurality of different conductors used as control inputs. In embodiments, this type of control interface may be ideal for control inputs that vary across a range, such as a volume control, a zoom control, and the like. However, this type of control interface may also be used for more discrete control signals (e.g. on/off control) where a predetermined threshold determines the state change of the control input.

In embodiments, the eyepiece may interface with a physical remote control device, such as a wireless track pad mouse, hand held remote control, body mounted remote control, remote control mounted on the eyepiece, and the like. The remote control device may be mounted on an external piece of equipment, such as for personal use, gaming, professional use, military use, and the like. For example, the remote control may be mounted on a weapon for a soldier, such as mounted on a pistol grip, on a muzzle shroud, on a fore grip, and the like, providing remote control to the soldier without the need to remove their hands from the weapon. The remote control may be removably mounted to the eyepiece.

In embodiments, a remote control for the eyepiece may be activated and/or controlled through a proximity sensor. A proximity sensor may be a sensor able to detect the presence of nearby objects without any physical contact. For example, a proximity sensor may emit an electromagnetic or electrostatic field, or a beam of electromagnetic radiation (infrared, for instance), and look for changes in the field or return signal. The object being sensed is often referred to as the proximity sensor's target. Different proximity sensor targets may demand different sensors. For example, a capacitive or photoelectric sensor might be suitable for a plastic target; an inductive proximity sensor requires a metal target. Other examples of proximity sensor technologies include capacitive displacement sensors, eddy-current, magnetic, photocell (reflective), laser, passive thermal infrared, passive optical, CCD, reflection of ionizing radiation, and the like. In embodiments, the proximity sensor may be integral to any of the control embodiments described herein, including physical remote controls, virtual mouse, interfaces mounted on the eyepiece, controls mounted on an external piece of equipment (e.g. a game controller, a weapon), and the like.

In embodiments, sensors for measuring a user's body motion may be used to control the eyepiece, or as an external input, such as using an inertial measurement unit (IMU), a 3-axis magnetometer, a 3-axis gyro, a 3-axis accelerometer, and the like. For instance, an sensor may be mounted on the hand(s) of the user, thereby enabling the use of the signals from the sensor for control the eyepiece, as described herein. In another instance, sensor signals may be received and interpreted by the eyepiece to assess and/or utilize the body motions of the user for purposes other than control. In an example, sensors mounted on each leg and each arm of the user may provide signals to the eyepiece that allow the eyepiece to measure the gait of the user. The gait of the user may then in turn be used to monitor the gait of the user over time, such as to monitor changes in physical behavior, improvement during physical therapy, changes due to a head trauma, and the like. In the instance of monitoring for a head trauma, the eyepiece may initially determine a baseline gait profile for the user, and then monitor the user over time, such as before and after a physical event (e.g. a sports-related collision, an explosion, an vehicle accident, and the like). In the case of an athlete or person in physical therapy, the eyepiece may be used periodically to measure the gait of the user, and maintain the measurements in a database for analysis. A running gait time profile may be produced, such as to monitor the user's gait for indications of physical traumas, physical improvements, and the like.

Figure 15B:
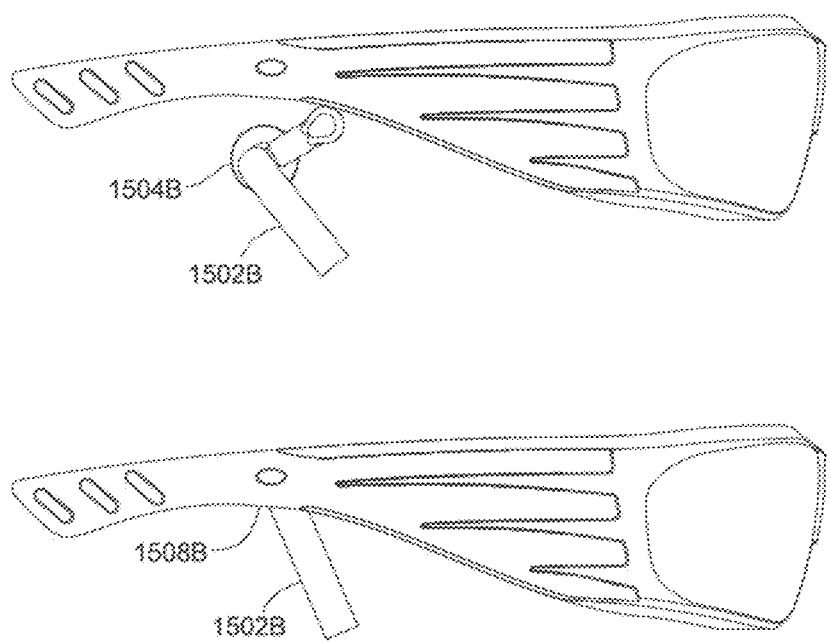
FIG. 15B depicts a facial actuation sensor as mounted on the eyepiece.

In embodiments, control of the eyepiece, and especially control of a cursor associated with displayed content to the user, may be enabled through the sensing of the motion of a facial feature, the tensing of a facial muscle, the clicking of the teeth, the motion of the jaw, and the like, of the user wearing the eyepiece through a facial actuation sensor 1502B. For instance, as shown in FIG. 15B, the eyepiece may have a facial actuation sensor as an extension from the eyepiece earphone assembly 1504B, from the arm 1508B of the eyepiece, and the like, where the facial actuation sensor may sense a force, a vibration, and the like associated with the motion of a facial feature. The facial actuation sensor may also be mounted separate from the eyepiece assembly, such as part of a standalone earpiece, where the sensor output of the earpiece and the facial actuation sensor may be either transferred to the eyepiece by either wired or wireless communication (e.g. Bluetooth or other communications protocol known to the art). The facial actuation sensor may also be attached to around the ear, in the mouth, on the face, on the neck, and the like. The facial actuation sensor may also be comprised of a plurality of sensors, such as to optimize the sensed motion of different facial or interior motions or actions. In embodiments, the facial actuation sensor may detect motions and interpret them as commands, or the raw signals may be sent to the eyepiece for interpretation. Commands may be commands for the control of eyepiece functions, controls associated with a cursor or pointer as provided as part of the display of content to the user, and the like. For example, a user may click their teeth once or twice to indicate a single or double click, such as normally associated with the click of a computer mouse. In another example, the user may tense a facial muscle to indicate a command, such as a selection associated with the projected image. In embodiments, the facial actuation sensor may utilize noise reduction processing to minimize the background motions of the face, the head, and the like, such as through adaptive signal processing technologies. A voice activity sensor may also be utilized to reduce interference, such as from the user, from other individuals nearby, from surrounding environmental noise, and the like. In an example, the facial actuation sensor may also improve communications and eliminate noise by detecting vibrations in the cheek of the user during speech, such as with multiple microphones to identify the background noise and eliminate it through noise cancellation, volume augmentation, and the like.

Figure 15C:
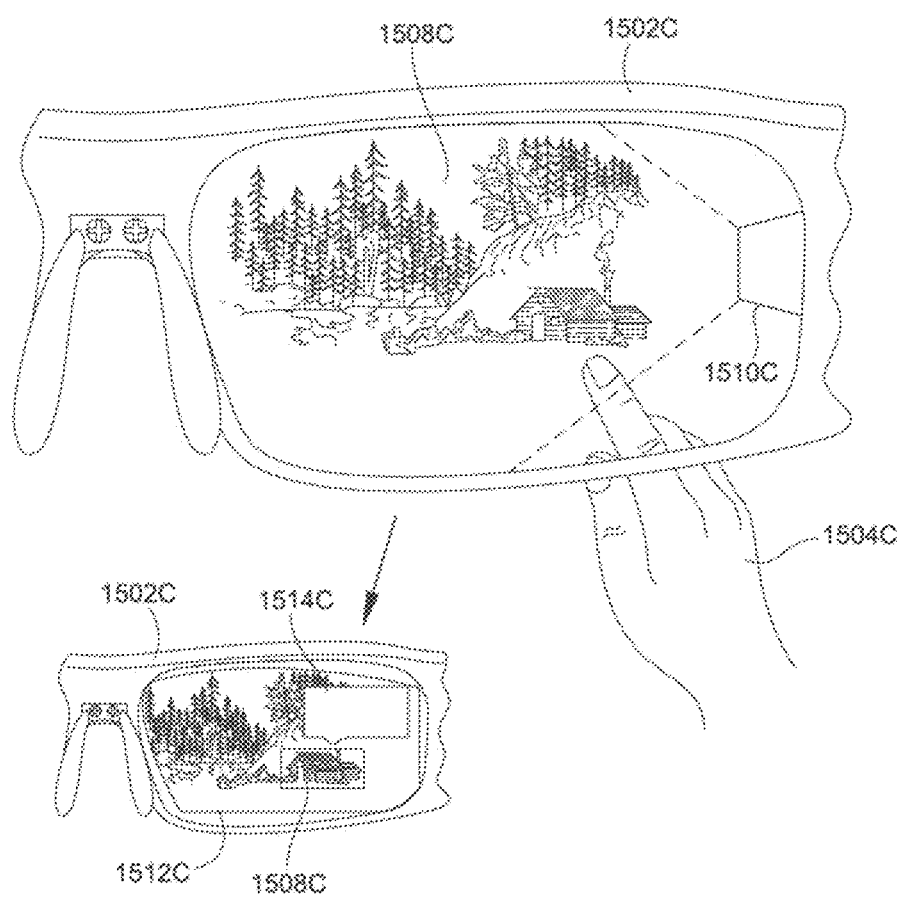
FIG. 15C depicts a hand pointing control of the eyepiece.

In embodiments, the user of the eyepiece may be able to obtain information on some environmental feature, location, object, and the like, viewed through the eyepiece by raising their hand into the field of view of the eyepiece and pointing at the object or position. For instance, the pointing finger of the user may indicate an environmental feature, where the finger is not only in the view of the eyepiece but also in the view of an embedded camera. The system may now be able to correlate the position of the pointing finger with the location of the environmental feature as seen by the camera. Additionally, the eyepiece may have position and orientation sensors, such as GPS and a magnetometer, to allow the system to know the location and line of sight of the user. From this, the system may be able to extrapolate the position information of the environmental feature, such as to provide the location information to the user, to overlay the position of the environmental information onto a 2D or 3D map, to further associate the established position information to correlate that position information to secondary information about that location (e.g. address, names of individuals at the address, name of a business at that location, coordinates of the location), and the like. Referring to FIG. 15C, in an example, the user is looking though the eyepiece 1502C and pointing with their hand 1504C at a house 1508C in their field of view, where an embedded camera 1510C has both the pointed hand 1504C and the house 1508C in its field of view. In this instance, the system is able to determine the location of the house 1508C and provide location information 1514C and a 3D map superimposed onto the user's view of the environment. In embodiments, the information associated with an environmental feature may be provided by an external facility, such as communicated with through a wireless communication connection, stored internal to the eyepiece, such as downloaded to the eyepiece for the current location, and the like. In embodiments, information provided to the wearer of the eyepiece may include any of a plurality of information related to the scene as viewed by the wearer, such as geographic information, point of interest information, social networking information (e.g. Twitter, Facebook, and the like information related to a person standing in front of the wearer augmented around the person, such as 'floating' around the person), profile information (e.g. such as stored in the wearer's contact list), historical information, consumer information, product information, retail information, safety information, advertisements, commerce information, security information, game related information, humorous annotations, news related information, and the like.

In embodiments, the user may be able to control their view perspective relative to a 3D projected image, such as a 3D projected image associated with the external environment, a 3D projected image that has been stored and retrieved, a 3D displayed movie (such as downloaded for viewing), and the like. For instance, and referring again to FIG. 15C, the user may be able to change the view perspective of the 3D displayed image 1512C, such as by turning their head, and where the live external environment and the 3D displayed image stay together even as the user turns their head, moves their position, and the like. In this way, the eyepiece may be able to provide an augmented reality by overlaying information onto the user's viewed external environment, such as the overlaid 3D displayed map 1512C, the location information 1514C, and the like, where the displayed map, information, and the like, may change as the user's view changes. In another instance, with 3D movies or 3D converted movies, the perspective of the viewer may be changed to put the viewer 'into' the movie environment with some control of the viewing perspective, where the user may be able to move their head around and have the view change in correspondence to the changed head position, where the user may be able to 'walk into' the image when they physically walk forward, have the perspective change as the user moves the gazing view of their eyes, and the like. In addition, additional image information may be provided, such as at the sides of the user's view that could be accessed by turning the head.

In embodiments, the user of one eyepiece may be able to synchronize their view of a projected image or video with at least the view of a second user of an eyepiece or other video display device. For instance, two separate eyepiece users may wish to view the same 3D map, game projection, point-of-interest projection, video, and the like, where the two viewers are not only seeing the same projected content, but where the projected content's view is synchronized between them. In an example, two users may want to jointly view a 3D map of a region, and the image is synchronized such that the one user may be able to point at a position on the 3D map that the other user is able to see and interact with. The two users may be able to move around the 3D map and share a virtual-physical interaction between the two users and the 3D map, and the like. Further, a group of eyepiece wearers may be able to jointly interact with a projection as a group. In this way, two or more users may be able to have a unified augmented reality experience through the coordination-synchronization of their eyepieces. Synchronization of two or more eyepieces may be provided by communication of position information between the eyepieces, such as absolute position information, relative position information, translation and rotational position information, and the like, such as from position sensors as described herein (e.g. gyroscopes, IMU, GPS, and the like). Communications between the eyepieces may be direct, through an Internet network, through the cell-network, through a satellite network, and the like. Processing of position information contributing to the synchronization may be executed in a master processor in a single eyepiece, collectively amongst a group of eyepieces, in remote server system, and the like, or any combination thereof. In embodiments, the coordinated, synchronized view of projected content between multiple eyepieces may provide an extended augmented reality experience from the individual to a plurality of individuals, where the plurality of individuals benefit from the group augmented reality experience. For example, a group of concertgoers may synchronize their eyepieces with a feed from the concert producers such that visual effects or audio may be pushed to people with eyepieces by the concert producer, performers, other audience members, and the like. In an example, the performer may have a master eyepiece and may control sending content to audience members. In one embodiment, the content may be the performer's view of the surrounding environment. The performer may be using the master eyepiece for applications as well, such as controlling an external lighting system, interacting with an augmented reality drum kit or sampling board, calling up song lyrics, and the like.

In embodiments, the image or video displayed on the eyepiece can be synchronized with images or video displayed on or captured by a connected device that has a communication link to the eyepiece or directly from the feed of a remote camera. The feed could be selected or another action could be initiated by a sensor input or control signal received from one of the connected devices, metadata sent by one of the other connected devices, or the like. Other video display devices may be other eyepieces, desktop computers, laptop computers, smartphones, tablet computers, televisions, or the like. The eyepieces, devices, and remote cameras could be connected by wide area, local area, metropolitan area, personal area, and cloud network communication links. The sensor input could be an audio sensor input, video sensor input, or the like. Other actions that could be initiated by receipt of the sensor input or control signal could include the initiating of an action such as tracking a target, sending a message, or initiating video synchronization as described elsewhere in this disclosure, and the like. For instance, the video captured by the eyepiece of a guard at a remote checkpoint or screening location could automatically be selected for display on the eyepiece of a supervisor, when a facial recognition application recognizes a person of interest in the video feed from the guard's eyepiece.

In embodiments, the eyepiece may utilize sound projection techniques to realize a direction of sound for the wearer of the eyepiece, such as with surround sound techniques. Realization of a direction of sound for a wearer may include the reproduction of the sound from the direction of origin, either in real-time or as a playback. It may include a visual or audible indicator to provide a direction for the source of sound. Sound projection techniques may be useful to an individual that has their hearing impaired or blocked, such as due to the user experiencing hearing loss, a user wearing headphones, a user wearing hearing protection, and the like. In this instance, the eyepiece may provide enhanced 3D audible reproduction. In an example, the wearer may have headphones on, and a gunshot has been fired. In this example, the eyepiece may be able to reproduce the 3D sound profile for the sound of the gunshot, thus allowing the wearer to respond to the gunshot knowing where the sound came from. In another example, a wearer with headphones, hearing loss, in a loud environment, and the like, may not otherwise be able to tell what's being said and/or the direction of the person speaking, but is provided with a 3D sound enhancement from the eyepiece (e.g. the wearer is listening to other proximate individuals through headphones and so does not have directionality information). In another example, a wearer may be in a loud ambient environment, or in an environment where periodic loud noises can occur. In this instance, the eyepiece may have the ability to cut off the loud sound to protect the wearer's hearing, or the sound could be so loud that the wearer can't tell where the sound came from, and further, now their ears could be ringing so loud they can't hear anything. To aid in this situation, the eyepiece may provide visible, auditory, vibration, and the like queues to the wearer to indicate the direction of the sound source. In embodiments, the eyepiece may provide "augmented" hearing where the wearer's ears are plugged to protect their ears from loud noises, but using the ear buds to generate a reproduction of sound to replace what's missing from the natural world. This artificial sound may then be used to give directionality to wirelessly transmitted communication that the operator couldn't hear naturally.

In embodiments, an example of a configuration for establishing directionality of a source sound may be point different microphones in different directions. For instance, at least one microphone may be used for the voice of the wearer, at least one microphone for the surrounding environment, at least one pointing down at the ground, and potentially in a plurality of different discrete directions. In this instance, the microphone pointing down may be subtracted to isolate other sounds, which may be combined with 3D sound surround, and augmented hearing techniques, as described herein.

In an example of a sound augmented system as part of the eyepiece, there are a number of users with eyepieces, such as in a noisy environment where all the users have 'plugged ears' as implemented through artificial noise blockage through the eyepiece ear buds. One of wearers may yell out that they need some piece of equipment. Because of all the ambient noise and the hearing protection the eyepiece creates, no one can hear the request for equipment. Here, the wearer making the verbal request has a filtered microphone close to their mouth, and they could wirelessly transmit the request to the others, where their eyepiece could relay a sound signal to the other user's eyepieces, and to the ear on the correct side, and the others would know to look to the right or left to see who has made the request. This system could be further enhanced with geo-locations of all the wearers, and a "virtual" surround sound system that uses the two ear buds to give the perception of 3D space (such as the SRS True Surround Technology).

In embodiments, auditory queues could also be computer generated so the communicating user doesn't need to verbalize their communication but can select it from a list of common commands, the computer generates the communication based on preconfigured conditions, and the like. In an example, the wearers may be in a situation where they don't want a display in front of their eyes but want to have ear buds in their ears. In this case, if they wanted to notify someone in a group to get up and follow them, they could just click a controller a certain number of times, or provide a visual hand gesturer with a camera, an IMU, and the like. The system may choose the 'follow me' command and transmit it to the other users with the communicating user's location for the 3D system to trick them into hearing from where they are actually sitting out of sight of them. In embodiments, directional information may be determined and/or provided through position information from the users of eyepieces.

The eyepiece may include facilities for providing a vibration sensation to the user, such as through vibration actuators in the frame or arms of the eyepiece structure, such as through mechanical vibration motors, piezoelectric vibration actuator, ultrasonic vibration actuator, and the like. The vibration may be provided to indicate a message indication to the user, as an indicator to a user that is sight-impaired (e.g. because of darkness, smoke, clouds, blindness), as part of a game, part of a simulation, and the like. Vibration actuators may be used separately or in conjunction with speakers in side-arms of the eyepiece to help create a 3D visual-sound-vibration virtual reality environment, such as for games, simulations, and the like. For instance, vibration actuators may be mounted in each side arm of the eyepiece such that when an application presents a projectile flying past the user's left side of their head, the left side vibration actuator is set to vibrate in such a way as to simulate the sensation of the projectile actually flying past the user. In addition, the speaker on that side arm may synchronously apply a sound that mimics the sound the projectile would make as it flies past the user's head. Vibration and/or speakers may be mounted on the eyepiece in such a way as to provide a 3D vibrational-audio experience to the user to augment the visual experience provided through the visually displayed content, such as in 3D visually displayed content. In this way, the user may be enveloped in a multi-sensory virtual 3D environment. In embodiments, the present disclosure may comprise an interactive head-mounted eyepiece worn by a user, wherein the eyepiece comprises an optical assembly through which the user views a surrounding environment and displayed content, an integrated image source adapted to introduce the content to the optical assembly, and an processing facility adapted to manage the functionality of the eyepiece, wherein the head-mounted eyepiece has a structure comprising a frame through which the user views the surrounding environment and a left and right side arm for supporting the frame on the head of the user, and a vibration actuator in each of the left and right side arm, each vibration actuator independently responsive to vibration commands from the processing facility. The vibration command may initiate a vibration in one of the vibration actuators in response to a virtual projectile as part of the displayed content, a virtual explosion, a message indication, a visual cue, a warning, and the like. The displayed content may be provided as part of the user playing a simulation, a game application, a utility application, and the like. The application calling the vibration command may be running locally on the eyepiece, in part or in whole through an external platform where the eyepiece has a communicative interconnection with the external platform, and the like. Further, the eyepiece may include an integrated speaker as described herein, such as in each of the left and right side arm, where the vibration command initiates a vibration in one of the vibration actuators in time synchronization with an auditory command to initiate a sound in the speaker on the same side arm as receiving the vibration command.

In embodiments, the eyepiece may provide aspects of signals intelligence (SIGINT), such as in the use of existing WiFi, 3G, Bluetooth, and the like communications signals to gather signals intelligence for devices and users in proximity to the wearer of the eyepiece. These signals may be from other eyepieces, such as to gather information about other known friendly users; other eyepieces that have been picked up by an unauthorized individual, such as through a signal that is generated when an unauthorized user tries to use the eyepiece; other communications devices (e.g. radios, cell phones, pagers, walky-talkies, and the like); electronic signals emanating from devices that may not be directly used for communications; and the like. Information gathered by the eyepiece may be direction information, position information, motion information, number of and/or rate of communications, and the like. Further, information may be gathered through the coordinated operations of multiple eyepieces, such as in the triangulation of a signal for determination of the signal's location.

Figure 15D:
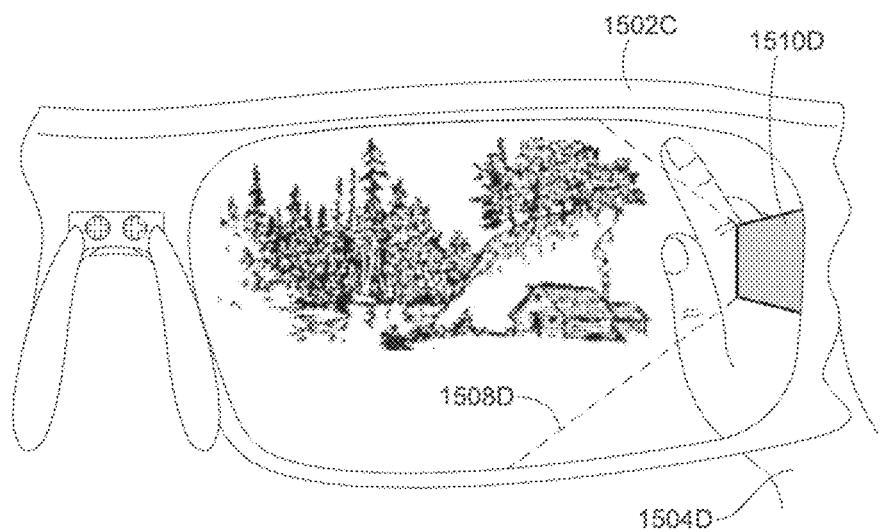
FIG. 15D depicts a hand pointing control of the eyepiece.

Referring to FIG. 15D, in embodiments the user of the eyepiece 1502D may be able to use multiple hand/finger points from their hand 1504D to define the field of view (FOV) 1508D of the camera 1510D relative to the see-thru view, such as for augmented reality applications. For instance, in the example shown, the user is utilizing their first finger and thumb to adjust the FOV 1508D of the camera 1510D of the eyepiece 1502D. The user may utilize other combinations to adjust the FOV 1508D, such as with combinations of fingers, fingers and thumb, combinations of fingers and thumbs from both hands, use of the palm(s), cupped hand(s), and the like. The use of multiple hand/finger points may enable the user to alter the FOV 1508 of the camera 1510D in much the same way as users of touch screens, where different points of the hand/finger establish points of the FOV to establish the desired view. In this instance however, there is no physical contact made between the user's hand(s) and the eyepiece. Here, the camera may be commanded to associate portions of the user's hand(s) to the establishing or changing of the FOV of the camera. The command may be any command type described herein, including and not limited to hand motions in the FOV of the camera, commands associated with physical interfaces on the eyepiece, commands associated with sensed motions near the eyepiece, commands received from a command interface on some portion of the user, and the like. The eyepiece may be able to recognize the finger/hand motions as the command, such as in some repetitive motion. In embodiments, the user may also utilize this technique to adjust some portion of the projected image, where the eyepiece relates the viewed image by the camera to some aspect of the projected image, such as the hand/finger points in view to the projected image of the user. For example, the user may be simultaneously viewing the external environment and a projected image, and the user utilizes this technique to change the projected viewing area, region, magnification, and the like. In embodiments, the user may perform a change of FOV for a plurality of reasons, including zooming in or out from a viewed scene in the live environment, zoom in or out from a viewed portion of the projected image, to change the viewing area allocated to the projected image, to change the perspective view of the environment or projected image, and the like.

In embodiments, the eyepiece may enable simultaneous FOVs. For example, simultaneous wide, medium, and narrow camera FOVs may be used, where the user can have different FOVs up simultaneously in view (i.e. wide to show the entire field, perhaps static, and narrow to focus on a particular target, perhaps moving with the eye or with a cursor).

Figure 15E:
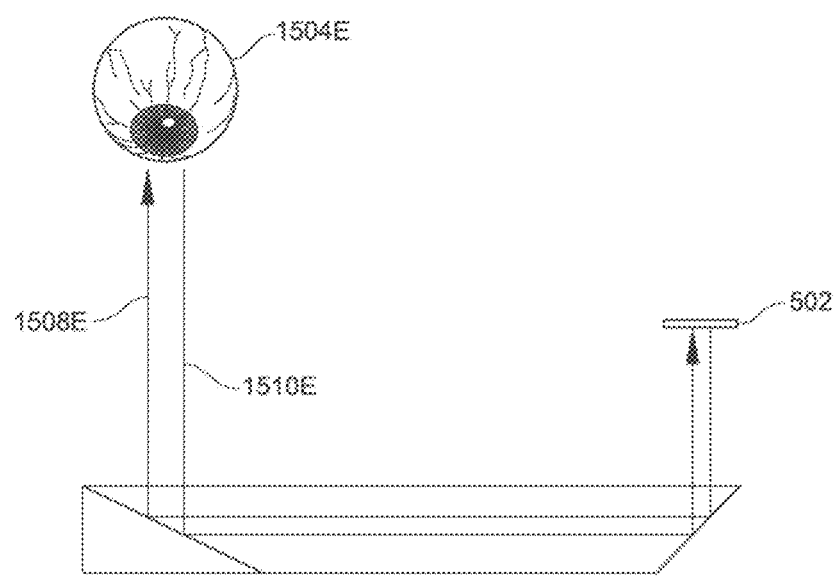
FIG. 15E depicts an example of eye tracking control.

In embodiments the eyepiece may be able to determine where the user is gazing, or the motion of the user's eye, by tracking the eye through reflected light off the user's eye. This information may then be used to help correlate the user's line of sight with respect to the projected image, a camera view, the external environment, and the like, and used in control techniques as described herein. For instance, the user may gaze at a location on the projected image and make a selection, such as with an external remote control or with some detected eye movement (e.g. blinking). In an example of this technique, and referring to FIG. 15E, transmitted light 1508E, such as infrared light, may be reflected 1510E from the eye 1504E and sensed at the optical display 502 (e.g. with a camera or other optical sensor). The information may then be analyzed to extract eye rotation from changes in reflections. In embodiments, an eye tracking facility may use the corneal reflection and the center of the pupil as features to track over time; use reflections from the front of the cornea and the back of the lens as features to track; image features from inside the eye, such as the retinal blood vessels, and follow these features as the eye rotates; and the like. Alternatively, the eyepiece may use other techniques to track the motions of the eye, such as with components surrounding the eye, mounted in contact lenses on the eye, and the like. For instance, a special contact lens may be provided to the user with an embedded optical component, such as a mirror, magnetic field sensor, and the like, for measuring the motion of the eye. In another instance, electric potentials may be measured and monitored with electrodes placed around the eyes, utilizing the steady electric potential field from the eye as a dipole, such as with its positive pole at the cornea and its negative pole at the retina. In this instance, the electric signal may be derived using contact electrodes placed on the skin around the eye, on the frame of the eyepiece, and the like. If the eye moves from the centre position towards the periphery, the retina approaches one electrode while the cornea approaches the opposing one. This change in the orientation of the dipole and consequently the electric potential field results in a change in the measured signal. By analyzing these changes eye movement may be tracked.

In another example of how eye gaze direction of the user and associated control may be applied involves placement (by the eyepiece) and optional selection (by the user) of a visual indicator in the user's peripheral vision, such as in order to reduce clutter in the narrow portion of the user's visual field around the gaze direction where the eye's highest visual input resides. Since the brain is limited as to how much information it can process at a time, and the brain pays the most attention to visual content close to the direction of gaze, the eyepiece may provide projected visual indicators in the periphery of vision as cues to the user. This way the brain may only have to process the detection of the indicator, and not the information associated with the indicator, thus decrease the potential for overloading the user with information. The indicator may be an icon, a picture, a color, symbol, a blinking object, and the like, and indicate an alert, an email arriving, an incoming phone call, a calendar event, an internal or external processing facility that requires attention from the user, and the like. With the visual indicator in the periphery, the user may become aware of it without being distracted by it. The user may then optionally decide to elevate the content associated with the visual cue in order to see more information, such as gazing over to the visual indicator, and by doing so, opening up its content. For example, an icon representing an incoming email may indicate an email being received. The user may notice the icon, and choose to ignore it (such as the icon disappearing after a period of time if not activated, such as by a gaze or some other control facility). Alternately, the user may notice the visual indicator and choose to 'active' it by gazing in the direction of the visual indicator. In the case of the email, when the eyepiece detects that the user's eye gaze is coincident with the location of the icon, the eyepiece may open up the email and reveal its content. In this way the user maintains control over what information is being paid attention to, and as a result, minimize distractions and maximize content usage efficiency.

In embodiments, and associated with certain optical configurations described herein, such as the frontlight LCoS, feedback between the two or more displays may ensure that the displays have the same brightness and contrast. In embodiments, cameras in each display may be employed. The current to the LEDs may be controlled and color balance may be obtained, such as by selecting LED's of similar quality, output, and or color (e.g. from similar bins), right and left pulse width modulation (PWM) values may be provided, and periodic calibration may be carried out. In embodiments, calibration of the power spectrum may be achieved. If the display is turned down because of high outside brightness, the user may know the calibration for each display. In embodiments, equal brightness, color saturation, color balance, hue and the like between the two displays may be created. This may prevent the user's brain from ignoring one display. In embodiments, a feedback system from the displays may be created that allows the user or another to regulate brightness and the like such that each display has a constant and or consistent brightness, color saturation, balance, hue and the like. In embodiments, there may be a brightness sensor on each display that may be color, RGB, white sensor, sensor for overall light, and the like. In embodiments, the sensor may be a power sensor that monitors or checks the power delivered to or consumed by the LED. The user or another may regulate one or more displays by turning the power to the LED up or down. This may be done during manufacturing and or may be done during the life of the eyepiece and or periodically. In embodiments, there may be a dynamic range aspect. As LEDs and/or power are dimmed down there may be a power algorithm that may be refined on one display so that both maintain consistent brightness. In embodiments the user and or manufacturer or the eyepiece may adjust the LEDs to follow the same brightness curve as the power is changed. There may be RGB LEDs and the LED curve may be matched between the two displays. Accordingly, the brightness, color saturation, color balance, hue and the like may be controlled over a dynamic range. In embodiments, such items may be measured and controlled during manufacturing, during a dynamic range, during the life of the glasses and the like. In embodiments, equal brightness, color saturation, color balance, hue and the like between the two displays may be actually created or created to be perceived by the user based on differences between the user's eyes. In various embodiments, adjustments of brightness, color saturation, color balance, hue and the like may be performed by a user, manufacturer, and or automatically performed by the eyepiece based on feedback, various program algorithms, and the like. In embodiments, sensor feedback may cause an automatic and or manual adjustment in at least one of brightness, color saturation, color balance, hue and the like.

In embodiments, a system may comprise an interactive head-mounted eyepiece worn by a user, wherein the eyepiece includes an optical assembly through which the user views a surrounding environment and displayed content, and an integrated image source for introducing the content to the optical assembly wherein the optical assembly comprises two or more displays, and wherein at least one of brightness, color saturation, color balance, and hue is regulated for at least one of the displays such that at least one of brightness, color saturation, color balance, and hue of the two or more displays is balanced relative to one another within a predetermined range. In embodiments, the regulation may comprise making at least one of brightness, color saturation, color balance, hue, and the like of the two or more displays relative to one another within a predetermined range. In embodiments, an adjustment of at least one of brightness, color saturation, color balance, hue, and the like may be made based on the detection of power delivered to the integrated image source. In embodiments the adjustment may be based on a power algorithm so that at least on of brightness, color saturation, color balance, hue, and the like is consistent between the two or more displays. In further embodiments, the adjustment may be based on a sensor of total optic sensor feedback. In embodiments, at least one of brightness, color saturation, color balance, hue, and the like may be regulated at least one of during manufacturing, during a dynamic range of output produced by the integrated image source, and the like. In embodiments, the system may be adapted to automatically check at least one of brightness, color saturation, color balance, hue, and the like of the two or more displays relative to one another periodically over the lifetime of the eyepiece. In embodiments, the system may be adapted to automatically check the at least one of brightness, color saturation, color balance, hue, and the like of the two more displays relative to one another and selectively set the at least one of brightness, color saturation, color balance, hue, and the like of the two more displays to a predetermined value. Furthermore, an embodiment of the system may be adapted to automatically check the at least one of brightness, color saturation, color balance, hue, and the like of the two or more displays relative to one another and selectively set the at least one of brightness, color saturation, color balance, hue, and the like of the two more displays to a predetermined value based on sensor feedback measurements.

In embodiments, and associated with certain optical configurations described herein, such as the frontlight LCoS, the contrast between the two or more displays may be adjusted to be equal, or equal as perceived by the user. In embodiments, contrast may be checked on each display and adjusted accordingly and may be regulated during the manufacturing process to calibrate and adjust the displays, and it may be measured in the manufacturing process, over a dynamic range, during the life of the glasses and the like. In embodiments, the contrast of the system may be automatically calibrated between the two displays as well as in comparison to the outside world. In embodiments, the user may compensate for the differences between his eyes. The contrast may be adjusted as necessary to compensate for a sight and or perception deficit of the user. In embodiments, the contrast ratio may be a function of how the optics module is assembled. Reducing stray light, as described herein, may address techniques for assembling to provide a high contrast ratio. In embodiments, various types of single pixel brightness and or multi pixel color detectors may be inserted into the optical train to sample some or all of the light that is not making it all the way to the eye box of the display. In embodiments, and depending on where the detector is placed in the optical path, the system may be provided with real time feedback to compensate for assembly tolerances, LED and LCoS panel yield, binning tolerances, Hot and Cold panel compensation and or maintain individual user calibrations. In embodiments, brightness and contrast of the displays may be managed through good manufacturing practices. Further, during manufacturing, quality analysis may be done to test and, as necessary, calibrate the displays and compensate as necessary. Additionally, over the life of the system as components wear out, or the system heats and cools during use, one may modify calibration with a look up table for compensation values. In various embodiments, adjustments of brightness, color saturation, color balance, hue, contrast and the like may be performed by a user, manufacturer, and or automatically performed by the eyepiece based on feedback, various program algorithms, and the like. In embodiments, sensor feedback may cause an automatic and or manual adjustment in at least one of brightness, color saturation, color balance, hue, contrast, and the like.

In embodiments, a system may comprise an interactive head-mounted eyepiece worn by a user, wherein the eyepiece includes an optical assembly through which the user views a surrounding environment and displayed content, and an integrated image source for introducing the content to the optical assembly wherein the optical assembly comprises two or more displays, and wherein the contrast is regulated for at least one of the displays such that the contrast of the two or more displays is balanced relative to one another within a predetermined range. In further embodiments, the contrast may be regulated such that it is equal between the two or more displays. In embodiments, contrast may be regulated during the manufacturing process, during a dynamic range of output produced by the integrated image source, and the like. In embodiments, the system may be adapted to automatically check the contrast of the two or more displays relative to one another periodically over the lifetime of the eyepiece. In embodiments, the system may be adapted to automatically check the contrast of the two or more displays relative to one another and selectively set the contrast of the two or more displays to a predetermined value. In embodiments, the system may be adapted to automatically check the contrast of the two or more displays relative to one another and selectively set the contrast of the two or more displays to a predetermined value based on sensor feedback measurements. In embodiments, the contrast may be regulated to compensate for a deficit of the user. In embodiments, the contrast may be regulated as a function of at least one of stray light and light produced by the integrated image source. In embodiments, the contrast may be regulated based on feedback from detectors in the optical path of the system. Further, the detectors may comprise at least one of a single pixel brightness and multi pixel color detectors. In embodiments, the system may be provided with real time feedback to compensate for at least one of assembly tolerances, LED, and LCoS panel yield, binning tolerances, Hot and cold panel compensation, and to maintain individual user calibrations. In embodiments, the calibration of contrast may be regulated based off of a look up table for one or more compensation values.

In an embodiment, certain optical configurations described herein, such as the frontlight LCoS, enable insertion of a camera in many locations along the optical train to put the camera directly on axis with the eye. For example, a camera sensor may be placed adjacent to the LCoS, such as the camera 10232 in FIG. 102B. This in turn enables measurement of the location, diameter, velocity and direction of the pupil and imaging of the iris directly. Such measurements and imaging may be used for secure login or loading user settings, detecting health conditions by measuring the size and/or thickness of capillaries, setting a placeholder/bookmark based on last gazed area in book, and the like. Data collected by the camera about the various components of the eye can be used to control user interfaces, determine stress levels, monitor alertness, detect reactions to external or projected stimulus and the like. Since the frontlit optics are sharp and compact, a camera with extremely small pixels may be placed in the optical train retaining the small overall size of the optics and ensuring a high resolution image. In embodiments, the camera may be placed in many parts of the optical path by inserting a beam splitter as in FIG. 185 but it could also enable placement of the camera on the LCoS PCB, embedded directly into the LCoS silicone substrate, or other optical train placement.

In embodiments where the camera is put directly on axis with the eye, the camera may be able to see or detect the eye or directly into the eye. In embodiments, the system can track eye movement, detect pupil dilation, measure location, diameter, velocity and direction of the pupil and mage the iris directly. In embodiments the camera may determine if the user is looking around the environment or if the user is controlling the eyepiece. For example only, the camera may sense patterns of eye movement that cause it to send a signal to track eye movement such that it senses predetermined control commands that the user may perform with his eye. By way of example, the camera may recognize that the user's eyes are reading something on the user interface based on a pattern of the user's eye movement. In such cases, the camera initiate detection of a particular set of eye commands to transmit to the eye piece to carry out a particular function such as opening email and the like. In embodiments, the camera may detect that a user may focus on an object in a predetermined manner to control the eyepiece, such as by focusing on an item for a prolonged period of time, focusing on an item, moving the eye quickly and then re-focusing on the item, and the like. As the camera detects patters of movement such as these, it may signal to the eye piece to perform a particular function. For example only, focusing, looking away and re-focusing may cause the camera to signal to the eye piece that the user intends to "double-click" on an item in the display. Of course, any such patterns and or algorithms may be used for controlling the device via user's eye movement. In embodiments, the camera may detect a particular pattern of movement and when such movement is detected when particular application is in use, the camera may send a particular signal to the eyepiece based on such combination. By way of example, if an email program is open and the user's eyes exhibit a pattern of consistent with reading, the camera may signal to the eye piece to open a particular email on which the user's eyes are focused. In various embodiments, commands for controlling the eyepiece may be initiated based on the detection of the camera.

In embodiments the camera's detection of location, diameter, velocity and direction of the pupil, imaging of the retina and or iris directly, and the like may allow for security measures. By way of example when a user puts on the eyepiece, the camera may perform a retina scan which identifies the user against a database either onboard the eyepiece or stored remotely therefrom. In embodiments, if the user is recognized as the owner of the glasses or as a user of the glasses, it may open up the applications, and provide access to the user. If their glasses do not recognize the user, they may lock or prevent all or partial functionality. I embodiments the user may not need such a password, and the eyepiece may perform this function automatically. In embodiments, when the user is not recognized, the camera may take identifying information about the wearer in the event the wearer has stolen the eyepiece.

In embodiments, the eyepiece may perform user diagnostics based on detection of eye movement, detection of location, diameter, velocity and direction of the pupil, imaging of the retina and or iris directly, and the like. For example, diagnostics may be based on pupil dilation. If, for instance, the user's pupil dilates in a manner consistent with one who is lying, the camera and or eyepiece may detect that the user is lying. Further, if the user has a concussion, the pupil may change size despite a given amount of light entering the eye. The eyepiece may alert the user if he has a concussion. In embodiments, the eyepiece may be given to a soldier, athlete and the like as they exit physical activity and the eye piece may be used to diagnose the user as, for instance, having a concussion. The eyepiece may have a database of users on board or separate from the eye piece that may have information stored as related to various users. In an embodiment, as a player comes off the field to the sidelines, he may wear the glasses to perform a retina scan to identify the user via a database and then diagnose or examine the user by detecting the user's pupil size and comparing to the size of a pupil expected for the given light conditions. If the user's data falls outside of the expected ranger, the glasses may tell the user that his pupils are consistent with having a concussion. Similar uses may be employed such as detecting possible drug intoxication, detecting retina damage, detecting eye conditions and the like.

In embodiments, organic light emitting diodes (OLEDs) may be used in applications for microdisplays and/or sensors herein, and may be used with a Fraunhofer system, such as OLEDCam, or otherwise in the detection of eye movement or otherwise used with the eyepiece for illuminating the user's eye and the like. In embodiments, the device for detecting eye movements may be placed along the optical train on axis with a user's. In embodiments, microscale optical emitters and receivers may be integrated into the same chip. They may be implemented in an array type structure as a bidirectional or unidirectional microdisplay. In embodiments, the device may present and/or capture images at the same time. The microdisplay may be the basis for a system for personalized information and present information to the user and recognize interaction by the user. The user may perceive the environment as usual, and additional information may be presented via the eyepiece equipped with the bidirectional display. The visual information may be adapted to the context of operation of the system and the user may interact by movements or actions of the eyes. In embodiments, a CMOS-Chip may include a microdisplay and a camera on one substrate with a center element of the being a nested active matrix consisting of OLED pixels and photo diodes. In embodiments, the pixel cell may consist of red-green-blue-white and red-green-blue-photodiode pixel cells, and the like.

In embodiments, a system may comprise an interactive head-mounted eyepiece worn by the user, wherein the eyepiece includes an optical assembly through which the user views a surrounding environment and displayed content, an integrated image source adapted to introduce the displayed content to the optical assembly, and a camera disposed in the optical assembly along an optical axis such that the camera may view at least a portion of an eye of the user. In embodiments, the camera may be adapted to capture an image of the eye, pupil, retina, eyelid, and or eyelashes. In embodiments, commands for controlling the eyepiece may be initiated based on at least on image captured by the camera. In embodiments, a diagnosis of the user may be based on at least on image captured by the camera. Identification of the user may also be based on at least one image captured by the camera. By way of example the diagnosis may include a diagnosis of a concussion. In embodiments of the system, the identification of the user may be deployed as security aspect of the eyepiece. In embodiments, the integrated image source may illuminate the eye during an image capture by the camera. Further, the light from the image source may be modulated during an image capture by the camera. In embodiments, the camera may comprise one or more organic light emitting diodes (OLED). In embodiments, the user's eye, and or other parts listed herein including the iris, pupil, eyelid, eyelash, and the like, may be illuminate by various lights, LEDs, OLEDs, and the like. In embodiments, illumination of the user's eye may be used for imaging techniques, capturing data of the eye, identification and the like.

In an embodiment, the system may comprise an interactive head-mounted eyepiece worn by a user, wherein the eyepiece includes an optical assembly though which the user views a surrounding environment and displayed content, and integrated image source adapted to introduce the displayed content to the optical assembly, and a device for detecting eye movements. In embodiments, the device for detecting eye movements may comprise microscale optical emitters and receivers integrated into the same chip. In embodiments, the device may comprise a CMOS-Chip including a microdisplay and a camera on one substrate. In embodiments, the device for detecting eye movements may be disposed along the optical train on axis with the user's eye.

In embodiments, a camera is disposed in the optical assembly along an optical axis such that the camera views at least a portion of an eye of the user and may image one or more of the eye, a pupil, a retina, an eyelid and eyelashes. The integrated processor and the camera are adapted to track eye movements of the user; measure at least one of pupil dilation, pupil location, pupil diameter, pupil velocity and pupil direction; distinguish user eye movements intended as control or commands from user eye movements for reading or gazing; use eye movements of the user as commands for the processor for controlling a function of the integrated processor or the interactive head-mounted eyepiece; and use eye movements of the user as commands to control a device external to the user and external to the interactive head-mounted eyepiece. A diagnosis or an identification of the user may be based on at least one image captured by the camera, such as concussion. Identification of the user may be deployed as a security aspect of the eyepiece. The system may include a user input interface to control or signal an external device based on eye movements from the user. The camera may be adapted to capture an image of both eyes, and wherein the images are compared to a database comprising other images of both eyes to indicate a diagnosis. The optical axis of the integrated image source and the optical axis of the camera may be different. At least a portion of the optical axis of the integrated image source and the optical axis of the camera may be the same.

A device, such as a camera, microscale optical emitters and receivers integrated into the same chip, or CMOS-Chip including a microdisplay and a camera on one substrate, in an augmented reality eyepiece may detect eye movements of the user. An integrated image source may be adapted to at least one of modulate light from an image source and illuminate the eye, during an image capture by the camera. The camera may include one or more organic light emitting diodes (OLED). The device for detecting eye movements may be along the optical train on axis with the user's eye or on a different axis from the user's eye. An integrated processor may be adapted to interpret eye movements of the user as commands for operating a device within the interactive head-mounted eyepiece or an external device.

A method of detecting eye movements of a user may include wearing a head-mounted eyepiece, the head-mounted eyepiece including an optical assembly through which the user views a surrounding environment and displayed content, an integrated processor and an integrated image source adapted to introduce the displayed content to the optical assembly, and a camera, detecting eye movements of the user with the camera and the integrated processor, and controlling a device through the eye movements and the integrated processor, wherein the camera detects movements of at least one eye of the user and interprets the movements as commands. The integrated processor may distinguish between eye movements as commands and eye movements intended for gazing. The method may include interpreting predetermined eye movements as a command to perform a particular function. The method may include scanning at least one eye of the user to determine an identification of the user. The method may include scanning at least one eye of the user to diagnose a medical condition of the user. The camera may include at least one organic light emitting diode (OLED). Specific eye movements may be interpreted as specific commands. Eye movements may be selected from the group consisting of blinking, repetitive blinking, blink count, blink rate, eye open-closed (slow blink), gaze tracking, eye movements to the side, up and down, side to side, through a sequence of positions, to a specific position, dwell time in a position, gazing toward a fixed object, and gaze through a certain portion of a lens of the head mounted eyepiece. The method may include controlling the device through eye movements and a user input interface. The method may include capturing a view of the surrounding environment with the camera or a second camera for displaying to the user.

In embodiments, the eyepiece may utilize sub-conscious control aspects, such as images in the wearer's periphery, images presented to the user at rates below conscious perception, sub-conscious perceptions to a viewed scene by the viewer, and the like. For instance, a wearer may be presented images through the eyepiece that are at a rate the wearer is unaware of, but is subconsciously made aware of as presented content, such as a reminder, an alert (e.g. an alert that calls on the wearer to increase a level of attention to something, but not so much so that the user needs a full conscious reminder), an indication related to the wearer's immediate environment (e.g. the eyepiece has detected something in the wearer's field of view that may have some interest to the wearer, and to which the indication draws the wearer's attention), and the like. In another instance, the eyepiece may provide indicators to the wearer through a brain activity monitoring interface, where electrical signals within the brain fire before a person realizes they've recognized an image. For instance, the brain activity-monitoring interface may include electroencephalogram (EEG) sensors (or the like) to monitor brain activity as the wearer is viewing the current environment. When the eyepiece, through the brain activity-monitoring interface, senses that the wearer has become 'aware' of an element of the surrounding environment, the eyepiece may provide conscious level feedback to the wearer to make the wearer more aware of the element. For example, a wearer may unconsciously become aware of seeing a familiar face in a crowd (e.g. a friend, a suspect, a celebrity), and the eyepiece provides a visual or audio indication to the wearer to bring the person more consciously to the attention of the wearer. In another example, the wearer may view a product that arouses their attention at a subconscious level, and the eyepiece provides a conscious indication to the wearer, more information about the product, an enhanced view of the product, a link to more information about the product, and the like. In embodiments, the ability for the eyepiece to extend the wearer's reality to a subconscious level may enable the eyepiece to provide the wearer with an augmented reality beyond their normal conscious experience with the world around them.

Figure 15F:
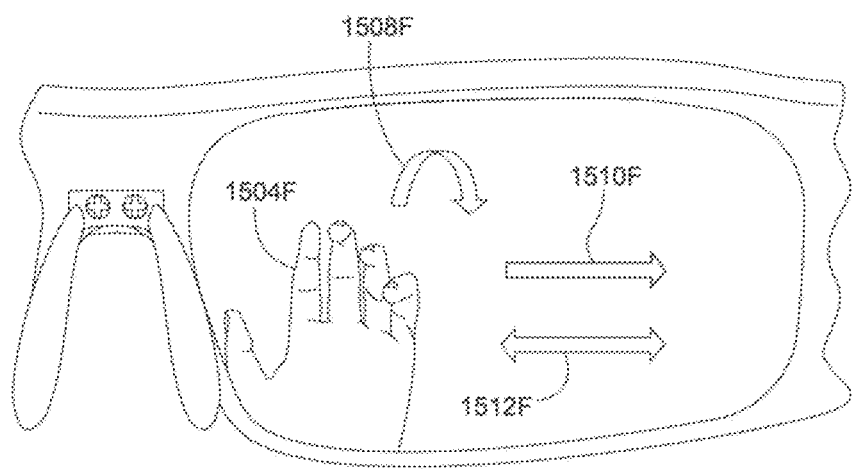
FIG. 15F depicts a hand positioning control of the eyepiece.

In embodiments, the eyepiece may have a plurality of modes of operation where control of the eyepiece is controlled at least in part by positions, shapes, motions of the hand, and the like. To provide this control the eyepiece may utilize hand recognition algorithms to detect the shape of the hand/fingers, and to then associate those hand configurations, possibly in combination with motions of the hand, as commands. Realistically, as there may be only a limited number of hand configurations and motions available to command the eyepiece, these hand configurations may need to be reused depending upon the mode of operation of the eyepiece. In embodiments, certain hand configurations or motions may be assigned for transitioning the eyepiece from one mode to the next, thereby allowing for the reuse of hand motions. For instance, and referring to FIG. 15F, the user's hand 1504F may be moved in view of a camera on the eyepiece, and the movement may then be interpreted as a different command depending upon the mode, such as a circular motion 1508F, a motion across the field of view 1510F, a back and forth motion 1512F, and the like. In a simplistic example, suppose there are two modes of operation, mode one for panning a view from the projected image and mode two for zooming the projected image. In this example the user may want to use a left-to-right finger-pointed hand motion to command a panning motion to the right. However, the user may also want to use a left-to-right finger-pointed hand motion to command a zooming of the image to greater magnification. To allow the dual use of this hand motion for both command types, the eyepiece may be configured to interpret the hand motion differently depending upon the mode the eyepiece is currently in, and where specific hand motions have been assigned for mode transitions. For instance, a clockwise rotational motion may indicate a transition from pan to zoom mode, and a counter-clockwise rotational motion may indicate a transition from zoom to pan mode. This example is meant to be illustrative and not limiting in anyway, where one skilled in the art will recognize how this general technique could be used to implement a variety of command/mode structures using the hand(s) and finger(s), such as hand-finger configurations-motions, two-hand configuration-motions, and the like.

In embodiments, a system may comprise an interactive head-mounted eyepiece worn by a user, wherein the eyepiece includes an optical assembly through which the user views a surrounding environment and displayed content, wherein the optical assembly comprises a corrective element that corrects the user's view of the surrounding environment, an integrated processor for handling content for display to the user, and an integrated image source for introducing the content to the optical assembly; and an integrated camera facility that images a gesture, wherein the integrated processor identifies and interprets the gesture as a command instruction. The control instruction may provide manipulation of the content for display, a command communicated to an external device, and the like.

In embodiments, control of the eyepiece may be enabled through eye movement, an action of the eye, and the like. For instance, there may be a camera on the eyepiece that views back to the wearer's eye(s), where eye movements or actions may be interpreted as command information, such as through blinking, repetitive blinking, blink count, blink rate, eye open-closed, gaze tracking, eye movements to the side, up and down, side to side, through a sequence of positions, to a specific position, dwell time in a position, gazing toward a fixed object (e.g. the corner of the lens of the eyepiece), through a certain portion of the lens, at a real-world object, and the like. In addition, eye control may enable the viewer to focus on a certain point on the displayed image from the eyepiece, and because the camera may be able to correlate the viewing direction of the eye to a point on the display, the eyepiece may be able to interpret commands through a combination of where the wearer is looking and an action by the wearer (e.g. blinking, touching an interface device, movement of a position sense device, and the like). For example, the viewer may be able to look at an object on the display, and select that object through the motion of a finger enabled through a position sense device.

In some embodiments, the glasses may be equipped with eye tracking devices for tracking movement of the user's eye, or preferably both eyes; alternatively, the glasses may be equipped with sensors for six-degree freedom of movement tracking, i.e., head movement tracking. These devices or sensors are available, for example, from Chronos Vision GmbH, Berlin, Germany and ISCAN, Woburn, Mass. Retinal scanners are also available for tracking eye movement. Retinal scanners may also be mounted in the augmented reality glasses and are available from a variety of companies, such as Tobii, Stockholm, Sweden, and SMI, Teltow, Germany, and ISCAN.

Figure 29A:
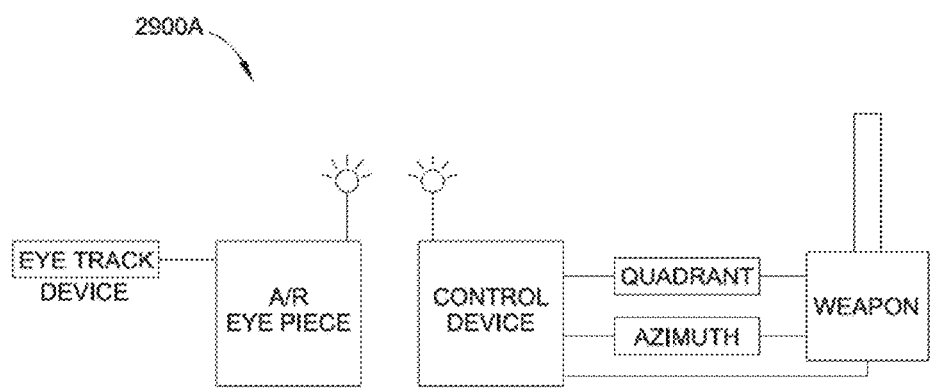
FIG. 29A depicts a control circuit for eye-tracking control of an external device.

The augmented reality eyepiece also includes a user input interface, as shown, to allow a user to control the device. Inputs used to control the device may include any of the sensors discussed above, and may also include a trackpad, one or more function keys and any other suitable local or remote device. For example, an eye tracking device may be used to control another device, such as a video game or external tracking device. As an example, FIG. 29A depicts a user with an augmented reality eyepiece equipped with an eye tracking device 2900A, discussed elsewhere in this document. The eye tracking device allows the eyepiece to track the direction of the user's eye or preferably, eyes, and send the movements to the controller of the eyepiece. Control system includes the augmented reality eyepiece and a control device for the weapon. The movements may then be transmitted to the control device for a weapon controlled by the control device, which may be within sight of the user. The movement of the user's eyes is then converted by suitable software to signals for controlling movement in the weapon, such as quadrant (range) and azimuth (direction). Additional controls may be used in conjunction with eye tracking, such as with the user's trackpad or function keys. The weapon may be large caliber, such as a howitzer or mortar, or may small caliber, such as a machine gun.

The movement of the user's eyes is then converted by suitable software to signals for controlling movement of the weapon, such as quadrant (range) and azimuth (direction) of the weapon. Additional controls may be used for single or continuous discharges of the weapon, such as with the user's trackpad or function keys. Alternatively, the weapon may be stationary and non-directional, such as an implanted mine or shape-charge, and may be protected by safety devices, such as by requiring specific encoded commands. The user of the augmented reality device may activate the weapon by transmitting the appropriate codes and commands, without using eye-tracking features.

In embodiments, control of the eyepiece may be enabled though gestures by the wearer. For instance, the eyepiece may have a camera that views outward (e.g. forward, to the side, down) and interprets gestures or movements of the hand of the wearer as control signals. Hand signals may include passing the hand past the camera, hand positions or sign language in front of the camera, pointing to a real-world object (such as to activate augmentation of the object), and the like. Hand motions may also be used to manipulate objects displayed on the inside of the translucent lens, such as moving an object, rotating an object, deleting an object, opening-closing a screen or window in the image, and the like. Although hand motions have been used in the preceding examples, any portion of the body or object held or worn by the wearer may also be utilized for gesture recognition by the eyepiece.

Figure 14A:
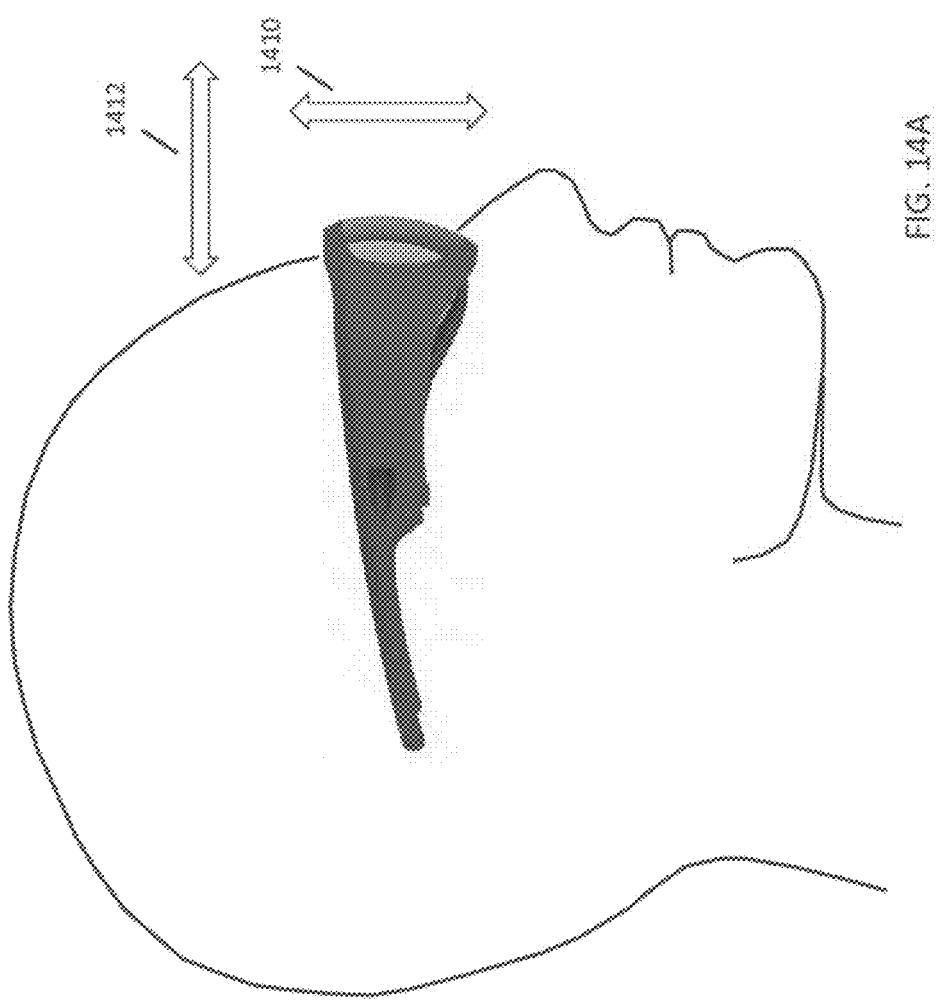
FIG. 14A depicts motions in an embodiment of the eyepiece featuring nod control.

In embodiments, head motion control may be used to send commands to the eyepiece, where motion sensors such as accelerometers, gyros, or any other sensor described herein, may be mounted on the wearer's head, on the eyepiece, in a hat, in a helmet, and the like. Referring to FIG. 14A, head motions may include quick motions of the head, such as jerking the head in a forward and/or backward motion 1412, in an up and/or down motion 1410, in a side to side motion as a nod, dwelling in a position, such as to the side, moving and holding in position, and the like. Motion sensors may be integrated into the eyepiece, mounted on the user's head or in a head covering (e.g. hat, helmet) by wired or wireless connection to the eyepiece, and the like. In embodiments, the user may wear the interactive head-mounted eyepiece, where the eyepiece includes an optical assembly through which the user views a surrounding environment and displayed content. The optical assembly may include a corrective element that corrects the user's view of the surrounding environment, an integrated processor for handling content for display to the user, and an integrated image source for introducing the content to the optical assembly. At least one of a plurality of head motion sensing control devices may be integrated or in association with the eyepiece that provide control commands to the processor as command instructions based upon sensing a predefined head motion characteristic. The head motion characteristic may be a nod of the user's head such that the nod is an overt motion dissimilar from ordinary head motions. The overt motion may be a jerking motion of the head. The control instructions may provide manipulation of the content for display, be communicated to control an external device, and the like. Head motion control may be used in combination with other control mechanisms, such as using another control mechanism as discussed herein to activate a command and for the head motion to execute it. For example, a wearer may want to move an object to the right, and through eye control, as discussed herein, select the object and activate head motion control. Then, by tipping their head to the right, the object may be commanded to move to the right, and the command terminated through eye control.

In embodiments, the eyepiece may be controlled through audio, such as through a microphone. Audio signals may include speech recognition, voice recognition, sound recognition, sound detection, and the like. Audio may be detected though a microphone on the eyepiece, a throat microphone, a jaw bone microphone, a boom microphone, a headphone, ear bud with microphone, and the like.

In embodiments, command inputs may provide for a plurality of control functions, such as turning on/off the eyepiece projector, turn on/off audio, turn on/off a camera, turn on/off augmented reality projection, turn on/off GPS, interaction with display (e.g. select/accept function displayed, replay of captured image or video, and the like), interaction with the real-world (e.g. capture image or video, turn a page of a displayed book, and the like), perform actions with an embedded or external mobile device (e.g. mobile phone, navigation device, music device, VoIP, and the like), browser controls for the Internet (e.g. submit, next result, and the like), email controls (e.g. read email, display text, text-to-speech, compose, select, and the like), GPS and navigation controls (e.g. save position, recall saved position, show directions, view location on map), and the like. In embodiments, the eyepiece, or component portions thereof, may be automatically turned on/off via a sensor indication, such as from an IR sensor, an accelerometer, a force sensor, a micro-switch, a capacitive sensor, through an eye-tracking detection facility, and the like. For example, the eyepiece may be automatically turned off when the user takes the eyepiece off their head by way of a capacitive sensor that senses the eyepiece is no longer in physical contact with the user's skin, such as at the bridge of the user's nose. One skilled in the art will appreciate other like configurations for sensing when the eyepiece has been taken off. In embodiments, the eyepiece may sense when detachable components are attached-detached from the eyepiece, and utilize this sensing to turn on/off aspects of the eyepiece. For example, a portion of the optics may be detachable, and when the optics portion is removed the power to that half of the eyepiece system is powered down to preserve power in the battery. The present disclosure may include a power management facility, where the power management facility controls power provided to select components of the eyepiece in correspondence to the sensor. The eyepiece may be mounted in a frame with a nose bridge and foldable arms, wherein hinges to the frame attach the foldable arms, and where the sensor may be mounted in the nose bridge of the frame, in the arm, in the hinge, and the like. The select component may be the image source, the processor, and the like. The power management facility may be in a sleep mode when the user is not wearing the eyepiece, where sleep mode may include a periodic reading of the sensor, where the power management facility transitions to a wake mode and powers on the eyepiece when it detects the user is wearing the eyepiece. The power management facility may reduce power to components based on usage of eyepiece functions, power remaining in an integrated battery, network availability, power consumption rate, and the like. The reduction of power may be based on a user preference profile. The user may override the reduction of power through a command. The user may be provided an indication through a user interface of the eyepiece when power is being reduced. The electrochromic density in the optical assembly may be increased if a brightness level of the image source is reduced as a result of reducing the power to the image source.

In embodiments, the eyepiece may provide 3D display imaging to the user, such as through conveying a stereoscopic, auto-stereoscopic, computer-generated holography, volumetric display image, stereograms/stereoscopes, view-sequential displays, electro-holographic displays, parallax "two view" displays and parallax panoramagrams, re-imaging systems, and the like, creating the perception of 3D depth to the viewer. Display of 3D images to the user may employ different images presented to the user's left and right eyes, such as where the left and right optical paths have some optical component that differentiates the image, where the projector facility is projecting different images to the user's left and right eye's, and the like. The optical path, including from the projector facility through the optical path to the user's eye, may include a graphical display device that forms a visual representation of an object in three physical dimensions. A processor, such as the integrated processor in the eyepiece or one in an external facility, may provide 3D image processing as at least a step in the generation of the 3D image to the user.

In embodiments, holographic projection technologies may be employed in the presentation of a 3D imaging effect to the user, such as computer-generated holography (CGH), a method of digitally generating holographic interference patterns. For instance, a holographic image may be projected by a holographic 3D display, such as a display that operates on the basis of interference of coherent light. Computer generated holograms have the advantage that the objects which one wants to show do not have to possess any physical reality at all, that is, they may be completely generated as a 'synthetic hologram'. There are a plurality of different methods for calculating the interference pattern for a CGH, including from the fields of holographic information and computational reduction as well as in computational and quantization techniques. For instance, the Fourier transform method and point source holograms are two examples of computational techniques. The Fourier transformation method may be used to simulate the propagation of each plane of depth of the object to the hologram plane, where the reconstruction of the image may occur in the far field. In an example process, there may be two steps, where first the light field in the far observer plane is calculated, and then the field is Fourier transformed back to the lens plane, where the wavefront to be reconstructed by the hologram is the superposition of the Fourier transforms of each object plane in depth. In another example, a target image may be multiplied by a phase pattern to which an inverse Fourier transform is applied. Intermediate holograms may then be generated by shifting this image product, and combined to create a final set. The final set of holograms may then be approximated to form kinoforms for sequential display to the user, where the kinoform is a phase hologram in which the phase modulation of the object wavefront is recorded as a surface-relief profile. In the point source hologram method the object is broken down in self-luminous points, where an elementary hologram is calculated for every point source and the final hologram is synthesized by superimposing all the elementary holograms.

In an embodiment, 3-D or holographic imagery may be enabled by a dual projector system where two projectors are stacked on top of each other for a 3D image output. Holographic projection mode may be entered by a control mechanism described herein or by capture of an image or signal, such as an outstretched hand with palm up, an SKU, an RFID reading, and the like. For example, a wearer of the eyepiece may view a letter 'X' on a piece of cardboard which causes the eyepiece to enter holographic mode and turning on the second, stacked projector. Selecting what hologram to display may be done with a control technique. The projector may project the hologram onto the cardboard over the letter 'X'. Associated software may track the position of the letter 'X' and move the projected image along with the movement of the letter 'X'. In another example, the eyepiece may scan a SKU, such as a SKU on a toy construction kit, and a 3-D image of the completed toy construction may be accessed from an online source or non-volatile memory. Interaction with the hologram, such as rotating it, zooming in/out, and the like, may be done using the control mechanisms described herein. Scanning may be enabled by associated bar code/SKU scanning software. In another example, a keyboard may be projected in space or on a surface. The holographic keyboard may be used in or to control any of the associated applications/functions.

In embodiments, eyepiece facilities may provide for locking the position of a virtual keyboard down relative to a real environmental object (e.g. a table, a wall, a vehicle dashboard, and the like) where the virtual keyboard then does not move as the wearer moves their head. In an example, and referring to FIG. 24, the user may be sitting at a table and wearing the eyepiece 2402, and wish to input text into an application, such as a word processing application, a web browser, a communications application, and the like. The user may be able to bring up a virtual keyboard 2408, or other interactive control element (e.g. virtual mouse, calculator, touch screen, and the like), to use for input. The user may provide a command for bringing up the virtual keyboard 2408, and use a hand gesture 2404 for indicating the fixed location of the virtual keyboard 2408. The virtual keyboard 2408 may then remain fixed in space relative to the outside environment, such as fixed to a location on the table 2410, where the eyepiece facilities keep the location of the virtual keyboard 2408 on the table 2410 even when the user turns their head. That is, the eyepiece 2402 may compensate for the user's head motion in order to keep the user's view of the virtual keyboard 2408 located on the table 2410. In embodiments, the user may wear the interactive head-mounted eyepiece, where the eyepiece includes an optical assembly through which the user views a surrounding environment and displayed content. The optical assembly may include a corrective element that corrects the user's view of the surrounding environment, an integrated processor for handling content for display to the user, and an integrated image source for introducing the content to the optical assembly. An integrated camera facility may be provided that images the surrounding environment, and identifies a user hand gesture as an interactive control element location command, such as a hand-finger configuration moved in a certain way, positioned in a certain way, and the like. The location of the interactive control element then may remain fixed in position with respect to an object in the surrounding environment, in response to the interactive control element location command, regardless of a change in the viewing direction of the user. In this way, the user may be able to utilize a virtual keyboard in much the same way they would a physical keyboard, where the virtual keyboard remains in the same location. However, in the case of the virtual keyboard there are not 'physical limitations', such as gravity, to limit where the user may locate the keyboard. For instance, the user could be standing next to a wall, and place the keyboard location on the wall, and the like. It will be appreciated by one skilled in the art that the 'virtual keyboard' technology may be applied to any controller, such as a virtual mouse, virtual touch pad, virtual game interface, virtual phone, virtual calculator, virtual paintbrush, virtual drawing pad, and the like. For example, a virtual touchpad may be visualized through the eyepiece to the user, and positioned by the user such as by use of hand gestures, and used in place of a physical touchpad.

In embodiments, eyepiece facilities may use visual techniques to render the projection of an object (e.g. virtual keyboard, keypad, calculator, notepad, joystick, control panel, book) onto a surface, such as by applying distortions like parallax, keystone, and the like. For example, the appearance of a keyboard projected onto a tabletop in front of the user with proper perspective may be aided through applying a keystone effect, where the projection as provided through the eyepiece to the user is distorted so that it looks like it is lying down on the surface of the table. In addition, these techniques may be applied dynamically, to provide the proper perspective even as the user moves around in relationship to the surface.

In embodiments, eyepiece facilities may provide for gesture recognition that may be used to provide a keyboard and mouse experience with the eyepiece. For instance, with images of a keyboard, mouse, and fingers overlaid on the lower part of the display, the system may be capable of tracking finger positions in real time to enable a virtual desktop. Through gesture recognition, tracking may be done without wires and external powered devices. In another instance, fingertip locations may be tracked through gesture recognition through the eyepiece without wires and external power, such as with gloves with passive RFID chips in each fingertip. In this instance, each RFID chip may have its own response characteristic, enabling a plurality of digits of the fingers to be read simultaneously. The RFID chips may be paired with the eyewear so that they are distinguishable from other RFID chips that may be operating nearby. The eyewear may provide the signals to activate the RFID chips and have two or more receiving antennas. Each receiving antenna may be connected to a phase-measurement circuit element that in turn provides input to a location-determining algorithm. The location-determining algorithm may also provide velocity and acceleration information, and the algorithm that ultimately may provide keyboard and mouse information to the eyepiece operating system. In embodiments, with two receiving antennas, the azimuthal positions of each fingertip can be determined with the phase difference between the receiving antennas. The relative phase difference between RFID chips may then be used to determine the radial positions of the fingertips.

In embodiments, eyepiece facilities may use visual techniques to render the projection of a previously taken medical scan onto the wearer's body, such as an x-ray, an ultrasound, an MRI, a PET scan, and the like. For example, and referring to FIG. 24A, the eyepiece may have access to an x-ray image taken of the wearer's hand. The eyepiece may then utilize its integrated camera to view the wear's hand 2402A, and overlay a projected image 2404A of the x-ray onto the hand. Further, the eyepiece may be able to maintain the image overlay as the wearer moves their hand and gaze relative to one other. In embodiments, this technique may also be implemented while the wearer is looking in the mirror, where the eyepiece transposes an image on top of the reflected image. This technique may be used as part of a diagnostic procedure, for rehabilitation during physical therapy, to encourage exercise and diet, to explain to a patient a diagnosis or condition, and the like. The images may be the images of the wearer, generic images from a database of images for medical conditions, and the like. The generic overlay may show some type of internal issue that is typical of a physical condition, a projection of what the body will look like if a certain routine is followed for a period of time, and the like. In embodiments, an external control device, such as pointer controller, may enable the manipulation of the image. Further, the overlay of the image may be synchronized between multiple people, each wearing an eyepiece, as described herein. For instance, a patient and a doctor may both project the image onto the patient's hand, where the doctor may now explain a physical ailment while the patient views the synchronized images of the projected scan and the doctor's explanation.

In embodiments, eyepiece facilities may provide for removing the portions of a virtual keyboard projection where intervening obstructions appear (e.g. the user's hand getting in the way, where it is not desired to project the keyboard onto the user's hand). In an example, and referring to FIG. 30, the eyepiece 3002 may provide a projected virtual keyboard 3008 to the wearer, such as onto a tabletop. The wearer may then reach 'over' the virtual keyboard 3008 to type. As the keyboard is merely a projected virtual keyboard, rather than a physical keyboard, without some sort of compensation to the projected image the projected virtual computer would be projected 'onto' the back of the user's hand. However, as in this example, the eyepiece may provide compensation to the projected image such that the portion of the wearer's hand 3004 that is obstructing the intended projection of the virtual keyboard onto the table may be removed from the projection. That is, it may not be desirable for portions of the keyboard projection 3008 to be visualized onto the user's hand, and so the eyepiece subtracts the portion of the virtual keyboard projection that is co-located with the wearer's hand 3004. In embodiments, the user may wear the interactive head-mounted eyepiece, where the eyepiece includes an optical assembly through which the user views a surrounding environment and displayed content. The optical assembly may include a corrective element that corrects the user's view of the surrounding environment, an integrated processor for handling content for display to the user, and an integrated image source for introducing the content to the optical assembly. The displayed content may include an interactive control element (e.g. virtual keyboard, virtual mouse, calculator, touch screen, and the like). An integrated camera facility may image a user's body part as it interacts with the interactive control element, wherein the processor removes a portion of the interactive control element by subtracting the portion of the interactive control element that is determined to be co-located with the imaged user body part based on the user's view. In embodiments, this technique of partial projected image removal may be applied to other projected images and obstructions, and is not meant to be restricted to this example of a hand over a virtual keyboard.

In embodiments, eyepiece facilities may provide for intervening obstructions for any virtual content that is displayed over "real" world content. If some reference frame is determined that places the content at some distance, then any object that passes between the virtual image and the viewer may be subtracted from the displayed content so as not to create a discontinuity for the user that is expecting the displayed information to exist at a certain distance away. In embodiments, variable focus techniques may also be used to increase the perception of a distance hierarchy amongst the viewed content.

In embodiments, eyepiece facilities may provide for the ability to determine an intended text input from a sequence of character contacts swiped across a virtual keypad, such as with the finger, a stylus, the entire hand, and the like. For example, and referring to FIG. 37, the eyepiece may be projecting a virtual keyboard 3700, where the user wishes to input the word 'wind'. Normally, the user would discretely press the key positions for 'w', then 'i', then 'n', and finally 'd', and a facility (camera, accelerometer, and the like, such as described herein) associated with the eyepiece would interpret each position as being the letter for that position. However, the system may also be able to monitor the movement, or swipe, of the user's finger or other pointing device across the virtual keyboard and determine best fit matches for the pointer movement. In the figure, the pointer has started at the character 'w' and swept a path 3704 though the characters e, r, t, y, u, i, k, n, b, v, f, and d where it stops. The eyepiece may observe this sequence and determine the sequence, such as through an input path analyzer, feed the sensed sequence into a word matching search facility, and output a best fit word, in this case 'wind' as text 3708. In embodiments, the eyepiece may monitor the motion of the pointing device across the keypad and determine the word more directly, such as though auto complete word matching, pattern recognition, object recognition, and the like, where some 'separator' indicates the space between words, such as a pause in the motion of the pointing device, a tap of the pointing device, a swirling motion of the pointing device, and the like. For instance, the entire swipe path may be used with pattern or object recognition algorithms to associate whole words with the discrete patterns formed by the user's finger as they move through each character to form words, with a pause between the movements as demarcations between the words. The eyepiece may provide the best-fit word, a listing of best-fit words, and the like. In embodiments, the user may wear the interactive head-mounted eyepiece, where the eyepiece includes an optical assembly through which the user views a surrounding environment and displayed content. The optical assembly may include a corrective element that corrects the user's view of the surrounding environment, an integrated processor for handling content for display to the user, and an integrated image source for introducing the content to the optical assembly. The displayed content may comprise an interactive keyboard control element (e.g. a virtual keyboard, calculator, touch screen, and the like), and where the keyboard control element is associated with an input path analyzer, a word matching search facility, and a keyboard input interface. The user may input text by sliding a pointing device (e.g. a finger, a stylus, and the like) across character keys of the keyboard input interface in a sliding motion through an approximate sequence of a word the user would like to input as text, wherein the input path analyzer determines the characters contacted in the input path, the word matching facility finds a best word match to the sequence of characters contacted and inputs the best word match as input text. In embodiments, the reference displayed content may be something other than a keyboard, such as a sketch pad for freehand text, or other interface references like a 4-way joystick pad for controlling a game or real robots and aircraft, and the like. Another example may be a virtual drum kit, such as with colored pads the user "taps" to make a sound. The eyepiece's ability to interpret patterns of motion across a surface may allow for projecting reference content in order to give the user something to point at and provide them with visual and/or audio feedback. In embodiments, the 'motion' detected by the eyepiece may be the motion of the user's eye as they look at the surface. For example, the eyepiece may have facilities for tracking the eye movement of the user, and by having both the content display locations of a projected virtual keyboard and the gazing direction of the user's eye, the eyepiece may be able to detect the line-of-sight motion of the user's eye across the keyboard, and then interpret the motions as words as described herein.

In embodiments, the eyepiece may provide the capability to command the eyepiece via hand gesture 'air lettering', such as the wearer using their finger to air swipe out a letter, word, and the like in view of an embedded eyepiece camera, where the eyepiece interprets the finger motion as letters, words, symbols for commanding, signatures, writing, emailing, texting, and the like. For instance, the wearer may use this technique to sign a document utilizing an 'air signature'. The wearer may use this technique to compose text, such as in an email, text, document, and the like. The wearer eyepiece may recognize a symbol made through the hand motion as a control command. In embodiments, the air lettering may be implemented through hand gesture recognition as interpreted by images captured through an eyepiece camera, or through other input control devices, such as via an inertial measurement unit (IMU) mounted in a device on the user's finger, hand, and the like, as described herein.

In embodiments, eyepiece facilities may provide for presenting displayed content corresponding to an identified marker indicative of the intention to display the content. That is, the eyepiece may be commanded to display certain content based upon sensing a predetermined external visual cue. The visual cue may be an image, an icon, a picture, face recognition, a hand configuration, a body configuration, and the like. The displayed content may be an interface device that is brought up for use, a navigation aid to help the user find a location once they get to some travel location, an advertisement when the eyepiece views a target image, an informational profile, and the like. In embodiments, visual marker cues and their associated content for display may be stored in memory on the eyepiece, in an external computer storage facility and imported as needed (such as by geographic location, proximity to a trigger target, command by the user, and the like), generated by a third-party, and the like. In embodiments, the user may wear the interactive head-mounted eyepiece, where the eyepiece includes an optical assembly through which the user views a surrounding environment and displayed content. The optical assembly may include a corrective element that corrects the user's view of the surrounding environment, an integrated processor for handling content for display to the user, and an integrated image source for introducing the content to the optical assembly. An integrated camera facility may be provided that images an external visual cue, wherein the integrated processor identifies and interprets the external visual cue as a command to display content associated with the visual cue. Referring to FIG. 38, in embodiments the visual cue 3812 may be included in a sign 3814 in the surrounding environment, where the projected content is associated with an advertisement. The sign may be a billboard, and the advertisement for a personalized advertisement based on a preferences profile of the user. The visual cue 3802,3808 may be a hand gesture, and the projected content a projected virtual keyboard 3804, 3810. For instance, the hand gesture may be a thumb and index finger gesture 3802 from a first user hand, and the virtual keyboard 3804 projected on the palm of the first user hand, and where the user is able to type on the virtual keyboard with a second user hand. The hand gesture 3808 may be a thumb and index finger gesture combination of both user hands, and the virtual keyboard 3810 projected between the user hands as configured in the hand gesture, where the user is able to type on the virtual keyboard using the thumbs of the user's hands. Visual cues may provide the wearer of the eyepiece with an automated resource for associating a predetermined external visual cue with a desired outcome in the way of projected content, thus freeing the wearer from searching for the cues themselves.

In embodiments, the eyepiece may include a visual recognition language translation facility for providing translations for visually presented content, such as for road signs, menus, billboards, store signs, books, magazines, and the like. The visual recognition language translation facility may utilize optical character recognition to identify letters from the content, match the strings of letters to words and phrases through a database of translations. This capability may be completely contained within the eyepiece, such as in an offline mode, or at least in part in an external computing facility, such as on an external server. For instance, a user may be in a foreign country, where the signs, menus, and the like are not understood by the wearer of the eyepiece, but for which the eyepiece is able to provide translations. These translations may appear as an annotation to the user, replace the foreign language words (such as on the sign) with the translation, provided through an audio translation to the user, and the like. In this way, the wearer won't have to take the effort to look up word translations, but rather they would be provided automatically. In an example, a user of the eyepiece may be Italian, and coming to the United States they have the need to interpret the large number of road signs in order to drive around safely. Referring to FIG. 38A, the Italian user of the eyepiece is viewing a U.S. stop sign 3802A. In this instance, the eyepiece may identify the letters on the sign, translate the word 'stop' in the Italian for stop, 'arresto', and make the stop sign 3804A appear to read the word 'arresto' rather than 'stop'. In embodiments, the eyepiece may also provide simple translation messages to the wearer, provide audio translations, provide a translation dictionary to the wearer, and the like. The present disclosure may comprise an interactive head-mounted eyepiece worn by a user, where the eyepiece includes an optical assembly through which the user views a surrounding environment and displayed content, and an integrated image source adapted to introduce the content to the optical assembly; an integrated camera for imaging text viewed within the surrounding environment; an optical character recognition facility to correlate one or more characters from the viewed text to one or more characters of a first language, and correlate the one or more characters of the first language to the one or more characters of the second language, wherein the integrated image source presents the one or more characters of the second language as displayed content, wherein the displayed content is locked in a position relative to the one or more characters from the viewed text. The presentation of the one or more characters of the second language may appear as an annotation to the user and placed as displayed content in relative to the originally viewed text. The presentation of the one or more characters of the second language may be superimposed onto the viewed location of the originally viewed text, such as the presentation of the one or more characters of the second language superimposed onto the originally viewed text matches the font characteristics of the originally viewed text. The viewed text is on a sign, a printed document, book, a road sign, a billboard, a menu, and the like. The optical character recognition facility may be incorporated in the eyepiece, provided external to the eyepiece, or provided in a combination of internally and externally. The one or more characters may be words, phrases, strings of alphanumeric characters, and the like. The one or more characters of the second language may be saved in an external facility and tagged so as to be made available to a second eyepiece viewing the same text, such as the tagging including a geographical location indication, an object identifier, and the like. In addition, the presentation of the one or more characters of the second language may be stored such that when the view of the text moves outside the view of the eyepiece it is recalled for presentation when the text moves back within the view of the eyepiece.

In one example, the eyepiece may be used in an adaptive environment, such as for blind users. In embodiments, the results of face recognition or object identification may be processed to obtain an audible result and can be presented as audio to a wearer of the glasses through associated earbuds/headphones. In other embodiments, the results of face recognition or object identification may be translated into haptic vibrations in the glasses or an associated controller. In an example, if someone stands in front of a user of the adaptive glasses, a camera may image the person and transmit the image to the integrated processor for processing by face recognition software or to face recognition software operating on a server or in the cloud. The results of the face recognition may be presented as written text in the display of the glasses for certain individuals, but for blind or poor vision users, the result may be processed to obtain audio. In other examples, object recognition may determine the user is approaching a curb, doorway, or other object and the glasses or controller would audibly or haptically warn the user. For poor vision users, the text on the display could be magnified or the contrast could be increased.

In embodiments, a GPS sensor may be used to determine a location of the user wearing the adaptive display. The GPS sensor may be accessed by a navigation application to audibly announce various points of interest to the user as they are approached or reached. In embodiments, the user may be audibly guided to an endpoint by the navigation application.

The eyepiece may be useful for various applications and markets. It should be understood that the control mechanisms described herein may be used to control the functions of the applications described herein. The eyepiece may run a single application at a time or multiple applications may run at a time. Switching between applications may be done with the control mechanisms described herein. The eyepiece may be used in military applications, gaming, image recognition applications, to view/order e-books, GPS Navigation (Position, Direction, Speed and ETA), Mobile TV, athletics (view pacing, ranking, and competition times; receive coaching), telemedicine, industrial inspection, aviation, shopping, inventory management tracking, firefighting (enabled by VIS/NIRSWIR sensor that sees through fog, haze, dark), outdoor/adventure, custom advertising, and the like. In an embodiment, the eyepiece may be used with e-mail, such as GMAIL in FIG. 7, the Internet, web browsing, viewing sports scores, video chat, and the like. In an embodiment, the eyepiece may be used for educational/training purposes, such as by displaying step by step guides, such as hands-free, wireless maintenance and repair instructions. For example, a video manual and/or instructions may be displayed in the field of view. In an embodiment, the eyepiece may be used in Fashion, Health, and Beauty. For example, potential outfits, hairstyles, or makeup may be projected onto a mirror image of a user. In an embodiment, the eyepiece may be used in Business Intelligence, Meetings, and Conferences. For example, a user's name tag can be scanned, their face run through a facial recognition system, or their spoken name searched in database to obtain biographical information. Scanned name tags, faces, and conversations may be recorded for subsequent viewing or filing.

In an embodiment, a "Mode" may be entered by the eyepiece. In the mode, certain applications may be available. For example, a consumer version of the eyepiece may have a Tourist Mode, Educational Mode, Internet Mode, TV Mode, Gaming Mode, Exercise Mode, Stylist Mode, Personal Assistant Mode, and the like.

A user of the augmented reality glasses may wish to participate in video calling or video conferencing while wearing the glasses. Many computers, both desktop and laptop have integrated cameras to facilitate using video calling and conferencing. Typically, software applications are used to integrate use of the camera with calling or conferencing features. With the augmented reality glasses providing much of the functionality of laptops and other computing devices, many users may wish to utilize video calling and video conferencing while on the move wearing the augmented reality glasses.

In an embodiment, a video calling or video conferencing application may work with a WiFi connection, or may be part of a 3G or 4G calling network associated with a user's cell phone. The camera for video calling or conferencing is placed on a device controller, such as a watch or other separate electronic computing device. Placing the video calling or conferencing camera on the augmented reality glasses is not feasible, as such placement would provide the user with a view only of themselves, and would not display the other participants in the conference or call. However, the user may choose to use the forward-facing camera to display their surroundings or another individual in the video call.

FIG. 32 depicts a typical camera 3200 for use in video calling or conferencing. Such cameras are typically small and could be mounted on a watch 3202, as shown in FIG. 32, cell phone or other portable computing device, including a laptop computer. Video calling works by connecting the device controller with the cell phone or other communications device. The devices utilize software compatible with the operating system of the glasses and the communications device or computing device. In an embodiment, the screen of the augmented reality glasses may display a list of options for making the call and the user may gesture using a pointing control device or use any other control technique described herein to select the video calling option on the screen of the augmented reality glasses.

FIG. 33 illustrates an embodiment 3300 of a block diagram of a video-calling camera. The camera incorporates a lens 3302, a CCD/CMOS sensor 3304, analog to digital converters for video signals, 3306, and audio signals, 3314. Microphone 3312 collects audio input. Both analog to digital converters 3306 and 3314 send their output signals to a signal enhancement module 3308. The signal enhancement module 3308 forwards the enhanced signal, which is a composite of both video and audio signals to interface 3310. Interface 3310 is connected to an IEEE 1394 standard bus interface, along with a control module 3316.

In operation, the video call camera depends on the signal capture which transforms the incident light, as well as incident sound into electrons. For light this process is performed by CCD or CMOS chip 3304. The microphone transforms sound into electrical impulses.

The first step in the process of generating an image for a video call is to digitize the image. The CCD or CMOS chip 3304 dissects the image and converts it into pixels. If a pixel has collected many photons, the voltage will be high. If the pixel has collected few photons, the voltage will be low. This voltage is an analog value. During the second step of digitization, the voltage is transformed into a digital value by the analog to digital converter 3306, which handles image processing. At this point, a raw digital image is available.

Audio captured by the microphone 3312 is also transformed into a voltage. This voltage is sent to the analog to digital converter 3314 where the analog values are transformed into digital values.

The next step is to enhance the signal so that it may be sent to viewers of the video call or conference. Signal enhancement includes creating color in the image using a color filter, located in front of the CCD or CMOS chip 3304. This filter is red, green, or blue and changes its color from pixel to pixel, and in an embodiment, may be a color filter array, or Bayer filter. These raw digital images are then enhanced by the filter to meet aesthetic requirements. Audio data may also be enhanced for a better calling experience.

In the final step before transmission, the image and audio data are compressed and output as a digital video stream, in an embodiment using a digital video camera. If a photo camera is used, single images may be output, and in a further embodiment, voice comments may be appended to the files. The enhancement of the raw digital data takes place away from the camera, and in an embodiment may occur in the device controller or computing device that the augmented reality glasses communicate with during a video call or conference.

Further embodiments may provide for portable cameras for use in industry, medicine, astronomy, microscopy, and other fields requiring specialized camera use. These cameras often forgo signal enhancement and output the raw digital image. These cameras may be mounted on other electronic devices or the user's hand for ease of use.

The camera interfaces to the augmented reality glasses and the device controller or computing device using an IEEE 1394 interface bus. This interface bus transmits time critical data, such as a video and data whose integrity is critically important, including parameters or files to manipulate data or transfer images.

In addition to the interface bus, protocols define the behavior of the devices associated with the video call or conference. The camera for use with the augmented reality glasses, may, in embodiments, employ one of the following protocols: AV/C, DCAM, or SBP-2.

AV/C is a protocol for Audio Video Control and defines the behavior of digital video devices, including video cameras and video recorders.

DCAM refers to the 1394 based Digital Camera Specification and defines the behavior of cameras that output uncompressed image data without audio.

SBP-2 refers to Serial Bus Protocol and defines the behavior of mass storage devices, such as hard drives or disks.

Devices that use the same protocol are able to communicate with each other. Thus, for video calling using the augmented reality glasses, the same protocol may be used by the video camera on the device controller and the augmented reality glasses. Because the augmented reality glasses, device controller, and camera use the same protocol, data may be exchanged among these devices. Files that may be transferred among devices include: image and audio files, image and audio data flows, parameters to control the camera, and the like.

In an embodiment, a user desiring to initiate a video call may select a video call option from a screen presented when the call process is initiated. The user selects by making a gesture using a pointing device, or gesture to signal the selection of the video call option. The user then positions the camera located on the device controller, wristwatch, or other separable electronic device so that the user's image is captured by the camera. The image is processed through the process described above and is then streamed to the augmented reality glasses and the other participants for display to the users.

In embodiments, the camera may be mounted on a cell phone, personal digital assistant, wristwatch, pendant, or other small portable device capable of being carried, worn, or mounted. The images or video captured by the camera may be streamed to the eyepiece. For example, when a camera is mounted on a rifle, a wearer may be able to image targets not in the line of sight and wirelessly receive imagery as a stream of displayed content to the eyepiece.

In embodiments, the present disclosure may provide the wearer with GPS-based content reception, as in FIG. 6. As noted, augmented reality glasses of the present disclosure may include memory, a global positioning system, a compass or other orienting device, and a camera. GPS-based computer programs available to the wearer may include a number of applications typically available from the Apple Inc. App Store for iPhone use. Similar versions of these programs are available for other brands of smart phone and may be applied to embodiments of the present disclosure. These programs include, for example, SREngine (scene recognition engine), NearestTube, TAT Augmented ID, Yelp, Layar, and TwittARound, as well as other more specialized applications, such as RealSki.

SREngine is a scene recognition engine that is able to identify objects viewed by the user's camera. It is a software engine able to recognize static scenes, such as scenes of architecture, structures, pictures, objects, rooms, and the like. It is then able to automatically apply a virtual "label" to the structures or objects according to what it recognizes. For example, the program may be called up by a user of the present disclosure when viewing a street scene, such as FIG. 6. Using a camera of the augmented reality glasses, the engine will recognize the Fontaines de la Concorde in Paris. The program will then summon a virtual label, shown in FIG. 6 as part of a virtual image 618 projected onto the lens 602. The label may be text only, as seen at the bottom of the image 618. Other labels applicable to this scene may include "fountain," "museum," "hotel," or the name of the columned building in the rear. Other programs of this type may include the Wikitude Ark. Travel Guide, Yelp and many others.

NearestTube, for example, uses the same technology to direct a user to the closest subway station in London, and other programs may perform the same function, or similar, in other cities. Layar is another application that uses the camera, a compass or direction, and GPS data to identify a user's location and field of view. With this information, an overlay or label may appear virtually to help orient and guide the user. Yelp and Monocle perform similar functions, but their databases are somewhat more specialized, helping to direct users in a similar manner to restaurants or to other service providers.

The user may control the glasses, and call up these functions, using any of the controls described in this patent. For example, the glasses may be equipped with a microphone to pick up voice commands from a user and process them using software contained with a memory of the glasses. The user may then respond to prompts from small speakers or earbuds also contained within the glasses frame. The glasses may also be equipped with a tiny track pad, similar to those found on smartphones. The trackpad may allow a user to move a pointer or indicator on the virtual screen within the AR glasses, similar to a touch screen. When the user reaches a desired point on the screen, the user depresses the track pad to indicate his or her selection. Thus, a user may call up a program, e.g., a travel guide, and then find his or her way through several menus, perhaps selecting a country, a city and then a category. The category selections may include, for example, hotels, shopping, museums, restaurants, and so forth. The user makes his or her selections and is then guided by the AR program. In one embodiment, the glasses also include a GPS locator, and the present country and city provides default locations that may be overridden.

In an embodiment, the eyepiece's object recognition software may process the images being received by the eyepiece's forward facing camera in order to determine what is in the field of view. In other embodiments, the GPS coordinates of the location as determined by the eyepiece's GPS may be enough to determine what is in the field of view. In other embodiments, an RFID or other beacon in the environment may be broadcasting a location. Any one or combination of the above may be used by the eyepiece to identify the location and the identity of what is in the field of view.

When an object is recognized, the resolution for imaging that object may be increased or images or video may be captured at low compression. Additionally, the resolution for other objects in the user's view may be decreased, or captured at a higher compression rate in order to decrease the needed bandwidth.

Once determined, content related to points of interest in the field of view may be overlaid on the real world image, such as social networking content, interactive tours, local information, and the like. Information and content related to movies, local information, weather, restaurants, restaurant availability, local events, local taxis, music, and the like may be accessed by the eyepiece and projected on to the lens of the eyepiece for the user to view and interact with. For example, as the user looks at the Eiffel Tower, the forward facing camera may take an image and send it for processing to the eyepiece's associated processor. Object recognition software may determine that the structure in the wearer's field of view is the Eiffel Tower. Alternatively, the GPS coordinates determined by the eyepiece's GPS may be searched in a database to determine that the coordinates match those of the Eiffel Tower. In any event, content may then be searched relating to the Eiffel Tower visitor's information, restaurants in the vicinity and in the Tower itself, local weather, local Metro information, local hotel information, other nearby tourist spots, and the like. Interacting with the content may be enabled by the control mechanisms described herein. In an embodiment, GPS-based content reception may be enabled when a Tourist Mode of the eyepiece is entered.

In an embodiment, the eyepiece may be used to view streaming video. For example, videos may be identified via search by GPS location, search by object recognition of an object in the field of view, a voice search, a holographic keyboard search, and the like. Continuing with the example of the Eiffel Tower, a video database may be searched via the GPS coordinates of the Tower or by the term 'Eiffel Tower' once it has been determined that is the structure in the field of view. Search results may include geo-tagged videos or videos associated with the Eiffel Tower. The videos may be scrolled or flipped through using the control techniques described herein. Videos of interest may be played using the control techniques described herein. The video may be laid over the real world scene or may be displayed on the lens out of the field of view. In an embodiment, the eyepiece may be darkened via the mechanisms described herein to enable higher contrast viewing. In another example, the eyepiece may be able to utilize a camera and network connectivity, such as described herein, to provide the wearer with streaming video conferencing capabilities. The streamed video could be video of at least one other video conference participant, a visual presentation, or the like. The streamed video could be automatically uploaded upon capture to a video storage location, without interaction by the user of the eyepiece. The streamed video could be uploaded to a physical or virtual storage location. The virtual storage location could be located at a single physical location or a cloud storage location. The streamed video of the video conference could also be modified by the eyepiece, where the modification could be based on a sensor input. The sensor input could be a visual sensor input or an audio sensor input. The visual sensor input could be an image of another participant of the video conference, a visual presentation, or the like. The audio sensor input could be the voice of a particular participant of the video conference.

In embodiments, the eyepiece may provide for an interface to accept wireless streaming media (e.g. video, audio, text messaging, phone call and calendar alerts) from an external facility, such as a smart phone, a tablet, a personal computer, an entertainment device, a portable music and video device, a home theater system, a home entertainment system, another eyepiece, and the like. The wireless streaming media may be through any of the wireless communication systems and protocols know in the art, such as Bluetooth, WiFi, wireless home network connection, wireless local area network (WLAN), wireless home digital interface (WHDI), cellular mobile telecommunications, and the like. The eyepiece may also use multiple wireless communications systems, such as one for streaming high data rate media (e.g. video), one for low data rate media (e.g. text messaging), one for command data between the external facility and the eyepiece, and the like. For example, high data rate video could be streamed via a WiFi DLNA (Digital Living Network Alliance) interface, and Bluetooth for low data rate applications, such as text messaging. In embodiments, the external facility may be provided with an application to support the interface with the eyepiece. For example, a mobile application may be made available to the user for interfacing their smart phone with the eyepiece. In embodiments, the external facility may be provided with a transmission facility to interface with the eyepiece. For example, a transmitter dongle could be provided to interface the user's smart phone to the eyepiece. Because streaming of media from an external device may place much of the processing requirements onto the external device, the eyepiece may require less on-board processing capabilities to accommodate the streaming media. For instance, an embodiment of the eyepiece for accommodating streaming media may comprise an interface for accepting the streaming media, buffering data, providing the streaming media to the optical assembly through which the user views a surrounding environment and displayed content, and the like. That is, an embodiment of the eyepiece for accepting streaming media may be a simplified version of other embodiments of the eyepiece as described herein, such as to act as display for the external facility. In an example, a user may be able to stream a video from their smart phone to a 'simplified version' of the eyepiece. However, it will be appreciated by one skilled in the art that any additional functions described herein may also be included to create embodiment versions of the eyepiece that span from the very simplest version of the eyepiece, such as acting solely as a display interface for the external facility, to a version that includes a full range of the capabilities described herein, such as where a wireless streaming interface is but one of the plurality of functions and capabilities provided by the eyepiece. For instance, control techniques, power saving techniques, applications, driving one or both displays with the streaming media, displaying in a 3D mode, and the like, as described herein, may be useful even in the simpler versions of the eyepiece in order to aid in the commanding modes of the streaming media, battery management for increased life, optional media viewing modes, and the like. Alternately, an ultra-simple version of the eyepiece may provide an embodiment that minimizes the cost and complexity of the eyepiece, such as where the interface between the external facility and the eyepiece is a wired interface. For example, an embodiment of the eyepiece may provide a wired interface between a user's smart phone or tablet and the eyepiece, where the processing capabilities of the eyepiece may now be restricted to only that processing required to present the streaming media to the optics assembly for viewing the content on the lens(es) of the eyepiece.

In other embodiments, an app running on a smart phone may act as a remote input device for the glasses. For example, a user interface, such as a keyboard, may allow users to type in characters via the smart phone. The app would make the phone look like a BLUETOOTH keyboard. The app could simply be a full screen blank app that transmits touches to a pseudo touch screen driver running on the glasses, such that the user could do pinch and drags using the smart phone as an actual physical place to do these motions and get tactile feedback to your hands and visual feedback in the glasses. Thus, more generic apps running on the glasses that utilize these types of input gestures could work well with the user using a smart phone touch screen. Command information may be accompanied by a visual indicator. For example, in order to know where your finger is when you are using the external device to control the glasses or a glasses app, a visual indication of the command information may be displayed in the glasses, such as a highlighted trace of the finger's motion. The present disclosure may comprise an interactive head-mounted eyepiece worn by a user, wherein the eyepiece includes an optical assembly through which the user views a surrounding environment and displayed content, and an integrated image source adapted to introduce the content to the optical assembly; an integrated processor; an external device that has a physical user interface and an application to turn the external device into a user interface for the eyepiece operable through the integrated processor, wherein the physical interaction with the external device is indicated in the displayed content. In embodiments, the external device may be a smart phone, a tablet, a mobile navigation device, and the like. The physical user interface may be a keypad, a touchpad, a control interface, and the like. For instance, the physical interface may be an iPhone, and the displayed content a virtual keyboard that displays the user's action on the iPhone keypad as actions on a virtual keypad as displayed content on the eyepiece, such as showing highlighted keys, an indication of key depression, and the like, on the virtual keypad as the user's finger action physically interacts with the iPhone's physical keypad. The finger action may be one of a selection of content and movement of displayed content. The manipulation may be a multiple finger action on the touch pad, such as a pinch manipulation to resize the displayed content on the eyepiece.

As noted, the user of augmented reality may receive content from an abundance of sources. A visitor or tourist may desire to limit the choices to local businesses or institutions; on the other hand, businesses seeking out visitors or tourists may wish to limit their offers or solicitations to persons who are in their area or location but who are visiting rather than local residents. Thus, in one embodiment, the visitor or tourist may limit his or her search only to local businesses, say those within certain geographic limits. These limits may be set via GPS criteria or by manually indicating a geographic restriction. For example, a person may require that sources of streaming content or ads be limited to those within a certain radius (a set number or km or miles) of the person. Alternatively, the criteria may require that the sources are limited to those within a certain city or province. These limits may be set by the augmented reality user just as a user of a computer at a home or office would limit his or her searches using a keyboard or a mouse; the entries for augmented reality users are simply made by voice, by hand motion, or other ways described elsewhere in the portions of this disclosure discussing controls.

In addition, the available content chosen by a user may be restricted or limited by the type of provider. For example, a user may restrict choices to those with a website operated by a government institution (.gov) or by a non-profit institution or organization (.org). In this way, a tourist or visitor who may be more interested in visiting government offices, museums, historical sites and the like, may find his or her choices less cluttered. The person may be more easily able to make decisions when the available choices have been pared down to a more reasonable number. The ability to quickly cut down the available choices is desirable in more urban areas, such as Paris or Washington, D.C., where there are many choices.

The user controls the glasses in any of the manners or modes described elsewhere in this patent. For example, the user may call up a desired program or application by voice or by indicating a choice on the virtual screen of the augmented reality glasses. The augmented glasses may respond to a track pad mounted on the frame of the glasses, as described above. Alternatively, the glasses may be responsive to one or more motion or position sensors mounted on the frame. The signals from the sensors are then sent to a microprocessor or microcontroller within the glasses, the glasses also providing any needed signal transducing or processing. Once the program of choice has begun, the user makes selections and enters a response by any of the methods discussed herein, such as signaling "yes" or "no" with a head movement, a hand gesture, a trackpad depression, or a voice command.

At the same time, content providers, that is, advertisers, may also wish to restrict their offerings to persons who are within a certain geographic area, e.g., their city limits. At the same time, an advertiser, perhaps a museum, may not wish to offer content to local persons, but may wish to reach visitors or out-of-towners. In another example, advertisements may not be presented when the user is home but may be presented when the user is traveling or away from home. The augmented reality devices discussed herein are desirably equipped with both GPS capability and telecommunications capability and an integrated processor for implementing geographic-based rules for advertisement presentation. It will be a simple matter for the museum to provide streaming content within a limited area by limiting its broadcast power. The museum, however, may provide the content through the Internet and its content may be available world-wide. In this instance, a user may receive content through an augmented reality device advising that the museum is open today and is available for touring.

The user may respond to the content by the augmented reality equivalent of clicking on a link for the museum. The augmented reality equivalent may be a voice indication, a hand or eye movement, or other sensory indication of the user's choice, or by using an associated body-mounted controller. The museum then receives a cookie indicating the identity of the user or at least the user's internet service provider (ISP). If the cookie indicates or suggests an internet service provider other than local providers, the museum server may then respond with advertisements or offers tailored to visitors. The cookie may also include an indication of a telecommunications link, e.g., a telephone number. If the telephone number is not a local number, this is an additional clue that the person responding is a visitor. The museum or other institution may then follow up with the content desired or suggested by its marketing department.

Another application of the augmented reality eyepiece takes advantage of a user's ability to control the eyepiece and its tools with a minimum use of the user's hands, using instead voice commands, gestures or motions. As noted above, a user may call upon the augmented reality eyepiece to retrieve information. This information may already be stored in a memory of the eyepiece, but may instead be located remotely, such as a database accessible over the Internet or perhaps via an intranet which is accessible only to employees of a particular company or organization. The eyepiece may thus be compared to a computer or to a display screen which can be viewed and heard at an extremely close range and generally controlled with a minimal use of one's hands.

Applications may thus include providing information on-the-spot to a mechanic or electronics technician. The technician can don the glasses when seeking information about a particular structure or problem encountered, for example, when repairing an engine or a power supply. Using voice commands, he or she may then access the database and search within the database for particular information, such as manuals or other repair and maintenance documents. The desired information may thus be promptly accessed and applied with a minimum of effort, allowing the technician to more quickly perform the needed repair or maintenance and to return the equipment to service. For mission-critical equipment, such time savings may also save lives, in addition to saving repair or maintenance costs.

The information imparted may include repair manuals and the like, but may also include a full range of audio-visual information, i.e., the eyepiece screen may display to the technician or mechanic a video of how to perform a particular task at the same time the person is attempting to perform the task. The augmented reality device also includes telecommunications capabilities, so the technician also has the ability to call on others to assist if there is some complication or unexpected difficulty with the task. This educational aspect of the present disclosure is not limited to maintenance and repair, but may be applied to any educational endeavor, such as secondary or post-secondary classes, continuing education courses or topics, seminars, and the like.

In an embodiment, a Wi-Fi enabled eyepiece may run a location-based application for geo-location of opted-in users. Users may opt-in by logging into the application on their phone and enabling broadcast of their location, or by enabling geo-location on their own eyepiece. As a wearer of the eyepiece scans people, and thus their opted-in device, the application may identify opted-in users and send an instruction to the projector to project an augmented reality indicator on an opted-in user in the user's field of view. For example, green rings may be placed around people who have opted-in to have their location seen. In another example, yellow rings may indicate people who have opted-in but don't meet some criteria, such as they do not have a FACEBOOK account, or that there are no mutual friends if they do have a FACEBOOK account.

Figure 16:
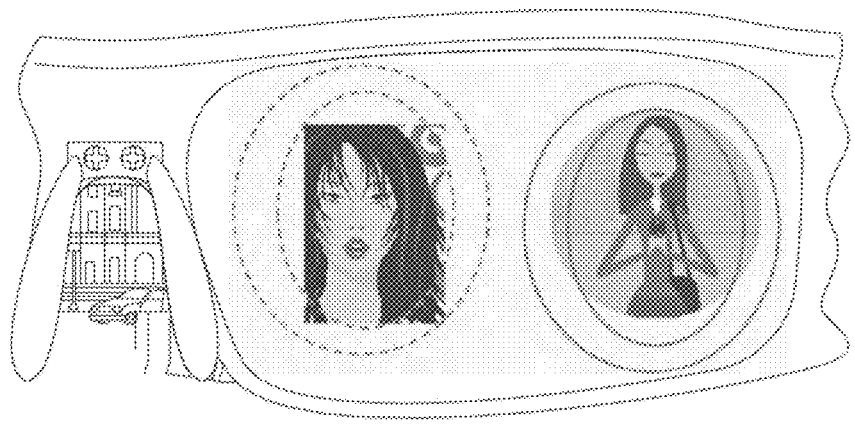
FIG. 16 depicts a location-based application mode of the eyepiece.

Some social networking, career networking, and dating applications may work in concert with the location-based application. Software resident on the eyepiece may coordinate data from the networking and dating sites and the location-based application. For example, TwittARound is one such program which makes use of a mounted camera to detect and label location-stamped tweets from other tweeters nearby. This will enable a person using the present disclosure to locate other nearby Twitter users. Alternatively, users may have to set their devices to coordinate information from various networking and dating sites. For example, the wearer of the eyepiece may want to see all E-HARMONY users who are broadcasting their location. If an opted-in user is identified by the eyepiece, an augmented reality indicator may be laid over the opted-in user. The indicator may take on a different appearance if the user has something in common with the wearer, many things in common with the user, and the like. For example, and referring to FIG. 16, two people are being viewed by the wearer. Both of the people are identified as E-HARMONY users by the rings placed around them. However, the woman shown with solid rings has more than one item in common with the wearer while the woman shown with dotted rings has no items in common with the wearer. Any available profile information may get accessed and displayed to the user.

In an embodiment, when the wearer directs the eyepiece in the direction of a user who has a networking account, such as FACEBOOK, TWITTER, BLIPPY, LINKEDIN, GOGGLE, WIKIPEDIA, and the like, the user's recent posts or profile information may be displayed to the wearer. For example, recent status updates, "tweets", "blips", and the like may get displayed, as mentioned above for TwittARound. In an embodiment, when the wearer points the eyepiece in a target user's direction, they may indicate interest in the user if the eyepiece is pointed for a duration of time and/or a gesture, head, eye, or audio control is activated. The target user may receive an indication of interest on their phone or in their glasses. If the target user had marked the wearer as interesting but was waiting on the wearer to show interest first, an indication may immediately pop up in the eyepiece of the target user's interest. A control mechanism may be used to capture an image and store the target user's information on associated non-volatile memory or in an online account.

In other applications for social networking, a facial recognition program, such as TAT Augmented ID, from TAT—The Astonishing Tribe, Malmo, Sweden, may be used. Such a program may be used to identify a person by his or her facial characteristics. This software uses facial recognition software to identify a person. Using other applications, such as photo identifying software from Filch, one can then identify the particular nearby person, and one can then download information from social networking sites with information about the person. This information may include the person's name and the profile the person has made available on sites such as Facebook, Twitter, and the like. This application may be used to refresh a user's memory of a person or to identify a nearby person, as well as to gather information about the person.

In other applications for social networking, the wearer may be able to utilize location-based facilities of the eyepiece to leave notes, comments, reviews, and the like, at locations, in association with people, places, products, and the like. For example, a person may be able to post a comment on a place they visited, where the posting may then be made available to others through the social network. In another example, a person may be able to post that comment at the location of the place such that the comment is available when another person comes to that location. In this way, a wearer may be able to access comments left by others when they come to the location. For instance, a wearer may come to the entrance to a restaurant, and be able to access reviews for the restaurant, such as sorted by some criteria (e.g. most recent review, age of reviewer, and the like).

A user may initiate the desired program by voice, by selecting a choice from a virtual touchscreen, as described above, by using a trackpad to select and choose the desired program, or by any of the control techniques described herein. Menu selections may then be made in a similar or complementary manner. Sensors or input devices mounted in convenient locations on the user's body may also be used, e.g., sensors and a track pad mounted on a wrist pad, on a glove, or even a discreet device, perhaps of the size of a smart phone or a personal digital assistant.

Applications of the present disclosure may provide the wearer with Internet access, such as for browsing, searching, shopping, entertainment, and the like, such as through a wireless communications interface to the eyepiece. For instance, a wearer may initiate a web search with a control gesture, such as through a control facility worn on some portion of the wearer's body (e.g. on the hand, the head, the foot), on some component being used by the wearer (e.g. a personal computer, a smart phone, a music player), on a piece of furniture near the wearer (e.g. a chair, a desk, a table, a lamp), and the like, where the image of the web search is projected for viewing by the wearer through the eyepiece. The wearer may then view the search through the eyepiece and control web interaction though the control facility.

In an example, a user may be wearing an embodiment configured as a pair of glasses, with the projected image of an Internet web browser provided through the glasses while retaining the ability to simultaneously view at least portions of the surrounding real environment. In this instance, the user may be wearing a motion sensitive control facility on their hand, where the control facility may transmit relative motion of the user's hand to the eyepiece as control motions for web control, such as similar to that of a mouse in a conventional personal computer configuration. It is understood that the user would be enabled to perform web actions in a similar fashion to that of a conventional personal computer configuration. In this case, the image of the web search is provided through the eyepiece while control for selection of actions to carry out the search is provided though motions of the hand. For instance, the overall motion of the hand may move a cursor within the projected image of the web search, the flick of the finger(s) may provide a selection action, and so forth. In this way, the wearer may be enabled to perform the desired web search, or any other Internet browser-enabled function, through an embodiment connected to the Internet. In one example, a user may have downloaded computer programs Yelp or Monocle, available from the App Store, or a similar product, such as NRU ("near you"), an application from Zagat to locate nearby restaurants or other stores, Google Earth, Wikipedia, or the like. The person may initiate a search, for example, for restaurants, or other providers of goods or services, such as hotels, repairmen, and the like, or information. When the desired information is found, locations are displayed or a distance and direction to a desired location is displayed. The display may take the form of a virtual label co-located with the real world object in the user's view.

Other applications from Layar (Amsterdam, the Netherlands) include a variety of "layers" tailored for specific information desired by a user. A layer may include restaurant information, information about a specific company, real estate listings, gas stations, and so forth. Using the information provided in a software application, such as a mobile application and a user's global positioning system (GPS), information may be presented on a screen of the glasses with tags having the desired information. Using the haptic controls or other control discussed elsewhere in this disclosure, a user may pivot or otherwise rotate his or her body and view buildings tagged with virtual tags containing information. If the user seeks restaurants, the screen will display restaurant information, such as name and location. If a user seeks a particular address, virtual tags will appear on buildings in the field of view of the wearer. The user may then make selections or choices by voice, by trackpad, by virtual touch screen, and so forth.

Applications of the present disclosure may provide a way for advertisements to be delivered to the wearer. For example, advertisements may be displayed to the viewer through the eyepiece as the viewer is going about his or her day, while browsing the Internet, conducting a web search, walking through a store, and the like. For instance, the user may be performing a web search, and through the web search the user is targeted with an advertisement. In this example, the advertisement may be projected in the same space as the projected web search, floating off to the side, above, or below the view angle of the wearer. In another example, advertisements may be triggered for delivery to the eyepiece when some advertising providing facility, perhaps one in proximity to the wearer, senses the presence of the eyepiece (e.g. through a wireless connection, RFID, and the like), and directs the advertisement to the eyepiece. In embodiments, the eyepiece may be used for tracking of advertisement interactions, such as the user seeing or interacting with a billboard, a promotion, an advertisement, and the like. For instance, user's behavior with respect to advertisements may be tracked, such as to provide benefits, rewards, and the like to the user. In an example, the user may be paid five dollars in virtual cash whenever they see a billboard. The eyepiece may provide impression tracking, such as based on seeing branded images (e.g. based on time, geography), and the like. As a result, offers may be targeted based on the location and the event related to the eyepiece, such as what the user saw, heard, interacted with, and the like. In embodiments, ad targeting may be based on historical behavior, such as based on what the user has interacted with in the past, patterns of interactions, and the like.

For example, the wearer may be window-shopping in Manhattan, where stores are equipped with such advertising providing facilities. As the wearer walks by the stores, the advertising providing facilities may trigger the delivery of an advertisement to the wearer based on a known location of the user determined by an integrated location sensor of the eyepiece, such as a GPS. In an embodiment, the location of the user may be further refined via other integrated sensors, such as a magnetometer to enable hyperlocal augmented reality advertising. For example, a user on a ground floor of a mall may receive certain advertisements if the magnetometer and GPS readings place the user in front of a particular store. When the user goes up one flight in the mall, the GPS location may remain the same, but the magnetometer reading may indicate a change in elevation of the user and a new placement of the user in front of a different store. In embodiments, one may store personal profile information such that the advertising providing facility is able to better match advertisements to the needs of the wearer, the wearer may provide preferences for advertisements, the wearer may block at least some of the advertisements, and the like. The wearer may also be able to pass advertisements, and associated discounts, on to friends. The wearer may communicate them directly to friends that are in close proximity and enabled with their own eyepiece; they may also communicate them through a wireless Internet connection, such as to a social network of friends, though email, SMS; and the like. The wearer may be connected to facilities and/or infrastructure that enables the communication of advertisements from a sponsor to the wearer; feedback from the wearer to an advertisement facility, the sponsor of the advertisement, and the like; to other users, such as friends and family, or someone in proximity to the wearer; to a store, such as locally on the eyepiece or in a remote site, such as on the Internet or on a user's home computer; and the like. These interconnectivity facilities may include integrated facilities to the eyepiece to provide the user's location and gaze direction, such as through the use of GPS, 3-axis sensors, magnetometer, gyros, accelerometers, and the like, for determining direction, speed, attitude (e.g. gaze direction) of the wearer. Interconnectivity facilities may provide telecommunications facilities, such as cellular link, a WiFi/MiFi bridge, and the like. For instance, the wearer may be able to communicate through an available WiFi link, through an integrated MiFi (or any other personal or group cellular link) to the cellular system, and the like. There may be facilities for the wearer to store advertisements for a later use. There may be facilities integrated with the wearer's eyepiece or located in local computer facilities that enable caching of advertisements, such as within a local area, where the cached advertisements may enable the delivery of the advertisements as the wearer nears the location associated with the advertisement. For example, local advertisements may be stored on a server that contains geo-located local advertisements and specials, and these advertisements may be delivered to the wearer individually as the wearer approaches a particular location, or a set of advertisements may be delivered to the wearer in bulk when the wearer enters a geographic area that is associated with the advertisements so that the advertisements are available when the user nears a particular location. The geographic location may be a city, a part of the city, a number of blocks, a single block, a street, a portion of the street, sidewalk, and the like, representing regional, local, hyper-local areas. Note that the preceding discussion uses the term advertisement, but one skilled in the art will appreciate that this can also mean an announcement, a broadcast, a circular, a commercial, a sponsored communication, an endorsement, a notice, a promotion, a bulletin, a message, and the like.

Figure 18:
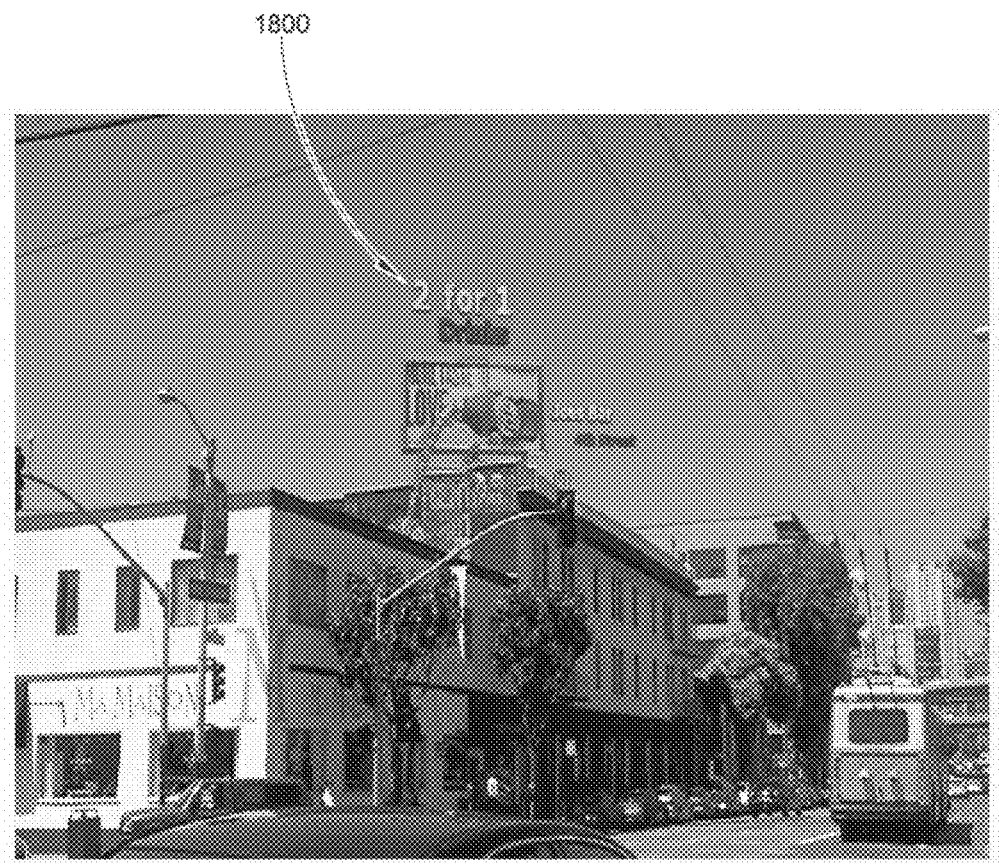
FIG. 18 depicts an augmented reality-enabled custom billboard.

FIGS. 18-20A depict ways to deliver custom messages to persons within a short distance of an establishment that wishes to send a message, such as a retail store. Referring to FIG. 18 now, embodiments may provide for a way to view custom billboards, such as when the wearer of the eyepiece is walking or driving, by applications as mentioned above for searching for providers of goods and services. As depicted in FIG. 18, the billboard 1800 shows an exemplary augmented reality-based advertisement displayed by a seller or a service provider. The exemplary advertisement, as depicted, may relate to an offer on drinks by a bar. For example, two drinks may be provided for the cost of just one drink. With such augmented reality-based advertisements and offers, the wearer's attention may be easily directed towards the billboards. The billboards may also provide details about location of the bar such as street address, floor number, phone number, and the like. In accordance with other embodiments, several devices other than eyepiece may be utilized to view the billboards. These devices may include without limitations smart phones, IPHONEs, IPADs, car windshields, user glasses, helmets, wristwatches, headphones, vehicle mounts, and the like. In accordance with an embodiment, a user (wearer in case the augmented reality technology is embedded in the eyepiece) may automatically receive offers or view a scene of the billboards as and when the user passes or drives by the road. In accordance with another embodiment, the user may receive offers or view the scene of the billboards based on his request.

Figure 19:
FIG. 19 depicts an augmented reality-enabled custom advertisement.

FIG. 19 illustrates two exemplary roadside billboards 1900 containing offers and advertisements from sellers or service providers that may be viewed in the augmented reality manner. The augmented advertisement may provide a live and near-to-reality perception to the user or the wearer.

Figure 20:
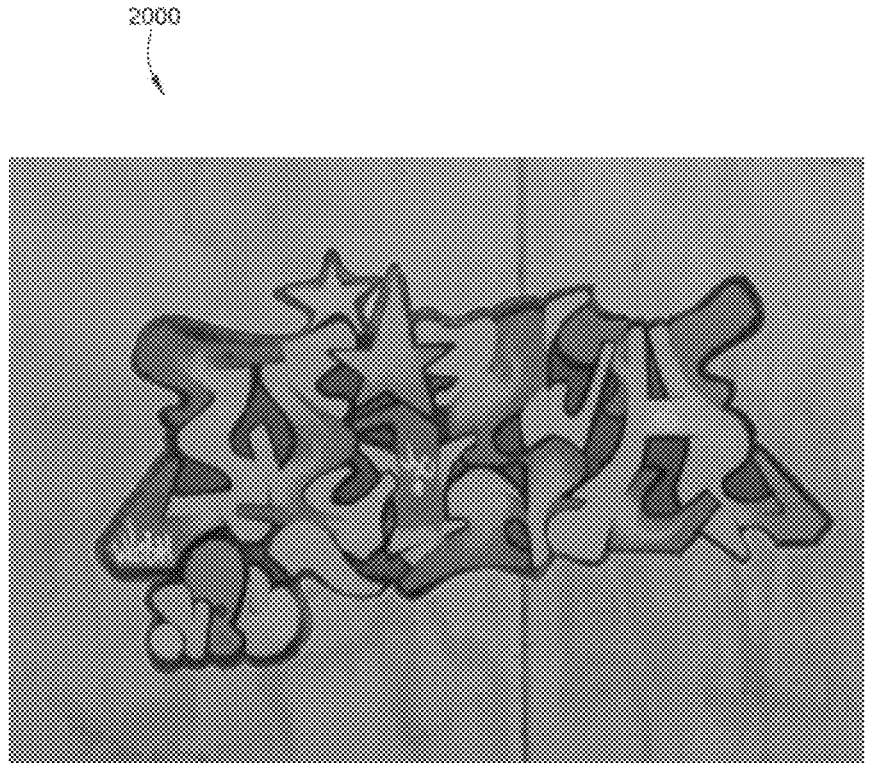
FIG. 20 an augmented reality-enabled custom artwork.
Figure 20A:
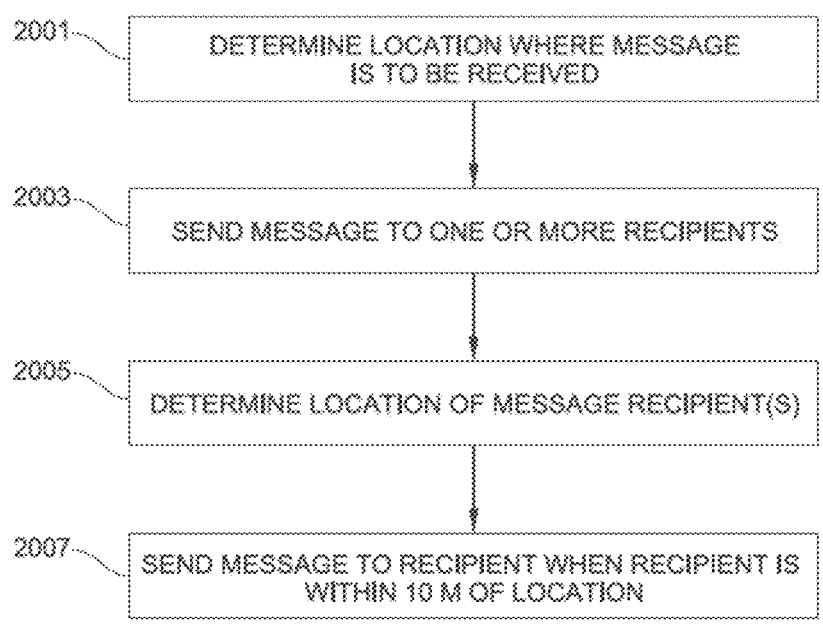
FIG. 20A depicts a method for posting messages to be transmitted when a viewer reaches a certain location.

As illustrated in FIG. 20, the augmented reality enabled device such as the camera lens provided in the eyepiece may be utilized to receive and/or view graffiti 2000, slogans, drawings, and the like, that may be displayed on the roadside or on top, side, front of the buildings and shops. The roadside billboards and the graffiti may have a visual (e.g. a code, a shape) or wireless indicator that may link the advertisement, or advertisement database, to the billboard. When the wearer nears and views the billboard, a projection of the billboard advertisement may then be provided to the wearer. In embodiments, one may also store personal profile information such that the advertisements may better match the needs of the wearer, the wearer may provide preferences for advertisements, the wearer may block at least some of the advertisements, and the like. In embodiments, the eyepiece may have brightness and contrast control over the eyepiece projected area of the billboard so as to improve readability for the advertisement, such as in a bright outside environment.

In other embodiments, users may post information or messages on a particular location, based on its GPS location or other indicator of location, such as a magnetometer reading. The intended viewer is able to see the message when the viewer is within a certain distance of the location, as explained with FIG. 20A. In a first step 2001 of the method FIG. 20A, a user decides the location where the message is to be received by persons to whom the message is sent. The message is then posted 2003, to be sent to the appropriate person or persons when the recipient is close to the intended "viewing area." Location of the wearers of the augmented reality eyepiece is continuously updated 2005 by the GPS system which forms a part of the eyepiece. When the GPS system determines that the wearer is within a certain distance of the desired viewing area, e.g., 10 meters, the message is then sent 2007 to the viewer. In one embodiment, the message then appears as e-mail or a text message to the recipient, or if the recipient is wearing an eyepiece, the message may appear in the eyepiece. Because the message is sent to the person based on the person's location, in one sense, the message may be displayed as "graffiti" on a building or feature at or near the specified location. Specific settings may be used to determine if all passersby to the "viewing area" can see the message or if only a specific person or group of people or devices with specific identifiers. For example, a soldier clearing a village may virtually mark a house as cleared by associating a message or identifier with the house, such as a big X marking the location of the house. The soldier may indicate that only other American soldiers may be able to receive the location-based content. When other American soldiers pass the house, they may receive an indication automatically, such as by seeing the virtual 'X' on the side of the house if they have an eyepiece or some other augmented reality-enabled device, or by receiving a message indicating that the house has been cleared. In another example, content related to safety applications may be streamed to the eyepiece, such as alerts, target identification, communications, and the like.

Embodiments may provide for a way to view information associated with products, such as in a store. Information may include nutritional information for food products, care instructions for clothing products, technical specifications for consumer electronics products, e-coupons, promotions, price comparisons with other like products, price comparisons with other stores, and the like. This information may be projected in relative position with the product, to the periphery of sight to the wearer, in relation to the store layout, and the like. The product may be identified visually through a SKU, a brand tag, and the like; transmitted by the product packaging, such as through an RFID tag on the product; transmitted by the store, such as based on the wearer's position in the store, in relative position to the products; and the like.

For example, a viewer may be walking through a clothing store, and as they walk are provided with information on the clothes on the rack, where the information is provided through the product's RFID tag. In embodiments, the information may be delivered as a list of information, as a graphic representation, as audio and/or video presentation, and the like. In another example, the wearer may be food shopping, and advertisement providing facilities may be providing information to the wearer in association with products in the wearer's proximity, the wearer may be provided information when they pick up the product and view the brand, product name, SKU, and the like. In this way, the wearer may be provided a more informative environment in which to effectively shop.

One embodiment may allow a user to receive or share information about shopping or an urban area through the use of the augmented reality enabled devices such as the camera lens fitted in the eyepiece of exemplary sunglasses. These embodiments will use augmented reality (AR) software applications such as those mentioned above in conjunction with searching for providers of goods and services. In one scenario, the wearer of the eyepiece may walk down a street or a market for shopping purposes. Further, the user may activate various modes that may assist in defining user preferences for a particular scenario or environment. For example the user may enter navigation mode through which the wearer may be guided across the streets and the market for shopping of the preferred accessories and products. The mode may be selected and various directions may be given by the wearer through various methods such as through text commands, voice commands, and the like. In an embodiment, the wearer may give a voice command to select the navigation mode which may result in the augmented display in front of the wearer. The augmented information may depict information pertinent to the location of various shops and vendors in the market, offers in various shops and by various vendors, current happy hours, current date and time and the like. Various sorts of options may also be displayed to the wearer. The wearer may scroll the options and walk down the street guided through the navigation mode. Based on options provided, the wearer may select a place that suits him the best for shopping based on such as offers and discounts and the like. In embodiments, the eyepiece may provide the ability to search, browse, select, save, share, receive advertisements, and the like for items of purchase, such as viewed through the eyepiece. For example, the wearer may search for an item across the Internet and make a purchase without making a phone call, such as through an application store, commerce application, and the like.

The wearer may give a voice command to navigate toward the place and the wearer may then be guided toward it. The wearer may also receive advertisements and offers automatically or based on request regarding current deals, promotions and events in the interested location such as a nearby shopping store. The advertisements, deals and offers may appear in proximity of the wearer and options may be displayed for purchasing desired products based on the advertisements, deals and offers. The wearer may for example select a product and purchase it through a Google checkout. A message or an email may appear on the eyepiece, similar to the one depicted in FIG. 7, with information that the transaction for the purchase of the product has been completed. A product delivery status/information may also be displayed. The wearer may further convey or alert friends and relatives regarding the offers and events through social networking platforms and may also ask them to join.

In embodiments, the user may wear the head-mounted eyepiece wherein the eyepiece includes an optical assembly through which the user may view a surrounding environment and displayed content. The displayed content may comprise one or more local advertisements. The location of the eyepiece may be determined by an integrated location sensor and the local advertisement may have a relevance to the location of the eyepiece. By way of example, the user's location may be determined via GPS, RFID, manual input, and the like. Further, the user may be walking by a coffee shop, and based on the user's proximity to the shop, an advertisement, similar to that depicted in FIG. 19, showing the store's brand 1900, such as the band for a fast food restaurant or coffee may appear in the user's field of view. The user may experience similar types of local advertisements as he or she moves about the surrounding environment.

In other embodiments, the eyepiece may contain a capacitive sensor capable of sensing whether the eyepiece is in contact with human skin. The sensor may be a capacitive sensor, a resistive sensor, an inductive sensor, an electromagnetic field sensor, or the like. Such sensor or group of sensors may be placed on the eyepiece and or eyepiece arm in such a manner that allows detection of when the glasses are being worn by a user. In other embodiments, sensors may be used to determine whether the eyepiece is in a position such that they may be worn by a user, for example, when the earpiece is in the unfolded position. Furthermore, local advertisements may be sent only when the eyepiece is in contact with human skin, in a wearable position, a combination of the two, actually worn by the user and the like. In other embodiments, the local advertisement may be sent in response to the eyepiece being powered on or in response to the eyepiece being powered on and worn by the user and the like. By way of example, an advertiser may choose to only send local advertisements when a user is in proximity to a particular establishment and when the user is actually wearing the glasses and they are powered on allowing the advertiser to target the advertisement to the user at the appropriate time.

In accordance with other embodiments, the local advertisement may be displayed to the user as a banner advertisement, two-dimensional graphic, text and the like. Further, the local advertisement may be associated with a physical aspect of the user's view of the surrounding environment. The local advertisement may also be displayed as an augmented reality advertisement wherein the advertisement is associated with a physical aspect of the surrounding environment. Such advertisement may be two or three-dimensional. By way of example, a local advertisement may be associated with a physical billboard as described further in FIG. 18 wherein the user's attention may be drawn to displayed content showing a beverage being poured from a billboard 1800 onto an actual building in the surrounding environment. The local advertisement may also contain sound that is displayed to the user through an earpiece, audio device or other means. Further, the local advertisement may be animated in embodiments. For example, the user may view the beverage flow from the billboard onto an adjacent building and, optionally, into the surrounding environment. Similarly, an advertisement may display any other type of motion as desired in the advertisement. Additionally, the local advertisement may be displayed as a three-dimensional object that may be associated with or interact with the surrounding environment. In embodiments where the advertisement is associated with an object in the user's view of the surrounding environment, the advertisement may remain associated with or in proximity to the object even as the user turns his head. For example, if an advertisement, such as the coffee cup as described in FIG. 19, is associated with a particular building, the coffee cup advertisement may remain associated with and in place over the building even as the user turns his head to look at another object in his environment.

In other embodiments, local advertisements may be displayed to the user based on a web search conducted by the user where the advertisement is displayed in the content of the web search results. For example, the user may search for "happy hour" as he is walking down the street, and in the content of the search results, a local advertisement may be displayed advertising a local bar's beer prices.

Further, the content of the local advertisement may be determined based on the user's personal information. The user's information may be made available to a web application, an advertising facility and the like. Further, a web application, advertising facility or the user's eyepiece may filter the advertising based on the user's personal information. Generally, for example, a user may store personal information about his likes and dislikes and such information may be used to direct advertising to the user's eyepiece. By way of specific example, the user may store data about his affinity for a local sports team, and as advertisements are made available, those advertisements with his favorite sports team may be given preference and pushed to the user. Similarly, a user's dislikes may be used to exclude certain advertisements from view. In various embodiments, the advertisements may be cashed on a server where the advertisement may be accessed by at least one of an advertising facility, web application and eyepiece and displayed to the user.

In various embodiments, the user may interact with any type of local advertisement in numerous ways. The user may request additional information related to a local advertisement by making at least one action of an eye movement, body movement and other gesture. For example, if an advertisement is displayed to the user, he may wave his hand over the advertisement in his field of view or move his eyes over the advertisement in order to select the particular advertisement to receive more information relating to such advertisement. Moreover, the user may choose to ignore the advertisement by any movement or control technology described herein such as through an eye movement, body movement, other gesture and the like. Further, the user may chose to ignore the advertisement by allowing it to be ignored by default by not selecting the advertisement for further interaction within a given period of time. For example, if the user chooses not to gesture for more information from the advertisement within five seconds of the advertisement being displayed, the advertisement may be ignored by default and disappear from the users view. Furthermore, the user may select to not allow local advertisements to be displayed whereby said user selects such an option on a graphical user interface or by turning such feature off via a control on said eyepiece.

In other embodiments, the eyepiece may include an audio device. Accordingly, the displayed content may comprise a local advertisement and audio such that the user is also able to hear a message or other sound effects as they relate to the local advertisement. By way of example, and referring again to FIG. 18, while the user sees the beer being poured, he will actually be able to hear an audio transmission corresponding to the actions in the advertisement. In this case, the user may hear the bottle open and then the sound of the liquid pouring out of the bottle and onto the rooftop. In yet other embodiments, a descriptive message may be played, or general information may be given as part of the advertisement, or both. In embodiments, any audio may be played as desired for the advertisement.

In accordance with another embodiment, social networking may be facilitated with the use of the augmented reality enabled devices such as a camera lens fitted in the eyepiece. This may be utilized to connect several users or other persons that may not have the augmented reality enabled device together who may share thoughts and ideas with each other. For instance, the wearer of the eyepiece may be sitting in a school campus along with other students. The wearer may connect with and send a message to a first student who may be present in a coffee shop. The wearer may ask the first student regarding persons interested in a particular subject such as environmental economics for example. As other students pass through the field of view of the wearer, the camera lens fitted inside the eyepiece may track and match the students to a networking database such as 'Google me' that may contain public profiles. Profiles of interested and relevant persons from the public database may appear and pop-up in front of the wearer on the eyepiece. Some of the profiles that may not be relevant may either be blocked or appear blocked to the user. The relevant profiles may be highlighted for quick reference of the wearer. The relevant profiles selected by the wearer may be interested in the subject environmental economics and the wearer may also connect with them. Further, they may also be connected with the first student. In this manner, a social network may be established by the wearer with the use of the eyepiece enabled with the feature of the augmented reality. The social networks managed by the wearer and the conversations therein may be saved for future reference.

The present disclosure may be applied in a real estate scenario with the use of the augmented reality enabled devices such as a camera lens fitted in an eyepiece. The wearer, in accordance with this embodiment, may want to get information about a place in which the user may be present at a particular time such as during driving, walking, jogging and the like. The wearer may, for instance, want to understand residential benefits and loss in that place. He may also want to get detailed information about the facilities in that place. Therefore, the wearer may utilize a map such as a Google online map and recognize the real estate that may be available there for lease or purchase. As noted above, the user may receive information about real estate for sale or rent using mobile Internet applications such as Layar. In one such application, information about buildings within the user's field of view is projected onto the inside of the glasses for consideration by the user. Options may be displayed to the wearer on the eyepiece lens for scrolling, such as with a trackpad mounted on a frame of the glasses. The wearer may select and receive information about the selected option. The augmented reality enabled scenes of the selected options may be displayed to the wearer and the wearer may be able to view pictures and take a facility tour in the virtual environment. The wearer may further receive information about real estate agents and fix an appointment with one of those. An email notification or a call notification may also be received on the eyepiece for confirmation of the appointment. If the wearer finds the selected real estate of worth, a deal may be made and that may be purchased by the wearer.

In accordance with another embodiment, customized and sponsored tours and travels may be enhanced through the use of the augmented reality-enabled devices, such as a camera lens fitted in the eyepiece. For instance, the wearer (as a tourist) may arrive in a city such as Paris and wants to receive tourism and sightseeing related information about the place to accordingly plan his visit for the consecutive days during his stay. The wearer may put on his eyepiece or operate any other augmented reality enabled device and give a voice or text command regarding his request. The augmented reality enabled eyepiece may locate wearer position through geo-sensing techniques and decide tourism preferences of the wearer. The eyepiece may receive and display customized information based on the request of the wearer on a screen. The customized tourism information may include information about art galleries and museums, monuments and historical places, shopping complexes, entertainment and nightlife spots, restaurants and bars, most popular tourist destinations and centers/attractions of tourism, most popular local/cultural/regional destinations and attractions, and the like without limitations. Based on user selection of one or more of these categories, the eyepiece may prompt the user with other questions such as time of stay, investment in tourism and the like. The wearer may respond through the voice command and in return receive customized tour information in an order as selected by the wearer. For example the wearer may give a priority to the art galleries over monuments. Accordingly, the information may be made available to the wearer. Further, a map may also appear in front of the wearer with different sets of tour options and with different priority rank such as:

Priority Rank 1: First tour Option (Champs Elyse, Louvre, Rodin, Museum, Famous Café)
Priority Rank 2: Second option
Priority Rank 3: Third Option The wearer, for instance, may select the first option since it is ranked as highest in priority based on wearer indicated preferences. Advertisements related to sponsors may pop up right after selection. Subsequently, a virtual tour may begin in the augmented reality manner that may be very close to the real environment. The wearer may for example take a 30 seconds tour to a vacation special to the Atlantis Resort in the Bahamas. The virtual 3D tour may include a quick look at the rooms, beach, public spaces, parks, facilities, and the like. The wearer may also experience shopping facilities in the area and receive offers and discounts in those places and shops. At the end of the day, the wearer might have experienced a whole day tour sitting in his chamber or hotel. Finally, the wearer may decide and schedule his plan accordingly.

Another embodiment may allow information concerning auto repairs and maintenance services with the use of the augmented reality enabled devices such as a camera lens fitted in the eyepiece. The wearer may receive advertisements related to auto repair shops and dealers by sending a voice command for the request. The request may, for example include a requirement of oil change in the vehicle/car. The eyepiece may receive information from the repair shop and display to the wearer. The eyepiece may pull up a 3D model of the wearer's vehicle and show the amount of oil left in the car through an augmented reality enabled scene/view. The eyepiece may show other relevant information also about the vehicle of the wearer such as maintenance requirements in other parts like brake pads. The wearer may see 3D view of the wearing brake pads and may be interested in getting those repaired or changed. Accordingly, the wearer may schedule an appointment with a vendor to fix the problem via using the integrated wireless communication capability of the eyepiece. The confirmation may be received through an email or an incoming call alert on the eyepiece camera lens.

In accordance with another embodiment, gift shopping may benefit through the use of the augmented reality enabled devices such as a camera lens fitted in the eyepiece. The wearer may post a request for a gift for some occasion through a text or voice command. The eyepiece may prompt the wearer to answer his preferences such as type of gifts, age group of the person to receive the gift, cost range of the gift and the like. Various options may be presented to the user based on the received preferences. For instance, the options presented to the wearer may be: Cookie basket, Wine and cheese basket, Chocolate assortment, Golfer's gift basket, and the like.

The available options may be scrolled by the wearer and the best fit option may be selected via the voice command or text command. For example, the wearer may select the Golfer's gift basket. A 3D view of the Golfer's gift basket along with a golf course may appear in front of the wearer. The virtual 3D view of the Golfer's gift basket and the golf course enabled through the augmented reality may be perceived very close to the real world environment. The wearer may finally respond to the address, location and other similar queries prompted through the eyepiece. A confirmation may then be received through an email or an incoming call alert on the eyepiece camera lens.

In various embodiments, a glasses platform may be used with various control mechanisms and take physical and informational inputs, perform processing functions, and control on-board and external features and systems, including based on feedback loops, to interact with content and execute e-commerce transactions. While such e-commerce and content scenarios are vast, some such scenarios include but are not limited to retail shopping environments, educational environments, transportation environments, home environments, event environments, dining/drinking environments, and outdoor environments. While these areas are described herein, various other scenarios would be apparent to one of ordinary skill in the art.

In embodiments, the glasses platform may be used in retail shopping environments. For example, the user may use the glasses to receive content related to an item and/or environment of interest. The user may receive and/or look up pricing information or alternative offers, product information such as SKU/barcodes, ratings, advertisements, GroupOn offers and the like in a retail shopping environment. In embodiments, the user may seek or obtain location information for a particular item. The user may also obtain information regarding loyalty program information related to a particular brand, item, and/ or shopping environment. Further, the user may use the glasses equipped with a camera, scanner, QR reader and the like to scan items into a shipping basket. Further, the user may use the eyepiece to detect the best item in a group of items. By way of example, the user may activate features of the glasses to visualize items in a particular fashion, such as with a program to determine or sense density or thickness of an item to find the best of the bunch. In embodiments, the user may us the glasses to negotiate the price of an item or name his preferred price. For example after scanning an item either virtually, with a scanner associated with the glasses, and the like the user may gesture, move his eyes, or use voice command or otherwise to name a price he will pay for the item. The user may further use the glasses to command that items be scanned and then pay via a payment method displayed or offered through a user interface. Such payment may be directed via hand gestures, eye movements and the like as described herein. Similarly, the user may redeem "points" or rewards during her shopping trip, and receive promotions related to a particular item and/or establishment, for example through GroupOn, and the like. Further, the user may employ image recognition with the glasses such that an item is recognized and an order is placed for the item in one interface. For example a program used with the glasses may allow the user to recognize a watch in a storefront using the glasses and thereby trigger an order placement menu for the item in the interface as the item is recognized. In additional embodiments, information may be input into the glasses platform by scanning bar codes, QR Codes, product labels, and the like. Promotion information such as process, signs, advertisements, coupons, and the like may be scanned, or otherwise received or recognized by the glasses as the user traverses a retail environment or as he is engaged in a retail interface with the glasses. The user may scan a loyalty card with the glasses for use in a transaction or otherwise input such information for use during a retail transaction. In embodiments, the glasses may aid in navigation and guidance. For example the user may be presented with a specific map of the store and may be provided with aisle content signs allowing the user to better navigate to items and to better navigate around the retail environment. The user may capture product images from the actual environment or download product images such that the image may be used to purchase an item, create notes for the item, generate or receive ratings, reviews and product information for the item and the like. Further, an object image and the geo-location application of the glasses may allow a user to receive the nearest location of the item, local reviews for the item, and the like. In embodiments, geo-location of the user may allow a particular object image to be generated or more appropriately recognized.

By way of more specific example, a system may comprise an interactive head-mounted eyepiece worn by the user, wherein the eyepiece includes a module for determining that the eyepiece is in proximity to a retail environment, and the system may comprise an optical assembly though which the user views the surrounding retail environment, a 3-D processing module for recognizing a feature of the environment and rendering a 3-D display of advertising content that is targeted to the retail location of the eyepiece on the head mounted eyepiece, an image-processing module for capturing and processing an image of the environment of the wearer of the head-mounted eyepiece, an integrated image source for introducing the content to the optical assembly, wherein the integrated image source renders the 3-D display as an overlay on the environment, and wherein the integrated image source presents a 3-D display of advertising content related to the retail environment. In embodiments, the 3-D processing module may be capable of locking a display element on the recognized feature of the environment, and the content may be presented with a relationship to the recognized feature in the display. In embodiments, the rendering of a 3-D display of advertising may be the result of at least on of scanning at least one of a bar code, QR code, product label product and the like. It may also be the product of purchasing a product, inputting an image of a product in the eyepiece, entering a location of the retail environment (or moving into a location of a retail environment), fixing the user's eyes on a product, and inputting loyalty program information in the eyepiece. In embodiments, a second 3-D display may be rendered as a result of at least one of scanning a product, purchasing a product, entering a location of the retail environment, and the like. In embodiments, the user may execute an e-commerce transaction via the eyepiece, and the transaction may include scanning items for purchase, selecting an item based on comparison with other items, negotiating a price, redeeming loyalty points, redeeming promotions, ordering an item and the like. In embodiments, the advertising may include the location of the item in proximity to the user. The location of the item may be shown in relation to the user's location, and the user may be given directions to the item. In embodiments, the eyepiece way be used for social networking and the eyepiece may employ facial recognition of another in the retail environment. Further, the eyepiece may be used to recognize the presence of a person in the environment and present social networking content related to a relationship between the wearer and the recognized person. Further, the user may send and or receive a friend request by gesturing with a part of his body. In embodiments, the user may compare prices of items via the advertisement. In embodiments, the advertisement may comprise audio content. In embodiments, recognizing a feature may include at least one of automated processing of the image containing the feature, pinging the feature with a signal, communicating with the feature, recognizing the feature by processing the location of the feature, retrieving information about the feature from a database, a user designation of the feature, and the like. Further, the user may designate a feature for holding the overlay content by interacting with a user interface of the eyepiece. In embodiments, the overlay may present the content on or in proximity to the recognized feature, and further embodiments, the recognized feature may be at least one of an item for purchase, an item on sale, a sign, an advertisement, an aisle, a location in a store, a kiosk, a service counter, a cash register, a television, a screen, shipping cart, and the like.

In embodiments, the glasses may be used in educational environments. By way of example, the glasses may display e-learning content such at that found in textbooks or otherwise. The glasses may allow the user to view, take, review items for testing. In embodiments, the user may be monitored while taking a test. The glasses may time the user as he moves through the material and may track the user's responses to adjust the exam as necessary based on the user's answers and/or progress through the test. In further embodiments, the user may view augmented reality (AR) overlays via the glasses. In embodiments, the AR overlay may include step-by-step guidance in a laboratory course, in a lecture, and the like. In embodiments, a virtual professor may be displayed allowing interaction via video, audio and chat. The user may view a blackboard/whiteboard notes via the glasses and he may input additional items on the board that may be shared with other users as they view the blackboard/whiteboard in the user interface or as the view an actual board such that AR notes may be added and or overlaid as the user views the particular blackboard/whiteboard. In embodiments, the glasses may provide a social networking platform for members of a class or educational section and provide social networking content for and about class members.

In embodiments, the glasses may be used with commerce in educational environments. By way of example, a user may use the glasses to purchase a program to or otherwise track content progression and course credit. Further, the user may monitor test and quiz grades and upcoming test and quiz administration dates, the user may download course credit/degree information, the user may capture assignments as discussed in class, listed on a syllabus, or otherwise and add the same to a calendar, and the user may meet a friend or class member by way of communicating with or about the other person via the glasses. In embodiments, the user may view his bill and tuition statements for review and tracking of the same. In embodiments, the user may purchase programs to do the same or he may use programs where the programs provide advertising in association with the same.

In further embodiments, the user may employ the glasses in an education environment. The user may scan test/quiz papers for viewing, manipulating or otherwise via the glasses. The user may scan or otherwise capture data associated with textbook content, manuals, and or worksheets, blackboard/whiteboard content for note taking and assignment tracking. The user may scan or capture data related to posters/signage. As such the user may track upcoming student meetings, inventory building descriptions, meeting places and the like. In embodiments, the user may capture faces of classmates, friends, interests and the like. In embodiments, the glasses may track a user's eye movement to validate interaction with content. In embodiments, the glasses may allow "Lifestride" or other pen functions in order to intake content and the like. The user may gesture notes and by way of moving a pen in communication with the glasses, the glasses may store the user's notes. In other embodiments, the user may gesture and the glasses may record notes based on such gesture, and in yet other embodiments, another sensor in association with a user's hand my allow notes to be recorded by the glasses as the user writes notes.

In embodiments, the system may comprise an interactive head-mounted eyepiece worn by the user, wherein the eyepiece includes a module for determining that the eyepiece is in proximity to an education environment. Further the system may comprise an optical assembly though which the user views the surrounding environment, a processing module for recognizing a feature of the environment and rendering education related content that relates to the environment, an image-processing module for capturing and processing an image of the environment of the wearer of the head-mounted eyepiece, the image processing module capable of locking a display element on the recognized feature of the environment, and an integrated image source for introducing the content to the optical assembly, wherein the integrated image source renders the education related content as an overlay on the environment, and wherein the content may be presented with a relationship to the recognized feature in the display. In embodiments, the integrated image source may present a display of transportation content related to the transportation environment and such relationship with a recognized feature may not be present. In embodiments, the rendering of educational content may be the result of scanning a bar code, QR code and the like, It may be the result of inputting an image of a textbook in the eyepiece, inputting an image of a handout in the eyepiece, recognizing a marker in the environment and entering a location of the education environment. In embodiments, the educational environment may be a classroom, exercise studio, auto garage, garage, outdoor environment, gymnasium, laboratory, factory, place of business, kitchen, a hospital, and the like. Further, the educational content may be text, textbook excerpt, instructions, video, audio, laboratory protocol, chemical structure, 3-D image, 3-D overlay, text overlay, classroom worksheet, test, recipe, lesson notes, medical chart, client file, safety notes, and exercise routine. In embodiments, the educational content may be associated or overlaid on an object in the environment. In embodiments, the object may be a whiteboard, blackboard, machine, automobile, aircraft, patient, textbook, a projector and the like. In embodiments, the system may be used for social networking, and further may employ facial recognition of at least one of a classmate, teacher, and the like in the environment. In embodiments, the user may send and/or receive a friend request by gesturing with a part of the user's body. In embodiments, the user may interact with the content for taking a test, completing an assignment, viewing a syllabus, viewing a lesson plan, practicing a technique, tracking course progression, tracking student credits, taking notes, recording notes, submitting questions, and the like. In embodiments, the overlay may present content on or in proximity to a recognized feature. Further, the recognized feature may be at least one of a poster, a blackboard, whiteboard, a screen, machine, automobile, aircraft, patient, textbook, projector, monitor, desk, a smart board, and the like. By way of example, a note may appear on a display that is framed by a blackboard; a movie may appear on the display in the spot where the screen is, a molecular display may appear over a blackboard, and the like. In embodiments, recognizing a feature may include at least one of automated processing of the image containing the feature, pinging the feature with a signal, communicating with the feature, recognizing the feature by processing the location of the feature, retrieving information about the feature by processing the location of the feature, retrieving information about the feature from a database, and user designation of the feature. Further, the user may designate a feature for holding the overlay content by interacting with a user interface of the eyepiece.

In embodiments, the glasses may be used in transportation environments. By way of example, the user may retrieve or capture content such as schedules, availability, delays and cancellations in relation to transportation. For example, as the user arrives at the airport, he may view his flight information via the glasses and see if his flight will be on time or delayed. In embodiments, the user may view his seat/class selection and select snack and meal preferences. He may check in via the glasses and he may switch or update his seat selection in embodiments via the glasses. In embodiments, a user pilot may be given step-by-step procedures for pre-flight checklist for FAA requirements. In embodiments, a train conductor, pilot and the like may be given guidance and navigation instructions in operating the train, plane and the like. In other embodiments, a user passenger may review safety information via the glasses, for example, the user may view pre-flight safety instructions where he is shown how to operate emergency equipment and the like. In embodiments, the user may use the glasses to book ancillary items such as a rental car, a hotel and the like. In embodiments, the user may book an in person tour and/or he may take a virtual tour of the area of interest via the glasses. He may view the surrounding environment of a destination to which he will travel such that he is familiar with the area prior to his arrival. In other embodiments, he may check and compare process of various items as well. The user may view and/or receive loyalty content such as the rewards available on a particular account, the points he may redeem and for what items and the like. The user may redeem loyalty points for while booking a flight, rental car, hotel and the like via the glasses. In embodiments, the user may employ the glasses for networking purposes in a travel or transportation environment. For example, the user may find out who the people on his particular flight or train are. The user may also use the glasses to view entertainment content during transit. By way of example, an inflight movie may be transmitted to the user's glasses. In embodiments, the user may view content related to various location and he may view AR landmarks and the like. By way of example, as the train or pane passes by a landscape, the user may view AR overlay of items of interest, such as landmarks, as associated with a particular area. In embodiments, the user may receive advertising content as he passes billboards/signage in transit. Furthermore, the user may receive personnel information as related to the transportation professionals involved with his transportation. By way of example the user may receive information related to a driver of a taxi to see his driver's record, or he may view the pilot's record of incidents and/or violations that may reflect on the pilot's safety rating.

Further, the user may use the glasses in transportation environments as related to commerce. For example the user may use the glasses to book a seat, redeem reward points for the same, schedule and pay for a meal during transit and the like. The user may find and book/pay for a flight, rent a car, book a hotel, taxi, bus and the like. The user may network with people related to his travel such as other passengers. In embodiments, the user may use the glasses to navigate. For example the user may be given maps of busses and taxis to show the best routes and methods to get around a city. The use may pay for applications for the same and or view ads associated with applications for the same. The user may interact with AR content in and around landmarks, and interact with advertising and promotions from AR-based billboards, signs and the like during his travel.

In embodiments, the user may input items into the glasses platform in a transportation environment. For example, he may scan his ticket to begin the check in process via use of the glasses. He may be provided with an instrument panel that displays the speed, fuel and GPS location during his transportation. The glasses may communicate with IT systems of a vehicle via Bluetooth to display the instrument panel and to provide information regarding the vehicle and or mode of transportation. In embodiments, the user may use the glasses to recognize faces of other passengers and/or store images of the same by inputting images into the glasses. The user may input landmark related content into the glasses for interaction or creating a database of the same for later recall. In embodiments, the user may input billboards/signs which may or may not be AR-based, for storage of and interaction with the same.

Furthermore, the system may comprise an interactive head-mounted eyepiece worn by the user, wherein the eyepiece includes a module for determining that the eyepiece is in proximity to a transportation environment, an optical assembly though which the user views the surrounding environment, a processing module for recognizing a feature of the environment and rendering transportation related content that relates to the transportation environment, an image-processing module for capturing and processing an image of the environment of the wearer of the head-mounted eyepiece, the image processing module capable of locking a display element on the recognized feature of the environment, and an integrated image source for introducing the content to the optical assembly, wherein the integrated image source renders the transportation content as an overlay on the environment and wherein the content may be presented with a relationship to the recognized feature in the display. In embodiments, the integrated image source may present a display of transportation content related to the transportation environment and such relationship with a recognized feature may not be present. In embodiments, the rendering of transportation content may be the result of scanning a bar code, QR code, a ticket, and the like, inputting an image of a ticket for transportation, entering a train, train station, cab stand, cab, airport, aircraft, boat, station, subway, subway station and the like. In embodiments, the transportation content may be a text, video, audio, 3-D image, 3-D overlay, text overlay, directions, schedules, maps, navigation, advertisement, location of points of interest, ancillary resources, safety instructions, flight instructions, operator checklists, FAA information, flight information arrival and departure time information, travel itinerary, and the like. In embodiment, ancillary resources may include resources for making hotel reservations, making car rental reservations, making dinner reservations, noting personal preferences, changing seat selection, finding local entertainment, scheduling local tours, and the like. In embodiments, the user may employ the eyepiece to purchase a pass for a flight, boat ride, train ride, the user may purchase value for a subway pass, reserve a taxi, view transportation schedules, compare travel pricing, retrieve directions, retrieve transportation routes, view current location in a map, view efficient routes for modes of transportation and the like. In embodiments, the content may be associated with a vehicle for displaying information about said vehicle wherein such information includes emergency exit information, maintenance information, operation information, instrument panel information, model information and the like. The system may be used for social networking, and the system may employ facial recognition of a traveler, an operator in the environment, and the like. The send may send and/or receive a friend request by gesturing with a part of his body. In embodiments, the eyepiece may be used to recognize the presence of a person in the environment and present social networking content related to a relationship between the wearer and the recognized person. In embodiments, the user may interact with a displayed advertisement to obtain additional information. In embodiments, the content may be an augmented environment (and the content may augment the environment) comprising any of visual instructions, audio instructions, visual markers an overlaid route plan for various reasons including for exiting the environment in an emergency, and the like. In embodiments, the overlay may present the content on or in proximity to the recognized feature. Further, the recognized feature may be at least one of a poster, train aircraft, cab, boat, subway train, screen, kiosk, map, window, and a wall. In embodiments, recognizing a feature may include at least one of automated processing of the image containing the feature, pinging the feature with a signal, communicating with the feature, recognizing the feature by processing the location of the feature, retrieving information about the feature from a database, user designation of the feature, and the like. Furthermore, the user may designate a feature for holding the overlay content by interacting with a user interface of the eyepiece.

In embodiments the glasses platform may be used in home environments. In embodiments the glasses may be used with content. For example the glasses may be used for entertainment where a user views media at home. The glasses may also be used to for shipping, for example, to generate grocery lists, and the like and to inventory items needed and stored and for checking the same. The user may employ the glasses for family coordination such as by paying bills via the glasses, making checklists of tasks to be done for the family, and the like. For example the glasses may be used for making and keeping doctors' appointments, upcoming soccer games, and the like. The glasses may be used for procedural guidance. By way of example the glasses may be used to guide the user in operating appliances, such as DVD play, VCR, remotes, and the like. Further the glasses may be used for security/and or safety. The user may activate an alarm system while in the home or away from the home to be sure it is on. The user may view home cameras while away and turn lights in the home on and off and the like. The user may be given instruction for emergency situations, for example, the user may be given instructions as to what to do during a fire, hurricane and the like. The user may turn on a feature of the glasses as described here in to see though smoke and the like. The user may employ the glasses to track and communicate with the family members during such an emergency. The glasses may provide lifesaving CPR guidance, 911 calling, and the like.

In embodiments, the glasses may be employed for commerce in a home environment. For example the user may employ the glasses to order food delivery, check on dry cleaning, order dry cleaning pick up and the like. The user may order entertainment content such as movies, videogames, and the like. In embodiments, the user may find and use guidance materials for house hold items, pay bills and the like. The user may view and act upon advertising and/or promotions while at home. For example if an ad is displayed in the glasses as the user is in the kitchen using a blender, an ad may prompt the user to find out more about a new blender and the user may select the add to learn more about the device.

In embodiments, the user may use the glasses in a home environment such that the user inputs information into the glasses. By way of example the user may input paperwork for storage, recall, interaction and the like. The user may input shopping lists, bills, checklists, manuals, mail and the like. The user may input advertising from a paper mail advertisement enabled for AR, a TV, radio and the like. The user may scan a paper ad in order to view or receive additional AR information associated with the ad. The user may input embedded symbol and/or ID's for example for identifying an appliance or other hardware. The user may input Wi-Fi network content to the glasses. Further, the user may input television content such as screens and Smart TV content. As such the user may be able to interact with such content via the glasses platform. The user may input remote control commands into the glasses platform such that the use will be enabled to operate various devices such as TVs, VCRs, DVD players, appliances, and the like. Further the user may input security system content such that the user is able to interact with and control the security system, cameras associated therewith, and the like. The user may view various camera feeds associated with the security system so that he may view various areas around the home environment via the glasses platform. The glasses may link up with such cameras via Bluetooth, via the Internet, a Wi-Fi connection and the like. The user may further be enabled to set alerts, turn off alerts, view alerts and interact with alerts associated with the security system.

Furthermore, the system may comprise an interactive head-mounted eyepiece worn by the user, wherein the eyepiece includes a module for determining that the eyepiece is in proximity to a home environment, an optical assembly though which the user views the surrounding home environment, a processing module for recognizing a feature of the environment and rendering home-related content that relates to the environment, an image-processing module for capturing and processing an image of the environment of the wearer of the head-mounted eyepiece, the image processing module capable of locking a display element on the recognized feature of the environment, and an integrated image source for introducing the content to the optical assembly, wherein the integrated image source may render the home-related content as an overlay on the environment, and wherein the content may be presented with a relationship to the recognized feature in the display. In embodiments, the integrated image source may present a display of content related to the environment and such relationship with a recognized feature and the content may not be present. In embodiments, the rendering of content may be the result of entering a home, fixing the user's eyes on an item in the home, recognizing with the eyepiece a marker in the environment, operating another device in the home, and the like. In embodiment, the content may include a user interface for operating a device such as a VCR, DVR, satellite receiver, set top box, video on demand device, audio equipment, video game console, alarm system, home computer, heating and cooling system and the like. In embodiments, the user may interact with the user interface via eye movement, hand gestures, head nod, and the like. In embodiments, the content may allow the user to complete the task of generating a shopping list, reviewing grocery inventory, paying bills, viewing bills, activating a device, operating lighting, generating virtual communications for family members and/or others, ordering deliveries, such as dry cleaning, food, and the like, acting on advertisements in the environment, and the like. In embodiments, the user may recognize the face of another approaching the home environment or in the home via the eyepiece. In embodiments, content may comprise instructions in an emergency setting, and the instruction may be at least one of audio, video, video instructions, and the like. In embodiments, the content may be an augmented environment, or it may augment the environment and comprise any of visual instruction, audio instructions, visual markers, overlaid route plan for exiting the environment in an emergency, and the like. In embodiments, the content may be generated in response to embedded symbols, television audio and/or video content, advertising, and the like. In embodiments, the content may be retrieved from user manuals stored in the eyepiece or downloaded from the internet, and the like. The content may comprise a 3-D advertisement, audio, video, text, and the like. In embodiments, recognizing a feature may include at least one of automated processing of the image containing the feature, pinging the feature with a signal, communicating with the feature, recognizing the feature by processing the location of the feature, retrieving information about the feature from a database, user designation of the feature, and the like. In embodiments, the user may designate a feature for holding the overlay content by interacting with a user interface of the eyepiece. In embodiments, he overlay may present the content on or in proximity to a recognized feature. Further, the recognized feature may be at least one of an appliance, note station, note pad, calendar, wall, electronic device, security system, room, door, doorway, key holder, and fixture.

In embodiments, the user may use the glasses in event environments. In various event environments, the user may use the glasses platform to interact with content. By way of example, the user may view schedules, ticketing information and/or availability of tickets/seating for events such as concerts, ball games, various entertainment, business events, and the like. The user may view or otherwise interaction with promotional information for an event. The user may view loyalty program content such as a point or reward value associated with an event, and the like. A user may be provided access to an event because of, or in association with, a loyalty program and the like. A user may be given the opportunity to view "bonus" material at an event because of loyalty status and the like. In embodiments, the user may view ancillary service and merchandise associated with the event, purchase the same and the like. In embodiments, the user may view AR content at an event such as a first down line, goal markers, interviews with the players/performers and the like. In embodiments, the user may view alternative video feeds, such as a sideline view when the user is in another seat in the stadium, a back stage view/video feed and the like.

In embodiments, the glasses may be used with commerce at event environments. By way of example the user may purchase/book tickets, view selected/available seats and the like. The user may book ancillary items such as purchasing a back stage pass, upgrading his seats and the like. In embodiments, the user may buy event related merchandise such as jerseys, concert shirts, posters and the like. The user may further redeem points such as those associated with a reward or frequent attendee program. In embodiments the user may purchase images and or view as a keepsake, memorabilia, such as an item digitally "signed" video from an event, a particular portion or entire game or event and the like. The user may view additional video of players and or performers or commentary during such event for additional cost or for free.

In embodiments, the user may input items and or data to the glasses platform in an event environment. In various embodiments, the user may input tickets/passes to find his seat, sign into the event, and the like. The user may input promotional materials, such as posters and signs, with AR enhancements for viewing and or interacting with the same. The user may input loyalty program information and may scan a card, and the like for a particular event. A such a user may interact with, provide data to, activate, and the like such an account in relation to the event. In embodiments, the user may input network content to the glasses via Wi-Fi, Bluetooth and the like.

Furthermore, the system may comprise an interactive head-mounted eyepiece worn by the user, wherein the eyepiece includes a module for determining that the eyepiece is in proximity to an event environment, an optical assembly though which the user views the surrounding event environment, a processing module for rendering a display of event content that is targeted to the event environment of the eyepiece on the head-mounted eyepiece, an image-processing module for capturing and processing an image of the environment of the wearer of the head-mounted eyepiece, the processing including recognizing a feature that relates to the event and storing the location of the feature, and an integrated image source for introducing the content to the optical assembly, wherein the integrated image source renders the event content as an overlay on the environment viewed by the eyepiece wearer and associates the content with the feature; wherein the integrated image source presents content related to the environment. In embodiments, the image processing module may be capable of locking a display element on the recognized feature of the environment, and the content may be presented with a relationship to the recognized feature in the display. In various embodiments, the rendering of content may be the result of at least one of entering the event environment, fixing the user's eyes on an items at the event, recognizing the feature in the environment, scanning a user's ticket, recognizing the presence of a person at the event, inputting an image from the event, and the like. In embodiments, the content may include augmented visual feeds including any of a first down line, field marker line, displays of performers, displays of performer's equipment, instant replays, enhanced views, live video, alternative views, advertisements related to the event, 3-D content, seat upgrade availability, and the like. In various embodiments, the content may include augmented audio feeds including any of player commentary, commentary audio, game sounds, enhanced performance sound, performer comments, live audio, and the like. The user may interact with the content via at least one of eye movement, hand gestures, head nods, and the like. In embodiments, the eyepiece may be used to recognize the presence of a person at the event and may present social networking content related to a relationship between the wearer and the recognized person. Further, the user may at least one of send and receive a friend request by gesturing with a part of the user's body such as with a head nod. The system may comprise a user interface for purchasing at least one of event items, images, and event views, and memorabilia digitally signed from the event. Further, the content may be generated in response to at least one of embedded symbols, television content, advertising, and the like. In embodiments, the content may include at least one of augmented video and audio of backstage, a locker room, dugout, bullpen, player's bench, and the like. In embodiments, the recognizing feature may include at least one of automated processing of the image containing the feature, pinging the feature with a signal, communicating with the feature, recognizing the feature by processing the location of the feature, retrieving information about the feature from a database, user designation of the feature, and the like. Further, the user may designate a feature for holding the overlay content by interacting with a user interface of the eyepiece. In embodiments, the overlay may present content on or in proximity to the recognized feature, and in embodiments, the recognized feature may be at least one of an object of game play including at least one of a field, a ball, a goal, a scoreboard, a jumbotron, a screen, a distance a ball has traveled, a path of a ball, stadium seats, and the like. In embodiments, the recognized feature may be an object of an artistic performance including at least one of a musician, an musical instrument, a stage, a sheet music stand, an actor, a set, a set prop, a curtain, and the like. In embodiments, the recognized feature is an object for concessions including at least one of a doll, a stuffed animal, a concert shirt, a food item, a beverage, a hat, an article of clothing, a beach towel, a toy, sports memorabilia, concert memorabilia, and the like.

In embodiments, the glasses platform may be used in a drinking/dining environment. For example, the glasses may be sued with content in a drinking/dining environment. In embodiments, the user may use the glasses to make reservations for seating and the like, to review possible seating availability, to view ratings, reviews, venue location and content and the like. The user may also view menu content and prices, comparisons between the venue and other venues, details regarding the foods and beverages such as reviews, nutrition content, how it's prepared and the like, wine ratings, automated wine parings and the like. The user may view social content, for example, may recognize or identify a person and or interact with patrons of the same venue. In embodiments, the user may view loyalty program content, such as dining point, as related to the user's account and or the particular venue. The user may use the glasses to translation items on the men, look up names and definitions of contents by search, and the like. The user may view video or images of menu items. In embodiments the user may view an AR version of the menu. In embodiments, the user may capture a menu image and view it with infinite focus, increase the magnification, adjust the contrast, lighting of the menu and the like. In embodiments, the user may look at the menu item and automatically pair sections of wines and beverages with ratings and prices and the like. The user may access a database of what he has had and what he liked and view reminders of past meals. In embodiments, the user may see a different item than he is consuming. For example, if the user orders a chopped salad, he may view this as a filet mignon and the like.

In embodiments, the glasses may be used in commerce in a drinking/dining environment. For example the glasses may be employed to find a venue, make or update a reservation, browse menus, select items of interest or for purchase from a menu, and to select items to order at a venue. The glasses may be used to pay for an item, share payment, calculate a tip, redeem points, and the like.

In embodiments, the glasses may be used in a drinking/dining environment to input data/items. In embodiments, the user may input content via Wi-Fi, Bluetooth, and the like. In embodiments, the user may input menus, signage and the like with AR enhancements to view and/or interact with the same. In embodiments, the user may input advertising content with AR enhancements to view and/or interact with the same. The user may input items for payment such as credit/debit cards, loyalty payments/redemption, and the like. Such input may be made via near field communication and the like. In embodiments, the user may pay via face recognition. In embodiments the glasses may be used to recognize the face of an employee and such payment may be sued based on such face recognition. In other embodiments, a user's face or a face of another individual may be recognized and an account may be debited to make payment based on the same.

In embodiments, the system may comprise, an interactive head-mounted eyepiece worn by a user, wherein the eyepiece includes a module for determining that the eyepiece is in proximity to at least one of an eating environment and a drinking environment, an optical assembly through which the user views the surrounding environment, a processing module for recognizing a feature of the environment and rendering at least one of eating and drinking related content that relates to the environment, an image-processing module for capturing and processing an image of the environment of the wearer of the head-mounted eyepiece, the image processing module capable of locking a display element on the recognized feature of the environment, and an integrated image source for introducing the content to the optical assembly, wherein the integrated image source renders the at least one of eating and drinking related content as an overlay on the environment and the content is presented with a relationship to the recognized feature in the display. In embodiments, the integrated image source may present a display of content related to the environment and such relationship with a recognized feature and the content may not be present. In embodiments, the rendering of content may be the result of at least one of entering the at least one of an eating environment and a drinking environment, fixing the user's eyes on a menu in the environment, opening a menu, recognizing a marker in the environment, focusing on signage in the environment, and the like. In embodiments, the content may include augmented menu content comprising at least one of ratings of the menu, comparisons of menu items, nutritional value of menu items, pairings of wine with menu items, images of menu items, audio description of menu items, video of menu items, enhanced magnification, contrast and lighting of menu items, and categorization of menu items based on geographic region, ingredients, ratings of items, whether the user has consumed the item before, and the like. In embodiments, the content may be received as a menu as the user waits to be seated. In embodiments, the user may interact with the content via at least one of eye movement, hand gestures, head nods, and the like. In embodiments, the user may place an order via the eyepiece. In embodiments, the user may pay the check, bill or a tab via the eyepiece. In embodiments, the eyepiece may be used for social networking and provide at least one of user reviews of the environment and facial recognition of another in the environment. In embodiments, the user may at least one of send and receive a friend request by gesturing with a part of the user's body. The content may comprise additional information regarding the menu items retrieved from the internet. In embodiments, the overlay may present content on or in a proximity to the recognized feature. In embodiments, the recognized features may be at least one of a poster, a frame, a menu board, a menu, a beverage container, a food presentation cart, a bar, a table, a window, a wall and the like. In embodiments, the recognizing a feature may include at least one of automated processing of the image containing the feature, pinging the feature with a signal, communicating with the feature, recognizing the feature by processing the location of the feature, retrieving information about the feature from a database, user designation of the feature, and the like. In embodiments, the user may designate a feature for holding the overlay content by interacting with a user interface of the eyepiece.

In embodiments, the glasses platform may be used in outdoor environments. In embodiments, the glasses may be used to interact with and or view content. The user may view navigation information such as trail locations, tome to destination, progress to a trial or down a trail, trail maps, AR overlay of trial obstacles that the user may not see otherwise, and the like. The user may be given conditions of the outdoor environment such as temperature, weather, sow conditions, fishing conditions, water level, tide conditions and the like. The user may use the glasses for communications such as coordination of groups by location, weather alerts, and the like as related to the outdoor environments. The user may gather information such as in order to identify plants, trees, animals, birds, sounds, birdcalls, and the like. In embodiments, the user may view an object and by asking the glasses "what is this" the user may be presented with content and or information about the object. In embodiments the user may obtain safety information such as whether something is edible, poisonous, dangerous and the like. For example, the user may pose the question "is this a dangerous snake" when viewed by the glasses and the glasses may then be used to provide the user with information about the snake such as that it has poisonous venom and the like. In embodiments, the user may use the glasses to identify and or receive content related to landmarks associated with an outdoor environment. Such landmarks may assist the user in navigating an environment, or learning about an environment. In embodiments, the user may use the glasses to view procedural guidance such as how to pitch a tent, tie a particular not, traverse difficult terrain, and the like. The user may ask, "How do I put up this tent" and the user may receive step-by-step instructions for the same. In embodiments, the user may view content about self, behavioral or a condition, or analysis for the same. The user may ask for updates from the glasses, such as "Am I dehydrated", "Am I hypothermic", "Am I hypoxic" and the like. Based on the results, the user may change his behavior to prevent a particular result or to promote a particular result. In embodiments, the user may view social content and environments regarding others experiences on a trail, experience blogs and the like. In embodiments, the user may be warned that a particular ski trail is for experts only, or the user may be further informed about the current conditions such as that there are severe ice patches at various parts of the trail.

In embodiments, the user may use the glasses as related to commerce in outdoor environments. The user may download relevant content as related to the environment. By way of example, the user may download trail maps, fishing maps, data about catching fish, skiing, snowboarding, and the like.

The user may schedule accommodations, order supplies, rent equipment, schedule a guide, tour, enter an event, obtain a license, for fishing, for example, a hunting permit or otherwise, and the like. The user may interact with a social network via the glasses in such a setting, for example, the user may join a training club, communicate with others who have been on a trail, or in a particular environment, and the like. The user may note and or track goal oriented achievements. For example the user may track or note goal of climbing Mount Whitney, may note goals for a charitable "fun run" and the like. The user may employ blog based commerce models and the like. In embodiments, the user may use social networking to raise funds for a particular outdoor event via the glasses platform.

In embodiments, the user may input content, data and the like into the glasses in, or related to an outdoor environment. In embodiments, the user may use a camera in the glasses for scene recognition, the user may employ GPS though the glasses to provide information related to or to navigate a particular environment. The user may send and receive communications to and from other users in the environment or send and receive communications related to the environment. The user may input landmark data, view landmark of the environment with AR enhancements, and the like. The user may input features such as leaves and flowers, make notes related the same, may capture pictures of the same and or learn about those in the environment. The user may capture images of items, animals and the like form the environment to learn more about them, store data related to the same, interact with AR content related to the same, and the like.

In embodiments, the system may comprise an interactive head-mounted eyepiece worn by a user, wherein the eyepiece includes a module for determining that the eyepiece is in proximity to an outdoor environment, an optical assembly through which the user views the surrounding outdoor environment, a processing module for rendering outdoor content that is targeted to the outdoor environment of the eyepiece on the head-mounted eyepiece, an image-processing module for capturing and processing an image of the environment of the wearer of the head-mounted eyepiece, the processing including recognizing a feature that relates to the event and storing the location of the feature, and an integrated image source for introducing the content to the optical assembly, wherein the integrated image source may render the outdoor content as an overlay on the environment viewed by the eyepiece wearer and may associate the content with the feature, wherein the integrated image source presents content related to the outdoor environment. In further embodiments, the image processing module may be capable of locking a display element on the recognized feature of the environment, and the content may be presented with a relationship to the recognized feature in the display. In embodiments, the content may be rendered as the result of at least one of entering the outdoor environment, fixing the user's eyes on an item in the environment, recognizing the feature in the environment, recognizing the presence of a person in the environment, inputting an image of the environment, focusing on signage in the environment, and the like. In embodiments, the content may include augmented environment content including at least one of overlaid trail information, time to destination information, user progress information, landmark information, safety information regarding the environment, location in the environment relative to other sources, and information regarding organisms in the environment. In embodiments, the content may include instruction for the user, and the instructions may be at least one of audio, video, image, 3D image, overlaid on an object, step-by-step instructions and the like. The user may interact with the content via at least one of eye movement, hand gestures, head nods and the like. The user may perform at least one of schedule accommodations, order supplies, rent equipment, schedule a tour, obtain a license or permit for an activity, input comments regarding the environment, and the like. Further, the content may augment at least one of camera inputs, GPS information, landmarks in the environment, and features in the outdoor environment. In embodiments, the eyepiece is used to recognize the presence of a person in the environment and presents social networking content related to a relationship between the wearer and the recognized person. Further, the user may at least one of send and receive a friend request by gesturing with a part of the user's body. In embodiments the content may be rendered based on an analysis of a user's condition. In embodiments, recognizing a feature may include at least one of automated processing of the image containing the feature, pinging the feature with a signal, communicating with the feature, recognizing the feature by processing the location of the feature, retrieving information about the feature from a database, user designation of the feature, and the like. Further, the user may designate a feature for holding the overlay content by interacting with a user interface of the eyepiece. In embodiments, the overlay may present the content on or in proximity to the recognized feature. Further, the recognized feature may be at least one of a plant, tree, bush, trail, rock, fence, path, clearing, campground, cabin, tent, mode of water transportation, water vehicle, and animal.

In embodiments, the user may use the glasses in exercise environments. In embodiments, the user may use the glasses to view, download or otherwise interact with content. For example the user may employ self-behavioral or condition analysis such as by asking the glasses, "Am I dehydrated?"; "Am I hypothermic?"; "Am I hypoxic?" and the like. In embodiments, the user may view health club oriented content such as club rates and offers, upcoming training sessions, and the like. The user may view training oriented content such as guidance and instructional content. For example, the user may view instructions, video, AR or otherwise, on how to do the squats, stretches, how to use equipment and the like. The user may view, review, and update blogs such as personal experience blogs related to the exercise environment.

In embodiments, the user may use the glasses in commerce in exercise environments. By way of example the user may pay for if for free, download a guidance program such as one related to an instruction, trainer or other guidance. In embodiments, the user may track success and or progress through the program to completion. In various embodiments, the applications may have advertisements associated with them to be displayed to the user. In embodiments, the user may use the glasses for ancillary equipment purchases and sales. For example the user may purchase new sneakers for increased arch support for running. In embodiments, the user may use the glasses for charitable events such as but not limited to a "fun run" or "climb Everest for charity X" where the user collects donations, and or views or updates blog entries for the same via the glasses platform.

In embodiments, the user may use the glasses for inputting information and or data in an exercise environment. In embodiments, the user may input data for performance tracking, input data via sensors, and input images and video. By way of example, only, the user may record another in a particular activity, and then use the video during his own training to perfect form, technique, and the like.

In embodiments, the system may comprise an interactive head-mounted eyepiece worn by a user, wherein the eyepiece includes a module for determining that the eyepiece wearer is at least one of exercising or is in proximity to an exercise environment, an optical assembly through which the user may view the surrounding exercise environment, a processing module for rendering exercise-related content on the head-mounted eyepiece, an image-processing module for capturing and processing an image of the environment of the wearer of the head-mounted eyepiece and recognizing a feature of the environment, an integrated image source for introducing the content to the optical assembly, wherein the integrated image source may render the exercise content as an overlay on the environment viewed by the user, wherein the overlay is fixed in proximity to the recognized feature as the user moves the eyepiece, and wherein the integrated image source presents content related to the exercise environment. In embodiments, the rendering of content may be the result of at least one of entering the exercise environment, fixing the user's eyes on an item in the environment, automatically recognizing a feature in the field of view of the eyepiece, engaging with a piece of equipment in the exercise environment, recognizing a marker in the environment, focusing on signage in the environment, and the like. In embodiments, the content may include augmented exercise content including at least one of training oriented content, club information content, instructions for exercise, information on upcoming classes and the like. In embodiments, the content may include at least one of 3-D content, audio, visual, video, and text content. The user may interact with the content via at least one of eye movement, hand gestures, head nods, and the like. In embodiments, content may include user information including at least one of vital signs heart rate, exercise time, lap time, best set time, historical user data, and the like. The content may allow the user to purchases a training session, time on a machine, more time at the club, drinks, health bars, and the like. In embodiments, the content may be an advertisement for at least one of an upcoming class, the health club, discount on items at a juice bar, for equipment sales and the like. Further, in embodiments, the eyepiece may be used for social networking wherein the eyepiece provides at least on of user reviews of the environment and facial recognition of another in the environment. Further, the user may at least one of send and receive a friend request by gesturing with a part of the user's body. In embodiments the user may send and receive friend requests to/from another member, trainer, instructor, and the like. In embodiments, the overlay may present content on or in proximity to the recognized feature. Further, the recognized feature may be at least one of a calendar, a wall, a window, a board, a mirror, a treadmill, a weight machine, a bicycle, a stationary bicycle, an elliptical machine an item of gymnastics equipment, a heavy bag, a track, a scoreboard, a goal, an area of a field, an area of a court, and the like. In embodiments, recognizing a feature may include at least one of automated processing of the image containing the feature, pinging the feature with a signal, communicating with the feature, recognizing the feature by processing the location of the feature, retrieving information about the feature from a database, user designation of the feature, and the like. In embodiments, the user may designate a feature for holding the overlay content by interacting with a user interface of the eyepiece, and the like.

Another application that may appeal to users is mobile on-line gaming using the augmented reality glasses. These games may be computer video games, such as those furnished by Electronic Arts Mobile, UbiSoft and Activision Blizzard, e.g., World of Warcraft® (WoW). Just as games and recreational applications are played on computers at home (rather than computers at work), augmented reality glasses may also use gaming applications. The screen may appear on an inside of the glasses so that a user may observe the game and participate in the game. In addition, controls for playing the game may be provided through a virtual game controller, such as a joystick, control module or mouse, described elsewhere herein. The game controller may include sensors or other output type elements attached to the user's hand, such as for feedback from the user through acceleration, vibration, force, pressure, electrical impulse, temperature, electric field sensing, and the like. Sensors and actuators may be attached to the user's hand by way of a wrap, ring, pad, glove, bracelet, and the like. As such, an eyepiece virtual mouse may allow the user to translate motions of the hand, wrist, and/or fingers into motions of the cursor on the eyepiece display, where "motions" may include slow movements, rapid motions, jerky motions, position, change in position, and the like, and may allow users to work in three dimensions, without the need for a physical surface, and including some or all of the six degrees of freedom.

Figure 27:
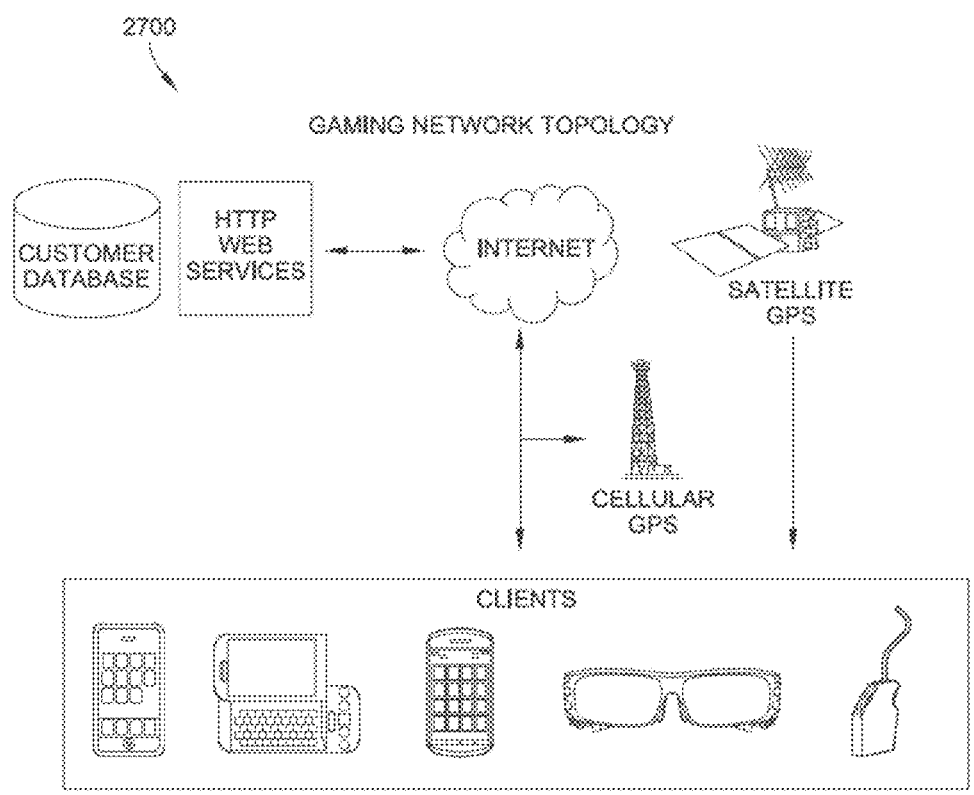
FIG. 27 depicts a gaming network.

As seen in FIG. 27, gaming application implementations 2700 may use both the internet and a GPS. In one embodiment, a game is downloaded from a customer database via a game provider, perhaps using their web services and the internet as shown, to a user computer or augmented reality glasses. At the same time, the glasses, which also have telecommunication capabilities, receive and send telecommunications and telemetry signals via a cellular tower and a satellite. Thus, an on-line gaming system has access to information about the user's location as well as the user's desired gaming activities.

Games may take advantage of this knowledge of the location of each player. For example, the games may build in features that use the player's location, via a GPS locator or magnetometer locator, to award points for reaching the location. The game may also send a message, e.g., display a clue, or a scene or images, when a player reaches a particular location. A message, for example, may be to go to a next destination, which is then provided to the player. Scenes or images may be provided as part of a struggle or an obstacle which must be overcome, or as an opportunity to earn game points. Thus, in one embodiment, augmented reality eyepieces or glasses may use the wearer's location to quicken and enliven computer-based video games.

Figure 28:
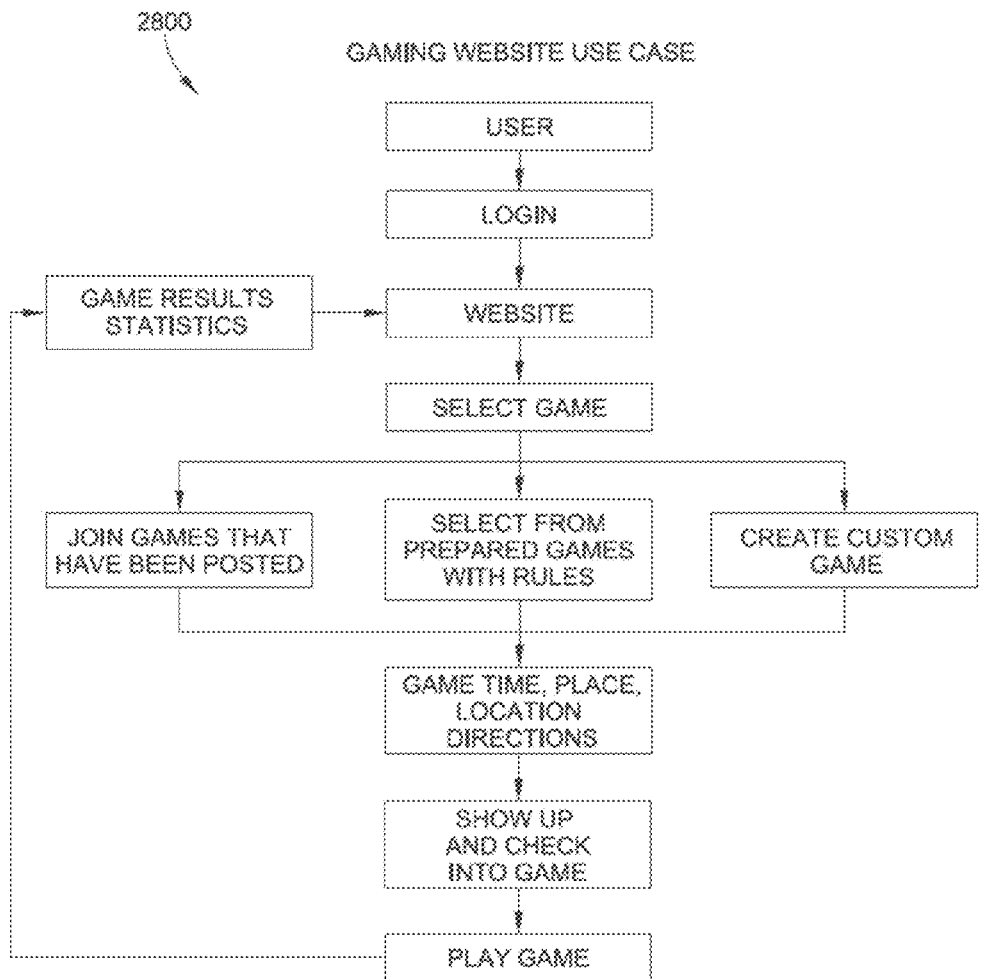
FIG. 28 depicts a method for gaming using augmented reality glasses.

One method of playing augmented reality games is depicted in FIG. 28. In this method 2800, a user logs into a website whereby access to a game is permitted. The game is selected. In one example, the user may join a game, if multiple player games are available and desired; alternatively, the user may create a custom game, perhaps using special roles the user desired. The game may be scheduled, and in some instances, players may select a particular time and place for the game, distribute directions to the site where the game will be played, etc. Later, the players meet and check into the game, with one or more players using the augmented reality glasses. Participants then play the game and if applicable, the game results and any statistics (scores of the players, game times, etc.) may be stored. Once the game has begun, the location may change for different players in the game, sending one player to one location and another player or players to a different location. The game may then have different scenarios for each player or group of players, based on their GPS or magnetometer-provided locations. Each player may also be sent different messages or images based on his or her role, his or her location, or both. Of course, each scenario may then lead to other situations, other interactions, directions to other locations, and so forth. In one sense, such a game mixes the reality of the player's location with the game in which the player is participating.

Games can range from simple games of the type that would be played in a palm of a player's hand, such as small, single player games. Alternatively, more complicated, multi-player games may also be played. In the former category are games such as SkySiege, A R Drone and Fire Fighter 360. In addition, multiplayer games are also easily envisioned. Since all players must log into the game, a particular game may be played by friends who log in and specify the other person or persons. The location of the players is also available, via GPS or other method. Sensors in the augmented reality glasses or in a game controller as described above, such as accelerometers, gyroscopes or even a magnetic compass, may also be used for orientation and game playing. An example is AR Invaders, available for iPhone applications from the App Store. Other games may be obtained from other vendors and for non-iPhone type systems, such as Layar, of Amsterdam and Paris SA, Paris, France, supplier of AR Drone, A R Flying Ace and AR Pursuit.

In embodiments, games may also be in 3D such that the user can experience 3D gaming. For example, when playing a 3D game, the user may view a virtual, augmented reality or other environment where the user is able to control his view perspective. The user may turn his head to view various aspects of the virtual environment or other environment. As such, when the user turns his head or makes other movements, he may view the game environment as if he were actually in such environment. For example, the perspective of the user may be such that the user is put 'into' a 3D game environment with at least some control over the viewing perspective where the user may be able to move his head and have the view of the game environment change in correspondence to the changed head position. Further, the user may be able to 'walk into' the game when he physically walks forward, and have the perspective change as the user moves. Further, the perspective may also change as the user moves the gazing view of his eyes, and the like. Additional image information may be provided, such as at the sides of the user's view that could be accessed by turning the head.

In embodiments, the 3D game environment may be projected onto the lenses of the glasses or viewed by other means. Further, the lenses may be opaque or transparent. In embodiments, the 3D game image may be associated with and incorporate the external environment of the user such that the user may be able to turn his head and the 3D image and external environment stay together. Further, such 3D gaming image and external environment associations may change such that the 3D image associates with more than one object or more than one part of an object in the external environment at various instances such that it appears to the user that the 3D image is interacting with various aspects or objects of the actual environment. By way of example, the user may view a 3D game monster climb up a building or on to an automobile where such building or automobile is an actual object in the user's environment. In such a game, the user may interact with the monster as part of the 3D gaming experience. The actual environment around the user may be part of the 3D gaming experience. In embodiments where the lenses are transparent, the user may interact in a 3D gaming environment while moving about his or her actual environment. The 3D game may incorporate elements of the user's environment into the game, it may be wholly fabricated by the game, or it may be a mixture of both.

In embodiments, the 3D images may be associated with or generated by an augmented reality program, 3D game software and the like or by other means. In embodiments where augmented reality is employed for the purpose of 3D gaming, a 3D image may appear or be perceived by the user based on the user's location or other data. Such an augmented reality application may provide for the user to interact with such 3D image or images to provide a 3D gaming environment when using the glasses. As the user changes his location, for example, play in the game may advance and various 3D elements of the game may become accessible or inaccessible to the viewer. By way of example, various 3D enemies of the user's game character may appear in the game based on the actual location of the user. The user may interact with or cause reactions from other users playing the game and or 3D elements associated with the other users playing the game. Such elements associated with users may include weapons, messages, currency, a 3D image of the user and the like. Based on a user's location or other data, he or she may encounter, view, or engage, by any means, other users and 3D elements associated with other users. In embodiments, 3D gaming may also be provided by software installed in or downloaded to the glasses where the user's location is or is not used.

In embodiments, the lenses may be opaque to provide the user with a virtual reality or other virtual 3D gaming experience where the user is 'put into' the game where the user's movements may change the viewing perspective of the 3D gaming environment for the user. The user may move through or explore the virtual environment through various body, head, and or eye movements, use of game controllers, one or more touch screens, or any of the control techniques described herein which may allow the user to navigate, manipulate, and interact with the 3D environment, and thereby play the 3D game.

In various embodiments, the user may navigate, interact with and manipulate the 3D game environment and experience 3D gaming via body, hand, finger, eye, or other movements, through the use of one or more wired or wireless controllers, one or more touch screens, any of the control techniques described herein, and the like.

In embodiments, internal and external facilities available to the eyepiece may provide for learning the behavior of a user of the eyepiece, and storing that learned behavior in a behavioral database to enable location-aware control, activity-aware control, predictive control, and the like. For example, a user may have events and/or tracking of actions recorded by the eyepiece, such as commands from the user, images sensed through a camera, GPS location of the user, sensor inputs over time, triggered actions by the user, communications to and from the user, user requests, web activity, music listened to, directions requested, recommendations used or provided, and the like. This behavioral data may be stored in a behavioral database, such as tagged with a user identifier or autonomously. The eyepiece may collect this data in a learn mode, collection mode, and the like. The eyepiece may utilize past data taken by the user to inform or remind the user of what they did before, or alternatively, the eyepiece may utilize the data to predict what eyepiece functions and applications the user may need based on past collected experiences. In this way, the eyepiece may act as an automated assistant to the user, for example, launching applications at the usual time the user launches them, turning off augmented reality and the GPS when nearing a location or entering a building, streaming in music when the user enters the gym, and the like. Alternately, the learned behavior and/or actions of a plurality of eyepiece users may be autonomously stored in a collective behavior database, where learned behaviors amongst the plurality of users are available to individual users based on similar conditions. For example, a user may be visiting a city, and waiting for a train on a platform, and the eyepiece of the user accesses the collective behavior database to determine what other users have done while waiting for the train, such as getting directions, searching for points of interest, listening to certain music, looking up the train schedule, contacting the city website for travel information, connecting to social networking sites for entertainment in the area, and the like. In this way, the eyepiece may be able to provide the user with an automated assistant with the benefit of many different user experiences. In embodiments, the learned behavior may be used to develop preference profiles, recommendations, advertisement targeting, social network contacts, behavior profiles for the user or groups of users, and the like, for/to the user.

In an embodiment, the augmented reality eyepiece or glasses may include one or more acoustic sensors for detecting sound 2900. An example is depicted above in FIG. 29. In one sense, acoustic sensors are similar to microphones, in that they detect sounds. Acoustic sensors typically have one or more frequency bandwidths at which they are more sensitive, and the sensors can thus be chosen for the intended application. Acoustic sensors are available from a variety of manufacturers and are available with appropriate transducers and other required circuitry. Manufacturers include ITT Electronic Systems, Salt Lake City, Utah, USA; Meggitt Sensing Systems, San Juan Capistrano, Calif., USA; and National Instruments, Austin, Tex., USA. Suitable microphones include those which comprise a single microphone as well as those which comprise an array of microphones, or a microphone array.

Acoustic sensors may include those using micro electromechanical systems (MEMS) technology. Because of the very fine structure in a MEMS sensor, the sensor is extremely sensitive and typically has a wide range of sensitivity. MEMS sensors are typically made using semiconductor manufacturing techniques. An element of a typical MEMS accelerometer is a moving beam structure composed of two sets of fingers. One set is fixed to a solid ground plane on a substrate; the other set is attached to a known mass mounted on springs that can move in response to an applied acceleration. This applied acceleration changes the capacitance between the fixed and moving beam fingers. The result is a very sensitive sensor. Such sensors are made, for example, by STMicroelectronics, Austin, Tex. and Honeywell International, Morristown N.J., USA.

In addition to identification, sound capabilities of the augmented reality devices may also be applied to locating an origin of a sound. As is well known, at least two sound or acoustic sensors are needed to locate a sound. The acoustic sensor will be equipped with appropriate transducers and signal processing circuits, such as a digital signal processor, for interpreting the signal and accomplishing a desired goal. One application for sound locating sensors may be to determine the origin of sounds from within an emergency location, such as a burning building, an automobile accident, and the like. Emergency workers equipped with embodiments described herein may each have one or more than one acoustic sensors or microphones embedded within the frame. Of course, the sensors could also be worn on the person's clothing or even attached to the person. In any event, the signals are transmitted to the controller of the augmented reality eyepiece. The eyepiece or glasses are equipped with GPS technology and may also be equipped with direction-finding capabilities; alternatively, with two sensors per person, the microcontroller can determine a direction from which the noise originated.

If there are two or more firefighters, or other emergency responders, their location is known from their GPS capabilities. Either of the two, or a fire chief, or the control headquarters, then knows the position of two responders and the direction from each responder to the detected noise. The exact point of origin of the noise can then be determined using known techniques and algorithms. See e.g., Acoustic Vector-Sensor Beamforming and Capon Direction Estimation, M. Hawkes and A. Nehorai, IEEE Transactions on Signal Processing, vol. 46, no. 9, September 1998, at 2291-2304; see also Cramer-Rao Bounds for Direction Finding by an Acoustic Vector Sensor Under Nonideal Gain-Phase Responses, Noncollocation or Nonorthogonal Orientation, P. K. Tam and K. T. Wong, IEEE Sensors Journal, vol. 9. No. 8, August 2009, at 969-982. The techniques used may include timing differences (differences in time of arrival of the parameter sensed), acoustic velocity differences, and sound pressure differences. Of course, acoustic sensors typically measure levels of sound pressure (e.g., in decibels), and these other parameters may be used in appropriate types of acoustic sensors, including acoustic emission sensors and ultrasonic sensors or transducers.

The appropriate algorithms and all other necessary programming may be stored in the microcontroller of the eyepiece, or in memory accessible to the eyepiece. Using more than one responder, or several responders, a likely location may then be determined, and the responders can attempt to locate the person to be rescued. In other applications, responders may use these acoustic capabilities to determine the location of a person of interest to law enforcement. In still other applications, a number of people on maneuvers may encounter hostile fire, including direct fire (line of sight) or indirect fire (out of line of sight, including high angle fire). The same techniques described here may be used to estimate a location of the hostile fire. If there are several persons in the area, the estimation may be more accurate, especially if the persons are separated at least to some extent, over a wider area. This may be an effective tool to direct counter-battery or counter-mortar fire against hostiles. Direct fire may also be used if the target is sufficiently close.

Figure 29B:
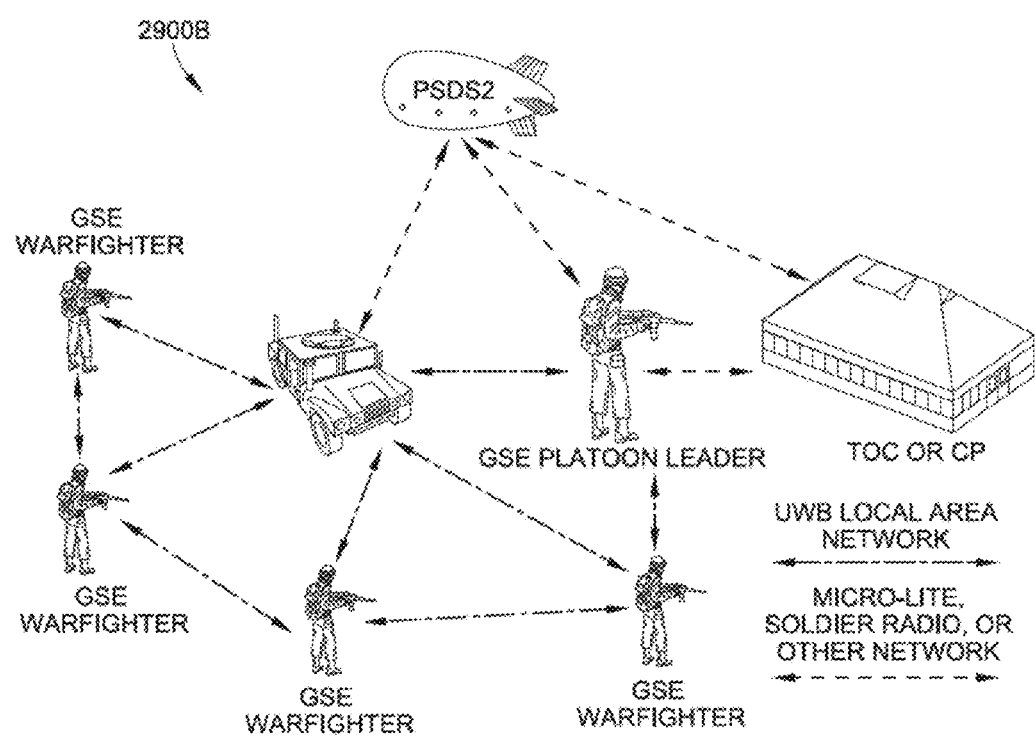
FIG. 29B depicts a communication network among users of augmented reality eyepieces.

An example using embodiments of the augmented reality eyepieces is depicted in FIG. 29B. In this example 2900B, numerous soldiers are on patrol, each equipped with augmented reality eyepieces, and are alert for hostile fire. The sounds detected by their acoustic sensors or microphones may be relayed to a squad vehicle as shown, to their platoon leader, or to a remote tactical operations center (TOC) or command post (CP). Alternatively, or in addition to these, the signals may also be sent to a mobile device, such as an airborne platform, as shown. Communications among the soldiers and the additional locations may be facilitated using a local area network, or other network. In addition, all the transmitted signals may be protected by encryption or other protective measures. One or more of the squad vehicle, the platoon commander, the mobile platform, the TOC or the CP will have an integration capability for combining the inputs from the several soldiers and determining a possible location of the hostile fire. The signals from each soldier will include the location of the soldier from a GPS capability inherent in the augmented reality glasses or eyepiece. The acoustic sensors on each soldier may indicate a possible direction of the noise. Using signals from several soldiers, the direction and possibly the location of the hostile fire may be determined. The soldiers may then neutralize the location.

In addition to microphones, the augmented reality eyepiece may be equipped with ear buds, which may be articulating ear buds, as mentioned elsewhere herein, and may be removably attached 1403, or may be equipped with an audio output jack 1401. The eyepiece and ear buds may be equipped to deliver noise-cancelling interference, allowing the user to better hear sounds delivered from the audio-video communications capabilities of the augmented reality eyepiece or glasses, and may feature automatic gain control. The speakers or ear buds of the augmented reality eyepiece may also connect with the full audio and visual capabilities of the device, with the ability to deliver high quality and clear sound from the included telecommunications device. As noted elsewhere herein, this includes radio or cellular telephone (smart phone) audio capabilities, and may also include complementary technologies, such as Bluetooth™ capabilities or related technologies, such as IEEE 802.11, for wireless personal area networks (WPAN).

Another aspect of the augmented audio capabilities includes speech recognition and identification capabilities. Speech recognition concerns understanding what is said while speech identification concerns understanding who the speaker is. Speech identification may work hand in hand with the facial recognition capabilities of these devices to more positively identify persons of interest. As described elsewhere in this document, a camera connected as part of the augmented reality eyepiece can unobtrusively focus on desired personnel, such as a single person in a crowd or multiple faces in a crowd. Using the camera and appropriate facial recognition software, an image of the person or people may be taken. The features of the image are then broken down into any number of measurements and statistics, and the results are compared to a database of known persons. An identity may then be made. In the same manner, a voice or voice sampling from the person of interest may be taken. The sample may be marked or tagged, e.g., at a particular time interval, and labeled, e.g., a description of the person's physical characteristics or a number. The voice sample may be compared to a database of known persons, and if the person's voice matches, then an identification may be made. In embodiments, multiple individuals of interest may by selected, such as for biometric identification. The multiple selection may be through the use of a cursor, a hand gesture, an eye movement, and the like. As a result of the multiple selection, information concerning the selected individuals may be provided to the user, such as through the display, through audio, and the like.

In embodiments where the camera is used for biometric identification of multiple people in a crowd, control technologies described herein may be used to select faces or irises for imaging. For example, a cursor selection using the hand-worn control device may be used to select multiple faces in a view of the user's surrounding environment. In another example, gaze tracking may be used to select which faces to select for biometric identification. In another example, the hand-worn control device may sense a gesture used to select the individuals, such as pointing at each individual.

In one embodiment, important characteristics of a particular person's speech may be understood from a sample or from many samples of the person's voice. The samples are typically broken into segments, frames and subframes. Typically, important characteristics include a fundamental frequency of the person's voice, energy, formants, speaking rate, and the like. These characteristics are analyzed by software which analyses the voice according to certain formulae or algorithms. This field is constantly changing and improving. However, currently such classifiers may include algorithms such as neural network classifiers, k-classifiers, hidden Markov models, Gaussian mixture models and pattern matching algorithms, among others.

Figure 31:
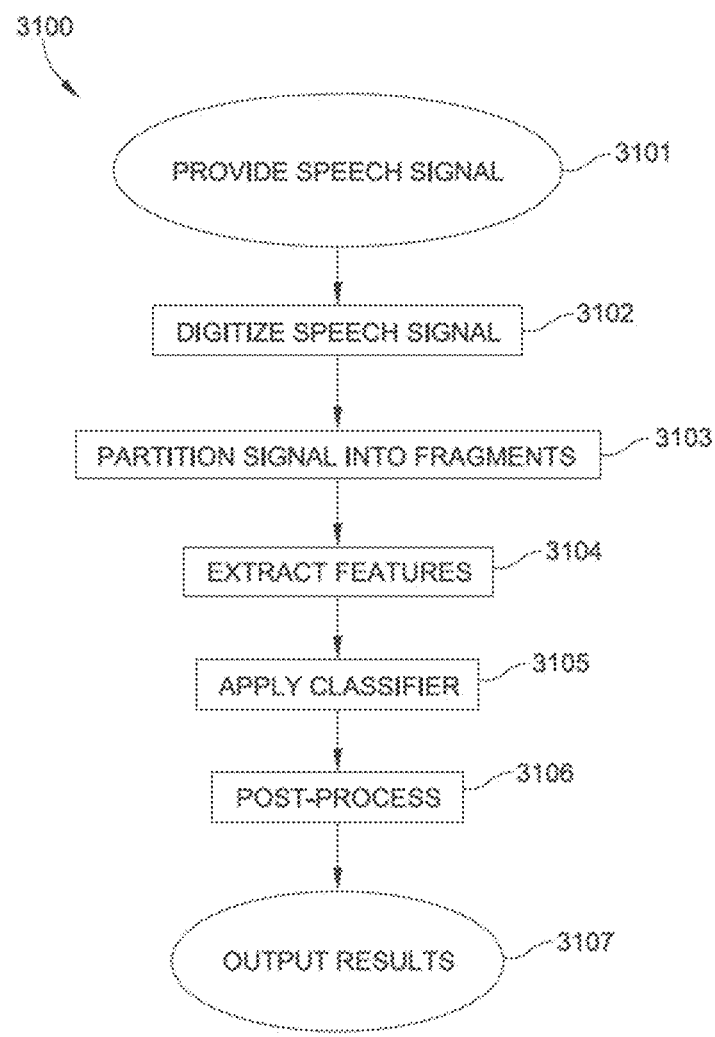
FIG. 31 depicts a flowchart for a method of identifying a person based on speech of the person as captured by microphones of the augmented reality device.

A general template 3100 for speech recognition and speaker identification is depicted in FIG. 31. A first step 3101 is to provide a speech signal. Ideally, one has a known sample from prior encounters with which to compare the signal. The signal is then digitized in step 3102 and is partitioned in step 3103 into fragments, such as segments, frames and subframes. Features and statistics of the speech sample are then generated and extracted in step 3104. The classifier, or more than one classifier, is then applied in step 3105 to determine general classifications of the sample. Post-processing of the sample may then be applied in step 3106, e.g., to compare the sample to known samples for possible matching and identification. The results may then be output in step 3107. The output may be directed to the person requesting the matching, and may also be recorded and sent to other persons and to one or more databases.

In an embodiment, the audio capabilities of the eyepiece include hearing protection with the associated earbuds. The audio processor of the eyepiece may enable automatic noise suppression, such as if a loud noise is detected near the wearer's head. Any of the control technologies described herein may be used with automatic noise suppression.

In an embodiment, the eyepiece may include a nitinol head strap. The head strap may be a thin band of curved metal which may either pull out from the arms of the eyepiece or rotate out and extend out to behind the head to secure the eyepiece to the head. In one embodiment, the tip of the nitinol strap may have a silicone cover such that the silicone cover is grasped to pull out from the ends of the arms. In embodiments, only one arm has a nitinol band, and it gets secured to the other arm to form a strap. In other embodiments, both arms have a nitinol band and both sides get pulled out to either get joined to form a strap or independently grasp a portion of the head to secure the eyepiece on the wearer's head. In embodiments, the eyepiece may have interchangeable equipment to attach the eyepiece to an individual's head, such as a joint where a head strap, glasses arms, helmet strap, helmet snap connection, and the like may be attached. For example, there may be a joint in the eyepiece near the user's temple where the eyepiece may attach to a strap, and where the strap may be disconnected so the user may attach arms to make the eyepiece take the form of glasses, attach to a helmet, and the like. In embodiments, the interchangeable equipment attaching the eyepiece to the user's head or to a helmet may include an embedded antenna. For example, a Nitinol head strap may have an embedded antenna inside, such as for a particular frequency, for a plurality of frequencies, and the like. In addition, the arm, strap, and the like, may contain RF absorbing foam in order to aid in the absorption of RF energy while the antenna is used in transmission.

Referring to FIG. 21, the eyepiece may include one or more adjustable wrap around extendable arms 2134. The adjustable wrap around extendable arms 2134 may secure the position of the eyepiece to the user's head. One or more of the extendable arms 2134 may be made out of a shape memory material. In embodiments, one or both of the arms may be made of nitinol and/or any shape-memory material. In other instances, the end of at least one of the wrap around extendable arms 2134 may be covered with silicone. Further, the adjustable wrap around extendable arms 2134 may extend from the end of an eyepiece arm 2116. They may extend telescopically and/or they may slide out from an end of the eyepiece arms. They may slide out from the interior of the eyepiece arms 2116 or they may slide along an exterior surface of the eyepiece arms 2116. Further, the extendable arms 2134 may meet and secure to each other. The extendable arms may also attach to another portion of the head mounted eyepiece to create a means for securing the eyepiece to the user's head. The wrap around extendable arms 2134 may meet to secure to each other, interlock, connect, magnetically couple, or secure by other means so as to provide a secure attachment to the user's head. In embodiments, the adjustable wrap around extendable arms

2134 may also be independently adjusted to attach to or grasp portions of the user's head. As such the independently adjustable arms may allow the user increased customizability for a personalized fit to secure the eyepiece to the user's head. Further, in embodiments, at least one of the wrap around extendable arms 2134 may be detachable from the head mounted eyepiece. In yet other embodiments, the wrap around extendable arms 2134 may be an add-on feature of the head mounted eyepiece. In such instances, the user may choose to put extendable, non-extendable or other arms on to the head mounted eyepiece. For example, the arms may be sold as a kit or part of a kit that allows the user to customize the eyepiece to his or her specific preferences. Accordingly, the user may customize that type of material from which the adjustable wrap around extendable arm 2134 is made by selecting a different kit with specific extendable arms suited to his preferences. Accordingly, the user may customize his eyepiece for his particular needs and preferences.

In yet other embodiments, an adjustable strap, 2142, may be attached to the eyepiece arms such that it extends around the back of the user's head in order to secure the eyepiece in place. The strap may be adjusted to a proper fit. It may be made out of any suitable material, including but not limited to rubber, silicone, plastic, cotton and the like.

In an embodiment, the eyepiece may be secured to the user's head by a plurality of other structures, such a rigid arm, a flexible arm, a gooseneck flex arm, a cable tensioned system, and the like. For instance, a flexible arm may be constructed from a flexible tubing, such as in a gooseneck configuration, where the flexible arm may be flexed into position to adjust to the fit of a given user, and where the flexible arm may be reshaped as needed. In another instance, a flexible arm may be constructed from a cable tensioned system, such as in a robotic finger configuration, having multiple joints connecting members that are bent into a curved shape with a pulling force applied to a cable running through the joints and members. In this case, the cable-driven system may implement an articulating ear horn for size adjustment and eyepiece headwear retention. The cable-tensioned system may have two or more linkages, the cable may be stainless steel, Nitinol-based, electro-actuated, ratcheted, wheel adjusted, and the like.

Embodiments of a cable-tensioned system 17800 are shown in FIGS. 178-179A&B. In embodiments, a cable tension system may comprise an ear horn 17802 comprised of two or more joints connecting members that may be bent to a curved shape with a pulling force applied to a cable 17804 running through the joints and/or members. In an erect position as shown in FIG. 178, the ear horn may be positioned straight along the user's head. The cable 17804 may be attached to and tightened via an adjustor 17808 whereby positioning the adjustor to increase tension in the cable 17804 causes the ear horn to bend or curve to shape to the user's head. By increasing such tension, the ear horn may stiffen and or become more rigid. By shaping to the user's head, the ear horn 17802 may adjust to a specific user's head and/or to assist in eyewear retention by securely holding eyewear to a user's head. In embodiments, as the tension of the cable 17804 increases, the ear horn becomes more rigid or less relaxed to position to the user's head, and as the tension is released in the cable 17804, the ear horn becomes more flexible allowing one or both of ear horns to straighten and/or to fold flat. In embodiments, the adjustor 17808 may be a ratcheted, electro-actuated, wheel adjusted, comprise a wedge slider, and the like. In embodiments, a wedge slider may be a tapered adjustment that may allow the position of one or more portions of the ear horn and/or eyepiece to be raised or lowered by pushing or pulling a tab or the like in or out to provide the adjustment. In embodiments, the ear horn 17804 may be constructed in a robotic finger configuration and shaped as shown in FIG. 179B. The adjustable ear horn as described herein may provide the benefit of securing the eyepiece to the user's head while providing the convenience of folding for ease of use. In embodiments, the ear horn may provide a wraparound head design where the ear horns of the right and left earpiece wrap around the user's head and touch or nearly touch in the back of the user's head. In embodiments, the ear horns may fasten to each other for added security. Such fastening may be through magnets on each ear horn, a hooking mechanism on the ear horn, and the like. In embodiments, the ear horns may wrap or contour partially or completely around the user's head and/or they may secure to the user's head by running along the side of the user's head and/or securing behind the user's ear. In embodiments, the ear horn may attach to an earpiece of an eyepiece such as the earpiece 2104 shown in FIG. 22. The ear horn may be permanently or removably attached to the earpiece. In embodiments, the ear horn may comprise a portion of the earpiece of an eyepiece as shown in FIG. 180, or it may comprise the entire earpiece (not shown). In embodiments, the adjustor 17808 may be positioned on the portion of the ear horn proximate to the eyepiece, on the end of the ear horn near or past the user's ear, or on any other piece of the ear horn and/or eyepiece. In embodiments one or both ear horns may be adjustable as described herein. In embodiments as described herein, an ear horn (shown by itself and without the eyepiece) may wrap and/or contour to the user's head as shown in FIG. 184.

In embodiments, a switchable attraction between multiple layers in a laminate may be used with the ear horns. For example one or more ear horns may comprise layers in a laminate and the attraction between layers may come from magnetic, electrostatic, and/or vacuum means. In embodiments, magnets may be used by rotating the poles to be in an attracting or repelling position allowing layers in laminate to attract to each other such that the ear horns stiffen and to repel each other such that the ear horns relax. In embodiments where laminate layers are close together, an electric voltage may be applied to create an electrostatic attraction that may be electrically switched. As the attraction is created, the ear horns may stiffen. When the voltage is removed, or the electrostatic attraction is switched, the ear horns may relax. In embodiments, a vacuum may be created by forcing two layers together which fit together and have a spring back in one or more portions of the layers that creates a cavity or void between the layers creating a vacuum. As the layers are forced together, they may allow the ear horn to stiffen. The vacuum seal may be broken to allow the ear horn to relax. In various embodiments, as the ear horns stiffen, they may provide a more rigid and/or secure retention of the eyepiece to the user's head. In embodiments, the ear horns may wrap or contour partially or completely around the user's head and/or they may secure to the user's head by running along the side of the user's head and/or securing behind the user's ear and/or to the back of the user's head. As the electrostatic voltage, magnetic attraction, and/or vacuum is adjusted, the ear horns may stiffen to allow the ear horns to secure to the user's head, and the ear horns may relax or release to straighten and/or to fold flat to a closed position.

In embodiments, one or more ear horns may comprise an inner rod and/or string structure where each ear horn further comprises a magnet. The magnet of each ear horn may connect to the other allowing the two ear horns to wrap around the user's head. The action of the magnets connecting to one another may allow the string and/or inner rod structure to tighten providing a more secure fit to the user's head. By connecting the magnets, in embodiments, inner rods of the ear horns may erect or become firmer to allow the ear horns to wrap around the user's head and/or inner strings of the ear horn may tighten and allow the ear horns to wrap around the user's head. In embodiments, the ear horns may wrap or contour partially or completely around the user's head and/or they may secure to the user's head by running along the side of the user's head and/or securing behind the user's ear. When the magnets are not connected, the ear horn may straighten and/or may be able to be folded flat.

In embodiments, one or more ear horns may utilize air pressure in chambers inside of the ear horns which may stiffen the ear horns. The air pressure may be increased to stiffen the ear horn. Such stiffening may allow the ear horns to adjust to and/or wrap around the user's head when the eyepiece is in use. In embodiments, the ear horns may wrap or contour partially or completely around the user's head and/or they may secure to the user's head by running along the side of the user's head and/or securing behind the user's ear. The air pressure may be decreased to relax the ear horns. When the ear horns are relaxed, they may be able to straighten and/or to be folded flat. The air pressure may be adjusted before or after being put on or taken off the user's head. In embodiments, the air pressure may be adjusted by a pump in the side frame that is operated by finger pressure or other means. In embodiments, pump may be adjusted via a user interface displayed in the glasses or by other means.

In various embodiments as described herein, stiffness of the ear horn may be related to thickness in a cubic relationship. By way of example, two unconnected layers may be twice as stiff as a single layer, but if the layers are connected into a single layer, the combined layer that is twice as thick will have the stiffness increased by eight times. As a further example, three single layers are three times as stiff as a single layer, but three layers connected together will be twenty-seven times as stiff as the single layer.

In embodiments, one or more ear horns may comprise inner and outer portions whereby the inner portion is formed from the one portion of the ear horn and the outer portion is formed from another portion of the ear horn as shown in FIG. 181. The inner and outer portions may fork from the ear horn or otherwise be formed from the ear horn to form two separate portions where one portion is an outer portion and the other is an inner portion. In embodiments, the inner portion may be in contact with the user's head while the outer portion may be in contact with the inner portion. In embodiments, the inner and outer portions may interlock as shown in the embodiment described in FIG. 182. The inner and outer portions may comprise interlocking groves, teeth or other means by which they interlock or fasten together. The upper and/or outer portion may comprise a tab or other protrusion by which the user may cause the inner and outer portions to no longer be locked together. In embodiments, the portions may be curved to a user's head. Further, the inner surface may push outward against the outer surface. By interlocking the inner and outer portions, the thickness of the portions may be doubled. Accordingly, by increasing the thickness of the ear horn portion, the stiffness may be increased. In embodiments, by doubling the thickness of the ear horn, the stiffness may be increased eight times as compared to the single layer. Stripping the outer layer may return the ear horn portions to a flexible condition thereby allowing the ear horns to be folded flat. In embodiments, the ear horns may be attached by magnets, clips, hooks, or by other means to secure to the user's head.

Furthermore, in embodiments, one or more ear horns may comprise three portions as depicted in FIG. 183. In such an embodiment, the ear horn may comprise an inner and outer portion as described in reference to FIGS. 181 and 182, however the embodiment may also include a middle portion 18302 such that the ear horn is comprised of three portions as shown in FIG. 183. The ear horn may further comprise one or more buttons, straps, interlocking groves, teeth, pins or other means to lock together the ear horn portions. One or more of the portions may comprise a tab or other protrusion by which the user may cause the inner and outer portions to no longer to be locked together by causing the teeth or other moans of locking the portions together to release. In embodiments, three unconnected layers may be three times as stiff as a single layer, but when the three layers are locked/connected together, the ear horn may be twenty-seven times as stiff as a single layer. When the three portions are unconnected or unlocked together, the ear horn may be flexible such that they may straighten and or fold flat. Further, while the portions are not locked together, the portions may slide over each other allowing them to be flexible and more easily stored when not in use and when the layers are locked or pinned together, they may not be able to slide over each other. The ear horn portions may reside in a sheath, tube or other structure comprising the ear horn such that the separate portions are not exposed. While ear horns of two and three portions have been described, one of ordinary skill in the art would understand that ear horns may be comprised of more than three portions, and/or of varying thicknesses, in various embodiments.

In various embodiments as described herein, the wrapping ear horns may fold flat. When the ear horns are folded to a closed position, as when the user is not using the eyepiece, the ear horns may straighten out so that they fold flatter and the ability for the ear horn to wrap or contour to the user's head and/or ear may not interfere with folding flat. In various embodiments as described herein, the ear horns may be folded and thereby straighten allowing the ear horn to become flat to allow the eyepiece to store in a flatter configuration. In various embodiments, the ear horns may straighten when released at the hinges or by other means thereby allowing the eyepiece to be folded flat. As described herein, in various embodiments, the ear horns may become less rigid allowing them to fold flat.

In embodiments, leveler pads may be used with one or more ear horns such that they may be able provide adjustment for ears that are in different vertical positions or to account for different positions of a user's ears or eyes. In embodiments, the pads may be placed on the ear horn at contact points of the user's ears to adjust the eyepiece to fit for different positions of the user's ears and/or eyes. In embodiments, the leveler pads may be adjusted via a wedge slider or by various means. The leveler pads may be a portion of the ear horn or the leveler pads may attach to the ear horns via clips, adhesive, friction, or other means.

In various embodiments described herein, the eyepiece and ear horns may be fitted with closed cell foam on one or more areas that come in contact with the user. The foam may provide the user with comfort while also preventing moisture and sweat from permeating the foam. Further the closed cell foam may provide a non-porous surface to prevent the eyepiece from carrying bacteria, microbes and other organisms and to prevent growth of the same. In various embodiments as described herein, foam may be ant-microbial and or antibacterial and/or treated with a substance for such purpose.

In an embodiment, the eyepiece may include security features, such as M-Shield Security, Secure content, DSM, Secure Runtime, IPsec, and the like. Other software features may include: User Interface, Apps, Framework, BSP, Codecs, Integration, Testing, System Validation, and the like.

In an embodiment, the eyepiece materials may be chosen to enable ruggedization.

In an embodiment, the eyepiece may be able to access a 3G access point that includes a 3G radio, an 802.11b connection and a Bluetooth connection to enable hopping data from a device to a 3G-enable embodiment of the eyepiece.

The present disclosure also relates to methods and apparatus for the capture of biometric data about individuals. The methods and apparatus provide wireless capture of fingerprints, iris patterns, facial structure and other unique biometric features of individuals and then send the data to a network or directly to the eyepiece. Data collected from an individual may also be compared with previously collected data and used to identify a particular individual.

In embodiments, the eyepiece 100 may be associated with mobile biometric devices, such as a biometric flashlight 7300, a biometric phone 5000, a biometric camera, a pocket biometric device 5400, an arm strap biometric device 5600, and the like, where the mobile biometrics device may act as a stand-alone device or in communications with the eyepiece, such as for control of the device, display of data from the device, storage of data, linking to an external system, linking to other eyepieces and/or other mobile biometrics devices, and the like. The mobile biometrics device may enable a soldier or other non-military personnel to collect or utilize existing biometrics to profile an individual. The device may provide for tracking, monitoring, and collecting biometric records such as including video, voice, gait, face, iris biometrics and the like. The device may provide for geo-location tags for collected data, such as with time, date, location, data-taking personnel, the environment, and the like. The device may be able to capture and record fingerprints, palm prints, scars, marks, tattoos, audio, video, annotations, and the like, such as utilizing a thin film sensor, recording, collecting, identifying, and verifying face, fingerprint, iris, latent fingerprints, latent palm prints, voice, pocket litter, and other identifying visible marks and environmental data. The device may be able to read prints wet or dry. The device may include a camera, such as with, IR illumination, UV illumination, and the like, with a capability to see through, dust, smoke, haze, and the like. The camera may support dynamic range extension, adaptive defect pixel correction, advanced sharpness enhancement, geometric distortion correction, advanced color management, hardware-based face detection, video stabilization, and the like. In embodiments, the camera output may be transmitted to the eyepiece for presentation to the soldier. The device may accommodate a plurality of other sensors, such as described herein, including an accelerometer, compass, ambient light, proximity, barometric and temperature sensors, and the like, depending on requirements. The device may also have a mosaic print sensor, as described herein, producing high resolution images of the whorls and pores of an individual's fingerprint, multiple finger prints simultaneously, palm print, and the like. A soldier may utilize a mobile biometrics device to more easily collect personnel information, such as for document and media exploitation (DOMEX). For instance, during an interview, enrollment, interrogations, and the like, operators may photograph and read identifying data or 'pocket litter' (e.g. passport, ID cards, personal documents, cell phone directories, pictures), take biometric data, and the like, into a person of interest profile that may be entered into a searchable secure database. In embodiments, biometric data may be filed using the most salient image plus manual entry, enabling partial data capture. Data may be automatically geo-located, time/date stamped, filed into a digital dossier, and the like, such as with a locally or network assigned global unique identifier (GUID). For instance, a face image may be captured at the scene of an IED bombing, the left iris image may be captured at a scene of a suicide bombing, latent fingerprints may be lifted from a sniper rifle, each taken from a different mobile biometrics device at different locations and times, and together identifying a person of interest from the multiple inputs, such as at a random vehicle inspection point.

Figure 39:
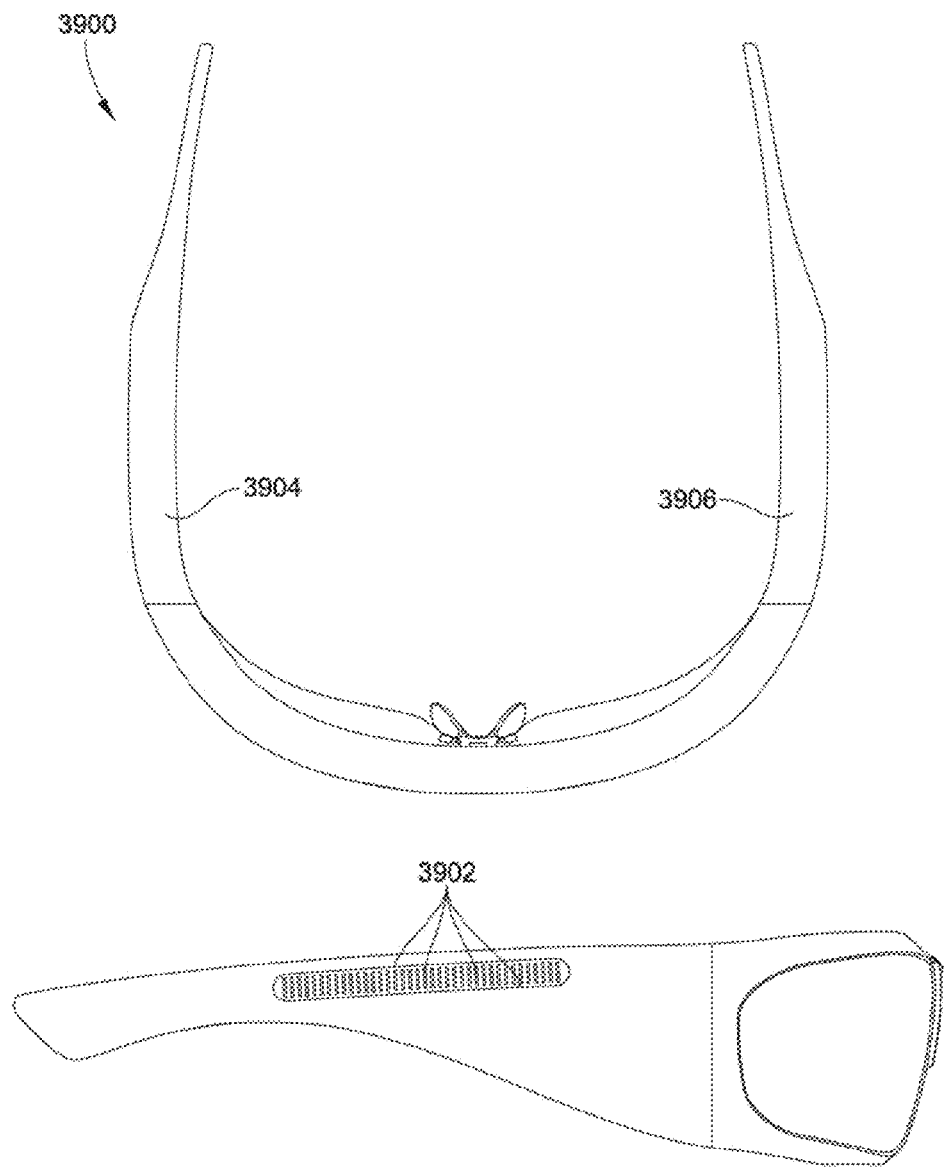
FIG. 39 illustrates glasses for biometric data capture according to an embodiment.

A further embodiment of the eyepiece may be used to provide biometric data collection and result reporting. Biometric data may be visual biometric data, such as facial biometric data or iris biometric data, or may be audio biometric data. FIG. 39 depicts an embodiment providing biometric data capture. The assembly, 3900 incorporates the eyepiece 100, discussed above in connection with FIG. 1. Eyepiece 100 provides an interactive head-mounted eyepiece that includes an optical assembly. Other eyepieces providing similar functionality may also be used. Eyepieces may also incorporate global positioning system capability to permit location information display and reporting.

The optical assembly allows a user to view the surrounding environment, including individuals in the vicinity of the wearer. An embodiment of the eyepiece allows a user to biometrically identify nearby individuals using facial images and iris images or both facial and iris images or audio samples. The eyepiece incorporates a corrective element that corrects a user's view of the surrounding environment and also displays content provided to the user through in integrated processor and image source. The integrated image source introduces the content to be displayed to the user to the optical assembly.

The eyepiece also includes an optical sensor for capturing biometric data. The integrated optical sensor, in an embodiment may incorporate a camera mounted on the eyepiece. This camera is used to capture biometric images of an individual near the user of the eyepiece. The user directs the optical sensor or the camera toward a nearby individual by positioning the eyepiece in the appropriate direction, which may be done just by looking at the individual. The user may select whether to capture one or more of a facial image, an iris image, or an audio sample.

The biometric data that may be captured by the eyepiece illustrated in FIG. 39 includes facial images for facial recognition, iris images for iris recognition, and audio samples for voice identification. The eyepiece 3900 incorporates multiple microphones 3902 in an end fire array disposed along both the right and left temples of the eyepiece. The microphone arrays 3902 are specifically tuned to enable capture of human voices in an environment with a high level of ambient noise. The microphones may be directional, steerable, and covert. Microphones 3902 provide selectable options for improved audio capture, including omni-directional operation, or directional beam operation. Directional beam operation allows a user to record audio samples from a specific individual by steering the microphone array in the direction of the subject individual. Adaptive microphone arrays may be created that will allow the operator to steer the directionality of the microphone array in three dimensions, where the directional beam may be adjusted in real time to maximize signal or minimize interfering noise for a non-stationary target. Array processing may allow summing of cardioid elements by analog or digital means, where there may be switching between omni and directional array operations. In embodiments, beam forming, array steering, adaptive array processing (speech source location), and the like, may be performed by the on-board processor. In an embodiment, the microphone may be capable of 10 dB directional recording.

Audio biometric capture is enhanced by incorporating phased array audio and video tracking for audio and video capture. Audio tracking allows for continuing to capture an audio sample when the target individual is moving in an environment with other noise sources. In embodiments, the user's voice may be subtracted from the audio track so as to enable a clearer rendition of the target individual, such as for distinguishing what is being said, to provide better location tracking, to provide better audio tracking, and the like.

To provide power for the display optics and biometric data collection the eyepiece 3900 also incorporates a lithium-ion battery 3904, that is capable of operating for over twelve hours on a single charge. In addition, the eyepiece 100 also incorporates a processor and solid-state memory 3906 for processing the captured biometric data. The processor and memory are configurable to function with any software or algorithm used as part of a biometric capture protocol or format, such as the .wav format.

A further embodiment of the eyepiece assembly 3900 provides an integrated communications facility that transmits the captured biometric data to a remote facility that stores the biometric data in a biometric data database. The biometric data database interprets the captured biometric data, interprets the data, and prepares content for display on the eyepiece.

In operation, a wearer of the eyepiece desiring to capture biometric data from a nearby observed individual positions himself or herself so that the individual appears in the field of view of the eyepiece. Once in position the user initiates capture of biometric information. Biometric information that may be captured includes iris images, facial images, and audio data.

In operation, a wearer of the eyepiece desiring to capture audio biometric data from a nearby observed individual positions himself or herself so that the individual appears is near the eyepiece, specifically, near the microphone arrays located in the eyepiece temples. Once in position the user initiates capture of audio biometric information. This audio biometric information consists of a recorded sample of the target individual speaking. Audio samples may be captured in conjunction with visual biometric data, such as iris and facial images.

To capture an iris image, the wearer/user observes the desired individual and positions the eyepiece such that the optical sensor assembly or camera may collect an image of the biometric parameters of the desired individual. Once captured the eyepiece processor and solid-state memory prepare the captured image for transmission to the remote computing facility for further processing.

The remote computing facility receives the transmitted biometric image and compares the transmitted image to previously captured biometric data of the same type. Iris or facial images are compared with previously collected iris or facial images to determine if the individual has been previously encountered and identified.

Once the comparison has been made, the remote computing facility transmits a report of the comparison to the wearer/user's eyepiece, for display. The report may indicate that the captured biometric image matches previously captured images. In such cases, the user receives a report including the identity of the individual, along with other identifying information or statistics. Not all captured biometric data allows for an unambiguous determination of identity. In such cases, the remote computing facility provides a report of findings and may request the user to collect additional biometric data, possibly of a different type, to aid in the identification and comparison process. Visual biometric data may be supplemented with audio biometric data as a further aid to identification.

Facial images are captured in a similar manner as iris images. The field of view is necessarily larger, due to the size of the images collected. This also permits to user to stand further off from the subject whose facial biometric data is being captured.

In operation the user may have originally captured a facial image of the individual. However, the facial image may be incomplete or inconclusive because the individual may be wearing clothing or other apparel, such as a hat, that obscures facial features. In such a case, the remote computing facility may request that a different type of biometric capture be used and additional images or data be transmitted. In the case described above, the user may be directed to obtain an iris image to supplement the captured facial image. In other instances, the additional requested data may be an audio sample of the individual's voice.

Figure 40:
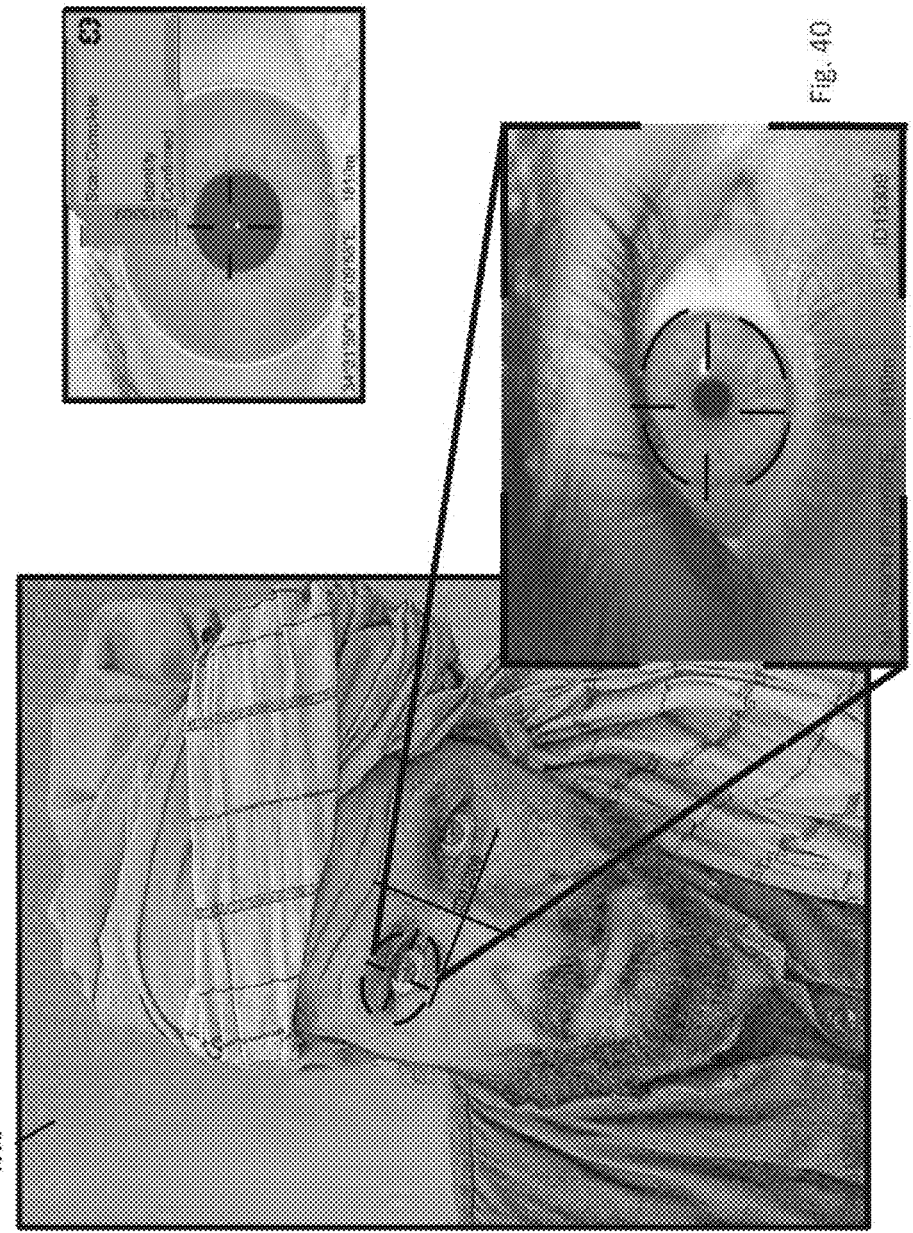
FIG. 40 illustrates iris recognition using the biometric data capture glasses according to an embodiment.

FIG. 40 illustrates capturing an iris image for iris recognition. The figure illustrates the focus parameters used to analyze the image and includes a geographical location of the individual at the time of biometric data capture. FIG. 40 also depicts a sample report that is displayed on the eyepiece.

Figure 41:
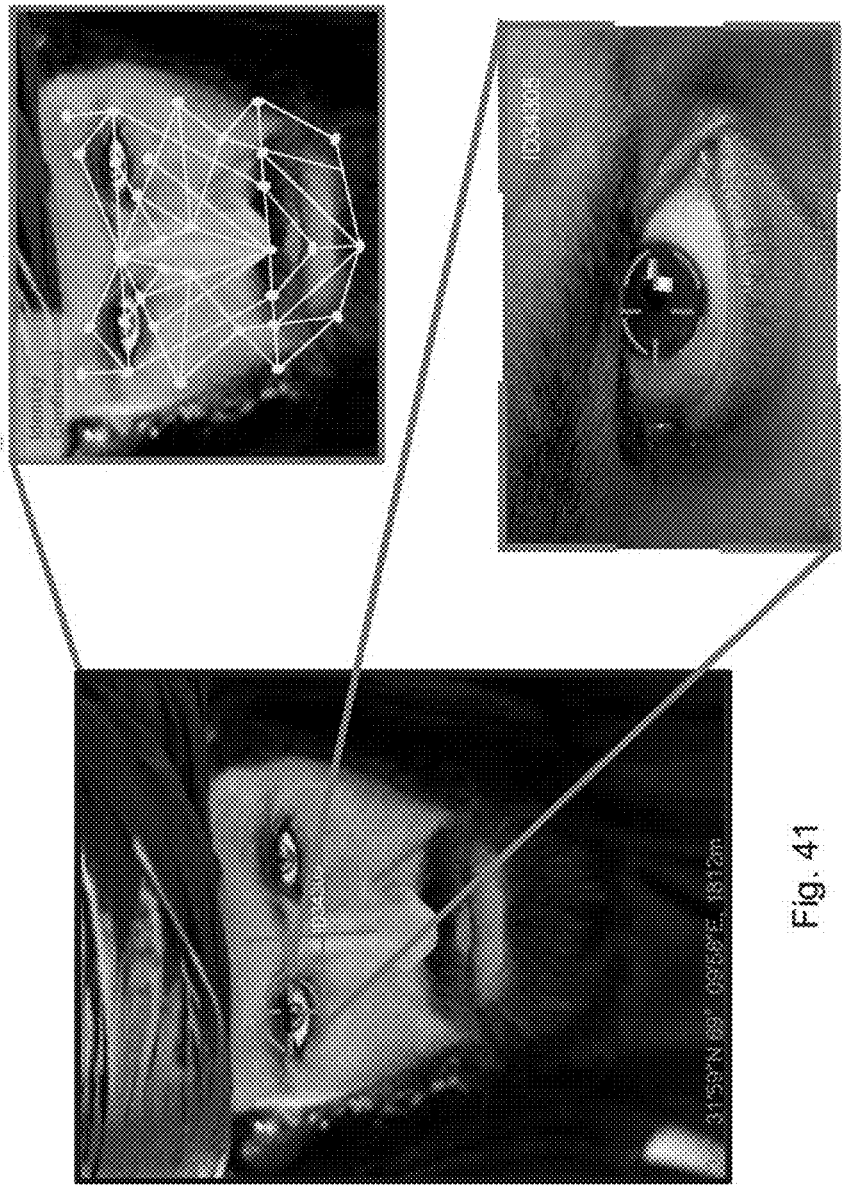
FIG. 41 depicts face and iris recognition according to an embodiment.

FIG. 41 illustrates capture of multiple types of biometric data, in this instance, facial and iris images. The capture may be done at the same time, or by request of the remote computing facility if a first type of biometric data leads to an inconclusive result.

Figure 42:
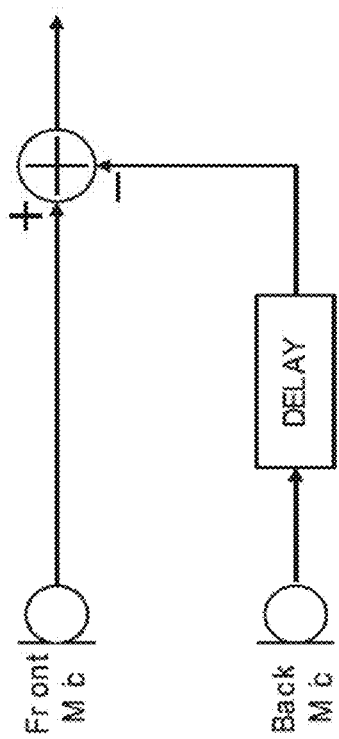
FIG. 42 illustrates use of dual omni-microphones according to an embodiment.
Figure 43:
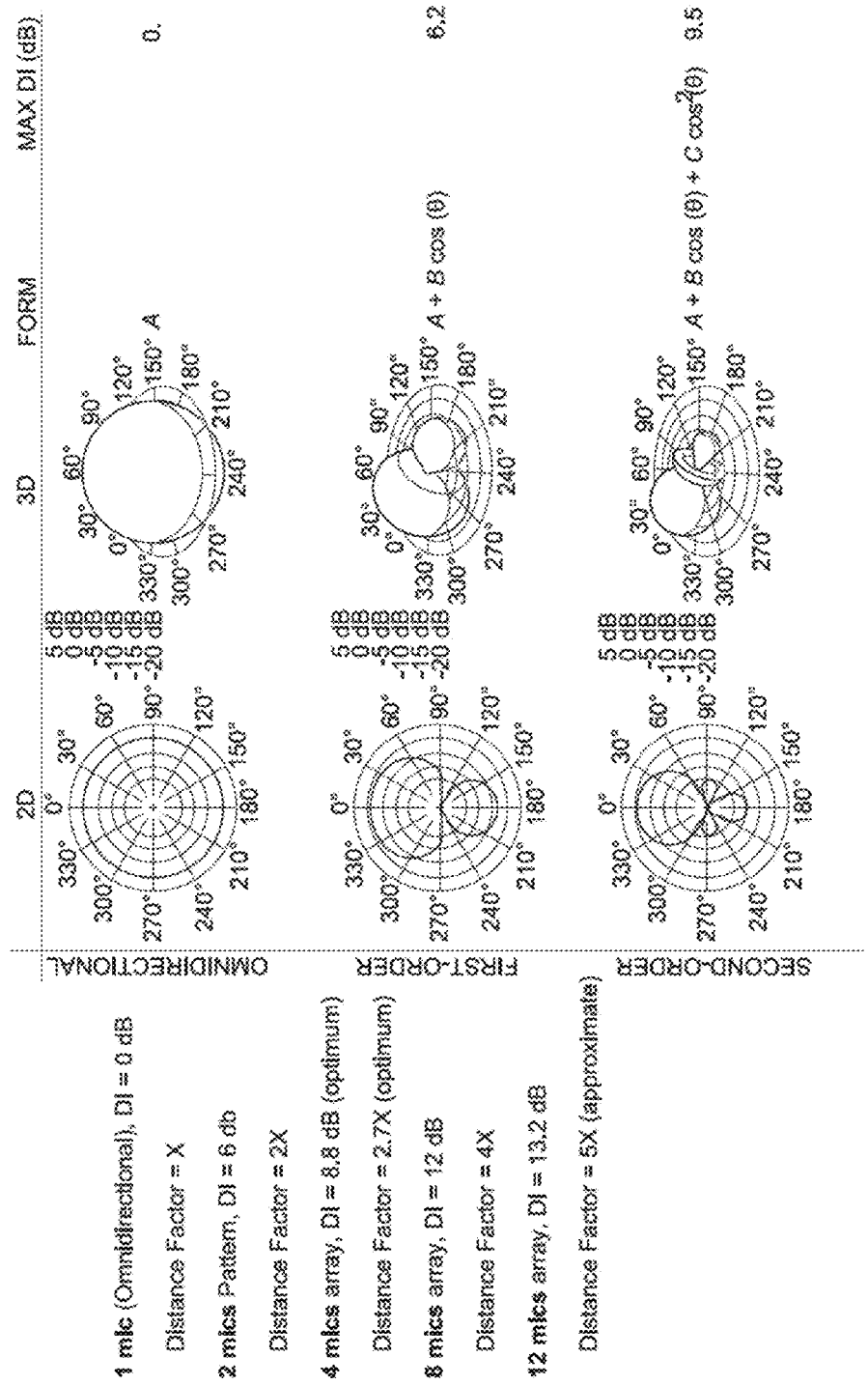
FIG. 43 depicts the directionality improvements with multiple microphones.

FIG. 42 shows the electrical configuration of the multiple microphone arrays contained in the temples of the eyepiece of FIG. 39. The endfire microphone arrays allow for greater discrimination of signals and better directionality at a greater distance. Signal processing is improved by incorporating a delay into the transmission line of the back microphone. The use of dual omni-directional microphones enables switching from an omni-directional microphone to a directional microphone. This allows for better direction finding for audio capture of a desired individual. FIG. 43 illustrates the directionality improvements available with different microphones.

As shown in the top portion of FIG. 43, a single omnidirectional microphone may be used. The microphone may be placed at a given distance from the source of the sound and the sound pressure or digital audio input (DI)_at the microphone will be at a given dB level. Instead of a single microphone, multiple microphones or an array of microphones may be used. For example, 2 microphones may be placed twice as far away from the source, for a distance factor of 2, with a sound pressure increase of 6 dB. Alternatively, 4 microphones may be used, at a distance factor of 2.7, with an 8.8 dB increase in sound pressure. Arrays may also be used. For example, an 8-microphone array at a distance factor of 4 may have a DI increase of 12 dB while a 12-microphone array at a distance factor of 5 may have a DI increase of 13.2 dB. The graphs in FIG. 43 depict the points which produce the same signal level at the microphone from a given sound pressure level at that point. As shown in FIG. 43, a first order supercardioid microphone may be used at the same distance, in this example having a 6.2 dB increase, while a second order. The multiple microphones may be arranged in a composite microphone array. Instead of using one standard high quality microphone to capture an audio sample, the eyepiece temple pieces house multiple microphones of different character. For example, this may be provided when the user is generating a biometric fingerprint of someone's voice for future capture and comparison. One example of multiple microphone use uses microphones from cut off cell phones to reproduce the exact electrical and acoustic properties of the individual's voice. This sample is stored for future comparison in a database. If the individual's voice is later captured, the earlier sample is available for comparison, and will be reported to the eyepiece user, as the acoustic properties of the two samples will match.

Figure 44:
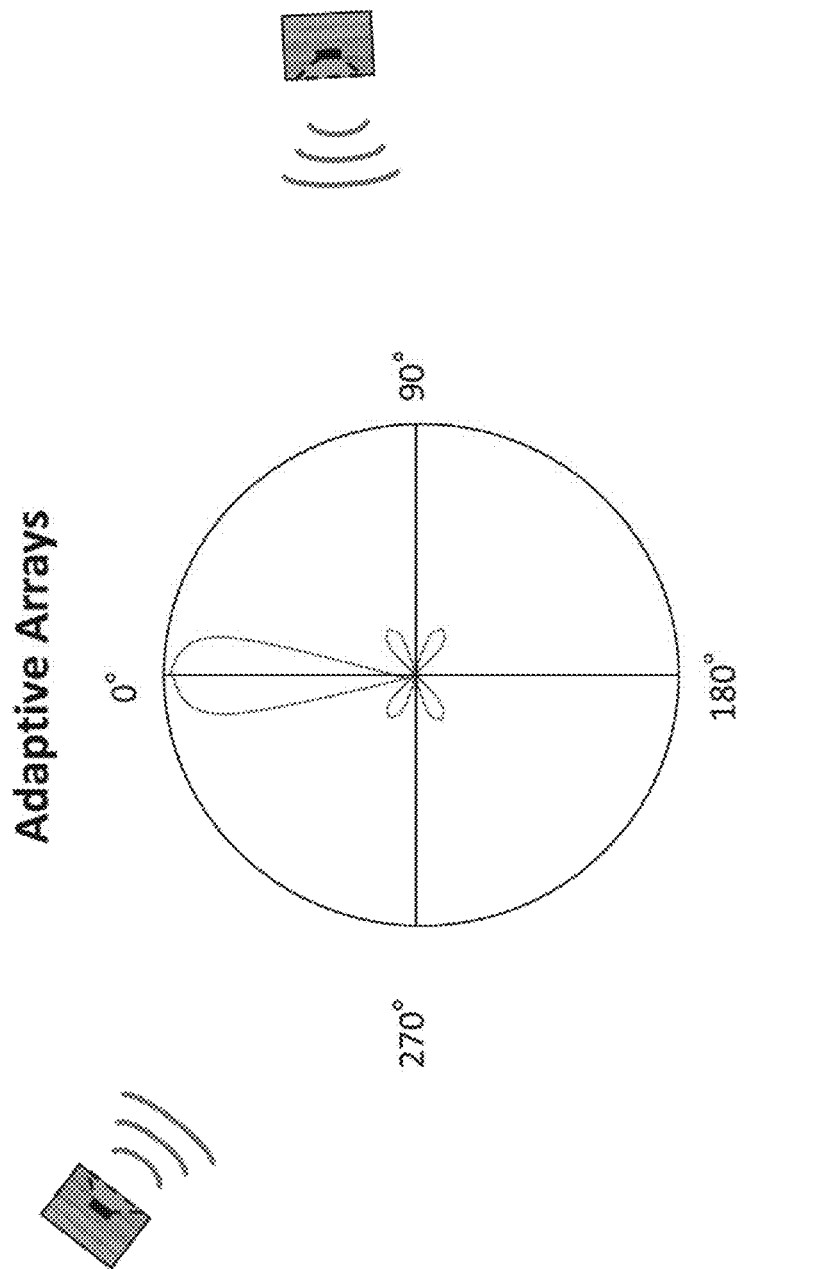
FIG. 44 shows the use of adaptive arrays to steer the audio capture facility according to an embodiment.

FIG. 44 shows the use of adaptive arrays to improve audio data capture. By modifying pre-existing algorithms for audio processing adaptive arrays can be created that allow the user to steer the directionality of the antenna in three dimensions. Adaptive array processing permits location of the source of the speech, thus tying the captured audio data to a specific individual. Array processing permits simple summing of the cardioid elements of the signal to be done either digitally or using analog techniques. In normal use, a user should switch the microphone between the omni-directional pattern and the directional array. The processor allows for beamforming, array steering and adaptive array processing, to be performed on the eyepiece. In embodiments, an audio phase array may be used for audio tracking of a specific individual. For instance, the user may lock onto the audio signature of an individual in the surrounding environment (such as acquired in real-time or from a database of sound signatures), and track the location of the individual without the need to maintain eye contact or the user moving their head. The location of the individual may be projected to the user through the eyepiece display. In embodiments, the tracking of an individual may also be provided through an embedded camera in the eyepiece, where the user would not be required to maintain eye contact with the individual, or move their head to follow. That is, in the case of either the audio or visual tracking, the eyepiece may be able to track the individual within the local environment, without the user needing to show an physical motion to indicate that tracking is taking place and even as the user moves their direction of view.

In an embodiment, the integrated camera may continuously record a video file, and the integrated microphone may continuously record an audio file. The integrated processor of the eyepiece may enable event tagging in long sections of the continuous audio or video recording. For example, a full day of passive recording may be tagged whenever an event, conversation, encounter, or other item of interest takes place. Tagging may be accomplished through the explicit press of a button, a noise or physical tap, a hand gesture, or any other control technique described herein. A marker may be placed in the audio or video file or stored in a metadata header. In embodiments, the marker may include the GPS coordinate of the event, conversation, encounter, or other item of interest. In other embodiments, the marker may be time-synced with a GPS log of the day. Other logic-based triggers can also tag the audio or video file such as proximity relationships to other users, devices, locations, or the like. Event tags may be active event tags that the user triggers manually, passive event tags that occur automatically (such as through preprogramming, through an event profile management facility, and the like), a location-sensitive tag triggered by the user's location, and the like. The event that triggers the event tag may be triggered by a sound, a sight, a visual marker, received from a network connection, an optical trigger, an acoustic trigger, a proximity trigger, a temporal trigger, a geo-spatial trigger, and the like. The event trigger may generate feedback to the user (such as an audio tone, a visual indicator, a message, and the like), store information (such as storing a file, document, entry in a listing, an audio file, a video file, and the like), generate an informational transmission, and the like.

In an embodiment, the eyepiece may be used as SigInt Glasses. Using one or more of an integrated WiFi, 3G or Bluetooth radios, the eyepiece may be used to conspicuously and passively gather signals intelligence for devices and individuals in the user's proximity. Signals intelligence may be gathered automatically or may be triggered when a particular device ID is in proximity, when a particular audio sample is detected, when a particular geo-location has been reached, and the like.

Various embodiments of tactical glasses may include standalone identification or collection of biometrics to geo-locate POIs, with visual biometrics (face, iris, walking gait) at a safe distance and positively identify POIs with robust sparse recognition algorithms for the face and iris. The glasses may include a hands free display for biometric computer interface to merge print and visual biometrics on one comprehensive display with augmented target highlighting and view matches and warnings without alerting the POI. The glasses may include location awareness, such as displaying current and average speeds plus routes and ETA to destination and pre-loading or recording trouble spots and ex-filtration routes. The glasses may include real-time networked tracking of blue and red forces to always know where your friendly's are, achieve visual separation range between blue and red forces, and geo-locate the enemy and share their location in real-time. A processor associated with the glasses may include capabilities for OCR translation and speech translation.

The tactical glasses can be used in combat to provide a graphical user interface projected on the lens that provides users with directions and augmented reality data on such things as team member positional data, map information of the area, SWIR/CMOS night vision, vehicular S/A for soldiers, geo locating laser range finder for geo-locating a POI or a target to >500 m with positional accuracy of typically less than two meters, S/A blue force range rings, Domex registration, AR field repair overlay, and real time UAV video. In one embodiment, the laser range finder may be a 1.55 micron eye-safe laser range finder.

The eyepiece may utilize GPS and inertial navigation (e.g. utilizing an inertial measurement unit) as described herein, such as described herein, to provide positional and directional accuracy. However, the eyepiece may utilize additional sensors and associated algorithms to enhance positional and directional accuracy, such as with a 3-axis digital compass, inclinometer, accelerometer, gyroscope, and the like. For instance, a military operation may require greater positional accuracy then is available from GPS, and so other navigation sensors may be utilized in combination to increase the positional accuracy of GPS.

The tactical glasses may feature enhanced resolution, such as 1280×1024 pixels, and may also feature auto-focus.

In dismounted and occupied enemy engagement missions, defeating a low-intensity, low-density, asymmetrical form of warfare is incumbent upon efficient information management. The tactical glasses system incorporates ES2 (every soldier is a sensor) capabilities through uncooperative data recording and intuitive tactical displays for a comprehensive picture of situational awareness.

In embodiments, the tactical glasses may include one or more waveguides being integrated into the frame. In some embodiments, the total internal reflection lens is attached to a pair of ballistic glasses in a monocular or binocular flip-up/flip-down arrangement. The tactical glasses may include omni-directional ear buds for advanced hearing and protection and a noise-cancelling boom microphone for communication phonetically differentiated commands.

In some embodiments, the waveguides may have contrast control. The contrast may be controlled using any of the control techniques described herein, such as gesture control, automatic sensor control, manual control using a temple mounted controller, and the like.

The tactical glasses may include a non-slip, adjustable elastic head-strap. The tactical glasses may include clip-in corrective lenses.

Figure 74:
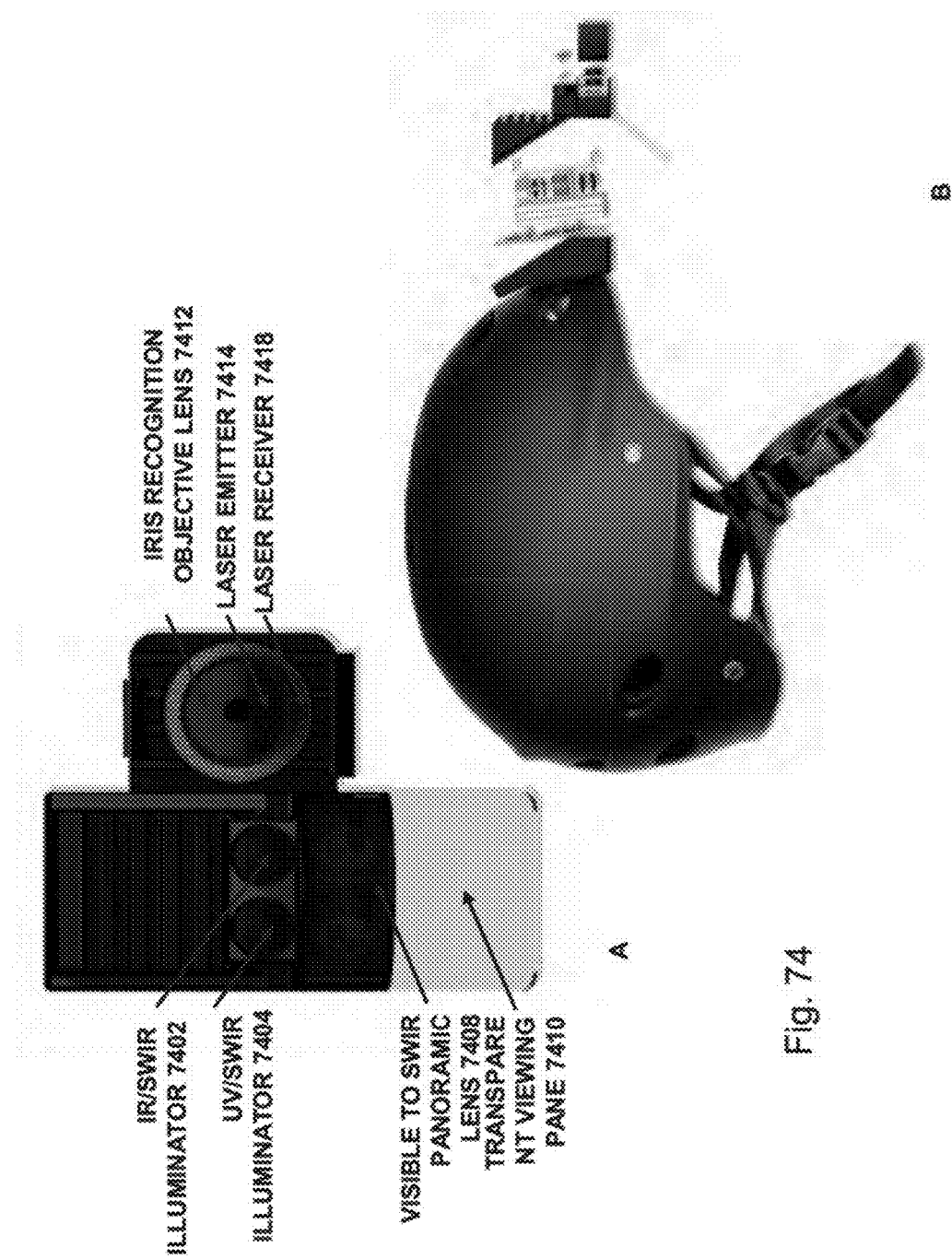
FIG. 74 depicts a helmet-mounted version of the eyepiece.

In some embodiments, the total internal reflection lens is attached to a device that is helmet-mounted, such as in FIG. 74, and may include a day/night, VIS/NIR/SWIR CMOS color camera. The device enables unimpeded "sight" of the threat as well as the soldier's own weapon with "see through", flip-up electro-optic projector image display. The helmet-mounted device, shown in FIG. 74A, may include an IR/SWIR illuminator 7402, UV/SWIR illuminator 7404, visible to SWIR panoramic lens 7408, visible to SWIR objective lens (not shown), transparent viewing pane 7410, iris recognition objective lens 7412, laser emitter 7414, laser receiver 7418, or any other sensor, processor, or technology described with respect to the eyepiece described herein, such as an integrated IMU, an eye-safe laser range finder, integrated GPS receiver, compass and inclinometer for positional accuracy, perspective control that changes the viewing angle of the image to match the eye position, electronic image stabilization and real-time enhancement, a library of threats stored onboard or remotely for access over a tactical network, and the like. A body-worn wireless computer may interface with the device in FIG. 74. The helmet-mounted device includes visible to SWIR projector optics, such as RGB microprojector optics. Multispectral IR and UV imaging helps spot fake or altered docs. The helmet-mounted device may be controlled with an encrypted wireless UWB wrist or weapon fore grip controller.

In an embodiment, the transparent viewing pane 7410 can rotate through 180° to project imagery onto a surface to share with others.

FIG. 74B shows a side view of the exploded device mounted to a helmet. The device may include a fully ambidextrous mount for mounting on the left or right side of the helmet. In some embodiments, two devices may be mounted on each of the left and right sides of the helmet to enable binocular vision. The device or devices may snap into a standard MICH or PRO-TECH helmet mount.

Today the warfighter cannot utilize fielded data devices effectively. The tactical glasses system combines a low profile form, lightweight materials and fast processers to make quick and accurate decisions in the field. The modular design of the system allows the devices to be effectively deployed to the individual, squad or company while retaining the ability to interoperate with any fielded computer. The tactical glasses system incorporates real-time dissemination of data. With the onboard computer interface the operator can view, upload or compare data in real time. This provides valuable situational and environmental data can be rapidly disseminated to all networked personnel as well as command posts (CPs) and tactical operations centers (TOCs).

FIGS. 75A and 75B in a front and side view, respectively, depict an exemplary embodiment of biometric and situational awareness glasses. This embodiment may include multiple field of view sensors 7502 for biometric collection situational awareness and augmented view user interface, fast locking GPS receiver and IMU, including 3-axis digital compass, gyroscope, accelerometer and inclinometer for positional and directional accuracy, 1.55 micron eye-safe laser range finder 7504 to assist biometric capture and targeting integrated digital video recorder storing two Flash SD cards, real-time electronic image stabilization and real-time image enhancement, library of threats stored in onboard mini-SD card or remotely loaded over a tactical network, flip-up photochromic lenses 7508, noise-cancelling flexible boom mike 7510 and 3-axis detachable stereo ear buds plus augmented hearing and protection system 7512. For example, the multiple field of view sensors 7502 may enable a 100°×40° FOV, which may be panoramic SXGA. For example, the sensors may be a VGA sensor, SXGA sensor, and a VGA sensor that generates a panoramic SXGA view with stitched 100°×40° FOV on a display of the glasses. The displays may be translucent with perspective control that changes the viewing angle of the image to match the eye position. This embodiment may also include SWIR detection to let wearers see 1064 nm and 1550 nm laser designators, invisible to the enemy and may feature ultra-low power 256-bit AES Encrypted connection between glasses, tactical radios and computers, instant 2× zoom, auto face tracking, face and iris recording, and recognition and GPS geo-location with a 1 m auto-recognition range. This embodiment may include a power supply, such as a 24 hour duration 4-AA alkaline, lithium and rechargeable battery box with its computer and memory expansion slots with a water- and dust-proof cord. In an embodiment, the glasses include a curved holographic wave guide.

In embodiments, the eyepiece may be able to sense lasers such as used in battlefield targeting. For instance, sensors in the eyepiece may be able to detect laser light in typical military-use laser transmission bands, such as 1064 nm, 1550 nm, and the like. In this way, the eyepiece may be able to detect whether their position is being targeted, if another location is being targeted, the location of a spotter using the laser as a targeting aid, and the like. Further, since the eyepiece may be able to sense laser light, such as directly or reflected, the soldier may not only detect enemy laser sources that have been directed or reflected to their position, but may supply the laser source themselves in order to locate optical surfaces (e.g. binoculars) in the battlefield scene. For example, the soldier scans the field with a laser and watches with the eyepiece for a reflected return of the laser as a possible location of an enemy viewing though binoculars. In embodiments, the eyepiece may continuously scan the surrounding environment for laser light, and provide feedback and/or action as a result of a detection, such as an audible alarm to the soldier, a location indicted through a visual indicator on the eyepiece display, and the like.

In some embodiments, a Pocket Camera may video record and captures still pictures, allowing the operator to record environmental data for analysis with a mobile, lightweight, rugged biometric device sized to be stored in a pocket. An embodiment may be 2.25"×3.5"×0.375" and capable of face capture at 10 feet, iris capture at 3 feet, recording voice, pocket litter, walking gait, and other identifying visible marks and environmental data in EFTS and EBTS compliant formatting compatible with any Iris/Face algorithm. The device is designed to pre-qualify and capture EFTS/EBTS/NIST/ISO/ITL 1-2007 compliant salient images to be matched and filed by any biometric matching software or user interface. The device may include a high definition video chip, 1 GHz processor with 533 Mhz DSP, GPS chip, active illumination and pre-qualification algorithms. In some embodiments, the Pocket Bio Cam may not incorporate a biometric watch list so it can be used at all echelons and/or for constabulary leave-behind operations. Data may be automatically geo-located and date/time stamped. In some embodiments, the device may operate Linux SE OS, meet MIL-STD-810 environmental standards, and be waterproof to 3 ft depth (about 1 m).

In an embodiment, a device for collection of fingerprints may be known as a bio-print device. The bio-print apparatus comprises a clear platen with two beveled edges. The platen is illuminated by a bank of LEDs and one or more cameras.

Multiple cameras are used and are closely disposed and directed to the beveled edge of the platen. A finger or palm is disposed over the platen and pressed against an upper surface of the platen, where the cameras capture the ridge pattern. The image is recorded using frustrated total internal reflection (FTIR). In FTIR, light escapes the platen across the air gap created by the ridges and valleys of the fingers or palm pressed against the platen.

Other embodiments are also possible. In one embodiment, multiple cameras are place in inverted 'V' s of a saw tooth pattern. In another embodiment, a rectangle is formed and uses light direct through one side and an array of cameras capture the images produced. The light enters the rectangle through the side of the rectangle, while the cameras are directly beneath the rectangle, enabling the cameras to capture the ridges and valleys illuminated by the light passing through the rectangle.

After the images are captured, software is used to stitch the images from the multiple cameras together. A custom FPGA may be used for the digital image processing.

Once captured and processed, the images may be streamed to a remote display, such as a smart phone, computer, hand-held device, or eyepiece, or other device.

The above description provides an overview of the operation of the methods and apparatus of the disclosure. Additional description and discussion of these and other embodiments is provided below.

Figure 45:
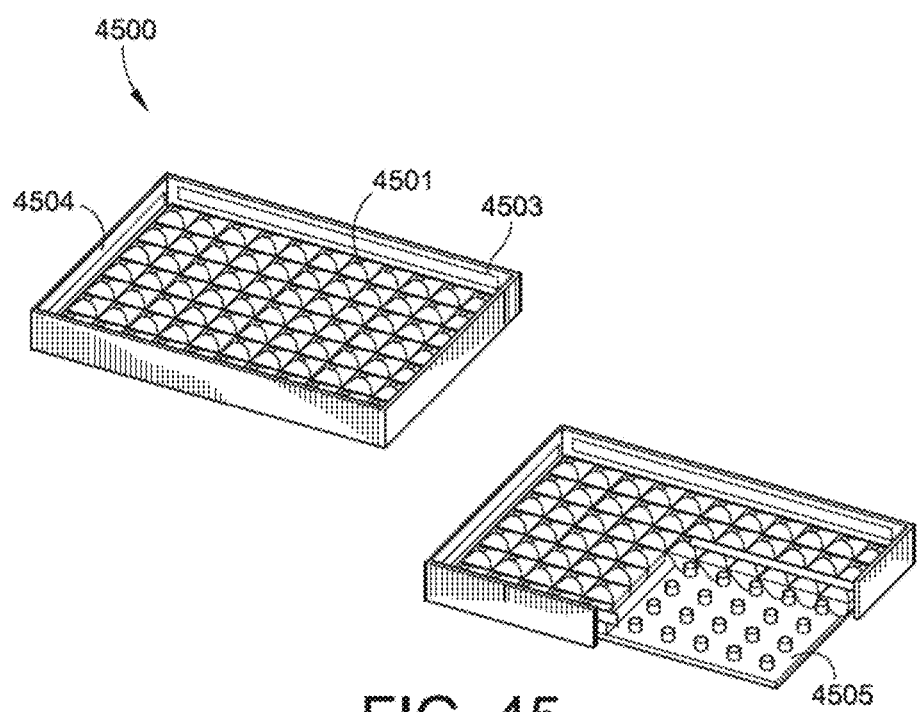
FIG. 45 shows the mosaic finger and palm enrollment system according to an embodiment.

FIG. 45 illustrates the construction and layout of an optics based finger and palm print system according to an embodiment. The optical array consists of approximately 60 wafer scale cameras 4502. The optics based system uses sequential perimeter illumination 4503, 4504 for high resolution imaging of the whorls and pores that comprise a finger or palm print. This configuration provides a low profile, lightweight, and extremely rugged configuration. Durability is enhanced with a scratch proof, transparent platen.

The mosaic print sensor uses a frustrated total internal reflection (FTIR) optical faceplate provides images to an array of wafer scale cameras mounted on a PCB like substrate 4505. The sensor may be scaled to any flat width and length with a depth of approximately ½". Size may vary from a plate small enough to capture just one finger roll print, up to a plate large enough to capture prints of both hands simultaneously.

The mosaic print sensor allows an operator to capture prints and compare the collected data against an on-board database. Data may also be uploaded and downloaded wirelessly. The unit may operate as a standalone unit or may be integrated with any biometric system.

In operation the mosaic print sensor offers high reliability in harsh environments with excessive sunlight. To provide this capability, multiple wafer scale optical sensors are digitally stitched together using pixel subtraction. The resulting images are engineered to be over 500 dots per inch (dpi). Power is supplied by a battery or by parasitically drawing power from other sources using a USB protocol. Formatting is EFTS, EBTS NIST, ISO, and ITL 1-2007 compliant.

Figure 46:
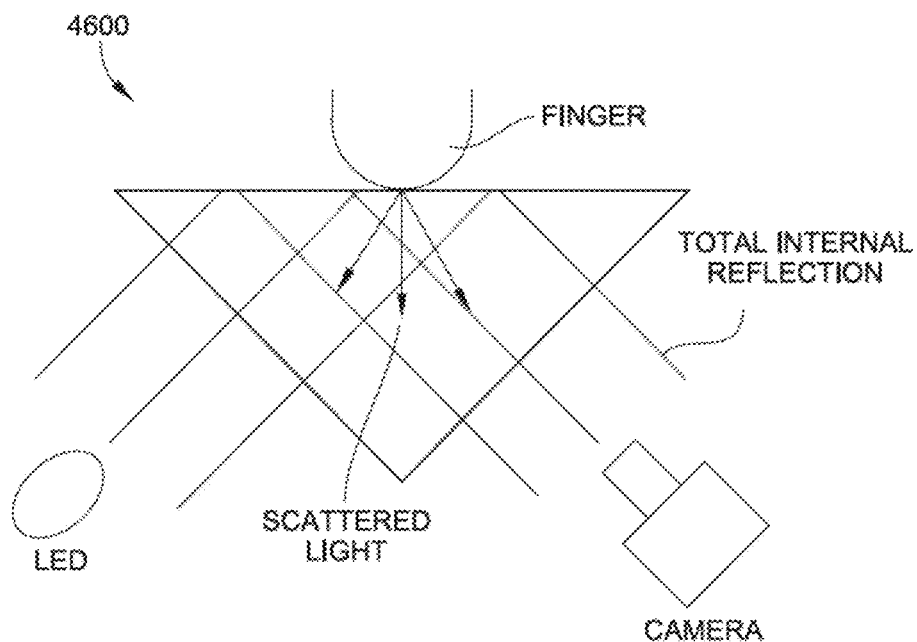
FIG. 46 illustrates the traditional optical approach used by other finger and palm print systems.

FIG. 46 illustrates the traditional optical approach used by other sensors. This approach is also based on FTIR (frustrated total internal reflection). In the figure, the fringes contact the prism and scatter the light. The camera captures the scattered light. The fringes on the finger being printed show as dark lines, while the valleys of the fingerprint show as bright lines.

Figure 47:
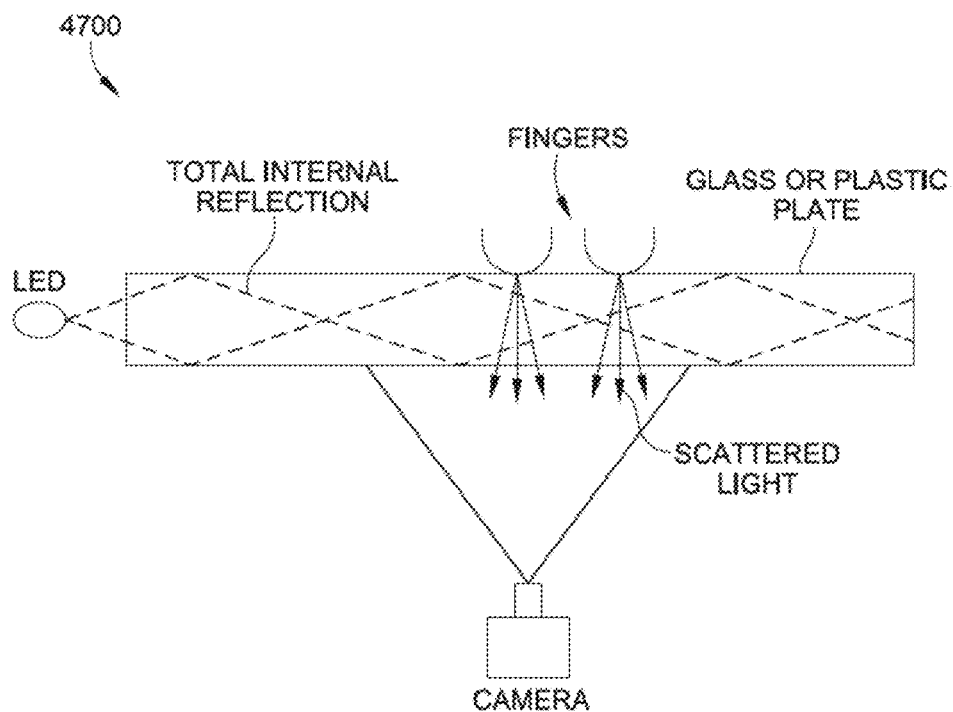
FIG. 47 shows the approach used by the mosaic sensor according to an embodiment.

FIG. 47 illustrates the approach used by the mosaic sensor 4700. The mosaic sensor also uses FTIR. However, the plate is illuminated from the side and the internal reflections are contained within the plate of the sensor. The fringes of the fingerprints whose images are being taken, shown at the top of the figure, contact the prism and scatter the light, allowing the camera to capture the scattered light. The fringes on the finger show as bright lines, whiles the valleys show as dark lines.

Figure 48:
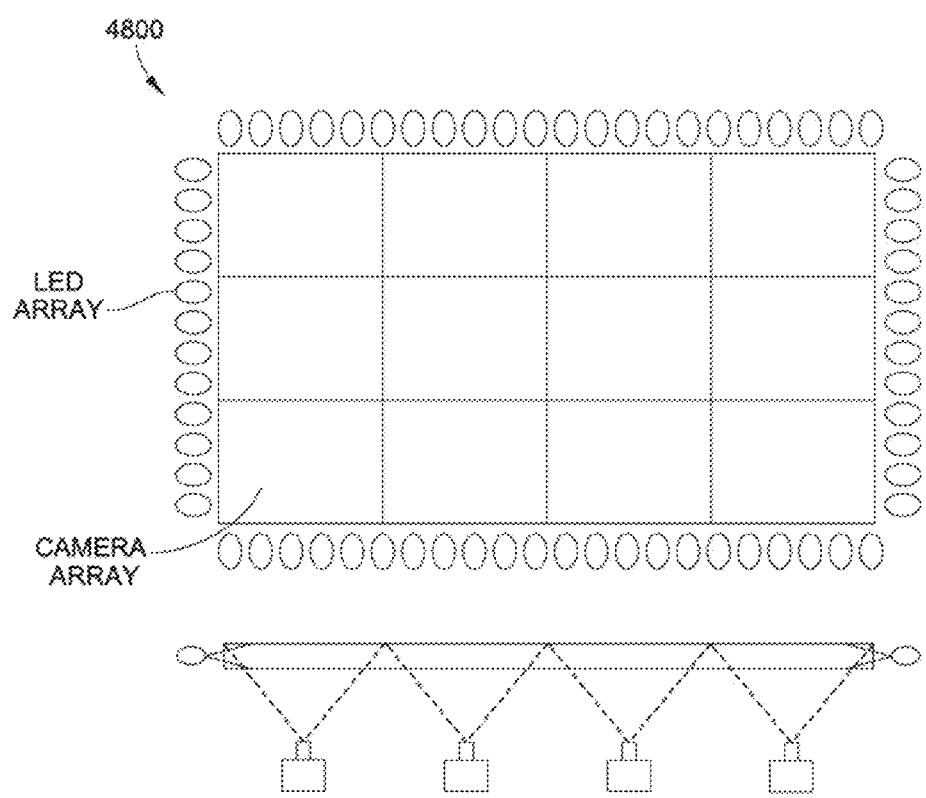
FIG. 48 depicts the device layout of the mosaic sensor according to an embodiment.

FIG. 48 depicts the layout of the mosaic sensor 4800. The LED array is arranged around the perimeter of the plate. Underneath the plate are the cameras used to capture the fingerprint image. The image is captured on this bottom plate, known as the capture plane. The capture plane is parallel to the sensor plane, where the fingers are placed. The thickness of the plate, the number of the cameras, and the number of the LEDs may vary, depending on the size of the active capturing area of the plate. The thickness of the plate may be reduced by adding mirrors that fold the optical path of the camera, reducing the thickness needed. Each camera should cover one inch of space with some pixels overlapping between the cameras. This allows the mosaic sensor to achieve 500 ppi. The cameras may have a field of view of 60 degrees; however, there may be significant distortion in the image.

FIG. 49 shows an embodiment 4900 of a camera field of view and the interaction of the multiple cameras used in the mosaic sensor. Each camera covers a small capturing area. This area depends on the camera field of view and the distance between the camera and the top surface of the plate. $\alpha$ is one half of the camera's horizontal field of view and $\beta$ is one half of the camera's vertical field of view.

Figure 50:
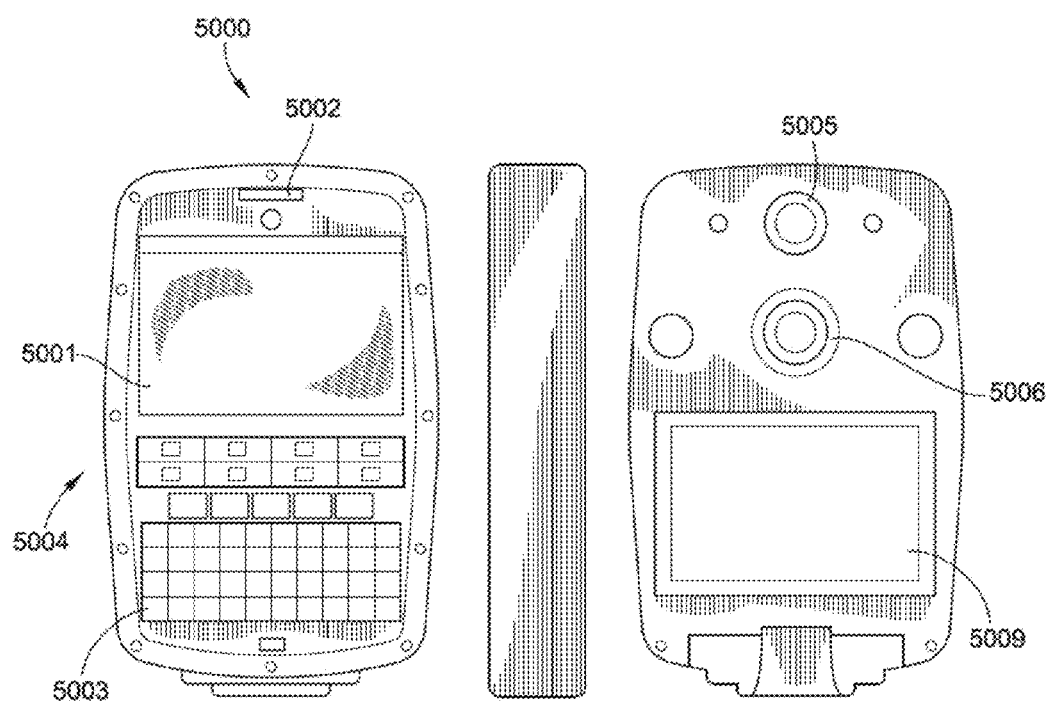
FIG. 50 shows the bio-phone and tactical computer according to an embodiment.

The mosaic sensor may be incorporated into a bio-phone and tactical computer as illustrated in FIG. 50. The bio-phone and tactical computer uses a completed mobile computer architecture that incorporates dual core processors, DSP, 3-D graphics accelerator, 3G-4G Wi-Lan (in accordance with 802.11a/b/g/n), Bluetooth 3.0, and a GPS receiver. The bio-phone and tactical computer delivers power equivalent to a standard laptop in a phone size package.

FIG. 50 illustrates the components of the bio-phone and tactical computer. The bio-phone and tactical computer assembly, 5000 provides a display screen 5001, speaker 5002 and keyboard 5003 contained within case 5004. These elements are visible on the front of the bio-phone and tactical computer assembly 5000. On the rear of the assembly 3800 are located a camera for iris imaging 5005, a camera for facial imaging and video recording 5006 and a bio-print fingerprint sensor 5009.

To provide secure communications and data transmission, the device incorporates selectable 256-bit AES encryption with COTS sensors and software for biometric pre-qualification for POI acquisition. This software is matched and filed by any approved biometric matching software for sending and receiving secure "perishable" voice, video, and data communications. In addition, the bio-phone supports Windows Mobile, Linux, and Android operating systems.

The bio-phone is a 3G-4G enabled hand-held device for reach back to web portals and biometric enabled watch list BEWL) databases. These databases allow for in-field comparison of captured biometric images and data. The device is designed to fit into a standard LBV or pocket. In embodiments, the biometrics phone and tactical computer may use a mobile computer architecture featuring dual core processors, DSP, 3-D graphics accelerator, 3G-4G, Wi-LAN (802.11a/b/g/n), Bluetooth 3.0, enabled for secure and civilian networks, GPS Receiver, WVGA sun-sight readable capacitance touchscreen display, capable of outputting stereoscopic 3D video, tactile backlit QWERTY keyboard, on-board storage, supporting multiple operating systems, and the like, that delivers laptop power in a light weight design.

Figure 52:
FIG. 52 illustrates a typical DOMEX collection.

The bio-phone can search, collect, enroll, and verify multiple types of biometric data, including face, iris, two-finger fingerprint, as well as biographic data. The device also records video, voice, gait, identifying marks, and pocket litter. Pocket litter includes a variety of small items normally carried in a pocket, wallet, or purse and may include such items as spare change, identification, passports, charge cards, and the like. FIG. 52 shows a typical collection of this type of information. Depicted in FIG. 52 are examples of a collection of pocket litter 5200. The types of items that may be included are personal documents and pictures 5201, books 5202, notebooks and paper, 5203, and documents, such as a passport 5204.

The biometrics phone and tactical computer may include a camera, such as a high definition still and video camera, capable of biometric data taking and video conferencing. In embodiments, the eyepiece camera and videoconference capabilities, as described herein, may be used in conjunction with the biometrics phone and tactical computer. For instance, a camera integrated into the eyepiece may capture images and communicate the images to the biometrics phone and tactical computer, and vice a versa. Data may be exchanged between the eyepiece and biometrics phone, network connectivity may be established by either, and shared, and the like. In addition, the biometric phone and tactical computer may be housed in a rugged, fully militarized construction, tolerant to a militarized temperature range, waterproof (such as to a depth of 5 m), and the like.

Figure 51:
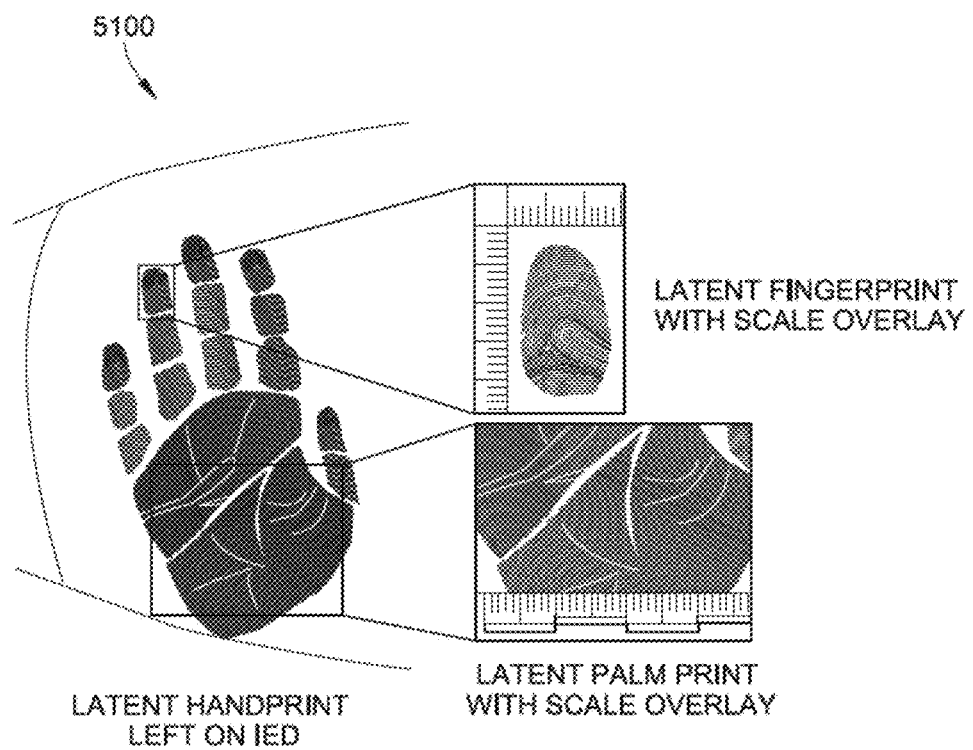
FIG. 51 shows the use of the bio-phone and tactical computer in capturing latent fingerprints and palm prints according to an embodiment.

FIG. 51 illustrates an embodiment 5100 of the use of the bio-phone to capture latent fingerprints and palm prints. Fingerprints and palm prints are captured at 1000 dpi with active illumination from an ultraviolet diode with scale overlay. Both fingerprint and palm prints 5100 may be captured using the bio-phone.

Figure 53:
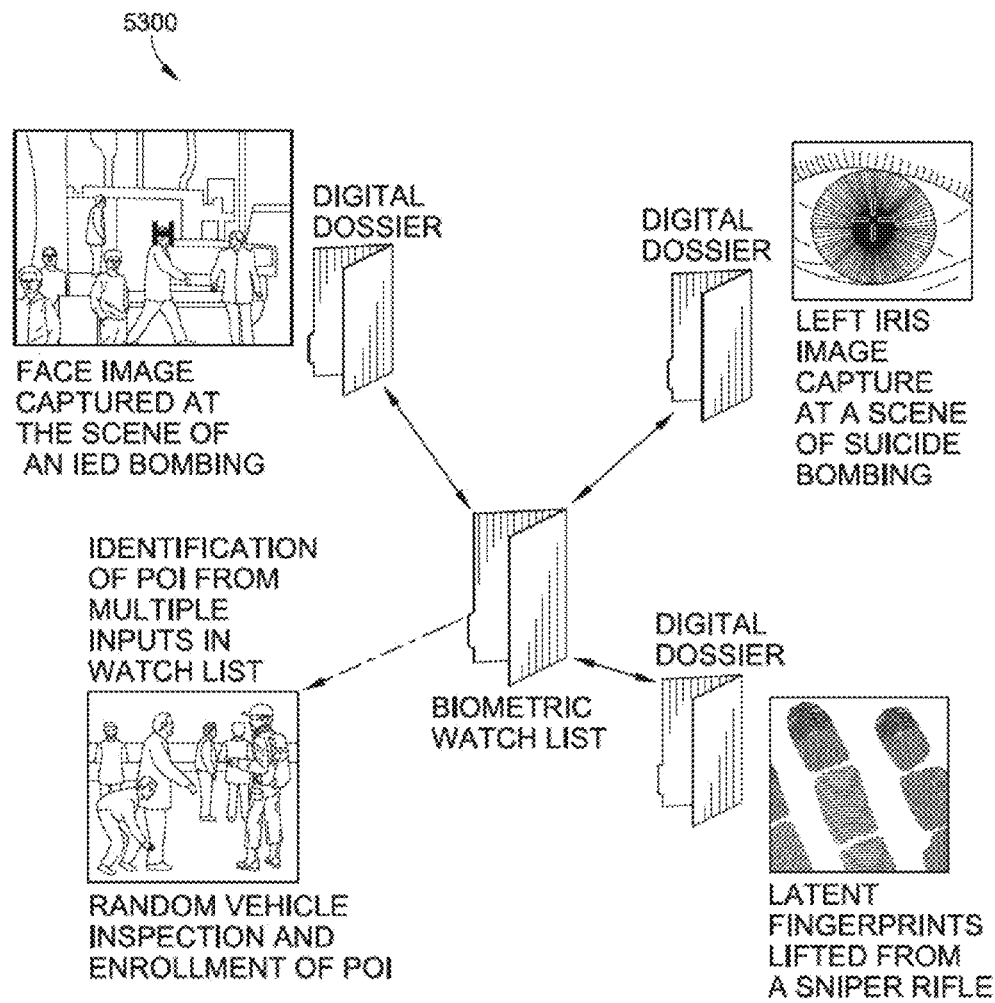
FIG. 53 shows the relationship between the biometric images captured using the bio-phone and tactical computer and a biometric watch list according to an embodiment.

Data collected by the bio-phone is automatically geo-located and date and time stamped using the GPS capability. Data may be uploaded or downloaded and compared against onboard or networked databases. This data transfer is facilitated by the 3G-4G, Wi-Lan, and Bluetooth capabilities of the device. Data entry may be done with the QWERTY keyboard, or other methods that may be provided, such as stylus or touch screen, or the like. Biometric data is filed after collection using the most salient image. Manual entry allows for partial data capture. FIG. 53 illustrates the interplay 5300 between the digital dossier images and the biometric watch list held at a database. The biometric watch list is used for comparing data captured in the field with previously captured data Formatting may use EFTS, EBTS NIST, ISO, and ITL 1-2007 formats to provide compatibility with a range and variety of databases for biometric data.

The specifications for the bio-phone and tactical computer are given below:
 Operating Temperature: −22° C. to +70° C.
 Connectivity I/O: 3G, 4G, WLAN a/b/g/n, Bluetooth 3.0, GPS, FM
 Connectivity Output: USB 2.0, HDMI, Ethernet
 Physical Dimensions: 6.875" (H)×4.875" (W)×1.2" (T)
 Weight: 1.75 lbs.
 Processor: Dual Core—1 GHz Processors, 600 MHz DSP, and 30M Polygon/sec 3-D Graphics Accelerator
 Display: 3,8" WVGA (800×480) Sunlight Readable, Transreflective, Capacitive Touch Screen, Scalable display output for connection to 3×1080p Hi-Def screens simultaneously.
 Operating System Windows Mobile, Linux, SE, Android
 Storage: 128 GB solid-state drive
 Additional Storage Dual SD Card slots for additional 128 GB storage.
 Memory: 4 GB RAM
 Camera: 3 Hi-Def Still and Video Cameras: Face, Iris, and Conference
  (User's Face)
 3D Support: Capable of outputting stereoscopic 3D video.
  Camera Sensor Support: Sensor dynamic range extension, Adaptive defect pixel correction, advanced sharpness enhancement, Geometric distortion correction, advanced management, HW based face detection, Video stabilization
 Biometrics: On-board optical, 2 fingerprint sensor, Face, DOMEX, and Iris cameras.
 Sensors: Can accommodate the addition of accelerometer, compass, ambient light, proximity, barometric, and temperature sensors, depending on requirements.
 Battery: <8 hrs, 1400 Mah, rechargeable Li-ion, hot swap battery pack.
 Power: Various power options for continuous operation.
 Software Features Face/gesture detection, noise filtering, pixel correction.
  Powerful display processor with multi-overlay, rotation, and resizing capabilities.
 Audio: On board microphone, speakers, and audio/video inputs.
 Keyboard: Full tactile QWERTY keyboard with adjustable backlight.

Additional devices and kits may also incorporate the mosaic sensors and may operate in conjunction with the bio-phone and tactical computer to provide a complete field solution for collection biometric data.

Figure 54:
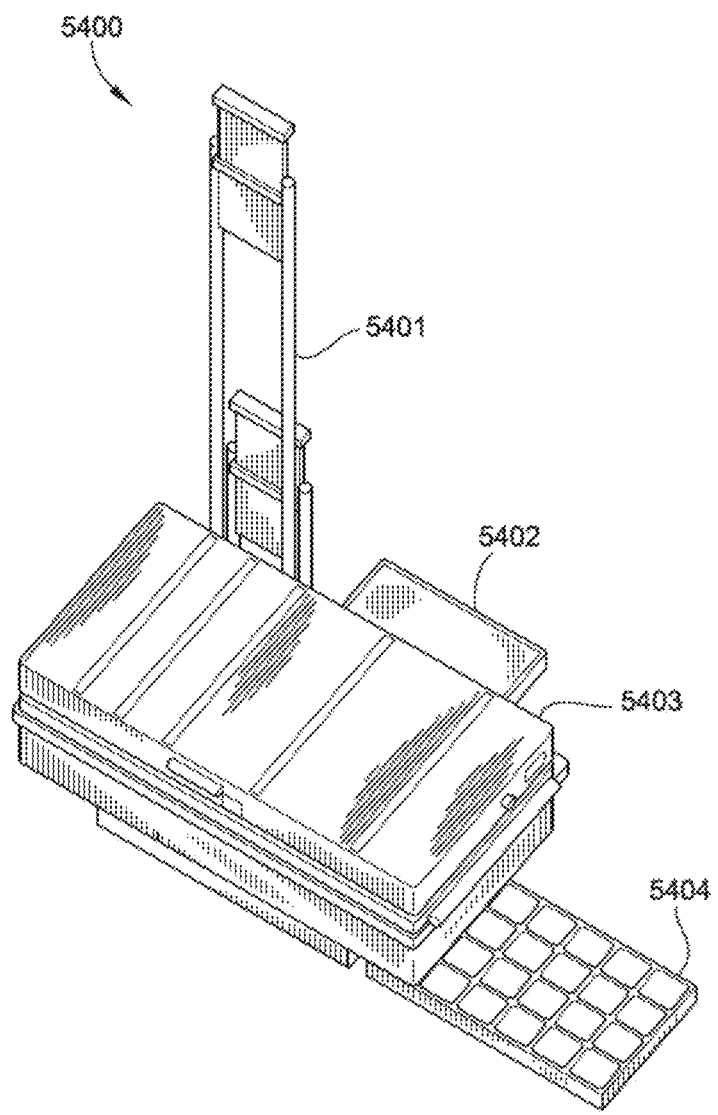
FIG. 54 illustrates a pocket bio-kit according to an embodiment.

One such device is the pocket bio-kit, illustrated in FIG. 54. The components of the pocket bio-kit 5400 include a GPS antenna 5401, a bio-print sensor 5402, keyboard 5404, all contained in case 5403. The specifications of the bio-kit are given below:
 Size: 6"×3"×1.5"
 Weight: 2 lbs. total
 Processor and Memory: 1 GHz OMAP processor
  650 MHz core
  3-D accelerator handling up to 18 million polygons/sec
  64 KB L2 cache
  166 MHz at 32 bit FSB
  1 GB embedded PoP memory expandable with up to 4 GB NAND
  64 GB solid state hard drive
 Display: 75 mm×50 mm, 640×480 (VGA) daylight readable LCD, anti-glare, anti-reflective, anti-scratch screen treatment
 Interface: USB 2.0
  10/100/1000 Ethernet
 Power: Battery operation: approximately 8 hours of continuous enrollments at roughly 5 minutes per enrollment.
 Embedded Capabilities: mosaic sensor optical fingerprint reader
  Digital iris camera with active IR illumination
  Digital face and DOMEX camera (visible) with flash
  Fast lock GPS The features of the bio-phone and tactical computer may also be provided in a bio-kit that provides for a biometric data collection system that folds into a rugged and compact case. Data is collected in biometric standard image and data formats that can be cross-referenced for near real-time data communication with Department of Defense Biometric Authoritative Databases.

Figure 55:
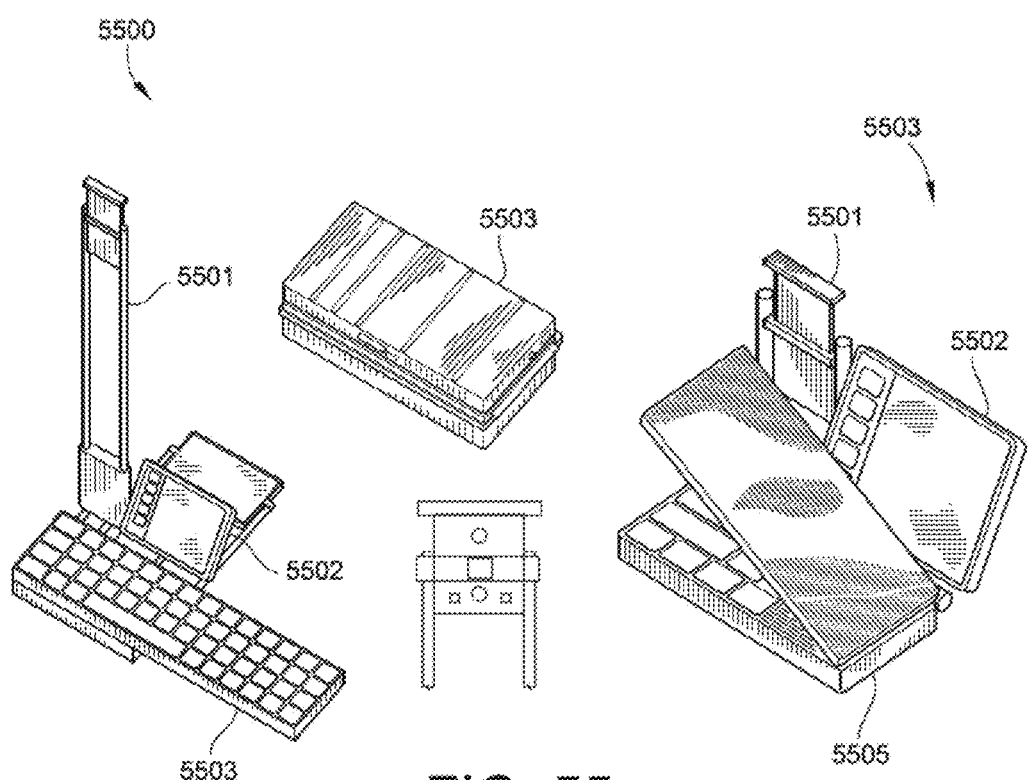
FIG. 55 shows the components of the pocket bio-kit according to an embodiment.

The pocket bio-kit shown in FIG. 55 can capture latent fingerprints and palm prints at 1,000 dpi with active illumination from an ultraviolet diode with scale overlay. The bio-kit holds 32 GB memory storage cards that are capable of interoperation with combat radios or computers for upload and download of data in real-time field conditions. Power is provided by lithium ion batteries. Components of the bio-kit assembly 5500 include a GPS antenna 5501, a bio-print sensor 5502, and a case 5503 with a base bottom 5505.

Biometric data collect is geo-located for monitoring and tracking individual movement. Finger and palm prints, iris images, face images, latent fingerprints, and video may be collected and enrolled in a database using the bio-kit. Algorithms for finger and palm prints, iris images, and face images facilitate these types of data collection. To aid in capturing iris images and latent fingerprint images simultaneously, the bio-kit has IR and UV diodes that actively illuminate an iris or latent fingerprint. In addition, the pocket bio-kit is also fully EFTS/EBTS compliant, including ITL 1-2007 and WSQ. The bio-kit meets MIL-STD-810 for operation in environmental extremes and uses a Linux operating system.

For capturing images, the bio-kit uses a high dynamic range camera with wave front coding for maximum depth of field, ensuring detail in latent fingerprints and iris images is captured. Once captured, real-time image enhancement software and image stabilization act to improve readability and provide superior visual discrimination.

The bio-kit is also capable of recording video and stores full-motion (30 fps) color video in an onboard "camcorder on chip."

The eyepiece 100 may interface with the mobile folding biometrics enrollment kit (aka bio-kit) 5500, a biometric data collection system that folds into a compact rugged case, such that unfolds into a mini workstation for fingerprints, iris and facial recognition, latent fingerprint, and the like biometric data as described herein. As is the case for the other mobile biometrics devices, the mobile folding biometrics enrollment kit 5500 may be used as a stand-alone device or in association with the eyepiece 100, as described herein. In an embodiment, the mobile folding biometrics enrollment kit may fold up to a small size such as 6"×3"×1.5" with weight such as 2 pounds. It may contain a processor, digital signal processor, 3D accelerator, fast syndrome-based hash (FSB) functions, solid state memory (e.g. package-on-package (PoP)), hard drive, display (e.g. 75 mm×50 mm, 640×480 (VGA) daylight-readable LCD anti-glare, anti-reflective, anti-scratch screen), USB, Ethernet, embedded battery, mosaic optical fingerprint reader, digital iris camera (such as with active IR illumination), digital face and DOMEX camera with flash, fast lock GPS, and the like. Data may be collected in biometric standard image and data formats that may be cross-referenced for a near real-time data communication with the DoD biometric authoritative databases. The device may be capable of collecting biometric data and geo-location of persons of interest for monitoring and tracking, wireless data upload/download using combat radio or computer with standard networking interface, and the like.

Figure 56:
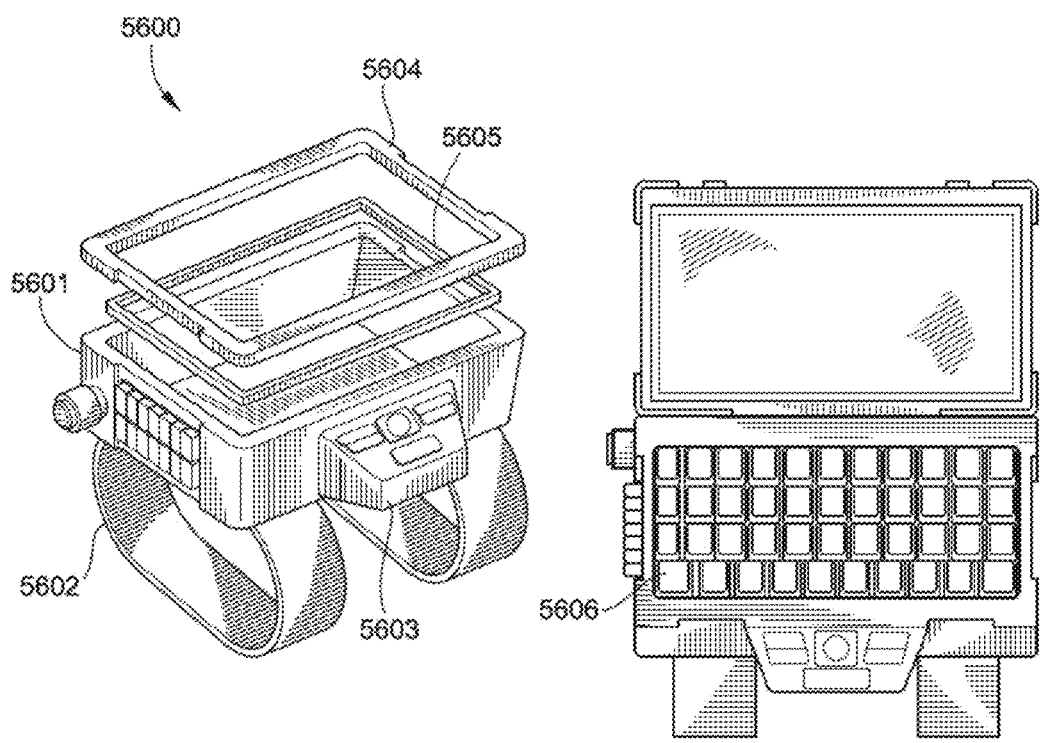
FIG. 56 depicts the fingerprint, palm print, geo-location and POI enrollment device according to an embodiment.

In addition to the bio-kit, the mosaic sensor may be incorporated into a wrist mounted fingerprint, palm print, geo-location, and POI enrollment device, shown in FIG. 56. The eyepiece 100 may interface with the biometric device 5600, a biometric data collection system that straps on a soldier's wrist or arm and folds open for fingerprints, iris recognition, computer, and the like biometric data as described herein. The device may have an integrated computer, keyboard, sunlight-readable display, biometric sensitive platen, and the like, so operators may rapidly and remotely store or compare data for collection and identification purposes. For instance, the arm strap biometric sensitive platen may be used to scan a palm, fingerprints, and the like. The device may provide geo-location tags for person of interest and collected data with time, date, location, and the like. As is the case for the other mobile biometrics devices, the biometric device 5600 may be used as a stand-alone device or in association with the eyepiece 100, as described herein. In an embodiment, the biometric device may be small and light to allow it to be comfortably worn on a soldier's arm, such as with dimensions 5"×2.5" for the active fingerprint and palm print sensor, and a weight of 16 ounces. There may be algorithms for fingerprint and palm capture. The device may include a processor, digital signal processor, a transceiver, a Qwerty key board, large weather-resistant pressure driven print sensor, sunlight readable transflective QVGA color backlit LCD display, internal power source, and the like.

In one embodiment, the wrist mounted assembly 5600 includes the following elements in case 5601: straps 5602, setting and on/off buttons 5603, protective cover for sensor 5604, pressure-driven sensor 4405, and a keyboard and LCD screen 5606.

The fingerprint, palm print, geo-location, and POI enrollments device includes an integrated computer, QWERTY keyboard, and display. The display is designed to allow easy operation in strong sunlight and uses an LCD screen or LED indicator to alert the operator of successful fingerprint and palm print capture. The display uses transflective QVGA color, with a backlit LCD screen to improve readability. The device is lightweight and compact, weighing 16 oz. and measuring 5"×2.5" at the mosaic sensor. This compact size and weight allows the device to slip into an LBV pocket or be strapped to a user's forearm, as shown in FIG. 56. As with other devices incorporating the mosaic sensor, all POIs are tagged with geo-location information at the time of capture.

The size of the sensor screen allows 10 fingers, palm, four-finger slap, and fingertip capture. The sensor incorporates a large pressure driven print sensor for rapid enrollment in any weather conditions as specified in MIL-STD-810, at a rate of 500 dpi. Software algorithms support both fingerprint and palm print capture modes and uses a Linux operating system for device management. Capture is rapid, due to the 720 MHz processor with 533 MHZ DSP. This processing capability delivers correctly formatted, salient images to any existing approved system software. In addition, the device is also fully EFTS/EBTS compliant, including ITL 1-2007 and WSQ.

As with other mosaic sensor devices, communication in wireless mode is possible using a removable UWB wireless 256-bit AES transceiver. This also provides secure upload and download to and from biometric databases stored off the device.

Power is supplied using lithium polymer or AA alkaline batteries.

Figure 57:
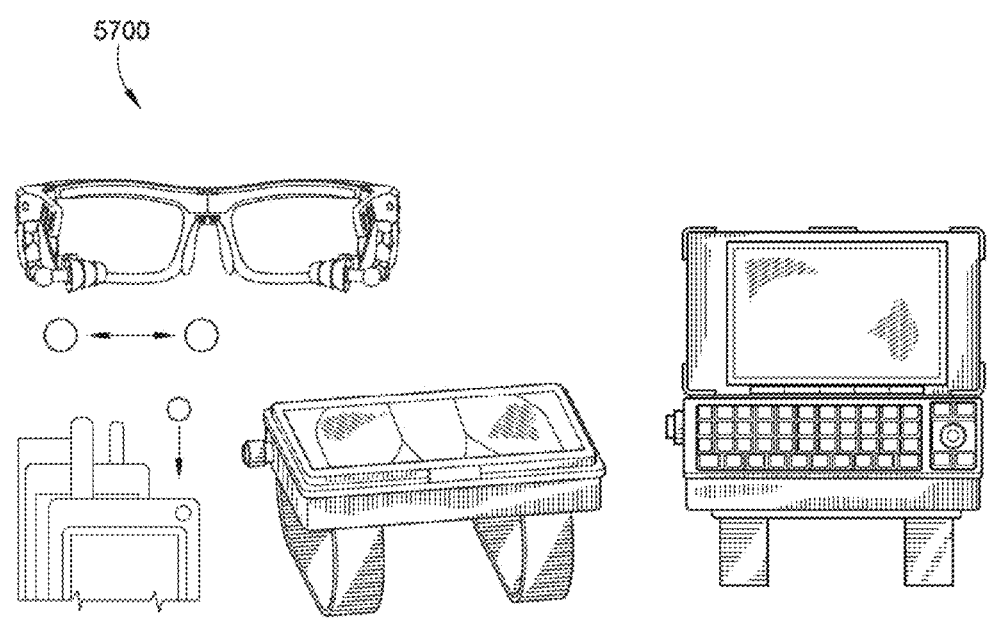
FIG. 57 shows a system for multi-modal biometric collection, identification, geo-location, and POI enrollment according to an embodiment.
Figure 57A:
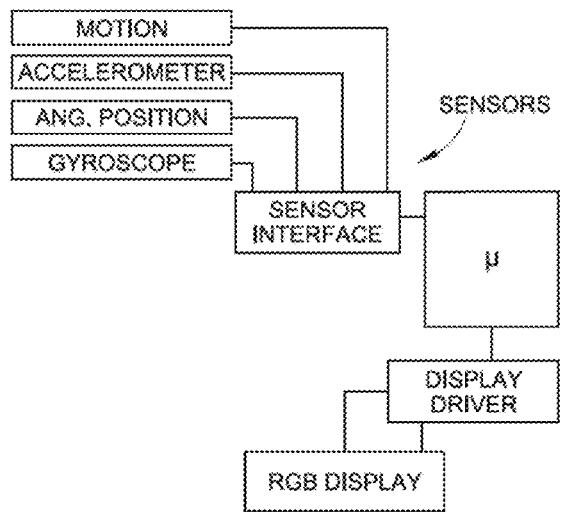
Figure 57B:
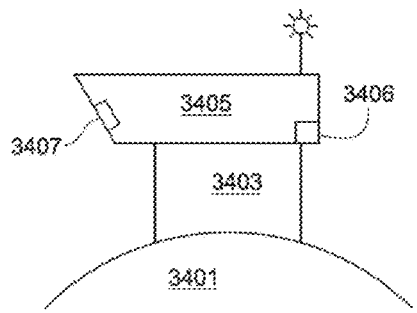
Figure 57C:
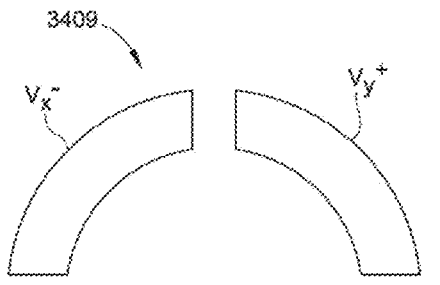
Figure 57D:
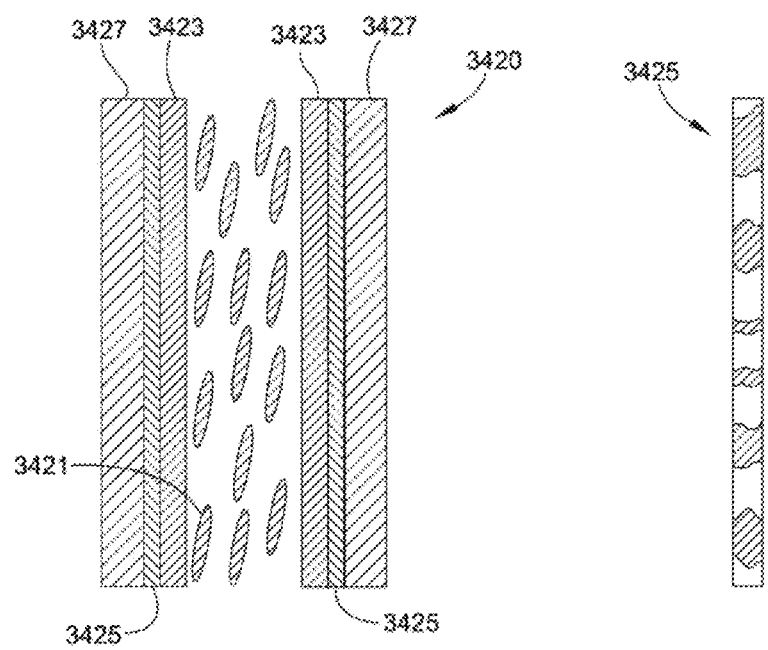
Figure 57E:
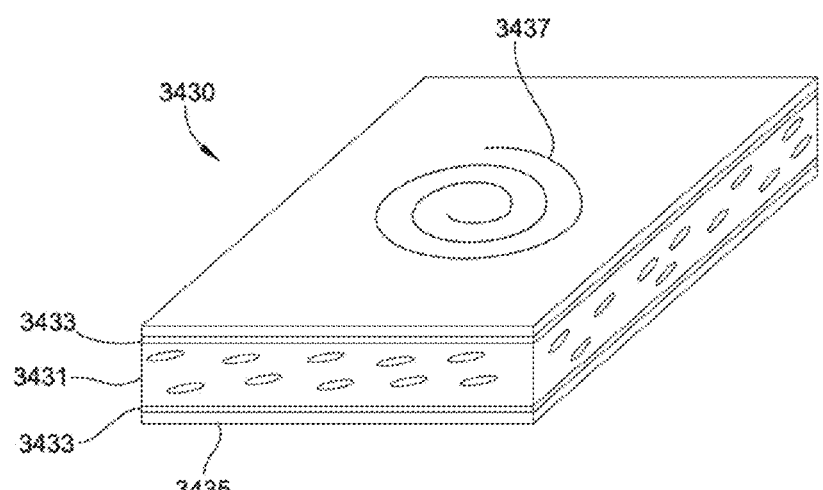

The wrist-mounted device described above may also be used in conjunction with other devices, including augmented reality eyepieces with data and video display, shown in FIG. 57. The assembly 5700 includes the following components: an eyepiece 5702, and a bio-print sensor device 5700. The augmented reality eyepiece provides redundant, binocular, stereo sensors and display and provides the ability to see in a variety of lighting conditions, from glaring sun at midday, to the extremely low light levels found at night Operation of the eyepiece is simple with a rotary switch located on the temple of the eyepiece a user can access data from a forearm computer or sensor, or a laptop device. The eyepiece also provides omni-directional earbuds for hearing protection and improved hearing. A noise cancelling boom microphone may also be integrated into the eyepiece to provide better communication of phonetically differentiated commands.

The eyepiece is capable of communicating wirelessly with the bio-phone sensor and forearm mounted devices using a 256-bit AES encrypted UWB. This also allows the device to communicate with a laptop or combat radio, as well as network to CPs, TOCs, and biometric databases. The eyepiece is ABIS, EBTS, EFTS, and JPEG 2000 compatible.

Similar to other mosaic sensor devices described above, the eyepiece uses a networked GPS to provide highly accurate geo-location of POIs, as well as a RF filter array.

In operation the low profile forearm mounted computer and tactical display integrate face, iris, fingerprint, palm print, and fingertip collection and identification. The device also records video, voice, gait, and other distinguishing characteristics. Facial and iris tracking is automatic, allowing the device to assist in recognizing non-cooperative POIs. With the transparent display provided by the eyepiece, the operator may also view sensor imagery, moving maps, superimposed applications with navigation, targeting, position or other information from sensors, UAVs, and the like, and data as well as the individual whose biometric data is being captured or other targets/POIs.

FIG. 58 illustrates a further embodiment of the fingerprint, palm print, geo-location, and POI enrollment device. The device is 16 oz. (approx. 450 g.) and uses a 5"×2.5" active fingerprint and palm print capacitance sensor. The sensor is capable of enrolling 10 fingers, a palm, 4 finger slap, and fingertip prints at 500 dpi. A 0.6-1 GHz processor with 430 MHz DSP provides rapid enrollment and data capture. The device is ABIS, EBTS, EFTS, and JPEG 2000 compatible and features networked GPS for highly accurate location of persons of interest. In addition, the device communicates wirelessly over a 256-bit AES encrypted UWB, laptop, or combat radio. Database information may also be stored on the device, allowing in the field comparison without uploading information. This onboard data may also be shared wirelessly with other devices, such as a laptop or combat radio.

A further embodiment of the wrist mounted bio-print sensor assembly 5800 includes the following elements: a bio-print sensor 5801, wrist strap 5802, keyboard 5803, and combat radio connector interface 5804.

Data may be stored on the forearm device since the device can utilize Mil-con data storage caps for increased storage capacity. Data entry is performed on the QWERTY keyboard and may be done wearing gloves.

The display is a transflective QVGA, color, backlit LCD display designed to be readable in sunlight. In addition to operation in strong sunlight, the device may be operated in a wide range of environments, as the device meets the requirements of MIL-STD-810 operation in environmental extremes.

Figure 59:
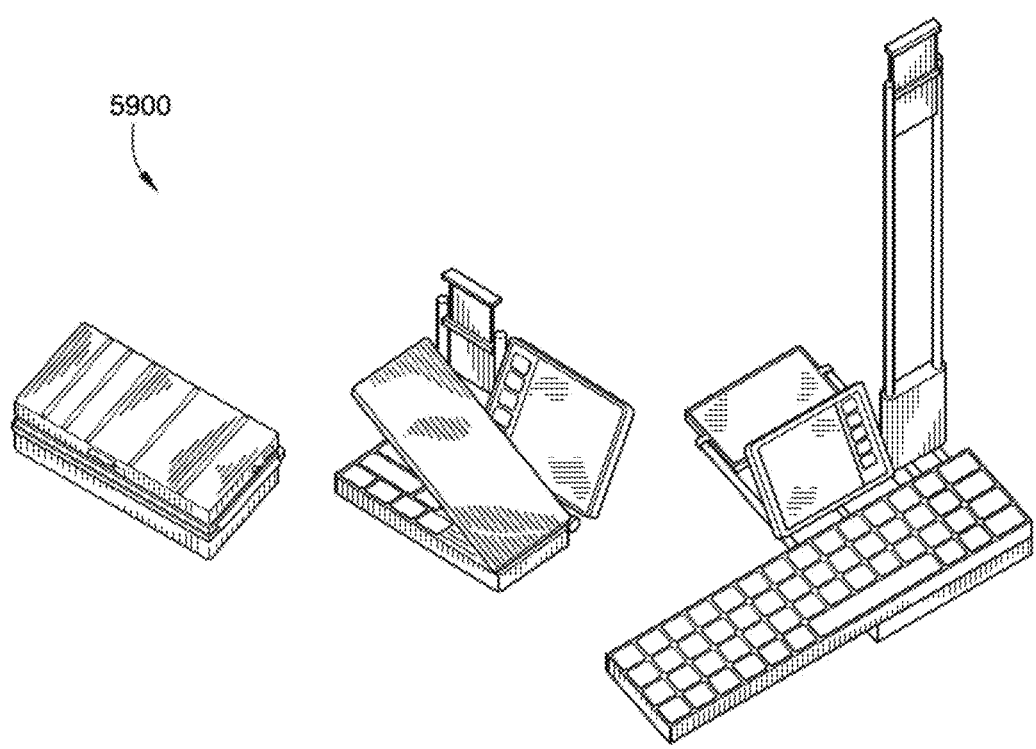
FIG. 59 shows a mobile folding biometric enrollment kit according to an embodiment.

The mosaic sensor described above may also be incorporated into a mobile, folding biometric enrollment kit, as shown in FIG. 59. The mobile folding biometric enrollment kit 5900 folds into itself and is sized to fit into a tactical vest pocket, having dimensions of 8×12×4 inches when unfolded.

Figure 60:
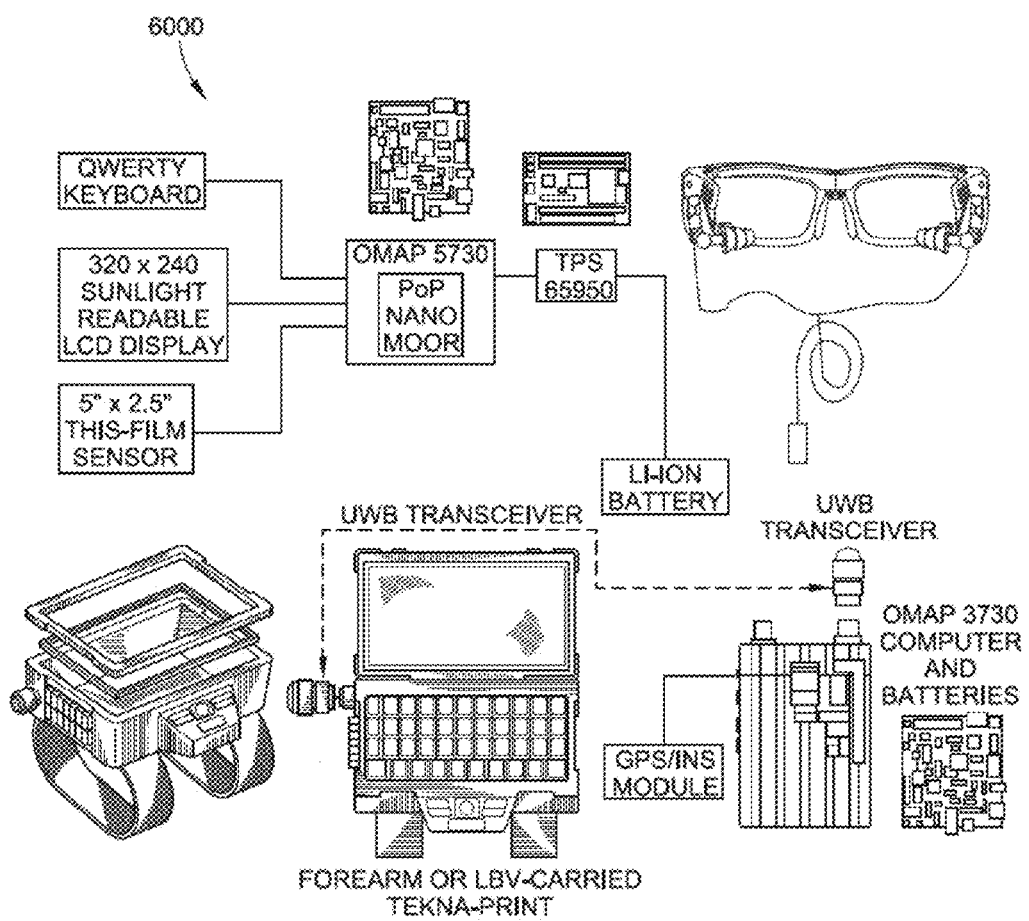
FIG. 60 is a high level system diagram of a biometric enrollment kit according to an embodiment.

FIG. 60 illustrates an embodiment 6000 of how the eyepiece and forearm mounted device may interface to provide a complete system for biometric data collection.

Figure 61:
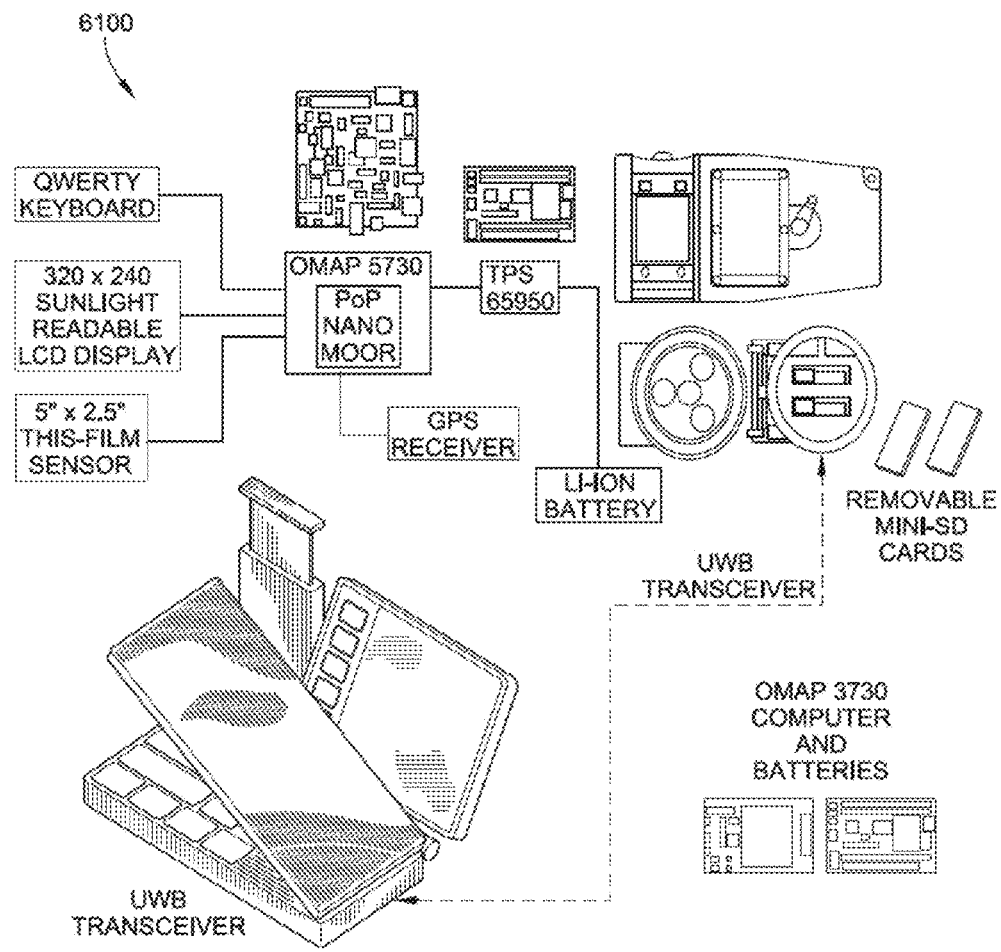
FIG. 61 is a system diagram of a folding biometric enrollment device according to an embodiment.

FIG. 61 provides a system diagram 6100 for a mobile folding biometric enrollment kit.

In operation the mobile folding biometric enrollment kit allows a user to search, collect, identify, verify, and enroll face, iris, palm print, fingertip, and biographic data for a subject and may also record voice samples, pocket litter, and other visible identifying marks. Once collected, the data is automatically geo-located, date, and time stamped. Collected data may be searched and compared against onboard and networked databases. For communicating with databases not onboard the device, wireless data up/download using combat radio or laptop computer with standard networking interface is provided. Formatting is compliant with EFTS, EBTS, NIST, ISO, and ITL 1-2007. Prequalified images may be sent directly to matching software as the device may use any matching and enrollment software.

The devices and systems incorporating described above provide a comprehensive solution for mobile biometric data collection, identification, and situational awareness. The devices are capable of collecting fingerprints, palm prints, fingertips, faces, irises, voice, and video data for recognition of uncooperative persons of interest (POI). Video is captured using high speed video to enable capture in unstable situations, such as from a moving video. Captured information may be readily shared and additional data entered via the keyboard. In addition, all data is tagged with date, time, and geo-location. This facilitates rapid dissemination of information necessary for situational awareness in potentially volatile environments. Additional data collection is possible with more personnel equipped with the devices, thus, demonstrating the idea that "every soldier is a sensor." Sharing is facilitated by integration of biometric devices with combat radios and battlefield computers.

In embodiments, the eyepiece may utilize flexible thin-film sensors, such as integrated into the eyepiece itself, into an external device that the eyepiece interfaces with, and the like. A thin film sensor may comprise a thin multi-layer electro-mechanical arrangement that produces an electrical signal when subjected to a sudden contact force or to continuously varying forces. Typical applications of electromechanical thin film sensors employ both on-off electrical switch sensing and the time-resolved sensing of forces. Thin-film sensors may include switches, force gauges, and the like, where thin film sensors may rely upon the effects of sudden electrical contact (switching), the gradual change of electrical resistance under the action of force, the gradual release of electrical charges under the action of stress forces, the generation of a gradual electromotive force across a conductor when, moving in a magnetic field, and the like. For example, flexible thin-film sensors may be utilized in force-pressure sensors with microscopic force sensitive pixels for two-dimensional force array sensors. This may be useful for touch screens for computers, smart-phones, notebooks, MP-3-like devices, especially those with military applications; screens for controlling anything under computer control including unmanned aerial vehicles (UAV), drones, mobile robots, exoskeleton-based devices; and the like. Thin-film sensors may be useful in security applications, such as in remote or local sensors for detecting intrusion, opening or closing of devices, doors, windows, equipment, and the like. Thin-film sensors may be useful for trip wire detection, such as with electronics and radio used in silent, remote trip-wire detectors. Thin-film sensors may be used in open-close detections, such as force sensors for detecting strain-stress in vehicle compartments, ship hulls, aircraft panels, and the like. Thin-film sensors may be useful as biometric sensors, such as in fingerprinting, palm-printing, fingertip printing, and the like. Thin-film sensors may be useful leak detection, such as detecting leaking tanks, storage facilities, and the like. Thin-film sensors may be useful in medical sensors, such as in detecting liquid or blood external to a body, and the like. These sensor applications are meant to be illustrative of the many applications thin-film sensors may be employed in association with control and monitoring of external devices through the eyepiece, and are not meant to be limiting in any way.

Figure 62:
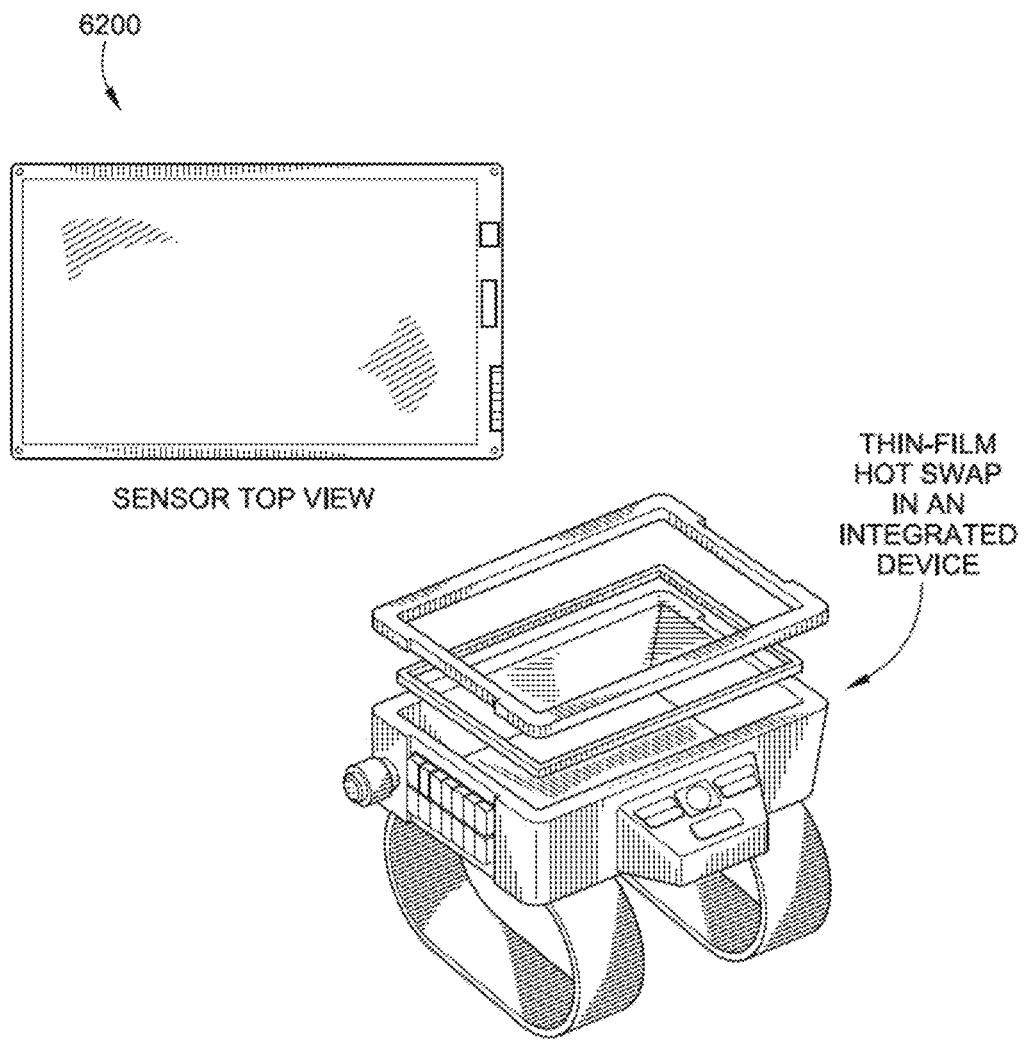
FIG. 62 shows a thin-film finger and palm print sensor according to an embodiment.

FIG. 62 illustrates an embodiment 6200 of a thin-film finger and palm print collection device. The device can record four fingerprint slaps and rolls, palm prints, and fingerprints to the NIST standard. Superior quality finger print images can be captured with either wet or dry hands. The device is reduced in weight and power consumption compared to other large sensors. In addition, the sensor is self-contained and is hot swappable. The configuration of the sensor may be varied to suit a variety of needs, and the sensor may be manufactured in various shapes and dimensions.

Figure 63:
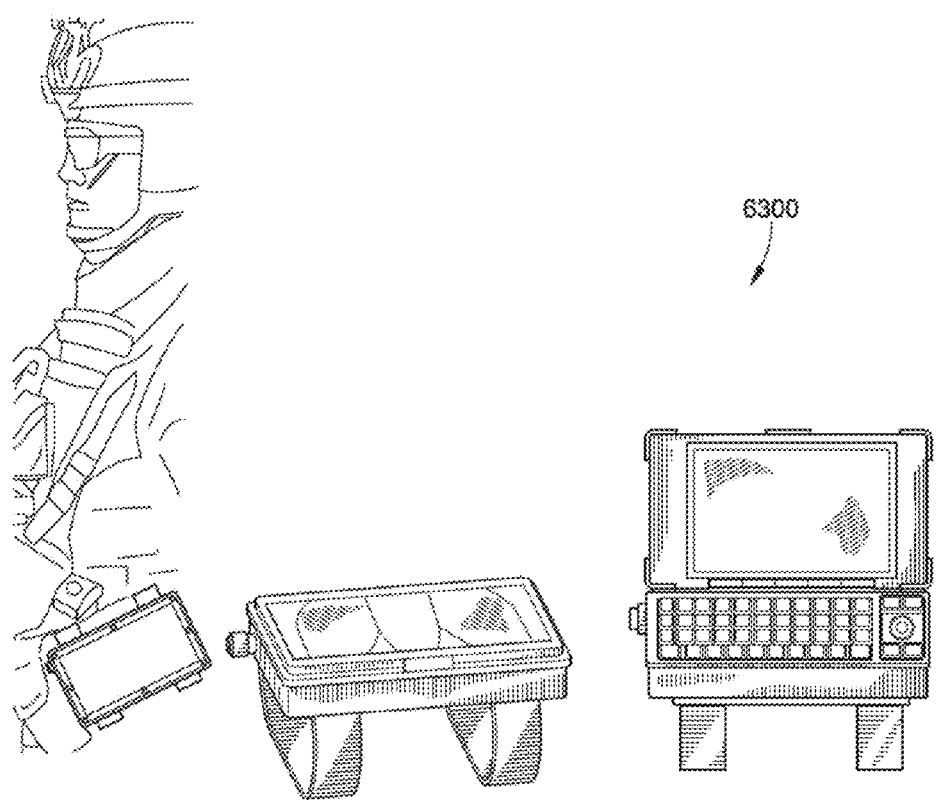
FIG. 63 shows a biometric collection device for finger, palm, and enrollment data collection according to an embodiment.

FIG. 63 depicts an embodiment 6300 of a finger, palm, and enrollment data collection device. This device records fingertip, roll, slap, and palm prints. A built in QWERTY keyboard allows entry of written enrollment data. As with the devices described above, all data is tagged with date, time, and geolocation of collection. A built in database provides on board matching of potential POIs against the built in database. Matching may also be performed with other databases over a battlefield network. This device can be integrated with the optical biometric collection eyepiece described above to support face and iris recognition.

Figure 64:
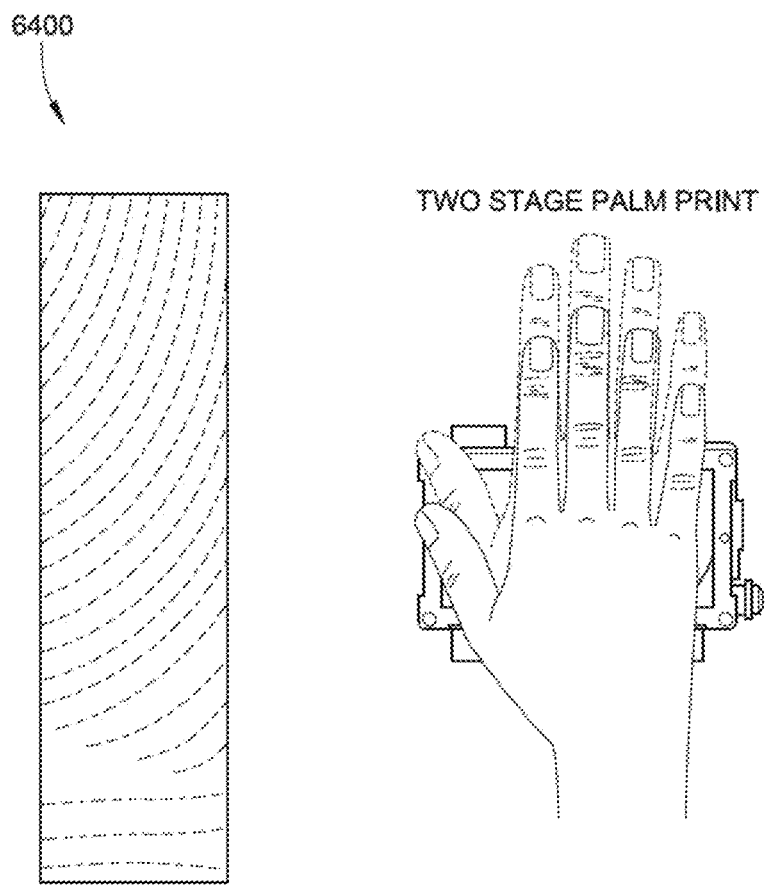
FIG. 64 illustrates capture of a two stage palm print according to an embodiment.
Figure 65:
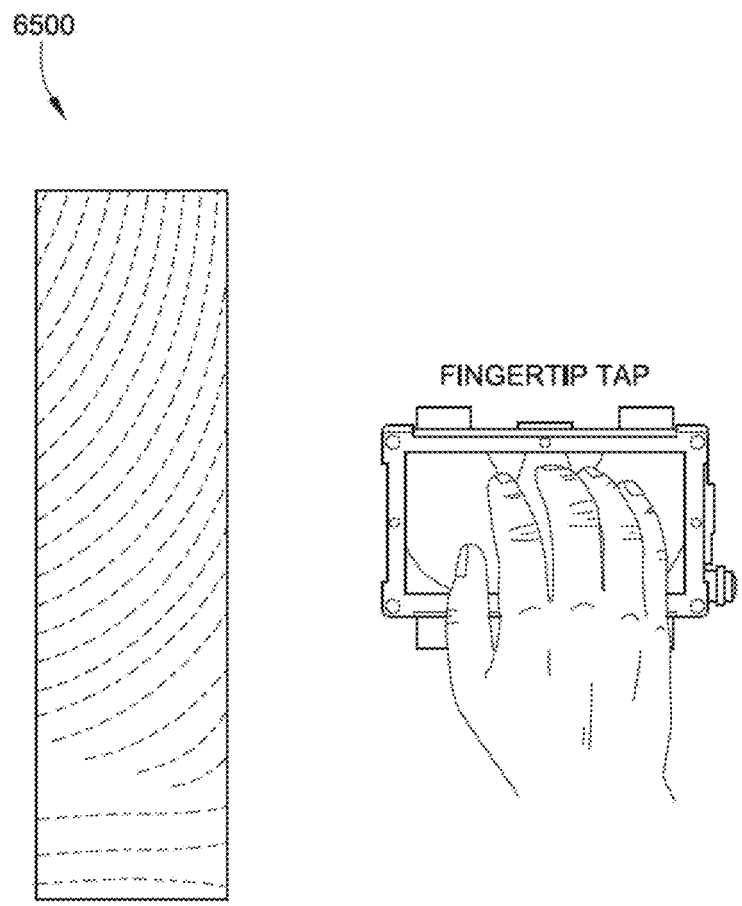
FIG. 65 illustrates capture of a fingertip tap according to an embodiment.
Figure 66:
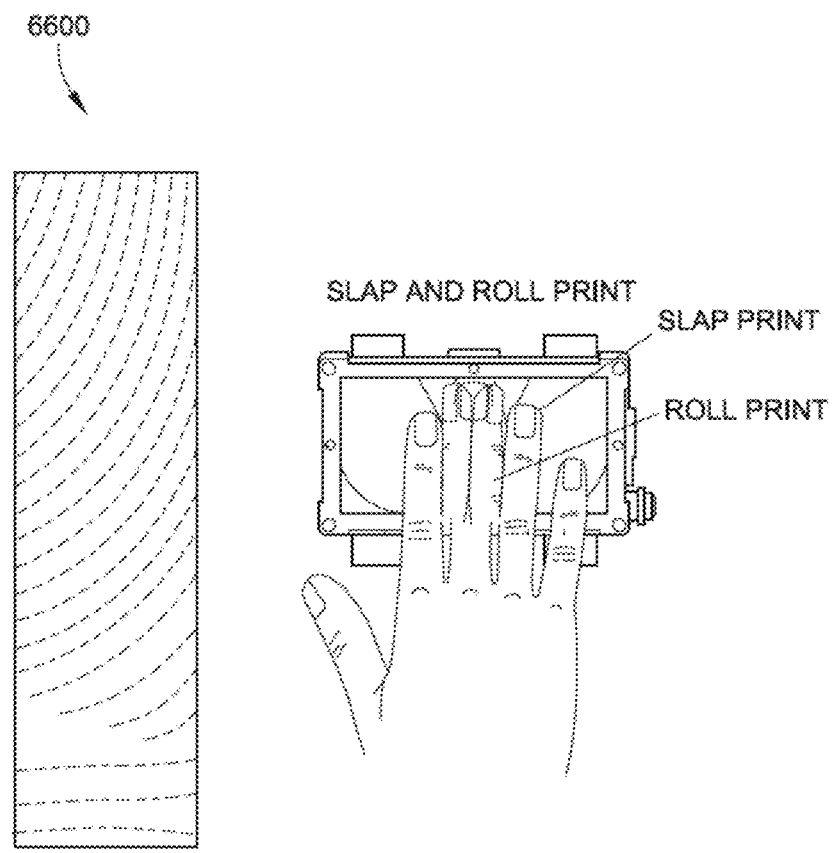
FIG. 66 illustrates capture of a slap and roll print according to an embodiment.

The specifications for the finger, palm, and enrollment device are given below:
Weight & Size: 16 oz. forearm straps or inserts into LBV pocket
5"×2.5" finger/palm print sensor
5.75"×2.75" QWERTY keyboard
3.5"×2.25" LCD display
One-handed operation
Environmental: Sensor operates in all weather conditions, −20° C. to +70° C.
Waterproofing: 1 m for 4 hours, operates without degradation
Biometric Collection: fingerprint and palm print collection, identification
Keyboard & LCD display for enrollment of POIs
Retains >30,000 full template portfolios (2 iris, 10 fingerprint, facial image, 35 fields of biographic information) for on board matching of POIs.
Tags all collected biometric data with time, date, and location
Pressure capacitance finger/palm print sensor
30 fps high contrast bitmap image
1000 dpi
Wireless: fully interoperable with combat radios, hand held or lap top computers and 256-bit AES encryption
Battery: dual 2000 mAh lithium polymer batteries
>12 hours, quick change battery in <15 seconds
Processing & Memory: 256 MB flash and 128 MB SDRA
supports 3 SD cards up to 32 GB each
600-1 GHZ ARM Cortex A8 processor
1 GB RAM FIGS. 64-66 depict use of the devices incorporating a sensor for collecting biometric data. FIG. 64 shows an embodiment 6400 of the capture of a two-stage palm print. FIG. 65 shows collection 6500 using a fingertip tap. FIG. 66 demonstrates an embodiment 6600 of a slap and roll print being collected.

The discussion above pertains to methods of gathering biometric data, such as fingerprints or palm prints using a platen or touch screen, as shown in FIGS. 66 and 62-66. This disclosure also includes methods and systems for touchless or contactless fingerprinting using polarized light. In one embodiment, fingerprints may be taken by persons using a polarized light source and retrieving images of the fingerprints using reflected polarized light in two planes. In another embodiment, fingerprints may be taken by persons using a light source and retrieving images of the fingerprints using multispectral processing, e.g., using two imagers at two different locations with different inputs. The different inputs may be caused by using different filters or different sensors/imagers. Applications of this technology may include biometric checks of unknown persons or subjects in which the safety of the persons doing the checking may be at issue.

Figure 67:
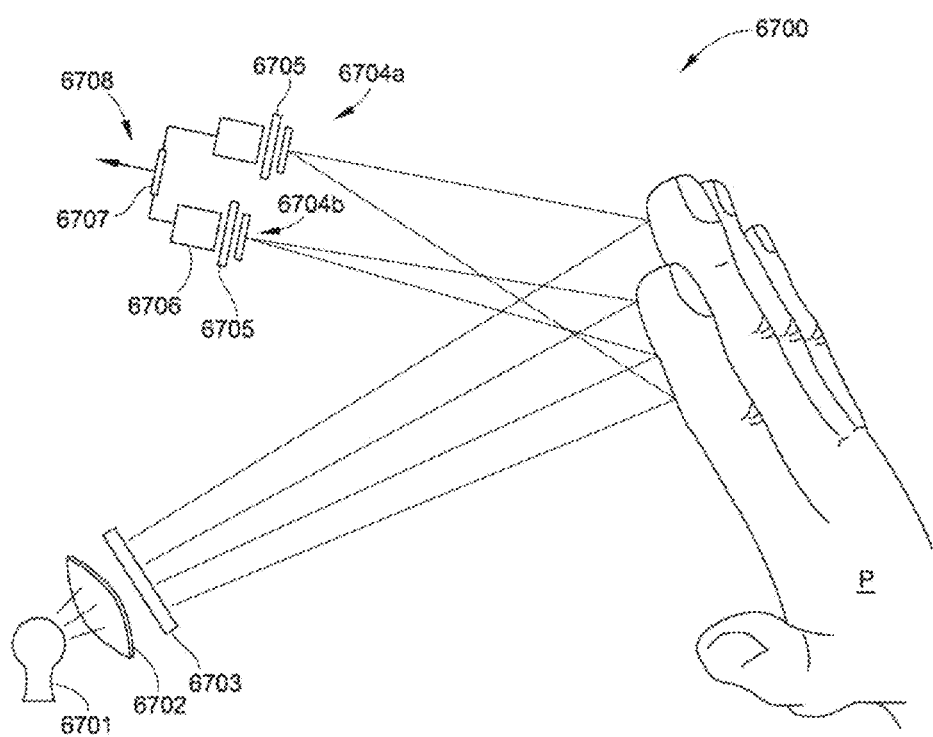
FIG. 67 depicts a system for taking contactless fingerprints, palmprints or other biometric prints.

In this method, an unknown person or subject may approach a checkpoint, for example, to be allowed further travel to his or her destination. As depicted in the system 6700 shown in FIG. 67, the person P and an appropriate body part, such as a hand, a palm P, or other part, are illuminated by a source of polarized light 6701. As is well known to those with skill in optical arts, the source of polarized light may simply be a lamp or other source of illumination with a polarizing filter to emit light that is polarized in one plane. The light travels to the person in an area which has been specified for non-contact fingerprinting, so that the polarized light impinges on the fingers or other body part of the person P. The incident polarized light is then reflected from the fingers or other body part and passes in all directions from the person. Two imagers or cameras 6704 receive the reflected light after the light has passed through optical elements such as a lens 6702 and a polarizing filter 6703. The cameras or imagers may be mounted on the augmented reality glasses, as discussed above with respect to FIG. 8F.

The light then passes from palm or finger or fingers of the person of interest to two different polarizing filters 6704a, 6704b and then to the imagers or cameras 6705. Light which has passed through the polarizing filters may have a 90° orientation difference (horizontal and vertical) or other orientation difference, such as 30°, 45°, 60° or 120°. The cameras may be digital cameras with appropriate digital imaging sensors to convert the incident light into appropriate signals. The signals are then processed by appropriate processing circuitry 6706, such as digital signal processors. The signals may then be combined in a conventional manner, such as by a digital microprocessor with memory 6707. The digital processor with appropriate memory is programmed to produce data suitable for an image of a palm, fingerprint, or other image as desired. The digital data from the imagers may then be combined in this process, for example, using the techniques of U.S. Pat. No. 6,249,616 and others. As noted above in the present disclosure, the combined "image" may then be checked against a database to determine an identity of the person. The augmented reality glasses may include such a database in the memory, or may refer the signals data elsewhere 6708 for comparison and checking.

Figure 68:
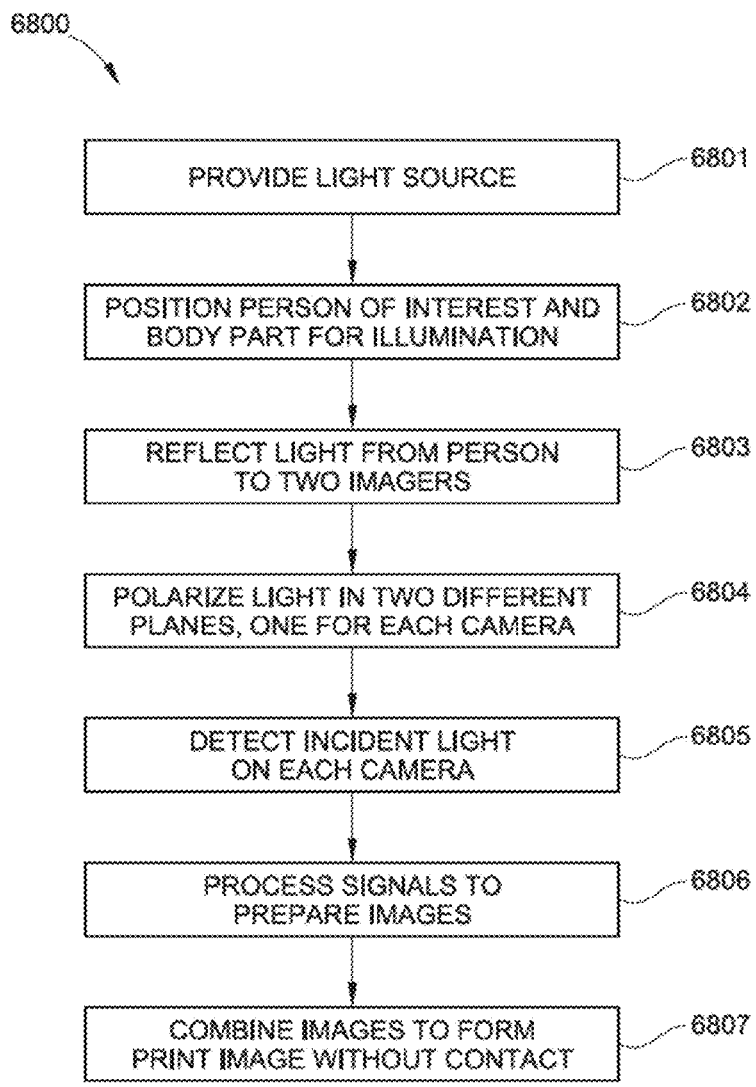
FIG. 68 depicts a process for taking contactless fingerprints, palmprints or other biometric prints.

A process for taking contactless fingerprints, palm prints or other biometric prints is disclosed in the flowchart of FIG. 68. In one embodiment, a polarized light source is provided 6801. In a second step 6802, the person of interest and the selected body part is positioned for illumination by the light. In another embodiment, it may be possible to use incident white light rather than using a polarized light source. When the image is ready to be taken, light is reflected 6803 from the person to two cameras or imagers. A polarizing filter is placed in front of each of the two cameras, so that the light received by the cameras is polarized 6804 in two different planes, such as in a horizontal and vertical plane. Each camera then detects 6805 the polarized light. The cameras or other sensors then convert the incidence of light into signals or data 6806 suitable for preparation of images. Finally, the images are then combined 6807 to form a very distinct, reliable print. The result is an image of very high quality that may be compared to digital databases to identify the person and to detect persons of interest.

It should be understood that while digital cameras are used in this contactless system, other imagers may be used, such as active pixel imagers, CMOS imagers, imagers that image in multiple wavelengths, CCD cameras, photo detector arrays, TFT imagers, and so forth. It should also be understood that while polarized light has been used to create two different images, other variations in the reflected light may also be used. For example, rather than using polarized light, white light may be used and then different filters applied to the imagers, such as a Bayer filter, a CYGM filter, or an RGBE filter. In other embodiments, it may be possible to dispense with a source of polarized light and instead use natural or white light rather than a source of polarized light.

The use of touchless or contactless fingerprinting has been under development for some time, as evidenced by earlier systems. For example, U.S. Pat. Appl. 2002/0106115 used polarized light in a non-contact system, but required a metallic coating on the fingers of the person being fingerprinted. Later systems, such as those described in U.S. Pat. No. 7,651,594 and U.S. Pat. Appl. Publ. 2008/0219522, required contact with a platen or other surface. The contactless system described herein does not require contact at the time of imaging, nor does it require prior contact, e.g., placing a coating or a reflective coating on the body part of interest. Of course, the positions of the imagers or cameras with respect to each other should be known for easier processing.

In use, the contactless fingerprint system may be employed at a checkpoint, such as a compound entrance, a building entrance, a roadside checkpoint or other convenient location. Such a location may be one where it is desirable to admit some persons and to refuse entrance or even detain other persons of interest. In practice, the system may make use of an external light source, such as a lamp, if polarized light is used. The cameras or other imagers used for the contactless imaging may be mounted on opposite sides of one set of augmented reality glasses (for one person). For example, a two-camera version is shown in FIG. 8F, with two cameras 870 mounted on frame 864. In this embodiment, the software for at least processing the image may be contained within a memory of the augmented reality glasses. Alternatively, the digital data from the cameras/imagers may be routed to a nearby datacenter for appropriate processing. This processing may include combining the digital data to form an image of the print. The processing may also include checking a database of known persons to determine whether the subject is of interest.

Another method of contactless fingerprinting utilizes quantum dot lasers to non-contact scan fingers and the hand to detect extremely low (parts per billion or even parts per trillion) concentrations of explosive compounds, as well as drug compounds. For example, the Quantum Dot or other kind of Laser, Laser Array may be mounted either in the back of the Bio-Phone or in the frame of the glasses so as to detect by very close proximity, but not touch, in order to prevent contamination from one subject to another. Thus, in addition to the capability of the glasses or other accessory devices to collect biometric data related to the iris, fingerprints, face and voice, an explosives or drugs contamination ID could also be collected.

Alternatively, one camera on each of two persons may be used, as seen in the camera 858 in FIG. 8F. In this configuration, the two persons would be relatively near so that their respective images would be suitably similar for combining by the appropriate software. For example, the two cameras 6705 in FIG. 67 may be mounted on two different pairs of augmented reality glasses, such as on two soldiers manning a checkpoint. Alternatively, the cameras may be mounted on a wall or on stationary parts of the checkpoint itself. The two images may then be combined by a remote processor with memory 6707, such as a computer system at the building checkpoint.

As discussed above, persons using the augmented reality glasses may be in constant contact with each other through at least one of many wireless technologies, especially if they are both on duty at a checkpoint. Accordingly, the data from the single cameras or from the two-camera version may be sent to a data center or other command post for the appropriate processing, followed by checking the database for a match of the palm print, fingerprint, iris print, and so forth. The data center may be conveniently located near the checkpoint. With the availability of modern computers and storage, the cost of providing multiple datacenters and wirelessly updating the software will not be a major cost consideration in such systems.

The touchless or contactless biometric data gathering discussed above may be controlled in several ways, such as the control techniques discussed else in this disclosure. For example, in one embodiment, a user may initiate a data-gathering session by pressing a touch pad on the glasses, or by giving a voice command. In another embodiment, the user may initiate a session by a hand movement or gesture or using any of the control techniques described herein. Any of these techniques may bring up a menu, from which the user may select an option, such as "begin data gathering session," "terminate data-gathering session," or "continue session." If a data-gathering session is selected, the computer-controlled menu may then offer menu choices for number of cameras, which cameras, and so forth, much as a user selects a printer. There may also be modes, such as a polarized light mode, a color filter mode, and so forth. After each selection, the system may complete a task or offer another choice, as appropriate. User intervention may also be required, such as turning on a source of polarized light or other light source, applying filters or polarizers, and so forth.

After fingerprints, palm prints, iris images or other desired data has been acquired, the menu may then offer selections as to which database to use for comparison, which device(s) to use for storage, etc. The touchless or contactless biometric data gathering system may be controlled by any of the methods described herein.

While the system and sensors have obvious uses in identifying potential persons of interest, there are positive battlefield uses as well. The fingerprint sensor may be used to call up a soldier's medical history, giving information immediately on allergies, blood type, and other time sensitive and treatment determining data quickly and easily, thus allowing proper treatment to be provided under battlefield conditions. This is especially helpful for patients who may be unconscious when initially treated and who may be missing identification tags.

A further embodiment of a device for capturing biometric data from individuals may incorporate a server to store and process biometric data collected. The biometric data captured may include a hand image with multiple fingers, a palm print, a face camera image, an iris image, an audio sample of an individual's voice, and a video of the individual's gait or movement. The collected data must be accessible to be useful.

Processing of the biometric data may be done locally or remotely at a separate server. Local processing may offer the option to capture raw images and audio and make the information available on demand from a computer host over a WiFi or USB link. As an alternative, another local processing method processes the images and then transmits the processed data over the Internet. This local processing includes the steps of finding the finger prints, rating the finger prints, finding the face and then cropping it, finding and then rating the iris, and other similar steps for audio and video data. While processing the data locally requires more complex code, it does offer the advantage of reduced data transmission over the Internet.

A scanner associated with the biometric data collection devices may use code that is compliant with the USB Image Device protocol that is a commonly used scanner standard. Other embodiments may use different scanner standards, depending on need.

When a WiFi network is used to transfer the data, the Bio-Print device, which is further described herein, can function or appear like a web server to the network. Each of the various types of images may be available by selecting or clicking on a web page link or button from a browser client. This web server functionality may be part of the Bio-Print device, specifically, included in the microcomputer functionality.

A web server may be a part of the Bio-Print microcomputer host, allowing for the Bio-Print device to author a web page that exposes captured data and also provides some controls. An additional embodiment of the browser application could provide controls to capture high resolution hand prints, face images, iris images, set the camera resolution, set the capture time for audio samples, and also enable a streaming connection, using a web cam, Skype, or similar mechanism. This connection could be attached to the audio and face camera.

A further embodiment provides a browser application that gives access to images and audio captured via file transfer protocol (FTP) or other protocol. A still further embodiment of the browser application may provide for automatic refreshes at a selectable rate to repeatedly grab preview images.

An additional embodiment provides local processing of captured biometric data using a microcomputer and provides additional controls to display a rating of the captured image, allowing a user to rate each of the prints found, retrieve faces captured, and also to retrieve cropped iris images and allow a user to rate each of the iris prints.

Yet another embodiment provides a USB port compatible with the Open Multimedia Application Platform (OMAP3) system. OMAP3 is a proprietary system on a chip for portable multimedia applications. The OMAP3 device port is equipped with a Remote Network Driver Interface Specification (RNDIS), a proprietary protocol that may be used on top of USB. These systems provide the capability that when a Bio-Print device is plugged into a Windows PC USB host port, the device shows up as an IP interface. This IP interface would be the same as over WiFi (TCP/IP web server). This allows for moving data off the microcomputer host and provides for display of the captured print.

An application on the microcomputer may implement the above by receiving data from an FPGA over the USB bus. Once received, JPEG content is created. This content may be written over a socket to a server running on a laptop, or be written to a file. Alternately, the server could receive the socket stream, pop the image, and leave it open in a window, thus creating a new window for each biometric capture. If the microcomputer runs Network File System (NFS), a protocol for use with Sun-based systems or SAMBA, a free software reimplementation that provides file and print services for Windows clients, the files captured may be shared and accessed by any client running NFS or System Management Bus (SMB), a PC communication bus implementation. In this embodiment, a JPEG viewer would display the files. The display client could include a laptop, augmented reality glasses, or a phone running the Android platform.

An additional embodiment provides for a server-side application offering the same services described above.

An alternative embodiment to a server-side application displays the results on the augmented reality glasses.

A further embodiment provides the microcomputer on a removable platform, similar to a mass storage device or streaming camera. The removable platform also incorporates an active USB serial port.

In embodiments, the eyepiece may include audio and/or visual sensors to capture sounds and/or visuals from 360 degrees around the wearer of an eyepiece. This may be from sensors mounted on the eyepiece itself, or coupled to sensors mounted on a vehicle that the wearer is in. For instance, sound sensors and/or cameras may be mounted to the outside of a vehicle, where the sensors are communicatively coupled to the eyepiece to provide a surround sound and/or sight 'view' of the surrounding environment. In addition, the sound system of the eyepiece may provide sound protection, canceling, augmentation, and the like, to help improve the hearing quality of the wearer while they are surrounded by extraneous or loud noise. In an example, a wearer may be coupled to cameras mounted on the vehicle they are driving. These cameras may then be in communication with the eyepiece, and provide a 360-degree view around the vehicle, such as provided in a projected graphical image through the eyepiece display to the wearer.

Figure 69:
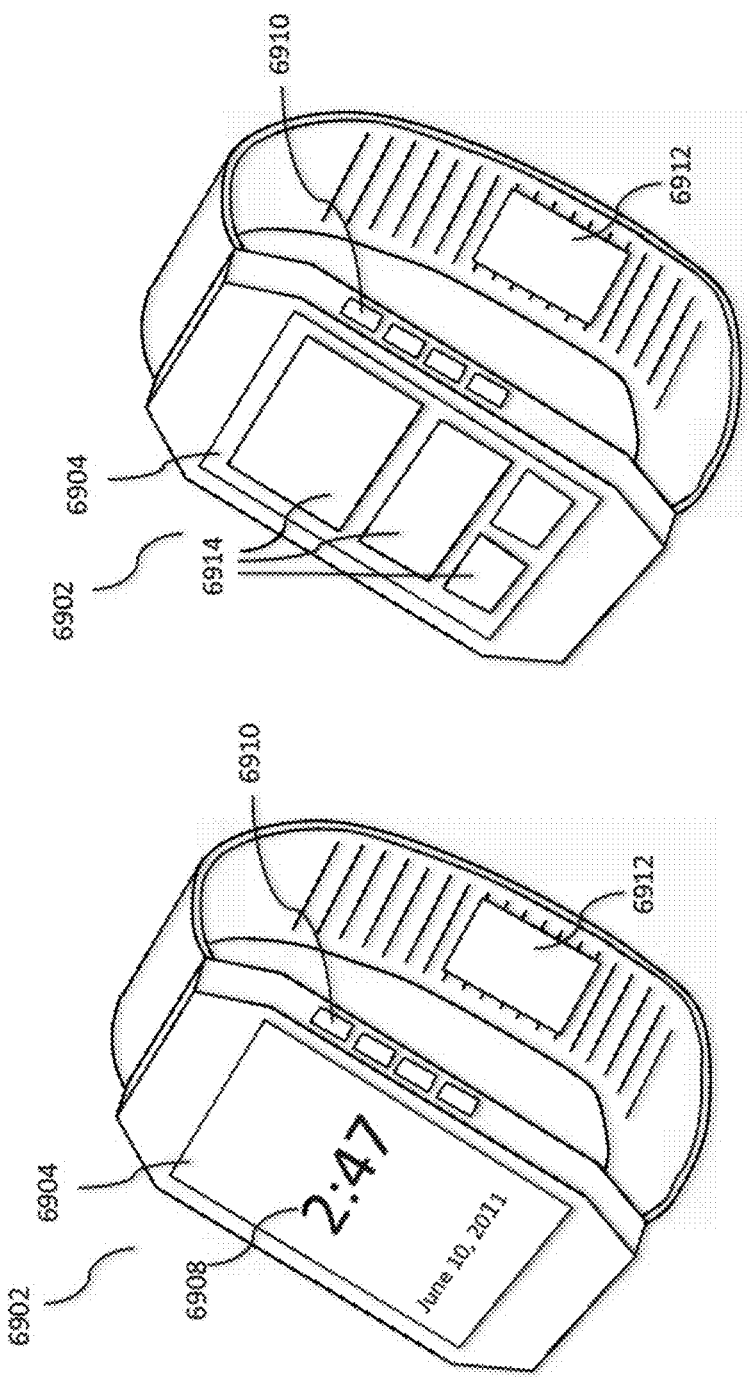
FIG. 69 depicts an embodiment of a watch controller.

In an example, and referring to FIG. 69, control aspects of the eyepiece may include a remote device in the form of a watch controller 6902, such as including a receiver and/or transmitter for interfacing with the eyepiece for messaging and/or controlling the eyepiece when the user is not wearing the eyepiece. The watch controller may include a camera, a fingerprint scanner, discrete control buttons, 2D control pad, an LCD screen, a capacitive touch screen for multi-touch control, a shake motor/piezo bumper to give tactile feedback, buttons with tactile feel, Bluetooth, camera, fingerprint scanner, accelerometer, and the like, such as provided in a control function area 6904 or on other functional portions 6910 of the watch controller 6902. For instance, a watch controller may have a standard watch display 6908, but additionally have functionality to control the eyepiece, such as through control functions 6914 in the control function area 6904. The watch controller may display and/or otherwise notify the user (e.g. vibration, audible sounds) of messages from the eyepiece, such an email, advertisements, calendar alerts, and the like, and show the content of the message that comes in from the eyepiece that the user is currently not wearing. A shake motor, piezo bumper, and the like, may provide tactile feedback to the touch screen control interface. The watch receiver may be able to provide virtual buttons and clicks in the control function area 6904 user interface, buzz and bump the user's wrist, and the like, when a message is received. Communications connectivity between the eyepiece and the watch receiver may be provided through Bluetooth, WiFi, Cell network, or any other communications interface known to the art. The watch controller may utilize an embedded camera for video-conferencing (such as described herein), iris scanning (e.g. for recording an image of the iris for storage in a database, for use in authentication in conjunction with an existing iris image in storage, and the like), picture taking, video, and the like. The watch controller may have a fingerprint scanner, such as described herein. The watch controller, or any other tactile interface described herein, may measure a user's pulse, such as through a pulse sensor 6912 (which may be located in the band, on the underside of the main body of the watch, and the like. In embodiments, the eyepiece and other control/tactile interface components may have pulse detection such that the pulse from different control interface components are monitored in a synchronized way, such as for health, activity monitoring, authorization, and the like. For example, a watch controller and the eyepiece may both have pulse monitoring, where the eyepiece is capable of sensing whether the two are in synchronization, if both match a previously measured profile (such as for authentication), and the like. Similarly, other biometrics may be used for authentication between multiple control interfaces and the eyepiece, such as with fingerprints, iris scans, pulse, health profile, and the like, where the eyepiece knows whether the same person is wearing the interface component (e.g. the watch controller) and the eyepiece. Biometric/health of a person may be determined by looking at IR LED view of the skin, for looking at subsurface pulse, and the like. In embodiments, multi-device authentication (e.g. token for Bluetooth handshake) may be used, such as using the sensors on both devices (e.g. fingerprint on both devices as a hash for the Bluetooth token), and the like.

In an embodiment, the watch controller may have a touch screen that may be useful for controlling the glasses even if they are not mounted on a user's face, such as if they are in a backpack. The transparent lens of the watch may have an OLED display with switchable mirrors affixed to the underside of the lens. In other embodiments, the watch controller lens may include an electric mirror or E-Ink display. In any event, the lens may cover a standard analog watch mechanism and the transparent lens including either the switchable mirrors or electric mirrors or e-ink display may be activated to display content. The watch may be used for gesture control with an integrated sensor that detects gestures. The watch may be used as an AR marker, such that when a camera of the glasses recognizes the watch, an app may be launched. One such app may be using the watch as a physical surface with an overlaid virtual image that effectively makes the watch a touch screen interface.

Figure 70B:
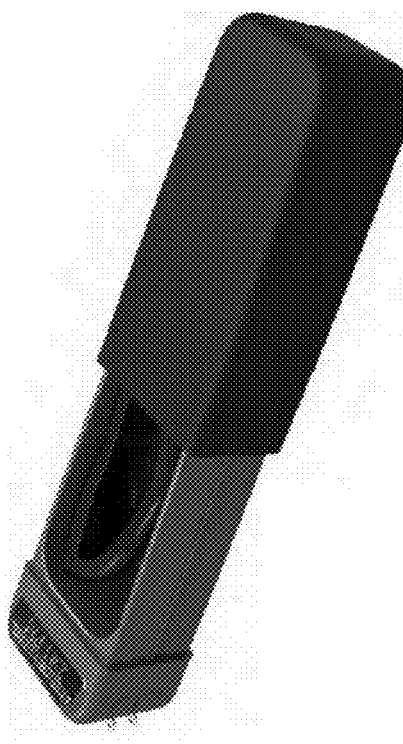
FIG. 70A-D depicts embodiment cases for the eyepiece, including capabilities for charging and integrated display.
Figure 70D:
Figure 70A:
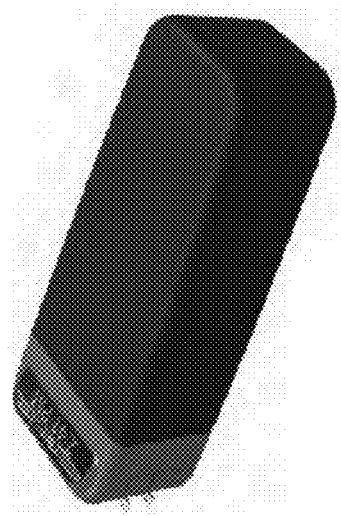
Figure 70C:

Referring to FIGS. 70A-70D, the eyepiece may be stored in an eyepiece carrying case, such as including a recharge capability, an integrated display, and the like. FIG. 70A depicts an embodiment of a case, shown closed, with integrated recharge AC plug and digital display, and FIG. 70B shows the same embodiment case open. FIG. 70C shows another embodiment case closed, and FIG. 70D shows the same embodiment open, where a digital display is shown through the cover. In embodiments, the case may have the ability to recharge the eyepiece while in the case, such as through an AC connection or battery (e.g. a rechargeable lithium-ion battery built into the carrying case for charging the eyepiece while away from AC power). Electrical power may be transferred to the eyepiece through a wired or wireless connection, such as though a wireless induction pad configuration between the case and the eyepiece. In embodiments, the case may include a digital display in communications with the eyepiece, such as through Bluetooth wireless, and the like. The display may provide information about the state of the eyepiece, such as messages received, battery level indication, notifications, and the like.

Referring to FIG. 71, the eyepiece 7120 may be used in conjunction with an unattended ground sensor unit 7102, such as formed as a stake 7104 that can be inserted in the ground 7118 by personnel, fired from a remote control helicopter, dropped by plane, and the like. The ground sensor unit 7102 may include a camera 7108, a controller 7110, a sensor 7112, and the like. Sensors 7112 may include a magnetic sensor, sound sensor, vibration sensor, thermal sensor, passive IR sensor, motion detector, GPS, real-time clock, and the like, and provide monitoring at the location of the ground sensor unit 7102. The camera 7108 may have a field of view 7114 in both azimuth and elevation, such as a full or partial 360-degree camera array in azimuth and +/−90 degrees in elevation. The ground sensor unit 7102 may capture a sensor and image data of an event(s) and transmit it over a wireless network connection to an eyepiece 7120. Further, the eyepiece may then transmit the data to an external communications facility 7122, such as a cell network, a satellite network, a WiFi network, to another eyepiece, and the like. In embodiments, ground sensor units 7102 may relay data from unit to unit, such as from 7102A to 7102B to 7102C. Further, the data may then be relayed from eyepiece 7120A to eyepiece 7120B and on to the communications facility 7122, such as in a backhaul data network. Data collected from a ground sensor unit 7102, or array of ground sensor units, may be shared with a plurality of eyepieces, such as from eyepiece to eyepiece, from the communications facility to the eyepiece, and the like, such that users of the eyepiece may utilize and share the data, either in its raw form or in a post-processed form (i.e. as a graphic display of the data through the eyepiece). In embodiments, the ground sensor units may be inexpensive, disposable, toy-grade, and the like. In embodiments, the ground sensor unit 7102 may provide backup for computer files from the eyepiece 7120.

Figure 72:
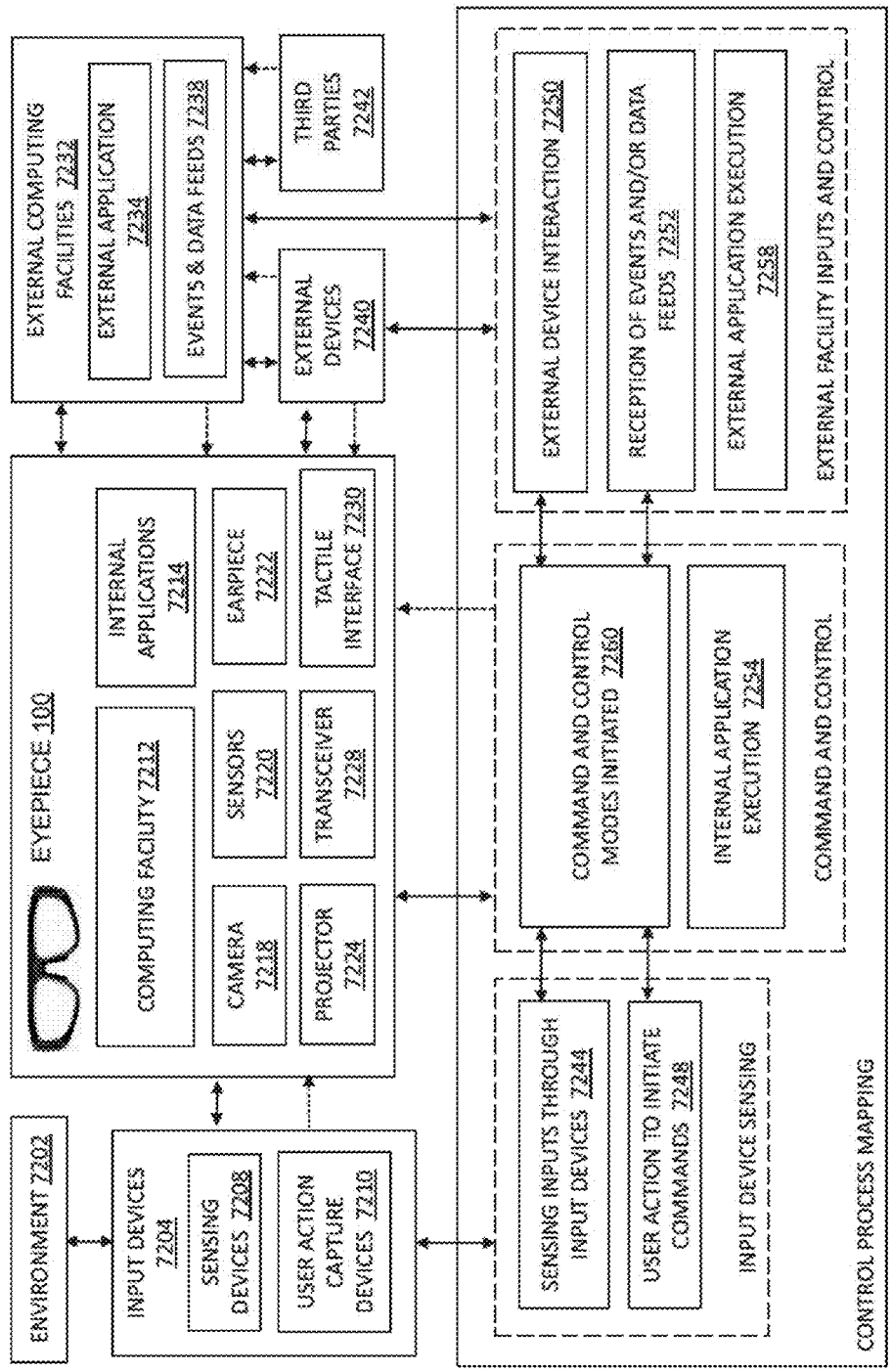
FIG. 72 depicts a block diagram of a control mapping system including the eyepiece.

Referring to FIG. 72, the eyepiece may provide control through facilities internal and external to the eyepiece, such as initiated from the surrounding environment 7202, input devices 7204, sensing devices 7208, user action capture devices 7210, internal processing facilities 7212, internal multimedia processing facilities, internal applications 7214, camera 7218, sensors 7220, earpiece 7222, projector 7224, through a transceiver 7228, through a tactile interface 7230, from external computing facilities 7232, external applications 7234, event and/or data feeds 7238, external devices 7240, third parties 7242, and the like. Command and control modes 7260 of the eyepiece may be initiated by sensing inputs through input devices 7244, user action 7248, external device interaction 7250, reception of events and/or data feeds 7252, internal application execution 7254, external application execution 7258, and the like. In embodiments, there may be a series of steps included in the execution control, including at least combinations of two of the following: events and/or data feeds, sensing inputs and/or sensing devices, user action capture inputs and/or outputs, user movements and/or actions for controlling and/or initiating commands, command and/or control modes and interfaces in which the inputs may be reflected, applications on the platform that may use commands to respond to inputs, communications and/or connection from the on-platform interface to external systems and/or devices, external devices, external applications, feedback 7262 to the user (such as related to external devices, external applications), and the like.

In embodiments, events and/or data feeds may include email, military related communications, calendar alerts, security events, safety events, financial events, personal events, a request for input, instruction, entering an activity state, entering a military engagement activity state, entering a type of environment, entering a hostile environment, entering a location, and the like, and combinations of the same.

In embodiments, sensing inputs and/or sensing devices may include a charge-coupled device, black silicon sensor, IR sensor, acoustic sensor, induction sensor, motion sensor, optical sensor, opacity sensor, proximity sensor, inductive sensor, Eddy-current sensor, passive infrared proximity sensor, radar, capacitance sensor, capacitive displacement sensor, hall-effect sensor, magnetic sensor, GPS sensor, thermal imaging sensor, thermocouple, thermistor, photoelectric sensor, ultrasonic sensor, infrared laser sensor, inertial motion sensor, MEMS internal motion sensor, ultrasonic 3D motion sensor, accelerometer, inclinometer, force sensor, piezoelectric sensor, rotary encoders, linear encoders, chemical sensor, ozone sensor, smoke sensor, heat sensor, magnetometer, carbon dioxide detector, carbon monoxide detector, oxygen sensor, glucose sensor, smoke detector, metal detector, rain sensor, altimeter, GPS, detection of being outside, detection of context, detection of activity, object detector (e.g. billboard), marker detector (e.g. geo-location marker for advertising), laser rangefinder, sonar, capacitance, optical response, heart rate sensor, RF/micropower impulse radio (MIR) sensor, and the like, and combinations of the same.

In embodiments, user action capture inputs and/or devices may include a head tracking system, camera, voice recognition system, body movement sensor (e.g. kinetic sensor), eye-gaze detection system, tongue touch pad, sip-and-puff systems, joystick, cursor, mouse, touch screen, touch sensor, finger tracking devices, 3D/2D mouse, inertial movement tracking, microphone, wearable sensor sets, robotic motion detection system, optical motion tracking system, laser motion tracking system, keyboard, virtual keyboard, virtual keyboard on a physical platform, context determination system, activity determination system (e.g. on a train, on a plane, walking, exercising, etc.) finger following camera, virtualized in-hand display, sign language system, trackball, hand-mounted camera, temple-located sensors, glasses-located sensors, Bluetooth communications, wireless communications, satellite communications, and the like, and combinations of the same.

In embodiments, user movements or actions for controlling or initiating commands may include head movement, head shake, head nod, head roll, forehead twitch, ear movement, eye movement, eye open, eye close, blink an eye, eye roll, hand movement, clench fist, open fist, shake fist, advance fist, retract fist, voice commands, sip or puff on straw, tongue movement, finger movement, one or more finger movements, extend finger crook finger, retract finger, extend thumb, make symbol with finger(s), make symbol with finger and thumb, depress finger of thumb, drag and drop with fingers, touch and drag, touch and drag with two fingers, wrist movement, wrist roll, wrist flap, arm movement, arm extend, arm retract, arm left turn signal, arm right turn signal, arms akimbo, arms extended, leg movement, leg kick, leg extend, leg curl, jumping jack, body movement walk, run turn left, turn right, about-face, twirl, arms up and twirl, arms down and twirl, one left out and twirl, twirl with various hand and arm positions, finger pinch and spread motions, finger movement (e.g. virtual typing), snapping, tapping hip motion, shoulder motion foot motions, swipe movements, sign language (e.g. ASL), and the like, and combinations of the same.

In embodiments, command and/or control modes and interfaces in which inputs can be reflected may include a graphical user interface (GUI), auditory command interface, clickable icons, navigable lists, virtual reality interface, augmented reality interface, heads-up display, semi-opaque display, 3D navigation interface, command line, virtual touch screen, robot control interface, typing (e.g. with persistent virtual keyboard locked in place), predictive and/or learning based user interface (e.g. learns what the wearer does in a 'training mode', and when and where they do it), simplified command mode (e.g. hand gestures to kick off an application, etc.), Bluetooth controllers, cursor hold, lock a virtual display, head movement around a located cursor, and the like, and combinations of the same.

In embodiments, applications on the eyepiece that can use commands and/or respond to inputs may include military applications, weapons control applications, military targeting applications, war game simulation, hand-to-hand fighting simulator, repair manual applications, tactical operations applications, mobile phone applications (e.g. iPhone apps), information processing, fingerprint capture, facial recognition, information display, information conveying, information gathering, iris capture, entertainment, easy access to information for pilots, locating objects in 3D in the real world, targeting for civilians, targeting for police, instructional, tutorial guidance without using hands (e.g. in maintenance, assembly, first aid, etc.), blind navigation assistance, communications, music, search, advertising, video, computer games, video, computer games, eBooks, advertising, shopping, e-commerce, videoconferencing, and the like, and combinations of the same.

In embodiments, communication and/or connection from the eyepiece interface to external systems and devices may include a microcontroller, microprocessor, digital signal processor, steering wheel control interface, joystick controller, motion and sensor resolvers, stepper controller, audio system controller, program to integrate sound and image signals, application programming interface (API), graphical user interface (GUI), navigation system controller, network router, network controller, reconciliation system, payment system, gaming device, pressure sensor, and the like.

In embodiments, external devices to be controlled may include a weapon, a weapon control system, a communications system, a bomb detection system, a bomb disarming system, a remote-controlled vehicle, a computer (and thus many devices able to be controlled by a computer), camera, projector, cell phone, tracking devices, display (e.g. computer, video, TV screen), video game, war game simulator, mobile gaming, pointing or tracking device, radio or sound system, range finder, audio system, iPod, smart phone, TV, entertainment system, computer controlled weapons system, drone, robot, automotive dashboard interfaces, lighting devices (e.g. mood lighting), exercise equipment, gaming platform (such as the gaming platform recognizing the user and preloading what they like to play), vehicles, storage-enabled devices, payment system, ATM, POS system, and the like.

In embodiments, applications in association with external devices may be military applications, weapons control applications, military targeting applications, war game simulation, hand-to-hand fighting simulator, repair manual applications, tactical operations applications, communications, information processing, fingerprint capture, facial recognition, iris capture, entertainment, easy access to information for pilots, locating objects in 3D in the real world, targeting for civilians, targeting for police, instructional, tutorial guidance without using hands (e.g. maintenance, assembly, first aid), blind navigation assistance, music, search, advertising, video, computer games, eBooks, automotive dashboard applications, advertising, military enemy targeting, shopping, e-commerce, and the like, and combinations of same.

In embodiments, feedback to the wearer related to external devices and applications may include visual display, heads-up display, bulls-eye or target tracking display, tonal output or sound warning, performance or rating indicator, score, mission accomplished indication, action complete indication, play of content, display of information, reports, data mining, recommendations, targeted advertisements, and the like.

In an example, control aspects of the eyepiece may include combinations of a head nod from a soldier as movement to initiate a silent command (such as during a combat engagement), through a graphical user interface for reflecting modes and/or interfaces in which the control input is reflected, a military application on the eyepiece that uses the commands and/or responds to the control input, an audio system controller to communicate and/or connect from the eyepiece interface to an external system or device, and the like. For instance, the soldier may be controlling a secure communications device through the eyepiece during a combat engagement, and wish to change some aspect of communications, such as a channel, a frequency, an encoding level, and the like, without making a sound and with minimal motion so as to minimize the chance of being heard or seen. In this instance, a nod of the soldier's head may be programmed to indicate the change, such as a quick nod forward to indicate the beginning of a transmission, a quick nod backward to indicate the end of a transmission, and the like. In addition, the eyepiece may be projecting a graphical user interface to the soldier for the secure communications device, such as showing what channel is active, what alternative channels are available, others in their team that are currently transmitting, and the like. The nod of the soldier may then be interpreted by processing facilities of the eyepiece as a change command, the command transmitted to the audio system controller, and the graphical user interface for the communications device showing the change. Further, certain nods/body motions may be interpreted as specific commands to be transmitted such that the eyepiece sends a pre-established communication without the soldier needing to be audible. That is, the soldier may be able to send pre-canned communications to their team though body motions (for example, as determined together with the team prior to the engagement). In this way, a soldier wearing and utilizing the facilities of the eyepiece may be able to connect and interface with the external secure communications device in a completely stealthy manner, maintaining silent communications with their team during engagement, even when out of sight with the team. In embodiments, other movements or actions for controlling or initiating commands, command and/or control modes and interfaces in which the inputs can be reflected, applications on platform that can use commands and/or respond to inputs, communication or connection from the on-platform interface to external systems and devices, and the like, as described herein, may also be applied.

In an example, control aspects of the eyepiece may include combinations of motion and position sensors as sensing inputs, an augmented reality interface as a command and control interface in which the inputs can be reflected to a soldier, a motion sensor and range finder for a weapon system as external devices to be controlled and information collected from, feedback to the soldier related to the external devices, and the like. For instance, a soldier wearing the eyepiece may be monitoring military movements within an environment with the motion sensor, and when the motion sensor is triggered an augmented reality interface may be projected to the wearer that helps identify a target, such as a person, vehicle, and the like for further monitoring and/or targeting. In addition, the range finder may be able to determine the range to the object and feedback that information to the soldier for use in targeting (such as manually, with the soldier executing a firing action; or automatically, with the weapon system receiving the information for targeting and the soldier providing a command to fire). In embodiments, the augmented reality interface may provide information to the soldier about the target, such as the location of the object on a 2D or 3D projected map, identity of the target from previously collected information (e.g. as stored in an object database, including face recognition, object recognition), coordinates of the target, night vision imaging of the target, and the like. In embodiments, the triggering of the motion detector may be interpreted by processing facilities of the eyepiece as a warning event, the command may be transmitted to the range finder to determine the location of the object, as well as to the speakers of the ear phones of the eyepiece to provide an audio warning to the soldier that a moving object has been sensed in the area being monitored. The audio warning plus visual indicators to the soldier may serve as inputs to the soldier that attention should be paid to the moving object, such as if the object has been identified as an object of interest to the soldier, such as through an accessed database for known combatants, known vehicle types, and the like. For instance, the soldier may be at a guard post monitoring the perimeter around the post at night. In this case, the environment may be dark, and the soldier may have fallen into a low attentive state, as it may be late at night, with all environmental conditions quiet. The eyepiece may then act as a sentry augmentation device, 'watching' from the soldier's personal perspective (as opposed to some external monitoring facility for the guard post). When the eyepiece senses movement, the soldier may be instantly alerted as well as guided to the location, range, identity, and the like, of the motion. In this way, the soldier may be able to react to avoid personal danger, to target fire to the located movement, and the like, as well as alert the post to potential danger. Further, if a firefight were to ensue, the soldier may have improved reaction time as a result of the warning from the eyepiece, with better decision making though information about the target, and minimizing the danger of being injured or the guard post from being infiltrated. In embodiments, other sensing inputs and/or sensing devices, command and/or control modes and interfaces in which the inputs can be reflected, useful external devices to be controlled, feedback related to external devices and/or external applications, and the like, as described herein, may also be applied.

In embodiments, the eyepiece may enable remote control of vehicles, such as a truck, robot, drone, helicopter, watercraft, and the like. For instance, a soldier wearing the eyepiece may be able to command through an internal communications interface for control of the vehicle. Vehicle control may be provided through voice commands, body movement (e.g. a soldier instrumented with movement sensors that are in interactive communication with the eyepiece, and interfaced through the eyepiece to control the vehicle), keyboard interface, and the like. In an example, a soldier wearing an eyepiece may provide remote control to a bomb disposal robot or vehicle, where commands are generated by the soldier though a command interface of the eyepiece, such as described herein. In another example, a soldier may command an aircraft, such as a remote control drone, remote control tactical counter-rotating helicopter, and the like. Again, the soldier may provide control of the remote control aircraft through control interfaces as described herein.

In an example, control aspects of the eyepiece may include combinations of a wearable sensor set as an action capture input for a soldier, utilizing a robot control interface as a command and control interface in which the inputs can be reflected, a drone or other robotic device as an external device to be controlled, and the like. For instance, the soldier wearing the eyepiece may be instrumented with a sensor set for the control of a military drone, such as with motion sensor inputs to control motion of the drone, hand recognition control for manipulation of control features of the drone (e.g. such as through a graphical user interface displayed through the eyepiece), voice command inputs for control of the drone, and the like. In embodiments, control of the drone through the eyepiece may include control of flight, control of on-board interrogation sensors (e.g. visible camera, IR camera, radar), threat avoidance, and the like. The soldier may be able to guide the drone to its intended target using body mounted sensors and picturing the actual battlefield through a virtual 2D/3D projected image, where flight, camera, monitoring controls are commanded though body motions of the soldier. In this way, the soldier may be able to maintain an individualistic, full visual immersion, of the flight and environment of the drone for greater intuitive control. The eyepiece may have a robot control interface for managing and reconciling the various control inputs from the soldier-worn sensor set, and for providing an interface for control of the drone. The drone may then be controlled remotely through physical action of the soldier, such as through a wireless connection to a military control center for drone control and management. In another similar example, a soldier may control a bomb-disarming robot that may be controlled through a soldier-worn sensor set and associated eyepiece robot control interface. For instance, the soldier may be provided with a graphical user interface that provides a 2D or 3D view of the environment around the bomb disarming robot, and where the sensor pack provides translation of the motion of the soldier (e.g. arms, hands, and the like) to motions of the robot. In this way, the soldier may be able to provide a remote control interface to the robot to better enable sensitive control during the delicate bomb disarming process. In embodiments, other user action capture inputs and/or devices, command and/or control modes and interfaces in which the inputs can be reflected, useful external devices to be controlled, and the like, as described herein, may also be applied.

In an example, control aspects of the eyepiece may include combinations of an event indication to the soldier as they enter a location, a predictive-learning based user interface as a command and control mode and/or interface in which the input occurrence of the event is reflected, a weapons control system as an external device to be controlled, and the like. For instance, an eyepiece may be programmed to learn the behavior of a soldier, such as what the soldier typically does when they enter a particular environment with a particular weapons control system, e.g. does the wearer turn on the system, arm the system, bring up visual displays for the system, and the like. From this learned behavior, the eyepiece may be able to make a prediction of what the soldier wants in the way of an eyepiece control function. For example, the soldier may be thrust into a combat situation, and needs the immediate use of a weapons control system. In this case, the eyepiece may sense the location and/or the identity of the weapons system as the soldier approaches, and configure/enable the weapons system to how the soldier typically configures the system when they are near the weapons control system, such as in previous uses of the weapons system where the eyepiece was in a learning mode, and commanding the weapons control system to turn on the system as last configured. In embodiments, the eyepiece may sense the location and/or identity of the weapons system through a plurality of methods and systems, such as through a vision system recognizing the location, an RFID system, a GPS system, and the like. In embodiments, the commanding of the weapons control system may be through a graphical user interface that provides the soldier with a visual for fire-control of the weapon system, an audio-voice command system interface that provides choices to the soldier and voice recognition for commanding, pre-determined automatic activation of a function, and the like. In embodiments, there may be a profile associated with such learned commanding, where the soldier is able to modify the learned profile and/or set preferences within the learned profile to help optimize automated actions, and the like. For example, the soldier may have separate weapon control profiles for weapons readiness (i.e. while on post and awaiting action) and for active weapons engagement with the enemy. The soldier may need to modify a profile to adjust to changing conditions associated with use of the weapon system, such as a change in fire command protocols, ammunition type, added capabilities of the weapon system, and the like. In embodiments, other events and/or data feeds, command and/or control modes and interfaces in which the inputs can be reflected, useful external devices to be controlled, and the like, as described herein, may also be applied.

In an example, control aspects of the eyepiece may include combinations of an individual responsibility event for a soldier (such as deployed in a theater of action, and managing their time) as an event and/or data feed, a voice recognition system as a user action capture input device, an auditory command interface as a command and control interface in which the inputs can be reflected, video-based communications as an application on the eyepiece that is used to respond to the input from the soldier, and the like. For instance, a soldier wearing the eyepiece may get a visual indication projected to them of a scheduled event for a group video supported communication between commanders. The soldier may then use a voice command to an auditory command interface on the eyepiece to bring up the contact information for the call, and voice command the group video communication to be initiated. In this way, the eyepiece may serve as a personal assistant for the soldier, bringing up scheduled events and providing the soldier with a hands-free command interface to execute the scheduled events. In addition, the eyepiece may provide for the visual interface for the group video communication, where the images of the other commanders are projected to the soldier through the eyepiece, and where an external camera is providing the soldier's video image through communicative connection to the eyepiece (such as with an external device with a camera, using a mirror with the internally integrated camera, and the like, as described herein). In this way, the eyepiece may provide a fully integrated personal assistant and phone/video-based communications platform, subsuming the functions of other traditionally separate electronics devices, such as the radio, mobile phone, a video-phone, a personal computer, a calendar, a hands-free command and control interface, and the like. In embodiments, other events and/or data feeds, user action capture inputs and/or devices, command and/or control modes and interfaces in which the inputs can be reflected, applications on platform that can use commands and/or respond to inputs, and the like, as described herein, may also be applied.

In an example, control aspects of the eyepiece may include combinations of a security event to a soldier as an event and/or data feed; a camera and touch screen as user action capture input devices; an information processing, fingerprint capture, facial recognition application on the eyepiece to respond to the inputs; a graphical user interface for communications and/or connection between the eyepiece and external systems and devices; and an external information processing, fingerprint capture, facial recognition application and database for access to external security facilities and connectivity, and the like. For instance, a soldier may receive a 'security event' while on post at a military checkpoint where a plurality of individuals is to be security checked and/or identified. In this case there may be a need for recording the biometrics of the individuals, such as because they don't show up in a security database, because of suspicious behavior, because they fit the profile of a member of a combatant, and the like. The soldier may then use biometric input devices, such as a camera for photographing faces and a touch screen for recording fingerprints, where the biometric inputs are managed though an internal information, processing, fingerprint capture, and facial recognition application on the eyepiece. In addition, the eyepiece may provide a graphical user interface as a communications connection to an external information, processing, fingerprint capture, and facial recognition application, where the graphical user interface provides data capture interfaces, external database access, people of interest database, and the like. The eyepiece may provide for an end-to-end security management facility, including monitoring for people of interest, input devices for taking biometric data, displaying inputs and database information, connectivity to external security and database applications, and the like. For instance, the soldier may be checking people through a military checkpoint, and the soldier has been commanded to collect facial images, such as with iris biometrics, for anyone that meets a profile and is not currently in a security database. As individuals approach the soldier, as in a line to pass through the checkpoint, the soldier's eyepiece takes high-resolution images of each individual for facial and/or iris recognition, such as checked though a database accessible through a network communication link. A person may be allowed to pass the checkpoint if they do not meet the profile (e.g. a young child), or is in the database with an indication that they are not considered a threat. A person may not be allowed to pass through the checkpoint, and is pulled aside, if the individual is indicated to be a threat or meets the profile and is not in the database. If they need to be entered into the security database, the soldier may be able to process the individual directly through facilities of the eyepiece or with the eyepiece controlling an external device, such as for collecting personal information for the individual, taking a close-up image of the individual's face and/or iris, recording fingerprints, and the like, such as described herein. In embodiments, other events and/or data feeds, user action capture inputs and/or devices, applications on platform that can use commands and/or respond to inputs, communication or connection from the on-platform interface to external systems and devices, applications for external devices, and the like, as described herein, may also be applied.

In an example, control aspects of the eyepiece may include combinations of a finger movement as a user action for a soldier initiating an eyepiece command, a clickable icon as a command and control mode and/or interface in which the user action can be reflected, an application on the eyepiece (e.g. weapons control, troop movements, intelligence data feed, and the like), a military application tracking API as a communication and/or connection from the eyepiece application to an external system, an external personnel tracking application, feedback to military personnel, and the like. For instance, a system for monitoring a soldier's selection of an on-eyepiece application may be implemented through an API such that the monitoring provides a service to the military for monitoring and tracking application usage, feedback to the soldier as to other applications available to them based on the monitored behavior, and the like. In the course of a day, the soldier may select an application for use and/or download, such as through a graphical user interface where clickable icons are presented, and to which the soldier may be able to select the icon based on a finger movement control implementation facility (such as a camera or inertial system through which the soldier's finger action is used as a control input, in this case to select the clickable icon). The selection may then be monitored through the military application tracking API that sends the selection, or stored number of selections (such as transmitting stored selections over a period of time), to the external personnel tracking application. The soldier's application selections, in this case 'virtual clicks', may then be analyzed for the purpose of optimizing usage, such as through increasing bandwidth, change of available applications, improvement to existing applications, and the like. Further, the external personnel tracking application may utilize the analysis to determine what the wearer's preferences are in terms of applications use, and send the wearer feedback in the form of recommendations of applications the wearer may be interested in, a preference profile, a list of what other similar military users are utilizing, and the like. In embodiments, the eyepiece may provide services to improve the soldier's experience with the eyepiece, such as with recommendations for usage that the soldier may benefit from, and the like, while aiding in guiding the military use of the eyepiece and applications thereof. For instance, a soldier that is new to using the eyepiece may not fully utilize its capabilities, such as in use of augmented reality interfaces, organizational applications, mission support, and the like. The eyepiece may have the capability to monitor the soldier's utilization, compare the utilization to utilization metrics (such as stored in an external eyepiece utilization facility), and provide feedback to the soldier in order to improve use and associated efficiency of the eyepiece, and the like. In embodiments, other user movements or actions for controlling or initiating commands, command and/or control modes and interfaces in which the inputs can be reflected, applications on platform that can use commands and/or respond to inputs, communication or connection from the on-platform interface to external systems and devices, applications for external devices, feedback related to external devices and/or external applications, and the like, as described herein, may also be applied.

In an example, control aspects of the eyepiece may include combinations of IR, thermal, force, carbon monoxide, and the like sensors as inputs; microphone as an additional input device; voice commands as an action by a soldier to initiate commands; a heads-up display as a command and control interface in which the inputs can be reflected; an instructional guidance application to provide guidance while reducing the need for the soldier to use their hands, such as in emergency repair in the field, maintenance, assembly, and the like; a visual display that provides feedback to the soldier based on the actions of the soldier and the sensor inputs; and the like. For instance, a soldier's vehicle may have been damaged in a firefight, leaving the soldier(s) stranded without immediate transport capabilities. The soldier may be able to bring up an instructional guidance application, as running through the eyepiece, to provide hands-free instruction and computer-based expert knowledge access to diagnosing the problem with the vehicle. In addition, the application may provide a tutorial for procedures not familiar to the soldier, such as restoring basic and temporary functionality of the vehicle. The eyepiece may also be monitoring various sensor inputs relevant to the diagnosis, such as an IR, thermal, force, ozone, carbon monoxide, and the like sensors, so that the sensor input may be accessible to the instructional application and/or directly accessible to the soldier. The application may also provide for a microphone through which voice commands may be accepted; a heads-up display for the display of instruction information, 2D or 3D depiction of the portion of the vehicle under repair; and the like. In embodiments, the eyepiece may be able to provide a hands-free virtual assistant to the soldier to assist them in the diagnosis and repair of the vehicle in order to re-establish a means for transport, allowing the soldier to re-engage the enemy or move to safety. In embodiments, other sensing inputs and/or sensing devices, user action capture inputs and/or devices, user movements or actions for controlling or initiating commands, command and/or control modes and interfaces in which the inputs can be reflected, applications on platform that can use commands and/or respond to inputs, feedback related to external devices and/or external applications, and the like, as described herein, may also be applied.

In an example, control aspects of the eyepiece may include combinations of the eyepiece entering an 'activity state', such as a 'military engagement' activity mode, e.g. the soldier commanding the eyepiece into a military engagement mode, or the eyepiece sensing it is in proximity to a military activity, perhaps even a predetermined or targeted engagement area through a received mission directive, which may have further been developed in part through self-monitoring and learning the wearer's general engagement assignment. Continuing with this example, entering an activity state e.g. a military engagement activity state, such as while driving in a vehicle into an encounter with the enemy or into hostile territory, may be combined with an object detector as a sensing input or sensing device, a head-mounted camera and/or eye-gaze detection system as a user action capture input, eye movement as a user movement or action for controlling or initiating commands, a 3D navigation interface as a command and control mode and/or interface in which the inputs can be reflected, an engagement management application on-board the eyepiece as an application for coordinating command inputs and user interface, a navigation system controller to communicate or connect with external systems or devices, a vehicle navigation system as an external device to be controlled and/or interfaced with, a military planning and execution facility as an external application for processing user actions with regard to a military directive, bulls-eye or target tracking system as feedback to the wearer as to enemy targeting opportunities within sight while driving, and the like. For instance, a soldier may enter a hostile environment while driving their vehicle, and the eyepiece, detecting the presence of the enemy engagement area (e.g. through GPS, direct viewing targets through an integrated camera, and the like) may enter a 'military engagement activity state' (such as enabled and/or approved by the soldier). The eyepiece may then detect an enemy vehicle, hostile dwelling, and the like with an object detector that locates an enemy targeting opportunity, such as through a head-mounted camera. Further, an eye-gaze detection system on the eyepiece may monitor where the soldier is looking, and possibly highlight information about a target at the location of the wearer's gaze, such as enemy personnel, enemy vehicle, enemy weapons, as well as friendly forces, where friend and foe are identified and differentiated. The soldier's eye movement may also be tracked, such as for changing targets of interest, or for command inputs (e.g. a quick nod indicating a selection command, a downward eye movement indicating a command for additional information, and the like). The eyepiece may invoke a 3D navigation interface projection to assist in providing the soldier with information associated with their surroundings, and a military engagement application for coordinating the military engagement activity state, such as taking inputs from the soldier, providing outputs to the 3D navigation interface, interfacing with external devices and applications, and the like. The eyepiece may for instance utilize a navigation system controller to interface with a vehicle navigation system, and thus may include the vehicle navigation system into the military engagement experience. Alternately, the eyepiece may use its own navigation system, such as in place of the vehicle system or to augment it, such as when the soldier gets out of the vehicle and wishes to have over-the-ground directions provided to them. As part of the military engagement activity state, the eyepiece may interface with an external military planning and execution facility, such as to provide current status, troop movements, weather conditions, friendly forces position and strength, and the like. In embodiments, the soldier, through entering an activity state, may be provided feedback associated with the activity state, such as for a military engagement activity state being supplied feedback in the form of information associated with an identified target. In embodiments, other events and/or data feeds, sensing inputs and/or sensing devices, user action capture inputs and/or devices, user movements or actions for controlling or initiating commands, command and/or control modes and interfaces in which the inputs can be reflected, applications on platform that can use commands and/or respond to inputs, communication or connection from the on-platform interface to external systems and devices, applications for external devices, feedback related to external devices and/or external applications, and the like, as described herein, may also be applied.

In an example, control aspects of the eyepiece may include combinations of a secure communications reception as a triggering event to a soldier, inertial movement tracking as a user action capture input device, drag-and-drop with fingers and swipe movements by the soldier as user movements or actions for controlling or initiating commands, navigable lists as a command and control interface in which the inputs can be reflected, information conveying as a type of application on the eyepiece that can use commands and respond to inputs, a reconciliation system as a communication or connection from the on-eyepiece interface to external systems and devices, iris capture and recognition system as an external application for external systems and devices, and the like. A soldier wearing the eyepiece may receive a secure communication, and the communication may come in to the eyepiece as an 'event' to the soldier, such as to trigger an operations mode of the eyepiece, with a visual and/or audible alert, to initiate an application or action on the eyepiece, and the like. The soldier may be able to react to the event through a plurality of control mechanisms, such as the wearer 'drag and dropping', swiping, and the like with their fingers and hands through a hand gesture interface (e.g. through a camera and hand gesture application on-board the eyepiece, where the wearer drags the email or information within the communication into a file, an application, another communication, and the like). The wearer may call up navigable lists as part of acting on the communication. The user may convey the information from the secure communication through an eyepiece application to external systems and devices, such as a reconciliation system for tracking communications and related actions. In embodiments, the eyepiece and/or secure access system may require identification verification, such as through biometric identity verification e.g. fingerprint capture, iris capture recognition, and the like. For instance, the soldier may receive a secure communication that is a security alert, where the secure communication comes with secure links to further information, and where the soldier is required to provide biometric authentication before being provided access. Once authenticated, the soldier may be able to use hand gestures in their response and manipulation of content available through the eyepiece, such as manipulating lists, links, data, images, and the like available directly from the communications and/or through the included links Providing the capability for the soldier to respond and manipulate content in association with the secure communication, may better allow the soldier to interact with the message and content in a manner that does not compromise any non-secure environment they may currently be in. In embodiments, other events and/or data feeds, user action capture inputs and/or devices, user movements or actions for controlling or initiating commands, command and/or control modes and interfaces in which the inputs can be reflected, applications on platform that can use commands and/or respond to inputs, communication or connection from the on-platform interface to external systems and devices, applications for external devices, and the like, as described herein, may also be applied.

In an example, control aspects of the eyepiece may include combinations of using an inertial user interface as a user action capture input device to provide military instruction to a soldier through the eyepiece to an external display device. For instance, a soldier, wearing the eyepiece, may wish to provide instruction to a group of other soldiers in the field from a briefing that has been made available to them through the facilities of the eyepiece. The soldier may be aided though the use of a physical 3D or 2D mouse (e.g. with inertial motion sensor, MEMS inertial sensor, ultrasonic 3D motion sensor, IR, ultrasonic, or capacitive tactile sensor, accelerometer, and the like), a virtual mouse, a virtual touch screen, a virtual keyboard, and the like to provide an interface for manipulating content in the briefing. The briefing may be viewable to and manipulated though the eyepiece, but also exported in real-time, such as to an external router that is connected to an external display device (e.g. computer monitor, projector, video screen, TV screen, and the like). As such, the eyepiece may provide a way for the soldier to have others view what they see through the eyepiece and as controlled through the control facilities of the eyepiece, allowing the soldier to export multimedia content associated with the briefing as enabled through the eyepiece to other non-eyepiece wearers. In an example, a mission briefing may be provided to a commander in the field, and the commander, through the eyepiece, may be able to brief their team with multimedia and augmented reality resources available through the eyepiece, as described herein, thus gaining the benefit that such visual resources provide. In embodiments, other sensing inputs and/or sensing devices, user action capture inputs and/or devices, command and/or control modes and interfaces in which the inputs can be reflected, communication or connection from the on-platform interface to external systems and devices, useful external devices to be controlled, feedback related to external devices and/or external applications, and the like, as described herein, may also be applied.

In an example, control aspects of the eyepiece may include combinations of a head nod as a user movement to initiating a command, a graphical user interface for reflecting modes and/or interfaces in which the control input is reflected, an entertainment application on the eyepiece that uses the commands and/or responds to the control input, an audio system controller to communicate and/or connect from the eyepiece interface to an external system or device, and the like. For instance, the wearer of the eyepiece may be controlling an audio player through the eyepiece, and wish to change to the next track. A nod of the wearer's head may be programmed in this instance to indicate a change in track. In addition, the eyepiece may be projecting a graphical user interface for the audio player to the wearer, such as showing what track is playing. The nod of the wearer may then be interpreted by processing facilities of the eyepiece as a change track command, the command may then be transmitted to the audio system controller for changing the track, and the graphical user interface for the audio player may then show a change of track to the wearer.

In an example, control aspects of the eyepiece may include combinations of a motion sensor as a sensing input, an augmented reality interface as a command and control interface in which the inputs can be reflected to the wearer, a range finder as an external device to be controlled and information collected from, and the like. For instance, the wearer of the eyepiece may be monitoring movements within an environment with a motion sensor, and when the motion sensor is triggered an augmented reality interface may be projected to the wearer that helps identify the object. In addition, other sensors may aid in the identification, such as a range finder to determine the range to the object. The augmented reality interface may provide information to the wearer about the object, such as the location of the object on a 2D or 3D projected map, identity of the object from previously collected information (e.g. as stored in an object database, including face recognition, object recognition), coordinates of the object, night vision imaging of the object, and the like. The triggering of the motion detector may be interpreted by processing facilities of the eyepiece as a warning event, the command may then be transmitted to the range finder to determine the location of the object, as well as to the speakers of the ear phones of the eyepiece to provide an audio warning to the wearer that a moving object has been sensed. The audio warning plus visual indicators to the wearer may serve as inputs to the wearer that attention should be paid to the moving object, such as if the object has been identified as an object of interest to the wearer.

In an example, control aspects of the eyepiece may include combinations of a wearable sensor set as a user action capture input, a robot control interface as a command and control interface in which the inputs can be reflected, a drone or other robotic device as an external device to be controlled, and the like. For instance, the wearer of the eyepiece may be instrumented up with a sensor set for the control of a drone, such as motion sensor inputs to control motion of the drown, hand recognition control for manipulation of control features of the drone (e.g. such as through a graphical user interface displayed through the eyepiece), voice command inputs for control of the drone, and the like. The eyepiece may have a robot control interface for managing and reconciling the various control inputs from the sensor set, and for providing an interface for control of the drone. The drone may then be controlled remotely through action of the wearer, such as through a wireless connection to a control center for drone control and management, to the drone more directly, and the like. In another similar example, a robot (e.g. a bomb disarming robot) may be controlled through the sensor set and eyepiece robot control interface. For instance, the wearer may be provided with a graphical user interface that provides a 2D or 3D view of the environment around the robot, and where the sensor pack provides translation of the motion of the wearer (e.g. arms, hands, and the like) to motions of the robot. In this way, the wearer may be able to provide a remote control interface to the robot.

In an example, control aspects of the eyepiece may include combinations of entering a location as an event to the eyepiece, a predictive-learning based user interface as a command and control mode and/or interface in which the input occurrence of the event is reflected, an entertainment system as an external device to be controlled, and the like. For instance, an eyepiece may be programmed to learn the behavior of the wearer, such as what the wearer typically does when they enter a room with an entertainment system, e.g. does the wearer turn on the television, the sound system, a game system, and the like. From this learned behavior, the eyepiece may be able to make a prediction of what the wearer wants in the way of an eyepiece control function. For example, walking into the living room, the eyepiece sensing the location and that the wearer typically turns on music through the entertainment system when they enter the room, and commanding the entertainment system to turn on the music that was last playing. In embodiments, the eyepiece may sense the location through a plurality of methods and systems, such as through a vision system recognizing the location, an RFID system, a GPS system, and the like. The commanding of the entertainment system may be through a graphical user interface that provides the wearer with choices, an audio-voice command system interface that provides choices to the wearer and voice recognition for commanding, an automatic activation of the command, and the like. There may be a profile associated with such learned commanding, where the wearer is able to modify the learned profile and/or set preferences within the learned profile to help optimize automated actions and the like.

In an example, control aspects of the eyepiece may include combinations of a personal event as an event and/or data feed, a voice recognition system as a user action capture input device, an auditory command interface as a command and control interface in which the inputs can be reflected, videoconferencing as an application on the eyepiece that is used to respond to the input from the wearer, and the like. For instance, a wearer may get a visual indication projected to them of a calendar event for a conference call. The user may then use a voice command to an auditory command interface on the eyepiece to bring up the dial-in information for the call, and voice command the videoconference to be initiated. In this way, the eyepiece may serve as a personal assistant, bringing up calendar events and providing the wearer with a hands-free command interface to execute the calendar events. In addition, the eyepiece may provide for the visual interface for the videoconference, where the image of others are projected to the wearer through the eyepiece, and where an external camera is providing the wearer's video image through communicative connection to the eyepiece. The eyepiece may provide a fully integrated personal assistant and phone/videoconferencing platform, subsuming the functions of other traditionally separate electronics devices, such as the mobile phone, the PDA, a calendar, a hands-free command and control interface, and the like.

In an example, control aspects of the eyepiece may include combinations of a security event as an event and/or data feed; a camera and touch screen as user action capture input devices; an information processing, fingerprint capture, facial recognition application on the eyepiece to respond to the inputs; a graphical user interface for communications and/or connection between the eyepiece and external systems and devices; and an external information processing, fingerprint capture, facial recognition application and database for access to external security facilities and connectivity, and the like. For instance, a security official may be dealing with a 'security event', which might be some checkpoint with many individuals to be security checked and/or identified, an individual that needs to be checked and/or identified, and the like, where there is a need identified for recording the biometrics of an individual (e.g. because they don't show up in a security database, because of suspicious behavior, and the like). The security official may then use biometric input devices, such as a camera for photographing faces and a touch screen for recording fingerprints, where the biometric inputs are managed though an internal information, processing, fingerprint capture, and facial recognition application on the eyepiece. In addition, the eyepiece may provide a graphical user interface as a communications connection to an external information, processing, fingerprint capture, and facial recognition application, where the graphical user interface provides data capture interfaces, external database access, people of interest database, and the like. The eyepiece may provide for an end-to-end security management facility, including monitoring for people of interest, input devices for taking biometric data, displaying inputs and database information, connectivity to external security and database applications, and the like.

In an example, control aspects of the eyepiece may include combinations of a finger movement as a user action for initiating a command, a clickable ion as a command and control mode and/or interface in which the user action can be reflected, an application on the eyepiece (e.g. phone application, music search, ads selection, and the like), an advertisement tracking API as a communication and/or connection from the eyepiece application to an external system, an external advertisement application, feedback to the user, and the like. For instance, a system for monitoring user selection of on-eyepiece applications may be implemented through an API such that the monitoring provides a service to an advertisement placement facility, feedback to the wearer as to other applications the wearer may be interested in based on the monitored behavior, and the like. In the course of a day, the wearer may select an application for use and/or download, such as through a graphical user interface where clickable icons are presented, and to which the wearer may be able to select the icon based on a finger movement control implementation facility (such as a camera or inertial system through which the wearer's finger action is used as a control input, in this case to select the clickable icon). The selection may then be monitored through the advertisement tracking API that sends the selection, or stored number of selections (such as transmitting stored selections over a period of time), to the external advertisement application. The wearer's application selections, in this case 'virtual clicks', may then be analyzed for the purpose of generating advertisement revenue, such as through advertisement placement back to the wearer, selling of the data to a third party advertisement facility, and the like. Further, the external advertisement application may utilize the analysis to determine what the wearer's preferences are in terms of applications use, and send the wearer feedback in the form of recommendations of applications the wearer may be interested in, a preference profile, a list of what other similar users are interested in downloading, and the like. In embodiments, the eyepiece may provide services to improve the wearer's experience with the eyepiece, such as with recommendations for downloads that the wearer may be interested in, with better targeted advertisements that the wearer may be interested in, and the like, while aiding in the generation of advertisement revenue for third-parties through an external advertisement application.

In an example, control aspects of the eyepiece may include combinations of body movement (e.g. kinetic sensor sensing head motion, cameras sensing hand motion, kinetic sensor sensing body motion) and touch sensors or audio as user action capture sensing devices (e.g. sensing a gaming device such as a steering wheel, a sword, and the like; sensing another player in the game; and the like), head and hand movement as user actions for controlling and/or initiating commands (e.g. through gesture control), a virtual reality interface as a command and control interface through which the inputs can be reflected, an information display as an application on the eyepiece that can respond to the inputs, a computer gaming device as an external device to be controlled through a gaming application, and the play of the gaming content to the wearer and performance, rating, score, and the like, as feedback to the user related to the external device and application. For instance, a wearer may be able to play an interactive computer game (e.g. on a computer, a computer-based gaming platform, a mobile gaming platform) in conjunction with the eyepiece, where the wearer's body movements are interpreted as control inputs, such as though body movement sensors, touch sensors, infrared sensors, IR camera, visible camera, and the like. In this way, movements of the wearer's body may be fed into the computer game, rather than using more traditional control inputs such as a handheld game controller. For example, the eyepiece may sense the motion of user's hands and the like through IR and/or visible cameras on the eyepiece and processed through on-board or external gesture recognition algorithms, the eyepiece may sense the motion of the user's head through motion sensors on the eyepiece (e.g. for sensing the user jumping, moving forward and back, side to side in response to the game), and the like. In an embodiment, the gestures may be captured by a downward facing camera, or a camera that is imaging downwards such as through the use of fold optics. In other embodiments, the camera may capture non-line of sight gestures for recognition. For example, a foviated or segmented camera can do motion tracking and room mapping when looking forward but has a quadrant or hemisphere looking down to capture gestures and user interface control commands with the users' hands at their side or in their lap that are non-parallel to the center axis of the display. Of course, hand gestures may be tracked as described herein, such as by using IMU sensors in a device (such as ring controller, a watch, a pistol grip, etc.), magnetic markers, RF tags, and the like. These body motion control inputs may then feed into a virtual reality interface and information display application on the eyepiece to provide the user with a visual depiction of the game environment, feed into a computer game platform to control the gaming platform from the user's motions, provided to both the virtual reality interface and information display of the eyepiece and the gaming platform to create an augmented reality game platform though the eyepiece, and the like. In embodiments, a control device or interactive control element used to sense body movement or otherwise show user interaction, may be removed from the computer image by a processor associated with the eyepiece. In cases where the sensor is not desired to be part of the game, all or part of the image of the control device may be removed from the image produced for gameplay. For example where the sensor is simply used to detect hand/limb movement, the sensor may be removed from the image generation, however, where the sensor or control device is an object related to game play, such as a sword, the object may be depicted as such in the game play or AR environment. In embodiments, the control device may be desired to be viewed in a location other than where it is in reality. For example, a target at which a user throws darts may be displayed at the end of a hall in front of a user instead of being displayed associated with the darts that the user is throwing. By further example, if the user never releases the dart in actual game play, the dart, as a control device, may be shown as traveling to the target based on the characteristics of the user's throw. In embodiments, the computer game may be run entirely on-board the eyepiece as a local gaming application, interfaced to an external game facility local to the wearer, interfaced to a networked gaming facility (e.g. a massively multiplayer online game, MMOG), a combination of on the eyepiece and through a gaming platform, and the like. In the case where the eyepiece is interfacing and controlling a local external game facility (e.g. a game platform in the wearer's home), the eyepiece application portion of game execution may provide the visual environment and information display to the wearer, and the external game facility may provide the game application execution. Alternately, the eyepiece may provide the user movement sensing interface and provide that information to the gaming platform, where the gaming platform then provides the visual interface of the game to the user. Alternately, the eyepiece may provide the user movement sensing interface where this information is used by both the eyepiece and the gaming platform to create an augmented reality gaming interface that combines the visual interface and the gaming platform in the gaming presentation to the user. In embodiments, AR applications may augment an advertisement or the like on the side of a building or other structure with objects passing by in the foreground. As the user drives by, the camera may notice that an object (such as a light pole on the edge of a street) is moving through the field of view faster than the augmented surface in the background. The display system may subtract part of the augmented image to preserve the virtual layering of content behind the image. This may require tight calibration of the parallax between the user's eyes, the displays and the camera. In embodiments, this technique may be used to produce a depth map. It would be clear to one skilled in the art that many different partitioning configurations between the processing provided by the eyepiece and processing provide by external facilities may be implemented. Further, the game implementation may extend to external gaming facilities across the Internet, such as with an MMOG. External facilities, whether local or across the Internet, may then provide feedback to the wearer, such as in providing at least a portion of the played content (e.g. the locally provided game projection combined with content from the external facilities and other players), performance indications, scores, rankings, and the like. In embodiments, the eyepiece may provide a user environment for computer games, where the eyepiece interfaces with external control inputs and external processing facilities, to create the next generation of gaming platform.

As an alternative to the eyepiece detecting body movement through sensors in direct physical connection to the wearer (e.g. kinetic sensors, body movement sensors, touch sensors), the eyepiece may incorporate an active remote sensing system for indirect sensing and interpreting of body movements of the wearer, such as though the use of a 3D active depth sensor utilizing projected IR, sonar, RF, energy and the like, to sense the position of the wearers hands, feet, and the like. The active 3D depth sensor may also be used in combination with a visible or IR camera on the eyepiece. The combination of camera and 3D depth sensor may provide 3D motion capture that is processed on the eyepiece to provide advanced gesture recognition. The 3D active depth sensor may include a source (e.g. IR laser projector) and receiving sensor (e.g. IR sensor). In embodiments, the camera and 3D active depth sensor may point downward, sideways, outward, with respect to the eyepiece line-of-sight in order to improve the system's visibility of the user's hands, feet, and the like. In embodiments, there may be a plurality of cameras on the eyepiece, such as one or more for imaging as described herein (e.g. one facing forward, one detecting eye motion, one facing backwards), one or more for sensing motion of the wearer for command and control of eyepiece functions, applications, external devices, and the like. In an example, the combination of depth sensor and camera may point downward to capture images and motions of the wearer's hands, where the eyepiece processor uses the inputs from the depth sensor and camera to track the hand movements (e.g. translation and rotation of a hand, motion of individual digits of the hand), computes the motion of the hand using a motion algorithm, and controls eyepiece functionality based on the detected motions and an on-board data base of functional commands as a function of detected motions. In embodiments, interpreted hand motions may be used for control of eyepiece functions, eyepiece application, control of external facilities through the eyepiece, input to an external gaming platform, input to an internal virtual reality game, and the like. In embodiments, the camera, 3D active depth sensor, and associated algorithms may be combined with the on-board microphone or array of microphones to detect both the sounds and the motions of the surrounding environment.

The present disclosure may comprise an interactive head-mounted eyepiece worn by a user, wherein the eyepiece includes an optical assembly that simultaneously provides the user with a view of a surrounding environment along a forward-looking line-of-sight and of displayed content introduced to the optical assembly from an integrated image source, and provides an integrated camera with a view of a surrounding environment along a downward-looking line-of-sight for user gesture recognition through an integrated gesture recognition facility. In embodiments, the gesture recognition facility may identify a motion that the eyepiece interprets as a command to the eyepiece. The motion may be a hand motion, an arm motion, a finger motion, a foot motion, a leg motion, and the like. The integrated camera may be able to view the forward-looking line-of-sight surrounding environment as well as the downward-looking line-of-sight for gesture recognition. The integrated camera may have a segmented optical element for simultaneously imaging the forward-looking line of sight and the downward-looking line-of-sight views. Further, the eyepiece may have an active sensing system for indirect sensing and interpreting of body movements of the user, where the active sensing system provides an active signal through the optical assembly along the downward-looking line-of-sight view. The active signal may be an IR, sonar, RF, and the like active signal. The active sensing system may include a 3D active depth sensor to sense the position of at least one of the user's hands, feet, body, and the like. The active sensing system may be used in conjunction with the integrated camera to further provide for user gesture recognition.

In embodiments, the eyepiece may include a dual mode for marker location and tracking. A GPS for general marker location near a POI may be created, and then another second marker may be created. The second marker may be generated through a sensor reading, image processing, image recognition, user feedback, and the like. This second marker may be used for tracking in between taking GPS readings. In embodiments, the second marker may be used to provide a distance to or from a point of interest. The dual marker system may provide the user with the distance, time and directions between two points. The point may be a point of interest for travel, transportation, business, commerce, and the like. The dual mode for marker location and tracking may allow the user to locate an item to purchase, an item to visit, a travel destination, a mode of transportation, and the like. Transportation items may include a user's automobile, a train, airport, taxi stand, taxi, subway, and the like. Items of commerce may include various items such as but not limited to, food, entertainment, shopping, clothes, books, services, and the like. In embodiments, the item to locate may be a tourist attraction, restaurant, park, street, and the like. There may be an ecosystem of markers, ranging from QR codes to a wide range of communication devices (routers and switches) or passive sensors (RFID tags that can be pinged), all of which might want to relay some relevant information to the glasses, whether a precise location that permits the back end network to figure out what content to deliver, or some content itself that is specific to the location of the marker. A single party could use two markers to help orient or triangulate the glasses, providing exact orientation and distance information that might be more difficult to get with some single markers (especially ones that are not visual themselves). In embodiments, two markers may be processed. The eyepiece may be able to recognize two markers in proximity/field of view, and to act on them, either simultaneously (e.g., for triangulation) or to assign one of them priority (e.g, a paid marker might take precedence over a non-paid marker in an advertising scenario; a safety-oriented marker might take precedence over an advertising marker, etc.). Markers may come from the glasses, but can also be placed by, for example, other glasses, or other systems (e.g., those of advertisers, government parties, etc., etc.)

In embodiments, a system may comprise an interactive head-mounted eyepiece worn by a user wherein the eyepiece wherein the eyepiece includes an optical assembly through which the user views a surrounding environment and displayed content, an integrated image source for introducing the content to the optical assembly, and an integrated processor that generates a marker for a point of interest based on a GPS reading and stores the marker in a memory of the eyepiece, wherein the integrated processor creates a second marker in relation to the GPS point and stores the second marker in the memory. In embodiments, the second marker may be generated through a least one of a sensor reading, image processing, image recognition, user feedback on a current location, and the like. The second marker may be used to calculate at least one of the distance, directions, and time to a point of interest. In embodiments, a point of interest may be at least one of a tourist attraction, restaurant, park, a street, and the like. In embodiments, the GPS point may be used with the second marker to provide at least one of the distance, directions, time to an item of commerce, and the like. In embodiments, the GPS point may be used with the second marker to provide at least one of the distance, directions, the time to a mode of transportation, the tracking of a mode of transportation, and the like. In such embodiments, the mode of transportation may include at least one of a train, subway, automobile, and the like. In embodiments of the system, the GPS point may be used with the second marker to provide tracking of a point of interest. In embodiments, the GPS point may be used with the second marker to provide tracking of an item of commerce. In embodiments, user feedback may be verbal input to the eyepiece. The second marker may be generated through various means. By way of example, the second marker may be based on processing of a still and or video image captured by the eyepiece to obtain location information for the subject of the image. In embodiments, the second marker may be based on data obtained from an internet search, scanning a QR code, bar code, an object, and the like.

In various embodiments, the eyepiece may comprise an earpiece to provide for augmented hearing where the user is able to hear his surrounding environment, but also additional audio. Such audio may include game content, sports commentary, and the like. In embodiments, microphones and or ear bud may play audio binaurally or otherwise. In embodiments, a bone conduction earpiece may be used with the eyepiece. Such earpieces may allow the user to have audio waves transmitted to the inner ear through the skull bones, thereby, by-passing the user's eardrum. In embodiments, the earpiece may be used with cheekbones just in front of the user's ears, and or other bones capable of transmitting audio. Accordingly a user may be enabled to monitor or listen to audio while being cognizant if his or her surroundings. In embodiments, the earpiece may also employ sounds lasers, whereby through the use of a laser, the earpiece emits sound waves. In embodiments, the earpiece may also employ a device that allows for a user to experience heightened volume and/or clarity of an external sound or of a sound generated by the earpiece. In various embodiments, the earpiece of the eyepiece may play, and or transmit audio from, radio, audio obtained wirelessly, audio via the internet, and the like. In embodiments, the eyepiece may also transmit satellite radio audio to the user.

In various embodiments, the eyepiece may comprise RF shielding for the brain and or other parts of the user's body. In embodiments, any portion of the eyepiece that transmits an electromagnet field may be shielded with barriers made of conductive or magnetic material or otherwise. In embodiments, the shield may comprise sheet metal, metal screen, metal foam, foam, and the like. Holes in the shield or mesh may be significantly smaller than the wavelength of the radiation that's being blocked or other radiation. In embodiments, the inside or other portion of the eyepiece and/or eyepiece enclosure may be coated with a metallic ink or other material to provide shielding. Such metals may be copper, nickel and the like in the form of very small particulates. Such metal may be sprayed on the enclosure. In further embodiments, such an RF shield may be worn by the user to prevent various frequencies from reaching his or her brain, eyes, or other parts of the body.

In embodiments, an interactive head-mounted eyepiece worn by a user may include an optical assembly though which the user views a surrounding environment and displayed content, and integrated image source for introducing the content toe the optical assembly, a radio element, and shielding wherein the radio element may radiate electromagnetic radiation and the shielding blocks the radiation from radiating out of the eyepiece form a portion of the eyepiece. In further embodiments the shielding may be positioned to protect the user from the radiation. Further, the shielding may be positioned to protect the user and another from the radiation. In embodiments, the shielding may shield at last a user's brain, a part of the user's head, another part of the user's body, and the like. In embodiments, the shielding may be comprised of at least one of a conductive material, magnetic material, sheet metal, metal screen, mesh, and metal foam. In embodiments described herein, the shielding may comprise holes smaller than the wavelength of a particular radiation, and the holes may be smaller than the wavelength of the radiation radiating out of the eyepiece. In embodiments, the shielding may comprise at least one of a metallic ink, copper ink, nickel ink, and the like. In embodiments, the shielding may coat the inside of the eyepiece. In embodiments, the shielding may be positioned in at least one of an arm of the eyepiece, in a forehead section of the eyepiece, and the like. In embodiments, the shielding may be positioned at least in a forehead section of the eyepiece and in an arm of the eyepiece. In embodiments the shielding may be worn by a user.

In an example, control aspects of the eyepiece may include combinations of IR, thermal, force, ozone, Carbon Monoxide, and the like sensors as inputs; microphone as an additional input device; voice commands as an action by the wearer to initiate commands; a heads-up display as a command and control interface in which the inputs can be reflected; an instructional guidance application to provide guidance while reducing the need for using their hands, such as in maintenance and assembly; a visual display that provides feedback to the wearer based on the actions of the wearer and the sensor inputs; and the like. For instance, a car mechanic may be the wearer of the eyepiece, where the mechanic is using the eyepiece to aid in the maintenance of a vehicle. An instructional guidance application, as running through the eyepiece, may provide hands-free instruction and computer-based expert knowledge access to the mechanic while diagnosing a problem on a vehicle. In addition, the application may provide a tutorial for procedures not familiar to the mechanic. The eyepiece may also be monitoring various sensor inputs relevant to the diagnosis and safety, such as an IR, thermal, force, ozone, Carbon Monoxide, and the like sensors, so that the sensor input may be accessible to the instructional application and/or directly accessible to the mechanic. The application may also provide for a microphone through which voice commands may be accepted; a heads-up display for the display of instruction information, 2D or 3D depiction of the portion of the vehicle under repair; feedback on time and cost of the repair; and the like. In embodiments, the eyepiece may be able to provide a hands-free virtual assistant to the mechanic to assist them in the diagnosis and repair of the vehicle.

In an example, control aspects of the eyepiece may include combinations of the eyepiece entering an 'activity state', such as a 'shopping' activity mode, e.g. the user commanding the eyepiece into a store shopping mode, or the eyepiece sensing it is in proximity to a shopping area, perhaps even a shopping area of interest to the wearer through a preference profile, which may have further been developed in part through self-monitoring and learning the wearer's shopping preferences. Continuing with this example, entering an activity state e.g. a shopping activity state, such as while driving in a car, may be combined with an object detector as a sensing input or sensing device, a head-mounted camera and/or eye-gaze detection system as a user action capture input, eye movement as a user movement or action for controlling or initiating commands, a 3D navigation interface as a command and control mode and/or interface in which the inputs can be reflected, an e-commerce application on-board the eyepiece as an application for coordinating command inputs and user interface, a navigation system controller to communicate or connect with external systems or devices, a vehicle navigation system as an external device to be controlled and/or interfaced with, an advertising facility as an external application for processing user actions with regard to an advertising database, bulls-eye or target tracking system as feedback to the wearer as to shopping opportunities within sight while driving, and the like. For instance, a wearer may enter a shopping district while driving their car, and the eyepiece, detecting the presence of the shopping district (e.g. through GPS, direct viewing targets through an integrated camera, and the like) may enter a 'shopping activity state' (such as enabled and/or approved by the wearer). The eyepiece may then detect a billboard, storefront, and the like with an object detector that locates a shopping opportunity, such as through a head-mounted camera. Further, an eye-gaze detection system on the eyepiece may monitor where the wearer is looking, and possibly highlight information about a target at the location of the wearer's gaze, such as sale items or specials currently available in a store. Eye movement of the wearer may also be tracked, such as for changing targets of interest, or for command inputs (e.g. a quick nod indicating a selection command, a downward eye movement indicating a command for additional information, and the like). For example, an iris or a retina of a user may be tracked to provide a control input. The eyepiece may invoke a 3D navigation interface projection to assist in providing the wearer information associated with their surroundings, and an e-commerce application for coordinating the shopping activity state, such as taking inputs from the wearer, providing outputs to the 3D navigation interface, interfacing with external devices and applications, and the like. The eyepiece may for instance utilize a navigation system controller to interface with a vehicle navigation system, and thus may include the vehicle navigation system into the shopping experience. Alternately, the eyepiece may use its own navigation system, such as in place of the vehicle system or to augment it, such as when the wearer gets out of the car and wishes to have walking directions provided to them. As part of the shopping activity state, the eyepiece may interface with an external advertising facility, such as to provide current deals, specials, pop-up ads for surrounding merchants, and the like. The external advertising facility may also be in connection with third-party advertisers, publishers, merchant support facilities, and the like, that may contribute to information provided to the wearer. In embodiments, the wearer, through entering an activity state, may be provided feedback associated with the activity state, such as for a shopping activity state being supplied feedback in the form of information associated with an identified target.

In an example, control aspects of the eyepiece may include combinations of email reception as a triggering event, inertial movement tracking as a user action capture input device, drag-and-drop with fingers and swipe movements as user movements or actions for controlling or initiating commands, navigable lists as a command and control interface in which the inputs can be reflected, information conveying as a type of application on the eyepiece that can use commands and respond to inputs, a payment system as a communication or connection from the on-eyepiece interface to external systems and devices, iris capture and recognition system as an external application for external systems and devices, and the like. For instance, a wearer may receive a bill via an email, and the email may come in to the eyepiece as an 'event' to the wearer, such as to trigger an operations mode of the eyepiece, with a visual and/or audible alert, to initiate an application on the eyepiece, and the like. The wearer may be able to react to the email event through a plurality of control mechanisms, such as the wearer 'drag and dropping', swiping, and the like with their fingers and hands through a hand gesture interface (e.g. through a camera and hand gesture application on-board the eyepiece, where the wearer drags the email or information within the email into a file, an application, another email, and the like). The wearer may call up navigable lists of bills to pay and the like. The user may convey the information from the email (e.g. billing information, account number, billed amount, and the like) through an eyepiece application to external systems and devices, such as a payment system for paying the bill. In embodiments, the eyepiece and/or payment system may require identification verification, such as through biometric identity verification e.g. fingerprint capture, iris capture recognition, and the like.

In an example, control aspects of the eyepiece may include combinations of using an inertial user interface as a user action capture input device to provide instruction through the eyepiece to an external display device. For instance, the wearer may wish to provide instruction to a group of individuals from a presentation available through the facilities of the eyepiece. The wearer may be aided though the use of a physical 3D or 2D mouse (e.g. with inertial motion sensor, MEMS inertial sensor, ultrasonic 3D motion sensor, accelerometer, and the like), a virtual mouse, a virtual touch screen, a virtual keyboard, and the like to provide an interface for manipulating content in the presentation. The presentation may be viewable to and manipulated though the eyepiece, but also exported in real-time, such as to an external router that is connected to an external display device (e.g. computer monitor, projector, video screen, TV screen, and the like). As such, the eyepiece may provide a way for the wearer to have others view what the wearer sees through the eyepiece and as controlled through the control facilities of the eyepiece, allowing the wearer to export the multimedia event enabled through the eyepiece to other non-eyepiece wearers.

In an example, control aspects of the eyepiece may include combinations of using an events/data feed and sensing inputs/sensing devices, such as where a security event plus an acoustic sensor may be implemented. There may be a security alert sent to a soldier and an acoustic sensor is utilized as an input device to monitor voice content in the surrounding environment, directionality of gunfire, and the like. For instance, a security alert is broadcast to all military personnel in a specific area, and with the warning, the eyepiece activates an application that monitors an embedded acoustic sensor array that analyzes loud sounds to identify the type of source for the sound, and direction from which the sound came. In embodiments, other events and/or data feeds, sensing inputs and/or sensing devices, and the like, as described herein, may also be applied.

In an example, control aspects of the eyepiece may include combinations of using an events/data feed and user action capture inputs/devices, such as for a request for an input plus use of a camera. A soldier may be in a location of interest and is sent a request for photos or video from their location, such as where the request is accompanied with instructions for what to photograph. For instance, the soldier is at a checkpoint, and at some central command post it is determined that an individual on interest may attempt to cross the checkpoint. Central command may then provide instructions to eyepiece users in proximity to the checkpoint to record and upload images and video, which may in embodiments be performed automatically without the soldier needing to manually turn on the camera. In embodiments, other events and/or data feeds, user action capture inputs and/or devices, and the like, as described herein, may also be applied.

In an example, control aspects of the eyepiece may include combinations of using an events/data feed and user movements or actions for controlling or initiating commands, such as when a soldier is entering an 'activity state' and they use a hand gesture for control. A soldier may be put in an activity state of readiness to engage the enemy, and the soldier uses hand gestures to silently command the eyepiece within an engagement command and control environment. For instance, the soldier may suddenly enter an enemy area as determined by new intelligence received that places the eyepiece in a heightened alert state. In this state it may be a requirement that silence may be required, and so the eyepiece transitions to a hand gesture command mode. In embodiments, other events and/or data feeds, user movements or actions for controlling or initiating commands, and the like, as described herein, may also be applied.

In an example, control aspects of the eyepiece may include combinations of using an events/data feed and command/control modes and interfaces in which the inputs can be reflected, such as entering a type of environment and the user of a virtual touch screen. A soldier may enter a weapons system area, and a virtual touch screen is made available to the wearer for at least a portion of the control of the weapons system. For instance, the soldier enters a weapons vehicle, and the eyepiece detecting the presence of the weapons system, and that the soldier is authorized to use the weapon, brings up a virtual fire control interface with virtual touch screen. In embodiments, other events and/or data feeds, command and/or control modes and interfaces in which the inputs can be reflected, and the like, as described herein, may also be applied.

In an example, control aspects of the eyepiece may include combinations of using an events/data feed and applications on platform that can use commands/respond to inputs, such as for a safety event in combination with easy access to information for pilots. A military pilot (or someone responsible for the flight checkout of a pilotless aircraft) may receive a safety event notification as they approach an aircraft prior to the aircraft taking off, and an application is brought up to walk them through the pre-flight checkout. For instance, a drone specialist approaches a drone to prepare it for launch, and an interactive checkout procedure is displayed to the soldier by the eyepiece. In addition, a communications channel may be opened to the pilot of the drone so they are included in the pre-flight checkout. In embodiments, other events and/or data feeds, applications on platform that can use commands and/or respond to inputs, and the like, as described herein, may also be applied.

In an example, control aspects of the eyepiece may include combinations of using an events/data feed and a communication or connection from the on-platform interface to external systems and devices, such as the soldier entering a location and a graphical user interface (GUI). A soldier may enter a location where they are required to interact with external devices, and where the external device is interfaced through the GIU. For instance, a soldier gets in a military transport, and the soldier is presented with a GUI that opens up an interactive interface that instructs the soldier on what they need to do during different phases of the transport. In embodiments, other events and/or data feeds, communication or connection from the on-platform interface to external systems and devices, and the like, as described herein, may also be applied.

In an example, control aspects of the eyepiece may include combinations of using an events/data feed and a useful external device to be controlled, such as for an instruction provided and a weapon system. A soldier may be provided instructions, or a feed of instructions, where at least one instruction pertains to the control of an external weapons system. For instance, a soldier may be operating a piece of artillery, and the eyepiece is providing them not only performance and procedural information in association with the weapon, but also provides a feed of instructions, corrections, and the like, associated with targeting. In embodiments, other events and/or data feeds, useful external devices to be controlled, and the like, as described herein, may also be applied.

In an example, control aspects of the eyepiece may include combinations of using an events/data feed and an application for a useful external device, such as in a security event/feed and biometrics capture/recognition. A soldier may be sent a security event notification through (such as through a security feed) to capture biometrics (fingerprints, iris scan, walking gait profile) of certain individuals, where the biometrics are stored, evaluated, analyzed, and the like, through an external biometrics application (such as served from a secure military network-based server/cloud). In embodiments, other events and/or data feeds, applications for external devices, and the like, as described herein, may also be applied.

In an example, control aspects of the eyepiece may include combinations of using an events/data feed and feedback to a soldier related to the external devices and applications, such as entering an activity state and the soldier being provided a display of information. A soldier may place the eyepiece into an activity state such as for military staging, readiness, action, debrief, and the like, and as feedback to being placed into the activity state the soldier receives a display of information pertaining to the entered state. For instance, a soldier enters into a staging state for a mission, where the eyepiece fetches information from a remote server as part of the tasks the soldier has to complete during staging, including securing equipment, additional training, and the like. In embodiments, other events and/or data feeds, feedback related to external devices and/or external applications, and the like, as described herein, may also be applied.

In an example, control aspects of the eyepiece may include combinations of using sensing inputs/sensing devices and user action capture inputs/devices, such as with an inertial motion sensor and head tracking system. The head motion of a soldier may be tracked through inertial motion sensor(s) in the eyepiece, such as for nod control of the eyepiece, view direction sensing for the eyepiece, and the like. For instance, the soldier may be a targeting a weapon system, and the eyepiece senses the gaze direction of the soldier's head through the inertial motion sensor(s) to provide continuous targeting of the weapon. Further, the weapon system may move continuously in response to the soldier's gaze direction, and so be continuously ready to fire on the target. In embodiments, other sensing inputs and/or sensing devices, user action capture inputs and/or devices, and the like, as described herein, may also be applied.

In an example, control aspects of the eyepiece may include combinations of using sensing inputs/sensing devices and user movements or actions for controlling or initiating commands, such as with an optical sensor and an eye shut, blink, and the like movement. The state of the soldier's eye may be sensed by an optical sensor that is included in the optical chain of the eyepiece, such as for using eye movement for control of the eyepiece. For instance, the soldier may be aiming their rifle, where the rifle has the capability to be fired through control commands from the eyepiece (such as in the case of a sniper, where commanding through the eyepiece may decrease the errors in targeting due to pulling the trigger manually). The soldier may then fire the weapon through a command initiated by the optical sensor detecting a predetermined eye movement, such as in a command profile kept on the eyepiece. In embodiments, other sensing inputs and/or sensing devices, user movements or actions for controlling or initiating commands, and the like, as described herein, may also be applied.

In an example, control aspects of the eyepiece may include combinations of using sensing inputs/sensing devices and command/control modes and interfaces in which the inputs can be reflected, such as with a proximity sensor and robotic control interface. A proximity sensor integrated into the eyepiece may be used to sense the soldier's proximity to a robotic control interface in order to activate and enable the use of the robotics. For instance, a soldier walks up to a bomb-detecting robot, and the robot automatically activates and initializes configuration for this particular soldier (e.g. configuring for the preferences of the soldier). In embodiments, other sensing inputs and/or sensing devices, command and/or control modes and interfaces in which the inputs can be reflected, and the like, as described herein, may also be applied.

In an example, control aspects of the eyepiece may include combinations of using sensing inputs/sensing devices and applications on platform that can use commands/respond to inputs, such as with an audio sensor and music/sound application. An audio sensor may monitor the ambient sound and initiate and/or adjust the volume for music, ambient sound, sound cancelling, and the like, to help counter an undesirable ambient sound. For instance, a soldier is loaded onto a transport and the engines of the transport are initially off. At this time the soldier may have no other duties except to rest, so they initiate music to help them rest. When the engines of the transport come on the music/sound application adjusts the volume and/or initiates additional sound cancelling audio in order to help keep the music input the same as before the engines started up. In embodiments, other sensing inputs and/or sensing devices, applications on platform that can use commands and/or respond to inputs, and the like, as described herein, may also be applied.

In an example, control aspects of the eyepiece may include combinations of using sensing inputs/sensing devices and communication or connection from the on-platform interface to external systems and devices, such as with a passive IR proximity sensor and external digital signal processor. A soldier may be monitoring a night scene with the passive IR proximity sensor, the sensor indicates a motion, and the eyepiece initiates a connection to an external digital signal processor for aiding in identifying the target from the proximity sensor data. Further, an IR imaging camera may be initiated to contribute additional data to the digital signal processor. In embodiments, other sensing inputs and/or sensing devices, communication or connection from the on-platform interface to external systems and devices, and the like, as described herein, may also be applied.

In an example, control aspects of the eyepiece may include combinations of using sensing inputs/sensing devices and useful external devices to be controlled, such as with an acoustic sensor and a weapons system, where an eyepiece being worn by a soldier senses a loud sound, such as may be an explosion or gun fire, and where the eyepiece then initiates the control of a weapons system for possible action against a target associated with the creation of the loud sound. For instance, a soldier is on guard duty, and gunfire is heard. The eyepiece may be able to detect the direction of the gunshot, and direct the soldier to the position from which the gunshot was made. In embodiments, other sensing inputs and/or sensing devices, useful external devices to be controlled, and the like, as described herein, may also be applied.

In an example, control aspects of the eyepiece may include combinations of using sensing inputs/sensing devices and applications for those useful external devices, such as with a camera and external application for instructions. The camera embedded in a soldier's eyepiece may view a target icon indicating that instructions are available, and the eyepiece accessing the external application for instructions. For instance, a soldier is delivered to a staging area, and upon entry the eyepiece camera views the icon, accesses the instructions externally, and provides the soldier with the instructions for what to do, where all the steps may be automatic so that the instructions are provided without the soldier being aware of the icon. In embodiments, other sensing inputs and/or sensing devices, applications for external devices, and the like, as described herein, may also be applied.

In an example, control aspects of the eyepiece may include combinations of using sensing inputs/sensing devices and feedback to user related to the external devices and applications, such as with a GPS sensor and a visual display from a remote application. The soldier may have an embedded GPS sensor that sends/streams location coordinates to a remote location facility/application that sends/streams a visual display of the surrounding physical environment to the eyepiece for display. For instance, a soldier may be constantly viewing the surrounding environment though the eyepiece, and by way of the embedded GPS sensor, is continuously streamed a visual display overlay that allows for the soldier to have an augmented reality view of the surrounding environment, even as the change locations. In embodiments, other sensing inputs and/or sensing devices, feedback related to external devices and/or external applications, and the like, as described herein, may also be applied.

In an example, control aspects of the eyepiece may include combinations of using user action capture inputs/devices and user movements or actions for controlling or initiating commands, such as with a body movement sensor (e.g. kinetic sensor) and an arm motion. The soldier may have body movement sensors attached to their arms, where the motion of their arms convey a command. For instance, a soldier may have kinetic sensors on their arms, and the motion of their arms are duplicated in an aircraft landing lighting system, such that the lights normally held by personnel aiding in a landing may be made to be larger and more visible. In embodiments, other user action capture inputs and/or devices, user movements or actions for controlling or initiating commands, and the like, as described herein, may also be applied.

In an example, control aspects of the eyepiece may include combinations of using user action capture inputs/devices and command/control modes and interfaces in which the inputs can be reflected, such as wearable sensor sets and a predictive learning-based user interface. A soldier may wear a sensor set where the data from the sensor set is continuously collected and fed to a machine-learning facility through a learning-based user interface, where the soldier may be able to accept, reject, modify, and the like, the learning from their motions and behaviors. For instance, a soldier may perform the same tasks in generally the same physical manner every Monday morning, and the machine-learning facility may establish a learned routine that it provides to the soldier on subsequent Monday mornings, such as a reminder to clean certain equipment, fill out certain forms, play certain music, meet with certain people, and the like. Further, the soldier may be able to modify the outcome of the learning through direct edits to the routine, such as in a learned behavior profile. In embodiments, other user action capture inputs and/or devices, command and/or control modes and interfaces in which the inputs can be reflected, and the like, as described herein, may also be applied.

In an example, control aspects of the eyepiece may include combinations of using user action capture inputs/devices and applications on platform that can use commands/respond to inputs, such as a finger-following camera and video application. A soldier may be able to control the direction that the eyepiece embedded camera is taking video through a resident video application. For instance, a soldier may be viewing a battle scene where they have need to be gazing in one direction, such as being watchful for new developments in the engagement, while filming in a different direction, such as the current point of engagement. In embodiments, other user action capture inputs and/or devices, applications on platform that can use commands and/or respond to inputs, and the like, as described herein, may also be applied.

In an example, control aspects of the eyepiece may include combinations of using user action capture inputs/devices and communication or connection from the on-platform interface to external systems and devices, such as a microphone and voice recognition input plus a steering wheel control interface. The soldier may be able to change aspects of the handling of a vehicle through voice commands received through the eyepiece and delivered to a vehicle's steering wheel control interface (such as through radio communications between the eyepiece and the steering wheel control interface). For instance, a soldier is driving a vehicle on a road, and so the vehicle has certain handling capabilities that are ideal for the road. But the vehicle also has other modes for diving under different conditions, such as off-road, in snow, in mud, in heavy rain, while in pursuit of another vehicle, and the like. In this instance, the soldier may be able to change the mode through voice command as the vehicle changes driving conditions. In embodiments, other user action capture inputs and/or devices, communication or connection from the on-platform interface to external systems and devices, and the like, as described herein, may also be applied.

In an example, control aspects of the eyepiece may include combinations of using user action capture inputs/devices and useful external devices to be controlled, such as a microphone and voice recognition input plus an automotive dashboard interface device. The soldier may use voice commands to control various devices associated with the dashboard of a vehicle, such as heating and ventilation, radio, music, lighting, trip computer, and the like. For instance, a soldier may be driving a vehicle on a mission, across rough terrain, such that they cannot let go of the steering wheel with either hand in order to manually control a vehicle dashboard device. In this instance, the soldier may be able to control the vehicle dashboard device through voice controls to the eyepiece. Voice commands through the eyepiece may be especially advantageous, such as opposed to voice control through a dashboard microphone system, because the military vehicle may be immersed in a very loud acoustic environment, and so using the microphone in the eyepiece may give substantially improved performance under such conditions. In embodiments, other user action capture inputs and/or devices, useful external devices to be controlled, and the like, as described herein, may also be applied.

In an example, control aspects of the eyepiece may include combinations of using user action capture inputs/devices and applications for useful external devices, such as with a joystick device and external entertainment application. A soldier may have access to a gaming joystick controller and is able to play a game through an external entertainment application, such as a multi-player game hosted on a network server. For instance, the soldier may be experiencing down time during a deployment, and on base they have access to a joystick device that interfaces to the eyepiece, and the eyepiece in turn to the external entertainment application. In embodiments, the soldier may be networked together with other military personnel across the network. The soldier may have stored preferences, a profile, and the like, associated with the game play. The external entertainment application may manage the game play of the soldier, such as in terms of their deployment, current state of readiness, required state of readiness, past history, ability level, command position, rank, geographic location, future deployment, and the like. In embodiments, other user action capture inputs and/or devices, applications for external devices, and the like, as described herein, may also be applied.

In an example, control aspects of the eyepiece may include combinations of using user action capture inputs/devices and feedback to the user related to external devices and applications, such as with an activity determination system and tonal output or sound warning. The soldier may have access to the activity determination system through the eyepiece to monitor and determine the soldier's state of activity, such as in extreme activity, at rest, bored, anxious, in exercise, and the like, and where the eyepiece may provide forms of tonal output or sound warning when conditions go out of limits in any way, such as pre-set, learned, as typical, and the like. For instance, the soldier may be monitored for current state of health during combat, and where the soldier and/or another individual (e.g. medic, hospital personnel, another member of the soldier's team, a command center, and the like) are provided an audible signal when health conditions enter a dangerous level, such as indicating that the soldier has been hurt in battle. As such, others may be alerted to the soldier's injuries, and would be able to attend to the injuries in a more time effective manner. In embodiments, other user action capture inputs and/or devices, feedback related to external devices and/or external applications, and the like, as described herein, may also be applied.

In an example, control aspects of the eyepiece may include combinations of using user movements or actions for controlling or initiating commands plus command/control modes and interfaces in which the inputs can be reflected, such as a clenched fist and Navigable list. A soldier may bring up a navigable list as projected content on the eyepiece display with a gesture such as a clenched fist, and the like. For instance, the eyepiece camera may be able to view the soldier's hand gesture(s), recognize and identify the hand gesture(s), and execute the command in terms of a pre-determined gesture-to-command database. In embodiments, hand gestures may include gestures of the hand, finger, arm, leg, and the like. In embodiments, other user movements or actions for controlling or initiating commands, command and/or control modes and interfaces in which the inputs can be reflected, and the like, as described herein, may also be applied.

In an example, control aspects of the eyepiece may include combinations of using user movements or actions for controlling or initiating commands plus applications on platform that can use commands/respond to inputs, such as a head nod and information display. The soldier may bring up an information display application with a gesture such as a headshake, arm motion, leg motion, eye motion, and the like. For instance, the soldier may wish to access an application, database, network connection, and the like, through the eyepiece, and is able to bring up a display application as part of a graphical user interface with the nod of their head (such as sensed though motion detectors in the eyepiece, on the soldier's head, on the soldier's helmet, and the like. In embodiments, other user movements or actions for controlling or initiating commands, applications on platform that can use commands and/or respond to inputs, and the like, as described herein, may also be applied.

In an example, control aspects of the eyepiece may include combinations of using user movements or actions for controlling or initiating commands plus communication or connection from the on-platform interface to external systems and devices, such as the blink of an eye and through an API to external applications. The soldier may be able to bring up an application program interface to access external applications, such as with the blink of an eye, a nod of the head, the movement of an arm or leg, and the like. For instance, the soldier may be able to access an external application through an API embedded in an eyepiece facility, and do so with the blink of an eye, such as detected though an optical monitoring capability through the optics system of the eyepiece. In embodiments, other user movements or actions for controlling or initiating commands, communication or connection from the on-platform interface to external systems and devices, and the like, as described herein, may also be applied.

In an example, control aspects of the eyepiece may include combinations of using user movements or actions for controlling or initiating commands and external devices to be controlled, such as through the tap of a foot accessing an external range finder device. A soldier may have a sensor such as a kinetic sensor on their shoe that will detect the motion of the soldier's foot, and the soldier uses a foot motion such as a tap of their foot to use an external range finder device to determine the range to an object such an enemy target. For instance, the soldier may be targeting a weapon system, and using both hands in the process. In this instance, commanding by way of a foot action through the eyepiece may allow for 'hands free' commanding. In embodiments, other user movements or actions for controlling or initiating commands, useful external devices to be controlled, and the like, as described herein, may also be applied.

In an example, control aspects of the eyepiece may include combinations of using user movements or actions for controlling or initiating commands plus applications for those useful external devices, such as making a symbol with a hand and an information conveying application. The soldier may utilize a hand formed symbol to trigger information shared through an external information conveying application, such as an external information feed, a photo/video sharing application, a text application, and the like. For instance, a soldier uses a hand signal to turn on the embedded camera and share the video stream with another person, to storage, and the like. In embodiments, other user movements or actions for controlling or initiating commands, applications for external devices, and the like, as described herein, may also be applied.

In an example, control aspects of the eyepiece may include combinations of using user movements or actions for controlling or initiating commands plus feedback to soldier as related to an external device and application, such as a headshake plus an audible alert. The soldier may be wearing an eyepiece equipped with an accelerometer (or like capable sensor for detecting g-force headshake), where when the soldier experiences a g-force headshake that is at a dangerously high level, an audible alert is sounded as feedback to the user, such as determined either as a part of on- or off-eyepiece applications. Further, the output of the accelerometer may be recorded and stored for analysis. For instance, the soldier may experience a g-force headshake from a proximate explosion, and the eyepiece may sense and record the sensor data associated with the headshake. Further, headshakes of a dangerous level may trigger automatic actions by the eyepiece, such as transmitting an alert to other soldiers and/or to a command center, begin monitoring and/or transmitting the health of the soldier from other body mounted sensors, provide audible instructions to the soldier related to their potential injuries, and the like. In embodiments, other user movements or actions for controlling or initiating commands, feedback related to external devices and/or external applications, and the like, as described herein, may also be applied.

In an example, control aspects of the eyepiece may include combinations of using command/control modes and interfaces in which the inputs can be reflected plus applications on platform that can use commands/respond to inputs, such as a graphical user interface plus various applications resident on the eyepiece. The eyepiece may provide a graphical user interface to the soldier and applications presented for selection. For instance, the soldier may have a graphical user interface projected by the eyepiece that provides different domains of application, such as military, personal, civil, and the like. In embodiments, other command and/or control modes and interfaces in which the inputs can be reflected, applications on platform that can use commands and/or respond to inputs, and the like, as described herein, may also be applied.

In an example, control aspects of the eyepiece may include combinations of using command/control modes and interfaces in which the inputs can be reflected plus a communication or connection from the on-platform interface to external systems and devices, such as a 3D navigation eyepiece interface plus navigation system controller interface to external system. The eyepiece may enter a navigation mode and connect to an external system through a navigation system controller interface. For instance, a soldier is in military maneuvers and brings up a preloaded 3D image of the surrounding terrain through the eyepiece navigation mode, and the eyepiece automatically connects to the external system for updates, current objects of interest such as overlaid by satellite images, and the like. In embodiments, other command and/or control modes and interfaces in which the inputs can be reflected, communication or connection from the on-platform interface to external systems and devices, and the like, as described herein, may also be applied.

In an example, control aspects of the eyepiece may include combinations of using command/control modes and interfaces in which the inputs can be reflected plus an external device to be controlled, such as an augmented reality interface plus external tracking device. The soldier's eyepiece may enter into an augmented reality mode and interface with an external tracking device to overlay information pertaining to the location of a traced object or person with an augmented reality display. For instance, the augmented reality mode may include a 3D map, and a person's location as determined by the external tracking device may be overlaid onto the map, and show a trail as the tracked person moves. In embodiments, other command and/or control modes and interfaces in which the inputs can be reflected, useful external devices to be controlled, and the like, as described herein, may also be applied.

In an example, control aspects of the eyepiece may include combinations of using command/control modes and interfaces in which the inputs can be reflected plus applications for those external devices, such as semi-opaque display mode plus simulation application. The eyepiece may be placed into a semi-opaque display mode to enhance the display of a simulation display application to the solder. For instance, the soldier is preparing for a mission, and before entering the field the soldier is provided a simulation of the mission environment, and since there is no real need for the user to see the real environment around them during the simulation, the eyepiece places the eyepiece into a semi-opaque display mode. In embodiments, other command and/or control modes and interfaces in which the inputs can be reflected, applications for external devices, and the like, as described herein, may also be applied.

In an example, control aspects of the eyepiece may include combinations of using command/control modes and interfaces in which the inputs can be reflected plus feedback to user related to the external devices and applications, such as an auditory command interface plus a tonal output feedback. The soldier may place the eyepiece into an auditory command interface mode and the eyepiece responds back with a tonal output as feedback from the system that the eyepiece is ready to receive the auditory commands. For instance, the auditory command interface may include at least portions of the auditory command interface in an external location, such as out on a network, and the tone is provided once the entire system is ready to accept auditory commands. In embodiments, other command and/or control modes and interfaces in which the inputs can be reflected, feedback related to external devices and/or external applications, and the like, as described herein, may also be applied.

In an example, control aspects of the eyepiece may include combinations of using applications on platform that can use commands/respond to inputs plus Communication or connection from the on-platform interface to external systems and devices, such as a communication application plus a network router, where the soldier is able to open up a communications application, and the eyepiece automatically searches for a network router for connectivity to a network utility. For instance, a soldier is in the field with their unit, and a new base camp is established. The soldier's eyepiece may be able to connect into the secure wireless connection once communications facilities have been established. Further, the eyepiece may alert the soldier once communications facilities have been established, even if the soldier has not yet attempted communications. In embodiments, other applications on platform that can use commands and/or respond to inputs, communication or connection from the on-platform interface to external systems and devices, and the like, as described herein, may also be applied.

In an example, control aspects of the eyepiece may include combinations of using applications on platform that can use commands/respond to inputs plus useful external devices to be controlled, such as a video application plus and external camera. The soldier may interface with deployed cameras, such as for surveillance in the field. For instance, mobile deployable cameras may be dropped from an aircraft, and the soldier then has connection to the cameras through the eyepiece video application. In embodiments, other applications on platform that can use commands and/or respond to inputs, useful external devices to be controlled, and the like, as described herein, may also be applied.

In an example, control aspects of the eyepiece may include combinations of using applications on platform that can use commands/respond to inputs plus applications for external devices, such as an on-eyepiece search application plus an external search application. A search application on the eyepiece may be augmented with an external search application. For instance, a soldier may be searching for the identity of an individual that is being questioned, and when the on-eyepiece search results in no find, the eyepiece connects with an external search facility. In embodiments, other applications on platform that can use commands and/or respond to inputs, applications for external devices, and the like, as described herein, may also be applied.

In an example, control aspects of the eyepiece may include combinations of using applications on platform that can use commands/respond to inputs plus feedback to the soldier as related to the external devices and applications, such as an entertainment application plus a performance indicator feedback. The entertainment application may be used as a resting mechanism for a soldier that needs to rest but may be otherwise anxious, and performance feedback is designed for the soldier in given environments, such as in a deployment when they need to rest but remain sharp, during down time when attentiveness is declining and needs to be brought back up, and the like. For instance, a soldier may be on a transport and about to enter an engagement. In this instance, an entertainment application may be an action-thinking game to heighten attention and aggressiveness, and where the performance indicator feedback is designed to maximize the soldier's desire to perform and to think through problems in a quick and efficient manner. In embodiments, other applications on platform that can use commands and/or respond to inputs, feedback related to external devices and/or external applications, and the like, as described herein, may also be applied.

In an example, control aspects of the eyepiece may include combinations of using a communication or connection from the on-platform interface to external systems and devices plus external devices to be controlled, such as an on-eyepiece processor interface to external facilities plus an external projector. The eyepiece processor may be able to connect to an external projector so that others may view the content available to the eyepiece. For instance, a soldier may be in the field and has access to content that they need to share with others who are not wearing an eyepiece, such as individuals not in the military. In this instance, the soldier's eyepiece may be able to interface with an external projector, and feed content from the eyepiece to the projector. In embodiments, the projector may be a pocket projector, a projector in a vehicle, in a conference room, remotely located, and the like. In embodiments the projector may also be integrated into the eyepiece, such that the content may be externally projected from the integrated projector. In embodiments, other communication or connection from the on-platform interface to external systems and devices, useful external devices to be controlled, and the like, as described herein, may also be applied.

In an example, control aspects of the eyepiece may include combinations of using a communication or connection from the on-platform interface to external systems and devices plus an application for external devices, such as an audio system controller interface plus an external sound system. The soldier may be able to connect the audio portion of the eyepiece facilities (e.g. music, audio playback, audio network files, and the like) to an external sound system. For instance, the soldier may be able to patch a communications being received by the eyepiece to a vehicle sound system so that others can hear. In embodiments, other communication or connection from the on-platform interface to external systems and devices, applications for external devices, and the like, as described herein, may also be applied.

In an example, control aspects of the eyepiece may include combinations of using a communication or connection from the on-platform interface to external systems and devices plus feedback to a soldier related to the external devices and applications, such as a stepper controller interface plus status feedback. The soldier may have access and control of a mechanism with digital stepper control through a stepper controller interface, where the mechanism provides feedback to the soldier as to the state of the mechanism. For instance, a solder working on removing a roadblock may have a lift mechanism on their vehicle, and the soldier may be able to directly interface with the lift mechanism through the eyepiece. In embodiments, other communication or connection from the on-platform interface to external systems and devices, feedback related to external devices and/or external applications, and the like, as described herein, may also be applied.

In an example, control aspects of the eyepiece may include combinations of using external devices to be controlled plus applications for those external devices, such as storage-enabled devices plus automatic backup applications. The soldier in the field may be provided data storage facilities and associated automatic backup applications. For instance, the storage facility may be located in a military vehicle, so that data may be backed up from a plurality of soldier's eyepieces to the vehicle, especially when a network link is not available to download to a remote backup site. A storage facility may be associated with an encampment, with a subset of soldiers in the field (e.g. in a pack), located on the soldier themselves, and the like. In embodiments, a local storage facility may upload the backup when network service connections become available. In embodiments, other useful external devices to be controlled, applications for external devices, and the like, as described herein, may also be applied.

In an example, control aspects of the eyepiece may include combinations of using external devices to be controlled plus feedback to a soldier related to external devices and applications, such as an external payment system plus feedback from the system. The soldier may have access to a military managed payment system, and where that system provides feedback to the soldier (e.g. receipts, account balance, account activity, and the like). For instance, the soldier may make payments to a vendor via the eyepiece where the eyepiece and external payment system exchange data, authorization, funds, and the like, and the payment system provides feedback data to the soldier. In embodiments, other useful external devices to be controlled, feedback related to external devices and/or external applications, and the like, as described herein, may also be applied.

In an example, control aspects of the eyepiece may include combinations of using applications for external devices plus feedback to a soldier related to external devices and applications, such as an information display from an external 3D mapping-rendering facility plus feedback along with the information display. The soldier may be able to have 3D mapping information data displayed through the eyepiece, where the mapping facility may provide feedback to the soldier, such as based on past information delivered, past information requested, requests from others in the area, based on changes associated with the geographical area, and the like. For instance, a soldier may be receiving a 3D map rendering from an external application, where the external application is also providing 3D map rendering to at least a second soldier in the same geographic area. The soldier may then receive feedback from the external facility related to the second soldier, such as their position depicted on the 3D map rendering, identity information, history of movement, and the like. In embodiments, other applications for external devices, feedback related to external devices and/or external applications, and the like, as described herein, may also be applied.

In embodiments, the eyepiece may provide a user with various forms of guidance in responding to medical situations. As a first example, the user may use the eyepiece for training purposes to simulate medical situations that may arise in combat, training, on or off duty and the like. The simulation may be geared towards a medical professional or non-medical personnel.

By way of example, a low level combat soldier may use the eyepiece to view a medical simulation as part of a training module to provide training for response to medical situations on the battlefield. The eyepiece may provide an augmented environment where the user views injuries overlaid on another solider to simulate those common or capable of being found on the battlefield. The soldier may then be prompted through a user interface to respond to the situation as presented. The user may be given step-by-step instructions of a course of action in providing emergency medical care on the field, or the user may carry out actions in response to the situation that are then corrected until the appropriate response is given.

Similarly, the eyepiece may provide a training environment for a medical professional. The eyepiece may present the user with a medical emergency or situation requiring a medical response for the purpose of training the medical professional. The eyepiece may play out common battle field scenarios for which the user must master appropriate responses and lifesaving techniques.

By way of example, the user may be presented with an augmented reality of a wounded soldier with a gunshot wound to the soldier's body. The medical professional may then act out the steps he feels to be the appropriate response for the situation, select steps through a user interface of the eyepiece that he feels are appropriate for the situation, input the steps into a user interface of the eyepiece, and the like. The user may act out the response through use of sensors and or an input device or he may input the steps of his response into a user interface via eye movements, hand gestures and the like. Similarly, he may select the appropriate steps as presented to him through the user interface via eye movements, hand gestures and the like. As actions are carried out and the user makes decisions about treatment, the user may be presented with additional guidance and instruction based on his performance. For example, if the user is presented with a soldier with a gunshot wound to the chest, and the user begins to lift the soldier to a dangerous position, the user may be given a warning or prompt to change his course of treatment. Alternatively, the user may be prompted with the correct steps in order to practice proper procedure. Further, the trainee may be presented with an example of a medical chart for the wounded soldier in the training situation where the user may have to base his decisions at least in part on what is contained in the medical chart. In various embodiments, the user's actions and performance may be recorded and or documented by the eyepiece for further critiquing and instruction after the training session has paused or otherwise stopped.

In embodiments, the eyepiece may provide a user with various forms of guidance in responding to actual medical situations in combat. By way of example, a non-trained soldier may be prompted with step-by-step lifesaving instructions for fellow soldiers in medical emergencies when a medic is not immediately present. When a fellow soldier is wounded, the user may input the type of injury, the eyepiece may detect the injury or a combination of these may occur. From there, the user may be provided with lifesaving instruction with which to treat the wounded soldier. Such instruction may be presented in the form of augmented reality in a stepwise process of instructions for the user. Further, the eyepiece may provide augmented visual aids to the user regarding location of vital organs near the wounded soldier's injury, an anatomical overlay of the soldier's body and the like. Further, the eyepiece may take video of the situation that is then sent back to a medic not in the field or on his way to the field, thereby allowing the medic to walk the untrained user through an appropriate lifesaving technique on the battlefield. Further, the wounded soldier's eyepiece may send vital information, such as information collected through integral or associated sensors, about the wounded soldier to the treating soldier's eyepiece to be sent to the medic or it may be sent directly to the medic in a remote location such that the treating soldier may provide the wounded solider with medical help based on the information gathered from the wounded soldier's eyepiece.

In other embodiments, when presented with a medical emergency on the battlefield, a trained medic may use the eyepiece to provide an anatomical overlay of the soldier's body so that he may respond more appropriately to the situation at hand. By way of example only and not to limit the present disclosure, if the wounded soldier is bleeding from a gunshot wound to the leg, the user may be presented with an augmented reality view of the soldier's arteries such that the user may determine whether an artery has been hit and how severe the wound may be. The user may be presented with the proper protocol via the eyepiece for the given wound so that he may check each step as he moves through treatment. Such protocol may also be presented to the user in an augmented reality, video, audio or other format. The eyepiece may provide the medic with protocols in the form of augmented reality instructions in a step-wise process. In embodiments, the user may also be presented with an augmented reality overlay of the wounded soldier's organs in order to guide the medic through any procedure such that the medic does not do additional harm to the soldier's organs during treatment. Further, the eyepiece may provide augmented visual aids to the user regarding location of vital organs near the wounded soldier's injury, an anatomical overlay of the soldier's body and the like.

In embodiments, the eyepiece may be used to scan the retina of the wounded soldier in order to pull up his medical chart on the battlefield. This may alert the medic to possible allergies to medication or other important issues that may provide a benefit during medical treatment.

Further, if the wounded soldier is wearing the eyepiece, the device may send information to the medic's glasses including the wounded soldier's heart rate, blood pressure, breathing stress, and the like. The eyepiece may also help the user observe the walking gait of a soldier to determine if the soldier has a head injury and they may help the user determine the location of bleeding or an injury. Such information may provide the user with information of possible medical treatment, and in embodiments, the proper protocol or a selection of protocols may be displayed to the user to help him in treating the patient.

In other embodiments, the eyepiece may allow the user to monitor other symptoms of the patient for a mental health status check. Similarly, the user can check to determine if the patient is exhibiting rapid eye movement and further may use the eyepiece to provide the patient with calming treatment such as providing the patient with eye movement exercises, breathing exercises, and the like. Further, the medic may be provided with information regarding the wounded soldier's vital signs and health data as it is collected from the wounded soldier's eyepiece and sent to the medic's eyepiece. This may provide the medic with real time data from the wounded soldier without having to determine such data on his own for example by taking the wounded soldier's blood pressure.

In various embodiments, the user may be provided with alerts from the eyepiece that tells him how far away an air or ground rescue is from his location on the battlefield. This may provide a medic with important information and alert him to whether certain procedures should or must be attempted given the time available in the situation, and it may provide an injured soldier with comfort knowing help is on the way or alert him that he may need other sources of help.

In other embodiments, the user may be provided alerts of his own vital signs if a problem is detected. For example, a soldier may be alerted if his blood pressure is too high, thereby alerting him that he must take medication or remove himself from combat if possible to return his blood pressure to a safe level. Also, the user may be alerted of other such personal data such as his pupil size, heart rate, waking gait change and the like in order to determine if the user is experiencing a medical problem. In other embodiments, a user's eyepiece may also alert medical personnel in another location of the user's medical status in order to send help for the user whether or not he knows he requires such help. Further, general data may be aggregated from multiple eyepieces in order to provide the commanding office with detailed information on his wounded soldiers, how many soldiers he has in combat, how many of those are wounded, and the like.

In various embodiments, a trained medical professional may use the eyepiece in medical responses out of combat as well. Such eyepiece may have similar uses as described above on or off the home base of the medic but outside of combat situations. In this way, the eyepiece may provide a user with a means to gain augmented reality assistance during a medical procedure, to document a medical procedure, perform a medical procedure at the guidance of a remote commanding officer via video and/or audio, and the like on or off a military base. This may provide assistance in a plurality of situations where the medic may need additional assistance. An example of this may occur when the medic is on duty on a training exercise, a calisthenics outing, a military hike and the like. Such assistance may be of importance when the medic is the only responder, when he is a new medic, approached with a new situation and the like.

In some embodiments, the eyepiece may provide user guidance in an environment related to a military transport plane. For example, the eyepiece may be used in such an environment when training, going into battle, on a reconnaissance or rescue mission, while moving equipment, performing maintenance on the plane and the like. Such use may be suited for personnel of various ranks and levels.

For illustrative purposes, a user may receive audio and visual information through the eyepiece while on the transport plane and going into a training exercise. The information may provide the user with details about the training mission such as the battle field conditions, weather conditions, mission instructions, map of the area and the like. The eyepiece may simulate actual battle scenarios to prepare the user for battle. The eyepiece may also record the user's responses and actions through various means. Such data gathering may allow the user to receive feedback about his performance. Further, the eyepiece may then change the simulation based on the results obtained during the training exercise to change the simulation while it is underway or to change future simulations for the user or various users.

In embodiments, the eyepiece may provide user guidance and or interaction on a military transport plane when going into battle. The user may receive audio and visual information about the mission as the user boards the plane. Check lists may be presented to the user for ensuring he has the appropriate materials and equipment of the mission. Further, instructions for securing equipment and proper use of safety harnesses may be presented along with information about the aircraft such as emergency exits, location of oxygen tanks, and safety devices. The user may be presented with instructions such as when to rest prior to the mission and have a drug administered for that purpose. The eyepiece may provide the user with noise cancellation for rest prior to mission, and then may alert the user when his rest is over and further mission preparation is to begin. Additional information may be provided such as a map of the battle area, number of vehicles and/or people on the field, weather conditions of the battle area and the like. The device may provide a link to other soldiers so that instructions and battle preparation may include soldier interaction where the commanding officer is heard by subordinates and the like. Further, information for each user may be formatted to suit his particular needs. For example, a commanding officer may receive higher level or more confidential information that may not be necessary to provide a lower ranking officer.

In embodiments, the user may use the eyepiece on a military transport plane in a reconnaissance or rescue mission where the eyepiece captures and stores various images and or video of places of interest as it flies over areas which may be used for gaining information about a potential ground battle area and the like. The eyepiece may be used to detect movement of people and vehicles on the ground and thereby detect enemy to be defeated or friendlies to be rescued or assisted. The eyepiece may provide the ability to apply tags to a map or images of areas flown over and searched giving a particular color coding for areas that have been searched or still need to be searched.

In embodiments, a user on a military transport plane may be provided with instructions and or a checklist for equipment to be stocked, the quantity and location to be moved and special handling instructions for various equipment. Alerts may be provided to the user for approaching vehicles as items are unloaded or loaded in order to ensure security.

For maintenance and safety of the military transport plane, the user may be provided with a preflight check for proper functioning of the aircraft. The pilot may be alerted if proper maintenance was not completed prior to mission. Further, the aircraft operators may be provided with a graphic overview or a list of the aircraft history to track the history of the aircraft maintenance.

In some embodiments, the eyepiece may provide user guidance in an environment related to a military fighter plane. For example, the eyepiece may be used in such an environment when training, going into battle, for maintenance and the like. Such use may be suited for personnel of various ranks and levels.

By way of example, a user may use the eyepiece for training for military fighter plane combat. The user may be presented with augmented reality situations that simulate combat situations in a particular military jet or plane. The user's responses and actions may be recorded and or analyzed to provide the user with additional information, critique and to alter training exercises based on past data.

In embodiments related to actual combat, the user may be presented with information showing him friendly and non-friendly aircraft surrounding and/or approaching him. The user may be presented information regarding the enemy aircraft such as top speed, maneuvering ability and missile range. In embodiments, the user may receive information relating to the presence of ground threats and may be alerted about the same. The eyepiece may sync to the user's aircraft and or aircraft instruments and gauges such that the pilot may see emergency alerts and additional information regarding the aircraft that may not normally be displayed in the cockpit. Further, the eyepiece may display the number of seconds to targeted area, the time to fire a missile or eject from the aircraft based on incoming threats. The eyepiece may suggest maneuvers for the pilot to preform based on the surrounding environment, potential threats and the like. In embodiments, the eyepiece may detect and display friendly aircraft even when such aircraft is in stealth mode.

In embodiments, the user may be provided with a preflight check for proper functioning of the fighter aircraft. The pilot may be alerted if proper routing maintenance was not completed prior to mission by linking with maintenance records, aircraft computers and otherwise. The eyepiece may allow the pilot to view history of the aircraft maintenance along with diagrams and schematics of the same.

In some embodiments, the eyepiece may provide user guidance in an environment related to a military helicopter. For example, the eyepiece may be used in such an environment when training, going into combat, for maintenance and the like. Such use may be suited for personnel of various ranks and levels.

By way of example, a user may use the eyepiece for training for military helicopter operation in combat or high stress situation. The user may be presented with augmented reality situations that simulate combat situations in a particular aircraft. The user's responses and actions may be recorded and or analyzed to provide the user with additional information, critique and to alter training exercises based on past data.

During training and/or combat a user's eyepiece may sync into the aircraft for alerts about the vital statistics and maintenance of the aircraft. The user may view program and safety procedures and emergency procedures for passengers as he boards the aircraft. Such procedures may show how to ride in the aircraft safely, how to operate the doors for entering and exiting the aircraft, the location of lifesaving equipment, among other information. In embodiments, the eyepiece may present the user with the location and/or position of threats such as those that could pose a danger to a helicopter during its typical flight. For example, the user may be presented with the location of low flying threats such as drones, other helicopters and the location of land threats. In embodiments, noise cancelling earphones and a multi-user user interface may be provided with the eyepiece allowing for communication during flight. In an event where the helicopter goes down, the user's eyepiece may transmit the location and helicopter information to a commanding officer and a rescue team. Further, use of night vision of the eyepiece during a low flying mission may enable a user to turn a high-powered helicopter spotlight off in order to search or find enemy without being detected.

In embodiments, and as described in various instances herein, the eyepiece may provide assistance in tracking the maintenance of the aircraft and to determine if proper routine maintenance has been performed. Further, and with other aircraft and vehicles mentioned herein, augmented reality may be used in the assistance of maintaining and working on the aircraft.

In some embodiments, the eyepiece may provide user guidance in an environment related to a military drone aircraft or robots. For example, the eyepiece may be used in such an environment in reconnaissance, capture and rescue missions, combat, in areas that pose particular danger to humans, and the like.

In embodiments, the eyepiece may provide video feed to the user regarding the drone's surrounding environment. Real time video may be displayed for up to the second information about various areas of interest. Gathering such information may provide a soldier with the knowledge of the number of enemy soldiers in the area, the layout of buildings and the like. Further, data may be gathered and sent to the eyepiece from the drone and or robot in order to gather intelligence on the location of persons of interest to be captured or rescued. By way of illustration, a user outside of a secure compound or bunker may use the drone and or robot to send back video or data feed to of the location, number and activity of persons in the secure compound in preparation of a capture or rescue.

In embodiments, use of the eyepiece with a drone and/or robot may allow a commanding officer to gather battlefield data during a mission to make plan changes and to give various instructions of the team depending on the data gathered. Further, the eyepiece and controls associated therewith may allow users to deploy weapons on the drone and/or robot via a user interface in the eyepiece. The data feed sent from the drone and/or robot may give the user information as to what weapons to deploy and when to deploy them.

In embodiments, the data gathered from the drone and/or robot may allow the user to get up close to potential hazardous situations. For example this may allow the user to investigate biological spills, bombs, alleyways, foxholes, and the like to provide the user with data of the situation and environment while keeping him out of direct harm's way.

In some embodiments, the eyepiece may provide user guidance in an environment related to a military ship at sea. For example, the eyepiece may be used in such an environment when training, going into battle, performing a search and rescue mission, performing disaster clean up, when performing maintenance and the like. Such use may be suited for personnel of various ranks and levels.

In embodiments, the eyepiece may be used in training to prepare users of various skill sets for performance of their job duties on the vessel. The training may include simulations testing the user's ability to navigate, control the ship and/or perform various tasks while in a combat situation, and the like. The user's responses and actions may be recorded and or analyzed to provide the user with additional information, critique and to alter training exercises based on past data.

In embodiments, the eyepiece may allow the user to view potential ship threats out on the horizon by providing him with an augmented reality view of the same. Such threats may be indicated by dots, graphics, or other means. Instructions may be sent to the user via the eyepiece regarding preparation for enemy engagement once the eyepiece detects a particular threat. Further, the user may view a map or video of the port where they will dock and be provided with enemy location. In embodiments, the eyepiece may allow the user to sync with the ship and/or weapon equipment to guide the user in the use of the equipment during battle. The user may be alerted by the eyepiece to where international and national water boundaries lie.

In embodiments where search and rescue is needed, the eyepiece may provide for tracking the current and/or for tagging the area of water recently searched. In embodiments where the current is tracked, this may provide the user information conveying the potential location or changed location of persons of interest to be rescued. Similarly, the eyepiece may be used in environments where the user must survey the surrounding environment. For example, the user may be alerted to significant shifts in water pressure and/or movement that may signal mantle movement and or the imminence of an upcoming disaster. Alerts may be sent to the user via the eyepiece regarding the shifting of the mantle, threat of earthquake and/or tsunami and the like. Such alerts may be provided by the eyepiece synching with devices on the ship, by tracking ocean water movement, current change, change in water pressure, a drop or increase of the surrounding water and the like.

In embodiments where military ships are deployed for disaster clean up, the eyepiece may be used in detecting areas of pollution, the speed of travel of the pollution and predictions of the depth and where the pollution will settle. In embodiments the eyepiece may be useful in detecting the parts per million of pollution and the variance thereon to determine the change in position of the volume of the pollution.

In various embodiments the eyepiece may provide a user with a program to check for proper functioning of the ship and the equipment thereon. Further, various operators of the ship may be alerted if proper routine maintenance was not completed prior to deployment. In embodiments the user may also be able to view the maintenance history of the ship along with the status of vital functioning of the ship.

In embodiments, the eyepiece may provide a user with various forms of guidance in the environment of a submarine. For example, the eyepiece may be used in such an environment when training, going into combat, for maintenance and the like. Such use may be suited for personnel of various ranks and levels.

By way of example, a user may use the eyepiece for training for submarine operation in combat or high stress situation. The user may be presented with augmented reality situations or otherwise that simulate combat situations in a particular submarine. The training program may be based on the user's rank such that his rank will determine the type of situation presented. The user's responses and actions may be recorded and or analyzed to provide the user with additional information, critique and to alter training exercises based on past data. In embodiments, the eyepiece may also train the user in maintaining the submarine, use of the submarine and proper safety procedures and the like.

In combat environments, the eyepiece may be used to provide the user with information relating to the user's depth, the location of the enemy and objects, friendlies and/or enemies on the surface. In embodiments, such information may be conveyed to the user in a visual representation, through audio and the like. In various embodiments the eyepiece may sync into and/or utilize devices and equipment of the submarine to gather data from GPS, sonar and the like to gather various information such as the location of other objects, submarines, and the like. The eyepiece may display instructions to the soldier regarding safety procedures, mission specifics, and the presences of enemies in the area. In embodiments, the device may communicate or sync with the ship and/or weapon equipment to guide the soldier in the use of such equipment and to provide a display relating to the particular equipment. Such display may include a visual and audio data relating to the equipment. By further way of example, the device may be used with the periscope to augment the user's visual picture and/or audio to show potential threats, places of interest, and information that may not otherwise be displayed by using the periscope such as the location of enemies out of view, national and international water boundaries, various threats, and the like.

The eyepiece may also be used in maintenance of the submarine. For example, it may provide the user with a pre journey check for proper functioning of the ship, it may alert the operation of proper routine maintenance was performed or not completed prior to the mission. Further, a user may be provided with a detailed history to review maintenance performed and the like. In embodiments, the eyepiece may also assist in maintaining the submarine by providing an augmented reality or other program that instructs the user in performing such maintenance.

In embodiments, the eyepiece may provide a user with various forms of guidance in the environment of a ship in port. For example, the eyepiece may be used in such an environment when training, going into combat, for maintenance and the like. Such use may be suited for personnel of various ranks and levels.

By way of example, a user may use the eyepiece for training for a ship in a port when in combat, under attach or a high stress situation. The user may be presented with augmented reality situations, or otherwise, that simulate combat situations that may be seen in a particular port and on such a ship. The training program may show various ports from around the world and the surrounding land data, data for the number of ally ships or enemy ships that may be in the port at a given time, and it may show the local fueling stations and the like. The training program may be based on the user's rank such that his rank will determine the type of situation presented. The user's responses and actions may be recorded and/or analyzed to provide the user with additional information, critique and to alter training exercises based on past data. In embodiments, the eyepiece may also train the user in maintaining and performing mechanical maintenance on the ship, use of the ship and proper safety procedures to employ on the ship and the like.

In combat environments, the eyepiece may be used to provide the user with information relating to the port where the user will or is docked. They user may be provided with information on the location or other visual representation of the enemy and or friendly ships in the port. In embodiments, the user may obtain alerts of approaching aircraft and enemy ships and the user may sync into the ship and/or weapon equipment to guide the user in using the equipment while providing information and/or display data about the equipment. Such data may include the amount and efficacy of particular ammunition and the like. The eyepiece may display instructions to the soldier regarding safety procedures, mission specifics, and the presences of enemies in the area. Such display may include visual and/or audio information.

The eyepiece may also be used in maintenance of the ship. For example, it may provide the user with a pre-journey check for proper functioning of the ship, it may alert the operation of proper routine maintenance was performed or not completed prior to the mission. Further, a user may be provided with a detailed history to review maintenance performed and the like. In embodiments, the eyepiece may also assist in maintaining the ship by providing an augmented reality or other program that instructs the user in performing such maintenance.

In other embodiments, the user may use the eyepiece or other device to gain biometric information of those coming into the port. Such information may provide the user's identity and allow the user to know if the person is a threat or someone of interest. In other embodiments, the user may scan an object or container imported into the port for potential threats in shipments of cargo and the like. The user may be able to detect hazardous material based on density or various other information collected by the sensors associated with the eyepiece or device. The eyepiece may record information or scan a document to determine whether the document may be counterfeit or altered in some way. This may assist the user in checking an individual's credentials, and it may be used to check the papers associated with particular pieces of cargo to alert the user to potential threats or issues that may be related to the cargo such as inaccurate manifests, counterfeit documents, and the like.

In embodiments, the eyepiece may provide a user with various forms of guidance when using a tank or other land vehicles. For example, the eyepiece may be used in such an environment when training, going into combat, for surveillance, group transport, for maintenance and the like. Such use may be suited for personnel of various ranks and levels.

By way of example, a user may use the eyepiece for training for using a tank or other ground vehicle when in combat, under attack or a high stress situation or otherwise. The user may be presented with augmented reality situations, or otherwise, that simulate combat situations that may be seen when in and/or operating a tank. The training program may test the user on proper equipment and weapon use and the like. The training program may be based on the user's rank such that his rank will determine the type of situation presented. The user's responses and actions may be recorded and/or analyzed to provide the user with additional information, critique and to alter training exercises based on past data. In embodiments, the eyepiece may also train the user in maintaining the tank, use of the tank and proper safety procedures to employ when in the tank or land vehicle and the like.

In combat environments, the eyepiece may be used to provide the user with information and/or visual representations relating to the location of the enemy and/or friendly vehicles on the landscape. In embodiments, the user may obtain alerts of approaching aircraft and enemy vehicles and the user may sync into the tank and/or weapon equipment to guide the user in using the equipment while providing information and/or display data about the equipment. Such data may include the amount and efficacy of particular ammunition and the like. The eyepiece may display instructions to the soldier regarding safety procedures, mission specifics, and the presences of enemies and friendlies in the area. Such display may include visual and audio information. In embodiments, the user may stream a 360-degree view from the surrounding environment outside of the tank by using he eyepiece to sync into a camera or other device with such a view. Video/audio feed may be provided to as many users inside of or outside of the tank/vehicle as necessary. This may allow the user to monitor vehicle and stationary threats. The eyepiece may communicate with the vehicle, and various vehicles, aircraft vessels and devices as described herein or otherwise apparent to one of ordinary skill in the art, to monitor vehicle statistics such as armor breach, engine status, and the like. The eyepiece may further provide GPS for navigational purposes, and use of Black Silicon or other technology as described herein to detect enemy and navigate to the environment at night and in times of less than optimal viewing and the like.

Further, the eyepiece may be used in the tank/land vehicle environment for surveillance. In embodiments, the user may be able to sync into cameras or other devices to get a 360-degree field of view to gather information. Night vision and/or SWIR and the like as described herein may be used for further information gathering where necessary. The user may use the eyepiece to detect heat signatures to survey the environment to detect potential threats, and may view soil density and the like to detect roadside bombs, vehicle tracks, various threats and the like.

In embodiments, the eyepiece may be used to facilitate group transport with a tank or other land vehicle. For example the user may be provided with a checklist that is visual, interactive or otherwise for items and personnel to be transported. The user may be able to track and update a manifest of items to track such as those in transport and the like. The user may be able to view maps of the surrounding area, scan papers and documents for identification of personnel, identify and track items associated with individuals in transport, view the itinerary/mission information of the individual in transport and the like.

The eyepiece may also be used in maintenance of the vehicle. For example, it may provide the user with a pre-journey check for proper functioning of the tank or other vehicle, it may alert the operation of proper routine maintenance was performed or not completed prior to the mission. Further, a user may be provided with a detailed history to review maintenance performed and the like. In embodiments, the eyepiece may also assist in maintaining the vehicle by providing an augmented reality or other program that instructs the user in performing such maintenance.

In embodiments, the eyepiece may provide a user with various forms of guidance when in an urban or suburban environment. For example, the eyepiece may be used in such environments when training, going into combat, for surveillance, and the like. Such use may be suited for personnel of various ranks and levels.

By way of example, a user may use the eyepiece for training when in combat, under attack or a high stress situation, when interacting with local people, and the like in an urban or suburban environment. The user may be presented with augmented reality situations, or otherwise, that simulate combat situations that may be seen when in such an environment. The training program may test the user on proper equipment and weapon use and the like. The training program may be based on the user's rank such that his rank will determine the type of situation presented. The user's responses and actions may be recorded and or analyzed to provide the user with additional information, critique and to alter training exercises based on past data. In embodiments, the user may view alternate scenarios of urban and suburban settings including actual buildings and layouts of buildings and areas of potential combat. The user may be provided with climate and weather information prior to going into the area, and may be apprised of the number of people in the area at a given time generally or at that time of day to prepare for possible attacks or other engagement. Further, the user may be provided with the location of individuals in, around and atop of buildings in a given area so that the user is prepared prior to entering the environment.

In urban and suburban environments, the eyepiece or other device may allow the user to survey the local people as well. The user may be able to gather face, iris, voice, and finger and palm print data of persons of interest. The user may be able to scan such data without the user's detection from 0-5 meters, a greater distance or right next the POI. In embodiments, the user may employ the eyepiece to see through smoke and/or destroyed environments, to note and record the presence of vehicles in the area, to record environment images for future use such as in battle plans, to note population density of an area at various times of day, the layout of various buildings and alleys, and the like. Furthermore, the user may gather and receive facts about a particular indigenous population with which the soldier will have contact.

The user may also employ the eyepiece or other device in urban/suburban environments when in combat. The device may allow the user to use geo location with a laser range finder to locate and kill an enemy target. In embodiments, it may give an aerial view of the surrounding environment and buildings. It may display enemy in the user's surrounding area and identify the location of individuals such as enemies or friendlies or those on the user's team. The user may use the eyepiece or other device to stay in contact with his home base, to view/hear instructions from commanding officers through the eyepiece where the instructions may be developed after viewing or hearing data from the user's environment. Further, the eyepiece may also allow the user to give orders to others on his team. In embodiments, the user may perform biometric data collection on those in the vicinity, record such information and/or retrieve information about them for use in combat. The user may link with other soldier devices for monitoring and using various equipment carried by the soldier. In embodiments, the eyepiece may alert the user for upcoming edges of buildings when on a roof top and alert when approaching a ground shift or ledge and the like. The use may be enabled to view a map overlay of the environment and the members of his team, and he may be able to detect nearby signals to be alerted and to alert others of possible enemies in the vicinity. In various embodiments, the user may use the eyepiece for communicating with other team members to execute a plan. Further, the user may use the eyepiece to detect enemies located in dark tunnels and other areas where they may be located.

The eyepiece may also be used in a desert environment. In addition to the general and/or applicable uses noted herein in relation to training, combat, survival, surveillance purposes, and the like, the eyepiece may be further employed in various use scenarios that may be encountered in environments such as a desert environment. By way of example, when going into combat or training, the user may use the eyepiece to correct impaired vision through sand storms in combat, surveillance, and training. Further, the eyepiece may simulate the poor visibility of sand storms and other desert dangers for the user in training mode. In combat, the eyepiece may assist the user in seeing or detecting the enemy in the presence of a sandstorm through various means as described above. Further, the user may be alerted to and/or be able to see the difference between sand clouds caused by vehicles and those generated by the wind in order to be alerted of potential enemy approach.

In various embodiments, the user may use the eyepiece to detect ground hazards and environmental hazards. For example the user may use the eyepiece to detect the edge of sand dunes, sand traps and the like. The user may also use the eyepiece to detect sand density to detect various hazards such as ground holes, cliffs, buried devices such as landmines and bombs, and the like. The user may be presented with a map of the desert to view the location of such hazards. In embodiments, the user may be provided a means by which to monitor his vital signs and to give him alerts when he is in danger to do the extreme environmental conditions such as heat during the day, cold at night, fluctuating temperatures, dehydration and the like. Such alerts and monitoring may be provided graphically in a user interface displayed in the eyepiece and/or via audio information.

In embodiments, the user may be presented with a map of the desert to view the location of his team, and he may use the eyepiece to detect nearby signals, or otherwise, to get alerts of possible enemy forces that may be displayed on the map or in an audio alert from an earpiece. In such embodiments, the user may have an advantage over his enemies as he may have the ability to determine the location of his team and enemies in sandstorms, buildings, vehicles and the like. The user may view a map of his location which may show areas in which the user has traveled recently as one color and new areas as another. In this way or through other means, the device may allow the user to not get lost and or stay moving in the proper direction. In embodiments, the user may be provided with a weather satellite overlay to warn the user of sand storms and hazardous weather.

The eyepiece may also be used in a wilderness environment. In addition to the general and/or applicable uses noted herein in relation to training, combat, survival, surveillance purposes, and the like, the eyepiece may be further employed in various use scenarios that may be encountered in environments such as a wilderness environment.

By way of example the user may use the eyepiece in training for preparation of being in the wilderness. For example the user may employ the eyepiece to simulate varying degrees of wilderness environments. In embodiments, the user may experience very thick and heavy trees/brush with dangerous animals about and in other training environments, he may be challenged with fewer places to hide from the enemy.

In combat, the user may use the eyepiece for various purposes. The user may use the eyepiece to detect freshly broken twigs and branches to detect recent enemy presence. Further, the user may use the eyepiece to detect dangerous cliffs, caves, changes in terrain, recently moved/disturbed dirt and the like. By way of example, by detecting the presence of recently disturbed dirt, which may be detected if it has a different density or heat signature from the surrounding dirt/leaves or which may be detected by other means, the user may be alerted to a trap, bomb or other dangerous device. In various environments described herein, the user may use the eyepiece to communicate with his team via a user interface or other means such that communication may remain silent and/or undetected by the enemy in close environments, open environments susceptible to echo, and the like. Also, in various environments, the user may employ night vision as described herein to detect the presence of enemies. The user may also view an overlay of trail maps and/or mountain trail maps in the eyepiece so that the user may view a path prior to encountering potentially dangerous terrain and or situations where the enemy may be located. In various environments as described herein, the eyepiece may also amplify the user's hearing for the detection of potential enemies.

In embodiments, a user may employ the eyepiece in a wilderness environment in a search and rescue use scenario. For example, the user may use the eyepiece to detect soil/leaf movement to determine if it's been disturbed for tracking human tracks and for finding a buried body. The user may view a map of the area which has been tagged to show areas already covered by air and or other team member searches to direct the user from areas already scoured and toward areas not searched. Further, the user may use the eyepiece for night vision for human and/or animal detection through trees, brush, thickets and the like. Further, by using the eyepiece to detect the presence of freshly broken twigs, the user may be able to detect the presence or recent presence of persons of interest when in a surveillance and/or rescue mission. In embodiments, the user may also view an overlay of trail maps and/or mountain trail maps in the eyepiece s so that the user may view a path prior to encountering potentially dangerous terrain and or situations.

In yet other embodiments, a user may employ the use of the eyepiece in a wilderness for living off of the land and survival-type situations. By way of example, the user may use the eyepiece to track animal presence and movement when hunting for food. Further, the user may use the eyepiece for detection of soil moisture and to detect the presence and location of a water supply. In embodiments, the eyepiece may also amplify the user's hearing to detect potential prey.

The eyepiece may also be used in an artic environment. In addition to the general and/or applicable uses noted herein in relation to training, combat, survival, surveillance purposes, and the like, the eyepiece may be further employed in various use scenarios that may be encountered in environments such as an arctic environment. For example, when in training, the eyepiece may simulate visual and audio white out conditions that a user may encounter in an arctic environment so that the user may adapt to operating under such stresses. Further, the eyepiece may provide the user with a program that simulates various conditions and scenarios due to extreme cold that he may encounter, and the program may track and display data related to the user's predicted loss of heat. Further, the program may adapt to simulate such conditions that the user would experience with such heat loss. In embodiments, the program may simulate the inability of the user to control his limbs properly which may manifest in a loss of weapon accuracy. In other embodiments, the user may be provided life-saving information and instructions about such things as burrowing in the snow for warmth, and various survival tips for artic conditions. In yet other embodiments, the eyepiece may sync into a vehicle such that the vehicle responds as if the vehicle were performing in a particular environment, for example with artic conditions and snow and ice. Accordingly the vehicle may respond to the user as such and the eyepiece may also simulate visual and audio as if the user were in such an environment.

In embodiments, the user may use the eyepiece in combat. The soldier may use the eyepiece to allow him to see through white out conditions. The user may be able to pull up an overlay map and/or audio that provides information of buildings ditches, land hazards and the like to allow the soldier to move around the environment safely. The eyepiece may alert the user to detections in the increase or decrease of snow density to let him know when the landmass under the snow has changed such as to denote a possible ditch, hole or other hazard, an object buried in the snow and the like. Further, in conditions where it is difficult to see, the user may be provided with the location of his team members and enemies whether or not snow has obstructed his view. The eyepiece may also provide heat signatures to display animals and individuals to the user in an artic environment. In embodiments, a user interface in the eyepiece may show a soldier's his vitals and give alerts when he is in danger doe to the surrounding extreme environmental conditions. Furthermore, the eyepiece may help the user operate a vehicle in snowy conditions by providing alerts from the vehicle to the user regarding transmission slipping, wheel spinning, and the like.

The eyepiece may also be used in a jungle environment. In addition to the general and/or applicable uses noted herein in relation to training, combat, survival, surveillance purposes, and the like, the eyepiece may be further employed in various use scenarios that may be encountered in environments such as a jungle environment. For example the eyepiece may be employed in training to provide the user with information regarding which plants may be eaten, which are poisonous and what insects and animals may present the user with danger. In embodiments, the eyepiece may simulate various noises and environments the user may encounter in the jungle so that when in battle the environment is not a distraction. Further, when in combat or an actual jungle environment, the user may be provided with a graphical overlay or other map to show him the surrounding area and/or to help him track where he's been and where he must go. It may alert him of allies and enemies in the area, and it may sense movement in order to alert the user of potential animals and/or insects nearby. Such alerts may help the user survive by avoiding attack and finding food. In other embodiments, the user may be provided with augmented reality data such as in the form of a graphical overlay that allows the user to compare a creature and/or animal to those encountered to help the user discern which are safe for eating, which are poisonous and the like. By having information that a particular creature is not a threat to the user, he may be spared of having to deploy a weapon when in stealth or quiet mode.

The eyepiece may also be used in relation to Special Forces missions. In addition to the general and/or applicable uses noted herein in relation to training, combat, survival, surveillance purposes, and the like, the eyepiece may be further employed in various use scenarios that may be encountered in relation to special forces missions. In embodiments, the eyepiece may be of particular use on stealth missions. For example, the user may communicate with his team in complete silence through a user interface that each member may see on his eyepiece. The user sharing information may navigate through the user interface with eye movements and/or a controller device and the like. As the user puts up instructions and/or navigates through the user interface and particular data concerning the information to convey, the other users may see the data as well. In embodiments, various users may be able to insert questions via the user interface to be answered by the instruction leader. In embodiments, a user may speak or launch other audio that all users may hear through their eyepiece or other device. This may allow users in various locations on the battlefield to communicate battle plans, instructions, questions, share information and the like and may allow them to do so without being detected.

In embodiments, the eyepiece may also be used for military fire-fighting. By way of example, the user may employ the eyepiece to run a simulation of firefighting scenarios. The device may employ augmented reality to simulate fire and structural damage to a building as time goes by and it may otherwise recreate life-like scenarios. As noted herein, the training program may monitor the user's progress and/or alter scenarios and training modules based on the user's actions. In embodiments, the eyepiece may be used in actual firefighting. The eyepiece may allow the user to see though smoke through various means as described herein. The user may view, download or otherwise, access a layout of the building, vessel, aircraft vehicle or structure that's on fire. In embodiments, the user will have an overview map or other map that displays where each team member is located. The eyepiece may monitor the user-worn or other devices during firefighting. The user may see his oxygen supply levels in his eyepiece and may be alerted as to when he should come out for more. The eyepiece may send notifications from the user's devices to the command outside of the structure to deploy new personnel to come in or out of the fire and to give status updates and alert of possible fire fighter danger. The user may have his vital signs displayed to determine if he is overheating, losing too much oxygen and the like. In embodiments, the eyepiece may be used to analyze whether cracks in beams or forming based on beam density, heat signatures and the like and inform the user of the structural integrity of the building or other environment. The eyepiece may provide automatic alerts when structural integrity is compromised.

In embodiments, the eyepiece may also be used for maintenance purposes. For example, the eyepiece may provide the user with a pre-mission and/or use checklist for proper functioning of the item to be used. It may alert the operator if proper maintenance has not been logged in the item's database. It may provide a virtual maintenance and/or performance history for the user to determine the safety of the item or of necessary measures to be taken for safety and/or performance. In embodiments, the eyepiece may be used to perform augmented reality programs and the like for training the user in weapon care and maintenance and for lessons in the mechanics of new and/or advanced equipment. In embodiments, the eyepiece may be used in maintenance and/or repair of various items such as weapons, vehicles, aircraft, devices and the like. The user may use the eyepiece to view an overlay of visual and/or audio instructions of the item to walk the user through maintenance without the need for a handheld manual. In embodiments, video, still images, 3D and/or 2D images, animated images, audio and the like may be used for such maintenance. In embodiments, the user may view an overlay and/or video of various images of the item such that the user is shown what parts to remove, in what order, and how, which parts to add, replace, repair, enhance and the like. In embodiments such maintenance programs may be augmented reality programs or otherwise. In embodiments, the user may use the eyepiece to connect with the machine or device to monitor the functioning and or vital statistics of the machine or device to assist in repair and/or to provide maintenance information. In embodiments, the user may be able to use the eyepiece to propose a next course of action during maintenance and the eyepiece may send the user information on the likelihood of such action harming the machine, helping to fix the machine, how and/or if the machine will function after the next step and the like. In embodiments, the eyepiece may be used for maintenance of all items, machines, vehicles, devices, aircraft and the like as mentioned herein or otherwise applicable to or encountered in a military environment.

The eyepiece may also be used in environments where the user has some degree of unfamiliarity with the language spoken. By way of example, a soldier may use the eyepiece and/or device to access near real-time translation of those speaking around him. Through the device's earpiece, he may hear a translation in his native language of one speaking to him. Further, he may record and translate comments made by prisoners and/or other detainees. In embodiments, the soldier may have a user interface that enables translating a phrase or providing translation to the user via an earpiece, via the user's eyepiece in a textual image or otherwise. In embodiments, the eyepiece may be used by a linguist to provide a skilled linguist with supplemental information regarding dialect spoken in a particular area or that which is being spoken by people near him. In embodiments, the linguist may use the eyepiece to record language samples for further comparison and/or study. Other experts may use the eyepiece to employ voice analysis to determine if the speaker is experiencing anger, shame, lying, and the like by monitoring inflection, tone, stutters and the like. This may give the listener native the speaker's intentions even when the listener and speaker speak different languages.

In embodiments, the eyepiece may allow the user to decipher body language and/or facial expressions or other biometric data from another. For example, the user may use the device to analyze a person's pupil dilation, eye blink rates, voice inflection, body movement and the like to determine if the person is lying, hostile, under stress, likely a threat, and the like. In embodiments, the eyepiece may also gather data such as that of facial expressions to detect and warn the user if the speaker is lying or likely making unreliable statements, hostile, and the like. In embodiments, the eyepiece may provide alerts to the user when interacting with a population or other individuals to warn about potential threatening individuals that may be disguised as non-combative or ordinary citizens or other individuals. User alerts may be audio and/or visual and may appear in the user's eyepiece in a user interface or overlaid in the user's vision and/or be associated with the surveyed individual in the user's line of vision. Such monitoring as described herein may be undetected as the user employs the eyepiece and/or device to gather the data from a distance or it may be performed up-close in a disguised or discrete fashion, or performed with the knowledge and/or consent of the individual in question.

The eyepiece may also be used when dealing with bombs and other hazardous environments. By way of example, the eyepiece may provide a user with alerts of soil density changes near the roadside which could alert the user and/or team of a buried bomb. In embodiments, similarly methods may be employed in various environments, such as testing the density of snow to determine if a bomb or other explosive may be found in artic environments and the like. In embodiments, the eyepiece may provide a density calculation to determine whether luggage and/or transport items tend to have an unexpected density or one that falls outside of a particular range for the items being transported. In embodiments, the eyepiece may provide a similar density calculation and provide an alert if the density is found to be one that falls within that expected for explosive devices, other weapons and the like. One skilled in the art will recognize that bomb detection may be employed via chemical sensors as well and/or means known in the art and may be employed by the eyepiece in various embodiments. In embodiments, the eyepiece may be useful in bomb disposal. The user may be provided with an augmented reality or other audio and/or visual overlay in order to gain instructions on how to diffuse the particular type of bomb present. Similar to the maintenance programs described above, the user may be provided with instructions for diffusing a bomb. In embodiments, if the bomb type is unknown a user interface may provide the user with instructions for safe handling and possible next steps to be taken. In embodiments, the user may be alerted of a potential bomb in the vicinity and may be presented with instructions for safe dealing with the situation such as how to safely flee the bomb area, how to safely exit a vehicle with a bomb, how closely the user may come to the bomb safely, how to diffuse the bomb via instructions appropriate for the situation and the user's skill level, and the like. In embodiments, the eyepiece may also provide a user with training in such hazardous environments and the like.

In embodiments, the eyepiece may detect various other hazards such as biological spills, chemical spills, and the like and provide the user with alerts of the hazardous situation. In embodiments, the user may also be provided with various instructions on diffusing the situation, getting to safety and keeping others safe in the environment and/or under such conditions. Although situations with bombs have been described, it is intended that the eyepiece may be used similarly in various hazardous and/or dangerous situations and to guard against and to neutralize and/or provide instruction and the like when such danger and hazards are encountered.

The eyepiece may be used in a general fitness and training environment in various embodiments. The eyepiece may provide the user with such information as the miles traveled during his run, hike, walk and the like. The eyepiece may provide the user with information such as the number of exercised performed, the calories burned, and the like. In embodiments, the eyepiece may provide virtual instructions to the user in relation to performing particular exercises correctly, and it may provide the user with additional exercises as needed or desired. Further, the eyepiece may provide a user interface or otherwise where physical benchmarks are disclosed for the soldier to meet the requirements for his particular program. Further, the eyepiece may provide data related to the amount and type of exercise needed to be carried out in order for user to meet such requirements. Such requirements may be geared toward Special Forces qualification, basic training, and the like. In embodiments, the user may work with virtual obstacles during the workout to prevent the user from setting up actual hurdles, obstacles and the like.

Although specific various environments and use scenarios have been described herein, such description is not intended to be limiting. Further, it is intended that the eyepiece may be used in various instances apparent to one of ordinary skill in the art. It is also intended that applicable uses of the eyepiece as noted for particular environments may be applied in various other environments even though not specifically mentioned therewith.

In embodiments, a user may access and/or otherwise manipulate a library of information stored on a secure digital (SD) card, Mini SD card, other memory, remotely loaded over a tactical network, or stored by other means. The library may be part of the user's equipment and/or it may be remotely accessible. The user's equipment may include a DVR or other means for storing information gathered by the user and the recorded data and/or feed may be transmitted elsewhere as desired. In embodiments, the library may include images of local threats, information and/or images of various persons listed as threats and the like. The library of threats may be stored in an onboard mini-SD card or other means. In embodiments, it may be remotely loaded over a tactical network. Furthermore, in embodiments, the library of information may contain programs and other information useful in the maintenance of military vehicles or the data may be of any variety or concerning any type of information. In various embodiments, the library of information may be used with a device such that data is transferred and/or sent to or from the storage medium and the user's device. By way of example, data may be sent to a user's eyepiece and from a stored library such that he is able to view images of local persons of interest. In embodiments, data may be sent to and from a library included in the soldier's equipment or located remotely and data may be sent to and from various devices as described here. Further, data may be sent between various devices as described herein and various libraries as described above.

In embodiments, military simulation and training may be employed. By way of example, gaming scenarios normally used for entertainment may be adapted and used for battlefield simulation and training. Various devices, such as the eyepiece described herein may be used for such purpose. Near field communications may be used in such simulation to alert personnel, present dangers, change strategy and scenario and for various other communication. Such information may be posted to share information where it is needed to give instruction and/or information. Various scenarios, training modules and the like may be run on the user's equipment. For example only, and not to limit the use of such training, a user's eyepiece may display an augmented reality battle environment. In embodiments, the user may act and react in such an environment as if he were actually in battle. The user may advance or regress depending on his performance. In various embodiments, the user's actions may be recorded for feedback to be provided based on his performance. In embodiments, the use may be provided with feedback independent of whether his performance was recorded. In embodiments, information posted as described above may be password or biometrically protected and or encrypted and instantly available or available after a particular period of time. Such information stored in electronic form may be updated instantly for all the change orders and updates that may be desired.

Near field communications or other means may also be used in training environments and for maintenance to share and post information where it is needed to give instruction and/or information. By way of example, information may be posed in classrooms, laboratories maintenance facilitates, repair bays, and the like or wherever it is needed for such training and instruction. A user's device, such as the eyepiece described herein, may allow such transmission and receipt of information. Information may be shared via augmented reality where a user encounters a particular area and once there he is notified of such information. Similarly as descried herein, near field communications may be used in maintenance. By way of example, information may be posted precisely where it is needed, such as in maintenance facilities, repair bays, associated with the item to be repaired, and the like. More specifically, and not to limit the present disclosure, repair instructions may be posted under the hood of a military vehicle and visible with the use of the soldier's eyepiece. Similarly, various instruction and training information may be shared with various users in any given training situation such as training for combat and/or training for military device maintenance. In embodiments, information posted as described above may be password or biometrics protected and or encrypted and instantly available or available after a particular period of time. Such information stored in electronic form may be updated instantly for all the change orders and updates that may be desired.

In embodiments, an application applied to the present disclosure may be for facial recognition or sparse facial recognition. Such sparse facial recognition may use one or more facial features to exclude possibilities in identifying persons of interest. Space facial recognition may have automatic obstruction masking and error and angle correction. In embodiments, and by way of example and not to limit the present disclosure, the eyepiece, flashlight and devices as described herein may allow for sparse facial recognition. This may work like human vision and quickly exclude regions or entire profiles that don't match by using sparse matching on all image vectors at once. This may make it almost impossible for false positives. Further, this may simultaneously utilize multiple images to enlarge the vector space and increase accuracy. This may work with either multiple database or multiple target images based on availability or operational requirement. In embodiments, a device may manually or automatically identify one or more specific clean features with minimal reduction in accuracy. By way of example, accuracy may be of various ranges and it may be at least 87.3% for a nose, 93.7% for an eye, and 98.3% for a mouth and chin. Further angle correction with facial reconstruction may be employed and, in embodiments, up to a 45 degree off angle correction with facial reconstruction may be achieved. This may be further enhanced with 3D image mapping technology. Further, obscured area masking and replacement may be employed. In embodiments, 97.5% and 93.5% obscured area masking and replacement may be achieved for sunglasses and a scarf respectively. In embodiments, the ideal input image may be 640 by 480. The target image may match reliably with less than 10% of the input resolution due to long range or atmospheric obscurants. Further, the specific ranges as noted above may be greater or lesser in various embodiments.

In various embodiments, the devices and/or networks described herein may be applied for the identification and or tracking of friends and/or allies. In embodiments, facial recognition may be employed to positively identify friends and or friendly forces. Further, real-time network tracking and/or real-time network tracking of blue and red forces may allow a user to know where his allies and/or friendlies are. In embodiments, there may be a visual separation range between blue and red forces and/or forces identified by various markers and/or means. Further, the user may be able to geo-locate the enemy and share the enemy's location in real-time. Further, the location of friendlies may be shared in real time as well. Devices used for such an application may be biometric collection glasses, eyepiece other devices as described herein and those known to one of ordinary skill in the art.

In embodiments, the devices and/or networks described herein may be applied in medical treatment in diagnosis. By way of example, such devices may enable medical personnel to make remote diagnoses. Further, and by way of example, when field medics arrive on a scene, or remotely, they may use a device such as a fingerprint sensor to instantaneously call up the soldier's medical history, allergies, blood type and other time sensitive medical data to apply the most effective treatment. In embodiment, such data may be called up via facial recognition, iris recognition, and the like of the soldier which may be accomplished via the eyepiece described herein or another device.

In embodiments, users may share various data via various networks and devices as described herein. By way of example, a 256-bit AES encrypted video wireless transceiver may bi-directionally share video between units and/or with a vehicle's computer. Further, biometric collection of data, enrollment, identification and verification of potential persons of interest, biometric data of persons of interest and the like may be shared locally and/or remotely over a wireless network. Further, such identification and verification of potential persons of interest may be accomplished or aided by the data shared locally and/or remotely over a wireless network. The line of biometric systems and devices as described herein may be enabled to share data over a network as well. In embodiments, data may be shared with, from and/or between various devices, individuals, vehicles, locations, units and the like. In embodiments there may be inter-unit and intra unit communication and data sharing. Data may be shared via, from and/or between existing communications assets, a mesh network or other network, a mil-con type ultra wide band transceiver caps with 256-bit encryption, a mil-con type cable, removable SD and/or microSD memory card, a Humvee, PSDS2, unmanned aerial vehicle, WBOTM, or other network relay, a combat radio, a mesh networked computer, devices such as but not limited to various devices described herein, a bio-phone 3G/4G networked computer, a digital dossier, tactical operating centers, command posts, DCSG-A, BAT servers, individuals and/or groups of individuals, and any eyepiece and/or device described herein and/or those known to persons skilled in the art and the like.

In embodiments, a device as described herein or other device may contain a viewing pane that reverses to project imagery on any surface for combat team viewing by a squad and/or team leader. The transparent viewing pane or other viewing pane may be rotated 180 degrees or another quantity of degrees in projection mode to share data with a team and/or various individuals. In embodiments, devices including but not limited to a monocular and binocular NVG may interface with all or virtually all tactical radios in use and allow the user to share live video, S/A, biometric data and other data in real-time or otherwise. Such devices as the binocular and monocular noted above may be a, VIS, NIR and/or SWIR binocular or monocular that may be self-contained, and comprise a color day/night vision and/or digital display with a compact, encrypted, wireless-enabled computer for interfacing with tactical radios. Various data may be shared over combat radios, mesh networks and long-range tactical networks in real time or near real time. Further, data may be organized into a digital dossier. Data of a person of interest (POI) may be organized into a digital dossier whether such POI rest was enrolled or not. Data that is shared, in embodiments, may be compared, manipulated and the like. While specific devices are mentioned, any device mentioned herein may be capable of sharing information as described herein and/or as would be recognized by one having ordinary skill in the art.

In embodiments, biometric data, video, and various other types of data may be collected via various devices, methods and means. For example, fingerprints and other data may be collected from weapons and other objects at a battle, terrorism and/or crime scene. Such collection may be captured by video or other means. A pocket bio cam, flashlight as described herein with built in still video camera, various other devices described herein, or other device may collect video, record, monitor, and collect and identify biometric photographic data. In embodiments, various devices may record, collect, identify and verify data and biometric data relating to the face, fingerprints, latent fingerprints, latent palm prints, iris, voice, pocket litter, scars, tattoos, and other identifying visible marks and environmental data. Data may be geo-located and date/time stamped. The device may capture EFTS/EBTS compliant salient images to be matched and filed by any biometric matching software. Further, video scanning and potential matching against a built-in or remote iris and facial database may be performed. In embodiments, various biometric data may be captured and/or compared against a database and/or it may be organized into a digital dossier. In embodiments, an imaging and detection system may provide for biometrics scanning and may allow facial tracking and iris recognition of multiple subjects. The subjects may be moving in or out of crowds at high speeds and may be identified immediately and local and/or remote storage and/or analysis may be performed on such images and/or data. In embodiments, devices may perform multi-modal biometric recognition. For example, a device may collect and identify a face and iris, an iris and latent fingerprints, various other combinations of biometric data, and the like. Further, a device may record video, voice, gait, fingerprints, latent fingerprints, palm prints, latent palm prints and the like and other distinguishing marks and/or movements. In various embodiments, biometric data may be filed using the most salient image plus manual entry, enabling partial data capture. Data may be automatically geo-located, time/date stamped and filed into a digital dossier with a locally or network assigned GUID. In embodiments, devices may record full livescan 4 fingerprint slaps and rolls, fingerprint slaps and rolls, palm prints, finger tips and finger prints. In embodiments, operators may collect and verify POIs with an onboard or remote database while overseeing indigenous forces. In embodiments, a device may access web portals and biometric enabled watch list databases and/or may contain existing biometric pre-qualification software for POI acquisition. In embodiments, biometrics may be matched and filed by any approved biometric matching software for sending and receiving secure perishable voice, video and data. A device may integrate and/or otherwise analyze biometric content. In embodiments, biometric data may be collected in biometric standard image and data formats that can be cross referenced for a near real or real time data communication with the Department of Defense Biometric Authoritative or other data base. In embodiments, a device may employ algorithms for detection, analysis, or otherwise in relation to finger and palm prints, iris and face images. A device, in embodiments, may illuminate an iris or latent fingerprint simultaneously for a comprehensive solution. In embodiments, a device may use high-speed video to capture salient images in unstable situations and may facilitate rapid dissemination of situational awareness with intuitive tactical display. Real time situational awareness may be provided to command posts and/or tactical operating centers. In embodiments, a device may allow every soldier to be a sensor and to observe and report. Collected data may be tagged with date, time and geo-location of collection. Further, biometric images may be NIST/ISO compliant, including ITL 1-2007. Further, in embodiments, a laser range finder may assist in biometric capture and targeting. A library of threats may be stored in onboard Mini-SD card or remotely loaded over a tactical network. In embodiments, devices may wirelessly transfer encrypted data between devices with a band transceiver and/or ultrawide band transceiver. A device may perform onboard matching of potential POI's against a built in database or securely over a battlefield network. Further, a device may employ high-speed video to capture salient images in all environmental conditions. Biometric profiles may be uploaded downloaded and searched in seconds or less. In embodiments, a user may employ a device to geo-locate a POI with visual biometrics at a safe distance and positively identify a POI with robust sparse recognition algorithms for the face, iris and the like. In embodiments, a user may merge and print a visual biometrics on one comprehensive display with augmented target highlighting and view matches and warnings without alerting the POI. Such display may be in various devices such as an eyepiece, handheld device and the like.

In embodiments, as indigenous persons filter through a controlled checkpoint and/or vehicle stops, an operator can collect, enroll, identify and verify POIs from a watch list using low profile face and iris biometrics. In embodiments, biometric collection and identification may take place at a crime scene. For example an operator may rapidly collect biometric data from all potential POIs at a bombing or other crime scene. The data may be collected, geo-tagged and stored in a digital dossier to compare POIs against past and future crime scenes. Further, biometric data may be collected in real time from POIs in house and building searches. Such data displayed may let the operator know whether to release detain or arrest a potential POI. In other embodiments, low profile collection of data and identification may occur in street environments or otherwise. A user may move through a market place for example and assimilate with the local population while collecting biometric, geo-location and/or environmental data with minimal visible impact. Furthermore, biometric data may be collected on the dead or wounded to identify whether they were or are a POI. In embodiments, a user may identify known or unknown POI's by facial identification, iris identification, fingerprint identification, visible identifying marks, and the like of the deceased or wounded, or others and keep a digital dossier updated with such data.

In embodiments, a laser range finder and/or inclinometer may be used to determine the location of persons of interest and/or improvised explosive devices, other items of interest, and the like. Various devices described herein may contain a digital compass, inclinometer and a laser range finder to provide geo-location of POIs, targets, IEDs, items of interest and the like. The geo-location of a POI and/or item of interest may be transmitted over networks, tactical networks, or otherwise, and such data may be shared among individuals. In embodiments, a device may allow an optical array and a laser range finder to geo-locate and range multiple POIs simultaneously with continuous observation of a group or crowd in the field in an uncontrolled environment. Further, in embodiments, a device may contain a laser range finder and designator to range and paint a target simultaneously with continuous observation of one or more targets. Further, in embodiments, a device may be soldier-worn, handheld or otherwise and include target geo-location with integrated laser range finder, digital compass, inclinometer and GPS receiver to locate the enemy in the field. In embodiments, a device may contain an integrated digital compass, inclinometer, MEMs Gyro and GPS receiver to record and display the soldier's position and direction of his sight. Further, various devices may include an integrated GPS receiver or other GPS receiver, IMU, 3-axis digital compass or other compass, laser range finder, gyroscope, micro-electro-mechanical system based gyroscope, accelerometer and/or an inclinometer for positional and directional accuracy and the like. Various devices and methods as described herein may enable a user to locate enemy and POIs in the field and share such information with friendlies via a network or other means.

In embodiments, users may be mesh networked or networked together with communications and geo-location. Further, each user may be provided with a pop-up, or other location map of all users or proximate users. This may provide the user with knowledge of where friendly forces are located. A described above, the location of enemies may be discovered. The location of enemies may be tracked and provided with a pop-up or other location map of enemies which may provide the user with knowledge of where friendly forces are located. Location of friendlies and enemies may be shared in real time. Users may be provided with a map depicting such locations. Such maps of the location and/or number of friendlies, enemies and combinations thereof may be displayed in the user's eyepiece or other device for viewing.

In embodiments, devices, methods, and applications may allow for hands-free, wireless, maintenance and repair visually and/or audio enhanced instructions. Such applications may include RFID sensing for parts location and kitting. In examples, a user may use a device for augmented reality guided field repair. Such field repair may be guided by hands-free, wireless, maintenance and repair instructions. A device, such as an eyepiece, projector, monocular and the like and/or other devices as described herein may display images of maintenance and repair procedures. In embodiments, such images may be still and/or video, animated, 3-D, 2-D, and the like. Further, the user may be provided with voice and/or audio annotation of such procedures. In embodiments, this application may be used in high threat environments where working undetected is a safety consideration. Augmented reality images and video may be projected on or otherwise overlaid on the actual object with which the user is working or in the user's field of view of the object to provide video, graphical, textual or other instructions of the procedure to be performed. In embodiments, a library of programs for various procedures may be downloaded and accessed wired or wirelessly from a body worn computer or from a remote device, database and/or server, and the like. Such programs may be used for actual maintenance or training purposes.

In embodiments, the devises, methods and descriptions found herein may provide for an inventory tracking system. In embodiments, such tracking system may allow a scan from up to 100 m distance to handle more than 1000 simultaneous links with 2 mb/s data rate. The system may give annotated audio and/or visual information regarding inventory tracking when viewing and/or in the vicinity of the inventory. In embodiments, devices may include an eyepiece, monocular, binocular and/or other devices as described herein and inventory tracking may use SWIR, SWIR color, and/or night vision technology, body worn wired or wireless computers, wireless UWB secure tags, RFID tags, a helmet/hardhat reader and display and the like. In embodiments, and by way of example only, a user may receive visual and/or audio information regarding inventory such as which items are to be destroyed, transferred, the quantity of items to be destroyed or transferred, where the items are to be transferred or disposed and the like. Further, such information may highlight, or otherwise provide a visual identification of the items in question along with instructions. Such information may be displayed on a user's eyepiece, projected onto an item, displayed on a digital or other display or monitor and the like. The items in question may be tagged via UWB and/or RFID tags, and/or augmented reality programs may be used to provide visualization and/or instruction to the user such that the various devices as described herein may provide the information as necessary for inventory tracking and management.

In various embodiments, SWIR, SWIR color, monocular, night vision, body worn wireless computer, the eyepiece as described herein and/or devices as described herein may be used when firefighting. In embodiments, a user may have increased visibility through smoke, and the location of various individuals may be displayed to the user by his device in an overlaid map or other map so that he may know the location of firefighters and/or others. The device may show real-time display of all firefighters' locations and provide hot spot detection of areas with temperatures of less than and greater than 200 degrees Celsius without triggering false alarms. Maps of the facility may also be provided by the device, displayed on the device, projected from the device and/or overlaid in the user's line of site through augmented reality or other means to help guide the user through the structure and/or environment.

Systems and devices as described herein may be configurable to any software and/or algorithm to conform to mission specific needs and/or system upgrades.

Figure 73:
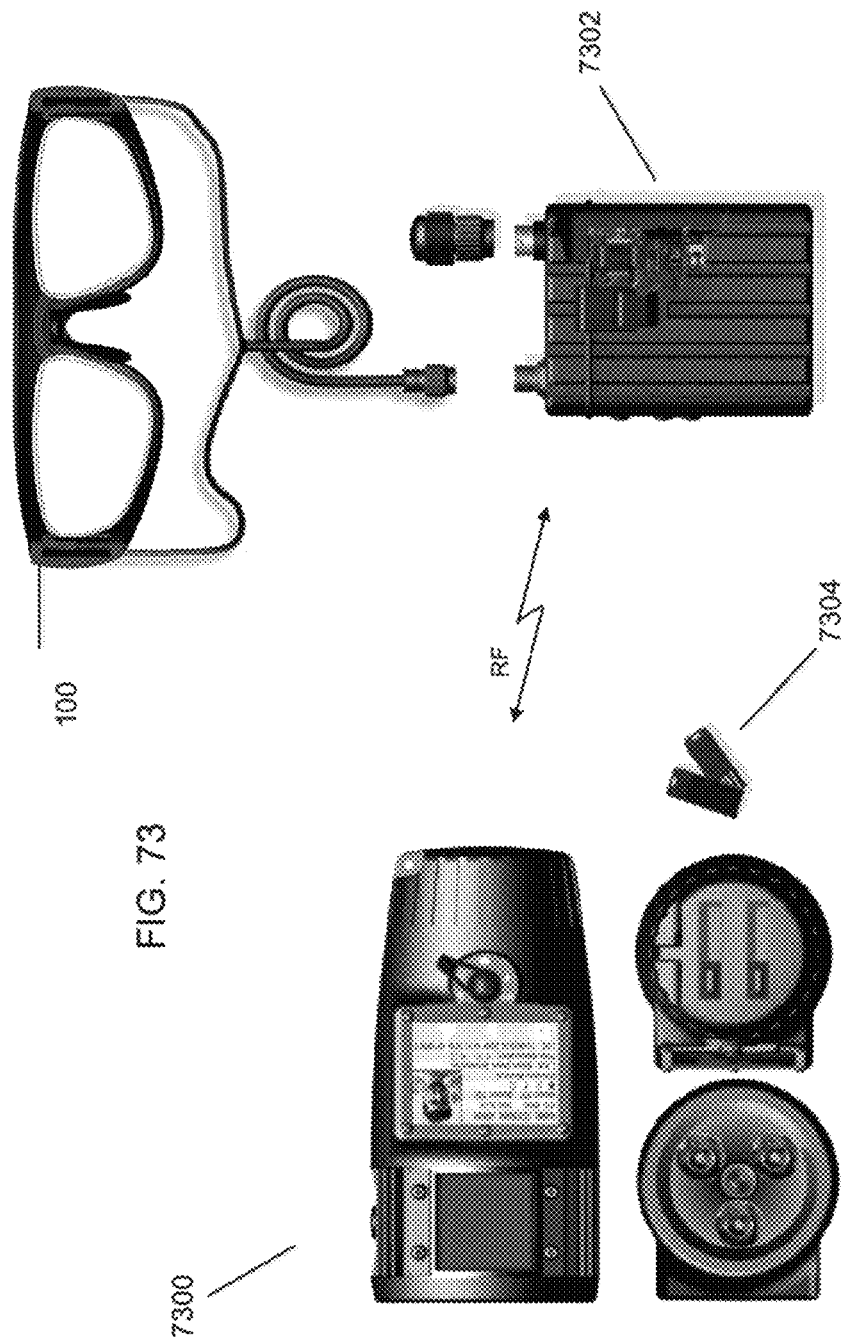
FIG. 73 depicts a biometric flashlight.

Referring to FIG. 73, the eyepiece 100 may interface with a 'biometric flashlight' 7300, such as including biometric data taking sensors for recording an individual's biometric signature(s) as well as the function and in the form factor of a typical handheld flashlight. The biometric flashlight may interface with the eyepiece directly, such as though a wireless connection directly from the biometric flashlight to the eyepiece 100, or as shown in the embodiment represented in FIG. 73, through an intermediate transceiver 7302 that interfaces wirelessly with the biometric flashlight, and through a wired or wireless interface from the transceiver to the eyepiece (e.g. where the transceiver device is worn, such as on the belt). Although other mobile biometric devices are depicted in figures without showing the transceiver, one skilled in the art will appreciate that any of the mobile biometric devices may be made to communicate with the eyepiece 100 indirectly through the transceiver 7300, directly to the eyepiece 100, or operate independently. Data may be transferred from the biometric flashlight to the eyepiece memory, to memory in the transceiver device, in removable storage cards 7304 as part of the biometric flashlight, and the like. The biometric flashlight may include an integrated camera and display, as described herein. In embodiments, the biometric flashlight may be used as a stand-alone device, without the eyepiece, where data is stored internally and information provided on a display. In this way, non-military personnel may more easily and securely use the biometric flashlight. The biometric flashlight may have a range for capturing curtain types of biometric data, such as a range of 1 meter, 3 meters, 10 meters, and the like. The camera may provide for monochrome or color images. In embodiments, the biometric flashlight may provide a covert biometric data collection flashlight-camera that may rapidly geo-locate, monitor and collect environmental and biometric data, for onboard or remote biometric matching. In an example use scenario, a soldier may be assigned to a guard post at nighttime. The soldier may utilize the biometric flashlight seemingly only as a typical flashlight, but where unbeknownst to the individuals being illuminated by the device, is also running and/or taking biometrics as part of a data collection and/or biometrics identification process.

Figure 76:
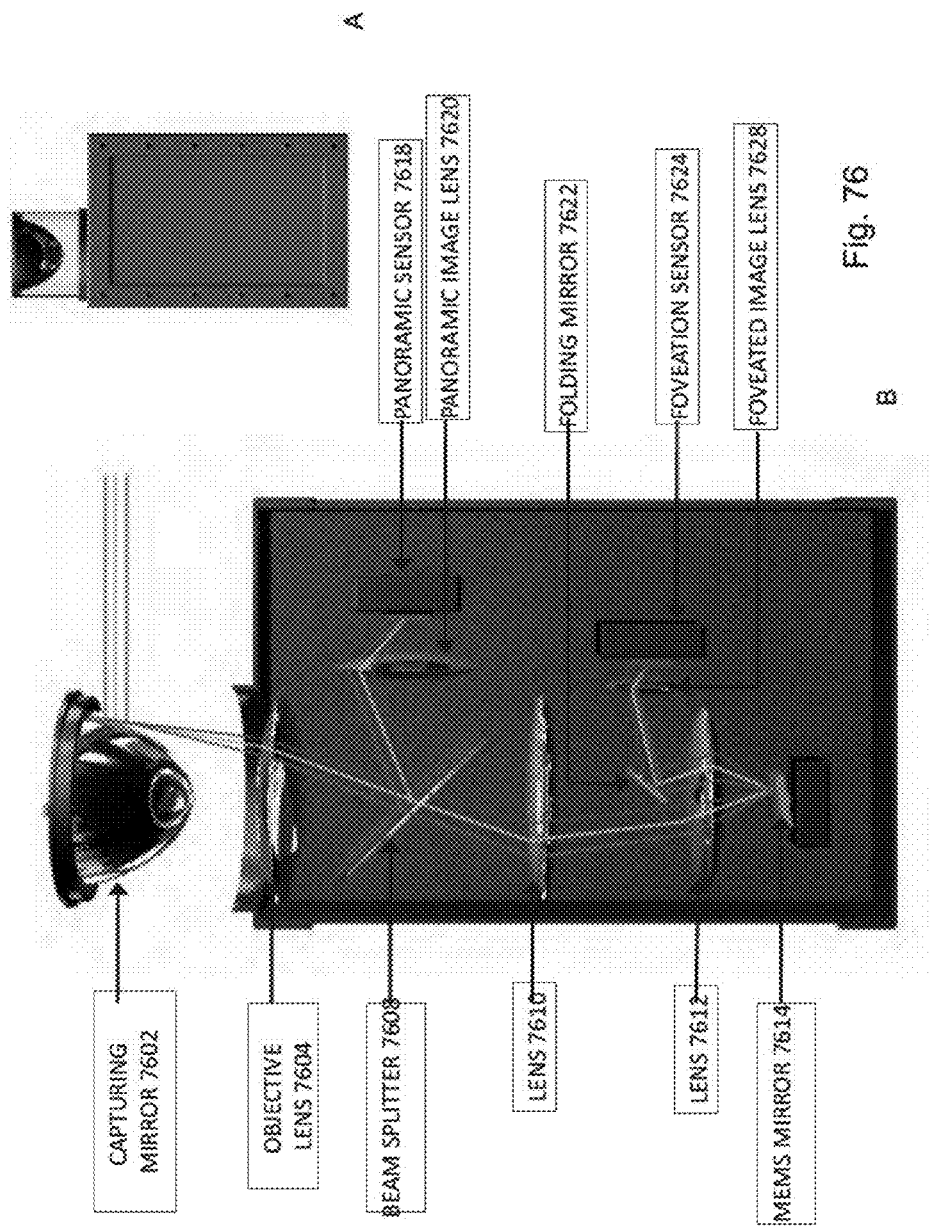
FIG. 76A depicts an assembled 360° imager and FIG. 76B depicts a cutaway view of the 360° imager.

Referring now to FIG. 76, a 360° imager utilizes digital foveated imaging to concentrates pixels to any given region, delivering a high resolution image of the specified region. Embodiments of the 360° imager may feature continuous 360°×40° panoramic FOV with super-high resolution foveated view and simultaneous and independent 10× optical zoom. The 360° imager may include dual 5 megapixel sensors and imaging capabilities of 30 fps and image acquisition time <100. The 360° imager may include a gyro-stabilized platform with independently stabilized image sensors. The 360° imager may have only one moving part and two imaging sensors that allows for reduced image processing bandwidth in a compact optical system design. The 360° image may also feature low angular resolution and high-speed video processing and may be sensor agnostic. The 360° image may be used as a surveillance fixture in a facility, on a mobile vehicle with a gyro stabilized platform, mounted on a traffic light or telephone pole, robot, aircraft, or other location that allows for persistent surveillance. Multiple users may independently and simultaneously view the environment imaged by the 360° imager. For example, imagery captured by the 360° imager may be displayed in the eyepiece to allow all recipients of the data, such as all occupants in a combat vehicle, to have real-time 360° situational awareness. The panoramic 360° imager may recognize a person at 100 meters and foveated 10× zoom can be used to read a license plate at 500 meters. The 360° imager allows constant recording of the environment and features an independent controllable foveated imager.

FIG. 76A depicts an assembled 360° imager and FIG. 76B depicts a cutaway view of the 360° imager. The 360° imager include a capturing mirror 7602, objective lens 7604, beam splitter 7608, lenses 7610 and 7612, MEMS mirror 7614, panoramic sensor 7618, panoramic image lens 7620, folding mirror 7622, foveation sensor 7624, and foveated image lens 7628. Imagery collected with the 360° imager may be geo-located and time and date stamped. Other sensors may be included in the 360° imager, such as thermal imaging sensor, NIR sensor, SWIR sensor, and the like. The MEMS mirror 7614 is a unique mirror prism that uses a single-viewpoint hemispherical capture system allowing for high and uniform resolution. The imager design enables <0.1° scanning accuracy, foveated distortion <1%, 50% MTF @ 400 lp/mm, and foveated acquisition <30 milliseconds.

The 360° imager may be part of a network with wireless or physical reach back to a TOC or database. For example, a user may use a display with a 360° imager driver to view imagery from a 360° imager wirelessly or using a wired connection, such as a mil-con type cable. The display may be a combat radio or mesh networked computer that is networked with a headquarters. Data from a database, such as a DoD authoritative database may be accessed by the combat radio or mesh networked computer, such as by using a removable memory storage card or through a networked connection.

Figure 77:
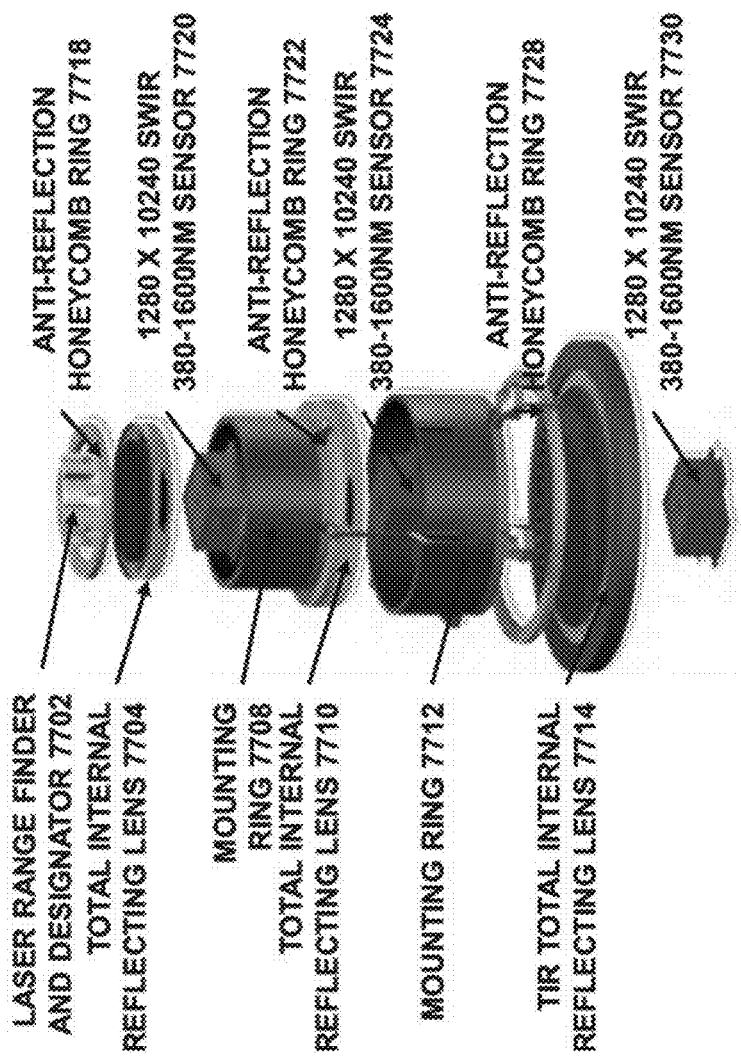
FIG. 77 depicts an exploded view of the multi-coincident view camera.

Referring now to FIG. 77, a multi-coincident view camera may be used for imaging. The feed from the multi-coincident view camera may be transmitted to the eyepiece 100 or any other suitable display device. In one embodiment, the multi-coincident view camera may be a fully-articulating, 3- or 4-coincident view, SWIR/LWIR imaging, and target designating system that allows simultaneous: wide, medium and narrow field-of-view surveillance, with each sensor at VGA or SXVGA resolution for day or night operations. The lightweight, gimbaled sensor array may be inertially stabilized as well as geo-referenced enabling a highly accurate sensor positioning and target designating with its NVG compatible laser pointer capability in all conditions. Its unique multiple and simultaneous fields-of-view enable wide area surveillance in the visible, near-infrared, short wave infrared and long wave infrared regions. It also permits a high resolution, narrow field-of-view for more precise target identification and designation with point-to-grid coordinates, when coupled with outputs from a digital compass, inclinometer and GPS receiver.

In one embodiment of the multi-coincident view camera, there may be separate, steerable, co-incident fields of view, such as 30°, 10° and 1°, with automated POI or multiple POIs tracking, face and iris recognition, onboard matching and communication wirelessly over 256-bit AES encrypted UWB with laptop, combat radio, or other networked or mesh-networked device. The camera may network to CP's, TOC's and biometric databases and may include a 3-axis, gyro-stabilized, high dynamic range, high resolution sensor to deliver the ability to see in conditions from a glaring sun to extremely low light. IDs may be made immediately and stored and analyzed locally or in remote storage. The camera may feature "look and locate" accurate geo-location of POI'S and threats, to >1,000 m distance, integrated 1550 nm, eye-safe laser range finder, networked GPS, 3-axis gyro, 3-axis magnetometer, accelerometer and inclinometer, electronic image enhancement and augmenting electronic stabilization aids in tracking, recording full-motion (30 fps) color video, be ABIS, EBTS, EFTS and JPEG 2000 compatible, and meet MIL-STD 810 for operation in environmental extremes. The camera may be mounted via a gimbaled ball system that integrates mobile uncooperative biometric collection and identification for a standoff biometric capture solution as well as laser range-finding and POI geo-location, such as at chokepoints, checkpoints, and facilities. Multi-modal biometric recognition includes collecting and identifying faces and irises and recording video, gait and other distinguishing marks or movements. The camera may include the capability to geo-location tag all POI's and collected data with time, date and location. The camera facilitates rapid dissemination of situational awareness to network-enabled units CP's and TOC's.

In another embodiment of the multi-coincident view camera, the camera features 3 separate, Color VGA SWIR Electro-optic Modules that provide co-incident 20°, 7.5° and 2.5° Fields of View and 1 LWIR Thermal Electro-optic Modules for broad area to pinpoint imaging of POIs and Targets in an ultra-compact configuration. The 3-axis, gyro-stabilized, high dynamic range, color VGA SWIR cameras deliver the ability to see in conditions from a glaring sun to extremely low light as well as through fog, smoke and haze—with no "blooming. Geo-location is obtained by integration of Micro-Electro-Mechanical System (MEMS) 3-axis gyroscopes and 3-axis accelerometers which augment the GPS receiver and magnetometer data. Integrated 1840 nm, eye-safe laser range finder and target designator, GPS receiver and IMU provide "look and locate", accurate geo-location of POIs and threats, to a 3 km distance. The camera displays and stores full-motion (30 fps) color video in its "camcorder on chip", and stores it on solid state, removable drives, for remote access during flight or for post-op review. Electronic image enhancement and augmenting electronic stabilization aids in tracking, geo-location range-finding and designation of POIs and targets. Thus, the eyepiece 100 delivers unimpeded "sight" of the threat by displaying the feed from the multi-coincident view camera. In certain embodiments of the eyepiece 100, the eyepiece 100 may also provide an unimpeded view of the soldier's own weapon with "see through", flip up/down, electro-optic display mechanism showing sensor imagery, moving maps, and data. In one embodiment, the flip up/down, electro-optic display mechanism may snap into any standard, MICH or PRO-TECH helmet's NVG mount.

FIG. 77 depicts an embodiment of a multi-coincident view camera, including laser range finder and designator 7702, total internal reflecting lens 7704, mounting ring 7708, total internal reflecting lens 7710, total internal reflecting lens 7714, anti-reflection honeycomb ring 7718, 1280×1024 SWIR 380-1600 nm sensor 7720, anti-reflection honeycomb ring 7722, 1280×1024 SWIR 380-1600 nm sensor 7724, anti-reflection honeycomb ring 7728, and 1280×1024 SWIR 380-1600 nm sensor 7730. Other embodiments may include additional TIR lenses, a FLIR sensor, and the like.

Figure 78A:
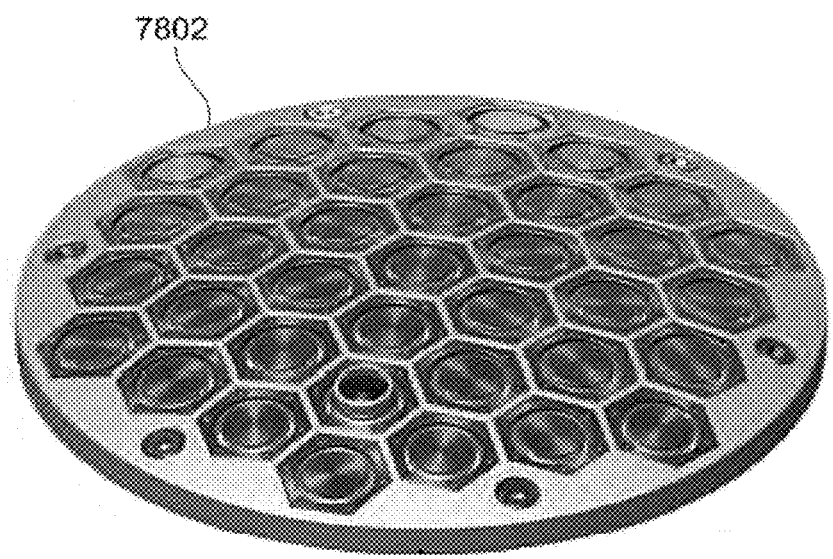
FIGS. 78A-78B depict a flight eye.
Figure 78B:
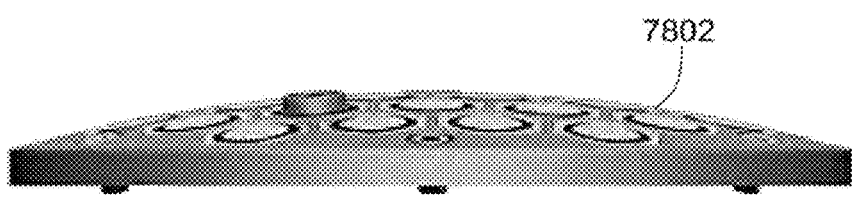

Referring to FIGS. 78A-78B, a flight eye is depicted. The feed from the flight eye may be transmitted to the eyepiece 100 or any other suitable display device. The flight eye may include multiple individual SWIR sensors mounted in a folded imager array with multiple FOVs. The flight eye is a low profile, surveillance and target designating system that enables a continuous image of a whole battlefield in a single flyover, with each sensor at VGA to SXGA resolution, day or night, through fog, smoke and haze. Its modular design allows selective, fixed resolution changes in any element from 1° to 30° for telephoto to wide angle imaging in any area of the array. Each SWIR imager's resolution is 1280×1024 and sensitive from 380-1600 nm. A multi-DSP array board "stiches" all the imagery together and auto-subtracts the overlapping pixels for a seamless image. A coincident 1064 nm laser designator and rangefinder 7802 can be mounted coincident with any imager, without blocking its FOV.

Figure 106:
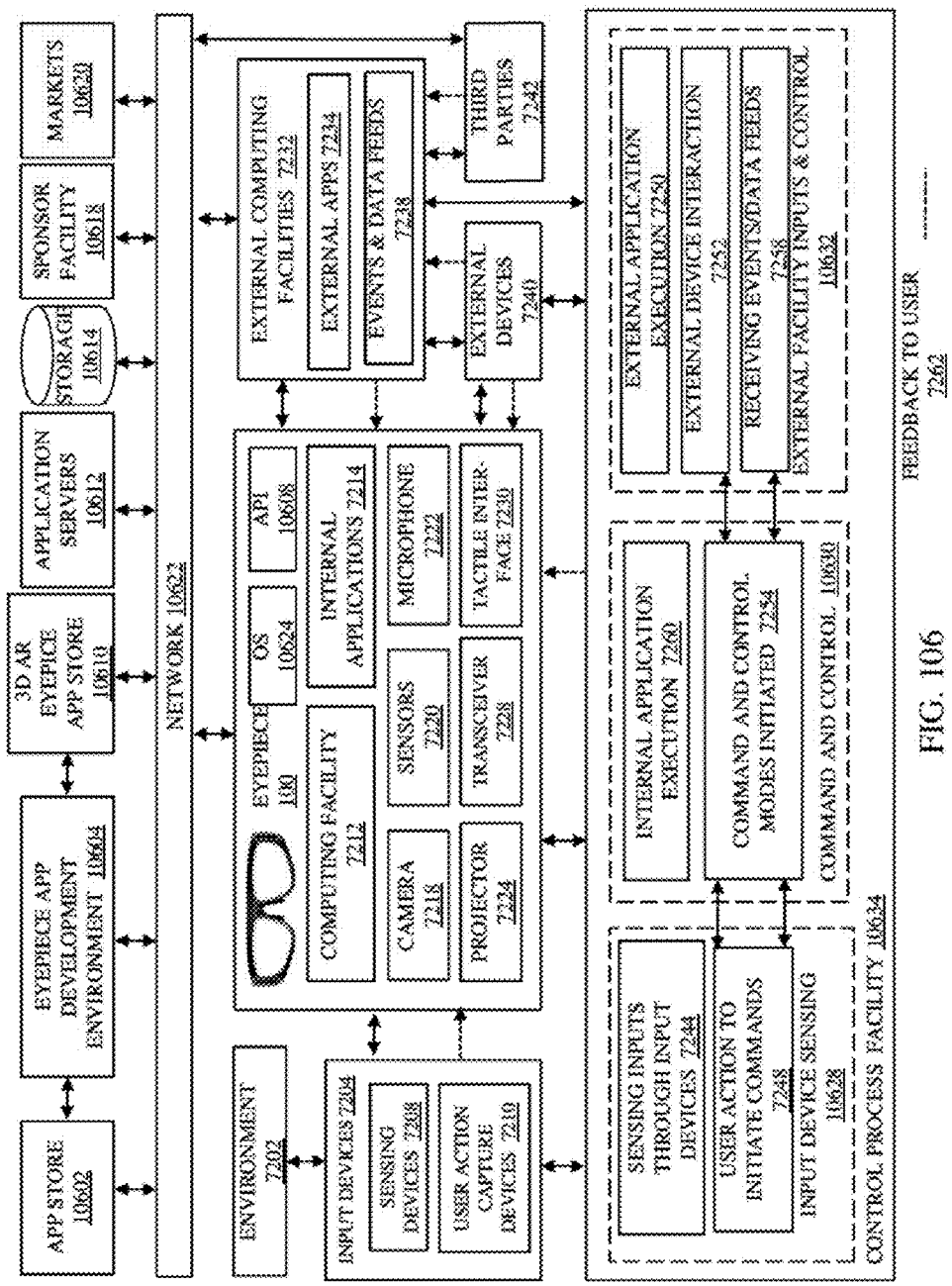

Referring to FIG. 106, the eyepiece 100 may operate in conjunction with software internal applications 7214 for the eyepiece that may be developed in association with an eyepiece application development environment 10604, where the eyepiece 100 may include a projection facility suitable to project an image onto a see-through or translucent lens, enabling the wearer of the eyepiece to view the surrounding environment as well as the displayed image as provided through the software internal application 7214. A processor, which may include a memory and an operating system (OS) 10624, may host the software internal application 7214, control interfaces between eyepiece command & control and the software application, control the projection facility, and the like.

In embodiments, the eyepiece 100 may include an operating system 10624 running on a multimedia computing facility 7212 that hosts an software internal application 7214, wherein the internal application 7214 may be a software application that has been developed by a third-party 7242 and provided for download to the eyepiece 100, such as from an app store 10602, a 3D AR eyepiece app store 10610, from third party networked application servers 10612, and the like. The internal application 7214 may interact with the eyepiece control process facility 10634 processes, such as in conjunction with an API 10608, through input devices 7204, external devices 7240, external computing facilities 7232, command and control 10630 facilities of the eyepiece, and the like. Internal applications 7214 may be made available to the eyepiece 100 through a network communications connection 10622, such as the Internet, a local area network (LAN), a mesh network with other eyepieces or mobile devices, a satellite communications link, a cellular network, and the like. Internal applications 7214 may be purchased through an applications store, such as the app store 10602, 3D AR eyepiece app store 10610, and the like. Internal applications 7214 may be provided through a 3D AR eyepiece store 10610, such as software internal applications 7214 specifically developed for the eyepiece 100.

An eyepiece applications development environment 10604 may be available for software developers to create new eyepiece applications (e.g. 3D applications), modify base applications to create new 3D application versions of the base application, and the like. The eyepiece application development environment 10604 may include a 3D application environment that is adapted to provide a developer with access to control schemes, UI parameters and other specifications available on the eyepiece once the finished application is loaded on or otherwise made functional for the eyepiece. The eyepiece may include API 10608 that is designed to facilitate communications between the finished application and the eyepiece computing systems. The application developer, within the developer's development environment may then focus on developing an application with certain functionality without concerning themselves with particulars of how to interact with the eyepiece hardware. The API may also make it more straightforward for a developer to modify an existing application to create a 3D application for use on the eyepiece 100. In embodiments, an internal application 7214 may utilize networked servers 10612 for client-server configurations, hybrid client-server configurations (e.g. running the internal application 7214 in part locally on the eyepiece 100 and in part on the application server 7214), hosting the application completely on the server, downloaded from the server, and the like. Network data storage 10614 may be provided in association with the internal application 7214, such as in further association with application servers 10612, purchased applications, and the like. In embodiments, internal applications 7214 may interact with a sponsor facility 10614, markets 10620, and the like, such as to provide sponsored advertisements in conjunction with the execution of the internal application 7214, to provide marketplace content to the user of the eyepiece 100, and the like.

In embodiments software and/or applications may be developed to be used with, or supplemental to the eyepiece. Applications for the eyepiece may be developed via an open source platform, a closed source platform, and/or a software development kit. The software development kit for developing applications for the eyepiece and software developed therefrom may be an open source or closed source. Applications may be developed that are compatible with Android, Apple, other platforms, and the like. Applications may be sold by or downloaded from an app store associated with the eyepiece, from an independent app store, and the like.

For example, an integrated processor of the eyepiece may run at least one software application and handle content for display to the user, and an integrated image source may introduce the content to the optical assembly of the eyepiece. The software application may provide interactive 3D content to the user through interaction with at least one of control and sensor facilities of the eyepiece.

In embodiments, the eyepiece may be used for various applications. The eyepiece may be used for consumer applications. For example only and not to provide an exhaustive list, the eyepiece may be used for or with tourism applications, educational applications, video applications, exercise applications, personal assistant applications, augmented reality applications, search applications, local search applications, navigations applications, movie applications, face recognition applications, place identifier applications, people identifier applications, text applications, instant messaging applications, email applications, things to do applications, social networking applications and the like. Social networking applications may include applications such as Facebook, Google+, and the like. In embodiments, the eyepiece may be used for enterprise applications. For example, and not to provide an exhaustive list, the eyepiece may be used for or with billing applications, customer relationship management applications, business intelligence applications, human resources management applications, form automation applications, office products applications, Microsoft Office, and the like. In embodiments, the eyepiece may be used for industrial applications. For example only an not to provide an exhaustive list, the eyepiece may be used for or with advanced product quality planning software applications, product part approval software applications, statistical process control applications, professional training applications and the like.

Figure 107:
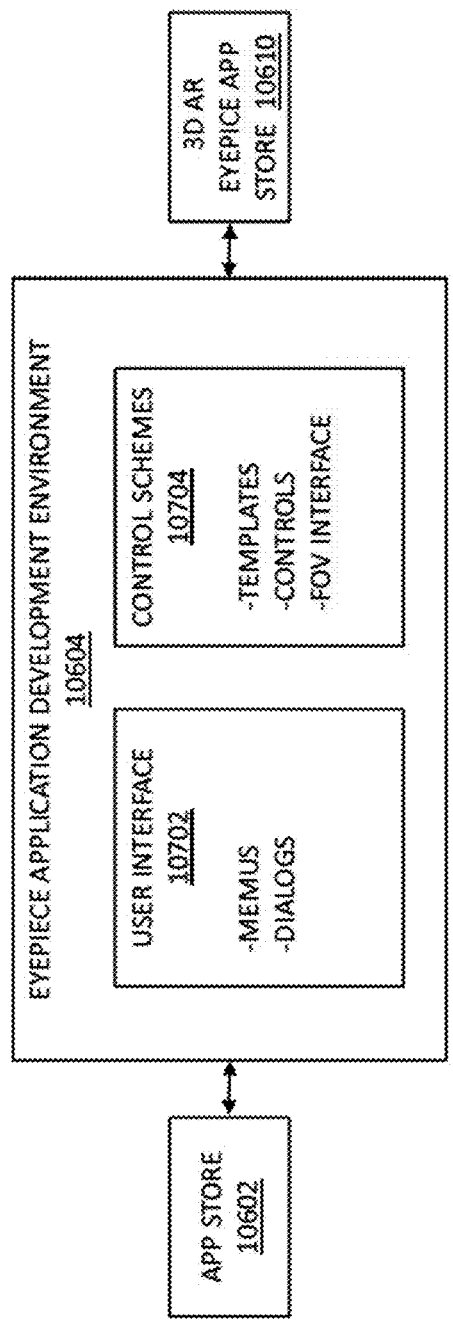

Referring to FIG. 107, the eyepiece application development environment 10604 may be used for development of applications that may be presented to the app store 10602, the 3D AR eyepiece app store 10610, and the like. The eyepiece application development environment 10604 may include a user interface 10702, access to control schemes 10704, and the like. For instance, a developer may utilize menus and dialog boxes within the user interface for accessing control schemes 10704 for selection so the application developer may choose a scheme. The developer may be able select a template scheme that generally operates the application, but may also have individual controls that may be selected for various functions that may override the template function scheme at a point in the application execution. The developer may also be able to utilize the user interface 10702 to develop applications with control schemes with a field of view (FOV) control, such as through a FOV interface. The FOV interface may provide a way to go between a FOV that shows both displays (for each eye) and a single display. In embodiments, 3D applications for the eyepiece may be designed within the single display view because the API 10610 will provide the translation which determines which display to be used for which content, although developers may be able to select a specific eye display for certain content. In embodiments, developers may be able to manually select and/or see what is going to be displayed in each eye, such as through the user interface 10702.

Figure 108:
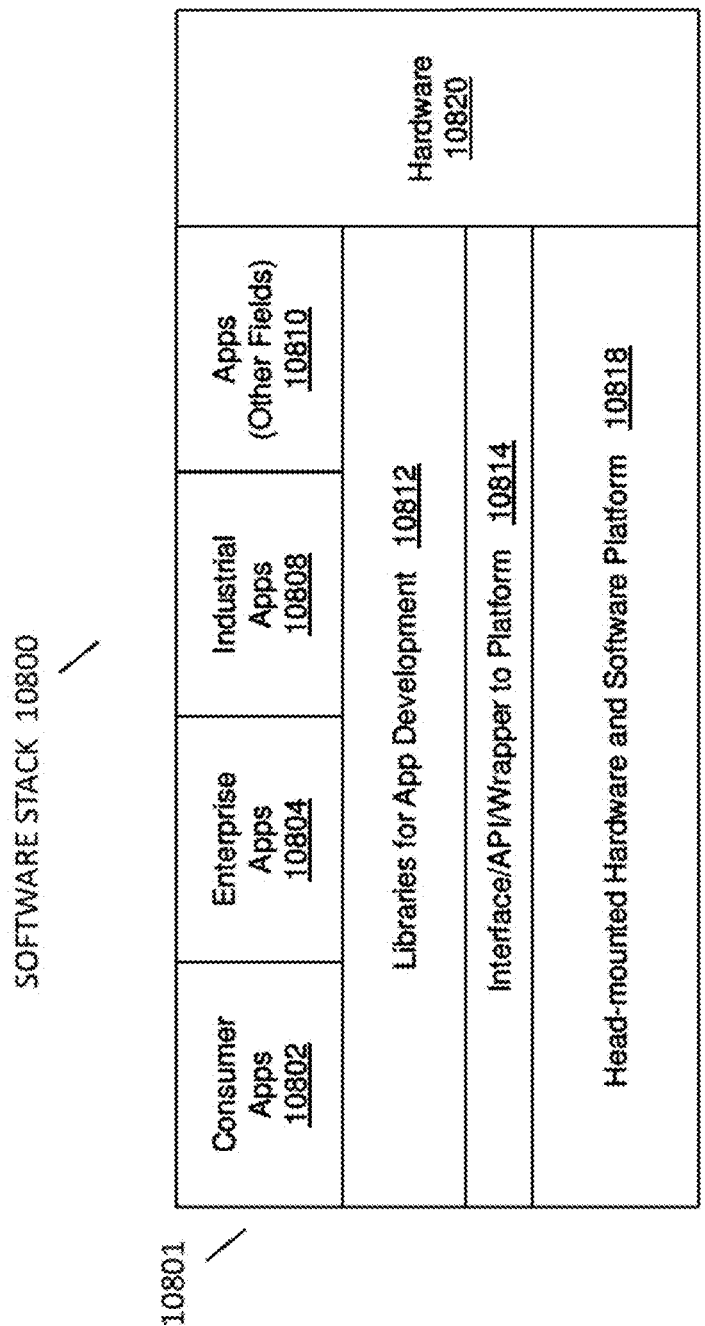

The eyepiece may have a software stack 10800 as described in FIG. 108. The software stack 10800 may have a head-mounted hardware and software platform layer 10818, an interface-API-wrapper to platform layer 10814, libraries for development 10812 layer, an applications layer 10801, and the like. The applications layer 10801 may in turn include consumer applications 10802, enterprise applications 10804, industrial applications 10808, and other like applications 10810. In addition, hardware 10820 associated with the execution or development of internal applications 7214 may also be incorporated into the software stack 10800.

In embodiments, the user experience may be optimized by ensuring that the augmented images are in focus with respect to the surrounding environment and that the displays are set at the appropriate brightness given the ambient light and the content being displayed.

In an embodiment, the eyepiece optical assembly may include an electro-optic module, aka display, for each eye that delivers content in a stereoscopic manner. In certain cases, a stereoscopic view is not desired. In embodiments, for certain content, only one display may be turned on or only one electro optic module may be included in the optical assembly. In other embodiments, the brightness of each display may be varied so that the brain ignores the dimmer display. An autobrightness control of the image source may control the brightness of the displayed content based on the brightness in the environment. The rate of brightness change may depend on the change in the environment. The rate of brightness change may be matched to the adaptation of the eye. The display content may be turned off for a period following a sudden change in environment brightness. The display content may be dimmed with a darkening of the environment. The display content may get brighter with a brightening of the environment.

When going from a bright environment to a dark environment, it takes a period of time for human eyes to adapt to the darkness. During this period of time, the eyes have only limited visibility of the dark environment. In some situations such as in security or law enforcement situations, it is important to be able to move from a bright environment to a dark environment and be able to rapidly determine what activities or objects are in the dark environment. However, it can take up to 20 minutes for a person's eyes to fully adapt to the dark environment. During this time, the person's vision of the environment is compromised which can lead to dangerous situations.

In some cases, a bright light such as a flashlight can be used to illuminate the dark environment. In other cases, it is possible to cover the person's eyes for a period of time prior to entering the dark environment to allow the eyes to partially adapt to the dark environment prior to entering the dark environment. However, in cases where a bright light cannot be used in the dark environment and it is not feasible to cover the person's eyes prior to entering the dark environment, a method to provide assisted viewing is needed to reduce the time where the person's vision is compromised during the transition from bright to dark.

Night vision goggles and binoculars are well known for providing images of dark environments. However, these devices provide an image of constant brightness and as such do not allow the user's eyes to adapt to the darkness so the device must be used continuously in the dark environment. As a result, these devices do not take advantage of the fact that people can see quite well in dark environments after their eyes are fully adapted the darkness.

U.S. Pat. No. 8,094,118 provides a method for adjusting the brightness of a display in correspondence to the brightness of the surrounding environment to conserve power. This method is directed at the perceived brightness of the display and does not relate to the adaptation of the user's eyes in transitions from bright to dark environments. In addition, the method does not assist the user with viewing the environment.

Therefore, the need persists for a method to assist people moving from bright to dark environments during the period when the person's eyes adapt to the darkness.

Head mounted displays with see-through capabilities provide a clear view of the scene in front of the user while also providing the ability to display an image, where the user sees a combined image comprised of the see-through view with the displayed image overlaid. The disclosure provides a method for providing an assisted view of the environment when the user is transitioning from a bright environment to a dark environment. The method uses a camera on the head mounted display to rapidly adjust capture conditions so that an image can be captured of the dark environment and the image is displayed to the user. The brightness of the displayed image is gradually reduced to enable the user's eyes to adapt to the dark environment.

FIG. 154 (taken from Hecht and Mandelbaum's data in the book edited by Davison, H., "The Eye" vol. 2, London Academic Press, 1962, Chapter 5 "Dark Adaptation and Night Vision", by Pirene, M. H.) shows a chart of a typical dark adaptation curve for a human eye, where the shaded area represents 80% of the group of subjects. In this chart the curve shows the lowest illuminance that can be observed at a particular time starting at time zero in a bright light environment and going to immediately to a dark environment where the lowest illuminance that can be observed is determined by showing the person spots of light of different illuminance over a field and the person reports the spots that can be seen after different times in darkness. As can be seen from the curve, the human eye, adapts over time so that lower illuminance spots can progressively be seen over a period of approximately 25 minutes. As noted on the chart in FIG. 154, there are actually two mechanisms that contribute to dark adaptation in the human eye. The cones in the eye (also known as photopic vision) adapt more quickly and at brighter conditions than the rods (also known as scotopic vision), which are relatively slow to adapt. As a result, the time to adapt in moving from a brighter condition to a darker condition can take a substantial period of time that depends on how dark the environment is. During the dark adaptation period, the person can be close to blind.

Table 2 provides typical illuminance values in units of both Lux and Lamberts for common lighting conditions. The range of illuminance for outside lighting conditions spans 9 orders of magnitude between bright sunlight and an overcast night without a moon. Illuminance values are also given for interior lighting conditions for comparison.

Table 2 shows typical levels of illuminance from the website: http://www.engineeringtoolbox.com/light-level-rooms-d_708.html

| Typical levels of brightness | Lux | Lambert |
|---|---|---|
| Sunlight | 107527 | 10.7527 |
| Full daylight | 10,752 | 1.0752 |
| Overcast day | 1075 | 0.1075 |
| Very dark day | 107 | 0.0107 |
| Twilight | 10.8 | 0.00108 |
| Deep twilight | 1.08 | 0.000108 |
| Full moon | 0.108 | 0.0000108 |
| Quarter moon | 0.0108 | 0.00000108 |
| Starlight | 0.0011 | 0.00000011 |
| Overcast night | 0.0001 | 0.00000001 |
| Supermarkets | 750 | 0.075 |

| Typical levels of brightness | Lux | Lambert |
|---|---|---|
| Normal office | 500 | 0.05 |
| Classroom | 250 | 0.025 |
| Warehouses | 150 | 0.015 |
| Dark public areas | 35 | 0.0035 |

Table 3 provides perceived brightness values in Brils when changing from one lighting condition where the eye is fully adapted, to a darker condition. The changes in lighting conditions shown relate to the illuminance values given in terms of Lamberts from, Table 2. The example given at the bottom of Table 3 is an illustration of a Bril, where the perceived brightness of 1 Bril is approximately the brightness provided outside on a clear night by a quarter moon, or 0.000001 Lambert, where the equation relating the perceived brightness in the human visual system to changes in lighting condition is provided in U.S. Pat. No. 8,094,118, the equation is given below as Equation 3 for reference.

$$B = \lambda (L/L_a) \sigma \quad \text{Equation 3}$$

where
$\sigma = 0.4 \log 10 (L_a) + 2.92$
$\lambda = 10^{2.0208} L_a^{0.336}$

In the other examples shown in Table 3, it is easy to see that many conditions encountered in real life result in situations where a change in lighting conditions results in perceived darkness. A variety of changes in lighting conditions and the perceived brightness when the change first happens are shown in Table 3. In many of these examples, the perceived brightness when first moving from the bright condition to the darker condition is well below the perceived brightness provided by a quarter moon after being fully dark adapted. Moving from daylight to a warehouse or a dark public area is particularly problematic and the eye is essentially blind for a period of time until it becomes adapted to the new lighting conditions. The disclosure described herein provides a method for assisting the human eye during transitions from bright conditions to darker conditions while the eye is adapting to the darker conditions.

Table 3 shows perceived levels of brightness when changing from a bright environment to a dark environment using Equation 3 and the illuminance values from Table 2:

| Perceived Brightness (brils) | σ | λ | Luminance (lamberts) | Adaptation luminance (lamberts) | Change in environment |
|---|---|---|---|---|---|
| 0.000005 | 3.32 | 227.4049951 | 0.05 | 10 | Sunny to office |
| 0.000000 | 3.32 | 227.4049951 | 0.015 | 10 | Sunny to warehouse |
| 0.016665 | 2.92 | 104.9059208 | 0.05 | 1 | Daylight to office |
| 0.000495 | 2.92 | 104.9059208 | 0.015 | 1 | Daylight to warehouse |
| 0.000007 | 2.92 | 104.9059208 | 0.0035 | 1 | Daylight to dark area |
| 0.000001 | 2.279176 | 30.37440945 | 0.0000108 | 0.025 | House to full moon |
| 1.011114 | 0.52 | 1.011113712 | 0.000001 | 0.000001 | Quarter moon |

FIG. 155 provides measured data on the rate of dark adaptation taken from the paper by Spillman L., Nowlan A. T., Bernholz C. D., "Dark Adaptation in the Presence of Waning Background Luminances", Journal of the Optical Society of America, Vol 62, No. 2, February 1972. FIG. 155 shows increment thresholds are measured against log background luminance decreasing linearly with time. Backgrounds changed over 7 log units within 3.5 min (□), 7 min (Δ), 14 min (○), 21 min (◊), and 3.5 min with no pre-exposure (■). Arrows indicate times of background extinction. Normal dark thresholds recorded in the absence of any background luminance (X) largely coincide with the curve for the steepest background slope and are omitted after becoming invariant.

The data in FIG. 155 are based on the measured rate at which the lowest detectable level (threshold) of illuminance on a lighted spot by a human eye progressively decreases as the eye becomes dark adapted (more sensitive) when the lighting conditions are changed from 0.325 Lamberts (partly cloudy day) to full darkness. The different curves shown in the chart of FIG. 155 are for lighting conditions where the change from bright to dark was done at different linear rates instead of immediately as shown in FIG. 154. The curves to the left side of the chart show a more rapid adaptation to the dark under conditions where the change from light to dark was done rapidly. As shown in FIG. 154 and supported by data show in FIG. 155, the typical time to dark adapt when moving directly from bright to full dark is approximately 15 minutes. What the data in FIG. 155 shows is that the brightness can be changed linearly over a period of 14 minutes with only a small penalty in terms of the time to dark adapt, the data in FIG. 155 shows the time to dark adapt increasing from 15 minutes for an immediate change to 19 minutes for a ramped change over 14 minutes. The disclosure herein provides a method of providing a displayed image of the dark environment with a brightness that progressively decreases with time so the user is provided with an observable image of the dark environment while still allowing the user's eyes to adapt to the dark environment. The method uses a camera that rapidly adjusts to the dark environment so that it can capture images of the dark environment. The captured images are provided to the user on a see-through head mounted display wherein the brightness of the images is progressively decreased over time so the user's eyes can dark adapt and the user can progressively see the environment with the see-through capability of the see-through head mounted display.

FIG. 156 is an illustration of a head mounted display device 15600 with see-through capabilities. The head mounted display device 15600 includes see-through displays 15602, one or more cameras 15604 and electronics 15608, wherein the electronics 15608 can include one or more of the following: a processor, a battery, a global positioning sensor (GPS), a direction sensor, data storage, a wireless communication system and a user interface.

In an embodiment, the head mounted display device 15600 with at least one camera 15604 or 15610 is used to provide an enhanced view of the dark environment on the see-through displays 15602 during the time that the user's eyes are adapting to the dark environment. The camera 15604 or 15610 can automatically adjust capture settings such as gain, ISO, resolution or pixel binning very rapidly with an auto-exposure system. In some embodiments, the lens of the camera 15604 or 15610 is changeable to enable improved image capture in a dark environment. The brightness of the images displayed on the see-through displays 15602 can be adjusted over time to match the adaptation of the eyes and any changing of photochromic materials that may be associated with the head mounted display device 15600. In this way, fast changing photochromic materials are not required. Photochromic materials with transition times to clear on the order of minutes are well suited to embodiments of the disclosure. In any case, the field of view of the displayed images of the environment should match the field of view of the head mounted display device 15600 to provide a display of the dark environment that is easy to interface within an augmented reality mode.

The disclosure provides a head mounted display device 15600 with one or more cameras 15604 or 15610 wherein captured images of the scene in front of the user can be displayed with a range of brightness over time. The cameras 15604 or 15610 and their associated auto-exposure systems can adjust to changes in brightness of the environment much faster than the user's eyes can adapt, typically under 1 second. In an embodiment, the cameras 15604 or 15610 capture images of the scene in front of the user and when the brightness of the scene changes rapidly from bright to dark, the captured images of the scene are displayed to the user on the see-through displays 15602. The brightness of the displayed images is decreased over time such that the user is provided with a bright image of the scene immediately after moving into the dark environment and the brightness is then decreased over time at a rate that allows the user's eyes to adapt to the darkness of the environment. FIG. 157 shows a graph of the brightness of the displayed image provided to the user over time, wherein t1 is the time when the brightness of the environment changes from bright to dark. Capture of images of the environment can begin at time t1 or before. After t1, the brightness of the displayed images is decreased until time t2 when the user's eyes are adapted to the dark environment. After time t2, the brightness of the displayed image is held constant at a level where the user can observe the environment in a see-through mode. In other embodiments of the disclosure, the brightness of the displayed image after time t2 is zero so that the user only observes the dark environment in a see-through mode. In a further embodiment of the disclosure, the image content of the displayed image changes after t2 from the captured images of the environment in front of the user, to other images or information such as augmented reality information e.g. instructions or directions. In yet another embodiment of the disclosure, if the environment is darker than a predetermined level, the brightness of the displayed image of the environment is decreased to a level which is maintained after time t2 thereby providing a version of night vision, wherein the night vision responds to rapid changes in environmental lighting and also provides longer term night vision when conditions are too dark for the eye to adapt to for the task at hand. The level of darkness wherein night vision imaging is provided after time t2 can be selected by the user in an operating mode setting, where tasks that require detection of more detail in the environment use settings which provide a brighter displayed image of the environment during night vision mode.

In a preferred embodiment, the brightness of the displayed image of the environment is decreased at a rate that corresponds to the rate that the user's eyes adapt to the dark environment, e.g. 14 minutes transition from a bright image to a dim image or no image corresponding to the curves shown in FIG. 155. In this way, the user is temporarily provided with an image of the environment while the user's eyes are adapting to the darkness, but the time to adapt to the dark environment is not extended substantially compared to the time to adapt without the displayed image.

In a further embodiment of the disclosure, the lens of the camera 15604 or 15610 is changed when the user enters the dark environment, to provide improved low light image capture capabilities. In this case, the camera 15604 or 15610 or another photoactive detector in the electronics 15608, detects the change from a bright environment to a dark environment, where the brightness of the environment is detected by an autoexposure sensor in electronics 15608 or by detecting a decrease in the pixel code values from the image sensor in the camera 15604 or 15610. The lens of the camera 15604 or 15610 is then changed to increase the light gathering capabilities or to enable the camera 15604 or 15610 to capture an infrared image. Example: light gathering capabilities can be increased by changing to a lens with a lower f#. Example: Infrared image capture can be enabled in the camera 15604 or 15610 by removing an infrared cut filter in the lens assembly, by moving the lens elements relative to one another to refocus or by changing one or more of the lens elements to an infrared lens element. In yet another embodiment, the image sensor in the camera 15604 or 15610 is changed to enable infrared image capture.

FIG. 158 shows a flowchart of a method of the disclosure. In Step 15802, the user moves from a bright environment to a dark environment. The camera 15604 (or another photoactive detector in the electronics 15608), detects the change in lighting conditions in the environment to dark conditions in Step 15804. In Step 15808, the capture conditions used by the camera 15604 or 15610 are adjusted by an auto-exposure system to enable image capture, and specifically video image capture, in the dark environment. In Step 15810, images of the environment are captured by the camera 15604 or 15610 and displayed on the see-through displays 15602 at a first brightness level, wherein the first brightness level of the displayed images is similar to the brightness perceived by the user in a see-through view of the environment immediately prior to the environment changing from bright to dark lighting conditions. Then in Step 15812, the brightness of the displayed images of the environment is decreased over time so that the user's eyes can dark adapt while viewing images of the environment. The decrease in brightness can be linear over the time period or nonlinear as shown in FIG. 157. The period of time over which the brightness of the images is decreased can correspond to the change in lighting conditions in the environment. Depending on how dark the environment is, in Step 15812, the brightness of the displayed images can be decreased to zero or maintained at a predetermined level to provide a version of night vision.

Example Scenario 1

A policeman working in daylight (approximately 1.0 Lambert), breaks down a door that leads to a somewhat dark room similar to the darkness in many restaurants (approximately 0.0035 Lambert) as shown from the data in Table 2. When the door opens, the policeman will perceive that the dark room is 0.000007 Bril or 10000× darker than the illuminance provided by a quarter moon as shown in the data in Table 3. In essence, he will not be able to see anything in the dark room. Based on the curves in FIG. 155, it will be approximately 1 minute before the policeman will be able to see anything in the dark room which is at 0.0035 Lambert (0.0035 Lamberts=0.54 Log milliLamberts). This is a dangerous situation as the eyes of the people in the dark room are already dark adapted so they will be able to see the policeman. In the case when the policeman is wearing a head mounted display device with a camera and see-through displays as described herein, images of the dark room can be presented to the policeman for approximately 1.5 minutes during the period of time that the policeman's eyes are dark adapting. After that time, the policeman can see the dark room through the see-through displays. The see-through displays can still be used to send instructions or other information to the policeman (as in an augmented reality imaging system) while he views the dark room through the see-through displays. Thus the head mounted display device of the disclosure provides the policeman instant vision in the dark room only as limited by the low light capabilities of the camera.

As long as the field of view presented in the displayed image closely matches the portion of the field of view of the policeman and the video images are live with only limited lag between capture and display, the policeman will be able to easily move around in the dark room using only the displayed image. The brightness of the displayed image is decreased over time as the policeman's eyes adapt to the dark room.

The camera can be a fairly standard digital camera with good low light performance operated in a high ISO and binned mode to provide video imaging down to partial moon light levels of lighting. Short wave infrared cameras or cameras with visible+near infrared imaging capabilities such as a camera with the infrared cut filter removed can be used to provide imaging down to darker levels. As indicated by the data shown in FIGS. 154 and 155, in very dark conditions it may be necessary to provide an image to the user for up to 25 minutes at which point the user's eyes will be fully dark adapted.

Example Scenario 2

A soldier inside a lighted house (illuminance 0.025 Lambert=0.40 Log milliLambert) opens a door and walks out into the night with a full moon (illuminance 0.00001 Lambert=−2 Log milliLambert). As can be seen from the numbers in Table 3, the perceived darkness when the soldier first steps into the night is full darkness with a brightness of 0.000001 Bril which is 1000000× darker than a night with a quarter moon when the eyes are fully adapted. The curves in FIG. 155 show that for this change in illuminance it will take the soldiers eyes approximately 2 minutes before objects can be seen in the darker conditions. As in the previous example, this can be a dangerous situation as the soldier is essentially blind for 2 minutes. The disclosure provides a see-through head mounted display, which captures images of the environment and displays them to the soldier to eliminate the period of blindness. In this case, the brightness of the images can be decreased over a period of 3-4 minutes so the soldier's eyes can dark adapt and at the end of that time, the soldier can operate with the head mounted display in a see-through mode or an augmented reality mode.

Instant visibility may be provided with the displayed image over the display field of view. A transition to see-through viewing is provided by gradually decreasing the brightness of the displayed image as the user's eyes adapt to the dark conditions.

This technique can also be used to compensate for photochromic lenses associated with the head mounted display device, which may not change to clear very quickly.

In alternate embodiments, the images presented to the user can be 2D captured by a single camera 15610 where the images presented to the eyes of the user are the same or 3D captured by stereo cameras 15604 wherein the images presented to the eyes of the user provide different perspectives of the scene. Other methods for producing stereo images such as using a lens with a split pupil or using a lens with a microlens array to enable light field imaging are also possible as is known to those skilled in the art.

The displayed image could also be tuned to different colors such as red or green to help the eye adapt to the darkness quicker as is commonly done in night vision binoculars.

In embodiments, the augmented reality eyepiece (AR) of the present disclosure is adapted to determine and/or compensate for the vergence of the user's eyes. Vergence is the simultaneous rotation of the user's eyes around a vertical axis to move their respective optical axes in opposite directions to obtain or maintain binocular vision. When a person looks at a closer object, the person's eyes move their respective optical axes inwardly toward the nose, a composite motion that is known as convergence. To look at a farther object, the person's eyes move their respective optical axes outwardly away from the nose, a composite motion that is known as divergence. The person's eyes diverge until their respective optical axes are essentially parallel to each other when the person is fixating on a point at infinity or very far away. Vergence works in conjunction with eye accommodation to permit a person to maintain a clear image of an object as the object moves relative to the person. Vergence compensation becomes important in situations where a virtual image, i.e., an AR image, such as a label or other information, is to be placed near to or overlap a real image or when a virtual image of an object is to be superimposed upon a real image of the object in order to make the placement of the virtual image correct with respect to the real image. Methods of the present disclosure for vergence compensation and/or determination are described herein and are collectively referred to as vergence methods.

The vergence methods may include a determination of the distance an object of interest from the user of the AR eyepiece and subsequent use of that distance to determine the vergence angle, i.e., the angle formed by the intersection of the optical axes of the user's eyes as they look at the object. The vergence angle is then used to determine the correct placement of the AR image with respect to the object, which may be in front of, behind, or at the matched to the object. For example, in a first set of vergence method embodiments, a single autofocus digital camera having an output signal is mounted in the AR eyepiece at some convenient location, e.g., in the bridge section or near one of the temples. The output of the camera is provided to a microprocessor within the AR eyepiece and/or transmitted to a remote processor. In either case, its signals relating to its autofocus capabilities are used to determine the distance to objects that the user may see when the user is looking straight ahead. This distance, along with the inter-pupillary distance of the user's eyes, is used to determine the vergence and the correct placement of a virtual image, e.g., a label, which may be desired for those objects. The distance and/or the vergence angle may also be used to determine the level of focus the virtual object is to have to be properly observable by the user. Optionally, additional information about that particular user's vergence characteristics may be input and stored in memory associated with the microprocessor and used to adjust the determination of the vergence.

In a second set of vergence method embodiments, an electronic range finder that is independent of a camera is incorporated into the AR eyepiece at some convenient location, e.g., in the bridge section or near one of the temples. In these embodiments, the output of the electronic range finder is used in the same manner as was the output of the autofocus camera described with regard to the first set of vergence method embodiments.

In a third set of vergence method embodiments, the AR eyepiece includes a plurality of range finding devices that may be autofocus cameras and/or electronic range finders. All of the plurality of devices may be aligned so as to determine the distance of objects in the same direction or one or more of the devices may be aligned differently from the other devices so that information about the distance to a variety of objects is obtainable. The outputs from one or more of the devices are input and analyzed in the same manner as was the output of the autofocus camera described with regard to the first set of vergence methods.

In a fourth set of vergence method embodiments, one or more range finding devices are employed in the manner discussed above. Additionally, the AR eyepiece includes one or more eye-tracking devices which are configured to track the movement and/or viewing direction of one or both of the user's eyes. The output of the eye-tracking devices is provided to a microprocessor within the AR eyepiece or may be transmitted to a remote processor. This output is used to determine the direction the user is viewing, and, when eye-tracking information from both eyes is available, to determine the vergence of the user's eyes. This direction and, if available, vergence information is then used alone or in conjunction with the vergence information determined from the range finding devices to determine placement, and optionally, the level of focus, of one or more virtual images related to one or more objects which the user may be viewing.

In a fifth set of vergence methods, one or more range finding device is directed away from the direction that is straight ahead of the user of the AR eyepiece. Distances to objects detected by the range finder device are used to display virtual images of the object in the manner described above. Although the user may or may not be aware of the virtual images when he is looking straight ahead, the user will be aware of the virtual images when the user looks in the direction of the objects to which they are related.

A calibration sequence may be used with any of the vergence method embodiments. The calibration sequence may employ steps of mechanical calibration nature, of an electronic calibration nature, or both. During the calibration sequence, the inter-pupilary distance of the user may be determined. Also, the user may be requested to look at a series of real or virtual objects having a range of real or virtual distances, e.g., from near to far, and the vergence of the eyes is measured either mechanically or electronically or both. The information from this calibration sequence may then be employed in the determinations of vergence, focusing, and/or virtual image placement when the AR eyepieces are in use. The calibration sequence is preferably employed when a user first puts on the AR eyepiece, but may be employed anytime the user believes that a recalibration would be helpful. Information correlating the user to that obtained during a calibration sequence may be stored for use whenever that particular user identifies himself to the AR eyepiece as its user, e.g., using any of the techniques described in this document.

It is to be noted that some range finding devices use range determining methodologies in which information received from a device's sensors is mapped upon a space-representing rectilinear or non-rectilinear grid. The information from the various sectors of the grid is inter-compared to determine the range distance. In the vergence method embodiments, the raw sensor information, the mapping information, the calculated distance, or any combination of these may be used in the determination of the placement and/or focus of the virtual image or images.

It is to be understood that the vergence method embodiments include the placement of a virtual image for one of the user's eyes or for both of the user's eyes. In some embodiments, one virtual image is provided to the user's left eye and a different virtual image is provided to the user's right eye. This would allow, for example, providing a virtual image or images to one eye while acquiring information from the other eye for sighting. In cases where multiple images are placed before the user, whether or not the images are the same or different, the placement may be simultaneous, at different times, or interlaced in time, e.g., the images are shown at a predetermined flicker rate or rates (e.g., 30, 60, and/or 180 Hz) with the image for the left eye being present when the image for the right eye is not and vice versa. In some embodiments, a virtual image is shown only to the person's dominant eye and in others a virtual image is shown only to the person's non-dominant eye. In some embodiments which employ images which are interlaced in time, virtual images of various objects which are located at various distances from the user are displayed in the manner described above; when the user looks from the real image of one object to the real image of another object, only the virtual image corresponding to the real image of the object being viewed will be seen by the user's brain. For example, by using a focusing mechanism operating at high rates, e.g. 30 to 60 Hertz, such as a piezo actuator attached to the LCOS or a variable focus lens inserted into the optical path, one or more of the same or different virtual images can be placed in more than one depth plane either to one or both of the user's eyes.

In some embodiments, the focal distance of the virtual image may be adjusted to provide the user with the illusion that the virtual image is at the desired distance. Such an adjustment is especially useful when images are being presented to both of the user's eyes and the relative lateral positions of the two images are adjusted for vergence. This adjustment may be accomplished, e.g., by adjusting the length of the optical path for the image displays or by the use of one or more variable lenses, which may be done in some embodiments of the present disclosure, for example, by raising or lowering the LCOS panel.

In embodiments, the disclosure provides methods for providing a depth cue with augmented reality virtual objects or virtual information that can convey a wide range of perceived depth to a broad range of individuals with different eye characteristics. These depth cue method embodiments of the present disclosure use differences in the lateral positioning or disparity of the augmented reality images provided to the two eyes of the individual to provide differences in the vergence of the virtual objects or virtual information that convey a sense of depth. One advantage of these methods is that the lateral shifting of the augmented reality images can be different for different portions of the augmented reality images so that the perceived depth is different for those portions. In addition, the lateral shifting can be done through image processing of the portions of the augmented reality images. The user can experience a full range of perceived depth through this method from as near as the individual can focus to infinity regardless of the individual's age.

In order to better understand these depth cue method embodiments of the present disclosure, it is useful to keep in mind that in some aspects of augmented reality, head mounted displays are used to add images of virtual objects or virtual information that is associated with the view of a scene as seen by a user. To add additional effects to the perception of the augmented reality it is useful to place the virtual objects or virtual information at a perceived depth in the scene. As an example, a virtual label can be placed onto an object in a scene, such as the name of a building. The perceived association of the virtual label with the building is enhanced if the label and the building are perceived by the user to be at the same depth in the scene. Head mounted displays with see-through capabilities are well suited to providing augmented reality information such as labels and objects because they provide the user with a clear view of the environment. However, for the augmented reality information to be of value, it must be easily associated with the objects in the environment and, as such, the positioning of the augmented reality information relative to the objects in the see-through view is important. While horizontal and vertical positioning of augmented reality information is relatively straight forward if the head mounted display has a camera that can be calibrated to the see-through view, the depth positioning is more complicated. U.S. Pat. No. 6,690,393 describes a method for positioning 2D labels in a 3D virtual world. However, this method is not directed at displays with a see-through view where the majority of the image the user sees is not provided digitally and, as such, the 3D location of objects is not known. U.S. Pat. No. 7,907,166 describes a robotic surgical system using a stereo viewer in which telestration graphics are overlaid onto stereo images of an operating site. However, similar to the method described in U.S. Pat. No. 6,690,393, this system uses captured images which are then manipulated to add graphics and, as such, does not address the unique situation with see-through displays wherein the majority of the image is not provided digitally and the relative locations of objects that the user sees are not known. Another prior art method for augmented reality is to adjust the focus of the virtual objects or virtual information so that the user perceives differences in focus depth that provide a depth cue to the user. As the user has to refocus his/her eyes to look at objects in the scene and to look at the virtual objects or virtual information, the user perceives an associated depth. However, the range of depth that can be associated with focus is limited by the accommodation that the user's eyes are capable of. This accommodation can be limited in some individuals particularly if the individual is older when eyes lose much of their accommodation range. In addition, the accommodation range is different depending on whether the user is near sighted or far-sighted. These factors make the result of using focus cues unreliable for a large population of user's with different ages and different eye characteristics. Therefore, the need persists beyond what is available in the prior art for a widely useable method for associating depth information with augmented reality.

Some of the depth cue method embodiments of the present disclosure are described in this and the following paragraphs with respect to FIG. 109 through FIG. 121. Head mounted displays with see-through capabilities provide a clear view of the scene in front of the user while also providing the ability to display an image, where the user sees a combined image comprised of the see-through view with the display image overlaid. The methods entail the displaying of 3D labels and other 3D information using the see-through display to aid the user in interpreting the environment surrounding the user. A stereo pair of images of the 3D labels and other 3D information may be presented to the left and right eyes of the user to position the 3D labels and other 3D information at different depths in the scene as perceived by the user. In this way, the 3D labels and other 3D information can be more easily associated with the see-through view and the surrounding environment.

Figure 109:
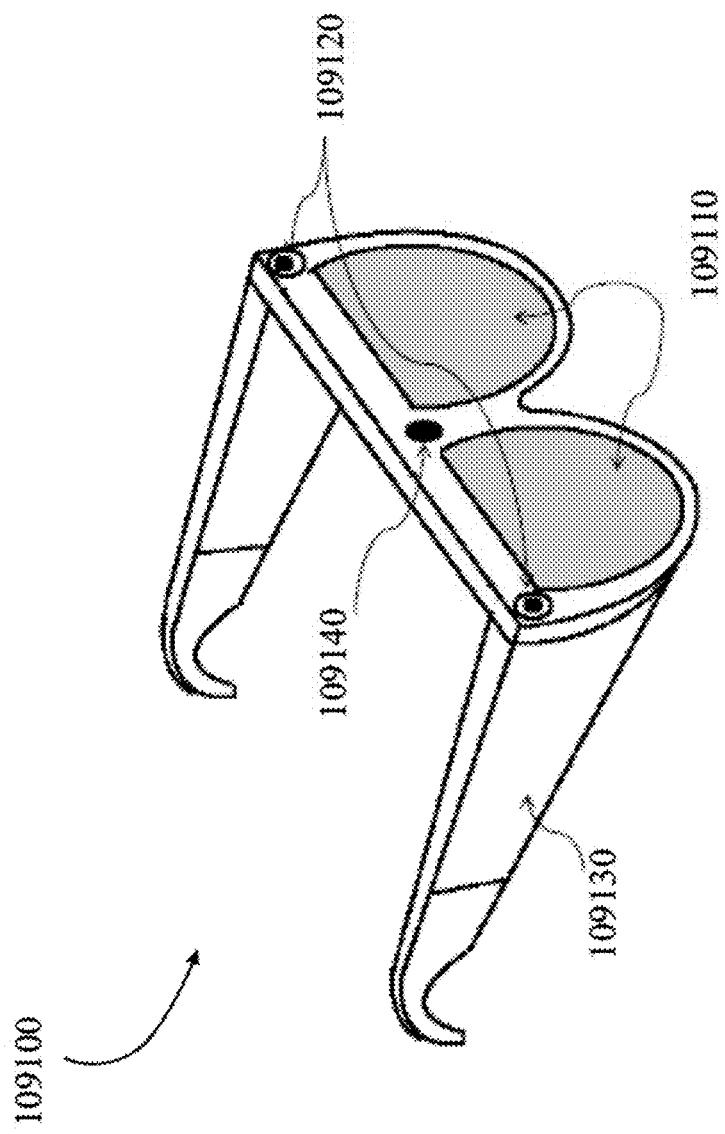

FIG. 109 is an illustration of a head mounted display device 109100 with see-through capabilities and is a special version of augmented reality eyepiece 100 shown in FIG. 1 and described throughout this document. The head mounted display device 109100 may include see-through displays 109110, stereo cameras 109120, electronics 109130, and range finder 109140. The electronics may include one or more of the following: a processor, a battery, a global positioning sensor (GPS), a direction sensor, data storage, a wireless communication system and a user interface.

FIG. 110 is an illustration of the scene in front of the user as seen by the user in the see-through view. A number of objects at different depths in the scene are shown for discussion. In FIG. 111 several of the objects in the scene have been identified and labeled. However, the labels are presented in two-dimensional (2D) fashion either by presenting the labels only to one eye of the user or by presenting the labels at the same positions in the image to each eye so the labels are coincident when viewed simultaneously. This type of labeling makes it more difficult to associate the labels with the objects particularly when there are foreground and background objects as the labels appear to be all located at the same perceived depth.

To make it easier to associate labels or other information with the desired objects or aspects of the environment, it is advantageous to present the labels or other information as three dimensional (3D) labels or other 3D information so that the information is perceived by the user to be at different depths. This may be done by presenting 3D labels or other 3D information in overlaid images to the two eyes of the user with a lateral shift in position between the images that are overlaid onto the see-through image so that the overlaid images have a perceived depth. This lateral shifting between images is also known as disparity to those skilled in stereo imaging and it causes the user to change the relative pointing of his/her eyes to align the images visually and this induces a perception of depth. The images with disparity are images of the 3D labels or other 3D information that are overlaid onto the see-through view of the scene seen by the user. By providing 3D labels with a large disparity, the user must align the optical axes of his/her eyes somewhat to bring the labels in the stereo images into alignment which gives a perception of the labels being located close to the user. The 3D labels that have a small disparity (or no disparity) can be visually aligned with the user's eyes looking straight ahead and this gives the perception of the 3D labels being located at a distance.

Figure 112:
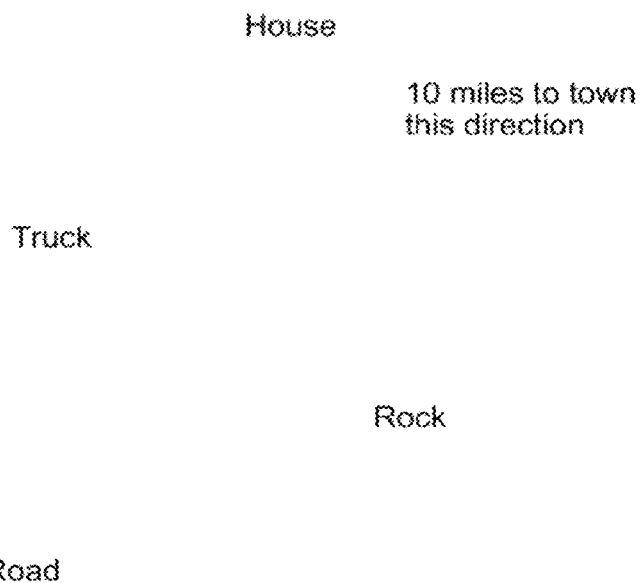
Figure 113:

FIGS. 112 and 113 illustrate a stereo image pair for 3D labels to be applied to the see-through view shown in FIG. 110. FIG. 112 is an image of the 3D labels shown to the user's left eye, while FIG. 113 is an image of the 3D labels shown to the user's right eye. Together, FIG. 112 and FIG. 113 provide a stereo pair of images. In this stereo pair, the lateral positioning of the 3D labels is different between images shown in FIG. 112 and FIG. 113. FIG. 114 provides an overlaid image of FIG. 112 and FIG. 113. For added clarity in FIG. 114, the 3D labels from FIG. 113 have been shown in grey while the 3D labels from FIG. 112 are shown in black. In the foreground of FIG. 114, the 3D labels from FIG. 113 are positioned to the left of the 3D labels from FIG. 112 with a relatively large disparity. In the background of FIG. 114, the 3D labels from FIG. 113 are coincident with and positioned on top of the 3D labels from FIG. 112 with no disparity. In the mid-ground region shown in FIG. 114, the 3D labels from FIG. 112 and FIG. 113 have a medium disparity. This relative disparity of the 3D labels as presented to the left and right eyes corresponds to the depth perceived by the user. By selecting a depth for the 3D labels that is coincident with the depth of the object in the scene that the 3D label is associated with makes it easy for the user to understand the connection between the 3D label and the object or other aspect of the environment that the user sees in the see-through view. FIG. 115 shows the see-through view of the scene with the 3D labels showing their disparity. However, when viewed in real life, the user would change the pointing direction of his/her eyes to make the 3D labels be coincident within each left/right set and it is this that provides the perception of depth to the user. The calculation of disparity is known to those skilled in the art. The equation for relating disparity and distance is given by the equation, Equation 1:

$$Z=Tf/d$$

where Z is the distance to the object from the stereo cameras, T is the separation distance between the stereo cameras, f is the focal length of the camera lens, and d is the disparity distance on the camera sensor between images of the same object in the scene. Rearranging the terms to solve for the disparity, the equation becomes Equation 2:

$$d=TF/Z$$

For example, for 7 mm focal length cameras which are separated by 120 mm and used in conjunctions with image sensors having center-to-center pixel distances of 2.2 micron, the disparities expressed in number of pixels a visual target point is shifted when one display is compared to the other are given in Table 1 for some representative distances (given in meters).

TABLE 1

| Distance (m) | Disparity (pixels) |
| --- | --- |
| 1 | 381.8 |
| 2 | 190.9 |
| 10 | 38.2 |
| 50 | 7.6 |
| 100 | 3.8 |
| 200 | 1.9 |

It is noted that sometimes in the art the disparity values for stereo images are described using numbers which range from negative to positive, wherein zero disparity is defined for an object at a selected distance from the observer which the observer would perceive as being in the mid-ground. The above-recited equations must be adapted to account for this shift of the zero point. When disparity values are described in this way, the disparities of a close object and a far object may be the same in magnitude and but opposite in sign.

FIG. 116 shows illustrations of the stereo pair of images captured by the stereo cameras 109120 on the head mounted display device 109100. Since these images are captured from different perspectives, they will have disparities that correspond to the distance from the head mounted display device 109100. In FIG. 117, the two images from FIG. 116 are overlaid to show the disparity between the images in the stereo pair. This disparity matches the disparity seen in the 3D labels shown for the objects in FIGS. 114 and 115. As such, the 3D labels will be perceived to be located at the same depth as the objects that they are intended to be associated with. FIG. 118 shows an illustration of the 3D labels as seen by the user as overlays to the see-through view seen with the left and right eyes.

FIG. 119 is a flowchart for a depth cue method embodiment of the present disclosure. In step 119010, the electronics 109130 in the head mounted display device 109100, determine the GPS location using the GPS for the head mounted display device 109100. In optional step 119020, the electronics 109130 determine the direction of view using an electronic compass. This enables the view location and view direction to be determined so that objects in the view and nearby objects can be located relative to the user's field of view by comparing the GPS location of the head mounted display device 109100 to databases of the GPS locations of other objects in the head mounted display device 109100 or by connecting to other databases using a wireless connection. In step 119030, objects of interest are identified relative to the user's field of view either by the electronics 109130 analyzing databases stored on the device 109100 or by wirelessly communicating in conjunction with another device. In step 119040, distances to the objects of interest are determined by comparing the GPS location of the head mounted display device 109100 to the GPS locations of the objects of interest. Labels relating names or other information about the objects of interest are then generated along with disparities to provide 3D labels at distances perceived by the user corresponding to the distances to the objects of interest in step 119050. FIG. 111 shows examples of labels comprising names, distances and descriptions for objects of interest in the user's field of view. In step 119060, the 3D labels for the objects of interest are displayed to the user's left and right eyes with the disparities to provide the 3D labels at the desired depths.

FIG. 120 is a flowchart for another a depth cue method embodiment of the present disclosure wherein steps similar to those in the steps of FIG. 119 have been numbered using the same reference numerals as used in FIG. 119. In step 120140, the distances and directions to the objects of interest relative to the user's field of view are determined either by the electronics 109130 on the device or in conjunction with a wirelessly connected other device. In step 120160, 3D labels are displayed to the user's left and right eyes with disparities to provide the 3D labels at the desired depths, and, in addition, the 3D labels are provided in the portions of the user's field of view that correspond to the direction to the objects of interest. FIG. 111 shows an example where the label for a distant object of interest is provided toward the rear of the user's field of view and in the direction toward the distant object of interest, shown in this example as the label "10 miles to town this direction." This feature provides a visual cue in the 3D information which makes it easy for the user to navigate to objects of interest. It should be noted that the 3D labels can be provided in front of other objects in the see-through field of view.

FIG. 121 is a flowchart for yet another depth cue method embodiment of the present disclosure. In this embodiment, distances to objects of interest in the scene are determined with a distance measuring device 109140 such as a rangefinder. In step 121010, one or more images are captured of a scene adjacent to the head mounted display device 109100 using stereo cameras 109120. Alternately, a single camera may be used to capture the one or more images of the scene. The one or more images of the scene can be different spectral types of images, for example, the images can be visible-light images, ultraviolet images, infrared images, or hyperspectral images. The image or images are analyzed in step 121020 to identify one or more objects of interest, wherein the analysis can be conducted by the electronics 109130 or the image can be sent wirelessly to another device for analysis. In step 121030, distances to objects of interest are determined using the distance measuring device 109140. Disparities correlating correlate distances of the objects of interest are determined in step 121040. In step 121050, labels or other information are determined for the objects of interest. In step 121060, the 3D labels or other 3D information are displayed for the objects of interest.

FIG. 122 is a flowchart for another depth cue method embodiment of the present disclosure. In this embodiment, the distances to objects in the scene are measured directly by using the stereo cameras to obtain a depth map of the scene. In step 122010, stereo cameras 109120 are used to capture one or more stereo image sets of the scene adjacent to the head mounted display device 109100. The one or more stereo image sets of the scene can be different spectral image types, for example, the stereo images can be visible-light images, ultraviolet images, infrared images, or hyperspectral images. The stereo image set or sets are analyzed in step 122020 to identify one or more objects of interest, wherein the analysis can be conducted by the electronics 109130 or the stereo image set or sets or can be sent wirelessly to another device for analysis. In step 122030, the images in the stereo image set or sets are compared to determine the disparities for the one or more objects of interest. In step 122040, labels or other related to the one or more objects of interest are determined. In step 122050, 3D labels and/or 3D information is displayed for the one or more objects of interest.

In embodiments, the present disclosure may provide for display content placement using camera focus distance information, such as utilizing an integrated camera operating in conjunction with an autofocus determination facility, wherein information relating to a distance to a real world object in the surrounding environment is extracted by an integrated processor from the autofocus determination facility, and where the integrated processor determines, based on the distance, a placement position for the content within a field of view of the optical assembly. The field of view may comprise two separately controllable fields of view, each aligned with one of the user's eyes, such that the user can view the surrounding area and content with both eyes and the placement position for the content comprises a placement position for each of the two separately controllable fields of view. The content may comprise two independent images where two independent images are to be placed separately in each of the two separately controllable fields of view, where the two independent images may form a 3D image when displayed to the user within the two separately controllable fields of view. The placement position may be determined by extracting a placement value from a table of placement values that correspond with distances to real world objects. The integrated processor may calculate the placement position.

In embodiments, the present disclosure may provide for a display content placement using range-finder information, such as with a range finder integrated with the eyepiece and operating to determine a distance to a real world object in the surrounding environment, and where the integrated processor determines, based on the distance, a placement position for the content within a field of view of the optical assembly. The field of view may comprise two separately controllable fields of view, each aligned with one of the user's eyes, such that the user can view the surrounding area and content with both eyes and the placement position for the content comprises a placement position for each of the two separately controllable fields of view. The content may comprise two independent images where two independent images are to be placed separately in each of the two separately controllable fields of view, where the two independent images may form a 3D image when displayed to the user within the two separately controllable fields of view. The placement position may be determined by extracting a placement value from a table of placement values that correspond with distances to real world objects. The integrated processor may calculate the placement position.

In embodiments, the present disclosure may display content placement using a plurality of range determination sensors, such as through utilization of a plurality of integrated range determination sensors operating to determine a distance to a real world object in the surrounding environment, and where an integrated processor determines, based on the distance, a placement position for the content within a field of view of the optical assembly. The field of view may comprise two separately controllable fields of view, each aligned with one of the user's eyes, such that the user can view the surrounding area and content with both eyes and the placement position for the content comprises a placement position for each of the two separately controllable fields of view. The content may comprise two independent images where two independent images are to be placed separately in each of the two separately controllable fields of view, where the two independent images may form a 3D image when displayed to the user within the two separately controllable fields of view. The placement position may be determined by extracting a placement value from a table of placement values that correspond with distances to real world objects. The integrated processor may calculate the placement position. In embodiments, the plurality of integrated range determination sensors may be camera sensors, range finders, and the like.

In embodiments, the present disclosure may display content placement using a combination of range determination sensors and user eye-tracking, such as through the utilization of a plurality of integrated sensors (e.g. camera, range finder) and eye-tracking information from an eye-tracking facility incorporated in conjunction with the optical assembly of the eyepiece, to establish an object's position with respect to viewing and object's position (e.g. angle to the object, distance to the object). In embodiments, the present disclosure may utilize other facilities related to the placement of content within a field of view of the optical assembly, such as location and placement of images in the user's peripheral vision, use of a calibration sequence, use of a grid to aid in the location and/or calibration, interlacing images to each eye for images at different distances, and the like.

In embodiments, the present disclosure may provide for display content control during movement of the eyepiece, such as through an integrated movement detection facility adapted to detect movements of the head-mounted eyepiece when worn by the user, and where the integrated processor determines a type of movement and reduces the appearance of the displayed content based on the type of movement. The type of movement may be jitter, fast movement, and the like. The reduction of appearance may be an elimination of the displayed content, a reduction in the brightness of the displayed content, a reduction in the contrast of the displayed content, a change in the focus of the displayed content, and the like.

Near field communications (NFC) allow for a short range wireless data exchange between an NFC reader and a passive NFC device, where the NFC reader acts as an 'initiator' of the communications (providing the power for the exchange) and the passive NFC device acts as a 'target' (harvesting power from the RF field from the NFC reader to provide data back to the reader). An example of this configuration may be an NFC reader device reading identification information from a tag, such as a clothing tag. Note that NFC is also compatible with radio frequency identification (RFID) technology. NFC wireless exchange of data may also be bi-directional if two electronics devices contain an NFC reader, and are brought in close proximity to each other. Examples of this configuration may be two NFC-enabled smart phones exchanging information between them (e.g. exchange of electronic business cards), an NFC-enabled smart phone exchanging information with an NFC-enabled point-of-service (POS) device (e.g. for electronic money transfer, such as with the GOGGLE WALLET mobile payment system), exchange of information between two NFC-enabled mobile game devices, and the like. Applications of NFC technology may include electronic money transfer, mobile payment, file sharing, electronic business card exchange, mobile gaming, social network connectivity, ticket purchasing, boarding pass check-in, POS, coupon collecting and/or redeeming, tour guide station initiator, ID card, keycard, key for a car or hotel, and the like. The NFC technology has a practical range of about 4 cm (theoretically about 20 cm), and so the initiator and target should be in close proximity for the communications to occur.

In an example, a user may store credit card information in their NFC-enabled smart phone, allowing them to make electronic money payments to a NFC-enabled POS device at a retail store by bringing their smart phone in close proximity to the POS device (again, such as implemented in the GOGGLE WALLET mobile payment system). In this way, the user does not need to pull out the actual credit card to make the transaction, as the credit card information is read from the smart phone by the POS device through the NFC connectivity. However, the user still has the inconvenience of having to take their smart phone out of their pocket or purse, hold it up close to the POS device, and then put their smart phone away again.

The present disclosure provides a more convenient solution for enabling NFC-enabled wireless transactions by providing the user with an NFC watch device, such as worn by the user on their wrist, which is then always conveniently available to hold up to another NFC-enabled device for data exchange. Although the present disclosure describes an embodiment of an NFC 'watch', it is not meant to be limiting in any way, and one skilled in the art would acknowledge alternate implementations that fulfill the spirit of the invention, such as implemented as a bracelet, a fob, a ring, and the like. Embodiments of the NFC watch may include a stand-alone NFC device, an NFC relay device, and the like, where the NFC relay device establishes communications with both an NFC target device (e.g. NFC-enabled POS device) as well as a second NFC-enabled device (e.g. a user's smart phone). For instance, in the case where the NFC watch is acting as a stand-alone NFC device, it may contain the information to be exchanged (e.g. credit card information). In the case where the NFC watch is acting as an NFC relay device, the watch may not contain the information to be exchanged, but rather, the information to be exchanged is stored in another electronics device that the NFC relay device is in communications with, such as a smart phone, a mobile computing device, a personal computer, and the like.

In embodiments, where the NFC watch is acting as an NFC relay device, the user may be able to leave their personal device (e.g. smart phone) in their pocket or purse, and simply bring the NFC watch close to the other NFC-enabled device for data exchange, where the NFC watch provides communications between the other NFC-enabled device and the user's personal device. For example, the user may be wearing the NFC watch on their wrist, and have their smart phone, containing their credit card information, stored in their pocket. When they approach an NFC-enabled POS device for electronic payment, the user may now be able to leave their smart phone stored away, and merely bring their NFC watch up to the POS device, where the NFC watch communicates with the user's smart phone over some non-proximate communications link (e.g. Bluetooth, WiFi, and the like). The NFC watch reads the user's credit card information from the smart phone, and transfers the data to the POS device. With this configuration, the user doesn't have to take out their smart phone at all, as they only have to bring their NFC watch close to the POS device to make the electronic payment, while maintaining all their personal and financial information centrally located in their smart phone.

In embodiments, and referring to FIG. 207, an NFC watch 20702 may provide the normal functions of a typical watch, such as a watch face 20704 for display of the time and date 20708, function buttons 20710, an embedded controller for watch functionality, and the like. But in addition, the NFC watch may provide for communications facilities, such as for near field communications to an NFC-enabled device, for mid-range communications (e.g. Bluetooth) to near-by electronics, for longer-range communications (e.g. WiFi) to electronics in the general vicinity, and the like. In embodiments, antennas 20712A-B for near field communications may be provided as an antenna 20712A in the watchband (e.g. with an NFC loop antenna), as an antenna 20712B in the watch body (e.g. with an NFC 'stamp' antenna), and the like. In the case where the antenna 20712A is located in the watchband, the user may operationally hold the watchband portion of the NFC watch close to the NFC-enabled target device for data exchange. In the case where the antenna 20712B is located in the watch body, the user may operationally hold the watch body portion of the NFC watch close to the NFC-enabled target device for data exchange. In embodiments, the watch display 20704 may also provide for a control interface 20718 that enables the user to input and/or select information, such as a credit card number for use in an electronic money exchange, a verification code, data for transfer, and the like, and where the control interface 20718 may include a display, control buttons, a 2D control pad, a touch screen, and the like.

Referring to FIG. 208, an example use scenario may include a user 20802 wearing an NFC watch 20702A acting as a stand-alone NFC device, where the NFC watch 20702A is held up to an NFC-enabled POS device 20084 for payment of purchase through an NFC communications link 20804A. In this case, the NFC watch 20702A contains the payment information to be exchanged with the NFC-enabled POS device 20804. In embodiments, the information contained in the NFC watch 20702A may have been previously input manually through the control interface 20718, through a wired or wireless connection to a computing facility (e.g. a mobile computing device, a smart phone, a personal computer), through a network connection (e.g. a local network connection, a WiFi connection), and the like.

Referring to FIG. 209, an example use scenario may include a user 20902 wearing an NFC watch 20702B acting as an NFC relay device that is in wireless communications 20908A with a smart phone 20908 in the user's pocket, and where the information for data exchange is contained in the user's smart phone 308. Without the use of the NFC watch, the user would have to take their smart phone out of their pocket and hold it up close to the NFC-enabled POS device for data exchange. With the present invention, the user 20902 may leave the smart phone 20908 in their pocket, and simply hold the NFC watch 20702B up to the NFC-enabled POS device 20804, where the NFC watch 20702B communicates 20804A with the NFC-enabled POS device 20804, thus enabling the transfer of information between the smart phone 308 and the NFC-enabled POS device 20804 via the two communication channels 20804A 20908A set up by the NFC watch 20702B. In this configuration, it may not be necessary for the smart phone 20908 to be NFC-enabled, as the only communications link required by the smart phone 20908 is to the NFC watch 20702B via the mid-range communications link 20908A, such as utilizing Bluetooth or the like.

In embodiments, the NFC watch may communicate with a plurality of other electronics facilities via non-NFC mid-range communications link(s), such as with personal computers, mobile computers, mobile communications devices, navigation devices, body-worn electronics devices, augmented reality eyewear, head-worn electronic devices, home entertainment devices, home security devices, home automation devices, a local network connection, a personal network connection, and the like. For instance, NFC watch may communicate with an eyepiece such as an eyepiece including optics enabling a see-through display on which may be displayed content served from an integrated processor and where aspects of the eyepiece may be controlled via sophisticated control techniques involving one or more of sensors, cameras, tactile interfaces, accessory devices, and the like. In embodiments, the NFC watch may interface with the glasses to present transaction details in the glasses. Glasses control systems may be used as an interface for any interactions needed in the transaction.

In embodiments, the NFC watch may provide computing resources, such as a microcontroller, memory, input-output devices independent of the communications links (e g memory card, wired connection), wireless connection to a local network for updates, programmability, and the like. For instance, the NFC relay device may provide memory to store a history of purchases, preferred items, a personal profile, sales offers, redemption codes, preferred customer ID, rewards information, loyalty program data, and the like.

The methods and systems described herein, especially the various embodiments of the inventive augmented reality eyepiece, may be adapted to communicate and receive communications by and/or through any electronic communications system or network. Examples of such electronic communication systems and networks types and their related protocols, topologies, network elements, etc., include the following: (1) wired networks such as: (a) wide area networks (WAN)—leased lines using protocols such as point-to-point (PPP), high-level data link control (HDLC), synchronous data link control (SDLC), and digital subscriber line; circuit switching using protocols such as PPP, and ISDN; packet switching using protocols such as frame relay, X.25 (pre-OSI stack), packet over synchronous optical networking/synchronous hierarchy (SONET/SDH), multi-protocol-label-switching (MPLS), switched multi-megabit data service (SMDS), Ethernet (e.g., 10 GB, 100 GB); cell relay using protocols such as the asynchronous transfer mode (ATM) protocol; and using network elements such as routers, switches, hubs, and firewalls; (b) Metropolitan Area Networking (MAN) using protocols such as ATM, fiber distributed network interface (FDDI), SMDS, Metro Ethernet, and Distributed-queue dual-bus (DQDB); using topologies such as star, bus, mesh, ring, and tree; and using network elements such as routers, switches, hubs, and firewalls; (c) local area networks (LAN), e.g., using high speed serial interface protocols such as Ethernet (e.g. Ethernet, Fast, 1 GB, 10 GB, and 100 GB); using topologies such as star and tree; and using network elements such as routers, switches, hubs, and firewalls; (d) personal area networks (PAN) using technologies such as USB and FireWire; (2) wireless networks such as: (a) wide area networks (WAN) using standards such as RTT (CDMA), EDGE (GSM), EV-DO (CDMA/TDMA), Flash-OFDM (Flash-OFDM), GPRS (GSM), HSPA D and U (UMTS/3GSM), LTE (3GPP), UMTS-TDD (UMTS/3GSM), WIMAX (802.16), satellite, mobile Internet, such as general 3G and general 4G; using network elements such as base station subsystem, network and switching subsystem, GPRS core network; operational support system, subscriber identify module (SIM), Universal Terrestrial Radio Access Network (UTRAN), and core network, and using interfaces such as W-CDMA (UTRA-FDD)-UMTS, ULTRA-TDD HCR-UMTS, TD-SCDMA-UMTS, User Equipment Interface-UMTS, Radio Resource Control (Radio Link Control, Media Access Control), Um Interface (Air interface for GSM with physical layer such as GMSK or 8PSK modulation, data link layer such as LAPDm, and network layer such as radio resource, mobility management, and call control); (b) Metropolitan Area Networks (MAN) using protocols such as WIMAX (802.16); Local Area Networks (LAN) using technologies such as Wi-Fi with modes such as Ad-hoc and Infrastructure, OSI layers such as SCMA/CA and subtechnologies such as OFDM and Spread Spectrum; and using network elements such as routers, switches, hubs, firewalls, access points, base stations, and with clients such as personal computers, laptop computers, Internet Protocol phones, mobile phones, and smart phones; (c) Personal Area Networks (PAN) using topologies such as star, tree, and mesh, and technologies such as (i) Bluetooth (e.g., using roles (such as master, slave, and simultaneous master/slave), protocol stacks (such as core protocols, cable replacement protocols, telephony control protocols, and adopted protocols), mandatory protocols (such as Link Management Protocol (LMP), Logical Link Control and Adaptation Protocol (L2CAP), Service Discovery Protocol (SDP)), pairing methods (such as legacy pairing and Simple Secure Pairing), air interface (such as license-free ISM band (2.402-2.480 GHz))), (ii) Infrared Data Association (IrDA) (e.g. using mandatory protocol stack layers (e.g., Infrared Physical Layer Specification (IrPHY), Infrared Link Access Protocol (IrLAP), Infrared Link Management Protocol (IrLMP)) or Optional Protocol Stack Layers (e.g., Tiny Transport Protocol (Tiny TP), Infrared Communications Protocol (IrCOMM), Object Exchange (OBEX), Infrared Local Area Network (IrLAN), IrSimple, and IrSimpleShot)), (iii) wireless USB, (iv) Z-Wave (e.g., having source-routed mesh network topology, one or more master controllers control routing and security, and FGSK modulation), (v) ZigBee (e.g. having physical and medium access control layers defined in 802.15.4 and components such as a network layer, an application layer, Zigbee device objects, and manufacturer-defined application objects, and using CSMA/CA), (vi) Body Area Network, and (vii) Wi-Fi; (3) Near Field Communications (NFC) such as those operating with peer to peer network types at 13.56 MHz, with ISO/IEC 18000-3 air interface and data rates of 106 Kbits/s-424 kbits/s and having passive and/or active communication modes. The methods and systems described herein, especially the various embodiments of the inventive augmented reality eyepiece, may be adapted to comply with any or all aspects of mobile device network management systems, such as policy management, user management, profile management, business intelligence, incident management, performance management, enterprise-class, multiplatform support mobile device management (including sub-aspects such as software and SaaS), security management (including sub-aspects such as certificate control (e.g., related to email, applications, Wi-Fi access, and VPN access), password enforcement, device wiping, remote locking, trail auditing/logging, centralized device configuration verification, jailbreak/rooted detection, secure container, and application wrapping), platform support (e.g., Android, iOS, Blackberry, Symbian, Windows mobile, and Windows phone), compliance management, software management (including such sub-aspects as application downloaders, application verifications, application update support, application patch support, application store support (e.g., enterprise applications and third party applications)), and hardware/device management (e.g., including device enrollment (e.g., ownership, staging, registration, user authentication, EULA development, and restriction development), external memory blocking, and configuration change history. The methods and systems described herein, especially the various embodiments of the inventive augmented reality eyepiece, may be adapted for use with any kind of private, community, or hybrid cloud computing network or cloud computing environment, including those which involve features of software as a service (SaaS), platform as a service (Paas), and/or infrastructure as a service (IaaS).

The methods and systems described herein may be deployed in part or in whole through a machine that executes computer software, program codes, and/or instructions on a processor. The processor may be part of a server, cloud server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, cloud servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, cloud servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

All documents referenced herein are hereby incorporated by reference.

What is claimed is:

1. An interactive head-mounted device, comprising:
   an optical assembly through which a surrounding environment is viewable;

an integrated processor for handling virtual content for display;

an integrated image source for introducing the virtual content to the optical assembly; and an environmental sensor;

wherein the integrated processor is adapted to initially display, via the integrated image source and the optical assembly, the virtual content with a display parameter having a first setting, and wherein the integrated processor is adapted to display, via the integrated image source and the optical assembly, the virtual content with the display parameter having a second setting, different from the first setting, responsive to a change in the surrounding environment as recognized by the environmental sensor.

2. The device of claim 1, wherein the virtual content is a video image.

3. The device of claim 2, wherein the display parameter is at least one of brightness, color saturation, color balance, color hue, video resolution, transparency, compression rate, frames per second rate, and playback speed.

4. The device of claim 1, wherein the environmental sensor includes at least one of a charge-coupled device, a black silicon sensor, an IR sensor, an acoustic sensor, an induction sensor, a motion sensor, an optical sensor, an opacity sensor, a proximity sensor, an inductive sensor, an Eddy-current sensor, a passive infrared proximity sensor, a radar, a capacitive displacement sensor, a hall-effect sensor, a magnetic sensor, a GPS sensor, a thermal imaging sensor, a thermocouple, a thermistor, a photoelectric sensor, an ultrasonic sensor, an infrared laser sensor, an inertial motion sensor, a MEMS internal motion sensor, an ultrasonic 3D motion sensor, an accelerometer, an inclinometer, a force sensor, a piezoelectric sensor, a rotary encoder, a linear encoder, a chemical sensor, an ozone sensor, a smoke sensor, a heat sensor, a magnetometer, a carbon dioxide detector, a carbon monoxide detector, an oxygen sensor, a glucose sensor, a smoke detector, a metal detector, a rain sensor, an altimeter, an activity sensor, an object detector, a marker detector, a laser rangefinder, a sonar, a capacitive sensor, a heart rate sensor, and an RF/micropower impulse radio (MIR) sensor.

5. The device of claim 2, wherein the video image is stopped from playing in response to an indication from an accelerometer input of the environmental sensor that a user's head is moving.

6. The device of claim 4, wherein an audio sensor input of the environmental sensor is generated by the speaking of at least one participant of a video conference.

7. The device of claim 2, wherein the video image is made more or less transparent in response to an indication from the environmental sensor that a user is moving.

8. An interactive head-mounted device, comprising:

an optical assembly through which a surrounding environment is viewable;

an integrated processor for handling virtual content for display;

an integrated image source for introducing the virtual content to the optical assembly; and an integrated virtual image capture facility that images an aspect of the surrounding environment and provides the virtual content for display;

wherein the integrated processor is adapted to initially display, via the integrated image source and the optical assembly, the virtual content with a display parameter having a first setting, and wherein the integrated processor is adapted to display, via the integrated image source and the optical assembly, the virtual content with the display parameter having a second setting, different from the first setting, responsive to a change in the surrounding environment as recognized by the integrated virtual image capture facility.

* * * * *